US009169316B2

(12) United States Patent
Baty et al.

(10) Patent No.: US 9,169,316 B2
(45) Date of Patent: Oct. 27, 2015

(54) PRODUCTION OF ANTIBODY FORMATS AND IMMUNOLOGICAL APPLICATIONS OF SAID FORMATS

(75) Inventors: Daniel Baty, Marseilles (FR); Ghislaine Behar, Marseilles (FR); Martine Chartier, Marseilles (FR); André Pelegrin, Montpellier (FR); Jean-luc Teillaud, Paris (FR); Isabelle Teulon, Saint Gely du Fesc (FR)

(73) Assignees: Centre National de la Recherche Scientifique-CNRS, Paris (FR); INSERM (Institut National de la Sante et de la Recherche Medicale), Paris (FR); Universite d'Aix Marseille, Marseilles (FR); Universite de Montpellier, Montpellier (FR); Institut Regional du Cancer de Montpellier-Val d'Aurelle, Montpellier (FR); Institut Paoli Calmettes, Marseilles (FR)

( * ) Notice: Subject to any disclaimer, the term of this patent is extended or adjusted under 35 U.S.C. 154(b) by 863 days.

(21) Appl. No.: 11/818,218

(22) Filed: Jun. 13, 2007

(65) Prior Publication Data

US 2009/0202979 A1 Aug. 13, 2009

Related U.S. Application Data

(63) Continuation of application No. PCT/FR2005/003151, filed on Dec. 15, 2005.

(30) Foreign Application Priority Data

Dec. 16, 2004 (FR) ..................................... 04 13433

(51) Int. Cl.
*A61K 39/395* (2006.01)
*C07K 16/30* (2006.01)
*C07K 16/00* (2006.01)
*C07K 16/28* (2006.01)

(52) U.S. Cl.
CPC .............. *C07K 16/00* (2013.01); *C07K 16/283* (2013.01); *C07K 16/3007* (2013.01); *C07K 2317/21* (2013.01); *C07K 2317/22* (2013.01); *C07K 2317/52* (2013.01); *C07K 2317/54* (2013.01); *C07K 2317/55* (2013.01)

(58) Field of Classification Search
None
See application file for complete search history.

(56) References Cited

U.S. PATENT DOCUMENTS

2002/0155604 A1 10/2002 Ledbetter et al.
2004/0253250 A1* 12/2004 Ledbetter et al. .......... 424/185.1
2007/0135621 A1 6/2007 Bourel et al.
2007/0298033 A1 12/2007 Gauthier et al.
2009/0053233 A1 2/2009 De Romeuf et al.
2009/0163410 A1 6/2009 Baty et al.

FOREIGN PATENT DOCUMENTS

EP 0 618 292 10/1994
WO WO 9425591 A1 * 11/1994
WO WO 2005075515 A2 * 8/2005

OTHER PUBLICATIONS

Paul. Fundamental Immunology, 3rd Edition, 1993. pp. 292-295.*
Rudikoff, Giusti, Cook, and Scharff. Single amino acid substitution altering antigen-binding specificity. Proceedings of the National Academy of Sciences, 1982. vol. 79, pp. 1979-1983.*
Colman. Effects of amino acid sequence changes on antibody-antigen interactions. Research in Immunology, 1994. vol. 145, pp. 33-36.*
Mac Callum, Martin and Thornton. Antibody-antigen interactions: contact analysis and binding site topography. Journal of Molecular Biology, 1996. vol. 262, pp. 732-745.*
Muyldermans and Lauwereys. Unique single-domain antigen binding fragments derived from naturally occurring camel heavy-chain antibodies. Journal of Molecular Recognition, 1999. vol. 12, pp. 131-140.*
Harmsen and Haard. Properties, production, and applications of camelid single-domain antibody fragments. Applied Microbiology and Biotechnology, 2007. vol. 77, pp. 13-22.*
De Pascalis, Iwahashi, Tamura, Padlan, Gonzales, Santos, Giuliano, Schuck, Schlom, and Kashmir. Grafting of abbreviated complementarity determining regions containing specificity determining residues essential for ligand contact to engineer a less immunogenic humanzied monoclonal antibody. Journal of Immunology, 2002. vol. 169, pp. 3076-3084.*
Casset, Roux, Mouchet, Bes, Chardes, Granier, Mani, Pugniere, Laune, Pau, Kaczorek, Lahana, and Rees. A peptide mimetic of an anti-CD4 monoclonal antibody by rational design. Biochemical and Biophysical Research Communications, 2003. vol. 307, pp. 198-205.*
Vajdos, Adams, Breece, Presta, De Vos, and Sidhu. Comprehensive functional maps of the antigen-binding site of an anti-ErbB2 antibody obtained with shotgun scanning mutagenesis. Journal of Molecular Biology, 2002. vol. 320, pp. 415-428.*
Wu, Nie, Huse, and Watkins. Humanization of a murine monoclonal antibody by simultaneous optimization of framework and CDR residues. Journal of Molecular Biology, 1999. vol. 294, pp. 151-162.*
Zhu, Hattori, Zhang, Jimenez, Ludwig, Dias, Kussie, Koo, Kim, Lu, Liu, Tejada, Friedrich, Bohlen, Witte, and Rafii. Inhibition of human leukemia in an animal model with human antibodies directed against Vascular Endothelial Growth Factor Receptor 2. Leukemia, 2003. vol. 17, pp. 604-611.*

(Continued)

*Primary Examiner* — Misook Yu
*Assistant Examiner* — Julie Wu
(74) *Attorney, Agent, or Firm* — McAndrews, Held & Malloy Ltd.

(57) ABSTRACT

The invention concerns an in-vitro method for introducing a targeted genome modification into an oocyte or an egg and a method for performing a random insertion in the genome of a host cell.

10 Claims, 93 Drawing Sheets

(56) References Cited

OTHER PUBLICATIONS

Cortez-Retamozo, Lauwereys, Hassanzadeh, Gobert, Conrath, Muyldermans, Baetselier, and Revets. Efficient tumor targeting by single-domain antibody fragments of camels. International Journal of Cancer, 2002. vol. 98, pp. 456-462.*
Wright, Shin, and Morrison. Genetically engineered antibodies: progress and prospects. Critical Reviews in Immunology, 1992. vol. 12, pp. 125-168.*
Mc Call, Adams, Amoroso, Nielsen, Zhang, Horak, Simmons, Schier, Marks, and Weiner. Isolation and characterization of an anti-CD16 single chain Fv fragment and construction of an anti-HER2/neu/anti-CD16 bispecific svFv that triggers CD16 dependent tumor cytolysis. Molecular Immunology, 1999. vol. 36, pp. 433-446).*
Frenken, Van Der Linden, Hermans, Bos, Ruuls, De Geus, and Verrips. Isolation of antigen specific Llama VHH antibody fragments and their high level secretion by *Saccharomyces cerevisiae*. Journal of Biotechnology, 2000. vol. 78, pp. 11-21.*
Rahbarizadeh, Rasaee, Forouzandeh, Allameh, Sarrami, Nasiry, and Sadeghizadeh. The production and characterization of novel heavy-chain antibodies against the tandem repeat region of MUC1 mucin. Immunological Investigations, 2005. vol. 34, pp. 431-452.*
Pluckthun et al (Immunotech, 1997, 3:83-105).*
Riechmann et al (J of Immunol Methods, 1999, 231:25-38).*
Roguska et al (Protein Engineering, 9:896-904).*
Zuo et al (Protein Engineering, 2000, 13:361-367).*
Muyldermans (Molecular Biotechnology, 2001, 74:277-302).*
MacCallum et al (Journal of Molecular Biology, 1996, 262:732-745).*
De Pascalis et al (Journal of Immunology, 2002, 169:3076-3084).*
Casset et al (Biochemistry and Biophysical Research Communication, 2003, 307:198-205).*
Vajdos et al (Journal of Molecular Biology, 2002, 320:415-428).*
Holm et al (Molecular Immunology, 2007:1075-1084).*
Chen et al (Journal of Molecular Biology, 1999, 293:865-881).*
Wu et al (Journal of Molecular Biology, 1999, 294:151-162).*
CREDO, 2013, valence.*
Padlan et al, 1995, FASEB J, 9:133-139.*
Müller Kristian M. et al; "The first constant domain ($C_H1$ and $C_L$) of an antibody used as heterodimerization domain for bispecific miniantibodies;" Federation of European Biochemical Societies—FEBS Letters 442; 1998; pp. 259-264.
International Search Report for PCT/FR2005/003151 dated Mar. 22, 2006, 2 pages.
Le Calvez, H. et al.; "Increased Efficiency of Alkaline Phosphatase Production Levels in *Escherichia coli* Using a Degenerate PelB Signal Sequence;" Gene, vol. 170, 1996; pp. 51-55.
Vely, F. et al.; "A New Set of Monoclonal Antibodies Against Human Fc γ RII (CD32) and Fc γ RIII (CD16): Characterization and Use in Various Assays;" Hybridoma, vol. 16. No. 6, 1997; pp. 519-528.
Le Calvez, H. et al.; "Paratope Characterization by Structural Modelling of Two Anti-Cortisol Single-Chain Variable Fragments Produced in *E. coli*;" Molecular Immunology, vol. 32, No. 3, 1995; pp. 185-198.
Vivier, E. et al.; "Signaling Function of Reconstituted CD16: ζ : γ Receptor Complex Isoforms;" International Immunology, vol. 4, No. 11, 1992; pp. 1313-1323.
Chomczynski, P. et al.; "Single-Step Method of RNA Isolation by Acid Guanidinium Thiocyanate-Phenol-Chloroform Extraction;" Analytical Biochemistry, vol. 162, 1987; pp. 156-159.
Ghahroudi, M. A. et al.; "Selection and Identification of Single Domain Antibody Fragments From Camel Heavy-Chain Antibodies;" FEBS Letters, vol. 414, 1997; pp. 521-526.
Terskikh, A. et al.; "Marked Increase in the Secretion of a Fully Antigenic Recombinant Carcinoembryonic Antigen Obtained by Deletion of its Hydrophobic Tail;" Molecular Immunology, vol. 30, No. 10, 1993; pp. 921-927.
Hamers-Casterman, C. et al.; "Naturally Occurring Antibodies Devoid of Light Chains;" Nature, vol. 363, Jun. 3, 1993; pp. 446-448.
Teillaud, C. et al.; "Soluble CD16 Binds Peripheral Blood Mononuclear Cells and Inhibits Pokeweed-Mitogen-Induced Responses;" Blood, vol. 82, No. 10, Nov. 15, 1993; pp. 3081-3090.

* cited by examiner

```
                    /          FR1          /    CDR1     /        FR2      /   CDR2   /            FR3                   /     CDR3      /    FR4
                    1         10        20       30        40        50         60        70        80        90        100           110
                    1234567890123456 789 01ab2345 6789012345 6789012345 678 901 2abc 3456789012345 67890123456789012abc 3456 78901234 567890 abcde 12 34567890123

VHH ANTI-CD16

CD16 c13
/SEQ ID N°73/       EVQLVQSGGGLVQPGGSLRLSCSFPG SIFSLTMG*** WYRQAPGKERELVT SAT*** PGGDTNYADFVKG RFTISRDNARSIIYLQMNSLKPEDTAVYYCYA RTRNMG***** TV WGQGTQVTVSS
/SEQ ID N°103/      EVQLVESGGGLVQPGGSLRLSCSFPG SIFSLTMG*** WYRQAPGKERELVT SAT*** PGGDTNYADFVKG RFTISRDNARSIIYLQMNSLKPEDTAVYYCYA RTRNMG***** TV WGQGTQVTVSS

CD16 c21
/SEQ ID N°74/       EVQLVQSGGELVQAGGSLRLSCAASG LTFSSYNMG** WFRRAPGKEREFVA SITW** SGRDTFYADSVKG RFTISRDNAKNTVYLQMSSLKPEDTAVYYCAA NPWPVAAPRSG TY WGQGTQVTVSS
/SEQ ID N°104/      EVQLVESGGELVQAGGSLRLSCAASG LTFSSYNMG** WFRRAPGKEREFVA SITW** SGRDTFYADSVKG RFTISRDNAKNTVYLQMSSLKPEDTAVYYCAA NPWPVAAPRSG TY WGQGTQVTVSS

CD16 c28
/SEQ ID N°75/       EVQLVESGGGLVQPGESLTLSCVVAG SIFSFAMS*** WYRQAPGKERELVA RIG*** SDDRVTYADSVKG RFTISRDNIKRTAGLQMNSLKPEDTAVYYCNA QTDLRDWTVR* EY WGQGTQVTVSS

CD16 c72
/SEQ ID N°76/       EVQLVESGGGLVQPGGSLITLSCVAAG SIFTFAMS*** WYRQAPRKERELVA RIG*** TDDETMYKDSVKG RFTISRDNVKRTAGLQMNNLKPEDTAVYYCNA RTDYRDWTVR* EY WGQGTQVTVSS

VHH ANTI-CEA

CEA 3
/SEQ ID N°77/       EVQLVESGGGLVQAGGSLRLSCTSST VTFTPYOMG** WYRQAPGKQRALVA DIST** GGSRTNYADFAKG RFTISRDDVKNTVYLQMNNLKPEDTAVYYCNT YYAMIGHA**** RN WGQGTQVTVSS

CEA 17
/SEQ ID N°78/       EVQLVESGGGFVQAGESLTLTLSCTSST LTFTPYRMA** WYRQAPGKQRDIVA DISSG* DGRTTNYADFAKG RFTISRDNIKNTVFLRMTNLKPEDTAVYYCNT FVSFVGIA*** RS WGQGTQVTVSS

CEA 25
/SEQ ID N°79/       EVQLVESGGGLVQAGDSLILTCISPT LTFTPYRMG** WYRQAPGKQRDIVA DISGG* DGRTTNYADFAKG RFTISRDNVKNAVVLQMNNLKPEDTALYYCNT YVALVGHA*** RS WGQGTQVTVSS

CEA 43
/SEQ ID N°80/       QVQLQESGGGLVQAGGSLRLSCTSST LTFTPYRMG** WYRQTPGKQRDIVA DISPG* DGSTKNYAGFAQG RFTISRDNIKNTVYLQMNDLKPEDTAVYYCNT YVAFVGRA*** RT WGQGTQVTVTS
/SEQ ID N°105/      EVQLVESGGGLVQAGGSLRLSCTSST LTFTPYRMG** WYRQTPGKQRDIVA DLSPG* DGSTKNYAGFAQG RFTISRDNIKNTVYLQMNDLKPEDTAVYYCNT YVAFVGRA*** RT WGQGTQVTVTS
```

Figure 1

VHH anti-CD16

CD16 c13

/SEQ ID N° 81/
GAGGTGCAGCTGGTGCAGTCTGGGGGAGGCTTGGTGCAGCCTGGGGGGTCTCTGAGACTCTCCTGTTCATTCCCTGGAAGCATCTTCAGTCTCA
CCATGGGCTGGTACCGTCAGGCTCCAGGGAAGGAGCGCGAGTTGGTCACAAGTGCTACTCCTGGTGGTGACACAAACTATGCAGACTTCGTGAA
GGGCCGATTCACCATCTCCAGAGACAACGCCAGGAGCATCATATATCTACAAATGAATAGCCTGAAACCTGAGGACACGGCCGTCTATTATTGT
TATGCACGTACGAGGAATTGGGGTACGGTCTGGGGCCAGGGGACCCAGGTCACCGTCTCCTCA

/SEQ ID N° 106/
GAGGTGCAGCTGGTGGAGTCTGGGGGAGGCTTGGTGCAGCCTGGGGGGTCTCTGAGACTCTCCTGTTCATTCCCTGGAAGCATCTTCAGTCTCA
CCATGGGCTGGTACCGTCAGGCTCCAGGGAAGGAGCGCGAGTTGGTCACAAGTGCTACTCCTGGTGGTGACACAAACTATGCAGACTTCGTGAA
GGGCCGATTCACCATCTCCAGAGACAACGCCAGGAGCATCATATATCTACAAATGAATAGCCTGAAACCTGAGGACACGGCCGTCTATTATTGT
TATGCACGTACGAGGAATTGGGGTACGGTCTGGGGCCAGGGGACCCAGGTCACCGTCTCCTCA

CD16 c21

/SEQ ID N° 82/
GAGGTGCAGCTGGTGCAGTCTGGGGGAGAGTTGGTGCAGGCTGGGGGCTCTCTGAGACTCTCCTGTGCAGCCTCTGGCCTCACCTTCAGTAGCT
ATAACATGGGCTGGTTCCGCCGGGCTCCAGGGAAGGAGCGTGAGTTTGTAGCATCTATTACCTGGAGTGGTCGGGACACATTCTATGCAGACTC
CGTGAAGGGCCGATTCACCATCTCCAGAGACAACGCCAAGAACACTGTTTATCTGCAAATGAGCAGCCTGAAACCTGAGGACACGGCCGTTTAT
TATTGTGCTGcAAAcCCCTGGCCAGTGGCGGCGCCACGTAGTGGCACCTACTGGGGCCAAGGGACCCAGGTCACCGTCTCCTCA

/SEQ ID N° 107/
GAGGTGCAGCTGGTGGAGTCTGGGGGAGAGTTGGTGCAGGCTGGGGGCTCTCTGAGACTCTCCTGTGCAGCCTCTGGCCTCACCTTCAGTAGCT
ATAACATGGGCTGGTTCCGCCGGGCTCCAGGGAAGGAGCGTGAGTTTGTAGCATCTATTACCTGGAGTGGTCGGGACACATTCTATGCAGACTC
CGTGAAGGGCCGATTCACCATCTCCAGAGACAACGCCAAGAACACTGTTTATCTGCAAATGAGCAGCCTGAAACCTGAGGACACGGCCGTTTAT
TATTGTGCTGCAAAcCCCTGGCCAGTGGCGGCGCCACGTAGTGGCACCTACTGGGGCCAAGGGACCCAGGTCACCGTCTCCTCA

CD16 c28

/SEQ ID N° 81/
GAGGTGCAGCTGGTGGAGTCTGGGGGAGGCTTAGTGCAGCCTGGGGAGTCTcTGACACTCTCCTGtGTAGTTGCTGGAAGCATCTTCAGCTTCG
CCATGAGCTGGTATCGCCAGGCTCCAGGAAAAGAGCGCGAATTGGTCGCACGTATTGGTTCGGATGATCGGGTAACGTACGCAGATTCCGTGAA
GGGCCGATTTACCATCTCCAGAGACAACATCAAGCGCACGGCGGGCCTGCAGATGAACAGCCTGAAACCTGAGGACACGGCCGTCTACTACTGC
AAtGcCCAAACAGATTTGAGGGATTGGACTGTGCGAGAGTACTGGGGCCAGGGGACCCAGGTCACCGTCTCCTCA

CD16 c72

/SEQ ID N° 81/
GAGGTGCAGCTGGTGGAGTCTGGGGGAGGCTTGGTGCAGCCTGGGGGGTCTCTGACACTCTCCTGTGTTGCCGCTGGAAGCATCTTCACCTTCG
CCATGAGCTGGTACCGCCAGGCTCCACGAAAAGAGCGCGAATTGGTCGCACGTATTGGTACGGATGACGAAACAATGTACAAAGACTCCGTGAA
GGGTCGATTCACCATCTCCAGAGACAACGTCAAGCGCACGGCGGGTCTGCAGATGAACAACCTGAAACCCGAGGACACGGCCGTCTACTACTGC
AATGCCCCGGACAGATTATAGGGACTGGACTGTCCGTGAGTACTGGGGCCAGGGGACCCAGGTCACCGTCTCCTCA

VHH anti-CEA

CEA 3

/SEQ ID N° 85/
GAGGTGCAGCTGGTGGAGTCTGGGGGAGGCTTGGTGCAGGCTGGGGGCTCTCTGAGACTCTCCTGTACCAGCTCTACGGTTACCTTCACTCCGT
ATCAAATGGGCTGGTACCGCCAGGCTCCAGGGAAGCAGCGTGCTTTGGTCGCAGATATTAGTACGGGTGGTAGCCGCACAAATTATGCGGATTT
CGCGAAGGGCCGATTCACCATCTCCAGAGACGACGTTAAGAACACGGTGTATCTGCAAATGAACAACCTGAAACCTGAGGACACGGCCGTCTAC
TActGTAACACCTACTACGCGATGATAGGGCATGCGCGTAATTGGGGCCAGGGGACCCAGGTCACTGTCTCCTCA

CEA 17

/SEQ ID N° 86/
GAGGTGCAGCTGGTGGAGTCTGGGGGAGGCTTCGTGCAGGCGGGGGAATCTCTGACGCTCTCCTGTACAagTTCTACACTGACCTTCACTCCGT
ATCGCATGGCCTGGTACCGCCAGGCTCCAGGGAAGCAGCGTGATTTAGTCGCGGATATTAGTAGTGGTGATGGTAGGACCACAAACTATGCGGA
CTTCGCGAAGGGCCGATTCACCATCTCCAGAGACAACATCAAGAACACGGTCTTTCTGCGAATGACTAACCTGAAACCTGAGGACACGGCCGTC
TACTACTGTAACACCTTCGTTTCGTTTGTGGGGATTGCGCGTTCTTGGGGCCAGGGGACCCAGGTCACTGTCTCCTCA

CEA 25

/SEQ ID N° 87/
GAGGTGCAGCTGGTGGAGTCTGGGGGAGGCTTGGTGCAGGCGGGGGACTCTCTGACACTGACCTGTACAAGCCCTACACTTACCTTCACTCCGT
ATCGCATGGGCTGGTACCGCCAAGCTCCAGGGAAGCAGCGTGATTTGGTCGCAGATATTAGTGGTGGTGATGGTCGTACCACAAACTATGCAGA
CTTCGCGAAGGGCCGATTCACCATCTCCAGAGACAACGTCAAGAACGCGGTCTATCTGCAAATGAACAACCTGAAACCTGAAGACACGGCCATT
TATTACTGTAACACCTACGTCGCGATTGTGGGCCATGCGCGTTCCTGGGGCCAGGGGACCCAGGTCACCGTCTCCTCA

CEA 43

/SEQ ID N° 88/
CAGGTGCAGCTGCAGGAGTCTGGGGGAGGCTTGGTGCAGGCGGGGGGCTCTCTGACACTCTCCTGCACAAGTTCTACACTTACCTTCACTCCGT
ATCGCATGGGCTGGTACCGCCAGACTCCAGGGAAGCAGCGTGATTTGGTCGCGGACATTAGTCCTGGTGATGGTAGTACCAAAAATTATGCAGG
CTTCGCGCAGGGCCGATTCACCATCTCCAGAGACAACATCAAGAACACGGTGTATCTGCAAATGAACGACCTGAAACCTGAGGACACGGCCGTC
TATTAcTGCAACACCTACGTCGCGTTTGTGGGGCGTGCGCGTACTTGGGGCCAGGGGACCCAGGTCACTGTCACCTCA

/SEQ ID N° 108/
GAGGTGCAGCTGGTGGAGTCTGGGGGAGGCTTGGTGCAGGCGGGGGGCTCTCTGACACTCTCCTGCACAAGTTCTACACTTACCTTCACTCCGT
ATCGCATGGGCTGGTACCGCCAGACTCCAGGGAAGCAGCGTGATTTGGTCGCGGACATTAGTCCTGGTGATGGTAGTACCAAAAATTATGCAGG
CTTCGCGCAGGGCCGATTCACCATCTCCAGAGACAACATCAAGAACACGGTGTATCTGCAAATGAACGACCTGAAACCTGAGGACACGGCCGTC
TATTAcTGCAACACCTACGTCGCGTTTGTGGGGCGTGCGCGTACTTGGGGCCAGGGGACCCAGGTCACTGTCACCTCA

Figure 2

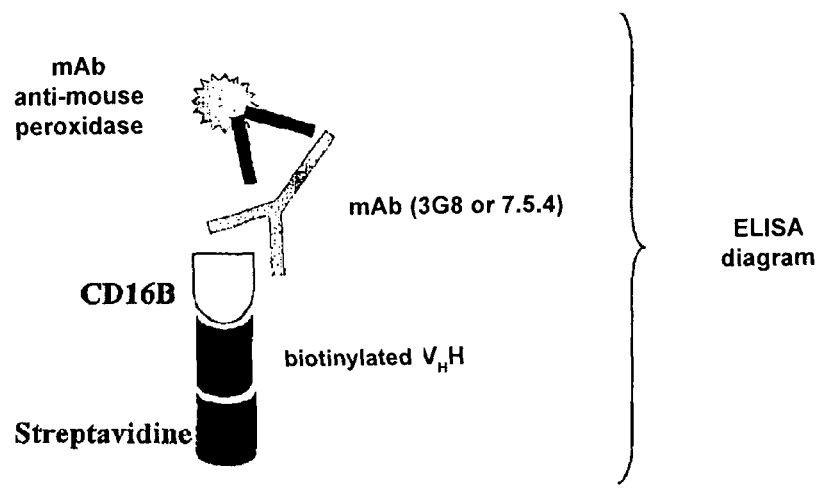
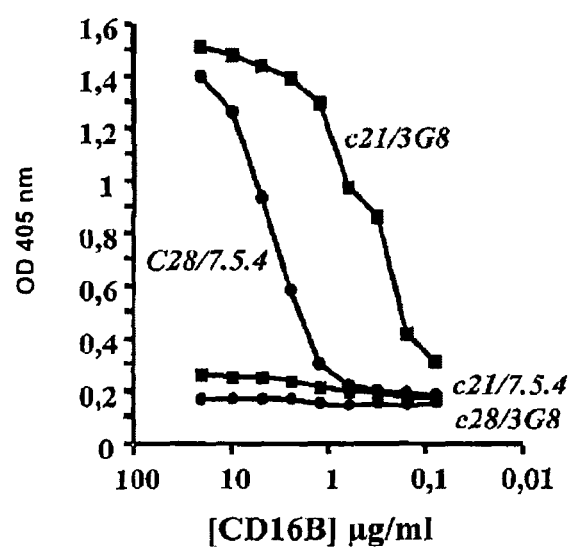
Figure 6

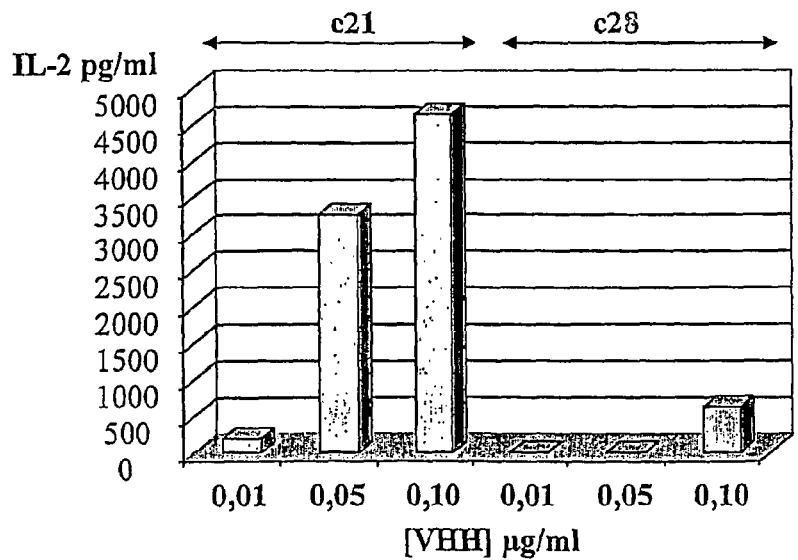
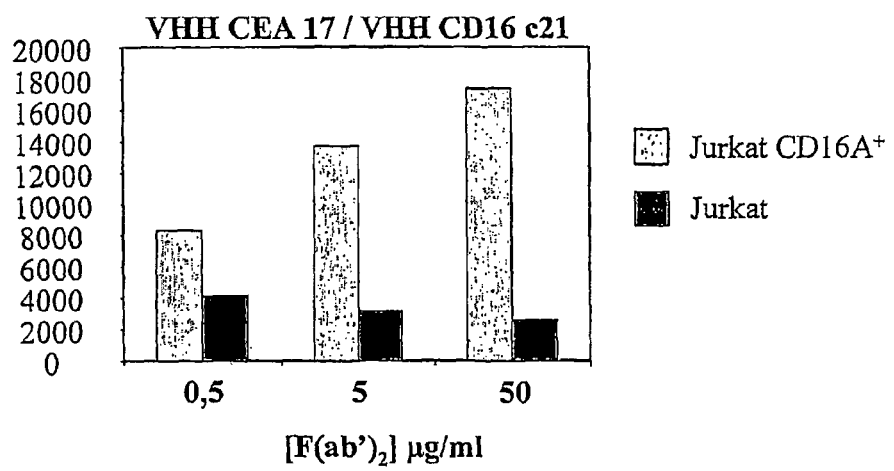
Figure 8

Figure 9 p55PhoA6HisGS/N- (SEQ ID NO:89)

ttgtttattttttctaaatacattcaaatatgtatccgctcatgagacaataaccctgataaatgcttca
ataatattgaa
aaaggaagagtatgagtattcaacatttccgtgtcgcccttattcccttttttgcggcatttttgccttc
ctgtttttgct
cacccagaaacgctggtgaaagtaaaagatgctgaagatcagttgggtgcacgagtgggttacatcgaa
ctggatctcaa
cagcggtaagatccttgagagttttcgcccgaagaacgttttccaatgatgagcacttttaaagttct
gctatgtggcg
cggtattatcccgtgttgacgccgggcaagagcaactcggtcgccgcatacactattctcagaatgact
tggttgagtac
tcaccagtcacagaaaagcatcttacggatggcatgacagtaagagaattatgcagtgctgccataacc
atgagtgataa
cactgcggccaacttacttctgacaacgatcggaggaccgaaggagctaaccgcttttttgcacaacat
gggggatcatg
taactcgccttgatcgttgggaaccggagctgaatgaagccataccaaacgacgagcgtgacaccacga
tgcctgtagca
atggcaacaacgttgcgcaaactattaactggcgaactacttactctagcttcccggcaacaattaata
gactggatgga
ggcggataaagttgcaggaccacttctgcgctcggcccttccggctggctggtttattgctgataaatc
tggagccggtg
agcgtgggtctcgcggtatcattgcagcactggggccagatggtaagccctcccgtatcgtagttatct
acacgacggg
agtcaggcaactatggatgaacgaaatagacagatcgctgagataggtgcctcactgattaagcattgg
taactgtcaga
ccaagtttactcatatatactttagattgatttaaaacttcattttttaatttaaaaggatctaggtgaa
gatcctttttg
ataatctcatgaccaaaatcccttaacgtgagttttcgttccactgagcgtcagacccccgtagaaaaga
tcaaaggatct
tcttgagatcctttttttctgcgcgtaatctgctgcttgcaaacaaaaaaaccaccgctaccagcggtg
gtttgtttgcc
ggatcaagagctaccaactctttttccgaaggtaactggcttcagcagagcgcagataccaaatactgt
ccttctagtgt
agccgtagttaggccaccacttcaagaactctgtagcaccgcctacatacctcgctctgctaatcctgt
taccagtggct
gctgccagtggcgataagtcgtgtcttaccggggttggactcaagacgatagttaccggataaggcgcag
cggtcgggctg
aacggggggttcgtgcacacagcccagcttggagcgaacgacctacaccgaactgagatacctacagcg
tgagcattgag
aaagcgccacgcttcccgaagggagaaaggcggacaggtatccggtaagcggcagggtcggaacaggag
agcgcacgagg
gagcttccaggggggaaacgcctggtatctttatagtcctgtcgggtttcgccacctctgacttgagcgt
cgatttttgtg
atgctcgtcagggggcggagcctatggaaaaacgccagcaacgcggcctttttacggttcctggcctt
ttgctggcctt
ttgctcacatgttctttcctgcgttatcccctgattctgtggataaccgtattaccgcctttgagtgag
ctgataccgct
cgccgcagccgaacgaccgagcgcagcgagtcagtgagcgaggaagcggaagagcgcctgatgcggtat
ttttctccttac
gcatctgtgcggtatttcacaccgcatatatggtgcactctcagtacaatctgctctgatgccgcatag
ttaagccagta
tacactccgctatcgctacgtgactgggtcatggctgcgccccgacacccgccaacacccgctgacgcg
ccctgacgggc
ttgtctgctcccggcatccgcttacagacaagctgtgaccgtctccgggagctgcatgtgtcagaggtt
ttcaccgtcat

Figure 9 (Cont.)

```
caccgaaacgcgcgaggcagctgcggtaaagctcatcagcgtggtcgtgaagcgattcacagatgtctg
cctgttcatcc
gcgtccagctcgttgagtttctccagaagcgttaatgtctggcttctgataaagcgggccatgttaagg
gcggttttttc
ctgtttggtcacttgatgcctccgtgtaagggggaatttctgttcatgggggtaatgataccgatgaaa
cgagagaggat
gctcacgatacgggttactgatgatgaacatgcccggttactggaacgttgtgagggtaaacaactggc
ggtatggatgc
ggcgggaccagagaaaaatcactcagggtcaatgccagcgcttcgttaatacagatgtaggtgttccac
agggtagccag
cagcatcctgcgatgcagatccggaacataatggtgcagggcgctgacttccgcgtttccagactttac
gaaacacggaa
accgaagaccattcatgttgttgctcaggtcgcagacgttttgcagcagcagtcgcttcacgttcgctc
gcgtatcggtg
attcattctgctaaccagtaaggcaacccgccagcctagccgggtcctcaacgacaggagcacgatca
tgcgcacccgt
ggccaggacccaacgctgcccgagatgcgccgcgtgcggctgctgagatggcggacgcgatggatatg
ttctgccaagg
gttggtttgcgcattcacagttctccgcaagaattgattggctccaattcttggagtggtgaatccgtt
agcgaggtgcc
gccggcttccattcaggtcgaggtggcccggctccatgcaccgcgacgcaacgcggggaggcagacaag
gtatagggcgg
cgcctacaatccatgccaacccgttccatgtgctcgccgaggcggcataaatcgccgtgacgatcagcg
gtccagtgatc
gaagttaggctggtaagagccgcgagcgatccttgaagctgtccctgatggtcgtcatctacctgcctg
gacagcatggc
ctgcaacgcggcatcccgatgccgccggaagcgagaagaatcataatggggaaggccatccagcctcg
cgtcgcgaacg
ccagcaagacgtagcccagcgcgtcggccagcttgcaattcgcgctaacttacattaattgcgttgcgc
tcactgcccgc
tttccagtcgggaaacctgtcgtgccagctgcattaatgaatcggccaacgcgcggggagaggcggttt
gcgtattgggc
gccagggtggttttctttcaccagtgagacgggcaacagctgattgcccttcaccgcctggccctga
gagagttgcag
caagcggtccacgctggttttgcccagcaggcgaaaatcctgtttgatggtggttgacggcgggatata
acatgagctgt
cttcgtatcgtcgtatcccactaccgagatatccgcaccaacgcgcagccggactcggtaatggcgc
gcattgcgccc
agcgccatctgatcgttggcaaccagcatcgcagtgggaacgatgccctcattcagcatttgcatggtt
tgttgaaaacc
ggacatggcactccagtcgccttcccgttccgctatcggctgaatttgattgcgagtgagatatttatg
ccagccagcca
gacgcagacgcgccgagacagaacttaatgggcccgctaacagcgcgatttgctggtgacccaatgcga
ccagatgctcc
acgcccagtcgcgtaccgtcttcatgggagaaaataatactgttgatgggtgtctggtcagagacatca
agaaataacgc
cggaacattagtgcaggcagcttccacagcaatggcatcctggtcatccagcggatagttaatgatcag
cccactgacgc
gttgcgcgagaagattgtgcaccgccgctttacaggcttcgacgccgcttcgttctaccatcgacacca
ccacgctggca
cccagttgatcggcgcgagatttaatcgccgcgacaatttgcgacggcgcgtgcagggccagactggag
gtggcaacgcc
aatcagcaacgactgtttgccgccagttgttgtgccacgcggttgggaatgtaattcagctccgcat
cgccgcttcca
cttttttccgcgttttcgcagaaacgtggctggcctggttcaccacgcgggaaacggtctgataagaga
caccggcatac
tctgcgacatcgtataacgttactggtttcacattcaccaccctgaattgactctcttcggggcgctat
catgccatacc
```

Figure 9 (Cont.)

```
gcgaaaggttttgcgccattcgatggtgtcaacgtaaatgcatgccgcttcgccttcgcgcgcgaattg
caagctgatcc
ggagcttatcgactgcacggtgcaccaatgcttctggcgtcaggcagccatcggaagctgtggtatggc
tgtgcaggtcg
taaatcactgcataattcgtgtcgctcaaggcgcactcccgttctggataatgttttttgcgccgacat
cataacggttc
tggcaaatattctgaaatgagctgttgacaattaatcatcggctcgtataatgtgtggaattgtgagcg
gataacaattt
cacacaggaaacaGAATTCcatATGAAATACCTATTACCAACAGCAGCAGCTGGGTTATTATTGCTCGC
TGCGCAGCCGG
CCATGGCGgccgatcctcgagagctcccgggCTGCAGcctgttctggaaaaccgggctgctcagggcg
atattactgca
cccggcggtgctcgccgtttaacgggtgatcagactgccgctctgcgtgattctcttagcgataaacct
gcaaaaaatat
tattttgctgattggcgatgggatgggggactcggaaattactgccgcacgtaattatgccgaaggtgc
gggcggctttt
ttaaaggtatagatgccttaccgcttaccgggcaatacactcactatgcgctgaataaaaaaaccggca
aaccggactac
gtcaccgactcggctgcatcagcaaccgctggtcaaccggtgtcaaaacctataacggcgcgctgggc
gtcgatattca
cgaaaaagatcacccaacgattctggaaatggcaaaagccgcaggtctggcgaccggtaacgtttctac
cgcagagttgc
aggatgccacgcccgctgcgctggtggcacatgtgacctcgcgcaaatgctacggtccgagcgcgacca
gtgaaaaatgt
ccgggtaacgctctggaaaaaggcggaaaaggatcgattaccgaacagctgcttaacgctcgtgccgac
gttacgcttgg
cggcggcgcaaaaaccttttgctgaaacggcaaccgctggtgaatggcagggaaaaacgctgcgtgaaca
ggcacaggcgc
gtggttatcagttggtgagcgatgctgcctcactgaattcggtgacggaagcgaatcagcaaaaacccc
tgcttggcctg
tttgctgacggcaatatgccagtgcgctggctaggaccgaaagcaacgtaCCACGGcaatatcgataag
cccgcagtcac
ctgtacgccaaatccgcaacgtaatgacagtgtaccaaccctggcgcagatgaccgacaaagccattga
attgttgagta
aaaatgagaaaggcttttttcctgcaagttgaaggtgcgtcaatcgataaacaggatcatgctgcgaatc
cttgtgggcaa
attgcgagacggtcgatctcgatgaagccgtacaacgggcgctggaattcgctaaaaaggagggtaac
acgctggtcat
agtcaccgctgatcacgccacgccagccagattgttgcgccggataccaaagctccgggcctcaccca
ggcgctaaata
ccaaagatggcgcagtgatggtgatgagttacgggaactccgaagaggattcacaagaacataccggca
gtcagttgcgt
attgcggcgtatggcccgcatgccgccaatgttgttggactgaccgaccagaccgatctcttctacacc
atgaaagccgc
tctgggctgaaaCATCATCATCACCATCACGGGAGCtaatAAGCTTctgttttggcggatgagagaag
attttcagcct
gatacagattaaatcagaacgcagaagcggtctgataaaacagaatttgcctggcggcagtagcgcggt
ggtcccacctg
acccatgccgaactcagaagtgaaacgccgtagcgccgatggtagtgtggggtctccccatgcgagag
tagggaactgc
caggcatcaaataaaacgaaaggctcagtcgaaagactgggcctttcgttttatctgttgtttgtcggt
gaacgctctcc
tgagtaggacaaatccgccgggagcggatttgaacgttgcgaagcaacggcccggaggaccctggcggg
caggacgcccg
ccataaactgccaggcatcaaattaagcagaaggccatcctgacggatggcctttttgcgtttctacaa
actctt
``` p55PhoA6HisGS/NAB<sup>-</sup> (SEQ ID NO:90)

Figure 9 (Cont.)

```
ttgtttatttttctaaatacattcaaatatgtatccgctcatgagacaataaccctgataaatgcttcaataa
ttgaa
aaaggaagagtatgagtattcaacatttccgtgtcgcccttattccttttttgcggcattttgccttcctgttt
ttgct
cacccagaaacgctggtgaaagtaaaagatgctgaagatcagttgggtgcacgagtgggttacatcgaactggat
ctcaa
cagcggtaagatccttgagagttttcgcccgaagaacgtttccaatgatgagcacttttaaagttctgctatg
tggcg
cggtattatcccgtgttgacgccgggcaagagcaactcggtcgccgcatacactattctcagaatgacttggttg
agtac
tcaccagtcacagaaaagcatcttacggatggcatgacagtaagagaattatgcagtgctgccataaccatgagt
gataa
cactgcggccaacttacttctgacaacgatcggaggaccgaaggagctaaccgcttttttgcacaacatgggggga
tcatg
taactcgccttgatcgttgggaaccggagctgaatgaagccataccaaacgacgagcgtgacaccacgatgcctg
tagca
atggcaacaacgttgcgcaaactattaactggcgaactacttactctagcttcccggcaacaattaatagactgg
atgga
ggcggataaagttgcaggaccacttctgcgctcggcccttccggctggctggtttattgctgataaatctggagc
cggtg
agcgtgggtctcgcggtatcattgcagcactgggccagatggtaagccctcccgtatcgtagttatctacacga
cgggg
agtcaggcaactatggatgaacgaaatagacagatcgctgagataggtgcctcactgattaagcattggtaactg
tcaga
ccaagtttactcatatatactttagattgatttaaaacttcatttttaatttaaaaggatctaggtgaagatcct
ttttg
ataatctcatgaccaaaatcccttaacgtgagttttcgttccactgagcgtcagaccccgtagaaaagatcaaag
gatct
tcttgagatcctttttttctgcgcgtaatctgctgcttgcaaacaaaaaaaccaccgctaccagcggtggtttgt
ttgcc
ggatcaagagctaccaactcttttttccgaaggtaactggcttcagcagagcgcagataccaaatactgtccttct
agtgt
agccgtagttaggccaccacttcaagaactctgtagcaccgcctacatacctcgctctgctaatcctgttaccag
tggct
gctgccagtggcgataagtcgtgtcttaccgggttggactcaagacgatagttaccggataaggcgcagcggtcg
ggctg
aacgggggttcgtgcacacagcccagcttggagcgaacgacctacaccgaactgagatacctacagcgtgagca
ttgag
aaagcgccacgcttcccgaagggagaaaggcggacaggtatccggtaagcggcagggtcggaacaggagagcgca
cgagg
gagcttccagggggaaacgcctggtatctttatagtcctgtcgggtttcgccacctctgacttgagcgtcgattt
ttgtg
atgctcgtcagggggcggagcctatggaaaaacgccagcaacgcggcctttttacggttcctggccttttgctg
gcctt
ttgctcacatgttctttcctgcgttatcccctgattctgtggataaccgtattaccgcctttgagtgagctgata
ccgct
cgccgcagccgaacgaccgagcgcagcgagtcagtgagcgaggaagcggaagagcgcctgatgcggtatttctc
cttac
gcatctgtgcggtatttcacaccgcatatggtgcactctcagtacaatctgctctgatgccgcatagttaagc
cagta
tacactccgctatcgctacgtgactgggtcatggctgcgccccgacacccgccaacacccgctgacgcgccctga
cgggc
ttgtctgctcccggcatccgcttacagacaagctgtgaccgtctccgggagctgcatgtgtcagaggttttcacc
gtcat
caccgaaacgcgcgaggcagctgcggtaaagctcatcagcgtggtcgtgaagcgattcacagatgtctgcctgtt
catcc
```

Figure 9 (Cont.)

```
gcgtccagctcgttgagtttctccagaagcgttaatgtctggcttctgataaagcgggccatgttaagggcggtt
ttttc
ctgtttggtcacttgatgcctccgtgtaagggggaatttctgttcatgggggtaatgataccgatgaaacgagag
aggat
gctcacgatacgggttactgatgatgaacatgcccggttactggaacgttgtgagggtaaacaactggcggtatg
gatgc
ggcgggaccagagaaaaatcactcagggtcaatgccagcgcttcgttaatacagatgtaggtgttccacagggta
gccag
cagcatcctgcgatgcagatccggaacataatggtgcagggcgctgacttccgcgtttccagactttacgaaaca
cggaa
accgaagaccattcatgttgttgctcaggtcgcagacgttttgcagcagcagtcgcttcacgttcgctcgcgtat
cggtg
attcattctgctaaccagtaaggcaaccccgccagcctagccgggtcctcaacgacaggagcacgatcatgcgca
cccgt
ggccaggacccaacgctgcccgagatgcgccgcgtgcggctgctggagatggcggacgcgatggatatgttctgc
caagg
gttggtttgcgcattcacagttctccgcaagaattgattggctccaattcttggagtggtgaatccgttagcgag
gtgcc
gccggcttccattcaggtcgaggtggcccggctccatgcaccgcgacgcaacgcggggaggcagacaaggtatag
ggcgg
cgcctacaatccatgccaacccgttccatgtgctcgccgaggcggcataaatcgccgtgacgatcagcggtccag
tgatc
gaagttaggctggtaagagccgcgagcgatccttgaagctgtccctgatggtcgtcatctacctgcctggacagc
atggc
ctgcaacgcgggcatcccgatgccgccggaagcgagaagaatcataatgggyaaggccatccagcctcgcgtcgc
gaacg
ccagcaagacgtagcccagcgcgtcggccagcttgcaattcgcgctaacttacattaattgcgttgcgctcactg
cccgc
tttccagtcgggaaacctgtcgtgccagctgcattaatgaatcggccaacgcgcggggagaggcggtttgcgtat
tgggc
gccagggtggttttctttcaccagtgagacgggcaacagctgattgcccttcaccgcctggccctgagagagt
tgcag
caagcggtccacgctggtttgccccagcaggcgaaaatcctgtttgatggtggttgacggcgggatataacatga
gctgt
cttcggtatcgtcgtatcccactaccgagatatccgcaccaacgcgcagcccggactcggtaatggcgcgcattg
cgccc
agcgccatctgatcgttggcaaccagcatcgcagtgggaacgatgccctcattcagcatttgcatggtttgttga
aaacc
ggacatggcactccagtcgccttcccgttccgctatcggctgaatttgattgcgagtgagatatttatgccagcc
agcca
gacgcagacgcgccgagacagaacttaatgggcccgctaacagcgcgatttgctggtgacccaatgcgaccagat
gctcc
acgcccagtcgcgtaccgtcttcatgggagaaaataatactgttgatgggtgtctggtcagagacatcaagaaat
aacgc
cggaacattagtgcaggcagcttccacagcaatggcatcctggtcatccagcggatagttaatgatcagcccact
gacgc
gttgcgcgagaagattgtgcaccgccgctttacaggcttcgacgccgcttcgttctaccatcgacaccaccacgc
tggca
cccagttgatcggcgcgagatttaatcgccgcgacaatttgcgacggcgcgtgcagggccagactggaggtggca
acgcc
aatcagcaacgactgtttgcccgccagttgttgtgccacgcggttgggaatgtaattcagctccgccatcgccgc
ttcca
ctttttcccgcgttttcgcagaaacgtggctggcctggttcaccacgcgggaaacggtctgataagagacaccgg
catac
tctgcgacatcgtataacgttactggtttcacattcaccaccctgaattgactctcttccgggcgctatcatgcc
atacc
gcgaaggttttgcgccattcgatggtgtcaacgtaaatgcatgccgcttcgccttcgcgcgcgaattgcaagct
gatcc
```

Figure 9 (Cont.)

```
ggagcttatcgactgcacggtgcaccaatgcttctggcgtcaggcagccatcggaagctgtggtatggctgtgca
ggtcg
taaatcactgcataattcgtgtcgctcaaggcgcactcccgttctggataatgttttttgcgccgacatcataac
ggttc
tggcaaatattctgaaatgagctgttgacaattaatcatcggctcgtataatgtgtggaattgtgagcggataac
aattt
cacacaggaaacaGAATTCcatATGAAATACCTATTACCAACAGCAGCAGCTGGGTTATTATTGCTCGCTGCGCA
GCCGG
CCATGGCGgccgatcctcgagagctcccgggCTGCAGcctgttctggaaaaccgggctgctcagggcgatatta
ctgca
cccggcggtgctcgccgtttaacgggtgatcagactgccgctctgcgtgattctcttagcgataaacctgcaaaa
aatat
tattttgctgattggcgatgggatggggactcggaaattactgccgcacgtaattatgccgaaggtgcgggcgg
ctttt
ttaaaggtatagatgccttaccgcttaccgggcaatacactcactatgcgctgaataaaaaaaccggcaaaccgg
actac
gtcaaccgactcggctgcatcagcaaccgcctggtcaacggtgtcaaaacctataacggcgcgctgggcgtcgat
attca
cgaaaaagatcacccaacgattctggaaatggcaaaagccgcaggtctggcgaccggtaacgtttctaccgcaga
gttgc
aggatgccacgcccgctgcgctggtggcacatgtgacctcgcgcaaatgctacggtccgagcgcgaccagtgaaa
aatgt
ccgggtaacgctctggaaaaaggcggaaaaggatcgattaccgaacagctgcttaacgctcgtgccgacgttacg
cttgg
cggcggcgcaaaaacctttgctgaaacggcaaccgctggtgaatggcagggaaaaacgctgcgtgaacaggcaca
ggcgc
gtggttatcagttggtgagcgatgctgcctcactgaattcggtgacggaagcgaatcagcaaaaaccctgcttg
gcctg
tttgctgacggcaatatgccagtgcgctggctaggaccgaaagcaacgtaCCACGGcaatatcgataagcccgca
gtcac
ctgtacgccaaatccgcaacgtaatgacagtgtaccaaccctggcgcagatgaccgacaaagccattgaattgtt
gagta
aaaatgagaaaggcttttcctgcaagttgaaggtgcgtcaatcgataaacaggatcatgctgcgaatccttgtg
ggcaa
attggcgagacggtcgatctcgatgaagccgtacaacgggcgctggaattcgctaaaaaggagggtaacacgctg
gtcat
agtcaccgctgatcacgccacgccagccagattgttgcgccggataccaaagctccgggcctcacccaggcgct
aaata
ccaaagatgcgcagtgatggtgatgagttacgggaactccgaagaggattcacaagaacataccggcagtcagt
tgcgt
attgcggcgtatggcccgcatgccgccaatgttgttggactgaccgaccagaccgatctcttctacaccatgaaa
gccgc
tctgggctgaaaCATCATCATCACCATCACGGGAGCtaatAAGCTTctgttttggcggatgagagaagatttc
agcct
gatacagattaaatcagaacgcagaagcggtctgataaaacagaatttgcctggcggcagtagcgcggtggtccc
acctg
acccatgccgaactcagaagtgaaacgccgtagcgccgatggtagtgtggggtctccccatgcgagagtaggga
actgc
caggcatcaaataaaacgaaaggctcagtcgaaagactgggcctttcgttttatctgttgtttgtcggtgaacgc
tctcc
tgagtaggacaaatccgccgggagcggatttgaacgttgcgaagcaacggcccggaggaccctggcgggcaggac
gcccg
ccataaactgccaggcatcaaattaagcagaaggccatcctgacggatggcctttttgcgtttctacaaactctt
``` p55/PhoA6HisG5'/NAB' (SEQ ID NO:91)

Figure 9 (Cont.)

```
ttgtttattttttctaaatacattcaaatatgtatccgctcatgagacaataaccctgataaatgcttcaataata
ttgaa
aaaggaagagtatgagtattcaacatttccgtgtcgccttattccctttttttgcggcattttgccttcctgttt
ttgct
cacccagaaacgctggtgaaagtaaaagatgctgaagatcagttgggtgcacgagtgggttacatcgaactggat
ctcaa
cagcggtaagatccttgagagttttcgccccgaagaacgttttccaatgatgagcacttttaaagttctgctatg
tggcg
cggtattatcccgtgttgacgccgggcaagagcaactcggtcgccgcatacactattctcagaatgacttggttg
agtac
tcaccagtcacagaaaagcatcttacggatggcatgacagtaagagaattatgcagtgctgccataaccatgagt
gataa
cactgcggccaacttacttctgacaacgatcggaggaccgaaggagctaaccgcttttttgcacaacatggggga
tcatg
taactcgccttgatcgttgggaaccggagctgaatgaagccataccaaacgacgagcgtgacaccacgatgcctg
tagca
atggcaacaacgttgcgcaaactattaactggcgaactacttactctagcttcccggcaacaattaatagactgg
atgga
ggcggataaagttgcaggaccacttctgcgctcggcccttccggctggctggtttattgctgataaatctggagc
cggtg
agcgtgggtctcgcggtatcattgcagcactggggccagatggtaagccctcccgtatcgtagttatctacacga
cgggg
agtcaggcaactatggatgaacgaaatagacagatcgctgagataggtgcctcactgattaagcattggtaactg
tcaga
ccaagtttactcatatatactttagattgatttaaaacttcatttttaatttaaaaggatctaggtgaagatcct
ttttg
ataatctcatgaccaaaatcccttaacgtgagttttcgttccactgagcgtcagacccgtagaaaagatcaaag
gatct
tcttgagatcctttttttctgcgcgtaatctgctgcttgcaaacaaaaaaaccaccgctaccagcggtggtttgt
ttgcc
ggatcaagagctaccaactcttttccgaaggtaactggcttcagcagagcgcagataccaaatactgtccttct
agtgt
agccgtagttaggccaccacttcaagaactctgtagcaccgcctacatacctcgctctgctaatcctgttaccag
tggct
gctgccagtggcgataagtcgtgtcttaccgggttggactcaagacgatagttaccggataaggcgcagcggtcg
ggctg
aacgggggttcgtgcacacagcccagcttggagcgaacgacctacaccgaactgagatacctacagcgtgagca
ttgag
aaagcgccacgcttcccgaagggagaaaggcggacaggtatccggtaagcggcagggtcggaacaggagagcgca
cgagg
gagcttccaggggggaaacgcctggtatctttatagtcctgtcgggtttcgccacctctgacttgagcgtcgattt
ttgtg
atgctcgtcaggggggcggagcctatggaaaaacgccagcaacgcggcctttttacggttcctggcctttgctg
gcctt
ttgctcacatgttctttcctgcgttatccctgattctgtggataaccgtattaccgcctttgagtgagctgata
ccgct
cgccgcagccgaacgaccgagcgcagcgagtcagtgagcgaggaagcggaagagcgcctgatgcggtattttctc
cttac
gcatctgtgcggtatttcacaccgcatatatggtgcactctcagtacaatctgctctgatgccgcatagttaagc
cagta
tacactccgctatcgctacgtgactgggtcatggctgcgccccgacaccgccaacacccgctgacgcgccctga
cgggc
ttgtctgctcccggcatccgcttacagacaagctgtgaccgtctccgggagctgcatgtgtcagaggttttcacc
gtcat
caccgaaacgcgcgaggcagctgcggtaaagctcatcagcgtggtcgtgaagcgattcacagatgtctgcctgtt
catcc
```

Figure 9 (Cont.)

```
gcgtccagctcgttgagtttctccagaagcgttaatgtctggcttctgataaagcgggccatgttaagggcggtt
ttttc
ctgtttggtcacttgatgcctccgtgtaagggggaatttctgttcatgggggtaatgataccgatgaaacgagag
aggat
gctcacgatacgggttactgatgatgaacatgcccggttactggaacgttgtgagggtaaacaactggcggtatg
gatgc
ggcgggaccagagaaaaatcactcagggtcaatgccagcgcttcgttaatacagatgtaggtgttccacagggta
gccag
cagcatcctgcgatgcagatccggaacataatggtgcagggcgctgacttccgcgtttccagactttacgaaaca
cggaa
accgaagaccattcatgttgttgctcaggtcgcagacgttttgcagcagcagtcgcttcacgttcgctcgcgtat
cggtg
attcattctgctaaccagtaaggcaaccccgccagcctagccgggtcctcaacgacaggagcacgatcatgcgca
cccgt
ggccaggacccaacgctgccgagatgcgccgcgtgcggctgctggagatggcggacgcgatggatatgttctgc
caagg
gttggtttgcgcattcacagttctccgcaagaattgattggctccaattcttggagtggtgaatccgttagcgag
gtgcc
gccggcttccattcaggtcgaggtggcccggctccatgcaccgcgacgcaacgcggggaggcagacaaggtatag
ggcgg
cgcctacaatccatgccaacccgttccatgtgctcgccgaggcggcataaatcgccgtgacgatcagcggtccag
tgatc
gaagttaggctggtaagagccgcgagcgatccttgaagctgtccctgatggtcgtcatctacctgcctggacagc
atggc
ctgcaaacgcgggcatcccgatgccgccggaagcgagaagaatcataatggggaaggccatccagcctcgcgtcgc
gaacg
ccagcaagacgtagcccagcgcgtcggccagcttgcaattcgcgctaacttacattaattgcgttgcgctcactg
cccgc
tttccagtcgggaaacctgtcgtgccagctgcattaatgaatcggccaacgcgcggggagaggcggtttgcgtat
tgggc
gccagggtggttttctttcaccagtgagacgggcaacagctgattgcccttcaccgcctggccctgagagagt
tgcag
caagcggtccacgctggtttgccccagcaggcgaaaatcctgtttgatggtggttgacggcgggatataacatga
gctgt
cttcggtatcgtcgtatcccactaccgagatatccgcaccaacgcgcagcccggactcggtaatggcgcgcattg
cgccc
agcgccatctgatcgttggcaaccagcatcgcagtgggaacgatgccctcattcagcatttgcatggtttgttga
aaacc
ggacatggcactccagtcgccttcccgttccgctatcggctgaatttgattgcgagtgagatatttatgccagcc
agcca
gacgcagacgcgccgagacagaacttaatggtcccgctaacagcgcgatttgctgatgacccaatgcgaccagat
gctcc
acgcccagtcgcgtaccgtcttcatggagaaaataatactgttgatgggtgtctggtcagagacatcaagaaat
aacgc
cggaacattagtgcaggcagcttccacagcaatggcatcctggtcatccagcggatagttaatgatcagcccact
gacgc
gttgcgcgagaagattgtgcaccgccgctttacaggcttcgacgccgcttcgttctaccatcgacaccaccacgc
tggca
cccagttgatcggcgcgagatttaatcgccgcgacaatttgcgacggcgcgtgcagggccagactggaggtggca
acgcc
aatcagcaacgactgtttgcccgccagttgttgtgccacgcggttgggaatgtaattcagctccgccatcgccgc
ttcca
cttttccgcgtttcgcagaaacgtggctggcctggttcaccacgcgggaaacggtctgataagagacaccgg
catac
tctgcgacatcgtataacgttactggtttcacattcaccaccctgaattgactctcttccgggcgctatcatgcc
atacc
gcgaaaggttttgcgccattcgatggtgtcaacgtaaatgcatgccgcttcgccttcgcgcgcgaattgcaagct
gatcc
```

Figure 9 (Cont.)

```
ggagcttatcgactgcacggtgcaccaatgcttctggcgtcaggcagccatcggaagctgtggtatggctgtgca
ggtcg
taaatcactgcataattcgtgtcgctcaaggcgcactcccgttctggataatgttttttgcgccgacatcataac
ggttc
tggcaaatattctgaaatgagctgttgacaattaatcatcggctcgtataatgtgtggaattgtgagcggataac
aattt
cacacaggaaacaGAATTCcatATGAAATACCTATTACCAACAGCAGCAGCTGGGTTATTATTGCTCGCTGCGCA
GCCGG
CCATGGCGgccggccgatcctcgagagctcccgggCTGCAGcctgttctggaaaaccgggctgctcagggcgat
attac
tgcaccggcggtgctcgccgtttaacgggtgatcagactgccgctctgcgtgattctcttagcgataaacctgc
aaaaa
atattattttgctgattggcgatgggatgggggactcggaaattactgccgcacgtaattatgccgaaggtgcgg
gcggc
ttttttaaaggtatagatgccttaccgcttaccgggcaatacactcactatgcgctgaataaaaaaacggcaaa
ccgga
ctacgtcaccgactcggctgcatcagcaaccgcctggtcaaccggtgtcaaaacctataacggcgcgctgggcgt
cgata
ttcacgaaaaagatcacccaacgattctggaaatggcaaaagccgcaggtctggcgaccggtaacgtttctaccg
cagag
ttgcaggatgccacgcccgctgcgctggtggcacatgtgacctcgcgcaaatgctacggtccgagcgcgaccagt
gaaaa
atgtccgggtaacgctctggaaaaaggcggaaaaggatcgattaccgaacagctgcttaacgctcgtgccgacgt
tacgc
ttggcggcggcgcaaaaacctttgctgaaacggcaaccgctggtgaatggcagggaaaaacgctgcgtgaacagg
cacag
gcgcgtggttatcagttggtgagcgatgctgcctcactgaattcggtgacggaagcgaatcagcaaaaaccctg
cttgg
cctgtttgctgacggcaatatgccagtgcgctggctaggaccgaaagcaacgtaCCACGGcaatatcgataagcc
cgcag
tcacctgtacgccaaatccgcaacgtaatgacagtgtaccaaccctggcgcagatgaccgacaaagccattgaat
tgttg
agtaaaaatgagaaaggcttttttcctgcaagttgaaggtgcgtcaatcgataaacaggatcatgctgcgaatcct
tgtgg
gcaaattggcgagacggtcgatctcgatgaagccgtacaacgggcgctggaattcgctaaaaaggagggtaacac
gctgg
tcatagtcaccgctgatcacgcccacgccagccagattgttgcgccggataccaaagctccgggcctcacccagg
cgcta
aataccaaagatggcgcagtgatggtgatgagttacgggaactccgaagaggattcacaagaacataccggcagt
cagtt
gcgtattgcggcgtatggcccgcatgccgccaatgttgttggactgaccgaccagaccgatctcttctacaccat
gaaag
ccgctctggggctgaaaCATCATCATCACCATCACGGGAGCtaatAAGCTTggctgttttggcggatgagagaag
atttt
cagcctgatacagattaaatcagaacgcagaagcggtctgataaaacagaatttgcctggcggcagtagcgcggt
ggtcc
cacctgacccatgccgaactcagaagtgaaacgccgtagcgccgatggtagtgtggggtctcccatgcgagag
taggg
aactgccaggcatcaaataaaacgaaaggctcagtcgaaagactgggcctttcgttttatctgttgtttgtcggt
gaacg
ctctcctgagtaggacaaatccgccgggagcggatttgaacgttgcgaagcaacggcccggaggaccctggcggg
cagga
cgcccgccataaactgccaggcatcaaattaagcagaaggccatcctgacggatggcctttttgcgtttctacaa
actct
t
``` p55/MCS1 (SEQ ID NO:92)

Figure 9 (Cont.)

```
ttgtttattttttctaaatacattcaaatatgtatccgctcatgagacaataaccctgataaatgcttcaataata
ttgaa
aaaggaagagtatgagtattcaacatttccgtgtcgcccttattccctttttgcggcatttttgccttcctgttt
ttgct
cacccagaaacgctggtgaaagtaaaagatgctgaagatcagttgggtgcacgagtgggttacatcgaactggat
ctcaa
cagcggtaagatccttgagagttttcgcccgaagaacgttttccaatgatgagcacttttaaagttctgctatg
tggcg
cggtattatcccgtgttgacgccgggcaagagcaactcggtcgccgcatacactattctcagaatgacttggttg
agtac
tcaccagtcacagaaaagcatcttacggatggcatgacagtaagagaattatgcagtgctgccataaccatgagt
gataa
cactgcggccaacttacttctgacaacgatcggaggaccgaaggagctaaccgcttttttgcacaacatggggga
tcatg
taactcgccttgatcgttgggaaccggagctgaatgaagccataccaaacgacgagcgtgacaccacgatgcctg
tagca
atggcaacaacgttgcgcaaactattaactggcgaactacttactctagcttcccggcaacaattaatagactgg
atgga
ggcggataaagttgcaggaccacttctgcgctcggcccttccggctggctggtttattgctgataaatctggagc
cggtg
agcgtgggtctcgcggtatcattgcagcactggggccagatggtaagccctcccgtatcgtagttatctacacga
cgggg
agtcaggcaactatggatgaacgaaatagacagatcgctgagataggtgcctcactgattaagcattggtaactg
tcaga
ccaagtttactcatatatactttagattgatttaaaacttcattttttaatttaaaaggatctaggtgaagatcct
ttttg
ataatctcatgaccaaaatcccttaacgtgagttttcgttccactgagcgtcagaccccgtagaaaagatcaaag
gatct
tcttgagatcctttttttctgcgcgtaatctgctgcttgcaaacaaaaaaaccaccgctaccagcggtggtttgt
ttgcc
ggatcaagagctaccaactctttttccgaaggtaactggcttcagcagagcgcagataccaaatactgtccttct
agtgt
agccgtagttaggccaccacttcaagaactctgtagcaccgcctacatacctcgctctgctaatcctgttaccag
tggct
gctgccagtggcgataagtcgtgtcttaccgggttggactcaagacgatagttaccggataaggcgcagcggtcg
ggctg
aacgggggttcgtgcacacagcccagcttggagcgaacgacctacaccgaactgagatacctacagcgtgagca
ttgag
aaagcgccacgcttcccgaagggagaaaggcggacaggtatccggtaagcggcagggtcggaacaggagagcgca
cgagg
gagcttccagggggaaacgcctggtatctttatagtcctgtcgggtttcgccacctctgacttgagcgtcgattt
ttgtg
atgctcgtcaggggggcggagcctatggaaaaacgccagcaacgcggcctttttacggttcctggccttttgctg
gcctt
ttgctcacatgttctttcctgcgttatcccctgattctgtggataaccgtattaccgcctttgagtgagctgata
ccgct
cgccgcagccgaacgaccgagcgcagcgagtcagtgagcgaggaagcggaagagcgcctgatgcggtattttctc
cttac
gcatctgtgcggtattcacaccgcatatatggtgcactctcagtacaatctgctctgatgccgcatagttaagc
cagta
tacactccgctatcgctacgtgactgggtcatggctgcgccccgacacccgccaacacccgctgacgcgccctga
cgggc
ttgtctgctcccggcatccgcttacagacaagctgtgaccgtctccgggagctgcatgtgtcagaggttttcacc
gtcat
caccgaaacgcgcgaggcagctgcggtaaagctcatcagcgtggtcgtgaagcgattcacagatgtctgcctgtt
catcc
```

Figure 9 (Cont.)

```
gcgtccagctcgttgagtttctccagaagcgttaatgtctggcttctgataaagcgggccatgttaagggcggtt
ttttc
ctgtttggtcacttgatgcctccgtgtaagggggaatttctgttcatgggggtaatgataccgatgaaacgagag
aggat
gctcacgatacgggttactgatgatgaacatgcccggttactggaacgttgtgagggtaaacaactggcggtatg
gatgc
ggcgggaccagagaaaaatcactcagggtcaatgccagcgcttcgttaatacagatgtaggtgttccacagggta
gccag
cagcatcctgcgatgcagatccggaacataatggtgcagggcgctgacttccgcgtttccagactttacgaaaca
cggaa
accgaagaccattcatgttgttgctcaggtcgcagacgttttgcagcagcagtcgcttcacgttcgctcgcgtat
cggtg
attcattctgctaaccagtaaggcaacccgccagcctagccgggtcctcaacgacaggagcacgatcatgcgca
cccgt
ggccaggacccaacgctgcccgagatgcgccgcgtgcggctgctggagatggcggacgcgatggatatgttctgc
caagg
gttggtttgcgcattcacagttctccgcaagaattgattggctccaattcttggagtggtgaatccgttagcgag
gtgcc
gccggcttccattcaggtcgaggtggcccggctccatgcacgcgacgcaacgcggggaggcagacaaggtatag
ggcgg
cgcctacaatccatgccaacccgttccatgtgctcgccgaggcggcataaatcgccgtgacgatcagcggtccag
tgatc
gaagttaggctggtaagagccgcgagcgatccttgaagctgtccctgatggtcgtcatctacctgcctggacagc
atggc
ctgcaacgcgggcatcccgatgccgccggaagcgagaagaatcataatggggaaggccatccagcctcgcgtcgc
gaacg
ccagcaagacgtagcccagcgcgtcggccagcttgcaattcgcgctaacttacattaattgcgttgcgctcactg
cccgc
tttccagtcgggaaacctgtcgtgccagctgcattaatgaatcggccaacgcgcggggagaggcggtttgcgtat
tgggc
gccaggtggttttctttcaccagtgagacgggcaacagctgattgccctcaccgcctggccctgagagt
tgcag
caagcggtccacgctggtttgcccagcaggcgaaaatcctgtttgatggtggttgacggcgggatataacatga
gctgt
cttcggtatcgtcgtatcccactaccgagatatccgcaccaacgcgcagcccggactcggtaatggcgcgcattg
cgccc
agcgccatctgatcgttggcaaccagcatcgcagtgggaacgatgccctcattcagcatttgcatggtttgttga
aaacc
ggacatggcactccagtcgccttcccgttccgctatcggctgaatttgattgcgagtgagatatttatgccagcc
agcca
gacgcagacgcgccgagacagaacttaatggTcccgctaacagcgcgatttgctgAtgacccaatgcgaccagat
gctcc
acgcccagtcgcgtaccgtcttcatgggagaaaataatactgttgatgggtgtctggtcagagacatcaagaaat
aacgc
cggaacattagtgcaggcagcttccacagcaatggcatcctggtcatccagcggatagttaatgatcagcccact
gacgc
gttgcgcgagaagattgtgcaccgccgctttacaggcttcgacgccgcttcgttctaccatcgacaccaccacgc
tggca
cccagttgatcggcgcgagatttaatcgccgcgacaatttgcgacggcgcgtgcagggccagactggaggtggca
acgcc
aatcagcaacgactgtttgcccgccagttgttgtgccacgcggttgggaatgtaattcagctccgccatcgccgc
ttcca
cttttccccgcgttttcgcagaaacgtggctggcctggttcaccacgcgggaaacggtctgataagagacaccgg
catac
tctgcgacatcgtataacgttactggtttcacattcaccaccctgaattgactctcttccgggcgctatcatgcc
atacc
gcgaaaggttttgcgccattcgatggtgtcaacgtaaatgcatgccgcttcgccttcgcgcgcgaattgcaagct
gatcc
```

Figure 9 (Cont.)

```
ggagcttatcgactgcacggtgcaccaatgcttctggcgtcaggcagccatcggaagctgtggtatggctgtgca
ggtcg
taaatcactgcataattcgtgtcgctcaaggcgcactcccgttctggataatgttttttgcgccgacatcataac
ggttc
tggcaaatattctgaaatgagctgttgacaattaatcatcggctcgtataatgtgtggaattgtgagcggataac
aattt
cacacaggaaacaGAATTCcatATGAAATACCTATTACCAACAGCAGCAGCTGGGTTATTATTGCTCGCTGCGCA
GCCGG
CCATGGcccaGGTCACCgtctcctcaaaCCGCGGaCTCGAGgcGGCCcagccGGCCatggccGCTAGCGCGGCCG
CTCTA
GAttAAGCTTggctgttttggcggatgagagaagattttcagcctgatacagattaaatcagaacgcagaagcgg
tctga
taaaacagaatttgcctggcggcagtagcgcggtggtcccacctgaccccatgccgaactcagaagtgaaacgcc
gtagc
gccgatggtagtgtggggtctcccatgcgagagtagggaactgccaggcatcaaataaaacgaaaggctcagtc
gaaag
actgggcctttcgttttatctgttgtttgtcggtgaacgctctcctgagtaggacaaatccgccgggagcggatt
tgaac
gttgcgaagcaacggcccggaggaccctggcgggcaggacgcccgccataaactgccaggcatcaaattaagcag
aaggc
catcctgacggatggcctttttgcgtttctacaaactctt
```

P55Flag/RBS/35 (SEQ ID NO:93)

```
ttgtttattttttctaaatacattcaaatatgtatccgctcatgagacaataaccctgataaatgcttcaataata
ttgaa
aaaggaagagtatgagtattcaacatttccgtgtcgcccttattccctttttttgcggcattttgccttcctgttt
ttgct
cacccagaaacgctggtgaaagtaaaagatgctgaagatcagttgggtgcacgagtgggttacatcgaactggat
ctcaa
cagcggtaagatccttgagagttttcgccccgaagaacgttttccaatgatgagcacttttaaagttctgctatg
tggcg
cggtattatcccgtgttgacgccgggcaagagcaactcggtcgccgcatacactattctcagaatgacttggttg
agtac
tcaccagtcacagaaaagcatcttacggatggcatgacagtaagagaattatgcagtgctgccataaccatgagt
gataa
cactgcggccaacttacttctgacaacgatcggaggaccgaaggagctaaccgcttttttgcacaacatggggga
tcatg
taactcgccttgatcgttgggaaccggagctgaatgaagccataccaaacgacgagcgtgacaccacgatgcctg
tagca
atggcaacaacgttgcgcaaactattaactggcgaactacttactctagcttcccggcaacaattaatagactgg
atgga
ggcggataaagttgcaggaccacttctgcgctcggcccttccggctggctggtttattgctgataaatctggagc
cggtg
agcgtgggtctcgcggtatcattgcagcactggggccagatggtaagccctcccgtatcgtagttatctacacga
cgggg
agtcaggcaactatggatgaacgaaatagacagatcgctgagataggtgcctcactgattaagcattggtaactg
tcaga
ccaagtttactcatatatactttagattgatttaaaacttcatttttaatttaaaaggatctaggtgaagatcct
ttttg
ataatctcatgaccaaaatcccttaacgtgagttttcgttccactgagcgtcagaccccgtagaaaagatcaaag
gatct
cttgagatcctttttttctgcgcgtaatctgctgcttgcaaacaaaaaaaccaccgctaccagcggtggtttgt
ttgcc
ggatcaagagctaccaactctttttccgaaggtaactggcttcagcagagcgcagataccaaatactgtccttct
agtgt
```

Figure 9 (Cont.)

```
agccgtagttaggccaccacttcaagaactctgtagcaccgcctacataectcgctctgctaatcctgttaccagtggct
gctgccagtggcgataagtcgtgtcttaccgggttggactcaagacgatagttaccggataaggcgcagcggtcgggctg
aacgggggttcgtgcacacagcccagcttggagcgaacgacctacaccgaactgagatacctacagcgtgagcattgag
aaagcgccacgcttcccgaagggagaaaggcggacaggtatccggtaagcggcagggtcggaacaggagagcgacgagg
gagcttccagggggaaacgcctggtatctttatagtcctgtcgggtttcgccacctctgacttgagcgtcgattttgtg
atgctcgtcagggggcggagcctatggaaaaacgccagcaacgcggcctttttacggttcctggccttttgctggcctt
ttgctcacatgttctttcctgcgttatcccctgattctgtggataaccgtattaccgcctttgagtgagctgataccgct
cgccgcagccgaacgaccgagcgcagcgagtcagtgagcgaggaagcggaagagcgcctgatgcggtatttctccttac
gcatctgtgcggtatttcacaccgcatatggtgcactctcagtacaatctgctctgatgccgcatagttaagccagta
tacactccgctatcgctacgtgactgggtcatggctgcgccccgacaccgccaacaccgctgacgcgcctgacgggc
ttgtctgctcccggcatccgcttacagacaagctgtgaccgtctccgggagctgcatgtgtcagaggttttcaccgtcat
caccgaaacgcgcgaggcagctgcggtaaagctcatcagcgtggtcgtgaagcgattcacagatgtctgcctgttcatcc
gcgtccagctcgttgagtttctccagaagcgttaatgtctggcttctgataaagcgggccatgttaagggcggttttttc
ctgtttggtcacttgatgcctccgtgtaagggggaatttctgttcatgggggtaatgataccgatgaaacgagagaggat
gctcacgatacgggttactgatgatgaacatgcccggttactggaacgttgtgagggtaaacaactggcggtatggatgc
ggcgggaccagagaaaaatcactcagggtcaatgccagcgcttcgttaatacagatgtaggtgttccacagggtagccag
cagcatcctgcgatgcagatccggaacataatggtgcagggcgctgacttccgcgtttccagactttacgaaacacggaa
accgaagaccattcatgttgttgctcaggtcgcagacgttttgcagcagcagtcgcttcacgttcgctcgcgtatcggtg
attcattctgctaaccagtaaggcaacccgccagcctagccgggtcctcaacgacaggagcacgatcatgcgcacccgt
ggccaggacccaacgctgcccgagatgcgccgcgtgcggctgctggagatggcggacgcgatggatatgttctgccaagg
gttggtttgcgcattcacagttctccgcaagaattgattggctccaattcttggagtggtgaatccgttagcgaggtgcc
gccggcttccattcaggtcgaggtggcccggctccatgcaccgcgacgcaacgcggggaggcagacaaggtatagggcgg
cgcctacaatccatgccaacccgttccatgtgctcgccgaggcggcataaatcgccgtgacgatcagcggtccagtgatc
gaagttaggctggtaagagccgcgagcgatccttgaagctgtccctgatggtcgtcatctacctgcctggacagcatggc
ctgcaacgcgggcatcccgatgccgccggaagcgagaagaatcataatggggaaggccatccagcctcgcgtcgcgaacg
ccagcaagacgtagcccagcgcgtcggccagcttgcaattcgcgctaacttacattaattgcgttgcgctcactgcccgc
tttccagtcgggaaacctgtcgtgccagctgcattaatgaatcggccaacgcgcggggagaggcggtttgcgtatgggc
gccagggtggttttttcttttcaccagtgagacgggcaacagctgattgcccttcaccgcctggccctgagagagttgcag
caagcggtccacgctggtttgccccagcaggcgaaaatcctgtttgatggtggttgacggcgggatataacatgagctgt
```

Figure 9 (Cont.)

```
cttcggtatcgtcgtatcccactaccgagatatccgcaccaacgcgcagcccggactcggtaatggcgcgcattg
cgccc
agcgccatctgatcgttggcaaccagcatcgcagtgggaacgatgccctcattcagcatttgcatggtttgttga
aaacc
ggacatggcactccagtcgccttcccgttccgctatcggctgaatttgattgcgagtgagatatttatgccagcc
agcca
gacgcagacgcgccgagacagaacttaatggTcccgctaacagcgcgatttgctgAtgacccaatgcgaccagat
gctcc
acgcccagtcgcgtaccgtcttcatgggagaaaataatactgttgatgggtgtctggtcagagacatcaagaaat
aacgc
cggaacattagtgcaggcagcttccacagcaatggcatcctggtcatccagcggatagttaatgatcagcccact
gacgc
gttgcgcgagaagattgtgcaccgccgctttacaggcttcgacgccgcttcgttctaccatcgacaccaccacgc
tggca
cccagttgatcggcgcgagatttaatcgccgcgacaatttgcgacggcgcgtgcagggccagactggaggtggca
acgcc
aatcagcaacgactgtttgcccgccagttgttgtgccacgcggttgggaatgtaattcagctccgccatcgccgc
ttcca
cttttccccgcgttttcgcagaaacgtggctggcctggttcaccacgcgggaaacggtctgataagagacaccgg
catac
tctgcgacatcgtataacgttactggtttcacattcaccaccctgaattgactctcttccgggcgctatcatgcc
atacc
gcgaaaggttttgcgccattcgatggtgtcaacgtaaatgcatgccgcttcgccttcgcgcgcgaattgcaagct
gatcc
ggagcttatcgactgcacggtgcaccaatgcttctggcgtcaggcagccatcggaagctgtggtatggctgtgca
ggtcg
taaatcactgcataattcgtgtcgctcaaggcgcactcccgttctggataatgttttttgcgccgacatcataac
ggttc
tggcaaatattctgaaatgagctgttgacaattaatcatcggctcgtataatgtgtggaattgtgagcggataac
aattt
cacacaggaaacaGAATTCcatATGAAATACCTATTACCAACAGCAGCAGCTGGGTTATTATTGCTCGCTGCGCA
GCCGG
CCATGGcccaGGTcACCgtctcctcaaaCCGCGGAGAGTGTgcaggtGATTACAAAGACGATGACGATAAGTAAT
AAacA
GGAAacagaaGtccatATGAAATACCTATTGCCTACGGCAGCCGCTGGATTGTTATTACTCGCGGCCcagccGGC
Catgg
ccGCTAGCGCGGCCGCTCTAGATTAAGCTTggctgttttggcggatgagagaagattttcagcctgatacagatt
aaatc
agaacgcagaagcggtctgataaaacagaatttgcctggcggcagtagcgcggtggtcccacctgacccatgcc
gaact
cagaagtgaaacgccgtagcgccgatggtagtgtggggtctcccatgcgagagtagggaactgccaggcatcaa
ataaa
acgaaaggctcagtcgaaagactgggcctttcgttttatctgttgtttgtcggtgaacgctctcctgagtaggac
aaatc
cgccgggagcggatttgaacgttgcgaagcaacggcccggaggacctggcgggcaggacgccgccataaactg
ccagg
catcaaattaagcagaaggccatcctgacggatggcctttttgcgtttctacaaactctt
```

P55Flag/RBS/35cmyc6HisGS (SEQ ID NO:94)

```
ttgtttattttttctaaatacattcaaatatgtatccgctcatgagacaataaccctgataaatgcttcaataata
ttgaa
aaaggaagagtatgagtattcaacatttccgtgtcgcccttattcccttttttgcggcatttgccttcctgttt
ttgct
cacccagaaacgctggtgaaagtaaaagatgctgaagatcagttgggtgcacgagtgggttacatcgaactggat
ctcaa
```

Figure 9 (Cont.)

```
cagcggtaagatccttgagagttttcgccccgaagaacgttttccaatgatgagcacttttaaagttctgctatg
tggcg
cggtattatcccgtgttgacgccgggcaagagcaactcggtcgccgcatacactattctcagaatgacttggttg
agtac
tcaccagtcacagaaaagcatcttacggatggcatgacagtaagagaattatgcagtgctgccataaccatgagt
gataa
cactgcggccaacttacttctgacaacgatcggaggaccgaaggagctaaccgcttttttgcacaacatggggga
tcatg
taactcgccttgatcgttgggaaccggagctgaatgaagccataccaaacgacgagcgtgacaccacgatgcctg
tagca
atggcaacaacgttgcgcaaactattaactggcgaactacttactctagcttccggcaacaattaatagactgg
atgga
ggcggataaagttgcaggaccacttctgcgctcggcccttccggctggctggtttattgctgataaatctggagc
cggtg
agcgtgggtctcgcggtatcattgcagcactgggccagatggtaagccctcccgtatcgtagttatctacacga
cgggg
agtcaggcaactatggatgaacgaaatagacagatcgctgagataggtgcctcactgattaagcattggtaactg
tcaga
ccaagtttactcatatatactttagattgatttaaaacttcattttctaatttaaaaggatctaggtgaagatcct
ttttg
ataatctcatgaccaaaatcccttaacgtgagttttcgttccactgagcgtcagacccgtagaaaagatcaaag
gatct
tcttgagatcctttttttctgcgcgtaatctgctgcttgcaaacaaaaaaaccaccgctaccagcggtggtttgt
ttgcc
ggatcaagagctaccaactcttttccgaaggtaactggcttcagcagagcgcagataccaaatactgtccttct
agtgt
agccgtagttaggccaccacttcaagaactctgtagcaccgcctacatacctcgctctgctaatcctgttaccag
tggct
gctgccagtggcgataagtcgtgtcttaccgggttggactcaagacgatagttaccggataaggcgcagcggtcg
ggctg
aacgggggttcgtgcacacagcccagcttggagcgaacgacctacaccgaactgagatacctacagcgtgagca
ttgag
aaagcgccacgcttcccgaagggagaaaggcggacaggtatccggtaagcggcagggtcggaacaggagagcgca
cgagg
gagcttccaggggggaaacgcctggtatctttatagtcctgtcgggtttcgccacctctgacttgagcgtcgattt
ttgtg
atgctcgtcagggggggcggagcctatggaaaaacgccagcaacgcggcctttttacggttcctggcttttgctg
gcctt
ttgctcacatgttctttcctgcgttatcccctgattctgtggataaccgtattaccgcctttgagtgagctgata
ccgct
cgccgcagccgaacgaccgagcgcagcgagtcagtgagcgaggaagcggaagagcgcctgatgcggtattttctc
cttac
gcatctgtgcggtatttcacaccgcatatatggtgcactctcagtacaatctgctctgatgccgcatagttaagc
cagta
tacactccgctatcgctacgtgactgggtcatggctgcgccccgacacccgccaacaccgctgacgcgccctga
cgggc
ttgtctgctcccggcatccgcttacagacaagctgtgaccgtctccgggagctgcatgtgtcagaggttttcacc
gtcat
caccgaaacgcgcgaggcagctgcggtaaagctcatcagcgtggtcgtgaagcgattcacagatgtctgcctgtt
catcc
gcgtccagctcgttgagtttctccagaagcgttaatgtctggcttctgataaagcgggccatgttaagggcggtt
ttttc
ctgtttggtcacttgatgcctccgtgtaaggggggaatttctgttcatgggggtaatgataccgatgaaacgagag
aggat
gctcacgatacgggttactgatgatgaacatgcccggttactggaacgttgtgagggtaaacaactggcggtatg
gatgc
ggcgggaccagagaaaaatcactcagggtcaatgccagcgcttcgttaatacagatgtaggtgttccacagggta
gccag
```

Figure 9 (Cont.)

```
cagcatcctgcgatgcagatccggaacataatggtgcaggycgctgacttccgcgtttccagactttacgaaaca
cggaa
accgaagaccattcatgttgttgctcaggtcgcagacgttttgcagcagcagtcgcttcacgttcgctcgcgtat
cggtg
attcattctgctaaccagtaaggcaacccgccagcctagccgggtcctcaacgacaggagcacgatcatgcgca
cccgt
ggccaggacccaacgctgcccgagatgcgccgcgtgcggctgctggagatggcggacgcgatggatatgttctgc
caagg
gttggtttgcgcattcacagttctccgcaagaattgattggctccaattcttggagtggtgaatccgttagcgag
gtgcc
gccggcttccattcaggtcgaggtggcccggctccatgcaccgcgacgcaacgcggggaggcagacaaggtatag
ggcgg
cgcctacaatccatgccaacccgttccatgtgctcgccgaggcggcataaatcgccgtgacgatcagcggtccag
tgatc
gaagttaggctggtaagagccgcgagcgatccttgaagctgtccctgatggtcgtcatctacctgcctggacagc
atggc
ctgcaacgcgggcatcccgatgccgccggaagcgagaagaatcataatggggaaggccatccagcctcgcgtcgc
gaacg
ccagcaagacgtagcccagcgcgtcggccagcttgcaattcgcgctaacttacattaattgcgttgcgctcactg
ccgc
tttccagtcgggaaacctgtcgtgccagctgcattaatgaatcggccaacgcgcggggagaggcggtttgcgtat
tgggc
gccagggtggttttttcttttcaccagtgagacgggcaacagctgattgcccttcaccgcctggccctgagagagt
tgcag
caagcggtccacgctggtttgccccagcaggcgaaaatcctgtttgatggtggttgacggcgggatataacatga
gctgt
cttcggtatcgtcgtatcccactaccgagatatccgcaccaacgcgcagcccggactcggtaatggcgcgcattg
cgccc
agcgccatctgatcgttggcaaccagcatcgcagtgggaacgatgccctcattcagcatttgcatggtttgttga
aaacc
ggacatggcactccagtcgccttcccgttccgctatcggctgaatttgattgcgagtgagatatttatgccagcc
agcca
gacgcagacgcgccgagacagaacttaatggTcccgctaacagcgcgatttgctgAtgacccaatgcgaccagat
gctcc
acgcccagtcgcgtaccgtcttcatgggagaaaataatactgttgatgggtgtctggtcagagacatcaagaaat
aacgc
cggaacattagtgcaggcagcttccacagcaatggcatcctggtcatccagcggatagttaatgatcagcccact
gacgc
gttgcgcgagaagattgtgcaccgccgctttacaggcttcgacgccgcttcgttctaccatcgacaccaccacgc
tggca
cccagttgatcggcgcgagatttaatcgccgcgacaatttgcgacggcgcgtgcagggccagactggaggtggca
acgcc
aatcagcaacgactgtttgcccgccagttgttgtgccacgcggttgggaatgtaattcagctccgccatcgccgc
ttcca
ctttttcccgcgtttcgcagaaacgtggctggcctggttcaccacgcgggaaacggtctgataagagacaccgg
catac
tctgcgacatcgtataacgttactggtttcacattcaccaccctgaattgactctcttccgggcgctatcatgcc
atacc
gcgaaaggttttgcgccattcgatggtgtcaacgtaaatgcatgccgcttcgccttcgcgcgcgaattgcaagct
gatcc
ggagcttatcgactgcacggtgcaccaatgcttctggcgtcaggcagccatcggaagctgtggtatggctgtgca
ggtcg
taaatcactgcataattcgtgtcgctcaaggcgcactcccgttctggataatgttttttgcgccgacatcataac
ggttc
tggcaaatattctgaaatgagctgttgacaattaatcatcggctcgtataatgtgtggaattgtgagcggataac
aattt
cacacaggaaacaGAATTCcatATGAAATACCTATTACCAACAGCAGCAGCTGGGTTATTATTGCTCGCTGCGCA
GCCGG
```

Figure 9 (Cont.)

CCATGGcccaGGTcACCgtctcctcaaaCCGCGGAGAGTGTgcaggtGATTACAAAGACGATGACGATAAGTAAT
AAacA
GGAAacagaaGtccatATGAAATACCTATTGCCTACGGCAGCCGCTGGATTGTTATTACTCGCGGCCcagccGGC
Catgg
ccGCTAGCGCGGCCGCAGAACAAAAACTCATCTCAGAAGAGGATCTGAATGGGGCCGTACATCACCACCATCATC
ATGGG
AGCTAAGCTTggctgttttggcggatgagagaagattttcagcctgatacagattaaatcagaacgcagaagcgg
tctga
taaaacagaattgcctggcggcagtagcgcggtggtcccacctgacccatgccgaactcagaagtgaaacgcc
gtagc
gccgatggtagtgtggggtctccccatgcgagagtagggaactgccaggcatcaaataaaacgaaaggctcagtc
gaaag
actgggcctttcgttttatctgttgtttgtcggtgaacgctctcctgagtaggacaaatccgccgggagcggatt
tgaac
gttgcgaagcaacggcccggaggaccctggcgggcaggacgcccgccataaactgccaggcatcaaattaagcag
aaggc
catcctgacggatggcctttttgcgtttctacaaactctt pHCH2CH3γ1-TAG (SEQ ID NO:95)

ttgtttattttttctaaatacattcaaatatgtatccgctcatgagacaataaccctgataaatgcttcaataata
ttgaa
aaggaagagtatgagtattcaacatttccgtgtcgcccttattcccttttttgcggcattttgccttcctgttt
ttgct
cacccagaaacgctggtgaaagtaaaagatgctgaagatcagttgggtgcacgagtgggttacatcgaactggat
ctcaa
cagcggtaagatccttgagagttttcgccccgaagaacgttttccaatgatgagcacttttaaagttctgctatg
tggcg
cggtattatcccgtgttgacgccgggcaagagcaactcggtcgccgcatacactattctcagaatgacttggttg
agtac
tcaccagtcacagaaaagcatcttacggatggcatgacagtaagagaattatgcagtgctgccataaccatgagt
gataa
cactgcggccaacttacttctgacaacgatcggaggaccgaaggagctaaccgcttttttgcacaacatggggga
tcatg
taactcgccttgatcgttgggaaccggagctgaatgaagccataccaaacgacgagcgtgacaccacgatgcctg
tagca
atggcaacaacgttgcgcaaactattaactggcgaactacttactctagcttcccggcaacaattaatagactgg
atgga
ggcggataaagttgcaggaccacttctgcgctcggcccttccggctggctggtttattgctgataaatctggagc
cggtg
agcgtgggtctcgcggtatcattgcagcactggggccagatggtaagccctcccgtatcgtagttatctacacga
cgggg
agtcaggcaactatggatgaacgaaatagacagatcgctgagataggtgcctcactgattaagcattggtaactg
tcaga
ccaagtttactcatatatactttagattgatttaaaacttcattttttaatttaaaaggatctaggtgaagatcct
ttttg
ataatctcatgaccaaaatcccttaacgtgagttttcgttccactgagcgtcagaccccgtagaaaagatcaaag
gatct
tcttgagatccttttttctgcgcgtaatctgctgcttgcaaacaaaaaaaccaccgctaccagcggtggtttgt
ttgcc
ggatcaagagctaccaactcttttccgaaggtaactggcttcagcagagcgcagataccaaatactgtccttct
agtgt
agccgtagttaggccaccacttcaagaactctgtagcaccgcctacatacctcgctctgctaatcctgttaccag
tggct
gctgccagtggcgataagtcgtgtcttaccgggttggactcaagacgatagttaccggataaggcgcagcggtcg
ggctg

Figure 9 (Cont.)

```
aacgggggggttcgtgcacacagcccagcttggagcgaacgacctacaccgaactgagatacctacagcgtgagca
ttgag
aaagcgccacgcttcccgaagggagaaaggcggacaggtatccggtaagcggcagggtcggaacaggagagcgca
cgagg
gagcttccaggggggaaacgcctggtatctttatagtcctgtcgggtttcgccacctctgacttgagcgtcgattt
ttgtg
atgctcgtcaggggggcggagcctatggaaaaacgccagcaacgcggccttttttacggttcctggccttttgctg
gcctt
ttgctcacatgttctttcctgcgttatccctgattctgtggataaccgtattaccgcctttgagtgagctgata
ccgct
cgccgcagccgaacgaccgagcgcagcgagtcagtgagcgaggaagcggaagagcgcctgatgcggtattttctc
cttac
gcatctgtgcggtatttcacaccgcatatatggtgcactctcagtacaatctgctctgatgccgcatagttaagc
cagta
tacactccgctatcgctacgtgactgggtcatggctgcgccccgacacccgccaacacccgctgacgcgcctga
cgggc
ttgtctgctcccggcatccgcttacagacaagctgtgaccgtctcccgggagctgcatgtgtcagaggttttcacc
gtcat
caccgaaacgcgcgaggcagctgcggtaaagctcatcagcgtggtcgtgaagcgattcacagatgtctgcctgtt
catcc
gcgtccagctcgttgagtttctccagaagcgttaatgtctggcttctgataaagcgggccatgttaagggcggtt
ttttc
ctgtttggtcacttgatgcctccgtgtaagggggaatttctgttcatgggggtaatgataccgatgaaacgagag
aggat
gctcacgatacgggttactgatgatgaacatgcccggttactggaacgttgtgagggtaaacaactggcggtatg
gatgc
ggcgggaccagagaaaaatcactcagggtcaatgccagcgcttcgttaatacagatgtaggtgttccacagggta
gccag
cagcatcctgcgatgcagatccggaacataatggtgcagggcgctgacttccgcgtttccagactttacgaaaca
cggaa
accgaagaccattcatgttgttgctcaggtcgcagacgttttgcagcagcagtcgcttcacgttcgctcgcgtat
cggtg
attcattctgctaaccagtaaggcaacccgccagcctagccgggtcctcaacgacaggagcacgatcatgcga
cccgt
ggccaggacccaacgctgcccgagatgcgccgcgtgcggctgctggagatggcggacgcgatggatatgttctgc
caagg
gttggtttgcgcattcacagttctccgcaagaattgattggctccaattcttggagtggtgaatccgttagcgag
gtgcc
gccggcttccattcaggtcgaggtggcccggctccatgcaccgcgacgcaacgcggggaggcagacaaggtatag
ggcgg
cgcctacaatccatgccaacccgttccatgtgctcgccgaggcggcataaatcgccgtgacgatcagcggtccag
tgatc
gaagttaggctggtaagagccgcgagcgatccttgaagctgtccctgatggtcgtcatctacctgcctggacagc
atggc
ctgcaacgcgggcatcccgatgccgccggaagcgagaagaatcataatggggaaggccatccagcctcgcgtcgc
gaacg
ccagcaagacgtagcccagcgcgtcggccagcttgcaattcgcgctaacttacattaattgcgttgcgctcactg
cccgc
tttccagtcgggaaacctgtcgtgccagctgcattaatgaatcggccaacgcgcggggagaggcggtttgcgtat
tgggc
gccagggtggttttttcttttcaccagtgagacgggcaacagctgattgcccttcaccgcctggccctgagagagt
tgcag
caagcggtccacgctggtttgccccagcaggcgaaaatcctgtttgatggtggttgacggcgggatataacatga
gctgt
cttcggtatcgtcgtatcccactaccgagatatccgcaccaacgcgcagcccggactcggtaatggcgcgcattg
cgccc
agcgccatctgatcgttggcaaccagcatcgcagtgggaacgatgccctcattcagcatttgcatggtttgttga
aaacc
```

Figure 9 (Cont.)

```
ggacatggcactccagtcgccttcccgttccgctatcggctgaatttgattgcgagtgagatatttatgccagcc
agcca
gacgcagacgcgccgagacagaacttaatggTcccgctaacagcgcgatttgctgAtgacccaatgcgaccagat
gctcc
acgcccagtcgcgtaccgtcttcatgggagaaaataatactgttgatgggtgtctggtcagagacatcaagaaat
aacgc
cggaacattagtgcaggcagcttccacagcaatggcatcctggtcatccagcggatagttaatgatcagcccact
gacgc
gttgcgcgagaagattgtgcaccgccgctttacaggcttcgacgccgcttcgttctaccatcgacaccaccacgc
tggca
cccagttgatcggcgcgagatttaatcgccgcgacaatttgcgacggcgcgtgcagggccagactggaggtggca
acgcc
aatcagcaacgactgtttgcccgccagttgttgtgccacgcggttgggaatgtaattcagctccgccatcgccgc
ttcca
ctttttcccgcgttttcgcagaaacgtggctggcctggttcaccacgcgggaaacggtctgataagagacaccgg
catac
tctgcgacatcgtataacgttactggtttcacattcaccaccctgaattgactctcttccgggcgctatcatgcc
atacc
gcgaaaggttttgcgccattcgatggtgtcaacgtaaatgcatgccgcttcgccttcgcgcgcgaattgcaagct
gatcc
ggagcttatcgactgcacggtgcaccaatgcttctggcgtcaggcagccatcggaagctgtggtatggctgtgca
ggtcg
taaatcactgcataattcgtgtcgctcaaggcgcactcccgttctggataatgttttttgcgccgacatcataac
ggttc
tggcaaatattctgaaatgagctgttgacaattaatcatcggctcgtataatgtgtggaattgtgagcggataac
aattt
cacacaggaaacaGAATTCatATGAAATACCTATTACCAACAGCAGCAGCTGGGTTATTATTGCTCGCTGCGCA
GCCGG
CCATGGcccaGGTcACCgtctcctcaGACAAAACTCACACATGCCCACCGTGCCCAgcacctgaactcctggggg
gaccg
tcagtcttcctcttccccccaaaacccaaggacacccctcatgatctcccggacccctgaggtcacatgcgtggtg
gtgga
cgtgagccacgaagaccctgaggtcaagttcaactggtacgtggacggcgtggaggtgcataatgccaagacaaa
gccgc
gggaggagcagtacaacagcacgtaccgggtggtcagcgtcctcaccgtcctgcaccaggactggctgaatggca
aggag
tacaagtgcaaggtctccaacaaagcccctcccagcccccatcgagaaaaccatctccaaagccaaaGGGCAGCCC
CGAGA
ACCACAGGTGTACACCCTGCCCCCATCCCGGGATGAGCTGACCAAGAACCAGGTCAGCCTGACCTGCCTGGTCAA
AGGCT
TCTATCCCAGCGACATCGCCGTGGAGTGGGAGAGCAATGGGCAGCCGGAGAACAACTACAAGACCACGCCTCCCG
TGCTG
GACTCCGACGGCTCCTTCTTCCTCTACAGCAAGCTCACCGTGGACAAGAGCAGGTGGCAGCAGGGGAACGTCTTC
TCATG
CTCCGTGATGCATGAGGCTCTGCACAACCACTACACGCAGAAGAGCCTCTCCCTGTCTCCGGGTAAAGCGGCCGC
AGAAC
AAAAACTCATCTCAGAAGAGGATCTGAATGGGGCCGTACATCACCACCATCATCATGGGAGCTAAGCTTggctgt
tttgg
cggatgagagaagattttcagcctgatacagattaaatcagaacgcagaagcggtctgataaaacagaatttgcc
tggcg
gcagtagcgcggtggtcccacctgaccccatgccgaactcagaagtgaaacgccgtagcgccgatggtagtgtgg
ggtct
ccccatgcgagagtagggaactgccaggcatcaaataaaacgaaaggctcagtcgaaagactgggcctttcgttt
tatct
gttgtttgtcggtgaacgctctcctgagtaggacaaatccgccgggagcggatttgaacgttgcgaagcaacggc
ccgga
ggaccctggcgggcaggacgcccgccataaactgccaggcatcaaattaagcagaaggccatcctgacggatggc
ctttt
```

Figure 9 (Cont.)

tgcgtttctacaaactctt pHCH2CH3γ1 (SEQ ID NO:96)

ttgtttatttttctaaatacattcaaatatgtatccgctcatgagacaataaccctgataaatgcttcaataatattgaa
aaaggaagagtatgagtattcaacatttccgtgtcgccttattccttttttgcggcatttgccttcctgttttttgct
cacccagaaacgctggtgaaagtaaaagatgctgaagatcagttgggtgcacgagtgggttacatcgaactggatctcaa
cagcggtaagatccttgagagttttcgccccgaagaacgttttccaatgatgagcacttttaaagttctgctatgtggcg
cggtattatcccgtgttgacgccgggcaagagcaactcggtcgccgcatacactattctcagaatgacttggttgagtac
tcaccagtcacagaaaagcatcttacggatggcatgacagtaagagaattatgcagtgctgccataaccatgagtgataa
cactgcggccaacttacttctgacaacgatcggaggaccgaaggagctaaccgcttttttgcacaacatggggatcatg
taactcgccttgatcgttgggaaccggagctgaatgaagccataccaaacgacgagcgtgacaccacgatgcctgtagca
atggcaacaacgttgcgcaaactattaactggcgaactacttactctagcttcccggcaacaattaatagactggatgga
ggcggataaagttgcaggaccacttctgcgctcggcccttccggctggctggtttattgctgataaatctggagccggtg
agcgtgggtctcgcggtatcattgcagcactggggccagatggtaagccctcccgtatcgtagttatctacacgacgggg
agtcaggcaactatggatgaacgaaatagacagatcgctgagataggtgcctcactgattaagcattggtaactgtcaga
ccaagtttactcatatatactttagattgatttaaaacttcattttttaatttaaaaggatctaggtgaagatcctttttg
ataatctcatgaccaaaatcccttaacgtgagttttcgttccactgagcgtcagaccccgtagaaaagatcaaaggatct
tcttgagatcctttttttctgcgcgtaatctgctgcttgcaaacaaaaaaaccaccgctaccagcggtggtttgtttgcc
ggatcaagagctaccaactctttttccgaaggtaactggcttcagcagagcgcagataccaaatactgtccttctagtgt
agccgtagttaggccaccacttcaagaactctgtagcaccgcctacatacctcgctctgctaatcctgttaccagtggct
gctgccagtggcgataagtcgtgtcttaccgggttggactcaagacgatagttaccggataaggcgcagcggtcgggctg
aacgggggttcgtgcacacagcccagcttggagcgaacgacctacaccgaactgagatacctacagcgtgagcattgag
aaagcgccacgcttcccgaagggagaaaggcggacaggtatccggtaagcggcagggtcggaacaggagagcgcacgagg
gagcttccaggggggaaacgcctggtatctttatagtcctgtcgggtttcgccacctctgacttgagcgtcgatttttgtg
atgctcgtcaggggggcggagcctatggaaaaacgccagcaacgcggcctttttacggttcctggccttttgctggcctt
ttgctcacatgttctttcctgcgttatcccctgattctgtggataaccgtattaccgcctttgagtgagctgataccgct
cgccgcagccgaacgaccgagcgcagcgagtcagtgagcgaggaagcggaagagcgcctgatgcggtatttctccttac
gcatctgtgcggtatttcacaccgcatatatggtgcactctcagtacaatctgctctgatgccgcatagttaagccagta
tacactccgctatcgctacgtgactgggtcatggctgcgccccgacacccgccaacacccgctgacgcgccctgacgggc

Figure 9 (Cont.)

```
ttgtctgctcccggcatccgcttacagacaagctgtgaccgtctccgggagctgcatgtgtcagaggttttcacc
gtcat
caccgaaacgcgcgaggcagctgcggtaaagctcatcagcgtggtcgtgaagcgattcacagatgtctgcctgtt
catcc
gcgtccagctcgttgagtttctccagaagcgttaatgtctggcttctgataaagcgggccatgttaagggcggtt
ttttc
ctgtttggtcacttgatgcctccgtgtaagggggaatttctgttcatgggggtaatgataccgatgaaacgagag
aggat
gctcacgatacgggttactgatgatgaacatgcccggttactggaacgttgtgagggtaaacaactggcggtatg
gatgc
ggcgggaccagagaaaaatcactcagggtcaatgccagcgcttcgttaatacagatgtaggtgttccacagggta
gccag
cagcatcctgcgatgcagatccggaacataatggtgcagggcgctgacttccgcgtttccagactttacgaaaca
cggaa
accgaagaccattcatgttgttgctcaggtcgcagacgttttgcagcagcagtcgcttcacgttcgctcgcgtat
cggtg
attcattctgctaaccagtaaggcaacccgccagcctagccgggtcctcaacgacaggagcacgatcatgcgca
cccgt
ggccaggaccaaacgctgcccgagatgcgccgcgtgcggctgctggagatggcggacgcgatggatatgttctgc
caagg
gttggtttgcgcattcacagttctccgcaagaattgattggctccaattcttggagtggtgaatccgttagcgag
gtgcc
gccggcttccattcaggtcgaggtggcccggctccatgcaccgcgacgcaacgcggggaggcagacaaggtatag
ggcgg
cgcctacaatccatgccaacccgttccatgtgctcgccgaggcggcataaatcgccgtgacgatcagcggtccag
tgatc
gaagttaggctggtaagagccgcgagcgatccttgaagctgtccctgatggtcgtcatctacctgcctggacagc
atggc
ctgcaacgcgggcatcccgatgccgccggaagcgagaagaatcataatggggaaggccatccagcctcgcgtcgc
gaacg
ccagcaagacgtagcccagcgcgtcggccagcttgcaattcgcgctaacttacattaattgcgttgcgctcactg
cccgc
tttccagtcgggaaacctgtcgtgccagctgcattaatgaatcggccaacgcgcggggagaggcggtttgcgtat
tgggc
gccagggtggttttcttttcaccagtgagacgggcaacagctgattgcccttcacgcctggccctgagagagt
tgcag
caagcggtccacgctggtttgcccagcaggcgaaaatcctgtttgatggtggttgacggcgggatataacatga
gctgt
cttcggtatcgtcgtatcccactaccgagatatccgcaccaacgcgcagcccggactcggtaatggcgcgcattg
cgccc
agcgccatctgatcgttggcaaccagcatcgcagtgggaacgatgccctcattcagcatttgcatggtttgttga
aaacc
ggacatggcactccagtcgccttcccgttccgctatcggctgaatttgattgcgagtgagatatttatgccagcc
agcca
gacgcagacgcgccgagacagaacttaatggTcccgctaacagcgcgatttgctgAtgaccccaatgcgaccagat
gctcc
acgcccagtcgcgtaccgtcttcatgggagaaaataatactgttgatggtgtctggtcagagacatcaagaaat
aacgc
cggaacattagtgcaggcagcttccacagcaatggcatcctggtcatccagcggatagttaatgatcagcccact
gacgc
gttgcgcgagaagattgtgcaccgccgctttacaggcttcgacgccgcttcgttctaccatcgacaccaccacgc
tggca
cccagttgatcggcgcgagatttaatcgccgcgacaatttgcgacggcgcgtgcagggccagactggaggtggca
acgcc
aatcagcaacgactgtttgcccgccagttgttgtgccacgcggttgggaatgtaattcagctccgccatcgccgc
ttcca
cttttttccgcgttttcgcagaaacgtggctggcctggttcaccacgcgggaaacggtctgataagagacaccgg
catac
```

Figure 9 (Cont.)

```
tctgcgacatcgtataacgttactggtttcacattcaccaccctgaattgactctcttccgggcgctatcatgcc
ataccc
gcgaaaggttttgcgccattcgatggtgtcaacgtaaatgcatgccgcttcgccttcgcgcgcgaattgcaagct
gatcc
ggagcttatcgactgcacggtgcaccaatgcttctggcgtcaggcagccatcggaagctgtggtatggctgtgca
ggtcg
taaatcactgcataattcgtgtcgctcaaggcgcactcccgttctggataatgttttttgcgccgacatcataac
ggttc
tggcaaatattctgaaatgagctgttgacaattaatcatcggctcgtataatgtgtggaattgtgagcggataac
aattt
cacacaggaaacaGAATTCcatATGAAATACCTATTACCAACAGCAGCAGCTGGGTTATTATTGCTCGCTGCGCA
GCCGG
CCATGGcccaGGTcACCgtctcctcaGACAAAACTCACACATGCCCACCGTGCCCAgcacctgaactcctggggg
gaccg
tcagtcttcctcttccccccaaaacccaaggacaccctcatgatctcccggacccctgaggtcacatgcgtggtg
gtgga
cgtgagccacgaagaccctgaggtcaagttcaactggtacgtggacggcgtggaggtgcataatgccaagacaaa
gccgc
gggaggagcagtacaacagcacgtaccgggtggtcagcgtcctcaccgtcctgcaccaggactggctgaatggca
aggag
tacaagtgcaaggtctccaacaaagccctcccagcccccatcgagaaaaccatctccaaagccaaaGGGCAGCCC
CGAGA
ACCACAGGTGTACACCCTGCCCCCATCCCGGGATGAGCTGACCAAGAACCAGGTCAGCCTGACCTGCCTGGTCAA
AGGCT
TCTATCCCAGCGACATCGCCGTGGAGTGGGAGAGCAATGGGCAGCCGGAGAACAACTACAAGACCACGCCTCCCG
TGCTG
GACTCCGACGGCTCCTTCTTCCTCTACAGCAAGCTCACCGTGGACAAGAGCAGGTGGCAGCAGGGGAACGTCTTC
TCATG
CTCCGTGATGCATGAGGCTCTGCACAACCACTACACGCAGAAGAGCCTCTCCCTGTCTCCGGGTAAATAAGCTTg
gctgt
tttggcggatgagagaagattttcagcctgatacagattaaatcagaacgcagaagcggtctgataaaacagaat
ttgcc
tggcggcagtagcgcggtggtcccacctgaccccatgccgaactcagaagtgaaacgccgtagcgccgatggtag
tgtgg
ggtctccccatgcgagagtagggaactgccaggcatcaaataaaacgaaaggctcagtcgaaagactgggcctt
cgttt
tatctgttgtttgtcggtgaacgctctcctgagtaggacaaatccgccgggagcggatttgaacgttgcgaagca
acggc
ccggaggaccctggcgggcaggacgcccgccataaactgccaggcatcaaattaagcagaaggccatcctgacgg
atggc
ctttttgcgtttctacaaactctt
```

P55CKFlag/RBS/35cmyc6HisGS (SEQ ID NO:97)

```
ttgtttattttttctaaatacattcaaatatgtatccgctcatgagacaataaccctgataaatgcttcaataata
ttgaa
aaggaagagtatgagtattcaacatttccgtgtcgcccttattccttttttgcggcattttgccttcctgttt
ttgct
cacccagaaacgctggtgaaagtaaaagatgctgaagatcagttgggtgcacgagtgggttacatcgaactggat
ctcaa
cagcggtaagatccttgagagttttcgccccgaagaacgttttccaatgatgagcacttttaaagttctgctatg
tggcg
cggtattatcccgtgttgacgccgggcaagagcaactcggtcgccgcatacactattctcagaatgacttggttg
agtac
tcaccagtcacagaaaagcatcttacggatggcatgacagtaagagaattatgcagtgctgccataaccatgagt
gataa
```

Figure 9 (Cont.)

```
cactgcggccaacttacttctgacaacgatcggaggaccgaaggagctaaccgcttttttgcacaacatgggggat
catg
taactcgccttgatcgttgggaaccggagctgaatgaagccataccaaacgacgagcgtgacaccacgatgcctg
tagca
atggcaacaacgttgcgcaaactattaactggcgaactacttactctagcttcccggcaacaattaatagactgg
atgga
ggcggataaagttgcaggaccacttctgcgctcggccttccggctggctggtttattgctgataaatctggagc
cggtg
agcgtgggtctcgcggtatcattgcagcactggggccagatggtaagccctcccgtatcgtagttatctacacga
cgggg
agtcaggcaactatggatgaacgaaatagacagatcgctgagataggtgcctcactgattaagcattggtaactg
tcaga
ccaagtttactcatatatactttagattgatttaaaacttcatttttaatttaaaaggatctaggtgaagatcct
ttttg
ataatctcatgaccaaatcccttaacgtgagttttcgttccactgagcgtcagacccgtagaaaagatcaaag
gatct
tcttgagatcctttttttctgcgcgtaatctgctgcttgcaaacaaaaaaaccaccgctaccagcggtggtttgt
ttgcc
ggatcaagagctaccaactctttttccgaaggtaactggcttcagcagagcgcagataccaaatactgtccttct
agtgt
agccgtagttaggccaccacttcaagaactctgtagcaccgcctacatacctcgctctgctaatcctgttaccag
tggct
gctgccagtggcgataagtcgtgtcttaccgggttggactcaagacgatagttaccggataaggcgcagcggtcg
ggctg
aacgggggttcgtgcacacagcccagcttggagcgaacgacctacaccgaactgagatacctacagcgtgagca
ttgag
aaagcgccacgcttcccgaagggagaaaggcggacaggtatccggtaagcggcagggtcggaacaggagagcgca
cgagg
gagcttccaggggaaacgcctggtatctttatagtcctgtcgggtttcgccacctctgacttgagcgtcgattt
ttgtg
atgctcgtcaggggggcggagcctatggaaaaacgccagcaacgcggcctttttacggttcctggccttttgctg
gcctt
ttgctcacatgttctttcctgcgttatcccctgattctgtggataaccgtattaccgcctttgagtgagctgata
ccgct
cgccgcagccgaacgaccgagcgcagcgagtcagtgagcgaggaagcggaagagcgcctgatgcggtattttctc
cttac
gcatctgtgcggtatttcacaccgcatatatggtgcactctcagtacaatctgctctgatgccgcatagttaagc
cagta
tacactccgctatcgctacgtgactgggtcatggctgcgccccgacacccgccaacacccgctgacgcgcctga
cgggc
ttgtctgctcccggcatccgcttacagacaagctgtgaccgtctccgggagctgcatgtgtcagaggttttcacc
gtcat
caccgaaacgcgcgaggcagctgcggtaaagctcatcagcgtggtcgtgaagcgattcacagatgtctgcctgtt
catcc
gcgtccagctcgttgagtttctccagaagcgttaatgtctggcttctgataaagcgggccatgttaagggcggtt
ttttc
ctgtttggtcacttgatgcctccgtgtaagggggaatttctgttcatggggtaatgataccgatgaaacgagag
aggat
gctcacgatacgggttactgatgatgaacatgcccggttactggaacgttgtgagggtaaacaactggcggtatg
gatgc
ggcgggaccagagaaaatcactcagggtcaatgccagcgcttcgttaatacagatgtaggtgttccacagggta
gccag
cagcatcctgcgatgcagatccggaacataatggtgcagggcgctgacttccgcgtttccagactttacgaaaca
cggaa
accgaagaccattcatgttgttgctcaggtcgcagacgttttgcagcagcagtcgcttcacgttcgctcgcgtat
cggtg
attcattctgctaaccagtaaggcaaccccgccagcctagccgggtcctcaacgacaggagcacgatcatgcgca
cccgt
```

Figure 9 (Cont.)

```
ggccaggacccaacgctgcccgagatgcgccgcgtgcggctgctggagatggcggacgcgatggatatgttctgc
caagg
gttggtttgcgcattcacagttctccgcaagaattgattggctccaattcttggagtggtgaatccgttagcgag
gtgcc
gccggcttccattcaggtcgaggtggcccggctccatgcaccgcgacgcaacgcggggaggcagacaaggtatag
ggcgg
cgcctacaatccatgccaacccgttccatgtgctcgccgaggcggcataaatcgccgtgacgatcagcggtccag
tgatc
gaagttaggctggtaagagccgcgagcgatccttgaagctgtccctgatggtcgtcatctacctgcctggacagc
atggc
ctgcaacgcgggcatcccgatgccgccggaagcgagaagaatcataatggggaaggccatccagcctcgcgtcgc
gaacg
ccagcaagacgtagcccagcgcgtcggccagcttgcaattcgcgctaacttacattaattgcgttgcgctcactg
cccgc
tttccagtcgggaaacctgtcgtgccagctgcattaatgaatcggccaacgcgcggggagaggcggtttgcgtat
tgggc
gccagggtggttttttcttttcaccagtgagacgggcaacagctgattgccttcaccgcctggccctgagagagt
tgcag
caagcggtccacgctggtttgcccagcaggcgaaaatcctgtttgatggtggttgacggcgggatataacatga
gctgt
cttcggtatcgtcgtatcccactaccgagatatccgcaccaacgcgcagcccggactcggtaatggcgcgcattg
cgccc
agcgccatctgatcgttggcaaccagcatcgcagtgggaacgatgccctcattcagcatttgcatggtttgttga
aaacc
ggacatggcactccagtcgccttcccgttccgctatcggctgaatttgattgcgagtgagatatttatgccagcc
agcca
gacgcagacgcgccgagacagaacttaatggTcccgctaacagcgcgatttgctgAtgacccaatgcgaccagat
gctcc
acgcccagtcgcgtaccgtcttcatgggagaaaataatactgttgatgggtgtctggtcagagacatcaagaaat
aacgc
cggaacattagtgcaggcagcttccacagcaatggcatcctggtcatccagcggatagttaatgatcagcccact
gacgc
gttgcgcgagaagattgtgcaccgccgctttacaggcttcgacgccgcttcgttctaccatcgacaccaccacgc
tggca
cccagttgatcggcgcgagatttaatcgccgcgacaatttgcgacggcgcgtgcagggccagactggaggtggca
acgcc
aatcagcaacgactgtttgcccgccagttgttgtgccacgcggttgggaatgtaattcagctccgccatcgccgc
ttcca
cttttcccgcgttttcgcagaaacgtggctggcctggttcaccacgcgggaaacggtctgataagagacaccgg
catac
tctgcgacatcgtataacgttactggtttcacattcaccaccctgaattgactctcttccgggcgctatcatgcc
atacc
gcgaaaggttttgcgccattcgatggtgtcaacgtaaatgcatgccgcttcgccttcgcgcgcgaattgcaagct
gatcc
ggagcttatcgactgcacggtgcaccaatgcttctggcgtcaggcagccatcggaagctgtggtatggctgtgca
ggtcg
taaatcactgcataattcgtgtcgctcaaggcgcactcccgttctggataatgttttttgcgccgacatcataac
ggttc
tggcaaatattctgaaatgagctgttgacaattaatcatcggctcgtataatgtgtggaattgtgagcggataac
aattt
cacacaggaaacaGAATTCcatATGAAATACCTATTACCAACAGCAGCAGCTGGGTTATTATTGCTCGCTGCGCA
GCCGG
CCATGGcccaGGTCACCGTCTCCTCAGGTACCGTGGCTGCACCATCTGTCTTCATCTTCCCGCCATCTGATGAGC
AGTTG
AAATCTGGAACTGCCTCTGTTGTGTGCCTGCTGAATAACTTCTATCCCAGAGAGGCCAAAGTACAGTGGAAGGTG
GATAA
CGCCCTCCAATCGGGTAACTCCCAGGAGAGTGTCACAGAGCAGGACAGCAAGGACAGCACCTACAGCCTCAGCAG
CACCC
```

Figure 9 (Cont.)

```
TGACGCTGAGCAAAGCAGACTACGAGAAACACAAAGTCTACGCCTGCGAAGTCACCCATCAGGGCCTGAGCTCGC
CGGTG
ACAAAGAGCTTCAACCGCGGAGAGTGTgcaggtGATTACAAAGACGATGACGATAAGTAATAAacAGGAAacaga
aGtcc
atATGAAATACCTATTGCCTACGGCAGCCGCTGGATTGTTATTACTCGCGGCCcagccGGCCatggccGCTAGCG
CGGCC
GCAGAACAAAAACTCATCTCAGAAGAGGATCTGAATGGGCCGTACATCACCACCATCATCATGGGAGCTAAGCT
Tggct
gttttggcggatgagagaagattttcagcctgatacagattaaatcagaacgcagaagcggtctgataaaacaga
atttg
cctggcggcagtagcgcggtggtcccacctgacccatgccgaactcagaagtgaaacgccgtagcgccgatggt
agtgt
ggggtctccccatgcgagagtagggaactgccaggcatcaaataaaacgaaaggctcagtcgaaagactgggcct
ttcgt
tttatctgttgtttgtcggtgaacgctctcctgagtaggacaaatccgccgggagcggatttgaacgttgcgaag
caacg
gcccggaggaccctggcgggcaggacgcccgccataaactgccaggcatcaaattaagcagaaggccatcctgac
ggatg
gccttttgcgtttctacaaactctt
``` pCKCH1γ1-TAG (SEQ ID NO:98)

```
ttgtttattttttctaaatacattcaaatatgtatccgctcatgagacaataaccctgataaatgcttcaataata
ttgaa
aaaggaagagtatgagtattcaacatttccgtgtcgcccttattccctttttttgcggcattttgccttcctgttt
ttgct
cacccagaaacgctggtgaaagtaaaagatgctgaagatcagttgggtgcacgagtgggttacatcgaactggat
ctcaa
cagcggtaagatccttgagagttttcgccccgaagaacgttttccaatgatgagcacttttaaagttctgctatg
tggcg
cggtattatcccgtgttgacgccgggcaagagcaactcggtcgccgcatacactattctcagaatgacttggttg
agtac
tcaccagtcacagaaaagcatcttacggatggcatgacagtaagagaattatgcagtgctgccataaccatgagt
gataa
cactgcggccaacttacttctgacaacgatcggaggaccgaaggagctaaccgcttttttgcacaacatggggga
tcatg
taactcgccttgatcgttgggaaccggagctgaatgaagccataccaaacgacgagcgtgacaccacgatgcctg
tagca
atggcaacaacgttgcgcaaactattaactggcgaactacttactctagcttcccggcaacaattaatagactgg
atgga
ggcggataaagttgcaggaccacttctgcgctcggcccttccggctggctggtttattgctgataaatctggagc
cggtg
agcgtgggtctcgcggtatcattgcagcactggggccagatggtaagccctcccgtatcgtagttatctacacga
cgggg
agtcaggcaactatggatgaacgaaatagacagatcgctgagataggtgcctcactgattaagcattggtaactg
tcaga
ccaagtttactcatatatactttagattgatttaaaacttcatttttaatttaaaaggatctaggtgaagatcct
ttttg
ataatctcatgaccaaaatcccttaacgtgagttttcgttccactgagcgtcagaccccgtagaaaagatcaaag
gatct
tcttgagatcctttttttctgcgcgtaatctgctgcttgcaaacaaaaaaaccaccgctaccagcggtggtttgt
ttgcc
ggatcaagagctaccaactctttttccgaaggtaactggcttcagcagagcgcagataccaaatactgtccttct
agtgt
agccgtagttaggccaccacttcaagaactctgtagcaccgcctacatacctcgctctgctaatcctgttaccag
tggct
```

Figure 9 (Cont.)

```
gctgccagtggcgataagtcgtgtcttaccgggttggactcaagacgatagttaccggataaggcgcagcggtcg
ggctg
aacgggggttcgtgcacacagcccagcttggagcgaacgacctacaccgaactgagatacctacagcgtgagca
ttgag
aaagcgccacgcttcccgaagggagaaaggcggacaggtatccggtaagcggcagggtcggaacaggagagcgca
cgagg
gagcttccaggggggaaacgcctggtatctttatagtcctgtcgggtttcgccacctctgacttgagcgtcgattt
ttgtg
atgctcgtcagggggcggagcctatggaaaaacgccagcaacgcggccttttttacggttcctggccttttgctg
gcctt
ttgctcacatgttcttttcctgcgttatccctgattctgtggataaccgtattaccgcctttgagtgagctgata
ccgct
cgccgcagccgaacgaccgagcgcagcgagtcagtgagcgaggaagcggaagagcgcctgatgcggtattttctc
cttac
gcatctgtgcggtatttcacaccgcatatatggtgcactctcagtacaatctgctctgatgccgcatagttaagc
cagta
tacactccgctatcgctacgtgactgggtcatggctgcgccccgacacccgccaacacccgctgacgcgcctga
cgggc
ttgtctgctcccggcatccgcttacagacaagctgtgaccgtctccgggagctgcatgtgtcagaggttttcacc
gtcat
caccgaaacgcgcgaggcagctgcggtaaagctcatcagcgtggtcgtgaagcgattcacagatgtctgcctgtt
catcc
gcgtccagctcgttgagtttctccagaagcgttaatgtctggcttctgataaagcgggccatgttaagggcggtt
ttttc
ctgtttggtcacttgatgcctccgtgtaaggggga atttctgttcatgggggta atgataccgatgaaacgagag
aggat
gctcacgatacgggttactgatgatgaacatgcccggttactggaacgttgtgagggtaaacaactggcggtatg
gatgc
ggcgggaccagagaaaaatcactcagggtcaatgccagcgcttcgttaatacagatgtaggtgttccacagggta
gccag
cagcatcctgcgatgcagatccggaacataatggtgcagggcgctgacttccgcgtttccagactttacgaaaca
cggaa
accgaagaccattcatgttgttgctcaggtcgcagacgttttgcagcagcagtcgcttcacgttcgctcgcgtat
cggtg
attcattctgctaaccagtaaggcaacccgccagcctagccgggtcctcaacgacaggagcacgatcatgcgca
cccgt
ggccaggacccaacgctgcccgagatgcgccgcgtgcggctgctggagatggcggacgcgatggatatgttctgc
caagg
gttggtttgcgcattcacagttctccgcaagaattgattggctccaattcttggagtggtgaatccgttagcgag
gtgcc
gccggcttccattcaggtcgaggtggccggctccatgcaccgcgacgcaacgcggggaggcagacaaggtatag
ggcgg
cgcctacaatccatgccaacccgttccatgtgctcgccgaggcggcataaatcgccgtgacgatcagcggtccag
tgatc
gaagttaggctggtaagagccgcgagcgatccttgaagctgtccctgatggtcgtcatctacctgcctggacagc
atggc
ctgcaacgcgggcatcccgatgccgccggaagcgagaagaatcataatggggaaggccatccagcctcgcgtcgc
gaacg
ccagcaagacgtagccagcgcgtcggccagcttgcaattcgcgctaacttacattaattgcgttgcgctcactg
cccgc
tttccagtcgggaaacctgtcgtgccagctgcattaatgaatcggccaacgcgcggggagaggcggtttgcgtat
tgggc
gccagggtggttttctttttcaccagtgagacgggcaacagctgattgcccttcaccgcctggccctgagagagt
tgcag
caagcggtccacgctggtttgccccagcaggcgaaaatcctgtttgatggtggttgacggcgggataacatga
gctgt
cttcggtatcgtcgtatcccactaccgagatatccgcaccaacgcgcagcccggactcggtaatggcgcgcattg
cgccc
```

Figure 9 (Cont.)

```
agcgccatctgatcgttggcaaccagcatcgcagtgggaacgatgccctcattcagcatttgcatggtttgttga
aaacc
ggacatggcactccagtcgccttcccgttccgctatcggctgaatttgattgcgagtgagatatttatgccagcc
agcca
gacgcagacgcgccgagacagaacttaatggTcccgctaacagcgcgatttgctgAtgacccaatgcgaccagat
gctcc
acgcccagtcgcgtaccgtcttcatgggagaaaataatactgttgatgggtgtctggtcagagacatcaagaaat
aacgc
cggaacattagtgcaggcagcttccacagcaatggcatcctggtcatccagcggatagttaatgatcagcccact
gacgc
gttgcgcgagaagattgtgcaccgccgctttacaggcttcgacgccgcttcgttctaccatcgacaccaccacgc
tggca
cccagttgatcggcgcgagatttaatcgccgcgacaatttgcgacggcgcgtgcagggccagactggaggtggca
acgcc
aatcagcaacgactgtttgcccgccagttgttgtgccacgcggttgggaatgtaattcagctccgccatcgccgc
ttcca
cttttccgcgttttcgcagaaacgtggctggcctggttcaccacgcgggaaacggtctgataagagacaccgg
catac
tctgcgacatcgtataacgttactggtttcacattcaccaccctgaattgactctcttccgggcgctatcatgcc
atacc
gcgaaaggttttgcgccattcgatggtgtcaacgtaaatgcatgccgcttcgccttcgcgcgcgaattgcaagct
gatcc
ggagcttatcgactgcacggtgcaccaatgcttctggcgtcaggcagccatcggaagctgtggtatggctgtgca
ggtcg
taaatcactgcataattcgtgtcgctcaaggcgcactcccgttctggataatgttttttgcgccgacatcataac
ggttc
tggcaaatattctgaaatgagctgttgacaattaatcatcggctcgtataatgtgtggaattgtgagcggataac
aattt
cacacaggaaacaGAATTCcatATGAAATACCTATTACCAACAGCAGCAGCTGGGTTATTATTGCTCGCTGCGCA
GCCGG
CCATGGcccaGGTCACCGTCTCCTCAGGTACCGTGGCTGCACCATCTGTCTTCATCTTCCCGCCATCTGATGAGC
AGTTG
AAATCTGGAACTGCCTCTGTTGTGTGCCTGCTGAATAACTTCTATCCCAGAGAGGCCAAAGTACAGTGGAAGGTG
GATAA
CGCCCTCCAATCGGGTAACTCCCAGGAGAGTGTCACAGAGCAGGACAGCAAGGACAGCACCTACAGCCTCAGCAG
CACCC
TGACGCTGAGCAAAGCAGACTACGAGAAACACAAAGTCTACGCCTGCGAAGTCACCCATCAGGGCCTGAGCTCGC
CGGTG
ACAAAGAGCTTCAACCGCGGAGAGTGTgcaggtGATTACAAAGACGATGACGATAAGTAATAAacAGGAAacaga
aGtcc
atATGAAATACCTATTGCCTACGGCAGCCGCTGGATTGTTATTACTCGCGGCCcagcCGGCCATGGCCGCTAGCA
CCAAG
GGCCCATCGGTCTTCCCCCTGGCACCCTCCTCCAAGAGCACCTCTGGGGGCACAGCGGCCCTGGGCTGCCTGGTC
AAGGA
CTACTTCCCCGAACCGGTGACGGTGTCGTGGAACTCAGGCGCCCTGACCAGCGGCGTGCACACCTTCCCGGCTGT
CCTAC
AGTCCTCAGGACTCTACTCCCTCAgcagcGTAGTGACCGTGCCCTCCAGCAGCTTGGGCACCCAGACCTACATCT
GCAAC
GTGAATCACAAGCCCAGCAACACCAAGGTGGACAAGAAAGTTGAGCCCAAATCTTGTGCGGCCGCAGAACAAAAA
CTCAT
CTCAGAAGAGGATCTGAATGGGGCCGTACATCACCACCATCATCATGGGAGCTAAGCTTggctgttttggcggat
gagag
aagatttttcagcctgatacagattaaatcagaacgcagaagcggtctgataaaacagaatttgcctggcggcagt
agcgc
ggtggtcccacctgacccatgccgaactcagaagtgaaacgccgtagcgccgatggtagtgtggggtctcccca
tgcga
gagtagggaactgccaggcatcaaataaaacgaaaggctcagtcgaaagactgggcctttcgttttatctgttgt
ttgtc
```

Figure 9 (Cont.)

ggtgaacgctctcctgagtaggacaaatccgccgggagcggatttgaacgttgcgaagcaacggcccggaggacc
ctggc
gggcaggacgcccgccataaactgccaggcatcaaattaagcagaaggccatcctgacggatggccttttgcgt
ttcta
caaactctt pCKCH1Hγ1-TAG (SEQ ID NO:99)

ttgtttattttttctaaatacattcaaatatgtatccgctcatgagacaataaccctgataaatgcttcaataata
ttgaa
aaaggaagagtatgagtattcaacatttccgtgtcgcccttattccctttttttgcggcattttgccttcctgttt
ttgct
cacccagaaacgctggtgaaagtaaaagatgctgaagatcagttgggtgcacgagtgggttacatcgaactggat
ctcaa
cagcggtaagatccttgagagttttcgccccgaagaacgttttccaatgatgagcacttttaaagttctgctatg
tggcg
cggtattatcccgtgttgacgccgggcaagagcaactcggtcgccgcatacactattctcagaatgacttggttg
agtac
tcaccagtcacagaaaagcatcttacggatggcatgacagtaagagaattatgcagtgctgccataaccatgagt
gataa
cactgcggccaacttacttctgacaacgatcggaggaccgaaggagctaaccgcttttttgcacaacatggggga
tcatg
taactcgccttgatcgttgggaaccggagctgaatgaagccataccaaacgacgagcgtgacaccacgatgcctg
tagca
atggcaacaacgttgcgcaaactattaactggcgaactacttactctagcttcccggcaacaattaatagactgg
atgga
ggcggataaagttgcaggaccacttctgcgctcggcccttccggctggctggtttattgctgataaatctggagc
cggtg
agcgtgggtctcgcggtatcattgcagcactggggccagatggtaagccctcccgtatcgtagttatctacacga
cgggg
agtcaggcaactatggatgaacgaaatagacagatcgctgagataggtgcctcactgattaagcattggtaactg
tcaga
ccaagtttactcatatatactttagattgatttaaaacttcattttttaatttaaaaggatctaggtgaagatcct
ttttg
ataatctcatgaccaaaatcccttaacgtgagttttcgttccactgagcgtcagaccccgtagaaaagatcaaag
gatct
tcttgagatcctttttttctgcgcgtaatctgctgcttgcaaacaaaaaaaccaccgctaccagcggtggtttgt
ttgcc
ggatcaagagctaccaactctttttccgaaggtaactggcttcagcagagcgcagataccaaatactgtccttct
agtgt
agccgtagttaggccaccacttcaagaactctgtagcaccgcctacatacctcgctctgctaatcctgttaccag
tggct
gctgccagtggcgataagtcgtgtcttaccgggttggactcaagacgatagttaccggataaggcgcagcggtcg
ggctg
aacggggggttcgtgcacacagcccagcttggagcgaacgacctacaccgaactgagatacctacagcgtgagca
ttgag
aaagcgccacgcttcccgaagggagaaaggcggacaggtatccggtaagcggcagggtcggaacaggagagcgca
cgagg
gagcttccaggggggaaacgcctggtatctttatagtcctgtcgggtttcgccacctctgacttgagcgtcgattt
ttgtg
atgctcgtcagggggggcggagcctatggaaaaacgccagcaacgcggcctttttacggttcctggccttttgctg
gcctt
ttgctcacatgttctttcctgcgttatcccctgattctgtggataaccgtattaccgcctttgagtgagctgata
ccgct
cgccgcagccgaacgaccgagcgcagcgagtcagtgagcgaggaagcggaagagcgcctgatgcggtattttctc
cttac

Figure 9 (Cont.)

```
gcatctgtgcggtatttcacaccgcatatatggtgcactctcagtacaatctgctctgatgccgcatagttaagc
cagta
tacactccgctatcgctacgtgactgggtcatggctgcgcccgacacccgccaacacccgctgacgcgccctga
cgggc
ttgtctgctcccggcatccgcttacagacaagctgtgaccgtctccgggagctgcatgtgtcagaggttttcacc
gtcat
caccgaaacgcgcgaggcagctgcggtaaagctcatcagcgtggtcgtgaagcgattcacagatgtctgcctgtt
catcc
gcgtccagctcgttgagtttctccagaagcgttaatgtctggcttctgataaagcgggccatgttaagggcggtt
ttttc
ctgtttggtcacttgatgcctccgtgtaagggggaatttctgttcatgggggtaatgataccgatgaaacgagag
aggat
gctcacgatacgggttactgatgatgaacatgcccggttactggaacgttgtgagggtaaacaactggcggtatg
gatgc
ggcgggaccagagaaaaatcactcagggtcaatgccagcgcttcgttaatacagatgtaggtgttccacagggta
gccag
cagcatcctgcgatgcagatccggaacataatggtgcagggcgctgacttccgcgtttccagactttacgaaaca
cggaa
accgaagaccattcatgttgttgctcaggtcgcagacgttttgcagcagcagtcgcttcacgttcgctcgcgtat
cggtg
attcattctgctaaccagtaaggcaacccgccagcctagccgggtcctcaacgacaggagcacgatcatgcgca
cccgt
ggccaggacccaacgctgcccgagatgcgccgcgtgcggctgctggagatggcggacgcgatggatatgttctgc
caagg
gttggtttgcgcattcacagttctccgcaagaattgattggctccaattcttggagtggtgaatccgttagcgag
gtgcc
gccggcttccattcaggtcgaggtggcccggctccatgcaccgcgacgcaacgcggggaggcagacaaggtatag
ggcgg
cgcctacaatccatgccaacccgttccatgtgctcgccgaggcggcataaatcgccgtgacgatcagcggtccag
tgatc
gaagttaggctggtaagagccgcgagcgatccttgaagctgtccctgatggtcgtcatctacctgcctggacagc
atggc
ctgcaacgcgggcatcccgatgccgccggaagcgagaagaatcataatggggaaggccatccagcctcgcgtcgc
gaacg
ccagcaagacgtagcccagcgcgtcggccagcttgcaattcgcgctaacttacattaattgcgttgcgctcactg
cccgc
tttccagtcgggaaacctgtcgtgccagctgcattaatgaatcggccaacgcgcggggagaggcggtttgcgtat
tgggc
gccagggtggttttctttcaccagtgagacgggcaacagctgattgcccttcaccgcctggccctgagagagt
tgcag
caagcggtccacgctggtttgcccagcaggcgaaaatcctgtttgatggtggttgacggcgggatataacatga
gctgt
cttcggtatcgtcgtatcccactaccgagatatccgcaccaacgcgcagcccggactcggtaatggcgcgcattg
cgccc
agcgccatctgatcgttggcaaccagcatcgcagtgggaacgatgccctcattcagcatttgcatggtttgttga
aaacc
ggacatggcactccagtcgccttcccgttccgctatcggctgaatttgattgcgagtgagatatttatgccagcc
agcca
gacgcagacgcgccgagacagaacttaatggTcccgctaacagcgcgatttgctgAtgacccaatgcgaccagat
gctcc
acgcccagtcgcgtaccgtcttcatgggagaaaataatactgttgatgggtgtctggtcagagacatcaagaaat
aacgc
cggaacattagtgcaggcagcttccacagcaatggcatcctggtcatccagcggatagttaatgatcagcccact
gacgc
gttgcgcgagaagattgtgcaccgccgctttacaggcttcgacgccgcttcgttctaccatcgacaccaccacgc
tggca
cccagttgatcggcgcgagatttaatcgccgcgacaatttgcgacggcgcgtgcagggcagactggaggtggca
acgcc
```

Figure 9 (Cont.)

```
aatcagcaacgactgtttgcccgccagttgttgtgccacgcggttgggaatgtaattcagctccgccatcgccgc
ttcca
cttttcccgcgttttcgcagaaacgtggctggcctggttcaccacgcgggaaacggtctgataagagacaccgg
catac
tctgcgacatcgtataacgttactggtttcacattcaccaccctgaattgactctcttccgggcgctatcatgcc
atacc
gcgaaaggttttgcgccattcgatggtgtcaacgtaaatgcatgccgcttcgccttcgcgcgcgaattgcaagct
gatcc
ggagcttatcgactgcacggtgcaccaatgcttctggcgtcaggcagccatcggaagctgtggtatggctgtgca
ggtcg
taaatcactgcataattcgtgtcgctcaaggcgcactcccgttctggataatgttttttgcgccgacatcataac
ggttc
tggcaaatattctgaaatgagctgttgacaattaatcatcggctcgtataatgtgtggaattgtgagcggataac
aattt
cacacaggaaacaGAATTCcatATGAAATACCTATTACCAACAGCAGCAGCTGGGTTATTATTGCTCGCTGCGCA
GCCGG
CCATGGcccaGGTCACCGTCTCCTCAGGTACCGTGGCTGCACCATCTGTCTTCATCTTCCCGCCATCTGATGAGC
AGTTG
AAATCTGGAACTGCCTCTGTTGTGTGCCTGCTGAATAACTTCTATCCCAGAGAGGCCAAAGTACAGTGGAAGGTG
GATAA
CGCCCTCCAATCGGGTAACTCCCAGGAGAGTGTCACAGAGCAGGACAGCAAGGACAGCACCTACAGCCTCAGCAG
CACCC
TGACGCTGAGCAAAGCAGACTACGAGAAACACAAAGTCTACGCCTGCGAAGTCACCCATCAGGGCCTGAGCTCGC
CGGTG
ACAAAGAGCTTCAACCGCGGAGAGTGTgcaggtGATTACAAAGACGATGACGATAAGTAATAAacAGGAAacaga
aGtcc
atATGAAATACCTATTGCCTACGGCAGCCGCTGGATTGTTATTACTCGCGGCCcagcCGGCCATGGCCGCTAGCA
CCAAG
GGCCCATCGGTCTTCCCCCTGGCACCCTCCTCCAAGAGCACCTCTGGGGGCACAGCGGCCCTGGGCTGCCTGGTC
AAGGA
CTACTTCCCCGAACCGGTGACGGTGTCGTGGAACTCAGGCGCCCTGACCAGCGGCGTGCACACCTTCCCGGCTGT
CCTAC
AGTCCTCAGGACTCTACTCCCTCAGCAGCGTAGTGACCGTGCCCTCCAGCAGCTTGGGCACCCAGACCTACATCT
GCAAC
GTGAATCACAAGCCCAGCAACACCAAGGTGGACAAGAAAGTTGAGCCCAAATCTTGTGACAAAACTCACACATGC
CCACC
GTGCCCAGCGGCCGCAGAACAAAAACTCATCTCAGAAGAGGATCTGAATGGGGCCGTACATCACCACCATCATCA
TGGGA
GCTAAGCTTggctgttttggcggatgagagaagatttcagcctgatacagattaaatcagaacgcagaagcggt
ctgat
aaaacagaatttgcctggcggcagtagcgcggtggtcccacctgaccccatgccgaactcagaagtgaaacgccg
tagcg
ccgatggtagtgtggggtctcccatgcgagagtagggaactgccaggcatcaaataaaacgaaaggctcagtcg
aaaga
ctgggcctttcgttttatctgttgtttgtcggtgaacgctctctgagtaggacaaatccgccgggagcggattt
gaacg
ttgcgaagcaacggcccggaggaccctggcgggcaggacgccgccataaactgccaggcatcaaattaagcaga
aggcc
atcctgacggatggcctttttgcgtttctacaaactctt pcKcH1γ1 (SEQ ID NO:100)

ttgtttattttttctaaatacattcaaatatgtatccgctcatgagacaataaccctgataaatgcttcaataata
ttgaa
aaaggaagagtatgagtattcaacatttccgtgtcgcccttattccctttttgcggcattttgccttcctgttt
ttgct
```

Figure 9 (Cont.)

```
cacccagaaacgctggtgaaagtaaaagatgctgaagatcagttgggtgcacgagtgggttacatcgaactggat
ctcaa
cagcggtaagatccttgagagttttcgcccgaagaacgttttccaatgatgagcacttttaaagttctgctatg
tggcg
cggtattatcccgtgttgacgccgggcaagagcaactcggtcgccgcatacactattctcagaatgacttggttg
agtac
tcaccagtcacagaaaagcatcttacggatggcatgacagtaagagaattatgcagtgctgccataaccatgagt
gataa
cactgcggccaacttacttctgacaacgatcggaggaccgaaggagctaaccgcttttttgcacaacatggggga
tcatg
taactcgccttgatcgttgggaaccggagctgaatgaagccataccaaacgacgagcgtgacaccacgatgcctg
tagca
atggcaacaacgttgcgcaaactattaactggcgaactacttactctagcttcccggcaacaattaatagactgg
atgga
ggcggataaagttgcaggaccacttctgcgctcggcccttccggctggctggtttattgctgataaatctggagc
cggtg
agcgtgggtctcgcggtatcattgcagcactggggccagatggtaagccctcccgtatcgtagttatctacacga
cgggg
agtcaggcaactatggatgaacgaaatagacagatcgctgagataggtgcctcactgattaagcattggtaactg
tcaga
ccaagtttactcatatatactttagattgatttaaaacttcatttttaatttaaaaggatctaggtgaagatcct
ttttg
ataatctcatgaccaaaatcccttaacgtgagttttcgttccactgagcgtcagacccgtagaaaagatcaaag
gatct
tcttgagatcctttttttctgcgcgtaatctgctgcttgcaaacaaaaaaaccaccgctaccagcggtggtttgt
ttgcc
ggatcaagagctaccaactctttttccgaaggtaactggcttcagcagagcgcagataccaaatactgtccttct
agtgt
agccgtagttaggccaccacttcaagaactctgtagcaccgcctacatacctcgctctgctaatcctgttaccag
tggct
gctgccagtggcgataagtcgtgtcttaccgggttggactcaagacgatagttaccggataaggcgcagcggtcg
ggctg
aacgggggttcgtgcacacagcccagcttggagcgaacgacctacaccgaactgagataccracagcgtgagca
ttgag
aaagcgccacgcttcccgaagggagaaaggcggacaggtatccggtaagcggcagggtcggaacaggagagcgca
cgagg
gagcttccaggggaaacgcctggtatctttatagtcctgtcgggtttcgccacctctgacttgagcgtcgattt
ttgtg
atgctcgtcaggggggcggagcctatggaaaaacgccagcaacgcggcctttttacggttcctggccttttgctg
gcctt
ttgctcacatgttctttcctgcgttatcccctgattctgtggataaccgtattaccgcctttgagtgagctgata
ccgct
cgccgcagccgaacgaccgagcgcagcgagtcagtgagcgaggaagcggaagagcgcctgatgcggtattttctc
cttac
gcatctgtgcggtatttcacaccgcatatatggtgcactctcagtacaatctgctctgatgccgcatagttaagc
cagta
tacactccgctatcgctacgtgactgggtcatggctgcgccccgacacccgccaacacccgctgacgcgccctga
cgggc
ttgtctgctcccggcatccgcttacagacaagctgtgaccgtctccgggagctgcatgtgtcagaggttttcacc
gtcat
caccgaaacgcgcgaggcagctgggtaaagctcatcagcgtggtcgtgaagcgattcacagatgtctgcctgtt
catcc
gcgtccagctcgttgagtttctccagaagcgttaatgtctggcttctgataaagcgggccatgttaagggcggtt
ttttc
ctgtttggtcacttgatgcctccgtgtaagggggaatttctgttcatgggggtaatgataccgatgaaacgagag
aggat
gctcacgatacgggttactgatgatgaacatgcccggttactggaacgttgtgagggtaaacaactggcggtatg
gatgc
```

Figure 9 (Cont.)

```
ggcgggaccagagaaaaatcactcagggtcaatgccagcgcttcgttaatacagatgtaggtgttccacagggta
gccag
cagcatcctgcgatgcagatccggaacataatggtgcagggcgctgacttccgcgtttccagactttacgaaaca
cggaa
accgaagaccattcatgttgttgctcaggtcgcagacgttttgcagcagcagtcgcttcacgttcgctcgcgtat
cggtg
attcattctgctaaccagtaaggcaacccgccagcctagtcgggtcctcaacgacaggagcacgatcatgcgca
cccgt
ggccaggacccaacgctgcccgagatgcgccgcgtgcggctgctggagatggcggacgcgatggatatgttctgc
caagg
gttggtttgcgcattcacagttctccgcaagaattgattggctccaattcttggagtggtgaatccgttagcgag
gtgcc
gccggcttccattcaggtcgaggtggcccggctccatgcaccgcgacgcaacgcggggaggcagacaaggtatag
ggcgg
cgcctacaatccatgccaacccgttccatgtgctcgccgaggcggcataaatcgccgtgacgatcagcggtccag
tgatc
gaagttaggctggtaagagccgcgagcgatccttgaagctgtccctgatggtcgtcatctacctgcctggacagc
atggc
ctgcaacgcgggcatcccgatgccgccggaagcgagaagaatcataatggggaaggccatccagcctcgcgtcgc
gaacg
ccagcaagacgtagcccagcgcgtcggccagcttgcaattcgcgctaacttacattaattgcgttgcgctcactg
cccgc
tttccagtcgggaaacctgtcgtgccagctgcattaatgaatcggccaacgcgcgggggagaggcggtttgcgtat
tgggc
gccagggtggttttcttttcaccagtgagacgggcaacagctgattgcccttcaccgcctggccctgagagagt
tgcag
caagcggtccacgctggtttgcccagcaggcgaaaatcctgtttgatggtggttgacggcgggatataacatga
gctgt
cttcggtatcgtcgtatcccactaccgagatatccgcaccaacgcgcagcccggactcggtaatggcgcgcattg
cgccc
agcgccatctgatcgttggcaaccagcatcgcagtgggaacgatgccctcattcagcatttgcatggtttgttga
aaacc
ggacatggcactccagtcgccttcccgttccgctatcggctgaatttgattgcgagtgagatatttatgccagcc
agcca
gacgcagacgcgccgagacagaacttaatggTcccgctaacagcgcgatttgctgAtgacccaatgcgaccagat
gctcc
acgcccagtcgcgtaccgtcttcatgggagaaaataatactgttgatgggtgtctggtcagagacatcaagaaat
aacgc
cggaacattagtgcaggcagcttccacagcaatggcatcctggtcatccagcggatagttaatgatcagcccact
gacgc
gttgcgcgagaagattgtgcaccgccgctttacaggcttcgacgccgcttcgttctaccatcgacaccaccacgc
tggca
cccagttgatcggcgcgagatttaatcgccgcgacaatttgcgacggcgcgtgcagggccagactggaggtggca
acgcc
aatcagcaacgactgtttgcccgccagttgttgtgccacgcggttgggaatgtaattcagctccgccatcgccgc
ttcca
cttttcccgcgttttcgcagaaacgtggctggcctggttcaccacgcgggaaacggtctgataagagacaccgg
catac
tctgcgacatcgtataacgttactggtttcacattcaccaccctgaattgactctcttccgggcgctatcatgcc
atacc
gcgaaaggttttgcgccattcgatggtgtcaacgtaaatgcatgccgcttcgccttcgcgcgcgaattgcaagct
gatcc
ggagcttatcgactgcacggtgcaccaatgcttctggcgtcaggcagccatcggaagctgtggtatggctgtgca
ggtcg
taaatcactgcataattcgtgtcgctcaaggcgcactccgttctggataatgttttttgcgccgacatcataac
ggttc
tggcaaatattctgaaatgagctgttgacaattaatcatcggctcgtataatgtgtggaattgtgagcggataac
aattt
```

Figure 9 (Cont.)

```
cacacaggaaacaGAATTCcatATGAAATACCTATTACCAACAGCAGCAGCTGGGTTATTATTGCTCGCTGCGCAGCCGG
CCATGGcccaGGTcACCGTCTCCTCAGGTACCGTGGCTGCACCATCTGTCTTCATCTTCCCGCCATCTGATGAGCAGTTG
AAATCTGGAACTGCCTCTGTTGTGTGCCTGCTGAATAACTTCTATCCCAGAGAGGCCAAAGTACAGTGGAAGGTGGATAA
CGCCCTCCAATCGGGTAACTCCCAGGAGAGTGTCACAGAGCAGGACAGCAAGGACAGCACCTACAGCCTCAGCAGCACCC
TGACGCTGAGCAAAGCAGACTACGAGAAACACAAAGTCTACGCCTGCGAAGTCACCCATCAGGGCCTGAGCTCGCCGGTG
ACAAAGAGCTTCAACCGCGGAGAGTGTTAATAAacAGGAAacagaaGtccatATGAAATACCTATTGCCTACGGCAGCCG
CTGGATTGTTATTACTCGCGGCCcagcCGGCCATGGCCGCTAGCACCAAGGGCCCATCGGTCTTCCCCCTGGCACCCTCC
TCCAAGAGCACCTCTGGGGGCACAGCGGCCCTGGGCTGCCTGGTCAAGGACTACTTCCCCGAACCGGTGACGGTGTCGTG
GAACTCAGGCGCCCTGACCAGCGGCGTGCACACCTTCCCGGCTGTCCTACAGTCCTCAGGACTCTACTCCCTCAgcagcG
TAGTGACCGTGCCCTCCAGCAGCTTGGGCACCCAGACCTACATCTGCAACGTGAATCACAAGCCCAGCAACACCAAGGTG
GACAAGAAAGTTGAGCCCAAATCTTGTTAAGCTTggctgttttggcggatgagagaagattttcagcctgatacagatta
aatcagaacgcagaagcggtctgataaaacagaatttgcctggcggcagtagcgcggtggtcccacctgaccccatgccg
aactcagaagtgaaacgccgtagcgccgatggtagtgtggggtctcccatgcgagagtagggaactgccaggcatcaaa
taaaacgaaaggctcagtcgaaagactgggcctttcgttttatctgttgtttgtcggtgaacgctctcctgagtaggaca
aatccgccgggagcggatttgaacgttgcgaagcaacggcccggaggaccctggcgggcaggacgcccgccataaactgc
caggcatcaaattaagcagaaggccatcctgacggatggcctttttgcgtttctacaaactctt
``` pCKcH1Hy1 (SEQ ID NO:101)

```
ttgtttattttttctaaatacattcaaatatgtatccgctcatgagacaataaccctgataaatgcttcaataatattgaa
aaaggaagagtatgagtattcaacatttccgtgtcgcccttattcccttttttgcggcattttgccttcctgttttgct
cacccagaaacgctggtgaaagtaaaagatgctgaagatcagttgggtgcacgagtgggttacatcgaactggatctcaa
cagcggtaagatccttgagagttttcgccccgaagaacgttttccaatgatgagcactttaaagttctgctatgtggcg
cggtattatcccgtgttgacgccgggcaagagcaactcggtcgccgcatacactattctcagaatgacttggttgagtac
tcaccagtcacagaaaagcatcttacggatggcatgacagtaagagaattatgcagtgctgccataaccatgagtgataa
cactgcggccaacttacttctgacaacgatcggaggaccgaaggagctaaccgcttttttgcacaacatggggatcatg
taactcgccttgatcgttgggaaccggagctgaatgaagccataccaaacgacgagcgtgacaccacgatgcctgtagca
atggcaacaacgttgcgcaaactattaactggcgaactacttactctagcttcccggcaacaattaatagactggatgga
ggcggataaagttgcaggaccacttctgcgctcggcccttccggctggctggtttattgctgataaatctggagccggtg
agcgtgggtctcgcggtatcattgcagcactggggccagatggtaagccctcccgtatcgtagttatctacacgacgggg
```

Figure 9 (Cont.)

```
agtcaggcaactatggatgaacgaaatagacagatcgctgagataggtgcctcactgattaagcattggtaactg
tcaga
ccaagtttactcatatatactttagattgatttaaaacttcattttttaatttaaaaggatctaggtgaagatcct
ttttg
ataatctcatgaccaaaatcccttaacgtgagttttcgttccactgagcgtcagacccgtagaaaagatcaaag
gatct
tcttgagatcctttttttctgcgcgtaatctgctgcttgcaaacaaaaaaaccacgctaccagcggtggtttgt
ttgcc
ggatcaagagctaccaactcttttccgaaggtaactggcttcagcagagcgcagataccaaatactgtccttct
agtgt
agccgtagttaggccaccacttcaagaactctgtagcaccgcctacatacctcgctctgctaatcctgttaccag
tggct
gctgccagtggcgataagtcgtgtcttaccgggttggactcaagacgatagttaccggataaggcgcagcggtcg
ggctg
aacgggggttcgtgcacacagcccagcttggagcgaacgacctacaccgaactgagatacctacagcgtgagca
ttgag
aaagcgccacgcttcccgaagggagaaaggcggacaggtatccggtaagcggcagggtcggaacaggagagcgca
cgagg
gagcttccagggggaaacgcctggtatctttatagtcctgtcgggtttcgccacctctgacttgagcgtcgattt
ttgtg
atgctcgtcagggggcggagcctatggaaaaacgccagcaacgcggcctttttacggttcctggccttttgctg
gcctt
ttgctcacatgttctttcctgcgttatcccctgattctgtggataaccgtattaccgcctttgagtgagctgata
ccgct
cgccgcagccgaacgaccgagcgcagcgagtcagtgagcgaggaagcggaagagcgcctgatgcggtattttctc
cttac
gcatctgtgcggtatttcacaccgcatatatggtgcactctcagtacaatctgctctgatgccgcatagttaagc
cagta
tacactccgctatcgctacgtgactgggtcatggctgcgccccgacacccgccaacacccgctgacgcgccctga
cgggc
ttgtctgctcccggcatccgcttacagacaagctgtgaccgtctccgggagctgcatgtgtcagaggttttcacc
gtcat
caccgaaacgcgcgaggcagctgcggtaaagctcatcagcgtggtcgtgaagcgattcacagatgtctgcctgtt
catcc
gcgtccagctcgttgagtttctccagaagcgttaatgtctggcttctgataaagcgggccatgttaagggcggtt
ttttc
ctgtttggtcacttgatgcctccgtgtaagggggaatttctgttcatgggggtaatgataccgatgaaacgagag
aggat
gctcacgatacgggttactgatgatgaacatgcccggttactggaacgttgtgagggtaaacaactggcggtatg
gatgc
ggcgggaccagagaaaaatcactcagggtcaatgccagcgcttcgttaatacagatgtaggtgttccacagggta
gccag
cagcatcctgcgatgcagatccggaacataatggtgcagggcgctgacttccgcgtttccagactttacgaaaca
cggaa
accgaagaccattcatgttgttgctcaggtcgcagacgttttgcagcagcagtcgcttcacgttcgctcgcgtat
cggtg
attcattctgctaaccagtaaggcaacccgccagcctagccgggtcctcaacgacaggagcacgatcatgcgca
cccgt
ggccaggacccaacgctgcccgagatgcgccgcgtgcggctgctggagatggcggacgcgatggatatgttctgc
caagg
gttggtttgcgcattcacagttctccgcaagaattgattggctccaattcttggagtggtgaatccgttagcgag
gtgcc
gccggcttccattcaggtcgaggtggcccggctccatgcaccgcgacgcaacgcggggaggcagacaaggtatag
ggcgg
cgcctacaatccatgccaacccgttccatgtgctcgccgaggcggcataaatcgccgtgacgatcagcggtccag
tgatc
gaagttaggctggtaagagccgcgagcgatccttgaagctgtccctgatggtcgtcatctacctgcctggacagc
atggc
```

Figure 9 (Cont.)

```
ctgcaacgcgggcatcccgatgccgccggaagcgagaagaatcataatggggaaggccatccagcctcgcgtcgc
gaacg
ccagcaagacgtagcccagcgcgtcggccagcttgcaattcgcgctaacttacattaattgcgttgcgctcactg
cccgc
tttccagtcgggaaacctgtcgtgccagctgcattaatgaatcggccaacgcgcggggagaggcggtttgcgtat
tgggc
gccagggtggttttctttcaccagtgagacgggcaacagctgattgcccttcaccgcctggccctgagagagt
tgcag
caagcggtccacgctggtttgcccagcaggcgaaaatcctgtttgatggtggttgacggcgggatataacatga
gctgt
cttcggtatcgtcgtatcccactaccgagatatccgcaccaacgcgcagcccggactcggtaatggcgcgcattg
cgccc
agcgccatctgatcgttggcaaccagcatcgcagtgggaacgatgccctcattcagcatttgcatggtttgttga
aaacc
ggacatggcactccagtcgccttcccgttccgctatcggctgaatttgattgcgagtgagatatttatgccagcc
agcca
gacgcagacgcgccgagacagaacttaatggTcccgctaacagcgcgatttgctgAtgacccaatgcgaccagat
gctcc
acgcccagtcgcgtaccgtcttcatgggagaaaataatactgttgatgggtgtctggtcagagacatcaagaaat
aacgc
cggaacattagtgcaggcagcttccacagcaatggcatcctggtcatccagcggatagttaatgatcagcccact
gacgc
gttgcgcgagaagattgtgcaccgccgctttacaggcttcgacgccgcttcgttctaccatcgacaccaccacgc
tggca
cccagttgatcggcgcgagatttaatcgccgcgacaatttgcgacggcgcgtgcagggccagactggaggtggca
acgcc
aatcagcaacgactgtttgcccgccagttgttgtgccacgcggttgggaatgtaattcagctccgccatcgccgc
ttcca
cttttcccgcgttttcgcagaaacgtggctggcctggttcaccacgcgggaaacggtctgataagagacaccgg
catac
tctgcgacatcgtataacgttactggtttcacattcaccaccctgaattgactctcttccgggcgctatcatgcc
atacc
gcgaaaggttttgcgccattcgatggtgtcaacgtaaatgcatgccgcttcgccttcgcgcgcgaattgcaagct
gatcc
ggagcttatcgactgcacggtgcaccaatgcttctggcgtcaggcagccatcggaagctgtggtatggctgtgca
ggtcg
taaatcactgcataattcgtgtcgctcaaggcgcactcccgttctggataatgttttttgcgccgacatcataac
ggttc
tggcaaatattctgaaatgagctgttgacaattaatcatcggctcgtataatgtgtggaattgtgagcggataac
aattt
cacacaggaaacaGAATTCcatATGAAATACCTATTACCAACAGCAGCAGCTGGGTTATTATTGCTCGCTGCGCA
GCCGG
CCATGGcccaGGTcACCGTCTCCTCAGGTACCGTGGCTGCACCATCTGTCTTCATCTTCCCGCCATCTGATGAGC
AGTTG
AAATCTGGAACTGCCTCTGTTGTGTGCCTGCTGAATAACTTCTATCCCAGAGAGGCCAAAGTACAGTGGAAGGTG
GATAA
CGCCCTCCAATCGGGTAACTCCCAGGAGAGTGTCACAGAGCAGGACAGCAAGGACAGCACCTACAGCCTCAGCAG
CACCC
TGACGCTGAGCAAAGCAGACTACGAGAAACACAAAGTCTACGCCTGCGAAGTCACCCATCAGGGCCTGAGCTCGC
CGGTG
ACAAAGAGCTTCAACCGCGGAGAGTGTTAATAAacAGGAAacagaaGtccatATGAAATACCTATTGCCTACGGC
AGCCG
CTGGATTGTTATTACTCGCGGCCCagcCGGCCATGGCCGCTAGCACCAAGGGCCCATCGGTCTTCCCCCTGGCAC
CCTCC
TCCAAGAGCACCTCTGGGGGCACAGCGGCCCTGGGCTGCCTGGTCAAGGACTACTTCCCCGAACCGGTGACGGTG
TCGTG
GAACTCAGGCGCCCTGACCAGCGGCGTGCACACCTTCCCGGCTGTCCTACAGTCCTCAGGACTCTACTCCCTCAG
CAGCG
```

Figure 9 (Cont.)

```
TAGTGACCGTGCCCTCCAGCAGCTTGGGCACCCAGACCTACATCTGCAACGTGAATCACAAGCCCAGCAACACCA
AGGTG
GACAAGAAAGTTGAGCCCAAATCTTGTGACAAAACTCACACATGCCCACCGTGCCCATAAGCTTggctgttttgg
cggat
gagagaagattttcagcctgatacagattaaatcagaacgcagaagcggtctgataaaacagaatttgcctggcg
gcagt
agcgcggtggtcccacctgacccatgccgaactcagaagtgaaacgccgtagcgccgatggtagtgtgggtct
cccca
tgcgagagtagggaactgccaggcatcaaataaaacgaaaggctcagtcgaaagactgggcctttcgttttatct
gttgt
ttgtcggtgaacgctctcctgagtaggacaaatccgccgggagcggatttgaacgttgcgaagcaacggcccga
ggacc
ctggcgggcaggacgcccgccataaactgccaggcatcaaattaagcagaaggccatcctgacggatggcctttt
tgcgt
ttctacaaactctt pMabγ1* (SEQ ID NO:102)

ttgtttattttttctaaatacattcaaatatgtatccgctcatgagacaataaccctgataaatgcttcaataata
ttgaa
aaaggaagagtatgagtattcaacatttccgtgtcgcccttattccctttttgcggcattttgccttcctgttt
ttgct
cacccagaaacgctggtgaaagtaaaagatgctgaagatcagttgggtgcacgagtgggttacatcgaactggat
ctcaa
cagcggtaagatccttgagagttttcgccccgaagaacgttttccaatgatgagcacttttaaagttctgctatg
tggcg
cggtattatcccgtgttgacgccgggcaagagcaactcggtcgccgcatacactattctcagaatgacttggttg
agtac
tcaccagtcacagaaaagcatcttacggatggcatgacagtaagagaattatgcagtgctgccataaccatgagt
gataa
cactgcggccaacttacttctgacaacgatcggaggaccgaaggagctaaccgcttttttgcacaacatggggga
tcatg
taactcgccttgatcgttgggaaccggagctgaatgaagccataccaaacgacgagcgtgacaccacgatgcctg
tagca
atggcaacaacgttgcgcaaactattaactggcgaactacttactctagcttcccggcaacaattaatagactgg
atgga
ggcggataaagttgcaggaccacttctgcgctcggcccttccggctggctggtttattgctgataaatctggagc
cggtg
agcgtgggtctcgcggtatcattgcagcactggggccagatggtaagccctcccgtatcgtagttatctacacga
cgggg
agtcaggcaactatggatgaacgaaatagacagatcgctgagataggtgcctcactgattaagcattggtaactg
tcaga
ccaagtttactcatatatactttagattgatttaaaacttcattttttaatttaaaaggatctaggtgaagatcct
ttttg
ataatctcatgaccaaaatcccttaacgtgagttttcgttccactgagcgtcagaccccgtagaaaagatcaaag
gatct
cttgagatcctttttttctgcgcgtaatctgctgcttgcaaacaaaaaaaccaccgctaccagcggtggtttgt
ttgcc
ggatcaagagctaccaactctttttccgaaggtaactggcttcagcagagcgcagataccaaatactgtccttct
agtgt
agccgtagttaggccaccacttcaagaactctgtagcaccgcctacatacctcgctctgctaatcctgttaccag
tggct
gctgccagtggcgataagtcgtgtcttaccgggttggactcaagacgatagttaccggataaggcgcagcggtcg
ggctg
aacgggggttcgtgcacacagcccagcttggagcgaacgacctacaccgaactgagatacctacagcgtgagca
ttgag
```

Figure 9 (Cont.)

```
aaagcgccacgcttcccgaagggagaaaggcggacaggtatccggtaagcggcagggtcggaacaggagagcgca
cgagg
gagcttccagggggaaacgcctggtatctttatagtcctgtcgggtttcgccacctctgacttgagcgtcgattt
ttgtg
atgctcgtcagggggcggagcctatggaaaaacgccagcaacgcggccttttacggttcctggccttttgctg
gcctt
ttgctcacatgttctttcctgcgttatccctgattctgtggataaccgtattaccgcctttgagtgagctgata
ccgct
cgccgcagccgaacgaccgagcgcagcgagtcagtgagcgaggaagcggaagagcgcctgatgcggtattttctc
cttac
gcatctgtgcggtatttcacaccgcatatatggtgcactctcagtacaatctgctctgatgccgcatagttaagc
cagta
tacactccgctatcgctacgtgactgggtcatggctgcgccccgacacccgccaacacccgctgacgcgcctga
cgggc
ttgtctgctcccggcatccgcttacagacaagctgtgaccgtctccgggagctgcatgtgtcagaggttttcacc
gtcat
caccgaaacgcgcgaggcagctgcggtaaagctcatcagcgtggtcgtgaagcgattcacagatgtctgcctgtt
catcc
gcgtccagctcgttgagtttctccagaagcgttaatgtctggcttctgataaagcgggccatgttaagggcggtt
ttttc
ctgtttggtcacttgatgcctccgtgtaagggggaatttctgttcatgggggtaatgataccgatgaaacgagag
aggat
gctcacgatacgggttactgatgatgaacatgcccggttactggaacgttgtgagggtaaacaactggcggtatg
gatgc
ggcgggaccagagaaaaatcactcagggtcaatgccagcgcttcgttaatacagatgtaggtgttccacagggta
gccag
cagcatcctgcgatgcagatccggaacataatggtgcagggcgctgacttccgcgtttccagactttacgaaaca
cggaa
accgaagaccattcatgttgttgctcaggtcgcagacgttttgcagcagcagtcgcttcacgttcgctcgcgtat
cggtg
attcattctgctaaccagtaaggcaacccgccagcctagccgggtcctcaacgacaggagcacgatcatgcgca
cccgt
ggccaggacccaacgctgcccgagatgcgccgcgtgcggctgctggagatggcggacgcgatggatatgttctgc
caagg
gttggtttgcgcattcacagttctccgcaagaattgattggctccaattcttggagtggtgaatccgttagcgag
gtgcc
gccggcttccattcaggtcgaggtggccccggctccatgcaccgcgacgcaacgcggggaggcagacaaggtatag
ggcgg
cgcctacaatccatgccaacccgttccatgtgctcgccgaggcggcataaatcgccgtgacgatcagcggtccag
tgatc
gaagttaggctggtaagagccgcgagcgatccttgaagctgtccctgatggtcgtcatctacctgcctggacagc
atggc
ctgcaacgcgggcatcccgatgccgccggaagcgagaagaatcataatggggaaggccatccagcctcgcgtcgc
gaacg
ccagcaagacgtagcccagcgcgtcggccagcttgcaattcgcgctaacttacattaattgcgttgcgctcactg
cccgc
tttccagtcgggaaacctgtcgtgccagctgcattaatgaatcggccaacgcgcggggagaggcggtttgcgtat
tgggc
gccagggtggttttcttttcaccagtgagacgggcaacagctgattgcccttcaccgcctggccctgagagagt
tgcag
caagcggtccacgctggtttgccccagcaggcgaaaatcctgtttgatggtggttgacggcgggatataacatga
gctgt
cttcggtatcgtcgtatcccactaccgagatatccgcaccaacgcgcagcccggactcggtaatggcgcgcattg
cgccc
agcgccatctgatcgttggcaaccagcatcgcagtgggaacgatgccctcattcagcatttgcatggtttgttga
aaacc
ggacatggcactccagtcgccttcccgttccgctatcggctgaatttgattgcgagtgagatatttatgccagcc
agcca
```

Figure 9 (Cont.)

```
gacgcagacgcgccgagacagaacttaatggTcccgctaacagcgcgatttgctgAtgacccaatgcgaccagat
gctcc
acgccagtcgcgtaccgtcttcatgggagaaaataatactgttgatgggtgtctggtcagagacatcaagaaat
aacgc
cggaacattagtgcaggcagcttccacagcaatggcatcctggtcatccagcggatagttaatgatcagcccact
gacgc
gttgcgcgagaagattgtgcaccgccgctttacaggcttcgacgccgcttcgttctaccatcgacaccaccacgc
tggca
cccagttgatcggcgcgagatttaatcgccgcgacaatttgcgacggcgcgtgcagggccagactggaggtggca
acgcc
aatcagcaacgactgtttgcccgccagttgttgtgccacgcggttgggaatgtaattcagctccgccatcgccgc
ttcca
cttttccccgcgttttcgcagaaacgtggctggcctggttcaccacgcgggaaacggtctgataagagacaccgg
catac
tctgcgacatcgtataacgttactggtttcacattcaccaccctgaattgactctcttccgggcgctatcatgcc
atacc
gcgaaaggttttgcgccattcgatggtgtcaacgtaaatgcatgccgcttcgccttcgcgcgcgaattgcaagct
gatcc
ggagcttatcgactgcacggtgcaccaatgcttctggcgtcaggcagccatcggaagctgtggtatggctgtgca
ggtcg
taaatcactgcataattcgtgtcgctcaaggcgcactcccgttctggataatgttttttgcgccgacatcataac
ggttc
tggcaaatattctgaaatgagctgttgacaattaatcatcggctcgtataatgtgtggaattgtgagcggataac
aattt
cacacaggaaacaGAATTCcatATGAAATACCTATTACCAACAGCAGCAGCTGGGTTATTATTGCTCGCTGCGCA
GCCGG
CCATGGcccaGGTcACCGTCTCCTCAGGTACCGTGGCTGCACCATCTGTCTTCATCTTCCCGCCATCTGATGAGC
AGTTG
AAATCTGGAACTGCCTCTGTTGTGTGCCTGCTGAATAACTTCTATCCCAGAGAGGCCAAAGTACAGTGGAAGGTG
GATAA
CGCCCTCCAATCGGGTAACTCCCAGGAGAGTGTCACAGAGCAGGACAGCAAGGACAGCACCTACAGCCTCAGCAG
CACCC
TGACGCTGAGCAAAGCAGACTACGAGAAACACAAAGTCTACGCCTGCGAAGTCACCCATCAGGGCCTGAGCTCGC
CGGTG
ACAAAGAGCTTCAACCGCGGAGAGTGTTAATAAaCAGGAAacagaaGtccatATGAAATACCTATTGCCTACGGC
AGCCG
CTGGATTGTTATTACTCGCGGCCcagcCGGCCATGGCCGCTAGCACCAAGGGCCCatcggtcttcccctggcac
cctcc
tccaagagcacctctggggcacagcggccctgggctgcctggtcaaggactacttccccgaaccggtgacggtg
tcgtg
gaactcaggcgccctgaccagcggcgtgcacaccttcccggctgtcctacagtcctcaggactctactccctcag
cagcg
tggtgaccgtgcctccagcagcttgggcacccagacctacatctgcaacgtgaatcacaagcccagcaacacca
aggtg
gacaagaaagttGAGCCCAAATCTTGTGACAAAACTCACACATGCCCACCGTGCCCAgcacctgaactcctgggg
ggacc
gtcagtcttcctcttccccccaaaacccaaggacaccctcatgatctcccggacccctgaggtcacatgcgtggt
ggtgg
acgtgagccacgaagaccctgaggtcaagttcaactggtacgtggacggcgtggaggtgcataatgccaagacaa
agccg
cgggaggagcagtacaacagcacgtaccgggtggtcagcgtcctcaccgtcctgcaccaggactggctgaatggc
aagga
gtacaagtgcaaggtctccaacaaagccctcccagcccccatcgagaaaaccatctccaaagccaaaGGGCAGCC
CCGAG
AACCACAGGTGTACACCCTGCCCCCATCCCGGGATGAGCTGACCAAGAACCAGGTCAGCCTGACCTGCCTGGTCA
AAGGC
TTCTATCCCAGCGACATCGCCGTGGAGTGGGAGAGCAATGGGCAGCCGGAGAACAACTACAAGACCACGCCTCCC
GTGCT
```

Figure 9 (Cont.)

```
GGACTCCGACGGCTCCTTCTTCCTCTACAGCAAGCTCACCGTGGACAAGAGCAGGTGGCAGCAGGGGAACGTCTT
CTCAT
GCTCCGTGATGCATGAGGCTCTGCACAACCACTACACGCAGAAGAGCCTCTCCCTGTCTCCGGGTAAATAAGCTT
ggctg
ttttggcggatgagagaagattttcagcctgatacagattaaatcagaacgcagaagcggtctgataaaacagaa
tttgc
ctggcggcagtagcgcggtggtcccacctgacoccatgccgaactcagaagtgaaacgccgtagcgccgatggta
gtgtg
gggtctccccatgcgagagtagggaactgccaggcatcaaataaaacgaaaggctcagtcgaaagactgggcctt
tcgtt
ttatctgttgtttgtcggtgaacgctctcctgagtaggacaaatccgccgggagcggatttgaacgttgcgaagc
aacgg
cccggaggaccctggcgggcaggacgcccgccataaactgccaggcatcaaattaagcagaaggccatcctgacg
gatgg
ccttttttgcgtttctacaaactctt
```

FIGURE 11 p55PhoA6HisGS/N⁻

SEQ ID N° 89
```
   1 ttgtttattt ttctaaatac attcaaatat gtatccgctc atgagacaat aaccctgata
  61 aatgcttcaa taatattgaa aaggaagag tatgagtatt caacatttcc gtgtcgccct
 121 tattcccttt tttgcggcat tttgccttcc tgtttttgct cacccagaaa cgctggtgaa
 181 agtaaaagat gctgaagatc agttgggtgc acgagtgggt tacatcgaac tggatctcaa
 241 cagcggtaag atccttgaga gttttcgccc cgaagaacgt tttccaatga tgagcacttt
 301 taaagttctg ctatgtggcg cggtattatc ccgtgttgac gccgggcaag agcaactcgg
 361 tcgccgcata cactattctc agaatgactt ggttgagtac tcaccagtca cagaaaagca
 421 tcttacggat ggcatgacag taagagaatt atgcagtgct gccataacca tgagtgataa
 481 cactgcggcc aacttacttc tgacaacgat cggaggaccg aaggagctaa ccgctttttt
 541 gcacaacatg ggggatcatg taactcgcct tgatcgttgg gaaccggagc tgaatgaagc
 601 cataccaaac gacgagcgtg acaccacgat gcctgtagca atggcaacaa cgttgcgcaa
 661 actattaact ggcgaactac ttactctagc ttcccggcaa caattaatag actggatgga
 721 ggcggataaa gttgcaggac cacttctgcg ctcggccctt ccggctggct ggtttattgc
 781 tgataaatct ggagccggtg agcgtgggtc tcgcggtatc attgcagcac tggggccaga
 841 tggtaagccc tcccgtatcg tagttatcta cacgacgggg agtcaggcaa ctatggatga
 901 acgaaataga cagatcgctg agataggtgc ctcactgatt aagcattggt aactgtcaga
 961 ccaagtttac tcatatatac tttagattga tttaaaactt cattttaat ttaaaaggat
1021 ctaggtgaag atccttttg ataatctcat gaccaaaatc ccttaacgtg agttttcgtt
1081 ccactgagcg tcagaccccg tagaaaagat caaaggatct tcttgagatc ctttttttct
1141 gcgcgtaatc tgctgcttgc aaacaaaaaa accaccgcta ccagcggtgg tttgtttgcc
1201 ggatcaagag ctaccaactc tttttccgaa ggtaactggc ttcagcagag cgcagatacc
1261 aaatactgtc cttctagtgt agccgtagtt aggccaccac ttcaagaact ctgtagcacc
1321 gcctacatac ctcgctctgc taatcctgtt accagtggct gctgccagtg gcgataagtc
1381 gtgtcttacc gggttggact caagacgata gttaccggat aaggcgcagc ggtcgggctg
1441 aacgggggggt tcgtgcacac agcccagctt ggagcgaacg acctacaccg aactgagata
1501 cctacagcgt gagcattgag aaagcgccac gcttcccgaa gggagaaagg cggacaggta
1561 tccggtaagc ggcagggtcg gaacaggaga gcgcacgagg gagcttccag gggaaacgc
1621 ctggtatctt tatagtcctg tcgggtttcg ccacctctga cttgagcgtc gatttttgtg
1681 atgctcgtca gggggggcgga gcctatggaa aaacgccagc aacgcggcct ttttacggtt
1741 cctggccttt tgctggcctt ttgctcacat gttctttcct gcgttatccc ctgattctgt
1801 ggataaccgt attaccgcct ttgagtgagc tgataccgct cgccgcagcc gaacgaccga
1861 gcgcagcgag tcagtgagcg aggaagcgga agagcgcctg atgcggtatt ttctccttac
1921 gcatctgtgc ggtatttcac accgcatata tggtgcactc tcagtacaat ctgctctgat
1981 gccgcatagt taagccagta tacactccgc tatcgctacg tgactgggtc atggctgcgc
2041 cccgacaccc gccaacaccc gctgacgcgc cctgacgggc ttgtctgctc ccggcatccg
2101 cttacagaca agctgtgacc gtctccggga gctgcatgtg tcagaggttt tcaccgtcat
2161 caccgaaacg cgcgaggcag ctgcggtaaa gctcatcagc gtggtcgtga gcgattcac
2221 agatgtctgc ctgttcatcc gcgtccagct cgttgagttt ctccagaagc gttaatgtct
2281 ggcttctgat aaagcgggcc atgttaaggg cggttttttc ctgtttggtc acttgatgcc
2341 tccgtgtaag ggggaatttc tgttcatggg ggtaatgata ccgatgaaac gagagaggat
2401 gctcacgata cgggttactg atgatgaaca tgcccggtta ctggaacgtt gtgagggtaa
2461 acaactggcg gtatggatgc ggcgggacca gagaaaaatc actcagggtc aatgccagcg
2521 cttcgttaat acagatgtag gtgttccaca gggtagccag cagcatcctg cgatgcagat
2581 ccggaacata atggtgcagg cgctgactt ccgcgtttcc agactttacg aaacacggaa
2641 accgaagacc attcatgttg ttgctcaggt cgcagacgtt ttgcagcagc agtcgcttca
2701 cgttcgctcg cgtatcggtg attcattctg ctaaccagta aggcaacccc gccagcctag
2761 ccgggtcctc aacgacagga gcacgatcat gcgcacccgt ggccaggacc caacgctgcc
2821 cgagatgcgc cgcgtgcggc tgctggagat ggcggacgcg atggatatgt tctgccaagg
2881 gttggtttgc gcattcacag ttctccgcaa gaattgattg ctccaattc ttggagtggt
2941 gaatccgtta gcgaggtgcc gccggcttcc attcaggtcg aggtggcccg gctccatgca
3001 ccgcgacgca acgcggggag gcagacaagg tatagggcgg cgcctacaat ccatgccaac
```

Figure 11 (Contd.)

```
3061 ccgttccatg tgctcgccga ggcggcataa atcgccgtga cgatcagcgg tccagtgatc
3121 gaagttaggc tggtaagagc cgcgagcgat ccttgaagct gtccctgatg gtcgtcatct
3181 acctgcctgg acagcatggc ctgcaacgcg ggcatcccga tgccgccgga agcgagaaga
3241 atcataatgg ggaaggccat ccagcctcgc gtcgcgaacg ccagcaagac gtagcccagc
3301 gcgtcggcca gcttgcaatt cgcgctaact tacattaatt gcgttgcgct cactgcccgc
3361 tttccagtcg ggaaacctgt cgtgccagct gcattaatga atcggccaac gcgcggggag
3421 aggcggtttg cgtattgggc gccagggtgg tttttctttt caccagtgag acgggcaaca
3481 gctgattgcc cttcaccgcc tggccctgag agagttgcag caagcggtcc acgctggttt
3541 gccccagcag gcgaaaatcc tgtttgatgg tggttgacgg cgggatataa catgagctgt
3601 cttcggtatc gtcgtatccc actaccgaga tatccgcacc aacgcgcagc ccggactcgg
3661 taatggcgcg cattgcgccc agcgccatct gatcgttggc aaccagcatc gcagtgggaa
3721 cgatgccctc attcagcatt tgcatggttt gttgaaaacc ggacatggca ctccagtcgc
3781 cttcccgttc cgctatcggc tgaatttgat tgcgagtgag atatttatgc cagccagcca
3841 gacgcagacg cgccgagaca gaacttaatg ggcccgctaa cagcgcgatt tgctggtgac
3901 ccaatgcgac cagatgctcc acgcccagtc gcgtaccgtc ttcatgggag aaaataatac
3961 tgttgatggg tgtctggtca gagacatcaa gaaataacgc cggaacatta gtgcaggcag
4021 cttccacagc aatggcatcc tggtcatcca gcggatagtt aatgatcagc ccactgacgc
4081 gttgcgcgag aagattgtgc accgccgctt tacaggcttc gacgccgctt cgttctacca
4141 tcgacaccac cacgctggca cccagttgat cggcgcgaga tttaatcgcc gcgacaattt
4201 gcgacggcgc gtgcagggcc agactggagg tgcaacgcc aatcagcaac gactgtttgc
4261 ccgccagttg ttgtgccacg cggttgggaa tgtaattcag ctccgccatc gccgcttcca
4321 cttttttccg cgttttcgca gaaacgtggc tggcctggtt caccacgcgg gaaacggtct
4381 gataagagac accggcatac tctgcgacat cgtataacgt tactgtttc acattcacca
4441 ccctgaattg actctcttcc gggcgctatc atgccatacc gcgaaaggtt ttgcgccatt
4501 cgatggtgtc aacgtaaatg catgccgctt cgccttcgcg cgcgaattgc aagctgatcc
4561 ggagcttatc gactgcacgg tgcaccaatg cttctggcgt caggcagcca tcggaagctg
4621 tggtatggct gtgcaggtcg taaatcactg cataattcgt gtcgctcaag gcgcactccc
4681 gttctggata atgttttttg cgccgacatc ataacggttc tggcaaatat tctgaaatga
4741 gctgttgaca attaatcatc ggctcgtata atgtgtggaa ttgtgagcgg ataacaattt
4801 cacacaggaa acagaattcc atatgaaata cctattacca acagcagcag ctgggttatt
4861 attgctcgct gcgcagccgg ccatggcggc cgatcctcga gagctcccgg gctgcagccc
4921 tgttctggaa aaccgggctg ctcagggcga tattactgca cccggcggtg ctcgccgttt
4981 aacgggtgat cagactgccg ctctgcgtga ttctcttagc gataaacctg caaaaaatat
5041 tattttgctg attggcgatg ggatgggga ctcgaaaatt actgccgcac gtaattatgc
5101 cgaaggtgcg ggcggctttt ttaaaggtat agatgcctta ccgcttaccg ggcaatacac
5161 tcactatgcg ctgaataaaa aaaccggcaa accggactac gtcaccgact cggctgcatc
5221 agcaaccgcc tggtcaaccg gtgtcaaaac ctataacggc gcgctgggcg tcgatattca
5281 cgaaaaagat cacccaacga ttctggaaat ggcaaagcc gcaggtctgg cgaccggtaa
5341 cgtttctacc gcagagttgc aggatgccac gcccgctgcg ctggtggcac atgtgacctc
5401 gcgcaaatgc tacggtccga gcgcgaccag tgaaaaatgt ccgggtaacg ctctggaaaa
5461 aggcggaaaa ggatcgatta ccgaacagct gcttaacgct cgtgccgacg ttacgcttgg
5521 cggcggcgca aaaaccttg ctgaaacggc aaccgctggt gaatggcagg gaaaaacgct
5581 gcgtgaacag gcacaggcgc gtggttatca gttggtgagc gatgctgcct cactgaattc
5641 ggtgacggga gcgaatcagc aaaaacccct gcttggcctg tttgctgacg gcaatatgcc
5701 agtgcgctgg ctaggaccga aagcaacgta ccacggcaat atcgataagc ccgcagtcac
5761 ctgtacgcca aatccgcaac gtaatgacag tgtaccaacc ctggcgcaga tgaccgacaa
5821 agccattgaa ttgttgagta aaaatgagaa aggcttttc ctgcaagttg aaggtgcgtc
5881 aatcgataaa caggatcatg ctgcgaatcc ttgtgggcaa attggcgaga cggtcgatct
5941 cgatgaagcc gtacaacggg cgctggaatt cgctaaaaag gagggtaaca cgctggtcat
6001 agtcaccgct gatcacgccc acgccagcca gattgttgcg ccggatacca agctccggg
6061 cctcacccag gcgctaaata ccaaagatgg cgcagtgatg gtgatgagtt acgggaactc
6121 cgaagaggat tcacaagaac ataccggcag tcagttgcgt attgcggcgt atggcccgca
6181 tgccgccaat gttgttggac tgaccgacca gaccgatctc ttctacacca tgaaagccgc
6241 tctggggctg aaacatcatc atcaccatca cgggagctaa taagcttctg ttttggcgga
6301 tgagagaaga ttttcagcct gatacagatt aaatcagaac gcagaagcgg tctgataaaa
6361 cagaatttgc ctgcggcaa tagcgcggtg gtcccacctg accccatgcc gaactcagaa
6421 gtgaaacgcc gtagcgccga tggtagtgtg gggtctcccc atgcgagagt agggaactgc
6481 caggcatcaa ataaaacgaa aggctcagtc gaaagactgg gcctttcgtt ttatctgttg
```

Figure 11 (Contd.)

```
6541 tttgtcggtg aacgctctcc tgagtaggac aaatccgccg ggagcggatt tgaacgttgc
6601 gaagcaacgg cccggaggac cctggcgggc aggacgcccg ccataaactg ccaggcatca
6661 aattaagcag aaggccatcc tgacggatgg ccttttttgcg tttctacaaa ctctt
``` p55PhoA6HisGS/NAB⁻

SEQ ID N° 90
```
   1 ttgtttattt ttctaaatac attcaaatat gtatccgctc atgagacaat aaccctgata
  61 aatgcttcaa taatattgaa aaggaagag tatgagtatt caacatttcc gtgtcgccct
 121 tattcccttt tttgcggcat tttgccttcc tgttttttgct cacccagaaa cgctggtgaa
 181 agtaaaagat gctgaagatc agttgggtgc acgagtgggt tacatcgaac tggatctcaa
 241 cagcggtaag atccttgaga gttttcgccc cgaagaacgt tttccaatga tgagcacttt
 301 taaagttctg ctatgtggcg cggtattatc ccgtgttgac gccgggcaag agcaactcgg
 361 tcgccgcata cactattctc agaatgactt ggttgagtac tcaccagtca cagaaaagca
 421 tcttacggat ggcatgacag taagagaatt atgcagtgct gccataacca tgagtgataa
 481 cactgcggcc aacttacttc tgacaacgat cggaggaccg aaggagctaa ccgcttttt
 541 gcacaacatg gggatcatg taactcgcct tgatcgttgg gaaccggagc tgaatgaagc
 601 cataccaaac gacgagcgtg acaccacgat gcctgtagca atggcaacaa cgttgcgcaa
 661 actattaact ggcgaactac ttactctagc ttcccggcaa caattaatag actggatgga
 721 ggcggataaa gttgcaggac cacttctgcg ctcggccctt ccggctggct ggtttattgc
 781 tgataaatct ggagccggtg agcgtgggtc tcgcggtatc attgcagcac tggggccaga
 841 tggtaagccc tcccgtatcg tagttatcta cacgacgggg agtcaggcaa ctatggatga
 901 acgaaataga cagatcgctg agataggtgc ctcactgatt aagcattggt aactgtcaga
 961 ccaagtttac tcatatatac tttagattga tttaaaactt cattttttaat ttaaaaggat
1021 ctaggtgaag atcctttttg ataatctcat gaccaaaatc ccttaacgtg agttttcgtt
1081 ccactgagcg tcagacccg tagaaaagat caaaggatct tcttgagatc cttttttct
1141 gcgcgtaatc tgctgcttgc aaacaaaaaa accaccgcta ccagcggtgg tttgtttgcc
1201 ggatcaagag ctaccaactc tttttccgaa ggtaactggc ttcagcagag cgcagatacc
1261 aaatactgtc cttctagtgt agccgtagtt aggccaccac ttcaagaact ctgtagcacc
1321 gcctacatac ctcgctctgc taatcctgtt accagtggct gctgccagtg gcgataagtc
1381 gtgtcttacc gggttggact caagacgata gttaccggat aaggcgcagc ggtcgggctg
1441 aacggggggt tcgtgcacac agcccagctt ggagcgaacg acctacaccg aactgagata
1501 cctacagcgt gagcattgag aaagcgccac gcttcccgaa gggagaaagg cggacaggta
1561 tccggtaagc ggcagggtcg gaacaggaga gcgcacgagg gagcttccag ggggaaacgc
1621 ctggtatctt tatagtcctg tcgggtttcg ccacctctga cttgagcgtc gatttttgtg
1681 atgctcgtca ggggggcgga gcctatggaa aaacgccagc aacgcggcct ttttacggtt
1741 cctggccttt tgctggcctt ttgctcacat gttctttcct gcgttatccc ctgattctgt
1801 ggataaccgt attaccgcct ttgagtgagc tgataccgct cgccgcagcc gaacgaccga
1861 gcgcagcgag tcagtgagcg aggaagcgga agagcgcctg atgcggtatt ttctccttac
1921 gcatctgtgc ggtatttcac accgcatata tggtgcactc tcagtacaat ctgctctgat
1981 gccgcatagt taagccagta taactccgc tatcgctacg tgactgggtc atggctgcgc
2041 cccgacaccc gccaacaccc gctgacgcgc cctgacgggc ttgtctgctc ccggcatccg
2101 cttacagaca agctgtgacc gtctccggga gctgcatgtg tcagaggttt tcaccgtcat
2161 caccgaaacg cgcgaggcag ctgcggtaaa gctcatcagc gtggtcgtga agcgattcac
2221 agatgtctgc ctgttcatcc gcgtccagct cgttgagttt ctccagaagc gttaatgtct
2281 ggcttctgat aaagcgggcc atgttaaggg cggttttttc ctgtttggtc acttgatgcc
2341 tccgtgtaag ggggaatttc tgttcatggg ggtaatgata ccgatgaaac gagagaggat
2401 gctcacgata cgggttactg atgatgaaca tgcccggtta ctggaacgtt gtgagggtaa
2461 acaactggcg gtatggatgc ggcgggacca gagaaaaatc actcagggtc aatgccagcg
2521 cttcgttaat acagatgtag gtgttccaca gggtagccag cagcatcctg cgatgcagat
2581 ccggaacata atggtgcagg gcgctgactt ccgcgtttcc agactttacg aaacacggaa
2641 accgaagacc attcatgttg ttgctcaggt cgcagacgtt tgcagcagc agtcgcttca
2701 cgttcgctcg cgtatcggtg attcattctg ctaaccagta aggcaacccc gccagcctag
2761 ccgggtcctc aacgacagga gcacgatcat gcgcacccgt ggccaggacc aacgctgcc
2821 cgagatgcgc cgcgtgcggc tgctggagat ggcggacgcg atggatatgt tctgccaagg
2881 gttggtttgc gcattcacag ttctccgcaa gaattgattg gctccaattc ttggagtggt
2941 gaatccgtta gcgaggtgcc gccggcttcc attcaggtcg aggtggcccg gctccatgca
3001 ccgcgacgca acgcggggag gcagacaagg tatagggcgg cgcctacaat ccatgccaac
```

Figure 11 (Contd.)

```
3061 ccgttccatg tgctcgccga ggcggcataa atcgccgtga cgatcagcgg tccagtgatc
3121 gaagttaggc tggtaagagc cgcgagcgat ccttgaagct gtccctgatg gtcgtcatct
3181 acctgcctgg acagcatggc ctgcaacgcg ggcatcccga tgccgccgga agcgagaaga
3241 atcataatgg ggaaggccat ccagcctcgc gtcgcgaacg ccagcaagac gtagcccagc
3301 gcgtcggcca gcttgcaatt cgcgctaact tacattaatt gcgttgcgct cactgcccgc
3361 tttccagtcg ggaaacctgt cgtgccagct gcattaatga atcggccaac gcgcggggag
3421 aggcggtttg cgtattgggc gccagggtgg ttttctttt caccagtgag acgggcaaca
3481 gctgattgcc cttcaccgcc tggccctgag agagttgcag caagcggtcc acgctggttt
3541 gccccagcag gcgaaaatcc tgtttgatgg tggttgacgg cgggatataa catgagctgt
3601 cttcggtatc gtcgtatccc actaccgaga tatccgcacc aacgcgcagc ccggactcgg
3661 taatggcgcg cattgcgccc agcgccatct gatcgttggc aaccagcatc gcagtgggaa
3721 cgatgccctc attcagcatt tgcatggttt gttgaaaacc ggacatggca ctccagtcgc
3781 cttccgttc cgctatcggc tgaatttgat tgcgagtgag atatttatgc cagccagcca
3841 gacgcagacg cgccgagaca gaacttaatg gtcccgctaa cagcgcgatt tgctgatgac
3901 ccaatgcgac cagatgctcc acgcccagtc gcgtaccgtc ttcatgggag aaaataatac
3961 tgttgatggg tgtctggtca gagacatcaa gaaataacgc cggaacatta gtgcaggcag
4021 cttccacagc aatggcatcc tggtcatcca gcggatagtt aatgatcagc ccactgacgc
4081 gttgcgcgag aagattgtgc accgccgctt tacaggcttc gacgccgctt cgttctacca
4141 tcgacaccac cacgctggca cccagttgat cggcgcgaga tttaatcgcc gcgacaattt
4201 gcgacggcgc gtgcagggcc agactggagg tggcaacgcc aatcagcaac gactgtttgc
4261 ccgccagttg ttgtgccacg cggttgggaa tgtaattcag ctccgccatc gccgcttcca
4321 cttttccg cgttttcgca gaaacgtggc tggcctggtt caccacgcgg gaaacggtct
4381 gataagagac accggcatac tctgcgacat cgtataacgt tactgtttc acattcacca
4441 ccctgaattg actctcttcc gggcgctatc atgccatacc gcgaaaggtt ttgcgccatt
4501 cgatggtgtc aacgtaaatg catgccgctt cgccttcgcg cgcgaattgc aagctgatcc
4561 ggagcttatc gactgcacgg tgcaccaatg cttctggcgt caggcagcca tcggaagctg
4621 tggtatggct gtgcaggtcg taaatcactg cataattcgt gtcgctcaag gcgcactccc
4681 gttctggata atgtttttg cgccgacatc ataacggttc tggcaaatat tctgaaatga
4741 gctgttgaca attaatcatc ggctcgtata atgtgtggaa ttgtgagcgg ataacaattt
4801 cacacaggaa acagaattcc atatgaaata cctattacca acagcagcag ctgggttatt
4861 attgctcgct gcgcagccgg ccatggcggc cgatcctcga gagctccgg gctgcagcc
4921 tgttctggaa aaccgggctg ctcagggcga tattactgca cccggcggtg ctcgccgttt
4981 aacgggtgat cagactgccg ctctgcgtga ttctcttagc gataaacctg caaaaaatat
5041 tattttgctg attggcgatg ggatggggga ctcggaaatt actgccgcac gtaattatgc
5101 cgaaggtgcg ggcggctttt ttaaaggtat agatgcctta ccgcttaccg ggcaatacac
5161 tcactatgcg ctgaataaaa aaaccggcaa accggactac gtcaccgact cggctgcatc
5221 agcaaccgcc tggtcaaccg tgtcaaaac ctataacggc gcgctgggcg tcgatattca
5281 cgaaaaagat cacccaacga ttctggaaat ggcaaaagcc gcaggtctgg cgaccggtaa
5341 cgttctacc gcagagttgc aggatgccac gcccgctgcg ctggtggcac atgtgacctc
5401 gcgcaaatgc tacggtccga gcgcgaccag tgaaaatgt ccgggtaacg ctctggaaaa
5461 aggcggaaaa ggatcgatta ccgaacagct gcttaacgct cgtgccgacg ttacgcttgg
5521 cggcggcgca aaaacctttg ctgaaacggc aaccgctggt gaatggcagg gaaaaacgct
5581 gcgtgaacag gcacaggcgc gtggttatca gttggtgagc gatgctgcct cactgaattc
5641 ggtgacggaa gcgaatcagc aaaaaccct gcttggcctg tttgctgacg gcaatatgcc
5701 agtgcgctgg ctaggaccga agcaacgta ccacggcaat atcgataagc ccgcagtcac
5761 ctgtacgcca aatccgcaac gtaatgacag tgtaccaacc ctggcgcaga tgaccgacaa
5821 agccattgaa ttgttgagta aaatgagaa ggcttttc ctgcaagttg aaggtgcgtc
5881 aatcgataaa caggatcatg ctgcgaatcc ttgtgggcaa attggcgaga cggtcgatct
5941 cgatgaagcc gtacaacggg cgctggaatt cgctaaaaag gagggtaaca cgctggtcat
6001 agtcaccgct gatcacgccc acgccagcca gattgttgcg ccggatacca agctccggg
6061 cctcacccag gcgctaaata ccaaagatgg cgcagtgatg gtgatgagtt acgggaactc
6121 cgaagaggat tcacaagaac ataccggcag tcagttgcgt attgcggcgt atggccgca
6181 tgccgccaat gttgttggac tgaccgacca gaccgatctc ttctacacca tgaaagccgc
6241 tctggggctg aaacatcatc atcaccatca cgggagctaa taagcttctg ttttggcgga
6301 tgagagaaga ttttcagcct gatacagatt aaatcagaac gcagaagcgg tctgataaaa
6361 cagaatttgc ctggcggcag tagcgcggtg gtcccacctg accccatgcc gaactcagaa
6421 gtgaaacgcc gtagcgccga tggtagtgtg gggtctcccc atgcgagagt agggaactgc
6481 caggcatcaa ataaaacgaa aggctcagtc gaaagactgg cctttcgtt ttatctgttg
```

Figure 11 (Contd.)

```
6541 tttgtcggtg aacgctctcc tgagtaggac aaatccgccg ggagcggatt tgaacgttgc
6601 gaagcaacgg cccggaggac cctggcgggc aggacgcccg ccataaactg ccaggcatca
6661 aattaagcag aaggccatcc tgacggatgg ccttttttgcg tttctacaaa ctctt
``` p55/PhoA6HisGS-/NAB-

SEQ ID N° 91
```
   1 ttgtttattt ttctaaatac attcaaatat gtatccgctc atgagacaat aaccctgata
  61 aatgcttcaa taatattgaa aaggaagag tatgagtatt caacatttcc gtgtcgccct
 121 tattcccttt tttgcggcat tttgccttcc tgtttttgct cacccagaaa cgctgtgaa
 181 agtaaaagat gctgaagatc agttgggtgc acgagtgggt tacatcgaac tggatctcaa
 241 cagcggtaag atccttgaga gttttcgccc cgaagaacgt tttccaatga tgagcacttt
 301 taaagttctg ctatgtggcg cggtattatc ccgtgttgac gccgggcaag agcaactcgg
 361 tcgccgcata cactattctc agaatgactt ggttgagtac tcaccagtca cagaaaagca
 421 tcttacggat ggcatgacag taagagaatt atgcagtgct gccataacca tgagtgataa
 481 cactgcggcc aacttacttc tgacaacgat cggaggaccg aaggagctaa ccgcttttt
 541 gcacaacatg gggatcatg taactcgcct tgatcgttgg gaaccggagc tgaatgaagc
 601 cataccaaac gacgagcgtg acaccacgat gcctgtagca atggcaacaa cgttgcgcaa
 661 actattaact ggcgaactac ttactctagc ttcccggcaa caattaatag actggatgga
 721 ggcggataaa gttgcaggac cacttctgcg ctcggccctt ccggctggct ggtttattgc
 781 tgataaatct ggagccggtg agcgtgggtc tcgcggtatc attgcagcac tggggccaga
 841 tggtaagccc tcccgtatcg tagttatcta cacgacgggg agtcaggcaa ctatggatga
 901 acgaaataga cagatcgctg agataggtgc ctcactgatt aagcattggt aactgtcaga
 961 ccaagtttac tcatatatac tttagattga tttaaaactt cattttaat ttaaaaggat
1021 ctaggtgaag atccttttg ataatctcat gaccaaaatc ccttaacgtg agttttcgtt
1081 ccactgagcg tcagacccg tagaaaagat caaaggatct tcttgagatc ctttttttct
1141 gcgcgtaatc tgctgcttgc aaacaaaaaa accaccgcta ccagcggtgg tttgtttgcc
1201 ggatcaagag ctaccaactc tttttccgaa ggtaactggc ttcagcagag cgcagatacc
1261 aaatactgcc cttctagtgt agccgtagtt aggccaccac ttcaagaact ctgtagcacc
1321 gcctacatac ctcgctctgc taatcctgtt accagtggct gctgccagtg gcgataagtc
1381 gtgtcttacc gggttggact caagacgata gttaccggat aaggcgcagc ggtcgggctg
1441 aacggggggt tcgtgcacac agcccagctt ggagcgaacg acctacaccg aactgagata
1501 cctacagcgt gagcattgag aaagcgccac gcttcccgaa gggagaaagg cggacaggta
1561 tccggtaagc ggcagggtcg gaacaggaga gcgcacgagg gagcttccag ggggaaacgc
1621 ctggtatctt tatagtcctg tcgggtttcg ccacctctga cttgagcgtc gatttttgtg
1681 atgctcgtca gggggggcgga gcctatggaa aaacgccagc aacgcggcct ttttacggtt
1741 cctggccttt tgctggcctt ttgctcacat gttctttcct gcgttatccc ctgattctgt
1801 ggataaccgt attaccgcct ttgagtgagc tgataccgct cgccgcagcc gaacgaccga
1861 gcgcagcgag tcagtgagcg aggaagcgga agagcgcctg atgcggtatt ttctccttac
1921 gcatctgtgc ggtatttcac accgcatata tggtgcactc tcagtacaat ctgctctgat
1981 gccgcatagt taagccagta tacactccgc tatcgctacg tgactgggtc atggctgcgc
2041 cccgacaccc gccaacaccc gctgacgcgc cctgacgggc ttgtctgctc ccggcatccg
2101 cttacagaca agctgtgacc gtctccggga gctgcatgtg tcagaggttt tcaccgtcat
2161 caccgaaacg cgcgaggcag ctgcggtaaa gctcatcagc gtggtcgtga agcgattcac
2221 agatgtctgc ctgttcatcc gcgtccagct cgttgagttt ctccagaagc gttaatgtct
2281 ggcttctgat aaagcgggcc atgttaaggg cggttttttc ctgtttggtc acttgatgcc
2341 tccgtgtaag ggggaatttc tgttcatggg ggtaatgata ccgatgaaac gagagaggat
2401 gctcacgata cgggttactg atgatgaaca tgcccggtta ctggaacgtt gtgagggtaa
2461 acaactggcg gtatggatgc ggcgggacca gagaaaaatc actcagggtc aatgccagcg
2521 cttcgttaat acagatgtag gtgttccaca gggtagccag cagcatcctg cgatgcagat
2581 ccggaacata atggtgcagg cgctgactt ccgcgtttcc agactttacg aaacacggaa
2641 accgaagacc attcatgttg ttgctcaggt cgcagacgtt ttgcagcagc agtcgcttca
2701 cgttcgctcg cgtatcggtg attcattctg ctaaccagta aggcaacccc gccagcctag
2761 ccgggtcctc aacgacagga gcacgatcat gcgcacccgt ggccaggacc caacgctgcc
2821 cgagatgcgc cgcgtgcggc tgctggagat ggcggacgcg atggatatgt tctgccaagg
2881 gttggtttgc gcattcacag ttctccgcaa gaattgattg gctccaattc ttggagtggt
2941 gaatccgtta gcgaggtgcc gccggcttcc attcaggtcg aggtggcccg gctccatgca
3001 ccgcgacgca acgcggggag gcagacaagg tataggcgg cgcctacaat ccatgccaac
```

Figure 11 (Contd.)

```
3061 ccgttccatg tgctcgccga ggcggcataa atcgccgtga cgatcagcgg tccagtgatc
3121 gaagttaggc tggtaagagc cgcgagcgat ccttgaagct gtccctgatg gtcgtcatct
3181 acctgcctgg acagcatggc ctgcaacgcg ggcatcccga tgccgccgga agcgagaaga
3241 atcataatgg ggaaggccat ccagcctcgc gtcgcgaacg ccagcaagac gtagcccagc
3301 gcgtcggcca gcttgcaatt cgcgctaact tacattaatt gcgttgcgct cactgcccgc
3361 tttccagtcg ggaaacctgt cgtgccagct gcattaatga atcggccaac gcgcggggag
3421 aggcggtttg cgtattgggc gccagggtgg ttttttcttt caccagtgag acgggcaaca
3481 gctgattgcc cttcaccgcc tggccctgag agagttgcag caagcggtcc acgctggttt
3541 gccccagcag gcgaaaatcc tgtttgatgg tggttgacgg cgggatataa catgagctgt
3601 cttcggtatc gtcgtatccc actaccgaga tatccgcacc aacgcgcagc ccggactcgg
3661 taatggcgcg cattgcgccc agcgccatct gatcgttggc aaccagcatc gcagtgggaa
3721 cgatgccctc attcagcatt tgcatggttt gttgaaaacc ggacatggca ctccagtcgc
3781 cttccgttc cgctatcggc tgaatttgat tgcgagtgag atatttatgc cagccagcca
3841 gacgcagacg cgccgagaca gaacttaatg gtcccgctaa cagcgcgatt tgctgatgac
3901 ccaatgcgac cagatgctcc acgcccagtc gcgtaccgtc ttcatgggag aaaataatac
3961 tgttgatggg tgtctggtca gagacatcaa gaaataacgc cggaacatta gtgcaggcag
4021 cttccacagc aatggcatcc tggtcatcca gcggatagtt aatgatcagc ccactgacgc
4081 gttgcgcgag aagattgtgc accgccgctt tacaggcttc gacgccgctt cgttctacca
4141 tcgacaccac cacgctggca cccagttgat cggcgcgaga tttaatcgcc gcgacaattt
4201 gcgacggcgc gtgcagggcc agactggagg tggcaacgcc aatcagcaac gactgtttgc
4261 ccgccagttg ttgtgccacg cggttgggaa tgtaattcag ctccgccatc gccgcttcca
4321 ctttttcccg cgttttcgca gaaacgtggc tggcctggtt caccacgcgg gaaacggtct
4381 gataagagac accggacatac tctgcgacat cgtataacgt tactggtttc acattcacca
4441 ccctgaattg actctcttcc gggcgctatc atgccatacc gcgaaaggtt ttgcgccatt
4501 cgatggtgtc aacgtaaatg catgccgctt cgccttcgcg cgcgaattgc aagctgatcc
4561 ggagcttatc gactgcacgg tgcaccaatg cttctggcgt caggcagcca tcggaagctg
4621 tggtatggct gtgcaggtcg taaatcactg cataattcgt gtcgctcaag gcgcactccc
4681 gttctggata atgttttttg cgccgacatc ataacggttc tggcaaatat tctgaaatga
4741 gctgttgaca attaatcatc ggctcgtata atgtgtggaa ttgtgagcgg ataacaattt
4801 cacacaggaa acagaattcc atatgaaata cctattacca acagcagcag ctgggttatt
4861 attgctcgct gcgcagccgg ccatggcggc cggccgatcc tcgagagctc ccgggctgca
4921 gccctgttct ggaaaaccgg gctgctcagg gcgatattac tgcacccggc ggtgctcgcc
4981 gtttaacggg tgatcagact gccgctctgc gtgattctct tagcgataaa cctgcaaaaa
5041 atattatttt gctgattggc gatgggatgg gggactcgga aattactgcc gcacgtaatt
5101 atgccgaagg tgcgggcggc ttttttaaag gtatagatgc cttaccgctt accgggcaat
5161 acactcacta tgcgctgaat aaaaaaaccg gcaaaccgga ctacgtcacc gactcggctg
5221 catcagcaac cgcctggtca accggtgtca aaacctataa cggcgcgctg ggcgtcgata
5281 ttcacgaaaa agatcaccca acgattctgg aaatggcaaa agccgcaggt ctggcgaccg
5341 gtaacgtttc taccgcagag ttgcaggatg ccacgcccgc tgcgctggtg gcacatgtga
5401 cctcgcgcaa atgctacggt ccgagcgcga ccagtgaaga atgtcgggt aacgctctgg
5461 aaaaaggcgc aaaaggatcg attaccgaac agctgcttaa cgctcgtgcc gacgttacgc
5521 ttggcggcgg cgcaaaaacc tttgctgaaa cggcaaccgc tggtgaatgg cagggaaaaa
5581 cgctgcgtga acaggcacag gcgcgtggtt atcagttggt gagcgatgct gcctcactga
5641 attcggtgac ggaagcgaat cagcaaaaac ccctgcttgg cctgtttgct gacggcaata
5701 tgccagtgcg ctggctagga ccgaaagcaa cgtaccacgg caatatcgat aagcccgcag
5761 tcacctgtac gccaaatccg caacgtaatg acagtgtacc aaccctggcg cagatgaccg
5821 acaaagccat tgaattgttg agtaaaaatg agaaaggctt ttcctgcaa gttgaaggtg
5881 cgtcaatcga taaacaggat catgctgcga atccttgtgg gcaaattggc gagacggtcg
5941 atctcgatga agccgtacaa cgggcgctgg aattgctaa aaggagggt aacacgctgg
6001 tcatagtcac cgctgatcac gccacgcca gccagattgt tgcgccggat accaaagctc
6061 cgggcctcac ccaggcgcta aataccaaag atggcgcagt gatggtgatg agttacggga
6121 actccgaaga ggattcacaa gaacataccg gcagtcagtt gcgtattgcg gcgtatggcc
6181 cgcatgccgc caatgttgtt ggactgaccg accagaccga tctcttctac accatgaaag
6241 ccgctctggg gctgaaacat catcatcacc atcacgggag ctaataagct tggctgtttt
6301 ggcggatgag agaagatttt cagcctgata cagattaaat cagaacgcag aagcggtctg
6361 ataaaacaga atttgcctg cggcagtagc gcggtggtcc cacctgaccc catgccgaac
6421 tcagaagtga aacgccgtag cgccgatggt agtgtggggt ctccccatgc gagagtaggg
6481 aactgccagg catcaaataa aacgaaaggc tcagtcgaaa gactgggcct ttcgttttat
```

Figure 11 (Contd.)

```
6541 ctgttgtttg tcggtgaacg ctctcctgag taggacaaat ccgccgggag cggatttgaa
6601 cgttgcgaag caacggcccg gaggaccctg gcgggcagga cgcccgccat aaactgccag
6661 gcatcaaatt aagcagaagg ccatcctgac ggatggcctt tttgcgtttc tacaaactct
6721 t
``` p55/MCS1

SEQ ID N° 92
```
   1 ttgtttattt ttctaaatac attcaaatat gtatccgctc atgagacaat aaccctgata
  61 aatgcttcaa taatattgaa aaaggaagag tatgagtatt caacatttcc gtgtcgccct
 121 tattcccttt tttgcggcat tttgccttcc tgtttttgct cacccagaaa cgctggtgaa
 181 agtaaaagat gctgaagatc agttgggtgc acgagtgggt tacatcgaac tggatctcaa
 241 cagcggtaag atccttgaga gttttcgccc cgaagaacgt tttccaatga tgagcacttt
 301 taaagttctg ctatgtggcg cggtattatc ccgtgttgac gccgggcaag agcaactcgg
 361 tcgccgcata cactattctc agaatgactt ggttgagtac tcaccagtca cagaaaagca
 421 tcttacggat ggcatgacag taagagaatt atgcagtgct gccataacca tgagtgataa
 481 cactgcggcc aacttacttc tgacaacgat cggaggaccg aaggagctaa ccgcttttt
 541 gcacaacatg ggggatcatg taactcgcct tgatcgttgg gaaccggagc tgaatgaagc
 601 cataccaaac gacgagcgtg acaccacgat gcctgtagca atggcaacaa cgttgcgcaa
 661 actattaact ggcgaactac ttactctagc ttcccggcaa caattaatag actggatgga
 721 ggcggataaa gttgcaggac cacttctgcg ctcggccctt ccggctggct ggtttattgc
 781 tgataaatct ggagccggtg agcgtgggtc tcgcggtatc attgcagcac tggggccaga
 841 tggtaagccc tcccgtatcg tagttatcta cacgacgggg agtcaggcaa ctatggatga
 901 acgaaataga cagatcgctg agataggtgc ctcactgatt aagcattggt aactgtcaga
 961 ccaagtttac tcatatatac tttagattga tttaaaactt catttttaat ttaaaaggat
1021 ctaggtgaag atcctttttg ataatctcat gaccaaaatc ccttaacgtg agttttcgtt
1081 ccactgagcg tcagaccccg tagaaaagat caaaggatct tcttgagatc ctttttttct
1141 gcgcgtaatc tgctgcttgc aaacaaaaaa accaccgcta ccagcggtgg tttgtttgcc
1201 ggatcaagag ctaccaactc tttttccgaa ggtaactggc ttcagcagag cgcagatacc
1261 aaatactgtc cttctagtgt agccgtagtt aggccaccac ttcaagaact ctgtagcacc
1321 gcctacatac ctcgctctgc taatcctgtt accagtggct gctgccagtg gcgataagtc
1381 gtgtcttacc gggttggact caagacgata gttaccggat aaggcgcagc ggtcgggctg
1441 aacggggggt tcgtgcacac agcccagctt ggagcgaacg acctacaccg aactgagata
1501 cctacagcgt gagcattgag aaagcgccac gcttcccgaa gggagaaagg cggacaggta
1561 tccggtaagc ggcagggtcg gaacaggaga gcgcacgagg gagcttccag ggggaaacgc
1621 ctggtatctt tatagtcctg tcgggtttcg ccacctctga cttgagcgtc gatttttgtg
1681 atgctcgtca ggggggcgga gcctatggaa aaacgccagc aacgcggcct ttttacggtt
1741 cctggccttt tgctggcctt ttgctcacat gttctttcct gcgttatccc ctgattctgt
1801 ggataaccgt attaccgcct ttgagtgagc tgataccgct cgccgcagcc gaacgaccga
1861 gcgcagcgag tcagtgagcg aggaagcgga gagcgcctg atgcggtatt ttctccttac
1921 gcatctgtgc ggtatttcac accgcatata tggtgcactc tcagtacaat ctgctctgat
1981 gccgcatagt taagccagta tacactccgc tatcgctacg tgactgggtc atggctgcgc
2041 cccgacaccc gccaacaccc gctgacgcgc cctgacgggc ttgtctgctc ccggcatccg
2101 cttacagaca agctgtgacc gtctccggga gctgcatgtg tcagaggttt tcaccgtcat
2161 caccgaaacg cgcgaggcag ctgccggtaaa gctcatcagc gtggtcgtga gcgattcac
2221 agatgtctgc ctgttcatcc gcgtccagct cgttgagttt ctccagaagc gttaatgtct
2281 ggcttctgat aaagcgggcc atgttaaggg cggttttttc ctgtttggtc acttgatgcc
2341 tccgtgtaag ggggaatttc tgttcatggg ggtaatgata ccgatgaaac gagagaggat
2401 gctcacgata cgggttactg atgatgaaca tgcccggtta ctggaacgtt gtgagggtaa
2461 acaactggcg gtatggatgc ggcgggacca gagaaaaatc actcagggtc aatgccagcg
2521 cttcgttaat acagatgtag tgttccaca gggtagccag cagcatcctg cgatgcagat
2581 ccggaacata atggtgcagg cgctgactt ccgcgtttcc agactttacg aaacacggaa
2641 accgaagacc attcatgttg ttgctcaggt cgcagacgtt tgcagcagc agtcgcttca
2701 cgttcgctcg cgtatcggtg attcattctg ctaaccagta aggcaacccc gccagcctag
2761 ccgggtcctc aacgacagga gcacgatcat gcgcacccgt ggccaggacc caacgctgcc
2821 cgagatgcgc cgcgtgcggc tgctggagat ggcggacgcg atggatatgt tctgccaagg
2881 gttggtttgc gcattcacag ttctccgcaa gaattgattg gctccaattc ttggagtggt
2941 gaatccgtta gcgaggtgcc gccggcttcc attcaggtcg aggtggcccg gctccatgca
```

Figure 11 (Contd.)

```
3001 ccgcgacgca acgcggggag gcagacaagg tatagggcgg cgcctacaat ccatgccaac
3061 ccgttccatg tgctcgccga ggcggcataa atcgcgtga cgatcagcgg tccagtgatc
3121 gaagttaggc tggtaagagc cgcgagcgat ccttgaagct gtccctgatg gtcgtcatct
3181 acctgcctgg acagcatggc ctgcaacgcg ggcatcccga tgccgccgga agcgagaaga
3241 atcataatgg ggaaggccat ccagcctcgc gtcgcgaacg ccagcaagac gtagcccagc
3301 gcgtcggcca gcttgcaatt cgcgctaact tacattaatt gcgttgcgct cactgcccgc
3361 tttccagtcg ggaaacctgt cgtgccagct gcattaatga atcggccaac gcgcggggag
3421 aggcggtttg cgtattgggc gccagggtgg ttttttcttt caccagtgag acgggcaaca
3481 gctgattgcc cttcaccgcc tggccctgag agagttgcag caagcggtcc acgctggttt
3541 gccccagcag gcgaaaatcc tgtttgatgg tggttgacgg cgggatataa catgagctgt
3601 cttcggtatc gtcgtatccc actaccgaga tatccgcacc aacgcgcagc ccggactcgg
3661 taatggcgcg cattgcgccc agcgccatct gatcgttggc aaccagcatc gcagtgggaa
3721 cgatgccctc attcagcatt tgcatggttt gttgaaaacc ggacatggca ctccagtcgc
3781 cttcccgttc cgctatcggc tgaatttgat tgcgagtgag atatttatgc cagccagcca
3841 gacgcagacg cgccgagaca gaacttaatg gtcccgctaa cagcgcgatt tgctgatgac
3901 ccaatgcgac cagatgctcc acgcccagtc gcgtaccgtc ttcatgggag aaaataatac
3961 tgttgatggg tgtctggtca gagacatcaa gaaataacgc cggaacatta gtgcaggcag
4021 cttccacagc aatggcatcc tggtcatcca gcggatagtt aatgatcagc ccactgacgc
4081 gttgcgcgag aagattgtgc accgccgctt tacaggcttc gacgccgctt cgttctacca
4141 tcgacaccac cacgctggca cccagttgat cggcgcgaga tttaatcgcc gcgacaattt
4201 gcgacggcgc gtgcagggcc agactggagg tggcaacgcc aatcagcaac gactgtttgc
4261 ccgccagttg ttgtgccacg cggttgggaa tgtaattcag ctccgccatc gccgcttca
4321 cttttcccg cgttttcgca gaaacgtggc tggcctggtt caccacgcgg gaaacggtct
4381 gataagagac accggcatac tctgcgacat cgtataacgt tactggtttc acattcacca
4441 ccctgaattg actctcttcc gggcgctatc atgccatacc gcgaaaggtt ttgcgccatt
4501 cgatggtgtc aacgtaaatg catgccgctt cgccttcgcg cgcgaattgc aagctgatcc
4561 ggagcttatc gactgcacgg tgcaccaatg cttctggcgt caggcagcca tcggaagctg
4621 tggtatggct gtgcaggtcg taaatcactg cataattcgt gtcgctcaag gcgcactccc
4681 gttctggata atgtttttg cgccgacatc ataacggttc tggcaaatat tctgaaatga
4741 gctgttgaca attaatcatc ggctcgtata atgtgtggaa ttgtgagcgg ataacaattt
4801 cacacaggaa acagaattcc atatgaaata cctattacca acagcagcag ctgggttatt
4861 attgctcgct gcgcagccgg ccatggccca ggtcaccgtc tcctcaaacc gcggactcga
4921 ggcggcccag ccggccatgg ccgctagcgc ggccgctcta gattaagctt ggctgttttg
4981 gcggatgaga gaagattttc agcctgatac agattaaatc agaacgcaga agcggtctga
5041 taaacagaa tttgcctggc ggcagtagcg cggtggtccc acctgacccc atgccgaact
5101 cagaagtgaa acgccgtagc gccgatggta gtgtggggtc tcccatgcg agagtaggga
5161 actgccaggc atcaaataaa acgaaaggct cagtcgaaag actgggcctt tcgttttatc
5221 tgttgtttgt cggtgaacgc tctcctgagt aggacaaatc cgccgggagc ggatttgaac
5281 gttgcgaagc aacggcccgg aggaccctgg cgggcaggac gcccgccata aactgccagg
5341 catcaaatta agcagaaggc catcctgacg gatggccttt ttgcgtttct acaaactctt
```

P55Flag/RBS/35

SEQ ID N° 93

```
  1 ttgtttattt ttctaaatac attcaaatat gtatccgctc atgagacaat aaccctgata
 61 aatgcttcaa taatattgaa aaggaagag tatgagtatt caacatttcc gtgtcgccct
121 tattcccttt tttgcggcat tttgccttcc tgttttgct cacccagaaa cgctggtgaa
181 agtaaaagat gctgaagatc agttgggtgc acgagtgggt tacatcgaac tggatctcaa
241 cagcggtaag atcctgaga gttttcgccc cgaagaacgt tttccaatga tgagcacttt
301 taaagttctg ctatgtggcg cggtattatc ccgtgttgac gccgggcaag agcaactcgg
361 tcgccgcata cactattctc agaatgactt ggttgagtac tcaccagtca cagaaaagca
421 tcttacggat ggcatgacag taagagaatt atgcagtgct gccataacca tgagtgataa
481 cactgcggcc aacttacttc tgacaacgat cggaggaccg aaggagctaa ccgcttttt
541 gcacaacatg gggatcatg taactcgcct tgatcgttgg gaaccggagc tgaatgaagc
601 cataccaaac gacgagcgtg acaccacgat gcctgtagca atggcaacaa cgttgcgcaa
661 actattaact ggcgaactac ttactctagc ttcccggcaa caattaatag actggatgga
721 ggcggataaa gttgcaggac cacttctgcg ctcggccctt ccggctggct ggtttattgc
781 tgataaatct ggagccggtg agcgtgggtc tcgcggtatc attgcagcac tggggccaga
```

Figure 11 (Contd.)

```
 841 tggtaagccc tcccgtatcg tagttatcta cacgacgggg agtcaggcaa ctatggatga
 901 acgaaataga cagatcgctg agataggtgc ctcactgatt aagcattggt aactgtcaga
 961 ccaagtttac tcatatatac tttagattga tttaaaactt cattttaat ttaaaaggat
1021 ctaggtgaag atccttttg ataatctcat gaccaaaatc ccttaacgtg agttttcgtt
1081 ccactgagcg tcagacccg tagaaaagat caaaggatct tcttgagatc ctttttttct
1141 gcgcgtaatc tgctgcttgc aaacaaaaaa accaccgcta ccagcggtgg tttgtttgcc
1201 ggatcaagag ctaccaactc ttttccgaa ggtaactggc ttcagcagag cgcagatacc
1261 aaatactgtc cttctagtgt agccgtagtt aggccaccac ttcaagaact ctgtagcacc
1321 gcctacatac ctcgctctgc taatcctgtt accagtggct gctgccagtg gcgataagtc
1381 gtgtcttacc gggttggact caagacgata gttaccggat aaggcgcagc ggtcgggctg
1441 aacggggggt tcgtgcacac agcccagctt ggagcgaacg acctacaccg aactgagata
1501 cctacagcgt gagcattgag aaagcgccac gcttcccgaa gggagaaagg cggacaggta
1561 tccggtaagc ggcagggtcg aacaggaga gcgcacgagg gagcttccag ggggaaacgc
1621 ctggtatctt tatagtcctg tcgggtttcg ccacctctga cttgagcgtc gattttgtg
1681 atgctcgtca gggggggcgga gcctatggaa aaacgccagc aacgcggcct ttttacggtt
1741 cctggccttt tgctggcctt ttgctcacat gttctttcct gcgttatccc ctgattctgt
1801 ggataaccgt attaccgcct ttgagtgagc tgataccgct cgccgcagcc gaacgaccga
1861 gcgcagcgag tcagtgagcg aggaagcgga agagcgcctg atgcggtatt ttctccttac
1921 gcatctgtgc ggtatttcac accgcatata tggtgcactc tcagtacaat ctgctctgat
1981 gccgcatagt taagccagta tacactccgc tatcgctacg tgactgggtc atggctgcgc
2041 cccgacaccc gccaacaccc gctgacgcgc cctgacgggc ttgtctgctc ccggcatccg
2101 cttacagaca agctgtgacc gtctccggga gctgcatgtg tcagaggttt tcaccgtcat
2161 caccgaaacg cgcgaggcag ctgcatcagc gtggtcgtga agcgattcac
2221 agatgtctgc ctgttcatcc gcgtccagct cgttgagttt ctccagaagc gttaatgtct
2281 ggcttctgat aaagcgggcc atgttaaggg cggttttttc ctgtttggtc acttgatgcc
2341 tccgtgtaag ggggaattc tgttcatggg ggtaatgata ccgatgaaac gagagaggat
2401 gctcacgata cgggttactg atgatgaaca tgcccggtta ctggaacgtt gtgagggtaa
2461 acaactggcg gtatggatgc ggcgggacca gagaaaaatc actcagggtc aatgccagcg
2521 cttcgttaat acagatgtag gtgttccaca gggtagccag cagcatcctg cgatgcagat
2581 ccggaacata atggtgcagg gcgctgactt ccgcgtttcc agactttacg aaacacggaa
2641 accgaagacc attcatgttg ttgctcaggt cgcagacgtt ttgcagcagc agtcgcttca
2701 cgttcgctcg cgtatcggtg attcattctg ctaaccagta aggcaacccc gccagcctag
2761 ccgggtcctc aacgacagga gcacgatcat gcgcacccgt ggccaggacc caacgctgcc
2821 cgagatgcgc cgcgtgcggc tgctggagat ggcggacgcg atggatatgt tctgccaagg
2881 gttggtttgc gcattcacag ttctccgcaa gaattgattg gctccaattc ttggagtggt
2941 gaatccgtta gcgaggtgcc gccggcttcc attcaggtcg aggtggcccg gctccatgca
3001 ccgcgacgca acgcggggag gcagacaagg tatagggcgg cgcctacaat ccatgccaac
3061 ccgttccatg tgctcgccga gcggcataa atcgccgtga cgatcagcgg tccagtgatc
3121 gaagttaggc tggtaagagc cgcgagcgat ccttgaagct gtccctgatg gtcgtcatct
3181 acctgcctgg acagcatggc ctgcaacgcg ggcatcccga tgccgccgga agcgagaaga
3241 atcataatgg ggaaggccat ccagcctcgc gtcgcgaacg ccagcaagac gtagcccagc
3301 gcgtcggcca gcttgcaatt cgcgctaact tacattaatt gcgttgcgct cactgcccgc
3361 tttccagtcg ggaaacctgt cgtgccagct gcattaatga atcggccaac gcgcggggag
3421 aggcggtttg cgtattgggc gccagggtgg tttttctttt caccagtgag acgggcaaca
3481 gctgattgcc cttcaccgcc tggccctgag agagttgcag caagcggtcc acgctggttt
3541 gccccagcag gcgaaaatcc tgtttgatgg tggttgacgg cgggatataa catgagctgt
3601 cttcggtatc gtcgtatccc actaccgaga tatccgcacc aacgcgcagc ccggactcgg
3661 taatgcgcg cattgcgccc agcgccatct gatcgttggc aaccagcatc gcagtgggaa
3721 cgatgccctc attcagcatt tgcatggttt gttgaaaacc ggacatggca ctccagtcgc
3781 cttcccgttc cgctatcggc tgaatttgat tgcgagtgag atatttatgc cagccagcca
3841 gacgcagacg cgccgagaca gaacttaatg gtcccgctaa cagcgcgatt tgctgatgac
3901 ccaatgcgac cagatgctcc acgcccagtc gcgtaccgtc ttcatgggag aaaataatac
3961 tgttgatggg tgtctggtca gagacatcaa gaaataacgc cggaacatta gtgcaggcag
4021 cttccacagc aatggcatcc tggtcatcca gcggatagtt aatgatcagc ccactgacgc
4081 gttgcgcgag aagattgtgc accgccgctt tacaggcttc gacgccgctt cgttctacca
4141 tcgacaccac cacgctggca cccagttgat cggcgcgaga tttaatcgcc gcgacaattt
4201 gcgacggcgc gtgcagggcc agactggagg tggcaacgcc aatcagcaac gactgtttgc
4261 ccgccagttg ttgtgccacg cggttgggaa tgtaattcag ctccgccatc gccgcttcca
```

Figure 11 (Contd.)

```
     4321 cttttttcccg cgtttttcgca gaaacgtggc tggcctggtt caccacgcgg gaaacggtct
     4381 gataagagac accggcatac tctgcgacat cgtataacgt tactggtttc acattcacca
     4441 ccctgaattg actctcttcc gggcgctatc atgccatacc gcgaaaggtt ttgcgccatt
     4501 cgatggtgtc aacgtaaatg catgccgctt cgccttcgcg cgcgaattgc aagctgatcc
     4561 ggagcttatc gactgcacgg tgcaccaatg cttctggcgt caggcagcca tcggaagctg
     4621 tggtatggct gtgcaggtcg taaatcactg cataattcgt gtcgctcaag gcgcactccc
     4681 gttctggata atgttttttg cgccgacatc ataacggttc tggcaaatat tctgaaatga
     4741 gctgttgaca attaatcatc ggctcgtata atgtgtggaa ttgtgagcgg ataacaattt
     4801 cacacaggaa acagaattcc atatgaaata cctattacca acagcagcag ctgggttatt
     4861 attgctcgct gcgcagccgg ccatggccca ggtcaccgtc tcctcaaacc gcggagagtg
     4921 tgcaggtgat tacaaagacg atgacgataa gtaataaaca ggaaacagaa gtccatatga
     4981 aatacctatt gcctacggca gccgctggat tgttattact cgcggcccag ccggccatgg
     5041 ccgctagcgc ggccgctcta gattaagctt ggctgttttg gcggatgaga gaagattttc
     5101 agcctgatac agattaaatc agaacgcaga gcggtctga taaaacagaa tttgcctggc
     5161 ggcagtagcg cggtggtccc acctgacccc atgccgaact cagaagtgaa acgccgtagc
     5221 gccgatggta gtgtggggtc tccccatgcg agagtaggga actgccaggc atcaaataaa
     5281 acgaaaggct cagtcgaaag actgggcctt tcgttttatc tgttgtttgt cggtgaacgc
     5341 tctcctgagt aggacaaatc cgccgggagc ggatttgaac gttgcgaagc aacggcccgg
     5401 aggaccctgg cgggcaggac gcccgccata aactgccagg catcaaatta agcagaaggc
     5461 catcctgacg gatggccttt ttgcgtttct acaaactctt SEQ ID N° 109
        1 ttgtttattt ttctaaatac attcaaatat gtatccgctc atgagacaat aaccctgata
       61 aatgcttcaa taatattgaa aaggaagag tatgagtatt caacatttcc gtgtcgccct
      121 tattcccttt tttgcggcat tttgccttcc tgttttttgct caccagaaa cgctggtgaa
      181 agtaaaagat gctgaagatc agttgggtgc acgagtgggt tacatcgaac tggatctcaa
      241 cagcggtaag atccttgaga gttttcgccc cgaagaacgt tttccaatga tgagcacttt
      301 taaagttctg ctatgtggcg cggtattatc ccgtgttgac gccgggcaag agcaactcgg
      361 tcgccgcata cactattctc agaatgactt ggttgagtac tcaccagtca cagaaaagca
      421 tcttacggat ggcatgacag taagagaatt atgcagtgct gccataacca tgagtgataa
      481 cactgcggcc aacttacttc tgacaacgat cggaggaccg aaggagctaa ccgcttttttt
      541 gcacaacatg ggggatcatg taactcgcct tgatcgttgg gaaccggagc tgaatgaagc
      601 cataccaaac gacgagcgtg acaccacgat gcctgtagca atggcaacaa cgttgcgcaa
      661 actattaact ggcgaactac ttactctagc ttcccggcaa caattaatag actggatgga
      721 ggcggataaa gttgcaggac cacttctgcg ctcggccctt ccggctggct ggtttattgc
      781 tgataaatct ggagccggtg agcgtgggtc tcgcggtatc attgcagcac tggggccaga
      841 tggtaagccc tcccgtatcg tagttatcta cacgacgggg agtcaggcaa ctatggatga
      901 acgaaataga cagatcgctg agataggtgc ctcactgatt aagcattggt aactgtcaga
      961 ccaagtttac tcatatatac tttagattga tttaaaactt cattttttaat ttaaaaggat
     1021 ctaggtgaag atcctttttg ataatctcat gaccaaaatc ccttaacgtg agttttcgtt
     1081 ccactgagcg tcagaccccg tagaaaagat caaaggatct tcttgagatc ctttttttct
     1141 gcgcgtaatc tgctgcttgc aaacaaaaaa accaccgcta ccagcggtgg tttgtttgcc
     1201 ggatcaagag ctaccaactc tttttccgaa ggtaactggc ttcagcagag cgcagatacc
     1261 aaatactgtc cttctagtgt agccgtagtt aggccaccac ttcaagaact ctgtagcacc
     1321 gcctacatac ctcgctctgc taatcctgtt accagtggct gctgccagtg gcgataagtc
     1381 gtgtcttacc gggttggact caagacgata gttaccggat aaggcgcagc ggtcgggctg
     1441 aacggggggt tcgtgcacac agcccagctt ggagcgaacg acctacaccg aactgagata
     1501 cctacagcgt gagcattgag aaagcgccac gcttcccgaa gggagaaagg cggacaggta
     1561 tccggtaagc ggcagggtcg aacaggaga gcgcacgagg gagcttccag ggggaaacgc
     1621 ctggtatctt tatagtcctg tcgggtttcg ccacctctga cttgagcgtc gatttttgtg
     1681 atgctcgtca ggggggcgga gcctatggaa aaacgccagc aacgcggcct ttttacggtt
     1741 cctggccttt tgctggcctt ttgctcacat gttctttcct gcgttatccc ctgattctgt
     1801 ggataaccgt attaccgcct ttgagtgagc tgataccgct cgccgcagcc gaacgaccga
     1861 gcgcagcgag tcagtgagcg aggaagcgga gagcgcctg atgcggtatt ttctccttac
     1921 gcatctgtgc ggtatttcac accgcatata tggtgcactc tcagtacaat ctgctctgat
     1981 gccgcatagt taagccagta tacactccgc tatcgctacg tgactgggtc atggctgcgc
     2041 cccgacaccc gccaacaccc gctgacgcgc cctgacgggc ttgtctgctc ccggcatccg
     2101 cttacagaca agctgtgacc gtctccggga gctgcatgtg tcagaggttt tcaccgtcat
```

Figure 11 (Contd.)

```
2161 caccgaaacg cgcgaggcag ctgcggtaaa gctcatcagc gtggtcgtga agcgattcac
2221 agatgtctgc ctgttcatcc gcgtccagct cgttgagttt ctccagaagc gttaatgtct
2281 ggcttctgat aaagcgggcc atgttaaggg cggtttttc ctgtttggtc acttgatgcc
2341 tccgtgtaag ggggaatttc tgttcatggg ggtaatgata ccgatgaaac gagagaggat
2401 gctcacgata cgggttactg atgatgaaca tgcccggtta ctgaacgtt gtgagggtaa
2461 acaactggcg gtatggatgc ggcgggacca gagaaaaatc actcagggtc aatgccagcg
2521 cttcgttaat acagatgtag gtgttccaca gggtagccag cagcatcctg cgatgcagat
2581 ccggaacata atggtgcagg cgctgactt ccgcgtttcc agactttacg aaacacggaa
2641 accgaagacc attcatgttg ttgctcaggt cgcagacgtt ttgcagcagc agtcgcttca
2701 cgttcgctcg cgtatcggtg attcattctg ctaaccagta aggcaacccc gccagcctag
2761 ccgggtcctc aacgacagga gcacgatcat gcgcacccgt ggccaggacc caacgctgcc
2821 cgagatgcgc cgcgtgcggc tgctggagat ggcggacgcg atggatatgt tctgccaagg
2881 gttggtttgc gcattcacag ttctccgcaa gaattgattg gctccaattc ttggagtggt
2941 gaatccgtta gcgaggtgcc gccggcttcc attcaggtcg aggtggcccg gctccatgca
3001 ccgcgacgca acgcggggag gcagacaagg tatagggcgg cgcctacaat ccatgccaac
3061 ccgttccatg tgctcgccga ggcggcataa atcgccgtga cgatcagcgg tccagtgatc
3121 gaagttaggc tggtaagagc cgcgagcgat ccttgaagct gtccctgatg gtcgtcatct
3181 acctgcctgg acagcatggc ctgcaacgcg ggcatcccga tgccgccgga agcgagaaga
3241 atcataatgg ggaaggccat ccagcctcgc gtcgcgaacg ccagcaagac gtagcccagc
3301 gcgtcggcca gcttgcaatt cgcgctaact tacattaatt gcgttgcgct cactgcccgc
3361 tttccagtcg ggaaacctgt cgtgccagct gcattaatga atcggccaac gcgcggggag
3421 aggcggtttg cgtattgggc gccagggtgg ttttctttt caccagtgag acgggcaaca
3481 gctgattgcc cttcaccgcc tggccctgag agagttgcag caagcggtcc acgctggttt
3541 gccccagcag gcgaaaatcc tgtttgatgg tggttgacgg cgggatataa catgagctgt
3601 cttcggtatc gtcgtatccc actaccgaga tatccgcacc aacgcgcagc ccggactcgg
3661 taatggcgcg cattgcgccc agcgccatct gatcgttggc aaccagcatc gcagtgggaa
3721 cgatgccctc attcagcatt tgcatggttt gttgaaaacc ggacatggca ctccagtcgc
3781 cttcccgttc cgctatcggc tgaatttgat tgcgagtgag atatttatgc cagccagcca
3841 gacgcagacg cgccgagaca gaacttaatg gtcccgctaa cagcgcgatt tgctgatgac
3901 ccaatgcgac cagatgctcc acgcccagtc gcgtaccgtc ttcatggag aaaataatac
3961 tgttgatggg tgtctggtca gagacatcaa gaaataacgc cggaacatta gtgcaggcag
4021 cttccacagc aatggcatcc tggtcatcca gcggatagtt aatgatcagc ccactgacgc
4081 gttgcgcgag aagattgtgc accgccgctt tacaggcttc gacgccgctt cgttctacca
4141 tcgacaccac cacgctggca cccagttgat cggcgcgaga tttaatcgcc gcgacaattt
4201 gcgacggcgc gtgcagggcc agactggagg tggcaacgcc aatcagcaac gactgtttgc
4261 ccgccagttg ttgtgccacg cggttgggaa tgtaattcag ctccgccatc gccgcttcca
4321 cttttttccg cgttttcgca gaaacgtggc tggcctggtt caccacgcgg gaaacggtct
4381 gataagagac accggcatac tctgcgacat cgtataacgt tactggtttc acattcacca
4441 ccctgaattg actctcttcc gggcgctatc atgccatacc gcgaaaggtt ttgcgccatt
4501 cgatggtgtc aacgtaaatg catgccgctt cgccttcgcg cgcgaattgc aagctgatcc
4561 ggagcttatc gactgcacgt tgcaccaatg cttctggcgt caggcagcca tcggaagctg
4621 tggtatggct gtgcaggtcg taaatcactg cataattcgt gtcgctcaag gcgcactccc
4681 gttctggata atgttttttg cgccgacatc ataacggttc tggcaaatat tctgaaatga
4741 gctgttgaca attaatcatc ggctcgtata atgtgtggaa ttgtgagcgg ataacaattt
4801 cacacaggaa acagaattcc atatgaaata cctattacca acagcagcag ctgggttatt
4861 attgctcgct gcgcaccgcg ccatgcaccg tgtcaccgtc tcctcaaacc gcggagagtg
4921 tgcaggtgat tacaaagacg atgacgataa gtaataaaca ggaaacagaa gtccatatga
4981 aatatctttt acctacggca gccgcaggtt tgttgttact cgcggccag ccggccatgg
5041 ccgctagcgc ggccgctcta gattaagctt ggctgttttg gcggatgaga aagattttc
5101 agcctgatac agattaaatc agaacgcaga agcggtctga taaaacagaa tttgcctggc
5161 ggcagtagcg cggtggtccc acctgacccc atgccgaact cagaagtgaa acgccgtagc
5221 gccgatggta gtgtggggtc tccccatgcg agagtaggga actgccaggc atcaaataaa
5281 acgaaaggct cagtcgaaag actgggcctt tcgttttatc tgttgtttgt cggtgaacgc
5341 tctcctgagt aggacaaatc cgccgggagc ggatttgaac gttgcgaagc aacggcccgg
5401 aggaccctgg cgggcaggac gccgccata aactgccagg catcaaatta agcagaaggc
5461 catcctgacg gatggccttt ttgcgtttct acaaactctt
```

P55Flag/RBS/35cmyc6HisGS

Figure 11 (Contd.)

SEQ ID N° 94
```
   1 ttgtttattt ttctaaatac attcaaatat gtatccgctc atgagacaat aaccctgata
  61 aatgcttcaa taatattgaa aaaggaagag tatgagtatt caacatttcc gtgtcgccct
 121 tattcccttt tttgcggcat tttgccttcc tgtttttgct cacccagaaa cgctggtgaa
 181 agtaaaagat gctgaagatc agttgggtgc acgagtgggt tacatcgaac tggatctcaa
 241 cagcggtaag atccttgaga gttttcgccc cgaagaacgt tttccaatga tgagcacttt
 301 taaagttctg ctatgtggcg cggtattatc ccgtgttgac gccgggcaag agcaactcgg
 361 tcgccgcata cactattctc agaatgactt ggttgagtac tcaccagtca cagaaaagca
 421 tcttacggat ggcatgacag taagagaatt atgcagtgct gccataacca tgagtgataa
 481 cactgcggcc aacttacttc tgacaacgat cggaggaccg aaggagctaa ccgcttttt
 541 gcacaacatg gggatcatg taactcgcct tgatcgttgg aaccggagc tgaatgaagc
 601 cataccaaac gacgagcgtg acaccacgat gcctgtagca atggcaacaa cgttgcgcaa
 661 actattaact ggcgaactac ttactctagc ttcccggcaa caattaatag actggatgga
 721 ggcggataaa gttgcaggac cacttctgcg ctcggccctt ccggctggct ggtttattgc
 781 tgataaatct ggagccggtg agcgtgggtc tcgcggtatc attgcagcac tggggccaga
 841 tggtaagccc tcccgtatcg tagttatcta cacgacgggg agtcaggcaa ctatggatga
 901 acgaaataga cagatcgctg agataggtgc ctcactgatt aagcattggt aactgtcaga
 961 ccaagtttac tcatatatac tttagattga tttaaaactt cattttaat ttaaaaggat
1021 ctaggtgaag atcctttttg ataatctcat gaccaaaatc ccttaacgtg agttttcgtt
1081 ccactgagcg tcagaccccg tagaaaagat caaaggatct tcttgagatc cttttttct
1141 gcgcgtaatc tgctgcttgc aaacaaaaaa accaccgcta ccagcggtgg tttgtttgcc
1201 ggatcaagag ctaccaactc ttttttccgaa ggtaactggc ttcagcagag cgcagatacc
1261 aaatactgtc cttctagtgt agccgtagtt aggccaccac ttcaagaact ctgtagcacc
1321 gcctacatac ctcgctctgc taatcctgtt accagtggct gctgccagtg gcgataagtc
1381 gtgtcttacc gggttggact caagacgata gttaccggat aaggcgcagc ggtcgggctg
1441 aacggggggt tcgtgcacac agcccagctt ggagcgaacg acctacaccg aactgagata
1501 cctacagcgt gagcattgag aaagcgccac gcttcccgaa gggagaaagg cggacaggta
1561 tccggtaagc ggcagggtcg gaacaggaga gcgcacgagg gagcttccag ggggaaacgc
1621 ctggtatctt tatagtcctg tcgggtttcg ccacctctga cttgagcgtc gatttttgtg
1681 atgctcgtca ggggggcgga gcctatggaa aaacgccagc aacgcggcct ttttacggtt
1741 cctggccttt tgctggcctt ttgctcacat gttctttcct gcgttatccc ctgattctgt
1801 ggataaccgt attaccgcct ttgagtgagc tgataccgct cgccgcagcc gaacgaccga
1861 gcgcagcgag tcagtgagcg aggaagcgga gagcgcctg atgcggtatt ttctccttac
1921 gcatctgtgc ggtatttcac accgcatata tggtgcactc tcagtacaat ctgctctgat
1981 gccgcatagt taagccagta tacactccgc tatcgctacg tgactgggtc atggctgcgc
2041 cccgacaccc gccaacaccc gctgacgcgc cctgacgggc ttgtctgctc ccggcatccg
2101 cttacagaca agctgtgacc gtctccggga gctgcatgtg tcagaggttt tcaccgtcat
2161 caccgaaacg cgcgaggcag ctgcggtaaa gctcatcagc gtggtcgtga agcgattcac
2221 agatgtctgc ctgttcatcc gcgtccagct cgttgagttt ctccagaagc gttaatgtct
2281 ggcttctgat aaagcgggcc atgttaaggg cggttttttc ctgtttggtc acttgatgcc
2341 tccgtgtaag ggggaatttc tgttcatggg ggtaatgata ccgatgaaac gagagaggat
2401 gctcacgata cgggttactg atgatgaaca tgcccggtta ctggaacgtt gtgagggtaa
2461 acaactggcg gtatggatgc ggcgggacca gagaaaaatc actcagggtc aatgccagcg
2521 cttcgttaat acagatgtag gtgttccaca gggtagccag cagcatcctg cgatgcagat
2581 ccggaacata atggtgcagg gcgctgactt ccgcgtttcc agactttacg aaacacggaa
2641 accgaagacc attcatgttg ttgctcaggt cgcagacgtt ttgcagcagc agtcgcttca
2701 cgttcgctcg cgtatcggtg attcattctg ctaaccagta aggcaacccc gccagcctag
2761 ccgggtcctc aacgacagga gcacgatcat gcgcacccgt ggccaggacc caacgctgcc
2821 cgagatgcgc cgcgtgcggc tgctggagat ggcggacgcg atggatatgt tctgccaagg
2881 gttggtttgc gcattcacag ttctccgcaa gaattgattg gctccaattc ttggagtggt
2941 gaatccgtta gcgaggtgcc gccggcttcc attcaggtcg aggtggcccg gctccatgca
3001 ccgcgacgca acgcggggag gcagacaagg tataggcgg cgcctacaat ccatgccaac
3061 ccgttccatg tgctcgccga ggcggcataa atcgccgtga cgatcagcgg tccagtgatc
3121 gaagttaggc tggtaagagc cgcgagcgat ccttgaagct gtccctgatg gtcgtcatct
3181 acctgcctgg acagcatggc ctgcaacgcg ggcatcccga tgccgccgga agcgagaaga
3241 atcataatgg ggaaggccat ccagcctcgc gtcgcgaacg ccagcaagac gtagcccagc
3301 gcgtcggcca gcttgcaatt cgcgctaact acattaatt gcgttgcgct cactgcccgc
```

Figure 11 (Contd.)

```
3361 tttccagtcg ggaaacctgt cgtgccagct gcattaatga atcggccaac gcgcggggag
3421 aggcggtttg cgtattgggc gccagggtgg tttttctttt caccagtgag acgggcaaca
3481 gctgattgcc cttcaccgcc tggccctgag agagttgcag caagcggtcc acgctggttt
3541 gccccagcag gcgaaaatcc tgtttgatgg tggttgacgg cgggatataa catgagctgt
3601 cttcggtatc gtcgtatccc actaccgaga tatccgcacc aacgcgcagc ccggactcgg
3661 taatggcgcg cattgcgccc agcgccatct gatcgttggc aaccagcatc gcagtgggaa
3721 cgatgccctc attcagcatt tgcatggttt gttgaaaacc ggacatggca ctccagtcgc
3781 cttcccgttc cgctatcggc tgaatttgat tgccagtgag atatttatgc cagccagcca
3841 gacgcagacg cgccgagaca gaacttaatg gtcccgctaa cagcgcgatt tgctgatgac
3901 ccaatgcgac cagatgctcc acgcccagtc gcgtaccgtc ttcatgggag aaaataatac
3961 tgttgatggg tgtctggtca gagacatcaa gaaataacgc cggaacatta gtgcaggcag
4021 cttccacagc aatggcatcc tggtcatcca gcggatagtt aatgatcagc ccactgacgc
4081 gttgcgcgag aagattgtgc accgccgctt tacaggcttc gacgccgctt cgttctacca
4141 tcgacaccac cacgctggca cccagttgat cggcgcgaga tttaatcgcc gcgacaattt
4201 gcgacggcgc gtgcagggcc agactggagg tgcaacgcc aatcagcaac gactgtttgc
4261 ccgccagttg ttgtgccacg cggttgggaa tgtaattcag ctccgccatc gccgcttcca
4321 cttttcccg cgttttcgca gaaacgtggc tggcctggtt caccacgcgg gaaacggtct
4381 gataagagac accggcatac tctgcgacat cgtataacgt tactggtttc acattcacca
4441 ccctgaattg actctcttcc gggcgctatc atgccatcc gcgaaaggtt ttgcgccatt
4501 cgatggtgtc aacgtaaatg catgccgctt cgccttcgcg cgcgaattgc aagctgatcc
4561 ggagcttatc gactgcacgg tgcaccaatg cttctggcgt caggcagcca tcggaagctg
4621 tggtatggct gtgcaggtcg taaatcactg cataattcgt gtcgctcaag gcgcactccc
4681 gttctggata atgtttttg cgccgacatc ataacggttc tggcaaatat tctgaaatga
4741 gctgttgaca attaatcatc ggctcgtata atgtgtggaa ttgtgagcgg ataacaattt
4801 cacacaggaa acagaattcc atatgaaata cctattacca acagcagcag ctgggttatt
4861 attgctcgct gcgcagccgg ccatggccca ggtcaccgtc tcctcaaacc gcggagagtg
4921 tgcaggtgat tacaaagacg atgacgataa gtaataaaca ggaaacagaa gtccatatga
4981 aataccatt gcctacggca gccgctggat tgttattact cgcggcccag ccggccatgg
5041 ccgctagcgc ggccgcagaa caaaaactca tctcagaaga ggatctgaat ggggccgtac
5101 atcaccacca tcatcatggg agctaagctt ggctgttttg gcggatgaga gaagattttc
5161 agcctgatac agattaaatc agaacgcaga agcggtctga taaaacagaa tttgcctggc
5221 ggcagtagcg cggtggtccc acctgacccc atgccgaact cagaagtgaa acgccgtagc
5281 gccgatggta gtgtgggtc tccccatgcg agagtaggga actgccaggc atcaaataaa
5341 acgaaaggct cagtcgaaag actgggcctt tcgttttatc tgttgtttgt cggtgaacgc
5401 tctcctgagt aggacaaatc cgccgggagc ggatttgaac gttgcgaagc aacggcccgg
5461 aggaccctgg cgggcaggac gccgccata aactgccagg catcaaatta agcagaaggc
5521 catcctgacg gatggccttt ttgcgtttct acaaactctt
```

SEQ ID N° 110

```
   1 ttgtttattt ttctaaatac attcaaatat gtatccgctc atgagacaat aaccctgata
  61 aatgcttcaa taatattgaa aaaggaagag tatgagtatt caacatttcc gtgtcgccct
 121 tattcccttt tttgcggcat tttgccttcc tgttttgct cacccagaaa cgctggtgaa
 181 agtaaaagat gctgaagatc agttgggtgc acgagtgggt tacatcgaac tggatctcaa
 241 cagcggtaag atccttgaga gttttcgccc cgaagaacgt tttccaatga tgagcacttt
 301 taaagttctg ctatgtggcg cggtattatc ccgtgttgac gccgggcaag agcaactcgg
 361 tcgccgcata cactattctc agaatgactt ggttgagtac tcaccagtca cagaaaagca
 421 tcttacggat ggcatgacag taagagaatt atgcagtgct gccataacca tgagtgataa
 481 cactgcggcc aacttacttc tgacaacgat cggaggaccg aaggagctaa ccgcttttt
 541 gcacaacatg gggatcatg taactcgcct tgatcgttgg gaacggagc tgaatgaagc
 601 cataccaaac gacgagcgtg acaccacgat gcctgtagca atggcaacaa cgttgcgcaa
 661 actattaact ggcgaactac ttactctagc ttcccggcaa caattaatag actggatgga
 721 ggcggataaa gttgcaggac cacttctgcg ctcggccctt ccggctggct ggtttattgc
 781 tgataaatct ggagccggtg agcgtgggtc tcgcggtatc attgcagcac tggggccaga
 841 tggtaagccc tcccgtatcg tagttatcta cacgacgggg agtcaggcaa ctatggatga
 901 acgaaataga cagatcgctg agataggtgc ctcactgatt aagcattggt aactgtcaga
 961 ccaagtttac tcatatatac tttagattga tttaaaactt catttttaat ttaaaaggat
1021 ctaggtgaag atccttttg ataatctcat gaccaaaatc ccttaacgtg agttttcgtt
1081 ccactgagcg tcagacccg tagaaaagat caaaggatct tcttgagatc ctttttttct
```

Figure 11 (Contd.)

```
1141 gcgcgtaatc tgctgcttgc aaacaaaaaa accaccgcta ccagcggtgg tttgtttgcc
1201 ggatcaagag ctaccaactc ttttccgaa ggtaactggc ttcagcagag cgcagatacc
1261 aaatactgtc cttctagtgt agccgtagtt aggccaccac ttcaagaact ctgtagcacc
1321 gcctacatac ctcgctctgc taatcctgtt accagtggct gctgccagtg gcgataagtc
1381 gtgtcttacc gggttggact caagacgata gttaccggat aaggcgcagc ggtcgggctg
1441 aacgggggt tcgtgcacac agcccagctt ggagcgaacg acctacaccg aactgagata
1501 cctacagcgt gagcattgag aaagcgccac gcttcccgaa gggagaaagg cggacaggta
1561 tccggtaagc ggcagggtcg gaacagggaa gcgcacgagg gagcttccag ggggaaacgc
1621 ctggtatctt tatagtcctg tcgggtttcg ccacctctga cttgagcgtc gatttttgtg
1681 atgctcgtca ggggggcgga gcctatggaa aaacgccagc aacgcggcct ttttacggtt
1741 cctggccttt tgctggcctt ttgctcacat gttctttcct gcgttatccc ctgattctgt
1801 ggataaccgt attaccgcct ttgagtgagc tgataccgct cgccgcagcc gaacgaccga
1861 gcgcagcgag tcagtgagcg aggaagcgga agagcgcctg atgcggtatt ttctccttac
1921 gcatctgtgc ggtatttcac accgcatata tggtgcactc tcagtacaat ctgctctgat
1981 gccgcatagt taagccagta tacactccgc tatcgctacg tgactgggtc atggctgcgc
2041 cccgacaccc gccaacaccc gctgacgcgc cctgacgggc ttgtctgctc ccggcatccg
2101 cttacagaca agctgtgacc gtctccggga gctgcatgtg tcagaggttt tcaccgtcat
2161 caccgaaacg cgcgaggcag ctgcggtaaa gctcatcagc gtggtcgtga agcgattcac
2221 agatgtctgc ctgttcatcc gcgtccagct cgttgagttt ctccagaagc gttaatgtct
2281 ggcttctgat aaagcgggcc atgttaaggg cggttttttc ctgtttggtc acttgatgcc
2341 tccgtgtaag ggggaatttc tgttcatggg ggtaatgata ccgatgaaac gagagaggat
2401 gctcacgata cgggttactg atgatgaaca tgcccggtta ctggaacgtt gtgagggtaa
2461 acaactggcg gtatggatgc ggcgggacca gagaaaaatc actcagggtc aatgccagcg
2521 cttcgttaat acagatgtag gtgttccaca gggtagccag cagcatcctg cgatgcagat
2581 ccggaacata atggtgcagg cgctgactt ccgcgtttcc agactttacg aaacacggaa
2641 accgaagacc attcatgttg ttgctcaggt cgcagacgtt ttgcagcagc agtcgcttca
2701 cgttcgctcg cgtatcggtg attcattctg ctaaccagta aggcaacccc gccagcctag
2761 ccgggtcctc aacgacagga gcacgatcat gcgcacccgt ggccaggacc aacgctgcc
2821 cgagatgcgc cgcgtgcggc tgctggagat ggcggacgcg atggatatgt tctgccaagg
2881 gttggtttgc gcattcacag ttctccgcaa gaattgattg ctccaattc ttggagtggt
2941 gaatccgtta gcgaggtgcc gccggcttcc attcaggtcg aggtggcccg gctccatgca
3001 ccgcgacgca acgcggggag gcagacaagg tatagggcgg cgcctacaat ccatgccaac
3061 ccgttccatg tgctcgccga ggcggcataa atcgccgtga cgatcagcgg tccagtgatc
3121 gaagttaggc tggtaagagc cgcgagcgat ccttgaagct gtccctgatg gtcgtcatct
3181 acctgcctgg acagcatggc ctgcaacgcg ggcatcccga tgccgccgga agcgagaaga
3241 atcataatgg ggaaggccat ccagcctcgc gtcgcgaacg ccagcaagac gtagcccagc
3301 gcgtcggcca gcttgcaatt cgcgctaact tacattaatt gcgttgcgct cactgcccgc
3361 tttccagtcg ggaaacctgt cgtgccagct gcattaatga atcggccaac gcgcggggag
3421 aggcggtttg cgtattgggc gccagggtgg ttttctttt caccagtgag acgggcaaca
3481 gctgattgcc cttcaccgcc tggccctgag agagttgcag caagcggtcc acgctggttt
3541 gccccagcag gcgaaaatcc tgtttgatgg tggttacgg cgggatataa catgagctgt
3601 cttcggtatc gtcgtatccc actaccgaga tatccgcacc aacgcgcagc ccggactcgg
3661 taatggcgcg cattgcgccc agcgccatct gatcgttggc aaccagcatc gcagtgggaa
3721 cgatgccctc attcagcatt tgcatggttt gttgaaaacc ggacatggca ctccagtcgc
3781 cttcccgttc cgctatcggc tgaatttgat tgcgagtgag atatttatgc cagccagcca
3841 gacgcagacg cgccgagaca gaacttaatg gtcccgctaa cagcgcgatt tgctgatgac
3901 ccaatgcgac cagatgctcc acgcccactca gcgtaccgtc ttcatgggag aaaataatac
3961 tgttgatggg tgtctgtca gagacatcaa gaaataacgc cggaacatta gtgcaggcag
4021 cttccacagc aatggcatcc tggtcatcca gcggatagtt aatgatcagc ccactgacgc
4081 gttgcgcgag aagattgtgc accgccgctt tacaggcttc gacgccgctt cgttctacca
4141 tcgacaccac cacgctggca cccagttgat cggcgcgaga tttaatcgcc gcgacaattt
4201 gcgacggcgc gtgcagggcc agactggagg tggcaacgcc aatcagcaac gactgtttgc
4261 ccgccagttg ttgtgccacg cggttggaa tgtaattcag ctccgccatc gccgcttcca
4321 cttttcccg cgttttcgca gaaacgtggc tggcctggtt caccacgcgg gaaacggtct
4381 gataagagac accggcatac tctgcgacat cgtataacgt tactggtttc acattcacca
4441 ccctgaattg actctcttcc gggcgctatc atgccatacc gcgaaaggtt ttgcgccatt
4501 cgatggtgtc aacgtaaatg catccgcctt cgcctcgcg cgcgaattgc aagctgatcc
4561 ggagcttatc gactgcacgg tgcaccaatg cttctggcgt caggcagcca tcggaagctg
```

Figure 11 (Contd.)

```
4621 tggtatggct gtgcaggtcg taaatcactg cataattcgt gtcgctcaag gcgcactccc
4681 gttctggata atgttttttg cgccgacatc ataacggttc tggcaaatat tctgaaatga
4741 gctgttgaca attaatcatc ggctcgtata atgtgtggaa ttgtgagcgg ataacaattt
4801 cacacaggaa acagaattcc atatgaaata cctattacca acagcagcag ctgggttatt
4861 attgctcgct gcgcagccgg ccatggccca ggtcaccgtc tcctcaaacc gcggagagtg
4921 tgcaggtgat tacaaagacg atgacgataa gtaataaaca ggaaacagaa gtccatatga
4981 aatatctttt acctacggca gccgcaggtt tgttgttact cgcggcccag ccggccatgg
5041 ccgctagcgc ggccgcagaa caaaaactca tctcagaaga ggatctgaat ggggccgtac
5101 atcaccacca tcatcatggg agctaagctt ggctgttttg gcggatgaga gaagattttc
5161 agcctgatac agattaaatc agaacgcaga agcggtctga taaaacagaa tttgcctggc
5221 ggcagtagcg cggtggtccc acctgacccc atgccgaact cagaagtgaa acgccgtagc
5281 gccgatggta gtgtggggtc tccccatgcg agagtaggga actgccaggc atcaaataaa
5341 acgaaaggct cagtcgaaag actgggcctt tcgttttatc tgttgtttgt cggtgaacgc
5401 tctcctgagt aggacaaatc cgccgggagc ggatttgaac gttgcgaagc aacggcccgg
5461 aggaccctgg cgggcaggac gcccgccata aactgccagg catcaaatta agcagaaggc
5521 catcctgacg gatggccttt ttgcgtttct acaaactctt
``` pHCH2CH3γ1-TAG

SEQ ID N° 95

```
   1 ttgtttattt ttctaaatac attcaaatat gtatccgctc atgagacaat aaccctgata
  61 aatgcttcaa taatattgaa aaggaagag tatgagtatt caacatttcc gtgtcgccct
 121 tattcccttt tttgcggcat tttgccttcc tgttttgct cacccagaaa cgctggtgaa
 181 agtaaaagat gctgaagatc agttgggtgc acgagtgggt tacatcgaac tggatctcaa
 241 cagcggtaag atccttgaga gttttcgccc cgaagaacgt tttccaatga tgagcacttt
 301 taaagttctg ctatgtggcg cggtattatc ccgtgttgac gccggacaag agcaactcgg
 361 tcgccgcata cactattctc agaatgactt ggttgagtac tcaccagtca cagaaaagca
 421 tcttacggat ggcatgacag taagagaatt atgcagtgct gccataacca tgagtgataa
 481 cactgcggcc aacttacttc tgacaacgat cggaggaccg aaggagctaa ccgcttttt
 541 gcacaacatg ggggatcatg taactcgcct tgatcgttgg gaaccggagc tgaatgaagc
 601 cataccaaac gacgagcgtg acaccacgat gcctgtagca atggcaacaa cgttgcgcaa
 661 actattaact ggcgaactac ttactctagc ttcccggcaa caattaatag actggatgga
 721 ggcggataaa gttgcaggac cacttctgcg ctcggccctt ccggctggct ggtttattgc
 781 tgataaatct ggagccggtg agcgtgggtc tcgcggtatc attgcagcac tggggccaga
 841 tggtaagccc tcccgtatcg tagttatcta cacgacgggg agtcaggcaa ctatggatga
 901 acgaaataga cagatcgctg agataggtgc ctcactgatt aagcattggt aactgtcaga
 961 ccaagtttac tcatatatac tttagattga tttaaaactt catttttaat ttaaaaggat
1021 ctaggtgaag atcctttttg ataatctcat gaccaaaatc ccttaacgtg agttttcgtt
1081 ccactgagcg tcagacccg tagaaaagat caaaggatct cttgagatc cttttttct
1141 gcgcgtaatc tgctgcttgc aaacaaaaaa accaccgcta ccagcggtgg tttgtttgcc
1201 ggatcaagag ctaccaactc tttttccgaa ggtaactggc ttcagcagag cgcagatacc
1261 aaatactgtc cttctagtgt agccgtagtt aggccaccac ttcaagaact ctgtagcacc
1321 gcctacatac ctcgctctgc taatcctgtt accagtggct gctgccagtg gcgataagtc
1381 gtgtcttacc gggttggact caagacgata gttaccggat aaggcgcagc ggtcgggctg
1441 aacggggggt tcgtgcacac agcccagctt ggagcgaacg acctacaccg aactgagata
1501 cctacagcgt gagcattgag aaagcgccac gcttcccgaa gggagaaagg cggacaggta
1561 tccggtaagc ggcagggtcg gaacaggaga gcgcacgagg gagcttccag ggggaaacgc
1621 ctggtatctt tatagtcctg tcgggtttcg ccacctctga cttgagcgtc gatttttgtg
1681 atgctcgtca gggggcgga gcctatggaa aaacgccagc aacgcggcct ttttacggtt
1741 cctggccttt tgctggcctt ttgctcacat gttctttcct gcgttatccc ctgattctgt
1801 ggataaccgt attaccgcct ttgagtgagc tgataccgct cgccgcagcc gaacgaccga
1861 gcgcagcgag tcagtgagcg aggaagcgga agagcgcctg atgcggtatt ttctccttac
1921 gcatctgtgc ggtatttcac accgcatata ggtgcactc tcagtacaat ctgctctgat
1981 gccgcatagt taagccagta tacactccgc tatcgctacg tgactgggtc atggctgcgc
2041 cccgacaccc gccaacaccc gctgacgcgc cctgacgggc ttgtctgctc cggcatccg
2101 cttacagaca agctgtgacc gtctccggga gctgcatgtg tcagaggttt tcaccgtcat
2161 caccgaaacg cgcgaggcag ctgcggtaaa gctcatcagc gtggtcgtga agcgattcac
```

Figure 11 (Contd.)

```
2221 agatgtctgc ctgttcatcc gcgtccagct cgttgagttt ctccagaagc gttaatgtct
2281 ggcttctgat aaagcgggcc atgttaaggg cggttttttc ctgtttggtc acttgatgcc
2341 tccgtgtaag ggggaatttc tgttcatggg ggtaatgata ccgatgaaac gagagaggat
2401 gctcacgata cgggttactg atgatgaaca tgcccggtta ctggaacgtt gtgagggtaa
2461 acaactggcg gtatggatgc ggcgggacca gagaaaaatc actcagggtc aatgccagcg
2521 cttcgttaat acagatgtag gtgttccaca gggtagccag cagcatcctg cgatgcagat
2581 ccggaacata atggtgcagg gcgctgactt ccgcgtttcc agactttacg aaacacggaa
2641 accgaagacc attcatgttg ttgctcaggt cgcagacgtt ttgcagcagc agtcgcttca
2701 cgttcgctcg cgtatcggtg attcattctg ctaaccagta aggcaacccc gccagcctag
2761 ccgggtcctc aacgacagga gcacgatcat gcgcacccgt ggccaggacc caacgctgcc
2821 cgagatgcgc cgcgtgcggc tgctggagat ggcggacgcg atggatatgt tctgccaagg
2881 gttggtttgc gcattcacag ttctccgcaa gaattgattg ctccaattc ttggagtggt
2941 gaatccgtta gcgaggtgcc gccggcttcc attcaggtcg aggtggcccg gctccatgca
3001 ccgcgacgca acgcggggag gcagacaagg tatagggcgg cgcctacaat ccatgccaac
3061 ccgttccatg tgctcgccga ggcggcataa atcgccgtga cgatcagcgg tccagtgatc
3121 gaagttaggc tggtaagagc cgcgagcgat ccttgaagct gtccctgatg gtcgtcatct
3181 acctgcctgg acagcatggc ctgcaacgcg ggcatcccga tgccgccgga agcgagaaga
3241 atcataatgg ggaaggccat ccagcctcgc gtcgcgaacg ccagcaagac gtagcccagc
3301 gcgtcggcca gcttgcaatt cgcgctaact tacattaatt gcgttgcgct cactgcccgc
3361 tttccagtcg ggaaacctgt cgtgccagct gcattaatga atcggccaac gcgcggggag
3421 aggcggtttg cgtattgggc gccagggtgg ttttctttt caccagtgag acgggcaaca
3481 gctgattgcc cttcaccgcc tggccctgag agagttgcag caagcggtcc acgctggttt
3541 gccccagcag gcgaaaatcc tgtttgatgg tggttgacgg cgggatataa catgagctgt
3601 cttcggtatc gtcgtatccc actaccgaga tatccgcacc aacgcgcagc ccggactcgg
3661 taatggcgcg cattgcgcc agcgccatct gatcgttgcc aaccagcatc gcagtgggaa
3721 cgatgccctc attcagcatt tgcatggttt gttgaaaacc ggacatggca ctccagtcgc
3781 cttcccgttc cgctatcggc tgaatttgat tgcgagtgag atatttatgc cagccagcca
3841 gacgcagacg cgccgagaca gaacttaatg gtcccgctaa cagcgcgatt tgctgatgac
3901 ccaatgcgac cagatgctcc acgcccagtc gcgtaccgtc ttcatgggag aaaataatac
3961 tgttgatggg tgtctggtca gagacatcaa gaaataacgc cggaacatta gtgcaggcag
4021 cttccacagc aatggcatcc tggtcatcca gcggatagtt aatgatcagc ccactgacgc
4081 gttgcgcgag aagattgtgc accgccgctt tacaggcttc gacgccgctt cgttctacca
4141 tcgacaccac cacgctggca cccagttgat cggcgcgaga tttaatcgcc gcgacaattt
4201 gcgacggcgc gtgcagggcc agactggagg tggcaacgcc aatcagcaac gactgtttgc
4261 ccgccagttg ttgtgccacg cggttgggaa tgtaattcag ctccgccatc gccgcttcca
4321 cttttttccg cgttttcgca gaaacgtggc tggcctggtt caccacgcgg gaaacggtct
4381 gataagagac accggcatac tctgcgacat cgtataacgt tactggtttc acattcacca
4441 ccctgaattg actctcttcc gggcgctatc atgccatacc gcgaaggtt ttgcgccatt
4501 cgatggtgtc aacgtaaatg catgccgctt cgccttcgcg cgcgaattgc aagctgatcc
4561 ggagcttatc gactgcacgg tgcaccaatg cttctggcgt caggcagcca tcggaagctg
4621 tggtatggct gtgcaggtcg taaatcactg cataattcgt gtcgctcaag gcgcactccc
4681 gttctggata atgttttttg cgccgacatc ataacggttc tggcaaatat tctgaaatga
4741 gctgttgaca attaatcatc ggctcgtata atgtgtggaa ttgtgagcgg ataacaattt
4801 cacacaggaa acagaattcc atatgaaata cctattacca acagcacag ctgggttatt
4861 attgctcgct gcgcagccgg ccatgcccca ggtcaccgtc tcctcagaca aaactcacac
4921 atgcccaccg tgcccagcac ctgaactcct gggggaccg tcagtcttcc tcttccccc
4981 aaaacccaag gacaccctca tgatctcccg gacccctgag gtcacatgcg tggtggtgga
5041 cgtgagccac gaagaccctg aggtcaagtt caactggtac gtggacggcg tggaggtgca
5101 taatgccaag acaaagccgc gggaggagca gtacaacagc acgtaccggg tggtcagcgt
5161 cctcaccgtc ctgcaccagg actggctgaa tggcaaggag tacaagtgca aggtctccaa
5221 caaagccctc ccagccccca tcgagaaaac catctccaaa gccaagggc agccccgaga
5281 accacaggtg tacaccctgc cccatcccg ggatgagctg accaagaacc aggtcagcct
5341 gacctgcctg gtcaaaggct tctatccag cgacatcgcc gtggagtggg agagcaatgg
5401 gcagccggag aacaactaca agaccacgcc tcccgtgctg gactccacg ctccttctt
5461 cctctacagc aagctcaccg tggacaagag caggtggcag caggggaacg tcttctcatg
5521 ctccgtgatg catgaggctc tgcacaacca ctacacgcag aagagcctct ccctgtctcc
5581 gggtaaagcg gccgcagaac aaaaactcat ctcagaagag gatctgaatg gggccgtaca
5641 tcaccaccat catcatggga gctaagcttg gctgttttgg cggatgagag aagattttca
```

Figure 11 (Contd.)

```
5701 gcctgataca gattaaatca gaacgcagaa gcggtctgat aaaacagaat ttgcctggcg
5761 gcagtagcgc ggtggtccca cctgacccca tgccgaactc agaagtgaaa cgccgtagcg
5821 ccgatggtag tgtggggtct ccccatgcga gagtagggaa ctgccaggca tcaaataaaa
5881 cgaaaggctc agtcgaaaga ctgggccttt cgttttatct gttgtttgtc ggtgaacgct
5941 ctcctgagta ggacaaatcc gccgggagcg gatttgaacg ttgcgaagca acggcccgga
6001 ggaccctggc gggcaggacg cccgccataa actgccaggc atcaaattaa gcagaaggcc
6061 atcctgacgg atggcctttt tgcgtttcta caaactctt
``` pHCH2CH3γ1

SEQ ID N° 96
```
   1 ttgtttattt ttctaaatac attcaaatat gtatccgctc atgagacaat aaccctgata
  61 aatgcttcaa taatattgaa aaggaagag tatgagtatt caacatttcc gtgtcgccct
 121 tattccctt tttgcggcat tttgccttcc tgtttttgct cacccagaaa cgctggtgaa
 181 agtaaaagat gctgaagatc agttgggtgc acgagtgggt tacatcgaac tggatctcaa
 241 cagcggtaag atccttgaga gttttcgccc cgaagaacgt tttccaatga tgagcacttt
 301 taaagttctg ctatgtggcg cggtattatc ccgtgttgac gccgggcaag agcaactcgg
 361 tcgccgcata cactattctc agaatgactt ggttgagtac tcaccagtca cagaaaagca
 421 tcttacggat ggcatgacag taagagaatt atgcagtgct gccataacca tgagtgataa
 481 cactgcggcc aacttacttc tgacaacgat cggaggaccg aaggagctaa ccgcttttt
 541 gcacaacatg ggggatcatg taactcgcct tgatcgttgg gaaccgagc tgaatgaagc
 601 cataccaaac gacgagcgtg acaccacgat gcctgtagca atggcaacaa cgttgcgcaa
 661 actattaact ggcgaactac ttactctagc ttcccggcaa caattaatag actggatgga
 721 ggcggataaa gttgcaggac cacttctgcg ctcggccctt ccggctggct ggtttattgc
 781 tgataaatct ggagccggtg agcgtgggtc tcgcggtatc attgcagcac tggggccaga
 841 tggtaagccc tcccgtatcg tagttatcta cacgacgggg agtcaggcaa ctatggatga
 901 acgaaataga cagatcgctg agataggtgc ctcactgatt aagcattggt aactgtcaga
 961 ccaagtttac tcatatatac tttagattga tttaaaactt cattttaat ttaaaaggat
1021 ctaggtgaag atcctttttg ataatctcat gaccaaaatc ccttaacgtg agttttcgtt
1081 ccactgagcg tcagacccg tagaaaagat caaaggatct tcttgagatc ctttttttct
1141 gcgcgtaatc tgctgcttgc aaacaaaaaa accaccgcta ccagcggtgg tttgtttgcc
1201 ggatcaagag ctaccaactc tttttccgaa ggtaactggc ttcagcagag cgcagatacc
1261 aaatactgtc cttctagtgt agccgtagtt aggccaccac ttcaagaact ctgtagcacc
1321 gcctacatac ctcgctctgc taatcctgtt accagtggct gctgccagtg gcgataagtc
1381 gtgtcttacc gggttggact caagacgata gttaccggat aaggcgcagc ggtcgggctg
1441 aacggggggt tcgtgcacac agcccagctt ggagcgaacg acctacaccg aactgagata
1501 cctacagcgt gagcattgag aaagcgccac gcttcccgaa gggagaaagg cggacaggta
1561 tccggtaagc ggcagggtcg gaacaggaga gcgcacgagg gagcttccag ggggaaacgc
1621 ctggtatctt tatagtcctg tcgggtttcg ccacctctga cttgagcgtc gatttttgtg
1681 atgctcgtca ggggggcgga gcctatggaa aaacgccagc aacgcggcct ttttacggtt
1741 cctggccttt tgctgccctt tgctcacat gttctttcct gcgttatccc ctgattctgt
1801 ggataaccgt attaccgcct ttgagtgagc tgataccgct cgccgcagcc gaacgaccga
1861 gcgcagcgag tcagtgagcg aggaagcgga agagcgcctg atgcggtatt tctccttac
1921 gcatctgtgc ggtatttcac accgcatata tggtgcactc tcagtacaat ctgctctgat
1981 gccgcatagt taagccagta tacactccgc tatcgctacg tgactgggtc atggctgcgc
2041 cccgacaccc gccaacaccc gctgacgcgc cctgacgggc ttgtctgctc ccggcatccg
2101 cttacagaca gctgtgacc gtctccggga gctgcatgtg tcagaggttt tcaccgtcat
2161 caccgaaacg cgcgaggcag ctgcggtaaa gctcatcagc gtggtcgtga agcgattcac
2221 agatgtctgc ctgttcatcc gcgtccagct cgttgagttt ctccagaagc gttaatgtct
2281 ggcttctgat aaagcgggcc atgttaaggg cggttttttc ctgtttggtc acttgatgcc
2341 tccgtgtaag ggggaatttc tgttcatggg gtaatgata ccgatgaaac gagagaggat
2401 gctcacgata cgggttactg atgatgaaca tgcccggtta ctggaacgtt gtgagggtaa
2461 acaactggcg gtatggatgc ggcgggacca gagaaaaatc actcagggtc aatgccagcg
2521 cttcgttaat acagatgtag gtgttccaca gggtagccag cagcatcctg cgatgcagat
2581 ccggaacata atggtgcagg gcgctgactt ccgcgtttcc agactttacg aaacacggaa
2641 accgaagacc attcatgttg ttgctcaggt cgcagacgtt tgcagcagc agtcgcttca
2701 cgttcgctcg cgtatcggtg attcattctg ctaaccagta aggcaacccc gccagcctag
2761 ccgggtcctc aacgacagga gcacgatcat gcgcacccgt ggccaggacc caacgctgcc
```

Figure 11 (Contd.)

```
2821 cgagatgcgc cgcgtgcggc tgctggagat ggcggacgcg atggatatgt tctgccaagg
2881 gttggtttgc gcattcacag ttctccgcaa gaattgattg gctccaattc ttggagtggt
2941 gaatccgtta gcgaggtgcc gccggcttcc attcaggtcg aggtggcccg gctccatgca
3001 ccgcgacgca acgcggggag gcagacaagg tatagggcgg cgcctacaat ccatgccaac
3061 ccgttccatg tgctcgccga ggcggcataa atcgccgtga cgatcagcgg tccagtgatc
3121 gaagttaggc tggtaagagc cgcgagcgat ccttgaagct gtccctgatg gtcgtcatct
3181 acctgcctgg acagcatggc ctgcaacgcg gcatcccga tgccgccgga agcgagaaga
3241 atcataatgg ggaaggccat ccagcctcgc gtcgcgaacg ccagcaagac gtagcccagc
3301 gcgtcggcca gcttgcaatt cgcgctaact tacattaatt gcgttgcgct cactgcccgc
3361 tttccagtcg ggaaacctgt cgtgccagct gcattaatga atcggccaac gcgcggggag
3421 aggcggtttg cgtattgggc gccagggtgg ttttctttt caccagtgag acgggcaaca
3481 gctgattgcc cttcaccgcc tggccctgag agagttgcag caagcggtcc acgctggttt
3541 gccccagcag gcgaaaatcc tgtttgatgg tggttgacgg cgggatataa catgagctgt
3601 cttcggtatc gtcgtatccc actaccgaga tatccgcacc aacgcgcagc ccggactcgg
3661 taatggcgcg cattgcgccc agcgccatct gatcgttggc aaccagcatc gcagtgggaa
3721 cgatgccctc attcagcatt tgcatggttt gttgaaaacc ggacatggca ctccagtcgc
3781 cttcccgttc cgctatcggc tgaatttgat tgcgagtgag atatttatgc cagccagcca
3841 gacgcagacg cgccgagaca gaacttaatg gtcccgctaa cagcgcgatt tgctgatgac
3901 ccaatgcgac cagatgctcc acgcccagtc gcgtaccgtc ttcatgggag aaaataatac
3961 tgttgatggg tgtctggtca gagacatcaa gaaataacgc cggaacatta gtgcaggcag
4021 cttccacagc aatggcatcc tggtcatcca gcggatagtt aatgatcagc ccactgacgc
4081 gttgcgcgag aagattgtgc accgccgctt tacaggcttc gacgccgctt cgttctacca
4141 tcgacaccac cacgctggca cccagttgat cggcgcgaga tttaatcgcc gcgacaattt
4201 gcgacggcgc gtgcagggcc agactggagg tggcaacgcc aatcagcaac gactgtttgc
4261 ccgccagttg ttgtgccacg cggttgggaa tgtaattcag ctccgccatc gccgcttcca
4321 cttttcccg cgttttcgca gaaacgtggc tggcctggtt caccacgcgg gaaacggtct
4381 gataagagac accggcatac tctgcgacat cgtataacgt tactggtttc acattcacca
4441 ccctgaattg actctcttcc gggcgctatc atgccatacc gcgaaaggtt ttgcgccatt
4501 cgatggtgtc aacgtaaatg catgccgctt cgccttcgcg cgcgaattgc aagctgatcc
4561 ggagcttatc gactgcacgg tgcaccaatg cttctggcgt caggcagcca tcggaagctg
4621 tggtatggct gtgcaggtcg taaatcactg cataattcgt gtcgctcaag gcgcactccc
4681 gttctggata atgttttttg cgccgacatc ataacggttc tggcaaatat tctgaaatga
4741 gctgttgaca attaatcatc ggctcgtata atgtgtggaa ttgtgagcgg ataacaattt
4801 cacacaggaa acagaattcc atatgaaata cctattacca acagcagcag ctgggttatt
4861 attgctcgct gcgcagccgg ccatggccca ggtcaccgtc tcctcagaca aaactcacac
4921 atgccaccg tgcccagcac ctgaactcct ggggggaccg tcagtcttcc tcttcccccc
4981 aaaacccaag gacaccctca tgatctcccg gacccctgag gtcacatgcg tggtggtgga
5041 cgtgagccac gaagacctg aggtcaagtt caactggtac gtggacggcg tggaggtgca
5101 taatgccaag acaaagccgc gggaggagca gtacaacagc acgtaccggg tggtcagcgt
5161 cctcaccgtc ctgcaccagg actggctgaa tggcaaggag tacaagtgca aggtctccaa
5221 caaagccctc ccagccccca tcgagaaaac catctccaaa gccaaaggc agccccgaga
5281 accacaggtg tacaccctgc ccccatcccg ggatgagctg accaagaacc aggtcagcct
5341 gacctgcctg gtcaaaggct tctatcccag cgacatcgcc gtggagtggg agagcaatgg
5401 gcagccggag aacaactaca agaccacgcc tcccgtgctg gactccgacg gctccttctt
5461 cctctacagc aagctcaccg tggacaagag caggtggcag cagggaacg tcttctcatg
5521 ctccgtgatg catgaggctc tgcacaacca ctacacgcag aagagcctct ccctgtctcc
5581 gggtaaataa gcttggctgt tttggcggat gagagaagat tttcagcctg atacagatta
5641 aatcagaacg cagaagcggt ctgataaaac agaatttgcc tggcggcagt agcgcggtgg
5701 tcccacctga ccccatgccg aactcagaag tgaaacgccg tagcgccgat ggtagtgtgg
5761 ggtctcccca tgcgagagta gggaactgcc aggcatcaaa taaaacgaaa ggctcagtcg
5821 aaagactggg cctttcgttt tatctgttgt ttgtcggtga acgctctcct gagtaggaca
5881 aatccgccgg gagcggattt gaacgttgcg aagcaacggc ccggaggacc ctggcgggca
5941 ggacgcccgc cataaactgc caggcatcaa attaagcaga aggccatcct gacggatggc
6001 cttttttgcgt ttctacaaac tctt
```

P55CKFlag/RBS/35cmyc6HisGS

SEQ ID N° 97

Figure 11 (Contd.)

```
   1 ttgtttattt ttctaaatac attcaaatat gtatccgctc atgagacaat aaccctgata
  61 aatgcttcaa taatattgaa aaaggaagag tatgagtatt caacatttcc gtgtcgccct
 121 tattcccttt tttgcggcat tttgccttcc tgtttttgct cacccagaaa cgctggtgaa
 181 agtaaaagat gctgaagatc agttgggtgc acgagtgggt tacatcgaac tggatctcaa
 241 cagcggtaag atccttgaga gtttcgccc cgaagaacgt tttccaatga tgagcacttt
 301 taaagttctg ctatgtggcg cggtattatc ccgtgttgac gccgggcaag agcaactcgg
 361 tcgccgcata cactattctc agaatgactt ggttgagtac tcaccagtca cagaaaagca
 421 tcttacggat ggcatgacag taagagaatt atgcagtgct gccataacca tgagtgataa
 481 cactgcggcc aacttacttc tgacaacgat cggaggaccg aaggagctaa ccgcttttt
 541 gcacaacatg ggggatcatg taactcgcct tgatcgttgg gaaccggagc tgaatgaagc
 601 cataccaaac gacgagcgtg acaccacgat gcctgtagca atggcaacaa cgttgcgcaa
 661 actattaact ggcgaactac ttactctagc ttcccggcaa caattaatag actggatgga
 721 ggcggataaa gttgcaggac cacttctgcg ctcggccctt ccggctggct ggtttattgc
 781 tgataaatct ggagccggtg agcgtgggtc tcgcggtatc attgcagcac tggggccaga
 841 tggtaagccc tcccgtatcg tagttatcta cacgacgggg agtcaggcaa ctatggatga
 901 acgaaataga cagatcgctg atataggtgc ctcactgatt aagcattggt aactgtcaga
 961 ccaagtttac tcatatatac tttagattga tttaaaactt cattttaat ttaaaaggat
1021 ctaggtgaag atccttttg ataatctcat gaccaaaatc ccttaacgtg agttttcgtt
1081 ccactgagcg tcagacccg tagaaaagat caaggatct tcttgagatc cttttttct
1141 gcgcgtaatc tgctgcttgc aaacaaaaaa accaccgcta ccagcggtgg tttgtttgcc
1201 ggatcaagag ctaccaactc ttttccgaa ggtaactggc ttcagcagag cgcagatacc
1261 aaatactgtc cttctagtgt agccgtagtt aggccaccac ttcaagaact ctgtagcacc
1321 gcctacatac ctcgctctgc taatcctgtt accagtggct gctgccagtg gcgataagtc
1381 gtgtcttacc gggttggact caagacgata gttaccggat aaggcgcagc ggtcgggctg
1441 aacgggggt tcgtgcacac agcccagctt ggagcgaacg acctacaccg aactgagata
1501 cctacagcgt gagcattgag aaagcgccac gcttcccgaa gggagaaagg cggacaggta
1561 tccggtaagc ggcagggtcg gaacaggaga gcgcacgagg gagcttccag ggggaaacgc
1621 ctggtatctt tatagtcctg tcgggtttcg ccacctctga cttgagcgtc gatttttgtg
1681 atgctcgtca ggggggcgga gcctatggaa aaacgccagc aacgcggcct ttttacggtt
1741 cctggccttt tgctggcctt ttgctcacat gttctttcct gcgttatccc ctgattctgt
1801 ggataaccgt attaccgcct ttgagtgagc tgataccgct cgccgcagcc gaacgaccga
1861 gcgcagcgag tcagtgagcg aggaagcgga agagcgcctg atgcggtatt ttctccttac
1921 gcatctgtgc ggtatttcac accgcatata tggtgcactc tcagtacaat ctgctctgat
1981 gccgcatagt taagccagta tacactccgc tatcgctacg tgactgggtc atggctgcgc
2041 cccgacaccc gccaacaccc gctgacgcgc cctgacgggc ttgtctgctc ccggcatccg
2101 cttacagaca agctgtgacc gtctccggga gctgcatgtg tcagaggttt tcaccgtcat
2161 caccgaaacg cgcgaggcag ctcggtaaa gctcatcagc gtggtcgtga agcgattcac
2221 agatgtctgc ctgttcatcc gcgtccagct cgttgagttt ctccagaagc gttaatgtct
2281 ggcttctgat aaagcgggcc atgttaaggg cggtttttc ctgtttggtc acttgatgcc
2341 tccgtgtaag ggggaatttc tgttcatggg ggtaatgata ccgatgaaac gagagaggat
2401 gctcacgata cgggttactg atgatgaaca tgcccggtta ctggaacgtt gtgagggtaa
2461 acaactggcg gtatggatgc ggcgggacca gagaaaaatc actcaggtc aatgccagcg
2521 cttcgttaat acagatgtag gtgttccaca gggtagccag cagcatcctg cgatgcagat
2581 ccggaacata atggtgcagg gcgctgactt ccgcgtttcc agactttacg aaacacggaa
2641 accgaagacc attcatgttg ttgctcaggt cgcagacgtt ttgcagcagc agtcgcttca
2701 cgttcgctcg cgtatcggtg attcattctg ctaaccagta aggcaacccc gccagcctag
2761 ccgggtcctc aacgacagga gcacgatcat gcgcacccgt ggccaggacc caacgctgcc
2821 cgagatgcgc cgcgtgcggc tgctggagat ggcggacgcg atggatatgt tctgccaagg
2881 gttggtttgc gcattcacag ttctccgcaa gaattgattg gctccaattc ttggagtggt
2941 gaatccgtta gcgaggtgcc gccggcttcc attcaggtcg aggtggcccg gctccatgca
3001 ccgcgacgca acgcggggag gcagacaagg tatagggcgg cgcctacaat ccatgccaac
3061 ccgttccatg tgctcgccga ggcggcataa atcgccgtga cgatcagcgg tccagtgatc
3121 gaagttaggc tggtaagagc cgcgagcgat ccttgaagct gtccctgatg gtcgtcatct
3181 acctgcctgg acagcatggc ctgcaacgcg gcatcccga tgccgccgga agcgagaaga
3241 atcataatgg ggaaggccat ccagcctcgc gtcgcgaacg ccagcaagac gtagcccagc
3301 gcgtcggcca gcttgcaatt cgcgctaact tacattaatt gcgttgcgct cactgccgc
3361 tttccagtcg ggaaacctgt cgtgccagct gcattaatga atcggccaac gcgcggggag
3421 aggcggtttg cgtattgggc gccagggtgg tttttctttt caccagtgag acgggcaaca
```

Figure 11 (Contd.)

```
3481 gctgattgcc cttcaccgcc tggccctgag agagttgcag caagcggtcc acgctggttt
3541 gccccagcag gcgaaaatcc tgtttgatgg tggttgacgg cgggatataa catgagctgt
3601 cttcggtatc gtcgtatccc actaccgaga tatccgcacc aacgcgcagc ccggactcgg
3661 taatggcgcg cattgcgccc agcgccatct gatcgttggc aaccagcatc gcagtgggaa
3721 cgatgccctc attcagcatt tgcatggttt gttgaaaacc ggacatggca ctccagtcgc
3781 cttccgttc cgctatcggc tgaatttgat tgcgagtgag atatttatgc cagccagcca
3841 gacgcagacg cgccgagaca gaacttaatg gtcccgctaa cagcgcgatt tgctgatgac
3901 ccaatgcgac cagatgctcc acgcccagtc gcgtaccgtc ttcatgggag aaaataatac
3961 tgttgatggg tgtctggtca gagacatcaa gaaataacgc cggaacatta gtgcaggcag
4021 cttccacagc aatggcatcc tggtcatcca gcggatagtt aatgatcagc ccactgacgc
4081 gttgcgcgag aagattgtgc accgccgctt tacaggcttc gacgccgctt cgttctacca
4141 tcgacaccac cacgctggca cccagttgat cggcgcgaga tttaatcgcc gcgacaattt
4201 gcgacggcgc gtgcagggcc agactggagg tggcaacgcc aatcagcaac gactgtttgc
4261 ccgccagttg ttgtgccacg cggttgggaa tgtaattcag ctccgccatc gccgcttcca
4321 cttttccccg cgttttcgca gaaacgtggc tggcctggtt caccacgcgg gaaacggtct
4381 gataagagac accggcatac tctgcgacat cgtataacgt tactggtttc acattcacca
4441 ccctgaattg actctcttcc gggcgctatc atgccatacc gcgaaaggtt ttgcgccatt
4501 cgatggtgtc aacgtaaatg catgccgctt cgccttcgcg cgcgaattgc aagctgatcc
4561 ggagcttatc gactgcacgg tgcaccaatg cttctggcgt caggcagcca tcggaagctg
4621 tggtatggct gtgcaggtcg taaatcactg cataattcgt gtcgctcaag gcgcactccc
4681 gttctggata atgttttttg cgccgacatc ataacggttc tgcaaatat tctgaaatga
4741 gctgttgaca attaatcatc ggctcgtata atgtgtggaa ttgtgagcgg ataacaattt
4801 cacacaggaa acagaattcc atatgaaata cctattacca acagcagcag ctgggttatt
4861 attgctcgct gcgcagccgg ccatggccca ggtcaccgtc tcctcaggta ccgtggctgc
4921 accatctgtc ttcatcttcc cgccatctga tgagcagttg aaatctggaa ctgcctctgt
4981 tgtgtgcctg ctgaataact tctatcccag agaggccaaa gtacagtgga aggtggataa
5041 cgccctccaa tcgggtaact cccaggagag tgtcacagag caggacagca aggacagcac
5101 ctacagcctc agcagcaccc tgacgctgag caaagcagac tacgagaaac acaaagtcta
5161 cgcctgcgaa gtcacccatc agggcctgag ctcgccggtg acaaagagct caaccgcgg
5221 agagtgtgca ggtgattaca aagacgatga cgataagtaa taaacaggaa acagaagtcc
5281 atatgaaata cctattgcct acggcagccg ctggattgtt attactcgcg gcccagccgg
5341 ccatggccgc tagcgcggcg gcagaacaaa aactcatctc agaagaggat ctgaatgggg
5401 ccgtacatca ccaccatcat catgggagct aagcttggct gttttggcgg atgagagaag
5461 attttcagcc tgatacagat taaatcagaa cgcagaagcg gtctgataaa acagaatttg
5521 cctggcggca gtagcgcggt ggtcccacct gaccccatgc cgaactcaga agtgaaacgc
5581 cgtagcgccg atggtagtgt ggggtctccc catgcgagag tagggaactg ccaggcatca
5641 aataaaacga aaggctcagt cgaaagactg gcctttcgt tttatctgtt gtttgtcggt
5701 gaacgctctc ctgagtagga caaatccgcc gggagcggat ttgaacgttg cgaagcaacg
5761 gcccggagga ccctggcggg caggacgccc gccataaact gccaggcatc aaattaagca
5821 gaaggccatc ctgacggatg gcctttttgc gtttctacaa actctt
```

```
SEQ ID N° 111
    1 ttgtttattt ttctaaatac attcaaatat gtatccgctc atgagacaat aaccctgata
   61 aatgcttcaa taatattgaa aaaggaagag tatgagtatt caacatttcc gtgtcgccct
  121 tattcccttt tttgcggcat tttgccttcc tgttttgct cacccagaaa cgctggtgaa
  181 agtaaaagat gctgaagatc agttgggtgc acgagtgggt tacatcgaac tggatctcaa
  241 cagcggtaag atccttgaga gttttcgccc cgaagaacgt tttccaatga tgagcacttt
  301 taaagttctg ctatgtggcg cggtattatc ccgtgttgac gccgggcaag agcaactcgg
  361 tcgccgcata cactattctc agaatgactt ggttgagtac tcaccagtca cagaaaagca
  421 tcttacggat ggcatgacag taagagaatt atgcagtgct gccataacca tgagtgataa
  481 cactgcggcc aacttacttc tgacaacgat cggaggaccg aaggagctaa ccgcttttt
  541 gcacaacatg gggatcatg taactcgcct tgatcgttgg gaaccggagc tgaatgaagc
  601 cataccaaac gacgagcgtg acaccacgat gcctgtagca atggcaacaa cgttgcgcaa
  661 actattaact ggcgaactac ttactctagc ttcccggcaa caattaatag actggatgga
  721 ggcggataaa gttgcaggac cacttctgcg ctcggccctt ccggctggct ggtttattgc
  781 tgataaatct ggagccggtg agcgtgggtc tcgcggtatc attgcagcac tggggccaga
  841 tggtaagccc tcccgtatcg tagttatcta cacgacgggg agtcaggcaa ctatggatga
  901 acgaaataga cagatcgctg agataggtgc ctcactgatt aagcattggt aactgtcaga
```

Figure 11 (Contd.)

```
 961 ccaagtttac tcatatatac tttagattga tttaaaactt catttttaat ttaaaaggat
1021 ctaggtgaag atcctttttg ataatctcat gaccaaaatc ccttaacgtg agttttcgtt
1081 ccactgagcg tcagaccccg tagaaaagat caaaggatct tcttgagatc ctttttttct
1141 gcgcgtaatc tgctgcttgc aaacaaaaaa accaccgcta ccagcggtgg tttgtttgcc
1201 ggatcaagag ctaccaactc ttttttccgaa ggtaactggc ttcagcagag cgcagatacc
1261 aaatactgtc cttctagtgt agccgtagtt aggccaccac ttcaagaact ctgtagcacc
1321 gcctacatac ctcgctctgc taatcctgtt accagtggct gctgccagtg gcgataagtc
1381 gtgtcttacc gggttggact caagacgata gttaccggat aaggcgcagc ggtcgggctg
1441 aacgggggggt tcgtgcacac agcccagctt ggagcgaacg acctacaccg aactgagata
1501 cctacagcgt gagcattgag aaagcgccac gcttcccgaa gggagaaagg cggacaggta
1561 tccggtaagc ggcagggtcg gaacaggaga cgcacgagg gagcttccag ggggaaacgc
1621 ctggtatctt tatagtcctg tcgggtttcg ccacctctga cttgagcgtc gatttttgtg
1681 atgctcgtca gggggggcgga gcctatggaa aaacgccagc aacgcggcct ttttacggtt
1741 cctggccttt tgctggcctt ttgctcacat gttctttcct gcgttatccc ctgattctgt
1801 ggataaccgt attaccgcct ttgagtgagc tgataccgct cgccgcagcc gaacgaccga
1861 gcgcagcgag tcagtgagcg aggaagcgga agagcgcctg atgcggtatt ttctccttac
1921 gcatctgtgc ggtatttcac accgcatata tggtgcactc tcagtacaat ctgctctgat
1981 gccgcatagt taagccagta tacactccgc tatcgctacg tgactgggtc atggctgcgc
2041 cccgacaccc gccaacaccc gctgacgcgc cctgacgggc ttgtctgctc ccggcatccg
2101 cttacagaca agctgtgacc gtctccggga gctgcatgtg tcagaggttt tcaccgtcat
2161 caccgaaacg cgcgaggcag ctgcggtaaa gctcatcagc gtggtcgtga agcgattcac
2221 agatgtctgc ctgttcatcc gcgtccagct cgttgagttt ctccagaagc gttaatgtct
2281 ggcttctgat aaagcgggcc atgttaaggg cggttttttc ctgtttggtc acttgatgcc
2341 tccgtgtaag ggggaatttc tgttcatggg ggtaatgata ccgatgaaac gagagaggat
2401 gctcacgata cgggttactg atgatgaaca tgcccggtta ctggaacgtt gtgagggtaa
2461 acaactggcg gtatggatgc ggcgggacca gagaaaaatc actcagggtc aatgccagcg
2521 cttcgttaat acagatgtag gtgttccaca gggtagccag cagcatcctg cgatgcagat
2581 ccggaacata atggtgcagg gcgctgactt ccgcgtttcc agactttacg aaacacggaa
2641 accgaagacc attcatgttg ttgctcaggt cgcagacgtt ttgcagcagc agtcgcttca
2701 cgttcgctcg cgtatcggtg attcattctg ctaaccagta aggcaacccc gccagcctag
2761 ccgggtcctc aacgacagga gcacgatcat ggcgcaccgt ggccaggacc caacgctgcc
2821 cgagatgcgc cgcgtgcggc tgctggagat ggcggacgcg atggatatgt tctgccaagg
2881 gttggtttgc gcattcacag ttctccgcaa gaattgattg gctccaattc ttggagtggt
2941 gaatccgtta gcgaggtgcc gccggcttcc attcaggtcg aggtggcccg gctccatgca
3001 ccgcgacgca acgcggggag gcagacaagg tatagggcgg cgcctacaat ccatgccaac
3061 ccgttccatg tgctcgccga ggcggcataa atcgccgtga cgatcagcgg tccagtgatc
3121 gaagttaggc tggtaagagc cgcgagcgat ccttgaagct gtccctgatg gtcgtcatct
3181 acctgcctgg acagcatggc ctgcaacgcg gcatcccga tgccgccgga agcgagaaga
3241 atcataatgg ggaaggccat ccagcctcgc gtcgcgaacg ccagcaagac gtagcccagc
3301 gcgtcggcca gcttgcaatt cgcgctaact tacattaatt gcgttgcgct cactgcccgc
3361 tttccagtcg ggaaacctgt cgtgccagct gcattaatga atcggccaac gcgcggggag
3421 aggcggtttg cgtattgggc gccaggtgg ttttcttttt caccagtgag acgggcaaca
3481 gctgattgcc cttcaccgcc tggccctgag agagttgcag caagcggtcc acgctggttt
3541 gccccagcag gcgaaaatcc tgtttgatgg tggttgacgg cgggatataa catgagctgt
3601 cttcggtatc gtcgtatccc actaccgaga tatccgcacc aacgcgcagc ccggactcgg
3661 taatggcgcg cattgcgccc agcgccatct gatcgttggc aaccagcatc gcagtgggaa
3721 cgatgccctc attcagcatt tgcatggttt gttgaaaacc ggacatggca ctccagtcgc
3781 cttcccgttc cgctatcggc tgaatttgat tgcgagtgag atatttatgc cagccagcca
3841 gacgcagacg cgccgagaca gaacttaatg gtccgctaa cagcgcgatt tgctgatgac
3901 ccaatgcgac cagatgctcc acgccagtc gcgtaccgtc ttcatggag aaaataatac
3961 tgttgatggg tgtctggtca gagacatcaa gaaataacgc cggaacatta gtgcaggcag
4021 cttccacagc aatggcatcc tggtcatcca gcggatagtt aatgatcagc ccactgacgc
4081 gttgcgcgag aagattgtgc accgccgctt tacaggcttc gacgccgctt cgttctacca
4141 tcgacaccac cacgctgca cccagttgat cggcgcgaga tttaatcgcc gcgacaattt
4201 gcgacgcgc gtgcagggcc agactggagg tggcaacgcc aatcagcaac gactgtttgc
4261 ccgccagttg ttgtgccacg cggttgggaa tgtaattcag ctccgccatc gccgcttcca
4321 cttttttcccg cgttttcgca gaaacgtggc tggcctggtt caccacgcgg gaaacggtct
4381 gataagagac accggcatac tctgcgacat cgtataacgt tactggtttc acattcacca
```

Figure 11 (Contd.)

```
4441 ccctgaattg actctcttcc gggcgctatc atgccatacc gcgaaaggtt ttgcgccatt
4501 cgatggtgtc aacgtaaatg catgccgctt cgccttcgcg cgcgaattgc aagctgatcc
4561 ggagcttatc gactgcacgg tgcaccaatg cttctggcgt caggcagcca tcggaagctg
4621 tggtatggct gtgcaggtcg taaatcactg cataattcgt gtcgctcaag gcgcactccc
4681 gttctggata atgtttttg cgccgacatc ataacggttc tggcaaatat tctgaaatga
4741 gctgttgaca attaatcatc ggctcgtata atgtgtggaa ttgtgagcgg ataacaattc
4801 cacacaggaa acagaattcc atatgaaata cctattacca acagcagcag ctgggttatt
4861 attgctcgct gcgcagccgg ccatggccca ggtcaccgtc tcctcacgta cggtggctgc
4921 accatctgtc ttcatcttcc cgccatctga tgagcagttg aaatctggaa ctgcctctgt
4981 tgtgtgcctg ctgaataact ctatcccag agaggccaaa gtacagtgga aggtggataa
5041 cgccctccaa tcgggtaact cccaggagag tgtcacagag caggacagca aggacagcac
5101 ctacagcctc agcagcaccc tgacgctgag caaagcagac tacgagaaac acaaagtcta
5161 cgcctgcgaa gtcacccatc agggcctgag ctcgccggtg acaaagagct tcaaccgcgg
5221 agagtgtgca ggtgattaca aagacgatga cgataagtaa taaacaggaa acagaagtcc
5281 atatgaaata tcttttacct acggcagccg caggttgtt gttactcgcg gcccagccgg
5341 ccatggccgc tagcgcggcc gcagaacaaa aactcatctc agaagaggat ctgaatgggg
5401 ccgtacatca ccaccatcat catggagct aagcttggct gttttggcgg atgagagaag
5461 attttcagcc tgatacagat taaatcagaa cgcagaagcg gtctgataaa acagaatttg
5521 cctggcggca gtagcgcggt ggtcccacct gaccccatgc cgaactcaga agtgaaacgc
5581 cgtagcgccg atggtagtgt ggggtctccc catgcgagag tagggaactg ccaggcatca
5641 aataaaacga aaggctcagt cgaaagactg ggcctttcgt tttatctgtt gtttgtcggt
5701 gaacgctctc ctgagtagga caaatccgcc gggagcggat ttgaacgttg cgaagcaacg
5761 gcccggagga ccctggcggg caggacgccc gccataaact gccaggcatc aaattaagca
5821 gaaggccatc ctgacggatg gcctttttgc gtttctacaa actctt
``` pcKcH1γ1-TAG

SEQ ID N° 98
```
   1 ttgtttattt ttctaaatac attcaaatat gtatccgctc atgagacaat aaccctgata
  61 aatgcttcaa taatattgaa aaaggaagag tatgagtatt caacatttcc gtgtcgccct
 121 tattcccttt tttgcggcat tttgccttcc tgttttgct cacccagaaa cgctggtgaa
 181 agtaaaagat gctgaagatc agttgggtgc acgagtgggt tacatcgaac tggatctcaa
 241 cagcggtaag atccttgaga gttttcgccc cgaagaacgt tttccaatga tgagcacttt
 301 taaagttctg ctatgtggcg cggtattatc ccgtgttgac gccgggcaag agcaactcgg
 361 tcgccgcata cactattctc agaatgactt ggttgagtac tcaccagtca cagaaaagca
 421 tcttacggat ggcatgacag taagagaatt atgcagtgct gccataacca tgagtgataa
 481 cactgcggcc aacttacttc tgacaacgat cggaggaccg aaggagctaa ccgcttttt
 541 gcacaacatg gggatcatg taactcgcct tgatcgttgg gaaccggagc tgaatgaagc
 601 cataccaaac gacgagcgt acaccacgat gcctgtagca atggcaacaa cgttgcgcaa
 661 actattaact ggcgaactac ttactctagc ttcccggcaa caattaatag actggatgga
 721 ggcggataaa gttgcaggac cacttctgcg ctcggccctt ccggctggct ggtttattgc
 781 tgataaatct ggagccggtg agcgtgggtc tcgcggtatc attgcagcac tggggccaga
 841 tggtaagccc tcccgtatcg tagttatcta cacgacgggg agtcaggcaa ctatggatga
 901 acgaaataga cagatcgctg agataggtgc ctcactgatt aagcattggt aactgtcaga
 961 ccaagtttac tcatatatac tttagattga tttaaaactt catttttaat ttaaaaggat
1021 ctaggtgaag atcctttttg ataatctcat gaccaaaatc ccttaacgtg agttttcgtt
1081 ccactgagcg tcagaccccg tagaaaagat caaaggatct tcttgagatc cttttttct
1141 gcgcgtaatc tgctgcttgc aaacaaaaaa accaccgcta ccagcggtgg tttgtttgcc
1201 ggatcaagag ctaccaactc tttttccgaa ggtaactggc ttcagcagag cgcagatacc
1261 aaatactgtc cttctagtgt agccgtagtt aggccaccac ttcaagaact ctgtagcacc
1321 gcctacatac ctcgctctgc taatcctgtt accagtggct gctgccagtg gcgataagtc
1381 gtgtcttacc gggttggact caagacgata gttaccggat aaggcgcagc ggtcgggctg
1441 aacggggggt tcgtgcacac agcccagctt ggagcgaacg acctacaccg aactgagata
1501 cctacagcgt gagcattgag aaagcgccac gcttcccgaa gggagaaagg cggacaggta
1561 tccggtaagc ggcaggtcg gaacaggaga gcgcacgagg gagcttccag ggggaaacgc
1621 ctggtatctt tatagtcctg tcgggtttcg ccacctctga cttgagcgtc gatttttgtg
1681 atgctcgtca gggggcgga gcctatggaa aaacgccagc aacgcggcct ttttacggtt
1741 cctggccttt tgctggcctt ttgctcacat gttctttcct gcgttatccc ctgattctgt
```

Figure 11 (Contd.)

```
1801 ggataaccgt attaccgcct ttgagtgagc tgataccgct cgccgcagcc gaacgaccga
1861 gcgcagcgag tcagtgagcg aggaagcgga agagcgcctg atgcggtatt ttctccttac
1921 gcatctgtgc ggtatttcac accgcatata tggtgcactc tcagtacaat ctgctctgat
1981 gccgcatagt taagccagta tacactccgc tatcgctacg tgactgggtc atggctgcgc
2041 cccgacaccc gccaacaccc gctgacgcgc cctgacgggc ttgtctgctc ccggcatccg
2101 cttacagaca agctgtgacc gtctccggga gctgcatgtg tcagaggttt tcaccgtcat
2161 caccgaaacg cgcgaggcag ctgcggtaaa gctcatcagc gtggtcgtga agcgattcac
2221 agatgtctgc ctgttcatcc gcgtccagct cgttgagttt ctccagaagc gttaatgtct
2281 ggcttctgat aaagcgggcc atgttaaggg cggttttttc ctgtttggtc acttgatgcc
2341 tccgtgtaag ggggaatttc tgttcatggg ggtaatgata ccgatgaaac gagagaggat
2401 gctcacgata cgggttactg atgatgaaca tgcccggtta ctggaacgtt gtgagggtaa
2461 acaactggcg gtatggatgc ggcgggacca gagaaaaatc actcagggtc aatgccagcg
2521 cttcgttaat acagatgtag gtgttccaca gggtagccag cagcatcctg cgatgcagat
2581 ccggaacata atggtgcagg gcgctgactt ccgcgtttcc agactttacg aaacacggaa
2641 accgaagacc attcatgttg ttgctcaggt cgcagacgtt ttgcagcagc agtcgcttca
2701 cgttcgctcg cgtatcggtg attcattctg ctaaccagta aggcaacccc gccagcctag
2761 ccgggtcctc aacgacagga gcacgatcat gcgcacccgt ggccaggacc aacgctgcc
2821 cgagatgcgc cgcgtgcggc tgctggagat ggcggacgcg atggatatgt tctgccaagg
2881 gttggtttgc gcattcacag ttctccgcaa gaattgattg gctccaattc ttggagtggt
2941 gaatccgtta gcgaggtgcc gccggcttcc attcaggtcg aggtggcccg gctccatgca
3001 ccgcgacgca acgcggggag gcagacaagg tatagggcgg cgcctacaat ccatgccaac
3061 ccgttccatg tgctcgccga ggcggcataa atcgccgtga cgatcagcgg tccagtgatc
3121 gaagttaggc tggtaagagc cgcgagcgat ccttgaagct gtccctgatg gtcgtcatct
3181 acctgcctgg acagcatggc ctgcaacgcg ggcatcccga tgccgccgga agcgagaaga
3241 atcataatgg ggaaggccat ccagcctcgc gtcgcgaacg ccagcaagac gtagcccagc
3301 gcgtcggcca gcttgcaatt cgcgctaact tacattaatt gcgttgcgct cactgcccgc
3361 tttccagtcg ggaaacctgt cgtgccagct gcattaatga atcggccaac gcgcgggag
3421 aggcggtttg cgtattgggc gccagggtgg ttttcttttt caccagtgag acgggcaaca
3481 gctgattgcc cttcaccgcc tggccctgag agagttgcag caagcggtcc acgctggttt
3541 gccccagcag gcgaaaatcc tgtttgatgg tggttgacgg cgggatataa catgagctgt
3601 cttcggtatc gtcgtatccc actaccgaga tatccgcacc aacgcgcagc ccggactcgg
3661 taatggcgcg cattcgcgcc agcgccatct gatcgttggc aaccagcatc gcagtgggaa
3721 cgatgccctc attcagcatt tgcatggttt gttgaaaacc ggacatggca ctccagtcgc
3781 cttcccgttc cgctatcggc tgaatttgat tgcgagtgag atatttatgc cagccagcca
3841 gacgcagacg cgccgagaca gaacttaatg gtcccgctaa cagcgcgatt tgctgatgac
3901 ccaatgcgac cagatgctcc acgcccagtc gcgtaccgtc ttcatgggag aaaataatac
3961 tgttgatggg tgtctggtca gagacatcaa gaaataacgc cggaacatta gtgcaggcag
4021 cttccacagc aatggcatcc tggtcatcca gcggatagtt aatgatcagc ccactgacgc
4081 gttgcgcgag aagattgtgc accgccgctt tacaggcttc gacgccgctt cgttctacca
4141 tcgacaccac cacgctggca cccagttgat cggcgcgaga tttaatcgcc gcgacaattt
4201 gcgacggcgc gtgcagggcc agactggagg tggcaacgcc aatcagcaac gactgtttgc
4261 ccgccagttg ttgtgccacg cggttgggaa tgtaattcag ctccgccatc gccgcttcca
4321 cttttcccg cgttttcgca gaaacgtggc tggcctggtt caccacgcgg gaaacggtct
4381 gataagagac accggcatac tctgcgacat cgtataacgt tactggtttc acattcacca
4441 ccctgaattg actctcttcc gggcgctatc atgccatacc gcgaaaggtt ttgcgccatt
4501 cgatggtgtc aacgtaaatg catgccgctt cgccttcgcg cgcgaattgc aagctgatcc
4561 ggagcttatc gactgcacgg tgcaccaatg cttctggcgt caggcagcca tcggaagctg
4621 tggtatggct gtgcaggtcg taaatcactg cataattcgt gtcgctcaag gcgcactccc
4681 gttctggata atgttttttg cgccgacatc ataacggttc tggcaaatat tctgaaatga
4741 gctgttgaca attaatcatc ggctcgtata atgtgtggaa ttgtgagcgg ataacaattt
4801 cacacaggaa acagaattcc atatgaaata cctattacca acagcagcag ctgggttatt
4861 attgctcgct gcgcagccgg ccatggccca ggtcaccgtc tcctcaggta ccgtggctgc
4921 accatctgtc ttcatcttcc cgccatctga tgagcagttg aaatctggaa ctgcctctgt
4981 tgtgtgcctg ctgaataact ctatcccag agaggccaaa gtacagtgga aggtggataa
5041 cgccctccaa gtgggtaact cccaggagag tgtcacagag caggacagca aggacagcac
5101 ctacagcctc agcagcaccc tgacgctgag caaagcagac tacgagaaac acaaagtcta
5161 cgcctgcgaa gtcacccatc agggcctgag ctcgccggtg acaaagagct tcaaccgcgg
5221 agagtgtgca ggtgattaca agacgatga cgataagtaa taaacaggaa acagaagtcc
```

Figure 11 (Contd.)

```
    5281 atatgaaata cctattgcct acggcagccg ctggattgtt attactgcg gcccagccgg
    5341 ccatggccgc tagcaccaag ggcccatcgg tcttccccct ggcaccctcc tccaagagca
    5401 cctctggggg cacagcggcc ctgggctgcc tggtcaagga ctacttcccc gaaccggtga
    5461 cggtgtcgtg gaactcaggc gccctgacca gcggcgtgca caccttcccg gctgtcctac
    5521 agtcctcagg actctactcc ctcagcagcg tagtgaccgt gccctccagc agcttgggca
    5581 cccagaccta catctgcaac gtgaatcaca agcccagcaa caccaaggtg gacaagaaag
    5641 ttgagcccaa atcttgtgcg gccgcagaac aaaaactcat ctcagaagag gatctgaatg
    5701 gggccgtaca tcaccaccat catcatggga gctaagcttg gctgttttgg cggatgagag
    5761 aagattttca gcctgataca gattaaatca gaacgcagaa gcggtctgat aaaacagaat
    5821 ttgcctggcg gcagtagcgc ggtggtccca cctgaccca tgccgaactc agaagtgaaa
    5881 cgccgtagcg ccgatggtag tgtggggtct cccccatgcga gagtagggaa ctgccaggca
    5941 tcaaataaaa cgaaaggctc agtcgaaaga ctgggccttt cgttttatct gttgtttgtc
    6001 ggtgaacgct ctcctgagta ggacaaatcc gccgggagcg gatttgaacg ttgcgaagca
    6061 acggcccgga ggaccctggg gggcaggacg cccgccataa actgccaggc atcaaattaa
    6121 gcagaaggcc atcctgacgg atggcctttt tgcgtttcta caaactctt SEQ ID N° 112
       1 ttgtttattt ttctaaatac attcaaatat gtatccgctc atgagacaat aaccctgata
      61 aatgcttcaa taatattgaa aaggaagag tatgagtatt caacatttcc gtgtcgccct
     121 tattcccttt tttgcggcat tttgccttcc tgttttttgct cacccagaaa cgctggtgaa
     181 agtaaaagat gctgaagatc agttgggtgc acgagtgggt tacatcgaac tggatctcaa
     241 cagcggtaag atccttgaga gttttcgccc cgaagaacgt tttccaatga tgagcacttt
     301 taaagttctg ctatgtggcg cggtattatc ccgtgttgac gccgggcaag agcaactcgg
     361 tcgccgcata cactattctc agaatgactt ggttgagtac tcaccagtca cagaaaagca
     421 tcttacggat ggcatgacag taagagaatt atgcagtgct gccataacca tgagtgataa
     481 cactgcggcc aacttacttc tgacaacgat cggaggaccg aaggagctaa ccgcttttttt
     541 gcacaacatg ggggatcatg taactcgcct tgatcgttgg gaaccggagc tgaatgaagc
     601 cataccaaac gacgagcgtg acaccacgat gcctgtagca atggcaacaa cgttgcgcaa
     661 actattaact ggcgaactac ttactctagc ttccggcaa caattaatag actggatgga
     721 ggcggataaa gttgcaggac cacttctgcg ctcggccctt ccggctggct ggtttattgc
     781 tgataaatct ggagccggtg agcgtgggtc tcgcggtatc attgcagcac tggggccaga
     841 tggtaagccc tcccgtatcg tagttatcta cacgacgggg agtcaggcaa ctatgatga
     901 acgaaataga cagatcgctg agataggtgc ctcactgatt aagcattggt aactgtcaga
     961 ccaagtttac tcatatatac tttagattga tttaaaactt cattttttaat ttaaaaggat
    1021 ctaggtgaag atccttttttg ataatctcat gaccaaaatc ccttaacgtg agttttcgtt
    1081 ccactgagcg tcagaccccg tagaaaagat caaaggatct tcttgagatc ctttttttct
    1141 gcgcgtaatc tgctgcttgc aaacaaaaaa accaccgcta ccagcggtgg tttgtttgcc
    1201 ggatcaagag ctaccaactc tttttccgaa ggtaactggc ttcagcagag cgcagatacc
    1261 aaatactgtc cttctagtgt agccgtagtt aggccaccac ttcaagaact ctgtagcacc
    1321 gcctacatac ctcgctctgc taatcctgtt accagtggct gctgccagtg gcgataagtc
    1381 gtgtcttacc gggttggact caagacgata gttaccggat aaggcgcagc ggtcgggctg
    1441 aacgggggt tcgtgcacac agcccagctt ggagcgaacg acctacaccg aactgagata
    1501 cctacagcgt gagcattgag aaagcgccac gcttcccgaa gggagaaagg cggacaggta
    1561 tccggtaagc ggcagggtcg gaacaggaga gcgcacgagg gagcttccag ggggaaacgc
    1621 ctggtatctt tatagtcctg tcgggtttcg ccacctctga cttgagcgtc gatttttgtg
    1681 atgctcgtca ggggggcgga gcctatggaa aaacgccagc aacgcggcct ttttacggtt
    1741 cctggccttt tgctggcctt tgctcacat gttctttcct gcgttatccc ctgattctgt
    1801 ggataaccgt attaccgcct ttgagtgagc tgataccgct cgccgcagcc gaacgaccga
    1861 gcgcagcgag tcagtgagcg aggaagcgga agagcgcctg atgcggtatt ttctccttac
    1921 gcatctgtgc ggtatttcac accgcatata tggtgcactc tcagtacaat ctgctctgat
    1981 gccgcatagt taagccagta tacactccgc tatcgctacg tgactgggtc atggctgcgc
    2041 cccgacaccc gccaacaccc gctgacgcgc cctgacgggc ttgtctgctc ccggcatccg
    2101 cttacagaca agctgtgacc gtctccggga ctgcatgtg tcagaggttt tcaccgtcat
    2161 caccgaaacg cgcgaggcag ctgcggtaaa gctcatcagc gtggtcgtga agcgattcac
    2221 agatgtctgc ctgttcatcc gcgtccagct cgttgagttt ctccagaagc gttaatgtct
    2281 ggcttctgat aaagcgggcc atgttaaggg cggttttttc ctgtttggtc acttgatgcc
    2341 tccgtgtaag ggggaatttc tgttcatggg ggtaatgata ccgatgaaac gagagaggat
    2401 gctcacgata cgggttactg atgatgaaca tgcccggtta ctggaacgtt gtgagggtaa
```

Figure 11 (Contd.)

```
2461 acaactggcg gtatggatgc ggcgggacca gagaaaaatc actcagggtc aatgccagcg
2521 cttcgttaat acagatgtag gtgttccaca gggtagccag cagcatcctg cgatgcagat
2581 ccggaacata atggtgcagg gcgctgactt ccgcgtttcc agactttacg aaacacggaa
2641 accgaagacc attcatgttg ttgctcaggt cgcagacgtt ttgcagcagc agtcgcttca
2701 cgttcgctcg cgtatcggtg attcattctg ctaaccagta aggcaacccc gccagcctag
2761 ccgggtcctc aacgacagga gcacgatcat gcgcacccgt ggccaggacc caacgctgcc
2821 cgagatgcgc cgcgtgcggc tgctggagat ggcggacgcg atggatatgt tctgccaagg
2881 gttggtttgc gcattcacag ttctccgcaa gaattgattg gctccaattc ttggagtggt
2941 gaatccgtta gcgaggtgcc gccggcttcc attcaggtcg aggtggcccg gctccatgca
3001 ccgcgacgca acgcggggag gcagacaagg tatagggcgg cgcctacaat ccatgccaac
3061 ccgttccatg tgctcgccga ggcggcataa atcgccgtga cgatcagcgg tccagtgatc
3121 gaagttaggc tggtaagagc cgcgagcgat ccttgaagct gtccctgatg gtcgtcatct
3181 acctgcctgg acagcatggc ctgcaacgcg ggcatcccga tgccgccgga agcgagaaga
3241 atcataatgg ggaaggccat ccagcctcgc gtcgcgaacg ccagcaagac gtagcccagc
3301 gcgtcggcca gcttgcaatt cgcgctaact tacattaatt gcgttgcgct cactgcccgc
3361 tttccagtcg ggaaacctgt cgtgccagct gcattaatga atcggccaac gcgcggggag
3421 aggcggtttg cgtattgggc gccagggtgg ttttttctttt caccagtgag acgggcaaca
3481 gctgattgcc cttcaccgcc tggccctgag agagttgcag caagcggtcc acgctggttt
3541 gccccagcag gcgaaaatcc tgtttgatgg tggttgacgg cgggatataa catgagctgt
3601 cttcggtatc gtcgtatccc actaccgaga tatccgcacc aacgcgcagc ccggactcgg
3661 taatggcgcg cattgcgccc agcgccatct gatcgttggc aaccagcatc gcagtgggaa
3721 cgatgccctc attcagcatt tgcatggttt gttgaaaacc ggacatggca ctccagtcgc
3781 cttcccgttc cgctatcggc tgaatttgat tgcgagtgag atatttatgc cagccagcca
3841 gacgcagacg cgccgagaca gaacttaatg gtcccgctaa cagcgcgatt tgctgatgac
3901 ccaatgcgac cagatgctcc acgcccagtc gcgtaccgtc ttcatgggag aaaataatac
3961 tgttgatggg tgtctggtca gagacatcaa gaaataacgc cggaacatta gtgcaggcag
4021 cttccacagc aatggcatcc tggtcatcca gcggatagtt aatgatcagc ccactgacgc
4081 gttgcgcgag aagattgtgc accgccgctt tacaggcttc gacgccgctt cgttctacca
4141 tcgacaccac cacgctggca cccagttgat cggcgcgaga tttaatcgcc gcgacaattt
4201 gcgacggcgc gtgcagggcc agactggagg tggcaacgcc aatcagcaac gactgtttgc
4261 ccgccagttg ttgtgccacg cggttgggaa tgtaattcag ctccgccatc gccgcttcca
4321 ctttttcccg cgttttcgca gaaacgtggc tggcctggtt caccacgcgg gaaacggtct
4381 gataagagac accggcatac tctgcgacat cgtataacgt tactggtttc acattcacca
4441 ccctgaattg actctcttcc gggcgctatc atgccatacc gcgaaaggtt ttgcgccatt
4501 cgatggtgtc aacgtaaatg catgccgctt cgccttcgcg cgcgaattgc aagctgatcc
4561 ggagcttatc gactgcacgg tgcaccaatg cttctggcgt caggcagcca tcggaagctg
4621 tggtatggct gtgcaggtcg taaatcactg cataattcgt gtcgctcaag gcgcactccc
4681 gttctggata atgttttttg cgccgacatc ataacggttc tggcaaatat tctgaaatga
4741 gctgttgaca attaatcatc ggctcgtata atgtgtggaa ttgtgagcgg ataacaattt
4801 cacacaggaa acagaattcc atatgaaata cctattacca acagcagcag ctgggttatt
4861 attgctcgct gcgcagccgg ccatggccca ggtcaccgtc tcctcacgta cggtggctgc
4921 accatctgtc ttcatcttcc cgccatctga tgagcagttg aaatctggaa ctgcctctgt
4981 tgtgtgcctg ctgaataact tctatcccag agaggccaaa gtacagtgga aggtggataa
5041 cgccctccaa tcgggtaact cccaggagag tgtcacagag caggacagca aggacagcac
5101 ctacagcctc agcagcaccc tgacgctgag caaagcagac tacgagaaac acaaagtcta
5161 cgcctgcgaa gtcacccatc agggcctgag ctcgccggtg acaaagagct tcaaccgcgg
5221 agagtgtgca ggtgattaca agacgatga cgataagtaa taaacaggaa acagaagtcc
5281 atatgaaata tcttttacct acggcagccg caggtttgtt gttactgcgg gcccagccgg
5341 ccatggccgc tagcaccaag ggcccatcgg tcttccccct ggcaccctcc tccaagagca
5401 cctctggggg cacagcggcc ctgggctgcc tggtcaagga ctacttcccc gaaccggtga
5461 cggtgtcgtg gaactcaggc gccctgacca gcggcgtgca caccttcccg gctgtcctac
5521 agtcctcagg actctactcc ctcagcagcg tagtgaccgt gccctccagc agcttgggca
5581 cccagaccta catctgcaac gtgaatcaca agcccagcaa caccaaggtg gacaagaaag
5641 ttgagcccaa atcttgtgcg gccgcagaac aaaaactcat ctcagaagag gatctgaatg
5701 gggccgtaca tcaccaccat catcatggga gctaagcttg gctgttttgg cggatgagag
5761 aagattttca gcctgataca gattaaatca gaacgcagaa gcggtctgat aaaacagaat
5821 ttgcctggcg gcagtagcgc ggtggtccca cctgacccca tgccgaactc agaagtgaaa
5881 cgccgtagcg ccgatggtag tgtggggtct ccccatgcga gagtagggaa ctgccaggca
```

Figure 11 (Contd.)

```
5941 tcaaataaaa cgaaaggctc agtcgaaaga ctgggccttt cgttttatct gttgtttgtc
6001 ggtgaacgct ctcctgagta ggacaaatcc gccgggagcg gatttgaacg ttgcgaagca
6061 acggcccgga ggaccctggc gggcaggacg cccgccataa actgccaggc atcaaattaa
6121 gcagaaggcc atcctgacgg atggcctttt tgcgtttcta caaactctt
``` pCKCH1Hγ1-TAG

SEQ ID N° 99
```
   1 ttgtttattt ttctaaatac attcaaatat gtatccgctc atgagacaat aaccctgata
  61 aatgcttcaa taatattgaa aaggaagag tatgagtatt caacatttcc gtgtcgccct
 121 tattcccttt tttgcggcat tttgccttcc tgttttgct cacccagaaa cgctggtgaa
 181 agtaaaagat gctgaagatc agttgggtgc acgagtgggt tacatcgaac tggatctcaa
 241 cagcggtaag atccttgaga gttttcgccc cgaagaacgt tttccaatga tgagcacttt
 301 taaagttctg ctatgtggcg cggtattatc ccgtgttgac gccgggcaag agcaactcgg
 361 tcgccgcata cactattctc agaatgactt ggttgagtac tcaccagtca cagaaaagca
 421 tcttacggat ggcatgacag taagagaatt atgcagtgct gccataacca tgagtgataa
 481 cactgcggcc aacttacttc tgacaacgat cggaggaccg aaggagctaa ccgcttttt
 541 gcacaacatg gggatcatg taactcgcct tgatcgttgg gaaccggagc tgaatgaagc
 601 cataccaaac gacgagcgtg acaccacgat gcctgtagca atggcaacaa cgttgcgcaa
 661 actattaact ggcgaactac ttactctagc ttcccggcaa caattaatag actggatgga
 721 ggcggataaa gttgcaggac cacttctgcg ctcggccctt ccggctggct ggtttattgc
 781 tgataaatct ggagccggtg agcgtgggtc tcgcggtatc attgcagcac tggggccaga
 841 tggtaagccc tcccgtatcg tagttatcta cacgacgggg agtcaggcaa ctatggatga
 901 acgaaataga cagatcgctg agataggtgc ctcactgatt aagcattggt aactgtcaga
 961 ccaagtttac tcatatatac tttagattga tttaaaactt cattttaat ttaaaaggat
1021 ctaggtgaag atccttttg ataatctcat gaccaaaatc ccttaacgtg agttttcgtt
1081 ccactgagcg tcagaccccg tagaaaagat caaaggatct tcttgagatc ctttttttct
1141 gcgcgtaatc tgctgcttgc aaacaaaaaa accaccgcta ccagcggtgg tttgtttgcc
1201 ggatcaagag ctaccaactc tttttccgaa ggtaactggc ttcagcagag cgcagatacc
1261 aaatactgtc cttctagtgt agccgtagtt aggccaccac ttcaagaact ctgtagcacc
1321 gcctacatac ctcgctctgc taatcctgtt accagtggct gctgccagtg gcgataagtc
1381 gtgtcttacc gggttggact caagacgata gttaccggat aaggcgcagc ggtcgggctg
1441 aacggggggt tcgtgcacac agcccagctt ggagcgaacg acctacaccg aactgagata
1501 cctacagcgt gagcattgag aaagcgccac gcttcccgaa gggagaaagg cggacaggta
1561 tccggtaagc ggcagggtcg gaacaggaga gcgcacgagg gagcttccag ggggaaacgc
1621 ctggtatctt tatagtcctg tcgggtttcg ccacctctga cttgagcgtc gatttttgtg
1681 atgctcgtca gggggcgga gcctatgaa aaacgccagc aacgcggcct ttttacggtt
1741 cctggccttt tgctggcctt ttgctcacat gttctttcct gcgttatccc ctgattctgt
1801 ggataaccgt attaccgcct ttgagtgagc tgataccgct cgccgcagcc gaacgaccga
1861 gcgcagcgag tcagtgagcg aggaagcgga agagcgcctg atgcggtatt ttctccttac
1921 gcatctgtgc ggtatttcac accgcatata tggtgcactc tcagtacaat ctgctctgat
1981 gccgcatagt taagccagta tacactccgc tatcgctacg tgactgggtc atggctgcgc
2041 cccgacaccc gccaacaccc gctgacgcgc cctgacgggc ttgtctgctc ccggcatccg
2101 cttacagaca agctgtgacc gtctccggga gctgcatgtg tcagaggttt tcaccgtcat
2161 caccgaaacg cgcgaggcag ctgcggtaaa gctcatcagc gtggtcgtga agcgattcac
2221 agatgtctgc ctgttcatcc gcgtccagct cgttgagttt ctccagaagc gttaatgtct
2281 ggcttctgat aaagcgggcc atgttaaggg cggttttttc ctgtttggtc acttgatgcc
2341 tccgtgtaag ggggaatttc tgttcatggg ggtaatgata ccgatgaaac gagagaggat
2401 gctcacgata cgggttactg atgatgaaca tgcccggtta ctggaacgtt gtgagggtaa
2461 acaactggcg gtatggatgc ggcgggacca gagaaaaatc actcagggtc aatgccagcg
2521 cttcgttaat acagatgtag tgttccaca gggtagccag cagcatcctg cgatgcagat
2581 ccggaacata atggtgcagg cgctgacttc cgcgtttcc agactttacg aaacacggaa
2641 accgaagacc attcatgttg ttgctcaggt cgcagacgtt ttgcagcagc agtcgcttca
2701 cgttcgctcg cgtatcggtg attcattctg ctaaccagta aggcaacccc gccagcctag
2761 ccgggtcctc aacgacagga gcacgatcat gcgcacccgt ggccaggacc aacgctgcc
2821 cgagatgcgc cgcgtgcggc tgctggagat gcggacgcg atgatatgt tctgccaagg
2881 gttggtttgc gcattcacag ttctccgcaa gaattgattg gctccaattc ttggagtggt
2941 gaatccgtta gcgaggtgcc gccggcttcc attcaggtcg aggtggcccg gctccatgca
```

Figure 11 (Contd.)

```
3001 ccgcgacgca acgcggggag gcagacaagg tatagggcgg cgcctacaat ccatgccaac
3061 ccgttccatg tgctcgccga ggcggcataa atcgccgtga cgatcagcgg tccagtgatc
3121 gaagttaggc tggtaagagc cgcgagcgat ccttgaagct gtccctgatg gtcgtcatct
3181 acctgcctgg acagcatggc ctgcaacgcg ggcatcccga tgccgccgga agcgagaaga
3241 atcataatgg ggaaggccat ccagcctcgc gtcgcgaacg ccagcaagac gtagcccagc
3301 gcgtcggcca gcttgcaatt cgcgctaact tacattaatt gcgttgcgct cactgcccgc
3361 tttccagtcg ggaaacctgt cgtgccagct gcattaatga atcggccaac gcgcggggag
3421 aggcggtttg cgtattgggc gccagggtgg ttttctttt caccagtgag acgggcaaca
3481 gctgattgcc cttcaccgcc tggccctgag agagttgcag caagcggtcc acgctggttt
3541 gccccagcag gcgaaaatcc tgtttgatgg tggttgacgg cgggatataa catgagctgt
3601 cttcggtatc gtcgtatccc actaccgaga tatccgcacc aacgcgcagc ccggactcgg
3661 taatggcgcg cattgcgccc agcgccatct gatcgttggc aaccagcatc gcagtgggaa
3721 cgatgccctc attcagcatt tgcatggttt gttgaaaacc ggacatggca ctccagtcgc
3781 cttcccgttc cgctatcggc tgaatttgat tgcgagtgag atatttatgc cagccagcca
3841 gacgcagacg cgccgagaca gaactaatg gtcccgctaa cagcgcgatt gctgatgac
3901 ccaatgcgac cagatgctcc acgccagtc gcgtaccgtc ttcatgggag aaaataatac
3961 tgttgatggg tgtctggtca gagacatcaa gaaataacgc cggaacatta gtgcaggcag
4021 cttccacagc aatggcatcc tggtcatcca gcggatagtt aatgatcagc ccactgacgc
4081 gttgcgcgag aagattgtgc accgccgctt tacaggcttc gacgccgctt cgttctacca
4141 tcgacaccac cacgctggca cccagttgat cggcgcgaga tttaatcgcc gcgacaattt
4201 gcgacggcgt gtgcagggcc agactggagg tggcaaccgc aatcagcaac gactgtttgc
4261 ccgccagttg ttgtgccacg cggttgggaa tgtaattcag ctccgccatc gccgcttcca
4321 cttttttccccg cgttttcgca gaaacgtggc tggcctggtt caccacgcgg gaaacggtct
4381 gataagagac accggcatac tctgcgacat cgtataacgt tactggtttc acattcacca
4441 ccctgaattg actctcttcc gggcgctatc atgccatacc gcgaaaggtt ttgcgccatt
4501 cgatggtgtc aacgtaaatg catgccgctt cgccttcgcg cgcgaattgc aagctgatcc
4561 ggagcttatc gactgcacgg tgcaccaatg cttctggcgt caggcagcca tcggaagctg
4621 tggtatggct gtgcaggtcg taaatcactg cataattcgt gtcgctcaag gcgcactccc
4681 gttctggata atgttttttg cgccgacatc ataacggttc tggcaaatat tctgaaatga
4741 gctgttgaca attaatcatc ggctcgtata atgtgtggaa ttgtgagcgg ataacaattt
4801 cacacaggaa acagaattcc atatgaaata cctattacca acagcagcag ctgggttatt
4861 attgctcgct gcgcagccgg ccatgcacgc ggtcacccgtc tcctcaggta ccgtggctgc
4921 accatctgtc ttcatcttcc cgccatctga tgagcagttg aaatctggaa ctgcctctgt
4981 tgtgtgcctg ctgaataact tctatcccag agaggccaaa gtacagtgga aggtggataa
5041 cgccctccaa tcgggtaact cccaggagag tgtcacagag caggacagca aggacagcac
5101 ctacagcctc agcagcaccc tgacgctgag caaagcagac tacgagaaac acaaagtcta
5161 cgcctgcgaa gtcacccatc agggcctgag ctcgccggtg acaaagagct tcaaccgcgg
5221 agagtgtgca ggtgattaca aagacgatga cgataagtaa taaacaggaa acagaagtcc
5281 atatgaaata cctattgcct acggcagccg ctggattgtt attactcgcg gcccagccgg
5341 ccatggccgc tagcaccaag ggcccatcgg tcttccccct ggcaccctcc tccaagagca
5401 cctctggggg cacagcggcc ctgggctgcc tggtcaagga ctacttcccc gaaccggtga
5461 cggtgtcgtg gaactcaggc gccctgacca gcggcgtgca caccttcccg gctgtcctac
5521 agtcctcagg actctactcc ctcagcagcg tagtgaccgt gcccctccagc agcttgggca
5581 cccagaccta catctgcaac gtgaatcaca agcccagcaa caccaaggtg gacaagaaag
5641 ttgagcccaa atcttgtgac aaaactcaca catgcccacc gtgccagcg gcgcagaac
5701 aaaaactcat ctcagaagag gatctgaatg gggccgtaca tcaccaccat catcatggga
5761 gctaagcttg gctgttttgg cggatgagag aagattttca gcctgataca gattaaatca
5821 gaacgcagaa gcggtctgat aaaacagaat ttgcctggcg gcagtagcgc ggtggtccca
5881 cctgacccca tgccgaactc agaagtgaaa cgccgtagcg ccgatggtag tgtgggtct
5941 cccatgcga gagtagggaa ctgccaggca tcaaataaaa cgaaaggctc agtcgaaaga
6001 ctgggccttt cgttttatct gttgtttgtc ggtgaacgct ctcctgagta ggacaaatcc
6061 gccggagcg gatttgaacg ttgcgaagca acggcccgga ggacctggc gggcaggacg
6121 ccgccataa actgccaggc atcaaattaa gcagaaggcc atcctgacgg atggcctttt
6181 tgcgtttcta caaactctt
```

SEQ ID N° 113
```
   1 ttgtttattt ttctaaatac attcaaatat gtatccgctc atgagacaat aaccctgata
  61 aatgcttcaa taatattgaa aaggaagag tatgagtatt caacatttcc gtgtcgccct
```

Figure 11 (Contd.)

```
 121 tattcccttt tttgcggcat tttgccttcc tgtttttgct cacccagaaa cgctggtgaa
 181 agtaaaagat gctgaagatc agttgggtgc acgagtgggt tacatcgaac tggatctcaa
 241 cagcggtaag atccttgaga gttttcgccc cgaagaacgt tttccaatga tgagcacttt
 301 taaagttctg ctatgtggcg cggtattatc ccgtgttgac gccggcaag agcaactcgg
 361 tcgccgcata cactattctc agaatgactt ggttgagtac tcaccagtca cagaaaagca
 421 tcttacggat ggcatgacag taagagaatt atgcagtgct gccataacca tgagtgataa
 481 cactgcggcc aacttacttc tgacaacgat cggaggaccg aaggagctaa ccgcttttt
 541 gcacaacatg ggggatcatg taactcgcct tgatcgttgg gaaccggagc tgaatgaagc
 601 cataccaaac gacgagcgtg acaccacgat gcctgtagca atggcaacaa cgttgcgcaa
 661 actattaact ggcgaactac ttactctagc ttcccggcaa caattaatag actggatgga
 721 ggcggataaa gttgcaggac cacttctgcg ctcggccctt ccggctggct ggtttattgc
 781 tgataaatct ggagccggtg agcgtgggtc tcgcggtatc attgcagcac tggggccaga
 841 tggtaagccc tcccgtatcg tagttatcta cacgacgggg agtcaggcaa ctatggatga
 901 acgaaataga cagatcgctg ataggtgc ctcactgatt aagcattggt aactgtcaga
 961 ccaagtttac tcatatatac tttagattga tttaaaactt cattttaat ttaaaggat
1021 ctaggtgaag atcctttttg ataatctcat gaccaaaatc ccttaacgtg agttttcgtt
1081 ccactgagcg tcagacccccg tagaaaagat caaggatct tcttgagatc cttttttct
1141 gcgcgtaatc tgctgcttgc aaacaaaaaa accaccgcta ccagcggtgg tttgtttgcc
1201 ggatcaagag ctaccaactc ttttccgaa ggtaactggc ttcagcagag cgcagatacc
1261 aaatactgtc cttctagtgt agccgtagtt aggccaccac ttcaagaact ctgtagcacc
1321 gcctacatac ctcgctctgc taatcctgtt accagtggct gctgccagtg gcgataagtc
1381 gtgtcttacc gggttggact caagacgata gttaccggat aaggcgcagc ggtcgggctg
1441 aacggggggt tcgtgcacac agcccagctt ggagcgaacg acctacaccg aactgagata
1501 cctacagcgt gagcattgag aaagcgccac gcttcccgaa gggagaaagg cggacaggta
1561 tccggtaagc ggcagggtcg aacaggaga gcgcacgagg gagcttccag ggggaaacgc
1621 ctggtatctt tatagtcctg tcgggtttcg ccacctctga cttgagcgtc gatttttgtg
1681 atgctcgtca gggggcgga gcctatggaa aaacgccagc aacgcggcct ttttacggtt
1741 cctggccttt tgctggcctt ttgctcacat gttctttcct gcgttatccc ctgattctgt
1801 ggataaccgt attaccgcct ttgagtgagc tgataccgct cgccgcagcc gaacgaccga
1861 gcgcagcgag tcagtgagcg aggaagcgga agagcgcctg atgcggtatt ttctccttac
1921 gcatctgtgc ggtatttcac accgcatata tggtgcactc tcagtacaat ctgctctgat
1981 gccgcatagt taagccagta tacactccgc tatcgctacg tgactgggtc atggctgcgc
2041 cccgacaccc gccaacaccc gctgacgcgc cctgacgggc ttgtctgctc ccggcatccg
2101 cttacagaca agctgtgacc gtctccggga gctgcatgtg tcagaggttt tcaccgtcat
2161 caccgaaacg cgcgaggcag ctgcggtaaa gctcatcagc gtggtcgtga gcgattcac
2221 agatgtctgc ctgttcatcc gcgtccagct cgttgagttt ctccagaagc gttaatgtct
2281 ggcttctgat aaagcgggcc atgttaaggg cggttttttc ctgtttggtc acttgatgcc
2341 tccgtgtaag ggggaatttc tgttcatggg ggtaatgata ccgatgaaac gagagaggat
2401 gctcacgata cgggttactg atgatgaaca tgcccggtta ctggaacgtt gtgagggtaa
2461 acaactggcg gtatgatgc ggcgggacca gagaaaaatc actcaggtc aatgccagcg
2521 cttcgttaat acagatgtag gtgttccaca gggtagccag cagcatcctg cgatgcagat
2581 ccggaacata atggtgcagg gcgctgactt ccgcgtttcc agactttacg aaacacggaa
2641 accgaagacc attcatgttg ttgctcaggt cgcagacgtt ttgcagcagc agtcgcttca
2701 cgttcgctcg cgtatcggtg attcattctg ctaaccagta aggcaacccc gccagcctag
2761 ccgggtcctc aacgacagga gcacgatcat gcgcacccgt ggccaggacc aacgctgcc
2821 cgagatgcgc cgcgtgcggc tgctggagat ggcggacgcg atggatatgt tctgccaagg
2881 gttggtttgc gcattcacag ttctccgcaa gaattgattg gctccaattc ttggagtggt
2941 gaatccgtta gcgaggtgcc gccggcttcc attcaggtcg aggtggcccg gctccatgca
3001 ccgcgacgca acgcggggag gcagacaagg tatagggcgg cgcctacaat ccatgccaac
3061 ccgttccatg tgctcgccga ggcggcataa atcgccgtga cgatcagcgg tccagtgatc
3121 gaagttaggc tggtaagagc cgcgagcgat ccttgaagct gtcctgatg gtcgtcatct
3181 acctgcctgg acagcatggc ctgcaacgcg ggcatcccga tgccgccgga agcgagaaga
3241 atcataatgg ggaaggccat ccagcctcgc gtcgcgaacg ccagcaagac gtagcccagc
3301 gcgtcggcca gcttgcaatt cgcgctaact tacattaatt gcgttgcgct cactgcccgc
3361 tttccagtcg ggaaacctgt cgtgccagct gcattaatga atcggccaac gcgcggggag
3421 aggcggtttg cgtattgggc gccagggtgg ttttcttttc accagtgag acgggcaaca
3481 gctgattgcc cttcaccgcc tggccctgag agagttgcag caagcggtcc acgctggttt
3541 gccccagcag gcgaaaatcc tgtttgatgg tggttgacgg cgggatataa catgagctgt
```

Figure 11 (Contd.)

```
3601 cttcggtatc gtcgtatccc actaccgaga tatccgcacc aacgcgcagc ccggactcgg
3661 taatggcgcg cattgcgccc agcgccatct gatcgttggc aaccagcatc gcagtgggaa
3721 cgatgccctc attcagcatt tgcatggttt gttgaaaacc ggacatggca ctccagtcgc
3781 cttcccgttc cgctatcggc tgaatttgat tgcgagtgag atatttatgc cagccagcca
3841 gacgcagacg cgccgagaca gaacttaatg gtcccgctaa cagcgcgatt tgctgatgac
3901 ccaatgcgac cagatgctcc acgcccagtc gcgtaccgtc ttcatgggag aaaataatac
3961 tgttgatggg tgtctggtca gagacatcaa gaataacgc cggaacatta gtgcaggcag
4021 cttccacagc aatggcatcc tggtcatcca gcggatagtt aatgatcagc ccactgacgc
4081 gttgcgcgag aagattgtgc accgccgctt tacaggcttc gacgccgctt cgttctacca
4141 tcgacaccac cacgctggca cccagttgat cggcgcgaga tttaatcgcc gcgacaattt
4201 gcgacggcgc gtgcagggcc agactggagg tggcaacgcc aatcagcaac gactgtttgc
4261 ccgccagttg ttgtgccacg cggttgggaa tgtaattcag ctccgccatc gccgcttcca
4321 cttttcccg cgtttcgca gaaacgtggc tggcctggtt caccacgcgg gaaacggtct
4381 gataagagac accggcatac tctgcgacat cgtataacgt tactggtttc acattcacca
4441 ccctgaattg actctcttcc gggcgctatc atgccatacc gcgaaaggtt ttgcgccatt
4501 cgatggtgtc aacgtaaatg catgccgctt cgccttcgcg cgcgaattgc aagctgatcc
4561 ggagcttatc gactgcacgg tgcaccaatg cttctggcgt caggcagcca tcggaagctg
4621 tggtatggct gtgcaggtcg taaatcactg cataattcgt gtcgctcaag gcgcactccc
4681 gttctggata atgtttttg cgccgacatc ataacggttc tggcaaatat tctgaaatga
4741 gctgttgaca attaatcatc ggctcgtata atgtgtggaa ttgtgagcgg ataacaattt
4801 cacacaggaa acagaattcc atatgaaata cctattacca acagcagcag ctgggttatt
4861 attgctcgct gcgcagccgg ccatggccca ggtcaccgtc tcctcacgta cggtggctgc
4921 accatctgtc ttcatcttcc cgccatctga tgagcagttg aaatctggaa ctgcctctgt
4981 tgtgtgcctg ctgaataact tctatcccag agaggccaaa gtacagtgga aggtggataa
5041 cgccctccaa tcgggtaact cccaggagag tgtcacagag caggacagca aggacagcac
5101 ctacagcctc agcagcaccc tgacgctgag caaagcagac tacgagaaac acaaagtcta
5161 cgcctgcgaa gtcacccatc agggcctgag ctcgccggtg acaaagagct tcaaccgcgg
5221 agagtgtgca ggtgattaca aagacgatga cgataagtaa taaacaggaa acagaagtcc
5281 atatgaaata tcttttacct acggcagccg caggtttgtt gttactcgcg gcccagccgg
5341 ccatggccgc tagcaccaag ggcccatcgg tcttccccct ggcaccctcc tccaagagca
5401 cctctggggg cacagcggcc ctgggctgcc tggtcaagga ctacttcccc gaaccggtga
5461 cggtgtcgtg gaactcaggc gccctgacca gcggcgtgca caccttcccg gctgtcctac
5521 agtcctcagg actctactcc ctcagcagcg tagtgaccgt gccctccagc agcttgggca
5581 cccagaccta catctgcaac gtgaatcaca agcccagcaa caccaaggtg gacaagaaag
5641 ttgagcccaa atcttgtgac aaaactcaca catgcccacc gtgcccagcg gccgcagaac
5701 aaaaactcat ctcagaagag gatctgaatg gggccgtaca tcaccaccat catcatggga
5761 gctaagcttg gctgttttgg cggatgagag aagattttca gcctgataca gattaaatca
5821 gaacgcagaa gcggtctgat aaaacagaat ttgcctggcg gcagtagcgc ggtggtccca
5881 cctgacccca tgccgaactc agaagtgaaa cgccgtagcg ccgatggtag tgtggggtct
5941 ccccatgcga gagtagggaa ctgccaggca tcaaataaaa cgaaaggctc agtcgaaaga
6001 ctgggccttt cgttttatct gttgtttgtc ggtgaacgct ctcctgagta ggacaaatcc
6061 gccggagcg gatttgaacg ttgcgaagca acggcccgga ggacctggc gggcaggacg
6121 cccgccataa actgccaggc atcaaattaa gcagaaggcc atcctgacgg atggccttt
6181 tgcgtttcta caaactctt
``` pCKCH1γ1

SEQ ID N° 100
```
   1 ttgtttattt ttctaaatac attcaaatat gtatccgctc atgagacaat aaccctgata
  61 aatgcttcaa taatattgaa aaggaagag tatgagtatt caacatttcc gtgtcgccct
 121 tattcccttt tttgcggcat tttgccttcc tgtttttgct cacccagaaa cgctggtgaa
 181 agtaaaagat gctgaagatc agttgggtgc acgagtgggt tacatcgaac tggatctcaa
 241 cagcggtaag atccttgaga gttttcgccc cgaagaacgt tttccaatga tgagcacttt
 301 taaagttctg ctatgtggcg cggtattatc ccgtgttgac gccgggcaag agcaactcgg
 361 tcgccgcata cactattctc agaatgactt ggttgagtac tcaccagtca cagaaaagca
 421 tcttacggat ggcatgacag taagagaatt atgcagtgct gccataacca tgagtgataa
 481 cactgcggcc aacttacttc tgacaacgat cggaggaccg aaggagctaa ccgcttttt
```

Figure 11 (Contd.)

```
 541 gcacaacatg ggggatcatg taactcgcct tgatcgttgg gaaccggagc tgaatgaagc
 601 cataccaaac gacgagcgtg acaccacgat gcctgtagca atggcaacaa cgttgcgcaa
 661 actattaact ggcgaactac ttactctagc ttcccggcaa caattaatag actggatgga
 721 ggcggataaa gttgcaggac cacttctgcg ctcggccctt ccggctggct ggtttattgc
 781 tgataaatct ggagccggtg agcgtgggtc tcgcggtatc attgcagcac tggggccaga
 841 tggtaagccc tcccgtatcg tagttatcta cacgacgggg agtcaggcaa ctatggatga
 901 acgaaataga cagatcgctg agataggtgc ctcactgatt aagcattggt aactgtcaga
 961 ccaagtttac tcatatatac tttagattga tttaaaactt cattttaat ttaaaaggat
1021 ctaggtgaag atccttttg ataatctcat gaccaaaatc ccttaacgtg agttttcgtt
1081 ccactgagcg tcagacccg tagaaaagat caaaggatct tcttgagatc ctttttttct
1141 gcgcgtaatc tgctgcttgc aaacaaaaaa accaccgcta ccagcggtgg tttgtttgcc
1201 ggatcaagag ctaccaactc tttttccgaa ggtaactggc ttcagcagag cgcagatacc
1261 aaatactgtc cttctagtgt agccgtagtt aggccaccac ttcaagaact ctgtagcacc
1321 gcctacatac ctcgctctgc taatcctgtt accagtggct gctgccagtg gcgataagtc
1381 gtgtcttacc gggttggact caagacgata gttaccggat aaggcgcagc ggtcgggctg
1441 aacgggggt tcgtgcacac agcccagctt ggagcgaacg acctacaccg aactgagata
1501 cctacagcgt gagcattgag aaagcgccac gcttcccgaa gggagaaagg cggacaggta
1561 tccggtaagc ggcagggtcg gaacaggaga gcgcacgagg gagcttccag ggggaaacgc
1621 ctggtatctt tatagtcctg tcgggtttcg ccacctctga cttgagcgtc gatttttgtg
1681 atgctcgtca gggggcgga gcctatggaa aaacgccagc aacgcggcct ttttacggtt
1741 cctggccttt tgctggcctt ttgctcacat gttctttcct gcgttatccc ctgattctgt
1801 ggataaccgt attaccgcct ttgagtgagc tgataccgct cgccgcagcc gaacgaccga
1861 gcgcagcgag tcagtgagcg aggaagcgga gagcgcctg atgcggtatt ttctccttac
1921 gcatctgtgc ggtatttcac accgcatata tggtgcactc tcagtacaat ctgctctgat
1981 gccgcatagt taagccagta tacactccgc tatcgctacg tgactgggtc atggctgcgc
2041 cccgacaccc gccaacaccc gctgacgcgc cctgacgggc ttgtctgctc ccggcatccg
2101 cttacagaca agctgtgacc gtctccggga gctgcatgtg tcagaggttt tcaccgtcat
2161 caccgaaacg cgcgaggcag ctgcggtaaa gctcatcagc gtggtcgtga gcgattcac
2221 agatgtctgc ctgttcatcc gcgtccagct cgttgagttt ctccagaagc gttaatgtct
2281 ggcttctgat aaagcgggcc atgttaaggg cggttttttc ctgtttggtc acttgatgcc
2341 tccgtgtaag ggggaattc tgttcatggg ggtaatgata ccgatgaaac gagagaggat
2401 gctcacgata cgggttactg atgatgaaca tgcccggtta ctggaacgtt gtgagggtaa
2461 acaactggcg gtatggatgc ggcgggacca gagaaaaatc actcagggtc aatgccagcg
2521 cttcgttaat acagatgtag gtgttccaca gggtagccag cagcatcctg cgatgcagat
2581 ccggaacata atggtgcagg gcgctgactt ccgcgtttcc agactttacg aaacacggaa
2641 accgaagacc attcatgttg ttgctcaggt cgcagacgtt tgcagcagc agtcgcttca
2701 cgttcgctcg cgtatcggtg attcattctg ctaaccagta aggcaacccc gccagcctag
2761 ccgggtcctc aacgacagga gcacgatcat gcgcacccgt ggccaggacc caacgctgcc
2821 cgagatgcgc cgcgtgcggc tgctggagat ggcggacgcg atggatatgt tctgccaagg
2881 gttggtttgc gcattcacag ttctccgcaa gaattgattg gctccaattc ttggagtggt
2941 gaatccgtta gcgaggtgcc gccggcttcc attcaggtcg aggtggcccg gctccatgca
3001 ccgcgacgca acgcggggag gcagacaagg tatagggcgg cgcctacaat ccatgccaac
3061 ccgttccatg tgctcgccga ggcggcataa atccgcgtga cgatcagcgg tccagtgatc
3121 gaagttaggc tggtaagagc cgcgagcgat ccttgaagct gtcctgatg gtcgtcatct
3181 acctgcctgg acagcatggc ctgcaacgcg ggcatcccga tgccgccgga agcgagaaga
3241 atcataatgg ggaaggccat ccagcctcgc gtcgcgaacg ccagcaagac gtagcccagc
3301 gcgtcggcca gcttgcaatt cgcgctaact tacattaatt gcgttgcgct cactgcccgc
3361 tttccagtcg ggaaacctgt cgtgccagct gcattaatga atcggccaac gcgcggggag
3421 aggcggtttg cgtattgggc gccagggtgg ttttctttt caccagtgag acgggcaaca
3481 gctgattgcc cttcaccgcc tggccctgag agagttgcag caagcggtcc acgctggttt
3541 gccccagcag gcgaaaatcc tgtttgatgg tggttacgg cgggatataa catgagctgt
3601 cttcggtatc gtcgtatccc actaccgaga tatccgcacc aacgcgcagc ccggactcgg
3661 taatggcgcg cattgcgccc agcgccatct gatcgttggc aaccagcatc gcagtgggaa
3721 cgatgccctc attcagcatt tgcatggttt gttgaaaacc ggacatggca ctccagtcgc
3781 cttcccgttc cgctatcggc tgaatttgat tgcgagtgag atatttatgc cagccagcca
3841 gacgcagacg cgccgagaca gaacttaatg gtccgctaa cagcgcgatt tgctgatgac
3901 ccaatgcgac cagatgctcc acgccagtc gcgtaccgtc ttcatgggag aaaataatac
3961 tgttgatggg tgtctggtca gagacatcaa gaaataacgc cggaacatta gtgcaggcag
```

Figure 11 (Contd.)

```
4021 cttccacagc aatggcatcc tggtcatcca gcggatagtt aatgatcagc ccactgacgc
4081 gttgcgcgag aagattgtgc accgccgctt tacaggcttc gacgccgctt cgttctacca
4141 tcgacaccac cacgctggca cccagttgat cggcgcgaga tttaatcgcc gcgacaattt
4201 gcgacggcgc gtgcagggcc agactggagg tggcaacgcc aatcagcaac gactgtttgc
4261 ccgccagttg ttgtgccacg cggttgggaa tgtaattcag ctccgccatc gccgcttcca
4321 cttttcccg cgttttcgca gaaacgtggc tggcctggtt caccacgcgg gaaacggtct
4381 gataagagac accggcatac tctgcgacat cgtataacgt tactggtttc acattcacca
4441 ccctgaattg actctcttcc gggcgctatc atgccatacc gcgaaaggtt ttgcgccatt
4501 cgatggtgtc aacgtaaatg catgccgctt cgccttcgcg cgcgaattgc aagctgatcc
4561 ggagcttatc gactgcacgg tgcaccaatg cttctggcgt caggcagcca tcggaagctg
4621 tggtatggct gtgcaggtcg taaatcactg cataattcgt gtcgctcaag gcgcactccc
4681 gttctggata atgttttttg cgccgacatc ataacggttc tggcaaatat tctgaaatga
4741 gctgttgaca attaatcatc ggctcgtata atgtgtggaa ttgtgagcgg ataacaattt
4801 cacacaggaa acagaattcc atatgaaata cctattacca acagcagcag ctgggttatt
4861 attgctcgct gcgcagccgg ccatggccca ggtcaccgtc tcctcaggta ccgtggctgc
4921 accatctgtc ttcatcttcc cgccatctga tgagcagttg aaatctggaa ctgcctctgt
4981 tgtgtgcctg ctgaataact tctatcccag agaggccaaa gtacagtgga aggtggataa
5041 cgccctccaa tcgggtaact cccaggagag tgtcacagag caggacagca aggacagcac
5101 ctacagcctc agcagcaccc tgacgctgag caaagcagac tacgagaaac acaaagtcta
5161 cgcctgcgaa gtcacccatc agggcctgag ctcgccggtg acaaagagct tcaaccgcgg
5221 agagtgttaa taaacaggaa acagaagtcc atatgaaata cctattgcct acggcagccg
5281 ctggattgtt attactcgcg gccagccgg ccatggccgc tagcaccaag ggcccatcgg
5341 tcttcccct ggcaccctcc tccaagagca cctctggggg cacagcggcc ctgggctgcc
5401 tggtcaagga ctacttcccc gaacggtga cggtgtcgtg gaactcaggc gccctgacca
5461 gcggcgtgca caccttcccg gctgtcctac agtcctcagg actctactcc ctcagcagcg
5521 tagtgaccgt gccctccagc agcttgggca cccagaccta catctgcaac gtgaatcaca
5581 agcccagcaa caccaaggtg gacaagaaag ttgagcccaa atcttgttaa gcttggctgt
5641 tttggcggat gagagaagat tttcagcctg atacagatta aatcagaacg cagaagcggt
5701 ctgataaaac agaatttgcc tggcggcagt agcgcggtgg tcccacctga ccccatgccg
5761 aactcagaag tgaaacgccg tagcgccgat ggtagtgtgg ggtctcccca tgcgagagta
5821 gggaactgcc aggcatcaaa taaaacgaaa ggctcagtcg aaagactggg cctttcgttt
5881 tatctgttgt ttgtcggtga acgctctcct gagtaggaca aatccgccgg gagcggattt
5941 gaacgttgcg aagcaacggc ccggaggacc ctggcgggca ggacgccgc cataaactgc
6001 caggcatcaa attaagcaga aggccatcct gacggatggc cttttgcgt ttctacaaac
6061 tctt SEQ ID N° 114
   1 ttgttattt ttctaaatac attcaaatat gtatccgctc atgagacaat aaccctgata
  61 aatgcttcaa taatattgaa aaggaagag tatgagtatt caacatttcc gtgtcgccct
 121 tattcccttt tttgcggcat tttgccttcc tgttttgct cacccagaaa cgctggtgaa
 181 agtaaaagat gctgaagatc agttgggtgc acgagtgggt tacatcgaac tggatctcaa
 241 cagcggtaag atccttgaga gttttcgccc cgaagaacgt tttccaatga tgagcacttt
 301 taaagttctg ctatgtggcg cggtattatc ccgtgttgac gccgggcaag agcaactcgg
 361 tcgccgcata cactattctc agaatgactt ggttgagtac tcaccagtca cagaaaagca
 421 tcttacggat ggcatgacag taagagaatt atgcagtgct gccataacca tgagtgataa
 481 cactgcggcc aacttacttc tgacaacgat cggaggaccg aaggagctaa ccgcttttt
 541 gcacaacatg gggatcatg taactcgcct tgatcgttgg gaaccggagc tgaatgaagc
 601 cataccaaac gacgagcgtg acaccacgat gcctgtagca atggcaacaa cgttgcgcaa
 661 actattaact ggcgaactac ttactctagc ttcccggcaa caattaatag actggatgga
 721 ggcggataaa gttgcaggac cacttctgcg ctcggccctt ccggctggct ggtttattgc
 781 tgataaatct ggagccggtg agcgtgggtc tcgcggtatc attgcagcac tggggccaga
 841 tggtaagccc tcccgtatcg tagttatcta cacgacgggg agtcaggcaa ctatggatga
 901 acgaaataga cagatcgctg agataggtgc ctcactgatt aagcattggt aactgtcaga
 961 ccaagtttac tcatatatac tttagattga tttaaaactt catttttaat ttaaaaggat
1021 ctaggtgaag atcctttttg ataatctcat gaccaaaatc ccttaacgtg agttttcgtt
1081 ccactgagcg tcagacccg tagaaagat caaggatct cttgagatc ctttttttct
1141 gcgcgtaatc tgctgcttgc aaacaaaaaa accaccgcta ccagcggtgg tttgtttgcc
1201 ggatcaagag ctaccaactc ttttccgaa ggtaactggc ttcagcagag cgcagatacc
```

Figure 11 (Contd.)

```
1261 aaatactgtc cttctagtgt agccgtagtt aggccaccac ttcaagaact ctgtagcacc
1321 gcctacatac ctcgctctgc taatcctgtt accagtggct gctgccagtg gcgataagtc
1381 gtgtcttacc gggttggact caagacgata gttaccggat aaggcgcagc ggtcgggctg
1441 aacgggggt tcgtgcacac agcccagctt ggagcgaacg acctacaccg aactgagata
1501 cctacagcgt gagcattgag aaagcgccac gcttcccgaa gggagaaagg cggacaggta
1561 tccggtaagc ggcagggtcg gaacaggaga gcgcacgagg gagcttccag ggggaaacgc
1621 ctggtatctt tatagtcctg tcgggtttcg ccacctctga cttgagcgtc gattttgtg
1681 atgctcgtca gggggcgga gcctatggaa aaacgccagc aacgcggcct ttttacggtt
1741 cctggccttt tgctggcctt ttgctcacat gttctttcct gcgttatccc ctgattctgt
1801 ggataaccgt attaccgcct ttgagtgagc tgataccgct cgccgcagcc gaacgaccga
1861 gcgcagcgag tcagtgagcg aggaagcgga agagcgcctg atgcggtatt ttctccttac
1921 gcatctgtgc ggtatttcac accgcatata tggtgcactc tcagtacaat ctgctctgat
1981 gccgcatagt taagccagta tacactccgc tatcgctacg tgactgggtc atggctgcgc
2041 cccgacaccc gccaacaccc gctgacgcgc cctgacgggc ttgtctgctc ccggcatccg
2101 cttacagaca agctgtgacc gtctccggga gctgcatgtg tcagaggttt tcaccgtcat
2161 caccgaaacg cgcgaggcag ctgcggtaaa gctcatcagc gtggtcgtga agcgattcac
2221 agatgtctgc ctgttcatcc gcgtccagct cgttgagttt ctccagaagc gttaatgtct
2281 ggcttctgat aaagcgggcc atgttaaggg cggttttttc ctgtttggtc acttgatgcc
2341 tccgtgtaag ggggaattc tgttcatggg ggtaatgata ccgatgaaac gagagaggat
2401 gctcacgata cgggttactg atgatgaaca tgcccggtta ctggaacgtt gtgagggtaa
2461 acaactggcg gtatggatgc ggcggacca gagaaaaatc actcaggtc aatgccagcg
2521 cttcgttaat acagatgtag gtgttccaca gggtagccag cagcatcctg cgatgcagat
2581 ccggaacata atggtgcagg gcgctgactt ccgcgtttcc agactttacg aaacacggaa
2641 accgaagacc attcatgttg ttgctcaggt cgcagacgtt ttgcagcagc agtcgcttca
2701 cgttcgctcg cgtatcggtg attcattctg ctaaccagta aggcaacccc gccagcctag
2761 ccgggtcctc aacgacagga gcacgatcat gcgcacccgt ggccaggacc caacgctgcc
2821 cgagatgcgc cgcgtgcggc tgctggagat ggcggacgcg atggatatgt tctgccaagg
2881 gttggtttgc gcattcacag ttctccgcaa gaattgattg gctccaattc ttggagtggt
2941 gaatccgtta gcgaggtgcc gccggcttcc attcaggtcg aggtggcccg gctccatgca
3001 ccgcgacgca acgcgggggag gcagacaagg tatagggcgg cgcctacaat ccatgccaac
3061 ccgttccatg tgctcgccga ggcggcataa atcgccgtga cgatcagcgg tccagtgatc
3121 gaagttaggc tggtaagagc cgcgagcgat ccttgaagct gtccctgatg gtcgtcatct
3181 acctgcctgg acagcatggc ctgcaacgcg ggcatcccga tgccgccgga agcgagaaga
3241 atcataatgg ggaaggccat ccagcctcgc gtcgcgaacg ccagcaagac gtagcccagc
3301 gcgtcggcca gcttgcaatt cgcgctaact tacattaatt gcgttgcgct cactgcccgc
3361 tttccagtcg ggaaacctgt cgtgccagct gcattaatga atcggccaac gcgcggggag
3421 aggcggtttg cgtattggc gccaggtgg ttttctttt caccagtgag acggcaaca
3481 gctgattgcc cttcaccgcc tggccctgag agagttgcag caagcggtcc acgctggttt
3541 gccccagcag gcgaaaatcc tgtttgatgg tggttgacgg cggatataa catgagctgt
3601 cttcggtatc gtcgtatccc actaccgaga tatccgcacc aacgcgcagc ccggactcgg
3661 taatggcgcg cattgcgccc agcgccatct gatcgttggc aaccagcatc gcagtgggaa
3721 cgatgccctc attcagcatt tgcatggttt gttgaaaacc ggacatggca ctccagtcgc
3781 cttcccgttc cgctatcggc tgaatttgat tgcgagtgag atatttatgc cagccagcca
3841 gacgcagacg cgccgagaca gaacttaatg gtcccgctaa cagcgcgatt tgctgatgac
3901 ccaatgcgac cagatgctcc acgcccagtc gcgtaccgtc ttcatgggag aaaataatac
3961 tgttgatggg tgtctggtca gagacatcaa gaaataacgc cggaacatta gtgcaggcag
4021 cttccacagc aatggcatcc tggtcatcca gcggatagtt aatgatcagc ccactgacgc
4081 gttgcgcgag aagattgtgc accgccgctt tacaggcttc gacgcgcttc cgttctacca
4141 tcgacaccac cacgctggca cccagttgat cggcgcgaga tttaatcgcc gcgacaattt
4201 gcgacggcgc gtgcagggcc agactggagg tggcaacgcc aatcagcaac gactgtttgc
4261 ccgccagttg ttgtgccacg cggttgggaa tgtaattcag ctccgccatc gccgcttcca
4321 cttttttccg cgttttcgca gaaacgtggc tggcctggtt caccacgcgg gaaacggtct
4381 gataagagac accggcatac tctgcgacat cgtataacgt tactggtttc acattcacca
4441 ccctgaattg actctcttcc gggcgctatc atgccatacc gcgaaaggtt ttgcgccatt
4501 cgatggtgtc aacgtaaatg catgccgctt cgccttcgcg cgcgaattgc aagctgatcc
4561 ggagcttatc gactgcacgg tgcaccaatg cttctggcgt caggcagcca tcggaagctg
4621 tggtatggct gtgcaggtcg taaatcactg cataattcgt gtcgctcaag gcgcactccc
4681 gttctggata atgttttttg cgccgacatc ataacggttc tggcaaatat tctgaaatga
```

Figure 11 (Contd.)

```
4741 gctgttgaca attaatcatc ggctcgtata atgtgtggaa ttgtgagcgg ataacaattt
4801 cacacaggaa acagaattcc atatgaaata cctattacca acagcagcag ctgggttatt
4861 attgctcgct gcgcagccgg ccatggccca ggtcaccgtc tcctcacgta cggtggctgc
4921 accatctgtc ttcatcttcc cgccatctga tgagcagttg aaatctggaa ctgcctctgt
4981 tgtgtgcctg ctgaataact tctatcccag agaggccaaa gtacagtgga aggtggataa
5041 cgccctccaa tcgggtaact cccaggagag tgtcacagag caggacagca aggacagcac
5101 ctacagcctc agcagcaccc tgacgctgag caaagcagac tacgagaaac acaaagtcta
5161 cgcctgcgaa gtcacccatc agggcctgag ctcgccggtg acaaagagct caaccgcgg
5221 agagtgttaa taaacaggaa acagaagtcc atatgaaata tcttttacct acggcagccg
5281 caggtttgtt gttactcgcg gcccagccgg ccatggccgc tagcaccaag ggcccatcgg
5341 tcttccccct ggcaccctcc tccaagagca cctctggggg cacagcggcc ctgggctgcc
5401 tggtcaagga ctacttcccc gaaccggtga cggtgtcgtg gaactcaggc gccctgacca
5461 gcggcgtgca caccttcccg gctgtcctac agtcctcagg actctactcc ctcagcagcg
5521 tagtgaccgt gccctccagc agcttgggca cccagaccta catctgcaac gtgaatcaca
5581 agcccagcaa caccaaggtg gacaagaaag ttgagcccaa atcttgttaa gcttggctgt
5641 tttggcggat gagagaagat tttcagcctg atacagatta aatcagaacg cagaagcggt
5701 ctgataaaac agaatttgcc tggcggcagt agcgcggtgg tcccacctga cccatgccg
5761 aactcagaag tgaaacgccg tagcgccgat ggtagtgtgg ggtctcccca tgcgagagta
5821 gggaactgcc aggcatcaaa taaaacgaaa ggctcagtcg aaagactggg cctttcgttt
5881 tatctgttgt ttgtcggtga acgctctcct gagtaggaca aatccgccgg gagcggattt
5941 gaacgttgcg aagcaacggc ccggaggacc ctgcgggca ggacgcccgc cataaactgc
6001 caggcatcaa attaagcaga aggccatcct gacggatggc cttttttgcgt tctacaaac
6061 tctt
``` pCKCH1Hγ1

SEQ ID N° 101
```
   1 ttgtttattt ttctaaatac attcaaatat gtatccgctc atgagacaat aaccctgata
  61 aatgcttcaa taatattgaa aaaggaagag tatgagtatt caacatttcc gtgtcgccct
 121 tattcccttt tttgcggcat tttgccttcc tgttttttgct cacccagaaa cgctggtgaa
 181 agtaaaagat gctgaagatc agttgggtgc acgagtgggt tacatcgaac tggatctcaa
 241 cagcggtaag atccttgaga gttttcgccc cgaagaacgt tttccaatga tgagcacttt
 301 taaagttctg ctatgtggcg cggtattatc ccgtgttgac gccgggcaag agcaactcgg
 361 tcgccgcata cactattctc agaatgactt ggttgagtac tcaccagtca cagaaaagca
 421 tcttacggat ggcatgacag taagagaatt atgcagtgct gccataacca tgagtgataa
 481 cactgcggcc aacttacttc tgacaacgat cggaggaccg aaggagctaa ccgcttttt
 541 gcacaacatg ggggatcatg taactcgcct tgatcgttgg gaaccggagc tgaatgaagc
 601 cataccaaac gacgagcgtg acaccacgat gcctgtagca atggcaacaa cgttgcgcaa
 661 actattaact ggcgaactac ttactctagc ttcccggcaa caattaatag actggatgga
 721 ggcggataaa gttgcaggac cacttctgcg ctcggccctt ccggctggct ggtttattgc
 781 tgataaatct ggagccggtg agcgtgggtc tcgcggtatc attgcagcac tggggccaga
 841 tggtaagccc tcccgtatcg tagttatcta cacgacgggg agtcaggcaa ctatggatga
 901 acgaaataga cagatcgctg agataggtgc ctcactgatt aagcattggt aactgtcaga
 961 ccaagtttac tcatatatac tttagattga tttaaaactt catttttaat ttaaaaggat
1021 ctaggtgaag atcctttttg ataatctcat gaccaaaatc ccttaacgtg agttttcgtt
1081 ccactgagcg tcagaccccg tagaaaagat caaaggatct tcttgagatc cttttttct
1141 gcgcgtaatc tgctgcttgc aaacaaaaaa accaccgcta ccagcggtgg tttgtttgcc
1201 ggatcaagag ctaccaactc ttttccgaa ggtaactggc ttcagcagag cgcagatacc
1261 aaatactgtc cttctagtgt agccgtagtt aggccaccac ttcaagaact ctgtagcacc
1321 gcctacatac ctcgctctgc taatcctgtt accagtggct gctgccagtg gcgataagtc
1381 gtgtcttacc gggttggact caagacgata gttaccggat aaggcgcagc ggtcgggctg
1441 aacggggggt tcgtgcacac agcccagctt ggagcgaacg acctacaccg aactgagata
1501 cctacagcgt gagcattgag aaagcgccac gcttcccgaa gggagaaagg cggacaggta
1561 tccggtaagc ggcagggtcg gaacaggaga gcgcacgagg gagcttccag ggggaaacgc
1621 ctggtatctt tatagtcctg tcgggtttcg ccacctctga cttgagcgtc gatttttgtg
1681 atgctcgtca gggggcgga gcctatggaa aaacgccagc aacgcggcct ttttacggtt
1741 cctggccttt tgctggcctt ttgctcacat gttctttcct gcgttatccc ctgattctgt
```

Figure 11 (Contd.)

```
1801 ggataaccgt attaccgcct ttgagtgagc tgataccgct cgccgcagcc gaacgaccga
1861 gcgcagcgag tcagtgagcg aggaagcgga agagcgcctg atgcggtatt ttctccttac
1921 gcatctgtgc ggtatttcac accgcatata tggtgcactc tcagtacaat ctgctctgat
1981 gccgcatagt taagccagta tacactccgc tatcgctacg tgactgggtc atggctgcgc
2041 cccgacaccc gccaacaccc gctgacgcgc cctgacgggc ttgtctgctc ccggcatccg
2101 cttacagaca agctgtgacc gtctccggga gctgcatgtg tcagaggttt tcaccgtcat
2161 caccgaaacg cgcgaggcag ctgcggtaaa gctcatcagc gtggtcgtga agcgattcac
2221 agatgtctgc ctgttcatcc gcgtccagct cgttgagttt ctccagaagc gttaatgtct
2281 ggcttctgat aaagcgggcc atgttaaggg cggttttttc ctgtttggtc acttgatgcc
2341 tccgtgtaag ggggaatttc tgttcatggg ggtaatgata ccgatgaaac gagagaggat
2401 gctcacgata cgggttactg atgatgaaca tgcccggtta ctggaacgtt gtgagggtaa
2461 acaactggcg gtatggatgc ggcgggacca gagaaaaatc actcagggtc aatgccagcg
2521 cttcgttaat acagatgtag gtgttccaca gggtagccag cagcatcctg cgatgcagat
2581 ccggaacata atggtgcagg gcgctgactt ccgcgtttcc agactttacg aaacacggaa
2641 accgaagacc attcatgttg ttgctcaggt cgcagacgtt ttgcagcagc agtcgcttca
2701 cgttcgctcg cgtatcggtg attcattctg ctaaccagta aggcaacccc gccagcctag
2761 ccgggtcctc aacgacagga gcacgatcat gcgcacccgt ggccaggacc caacgctgcc
2821 cgagatgcgc cgcgtgcggc tgctggagat ggcggacgcg atggatatgt tctgccaagg
2881 gttggtttgc gcattcacag ttctccgcaa gaattgattg gctccaattc ttggagtggt
2941 gaatccgtta gcgaggtgcc gccggcttcc attcaggtcg aggtggcccg gctccatgca
3001 ccgcgacgca acgcggggag gcagacaagg tatagggcgg cgcctacaat ccatgccaac
3061 ccgttccatg tgctcgccga ggcggcataa atcgccgtga cgatcagcgg tccagtgatc
3121 gaagttaggc tggtaagagc cgcgagcgat ccttgaagct gtccctgatg gtcgtcatct
3181 acctgcctgg acagcatggc ctgaacgcg ggcatcccga tgccgccgga agcgagaaga
3241 atcataatgg ggaaggccat ccagcctcgc gtcgcgaacg ccagcaagac gtagcccagc
3301 gcgtcggcca gcttgcaatt cgcgctaact tacattaatt gcgttgcgct cactgcccgc
3361 tttccagtcg ggaaacctgt cgtgccagct gcattaatga atcggccaac gcgcggggag
3421 aggcggtttg cgtattgggc gccagggtgg ttttttcttt caccagtgag acgggcaaca
3481 gctgattgcc cttcaccgcc tggccctgag agagttgcag caagcggtcc acgctggttt
3541 gccccagcag gcgaaaatcc tgtttgatgg tggttgacgg cgggatataa catgagctgt
3601 cttcggtatc gtcgtatccc actaccgaga tatccgcacc aacgcgcagc ccggactcgg
3661 taatggcgcg cattgcgccc agcgccatct gatcgttggc aaccagcatc gcagtgggaa
3721 cgatgccctc attcagcatt tgcatggttt gttgaaaacc ggacatggca ctccagtcgc
3781 cttcccgttc cgctatcggc tgaatttgat tgcgagtgag atatttatgc cagccagcca
3841 gacgcagacg cgccgagaca gaacttaatg gtcccgctaa cagcgcgatt tgctgatgac
3901 ccaatgcgac cagatgctcc acgcccagtc gcgtaccgtc ttcatgggag aaaataatac
3961 tgttgatggg tgtctggtca gagacatcaa gaaataacgc cggaacatta gtgcaggcag
4021 cttccacagc aatggcatcc tggtcatcca gcggatagtt aatgatcagc ccactgacgc
4081 gttgcgcgag aagattgtgc accgccgctt tacaggcttc gacgccgctt cgttctacca
4141 tcgacaccac cacgctggca cccagttgat cggcgcgaga tttaatcgcc gcgacaattt
4201 gcgacgcgc gtgcagggcc agactggagg tggcaacgcc aatcagcaac gactgtttgc
4261 ccgccagttg ttgtgccacg cggttgggaa tgtaattcag ctccgccatc gccgcttcca
4321 cttttttccg cgttttcgca gaaacgtggc tggcctggtt caccacgcgg gaaacggtct
4381 gataagagac accggcatac tctgcgacat cgtataacgt tactggtttc acattcacca
4441 ccctgaattg actctcttcc gggcgctatc atgccatacc gcgaaaggtt ttgcgccatt
4501 cgatggtgtc aacgtaaatg catgccgctt cgccttcgcg gcgaattgc aagctgatcc
4561 ggagcttatc gactgcacgg tgcaccaatg cttctggcgt caggcagcca tcggaagctg
4621 tggtatggct gtgcaggtcg taaatcactg cataattcgt gtcgctcaag gcgcactccc
4681 gttctggata atgttttttg cgccgacatc ataacggttc tggcaaatat tctgaaatga
4741 gctgttgaca attaatcatc ggctcgtata atgtgtggaa ttgtgagcgg ataacaattt
4801 cacacaggaa acagaattcc atatgaaata cctattacca acagcagcag ctgggttatt
4861 attgctcgct gcgcagccgg ccatgcccca ggtcaccgtc tcctcaggta ccgtggctgc
4921 accatctgtc ttcatcttcc cgccatctga tgagcagttg aaatctggaa ctgcctctgt
4981 tgtgtgcctg ctgaataact ctatcccag agaggccaaa gtacagtgga aggtggataa
5041 cgccctccaa tcgggtaact cccaggagag tgtcacagag caggacagca aggacagcac
5101 ctacagcctc agcagcaccc tgacgctgag caaagcagac tacgagaaac acaaagtcta
5161 cgcctgcgaa gtcacccatc agggcctgag ctcgccggtg acaaagagct tcaaccgcgg
5221 agagtgttaa taaacaggaa acagaagtcc atatgaaata cctattgcct acggcagccg
```

Figure 11 (Contd.)

```
     5281 ctggattgtt attactcgcg gcccagccgg ccatggccgc tagcaccaag ggcccatcgg
     5341 tcttcccct  ggcaccctcc tccaagagca cctctggggg cacagcggcc ctgggctgcc
     5401 tggtcaagga ctacttcccc gaaccggtga cggtgtcgtg gaactcaggc gccctgacca
     5461 gcggcgtgca caccttcccg gctgtcctac agtcctcagg actctactcc ctcagcagcg
     5521 tagtgaccgt gccctccagc agcttgggca cccagaccta catctgcaac gtgaatcaca
     5581 agcccagcaa caccaaggtg gacaagaaag ttgagcccaa atcttgtgac aaaactcaca
     5641 catgcccacc gtgcccataa gcttggctgt tttggcggat gagagaagat tttcagcctg
     5701 atacagatta aatcagaacg cagaagcggt ctgataaaac agaatttgcc tggcggcagt
     5761 agcgcggtgg tcccacctga ccccatgccg aactcagaag tgaaacgccg tagcgccgat
     5821 ggtagtgtgg ggtctcccca tgcgagagta gggaactgcc aggcatcaaa taaaacgaaa
     5881 ggctcagtcg aaagactggg cctttcgttt tatctgttgt ttgtcggtga acgctctcct
     5941 gagtaggaca aatccgccgg gagcggattt gaacgttgcg aagcaacggc ccggaggacc
     6001 ctggcgggca ggacgccgc  cataaactgc caggcatcaa attaagcaga aggccatcct
     6061 gacggatggc cttttgcgt  ttctacaaac tctt SEQ ID N° 115
        1 ttgtttattt ttctaaatac attcaaatat gtatccgctc atgagacaat aaccctgata
       61 aatgcttcaa taatattgaa aaggaagag  tatgagtatt caacatttcc gtgtcgccct
      121 tattcccttt tttgcggcat tttgccttcc tgttttttgct cacccagaaa cgctggtgaa
      181 agtaaaagat gctgaagatc agttgggtgc acgagtgggt tacatcgaac tggatctcaa
      241 cagcggtaag atccttgaga gttttcgccc cgaagaacgt tttccaatga tgagcacttt
      301 taaagttctg ctatgtggcg cggtattatc ccgtgttgac gccgggcaag agcaactcgg
      361 tcgccgcata cactattctc agaatgactt ggttgagtac tcaccagtca cagaaaagca
      421 tcttacggat ggcatgacag taagagaatt atgcagtgct gccataacca tgagtgataa
      481 cactgcggcc aacttacttc tgacaacgat cggaggaccg aaggagctaa ccgcttttt
      541 gcacaacatg gggatcatg  taactcgcct tgatcgttgg gaaccgagc  tgaatgaagc
      601 cataccaaac gacgagcgtg acaccacgat gcctgtagca atggcaacaa cgttgcgcaa
      661 actattaact ggcgaactac ttactctagc ttcccggcaa caattaatag actgcatgga
      721 ggcggataaa gttgcaggac cacttctgcg ctcggccctt ccggctggct ggtttattgc
      781 tgataaatct ggagccggtg agcgtgggtc tcgcggtatc attgcagcac tggggccaga
      841 tggtaagccc tcccgtatcg tagttatcta cacgacgggg agtcaggcaa ctatggatga
      901 acgaaataga cagatcgctg agataggtgc ctcactgatt aagcattggt aactgtcaga
      961 ccaagtttac tcatatatac tttagattga tttaaaactt catttttaat ttaaaaggat
     1021 ctaggtgaag atcctttttg ataatctcat gaccaaaatc ccttaacgtg agttttcgtt
     1081 ccactgagcg tcagaccccg tagaaaagat caaaggatct cttgagatc  cttttttct
     1141 gcgcgtaatc tgctgcttgc aaacaaaaaa accaccgcta ccagcggtgg tttgtttgcc
     1201 ggatcaagag ctaccaactc tttttccgaa ggtaactggc ttcagcagag cgcagatacc
     1261 aaatactgtc cttctagtgt agccgtagtt aggccaccac ttcaagaact ctgtagcacc
     1321 gcctacatac ctcgctctgc taatcctgtt accagtggct gctgccagtg gcgataagtc
     1381 gtgtcttacc gggttggact caagacgata gttaccggat aaggcgcagc ggtcgggctg
     1441 aacggggggt tcgtgcacac agcccagctt ggagcgaacg acctacaccg aactgagata
     1501 cctacagcgt gagcattgag aaagcgccac gcttcccgaa gggagaaagg cggacaggta
     1561 tccggtaagc ggcagggtcg gaacaggaga gcgcacgagg gagcttccag ggggaaacgc
     1621 ctggtatctt tatagtcctg tcgggtttcg ccacctctga cttgagcgtc gatttttgtg
     1681 atgctcgtca gggggcgga  gcctatgaa  aaacgccagc aacgcggcct ttttacggtt
     1741 cctggccttt tgctggcctt ttgctcacat gttctttcct gcgttatccc ctgattctgt
     1801 ggataaccgt attaccgcct ttgagtgagc tgataccgct cgccgcagcc gaacgaccga
     1861 gcgcagcgag tcagtgagcg aggaagcgga agagcgcctg atgcggtatt ttctccttac
     1921 gcatctgtgc ggtatttcac accgcatata tggtgcactc tcagtacaat ctgctctgat
     1981 gccgcatagt taagccagta tacactccgc tatcgctacg tgactgggtc atggctgcgc
     2041 cccgacaccc gccaacaccc gctgacgcgc cctgacgggc ttgtctgctc ccggcatccg
     2101 cttacagaca agctgtgacc gtctccggga gctgcatgtg tcagaggttt tcaccgtcat
     2161 caccgaaacg cgcgaggcag ctgcggtaaa gctcatcagc gtggtcgtga agcgattcac
     2221 agatgtctgc ctgttcatcc gcgtccagct cgttgagttt ctccagaagc gttaatgtct
     2281 ggcttctgat aaagcgggcc atgttaaggg cggttttttc ctgtttggtc acttgatgcc
     2341 tccgtgtaag ggggaatttc tgttcatggg ggtaatgata ccgatgaaac gagagaggat
     2401 gctcacgata cgggttactg atgatgaaca tgcccggtta ctggaacgtt gtgagggtaa
     2461 acaactggcg gtatggatgc ggcgggacca gagaaaaatc actcagggtc aatgccagcg
```

Figure 11 (Contd.)

```
2521 cttcgttaat acagatgtag gtgttccaca gggtagccag cagcatcctg cgatgcagat
2581 ccggaacata atggtgcagg gcgctgactt ccgcgtttcc agactttacg aaacacggaa
2641 accgaagacc attcatgttg ttgctcaggt cgcagacgtt ttgcagcagc agtcgcttca
2701 cgttcgctcg cgtatcggtg attcattctg ctaaccagta aggcaacccc gccagcctag
2761 ccgggtcctc aacgacagga gcacgatcat gcgcacccgt ggccaggacc caacgctgcc
2821 cgagatgcgc cgcgtgcggc tgctggagat ggcggacgcg atggatatgt tctgccaagg
2881 gttggtttgc gcattcacag ttctccgcaa gaattgattg gctccaattc ttggagtggt
2941 gaatccgtta gcgaggtgcc gccggcttcc attcaggtcg aggtggcccg gctccatgca
3001 ccgcgacgca acgcggggag gcagacaagg tatagggcgg cgcctacaat ccatgccaac
3061 ccgttccatg tgctcgccga ggcggcataa atcgccgtga cgatcagcgg tccagtgatc
3121 gaagttaggc tggtaagagc cgcgagcgat ccttgaagct gtccctgatg gtcgtcatct
3181 acctgcctgg acagcatggc ctgcaacgcg ggcatcccga tgccgccgga agcgagaaga
3241 atcataatgg ggaaggccat ccagcctcgc gtcgcgaacg ccagcaagac gtagcccagc
3301 gcgtcggcca gcttgcaatt cgcgctaact tacattaatt gcgttgcgct cactgcccgc
3361 tttccagtcg ggaaacctgt cgtgccagct gcattaatga atcggccaac gcgcgggag
3421 aggcggtttg cgtattgggc gccagggtgg ttttttcttt caccagtgag acgggcaaca
3481 gctgattgcc cttcaccgcc tggccctgag agagttgcag caagcggtcc acgctggttt
3541 gccccagcag gcgaaaatcc tgtttgatgg tggttgacgg cgggatataa catgagctgt
3601 cttcggtatc gtcgtatccc actaccgaga tatccgcacc aacgcgcagc ccggactcgg
3661 taatggcgcg cattgcgccc agcgccatct gatcgttggc aaccagcatc gcagtgggaa
3721 cgatgccctc attcagcatt tgcatggttt gttgaaaacc ggacatggca ctccagtcgc
3781 cttcccgttc cgctatcggc tgaatttgat tgcgagtgag atatttatgc cagccagcca
3841 gacgcagacg cgccgagaca gaacttaatg gtcccgctaa cagcgcgatt tgctgatgac
3901 ccaatgcgac cagatgctcc acgcccagtc gcgtaccgtc ttcatgggag aaaataatac
3961 tgttgatggg tgtctggtca gagacatcaa gaaataacgc cggaacatta gtgcaggcag
4021 cttccacagc aatggcatcc tggtcatcca gcggatagtt aatgatcagc ccactgacgc
4081 gttgcgcgag aagattgtgc accgccgctt tacaggcttc gacgccgctt cgttctacca
4141 tcgacaccac cacgctggca cccagttgat cggcgcgaga tttaatcgcc gcgacaattt
4201 gcgacgcgc gtgcagggcc agactggagg tggcaaccgc aatcagcaac gactgtttgc
4261 ccgccagttg ttgtgccacg cggttgggaa tgtaattcag ctccgccatc gccgcttcca
4321 cttttttccg cgttttcgca gaaacgtggc tggcctggtt caccacgcgg gaaacggtct
4381 gataagagac accggcatac tctgcgacat cgtataacgt tactggtttc acattcacca
4441 ccctgaattg actctcttcc gggcgctatc atgccatacc gcgaaaggtt ttgcgccatt
4501 cgatggtgtc aacgtaaatg catgccgctt cgccttcgcg cgcgaattgc aagctgatcc
4561 ggagcttatc gactgcacgg tgcaccaatg cttctggcgt caggcagcca tcggaagctg
4621 tggtatggct gtgcaggtcg taaatcactg cataattcgt gtcgctcaag gcgcactccc
4681 gttctggata atgttttttg cgccgacatc ataacggttc tggcaaatat tctgaaatga
4741 gctgttgaca attaatcatc ggctcgtata atgtgtggaa ttgtgagcgg ataacaattt
4801 cacacaggaa acagaattcc atatgaaata cctattacca acagcagcag ctgggttatt
4861 attgctcgct gcgcagccgg ccatggccca ggtcaccgtc tcctcacgta cggtggctgc
4921 accatctgtc ttcatcttcc cgccatctga tgagcagttg aaatctggaa ctgcctctgt
4981 tgtgtgcctg ctgaataact tctatcccag agaggccaaa gtacagtgga aggtggataa
5041 cgccctccaa tcgggtaact cccaggagag tgtcacagag caggacagca aggacagcac
5101 ctacagcctc agcagcaccc tgacgctgag caaagcagac tacgagaaac acaaagtcta
5161 cgcctgcgaa gtcacccatc agggcctgag ctcgccggtg acaaagagct caaccgcgg
5221 agagtgttaa taaacaggaa acagaagtcc atatgaaata tctttttacct acggcagccg
5281 caggtttgtt gttactcgcg gccagccgg ccatgccgc tagcaccaag gcccatcgg
5341 tcttcccct ggcaccctcc tccaagagca cctctggggg cacagcggcc ctgggctgcc
5401 tggtcaagga ctacttcccg gaaccggtga cggtgtcgtg gaactcaggc gccctgacca
5461 gcggcgtgca caccttcccg gctgtcctac agtcctcagg actctactcc ctcagcagcg
5521 tagtgaccgt gccctccagc agcttgggca cccagaccta catctgcaac gtgaatcaca
5581 agcccagcaa caccaaggtg gacaagaaag ttgagcccaa atcttgtgac aaaactcaca
5641 catgcccacc gtgcccataa gcttggctgt tttggcggat gagagaagat tttcagcctg
5701 atacagatta aatcagaacg cagaagcggt ctgataaaac agaatttgcc tggcggcagt
5761 agcgcggtgg tcccacctga ccccatgccg aactcagaag tgaaacgccg tagcgccgat
5821 ggtagtgtgg ggtctcccca tgcgagagta gggaactgcc aggcatcaaa taaaacgaaa
5881 ggctcagtcg aaagactggg cctttcgttt tatctgttgt ttgtcggtga acgctctcct
5941 gagtaggaca aatccgccgg gagcggattt gaacgttgcg aagcaacggc ccggaggacc
```

Figure 11 (Contd.)

```
6001 ctggcgggca ggacgcccgc cataaactgc caggcatcaa attaagcaga aggccatcct
6061 gacggatggc cttttgcgt ttctacaaac tctt
``` pMabγ1*

SEQ ID N° 102
```
   1 ttgtttattt ttctaaatac attcaaatat gtatccgctc atgagacaat aaccctgata
  61 aatgcttcaa taatattgaa aaaggaagag tatgagtatt caacatttcc gtgtcgccct
 121 tattcccttt tttgcggcat tttgccttcc tgttttgct cacccagaaa cgctggtgaa
 181 agtaaaagat gctgaagatc agttgggtgc acgagtgggt tacatcgaac tggatctcaa
 241 cagcggtaag atccttgaga gttttcgccc cgaagaacgt tttccaatga tgagcacttt
 301 taaagttctg ctatgtggcg cggtattatc ccgtgttgac gccgggcaag agcaactcgg
 361 tcgccgcata cactattctc agaatgactt ggttgagtac tcaccagtca cagaaaagca
 421 tcttacggat ggcatgacag taagagaatt atgcagtgct gccataacca tgagtgataa
 481 cactgcggcc aacttacttc tgacaacgat cggaggaccg aaggagctaa ccgcttttt
 541 gcacaacatg gggatcatg taactcgcct tgatcgttgg gaaccggagc tgaatgaagc
 601 cataccaaac gacgagcgtg acaccacgat gcctgtagca atggcaacaa cgttgcgcaa
 661 actattaact ggcgaactac ttactctagc ttcccggcaa caattaatag actggatgga
 721 ggcggataaa gttgcaggac cacttctgcg ctcggccctt ccggctggct ggtttattgc
 781 tgataaatct ggagccggtg agcgtgggtc tcgcggtatc attgcagcac tggggccaga
 841 tggtaagccc tcccgtatcg tagttatcta cacgacgggg agtcaggcaa ctatggatga
 901 acgaaataga cagatcgctg atataggtgc ctcactgatt aagcattggt aactgtcaga
 961 ccaagtttac tcatatatac tttagattga tttaaaactt catttttaat ttaaaaggat
1021 ctaggtgaag atcctttttg ataatctcat gaccaaaatc ccttaacgtg agttttcgtt
1081 ccactgagcg tcagacccg tagaaaagat caaggatct tcttgagatc ctttttttct
1141 gcgcgtaatc tgctgcttgc aaacaaaaaa accaccgcta ccagcggtgg tttgtttgcc
1201 ggatcaagag ctaccaactc ttttccgaa ggtaactggc ttcagcagag cgcagatacc
1261 aaatactgtc cttctagtgt agccgtagtt aggccaccac ttcaagaact ctgtagcacc
1321 gcctacatac ctcgctctgc taatcctgtt accagtggct gctgccagtg gcgataagtc
1381 gtgtcttacc gggttggact caagacgata gttaccggat aaggcgcagc ggtcgggctg
1441 aacggggggt tcgtgcacac agcccagctt ggagcgaacg acctacaccg aactgagata
1501 cctacagcgt gagcattgag aaagcgccac gcttcccgaa gggagaaagg cggacaggta
1561 tccggtaagc ggcagggtcg aacaggaga gcgcacgagg gagcttccag ggggaaacgc
1621 ctggtatctt tatagtcctg tcgggtttcg ccacctctga cttgagcgtc gatttttgtg
1681 atgctcgtca ggggggcgga gcctatgaa aaacgccagc aacgcggcct ttttacggtt
1741 cctggccttt tgctggcctt ttgctcacat gttctttcct gcgttatccc ctgattctgt
1801 ggataaccgt attaccgcct ttgagtgagc tgataccgct cgccgcagcc gaacgaccga
1861 gcgcagcgag tcagtgagcg aggaagcgga agagcgcctg atgcggtatt ttctccttac
1921 gcatctgtgc ggtatttcac accgcatata tggtgcactc tcagtacaat ctgctctgat
1981 gccgcatagt taagccagta tacactccgc tatcgctacg tgactgggtc atggctgcgc
2041 cccgacaccc gccaacaccc gctgacgcgc cctgacgggc ttgtctgctc ccggcatccg
2101 cttacagaca agctgtgacc gtctccggga gctgcatgtg tcagaggttt tcaccgtcat
2161 caccgaaacg cgcgaggcag ctgcggtaaa gctcatcagc gtggtcgtga agcgattcac
2221 agatgtctgc ctgttcatcc gcgtccagct cgttgagttt ctccagaagc gttaatgtct
2281 ggcttctgat aaagcgggcc atgttaaggg cggttttttc ctgtttggtc acttgatgcc
2341 tccgtgtaag ggggaatttc tgttcatggg gtaatgata ccgatgaaac gagagaggat
2401 gctcacgata cgggttactg atgatgaaca tgcccggtta ctggaacgtt gtgagggtaa
2461 acaactggcg gtatggatgc ggcgggacca gagaaaaatc actcagggtc aatgccagcg
2521 cttcgttaat acagatgtag gtgttccaca gggtagccag cagcatcctg cgatgcagat
2581 ccggaacata atggtgcagg gcgctgactt ccgcgtttcc agactttacg aaacacggaa
2641 accgaagacc attcatgttg ttgctcaggt cgcagacgtt ttgcagcagc agtcgcttca
2701 cgttcgctcg cgtatcggtg attcattctg ctaaccagta aggcaacccc gccagcctag
2761 ccgggtcctc aacgacagga gcacgatcat gcgcacccgt ggccaggacc caacgctgcc
2821 cgagatgcgc cgcgtgcggc tgctggagat ggcggacgcg atggatatgt tctgccaagg
2881 gttggtttgc gcattcacag ttctccgcaa gaattgattg gctccaattc ttggagtggt
2941 gaatccgtta gcgaggtgcc gccggcttcc attcaggtcg aggtggcccg gctccatgca
3001 ccgcgacgca acgcggggag gcagacaagg tatagggcgg cgcctacaat ccatgccaac
```

Figure 11 (Contd.)

```
3061 ccgttccatg tgctcgccga ggcggcataa atcgccgtga cgatcagcgg tccagtgatc
3121 gaagttaggc tggtaagagc cgcgagcgat ccttgaagct gtccctgatg gtcgtcatct
3181 acctgctgg acagcatggc ctgcaacgcg ggcatcccga tgccgccgga agcgagaaga
3241 atcataatgg ggaaggccat ccagcctcgc gtcgcgaacg ccagcaagac gtagcccagc
3301 gcgtcggcca gcttgcaatt cgcgctaact tacattaatt gcgttgcgct cactgccgc
3361 tttccagtcg ggaaacctgt cgtgccagct gcattaatga atcggccaac gcgcggggag
3421 aggcggtttg cgtattgggc gccagggtgg ttttcttt caccagtgag acgggcaaca
3481 gctgattgcc cttcaccgcc tggccctgag agagttgcag caagcggtcc acgctggttt
3541 gccccagcag gcgaaaatcc tgtttgatgg tggttgacgg cgggatataa catgagctgt
3601 cttcggtatc gtcgtatccc actaccgaga tatccgcacc aacgcgcagc ccggactcgg
3661 taatggcgcg cattgcgccc agcgccatct gatcgttggc aaccagcatc gcagtgggaa
3721 cgatgccctc attcagcatt tgcatggttt gttgaaaacc ggacatggca ctccagtcgc
3781 cttccgttc cgctatcggc tgaatttgat tgcgagtgag atatttatgc cagccagcca
3841 gacgcagacg cgccgagaca gaacttaatg gtcccgctaa cagcgcgatt tgctgatgac
3901 ccaatgcgac cagatgctcc acgcccagtc gcgtaccgtc ttcatgggag aaaataatac
3961 tgttgatggg tgtctggtca gagacatcaa gaataacgc cggaacatta gtgcaggcag
4021 cttccacagc aatgccatcc tggtcatcca gcggatagtt aatgatcagc ccactgacgc
4081 gttgcgcgag aagattgtgc accgccgctt tacaggcttc gacgccgctt cgttctacca
4141 tcgacaccac cacgctggca cccagttgat cggcgcgaga tttaatcgcc gcgacaattt
4201 gcgacggcgc gtgcagggcc agactggagg tggcaacgcc aatcagcaac gactgtttgc
4261 ccgccagttg ttgtgccacg cggttgggaa tgtaattcag ctccgccatc gccgcttcca
4321 cttttcccg cgttttcgca gaaacgtggc tggcctggtt caccacgcgg gaaacggtct
4381 gataagagac accggcatac tctgcgacat cgtataacgt tactggttc acattcacca
4441 ccctgaattg actctcttcc gggcgctatc atgccatacc gcgaaaggtt ttgcgccatt
4501 cgatggtgtc aacgtaaatg catgccgctt cgccttcgcg cgcgaattgc aagctgatcc
4561 ggagcttatc gactgcacgg tgcaccaatg cttctggcgt caggcagcca tcggaagctg
4621 tggtatggct gtgcaggtcg taatcactg cataattcgt gtcgctcaag gcgcactccc
4681 gttctggata atgtttttg cgccgacatc ataacggttc tggcaaatat tctgaaatga
4741 gctgttgaca attaatcatc ggctcgtata atgtgtggaa ttgtgagcgg ataacaattt
4801 cacacaggaa acagaattcc atatgaaata cctattacca acagcagcag ctgggttatt
4861 attgctcgct gcgcagccgg ccatggccca ggtcaccgtc tcctcaggta ccgtggctgc
4921 accatctgtc ttcatcttcc cgccatctga tgagcagttg aaatctggaa ctgcctctgt
4981 tgtgtgcctg ctgaataact tctatcccag agaggccaaa gtacagtgga aggtggataa
5041 cgccctccaa tcgggtaact cccaggagag tgtcacagag caggacagca aggacagcac
5101 ctacagcctc agcagcaccc tgacgctgag caaagcagac tacgagaaac acaaagtcta
5161 cgcctgcgaa gtcacccatc agggcctgag ctcgccggtg acaaagagct caaccgcgg
5221 agagtgttaa taaacaggaa acagaagtcc atatgaaata cctattgcct acggcagccg
5281 ctggattgtt attactcgcg gccagccgg ccatggccgc tagcaccaag ggcccatcgg
5341 tcttcccct ggcaccctcc tccaagagca cctctggggg cacagcggcc ctgggctgcc
5401 tggtcaagga ctacttcccc gaaccggtga cggtgtcgtg gaactcaggc gccctgacca
5461 gcggcgtgca caccttccg gctgtcctac agtcctcagg actctactcc ctcagcagcg
5521 tggtgaccgt gccctccagc agcttgggca cccagaccta catctgcaac gtgaatcaca
5581 agcccagcaa caccaaggtg gacaagaaag ttgagcccaa atcttgtgac aaaactcaca
5641 catgcccacc gtgcccagca cctgaactcc tggggggacc gtcagtcttc ctcttccccc
5701 caaacccaa ggacaccctc atgatctccc ggacccctga ggtcacatgc gtggtggtgg
5761 acgtgagcca cgaagaccct gaggtcaagt tcaactggta cgtggacggc gtggaggtgc
5821 ataatgccaa gacaaagccg cgggaggagc agtacaacag cacgtaccgg gtggtcagcg
5881 tcctcaccgt cctgcaccag gactggctga atggcaagga gtacaagtgc aaggtctcca
5941 acaaagccct cccagccccc atcgagaaaa ccatctccaa agccaaaggg cagccccgag
6001 aaccacaggt gtacaccctg cccccatccc gggatgagct gaccaagaac caggtcagcc
6061 tgacctgcct ggtcaaaggc ttctatccca gcgacatcgc cgtggagtgg gagagcaatg
6121 ggcagccgga gaacaactac aagaccacgc ctcccgtgct ggactccgac ggctccttct
6181 tcctctacag caagctcacc gtggacaaga gcaggtggca gaggggaac gtcttctcat
6241 gctccgtgat gcatgaggct ctgcacaacc actacacgca gaagagcctc tccctgtctc
6301 cgggtaaata gcttggctg ttttggcgga tgagaagaa ttttcagcct gatacagatt
6361 aaatcagaac gcagaagcgg tctgataaaa cagaatttgc ctggcggcag tagcgcggtg
6421 gtcccacctg acccatgcc gaactcagaa gtgaaacgcc gtagcgccga tggtagtgtg
6481 gggtctcccc atgcgagagt agggaactgc caggcatcaa ataaaacgaa aggctcagtc
```

Figure 11 (Contd.)

```
    6541 gaaagactgg gcctttcgtt ttatctgttg tttgtcggtg aacgctctcc tgagtaggac
    6601 aaatccgccg ggagcggatt tgaacgttgc gaagcaacgg cccggaggac cctggcgggc
    6661 aggacgcccg ccataaactg ccaggcatca aattaagcag aaggccatcc tgacggatgg
    6721 ccttttgcg tttctacaaa ctctt SEQ ID N° 116
       1 ttgtttattt ttctaaatac attcaaatat gtatccgctc atgagacaat aaccctgata
      61 aatgcttcaa taatattgaa aaggaagag tatgagtatt caacatttcc gtgtcgccct
     121 tattccctt tttgcggcat tttgccttcc tgttttgct cacccagaaa cgctggtgaa
     181 agtaaaagat gctgaagatc agttgggtgc acgagtgggt tacatcgaac tggatctcaa
     241 cagcggtaag atccttgaga gttttcgccc cgaagaacgt tttccaatga tgagcacttt
     301 taaagttctg ctatgtggcg cggtattatc ccgtgttgac gccgggcaag agcaactcgg
     361 tcgccgcata cactattctc agaatgactt ggttgagtac tcaccagtca cagaaaagca
     421 tcttacggat ggcatgacag taagagaatt atgcagtgct gccataacca tgagtgataa
     481 cactgcggcc aacttacttc tgacaacgat cggaggaccg aaggagctaa ccgcttttt
     541 gcacaacatg gggatcatg taactcgcct tgatcgttgg aaccggagc tgaatgaagc
     601 cataccaaac gacgagcgtg acaccacgat gcctgtagca atggcaacaa cgttgcgcaa
     661 actattaact ggcgaactac ttactctagc ttcccggcaa caattaatag actggatgga
     721 ggcggataaa gttgcaggac cacttctgcg ctcggccctt ccggctggct ggtttattgc
     781 tgataaatct ggagccggtg agcgtgggtc tcgcggtatc attgcagcac tggggccaga
     841 tggtaagccc tcccgtatcg tagttatcta cacgacgggg agtcaggcaa ctatggatga
     901 acgaaataga cagatcgctg agataggtgc ctcactgatt aagcattggt aactgtcaga
     961 ccaagtttac tcatatatac tttagattga tttaaaactt cattttaat ttaaaaggat
    1021 ctaggtgaag atcctttttg ataatctcat gaccaaaatc ccttaacgtg agttttcgtt
    1081 ccactgagcg tcagaccccg tagaaaagat caaaggatct tcttgagatc cttttttct
    1141 gcgcgtaatc tgctgcttgc aaacaaaaaa accaccgcta ccagcggtgg tttgtttgcc
    1201 ggatcaagag ctaccaactc tttttccgaa ggtaactggc ttcagcagag cgcagatacc
    1261 aaatactgtc cttctagtgt agccgtagtt aggccaccac ttcaagaact ctgtagcacc
    1321 gcctacatac ctcgctctgc taatcctgtt accagtggct gctgccagtg gcgataagtc
    1381 gtgtcttacc gggttggact caagacgata gttaccggat aaggcgcagc ggtcgggctg
    1441 aacgggggt tcgtgcacac agcccagctt ggagcgaacg acctacaccg aactgagata
    1501 cctacagcgt gagcattgag aaagcgccac gcttcccgaa gggagaaagg cggacaggta
    1561 tccggtaagc ggcagggtcg gaacaggaga gcgcacgagg gagcttccag ggggaaacgc
    1621 ctggtatctt tatagtcctg tcgggtttcg ccacctctga cttgagcgtc gatttttgtg
    1681 atgctcgtca ggggggcgga gcctatggaa aaacgccagc aacgcggcct ttttacggtt
    1741 cctggccttt tgctggcctt ttgctcacat gttctttcct gcgttatccc ctgattctgt
    1801 ggataaccgt attaccgcct ttgagtgagc tgataccgct cgccgcagcc gaacgaccga
    1861 gcgcagcgag tcagtgagcg aggaagcgga agagcgcctg atgcggtatt ttctccttac
    1921 gcatctgtgc ggtatttcac accgcatata tggtgcactc tcagtacaat ctgctctgat
    1981 gccgcatagt taagccagta tacactccgc tatcgctacg tgactgggtc atggctgcgc
    2041 cccgacaccc gccaacaccc gctgacgcgc cctgacgggc ttgtctgctc ccggcatccg
    2101 cttacagaca agctgtgacc gtctccggga gctgcatgtg tcagaggttt tcaccgtcat
    2161 caccgaaacg cgcgaggcag ctgcggtaaa gctcatcagc gtggtcgtga gcgattcac
    2221 agatgtctgc ctgttcatcc gcgtccagct cgttgagttt ctccagaagc gttaatgtct
    2281 ggcttctgat aaagcgggcc atgttaaggg cggttttttc ctgtttggtc acttgatgcc
    2341 tccgtgtaag ggggaatttc tgttcatggg ggtaatgata ccgatgaaac gagagaggat
    2401 gctcacgata cgggttactg atgatgaaca tgcccggtta ctggaacgtt gtgagggtaa
    2461 acaactggcg gtatggatgc ggcgggacca gagaaaaatc actcagggtc aatgccagcg
    2521 cttcgttaat acagatgtag tgttccaca gggtagccag cagcatcctg cgatgcagat
    2581 ccggaacata atggtgcagg gcgctgactt ccgcgtttcc agactttacg aaacacggaa
    2641 accgaagacc attcatgttg ttgctcaggt cgcagacgtt ttgcagcagc agtcgcttca
    2701 cgttcgctcg cgtatcggtg attcattctg ctaaccagta aggcaacccc gccagcctag
    2761 ccgggtcctc aacgacagga gcacgatcat gcgcacccgt ggccaggacc caacgctgcc
    2821 cgagatgcgc cgcgtgcggc tgctggagat ggcggacgcg atggatatgt tctgccaagg
    2881 gttggtttgc gcattcacag ttctccgcaa gaattgattg gctccaattc ttggagtggt
    2941 gaatccgtta gcgaggtgcc gccggcttcc attcaggtcg aggtggcccg gctccatgca
    3001 ccgcgacgca acgcgggag gcagacaagg tatagggcgg cgcctacaat ccatgccaac
    3061 ccgttccatg tgctcgccga ggcggcataa atcgccgtga cgatcagcgg tccagtgatc
```

Figure 11 (Contd.)

```
3121 gaagttaggc tggtaagagc cgcgagcgat ccttgaagct gtccctgatg gtcgtcatct
3181 acctgcctgg acagcatggc ctgcaacgcg ggcatcccga tgccgccgga agcgagaaga
3241 atcataatgg ggaaggccat ccagcctcgc gtcgcgaacg ccagcaagac gtagcccagc
3301 gcgtcggcca gcttgcaatt cgcgctaact tacattaatt gcgttgcgct cactgcccgc
3361 tttccagtcg ggaaacctgt cgtgccagct gcattaatga atcggccaac gcgcggggag
3421 aggcggtttg cgtattgggc gccagggtgg ttttctttt caccagtgag acgggcaaca
3481 gctgattgcc cttcaccgcc tggccctgag agagttgcag caagcggtcc acgctggttt
3541 gccccagcag gcgaaaatcc tgtttgatgg tggttgacgg cgggatataa catgagctgt
3601 cttcggtatc gtcgtatccc actaccgaga tatccgcacc aacgcgcagc ccggactcgg
3661 taatggcgcg cattgcgccc agcgccatct gatcgttggc aaccagcatc gcagtgggaa
3721 cgatgccctc attcagcatt tgcatggttt gttgaaaacc ggacatggca ctccagtcgc
3781 cttccgttc cgctatcggc tgaatttgat tgcgagtgag atatttatgc cagccagcca
3841 gacgcagacg cgccgagaca gaacttaatg gtcccgctaa cagcgcgatt tgctgatgac
3901 ccaatgcgac cagatgctcc acgcccagtc gcgtaccgtc ttcatgggag aaaataatac
3961 tgttgatggg tgtctggtca gagacatcaa gaaataacgc cggaacatta gtgcaggcag
4021 cttccacagc aatggcatcc tggtcatcca gcggatagtt aatgatcagc ccactgacgc
4081 gttgcgcgag aagattgtgc accgccgctt tacaggcttc gacgccgctt cgttctacca
4141 tcgacaccac cacgctggca cccagttgat cggcgcgaga tttaatcgcc gcgacaattt
4201 gcgacggcgc gtgcagggcc agactggagg tggcaacgcc aatcagcaac gactgtttgc
4261 ccgccagttg ttgtgccacg cggttgggaa tgtaattcag ctccgccatc gccgcttcca
4321 ctttttcccg cgttttcgca gaaacgtggc tggcctggtt caccacgcgg gaaacggtct
4381 gataagagac accggcatac tctgcgacat cgtataacgt tactggtttc acattcacca
4441 ccctgaattg actctcttcc gggcgctatc atgccatacc gcgaaaggtt ttgcgccatt
4501 cgatggtgtc aacgtaaatg catgccgctt cgccttcgcg cgcgaattgc aagctgatcc
4561 ggagcttatc gactgcacgg tgcaccaatg cttctggcgt caggcagcca tcggaagctg
4621 tggtatggct gtgcaggtcg taaatcactg cataattcgt gtcgctcaag gcgcactccc
4681 gttctggata atgttttttg cgccgacatc ataacggttc tggcaaatat tctgaaatga
4741 gctgttgaca attaatcatc ggctcgtata atgtgtggaa ttgtgagcgg ataacaattt
4801 cacacaggaa acagaattcc atatgaaata cctattacca acagcagcag ctgggttatt
4861 attgctcgct gcgcagccgg ccatggccca ggtcaccgtc tcctcacgta cggtggctgc
4921 accatctgtc ttcatcttcc cgccatctga tgagcagttg aaatctggaa ctgcctctgt
4981 tgtgtgcctg ctgaataact ctatcccag agaggccaaa gtacagtgga aggtggataa
5041 cgccctccaa tcgggtaact cccaggagag tgtcacagag caggacagca aggacagcac
5101 ctacagcctc agcagcaccc tgacgctgag caaagcagac tacgagaaac acaagtcta
5161 cgcctgcgaa gtcacccatc agggcctgag ctcgccggtg acaaagagct tcaaccgcgg
5221 agagtgttaa taaacaggaa acagaagtcc atatgaaata tcttttacct acggcagccg
5281 caggtttgtt gttactcgcg gcccagccgg ccatggccgc tagcaccaag ggcccatcgg
5341 tcttcccct ggcaccctcc tccaagagca cctctggggg cacagcggcc ctgggctgcc
5401 tggtcaagga ctacttcccc gaaccggtga cggtgtcgtg gaactcaggc gccctgacca
5461 gcggcgtgca caccttccg gctgtcctac agtcctcagg actctactcc ctcagcagcg
5521 tggtgaccgt gccctccagc agcttgggca cccagaccta catctgcaac gtgaatcaca
5581 agcccagcaa caccaaggtg gacaagaaag ttgagccaa atcttgtgac aaaactcaca
5641 catgcccacc gtgcccagca cctgaactcc tggggggacc gtcagtcttc ctcttccccc
5701 caaacccaa ggacaccctc atgatctccc ggacccctga ggtcacatgc gtggtggtgg
5761 acgtgagcca cgaagaccct gaggtcaagt tcaactggta cgtggacggc gtggaggtgc
5821 ataatgccaa gacaaagccg cgggaggagc agtacaacag cacgtaccgg gtggtcagcg
5881 tcctcaccgt cctgcaccag gactggctga atggcaagga gtacaagtgc aaggtctcca
5941 acaaagccct cccagccccc atcgagaaaa ccatctccaa agccaaaggg cagccccgag
6001 aaccacaggt gtacaccctg cccccatccc gggatgagct gaccaagaac caggtcagcc
6061 tgacctgcct ggtcaaaggc ttctatccca gcgacatcgc cgtggagtgg gagagcaatg
6121 ggcagccgga gaacaactac aagaccacgc ctcccgtgct ggactccgac ggctccttct
6181 tcctctacag caagctcacc gtggacaaga gcaggtggca gcaggggaac gtcttctcat
6241 gctccgtgat gcatgaggct ctgcacaacc actacacgca gaagagcctc tccctgtctc
6301 cgggtaaata agcttggctg ttttggcgga tgagagaaga ttttcagcct gatacagatt
6361 aaatcagaac gcagaagcgg tctgataaaa cagaatttgc ctggcggcag tagcgcggtg
6421 gtcccacctg acccatgcc gaactcagaa gtgaaacgcc gtagcgccga tggtagtgtg
6481 gggtctcccc atgcgagagt agggaactgc caggcatcaa ataaaacgaa aggctcagtc
6541 gaaagactgg gcctttcgtt ttatctgttg tttgtcggtg aacgctctcc tgagtaggac
```

Figure 11 (Contd.)

```
6601 aaatccgccg ggagcggatt tgaacgttgc gaagcaacgg cccggaggac cctggcgggc
6661 aggacgcccg ccataaactg ccaggcatca aattaagcag aaggccatcc tgacggatgg
6721 ccttttttgcg tttctacaaa ctctt
```

Fab type:
VHH1-CL/VHH2-CH1γ1
(cloning of VHH in the plasmids
pCkCH1γ1-TAG or PCkCH1γ1)

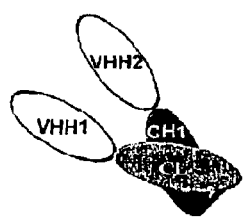

Combinations:

| VHH1 | A | A |
|---|---|---|
| VHH2 | A | B |

Formats:
AA = monospecific, bivalent
AB = bispecific or biepitopic, monovalent

F(ab')2 type:
VHH1-CL/VHH2-CH1Hγ1
(cloning of VHH in the plasmids
pCkCH1Hγ1-TAG or pCkCH1Hγ1)

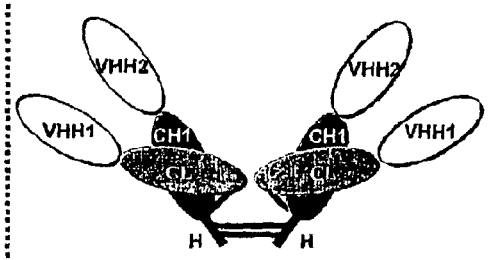

Combinations:

| VHH1 | Ax2 | Ax2 |
|---|---|---|
| VHH2 | Ax2 | Bx2 |

Formats:
A4: monospecific, tetravalent
A2B2 = bispecific or biepitopic, bivalent Combinations:

| VHH1 | A | A | A | A | A | A | A | B | A |
|---|---|---|---|---|---|---|---|---|---|
| VHH2 | A | B | A | A | A | B | B | A | B |
| VHH3 | A | A | B | A | B | B | A | C | A | C |
| VHH4 | A | B | B | B | A | C | C | A | C | D |

Formats: of the tetravalent monospecific (AAAA) to the tetraspecific or monovalent tetraepitopic (ABCD) passing by all of the other possible formats (refer to nomenclature and definitions above)

Reduction of the disulphide bridges of a type F(ab')2 fragment and another type F(ab')2 fragment, then reassembly by a bridging agent.

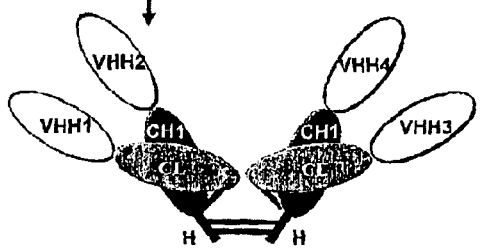

Figure 12A

Type (HCH2CH3)2:
VHH-HCH2CH3
(cloning of VHH in the plasmids
pHC2CH3γ1-TAG or pHCH2CH3γ1)
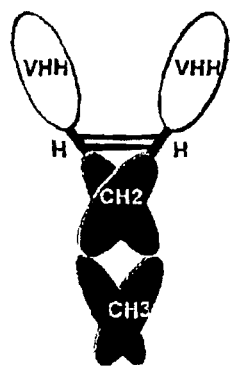
| Combinations: | | |
|---|---|---|
| VHH | A | A |
Formats:
A2 = monospecific, bivalent
Type mAb*
VHH1-CL/VHH2-CH1HCH2CH3 γ1
(cloning of VHH in the plasmid
pCkCH1CH2CH3γ1)
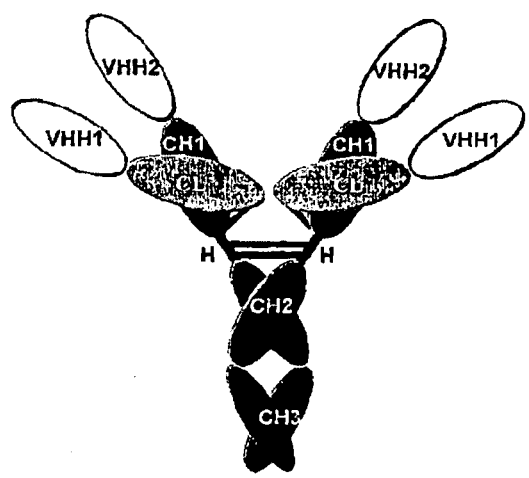
| Combinations: | | |
|---|---|---|
| VHH1 | Ax2 | Ax2 |
| VHH2 | Ax2 | Bx2 |
Formats:
A4 = monospecific, tetravalent
A2B2 = bispecific or biepitopic, bivalent
Figure 12B

PRODUCTION OF ANTIBODY FORMATS AND IMMUNOLOGICAL APPLICATIONS OF SAID FORMATS

CROSS-REFERENCE TO RELATED APPLICATIONS

This application is a continuation of PCT Serial No. PCT/FR2005/003151, filed Dec. 15, 2005, which claims priority to French Application Serial No. 04/13433, filed Dec. 16, 2004, both of which are incorporated by reference herein.

BACKGROUND AND SUMMARY

The invention relates to the production of antibody formats and their immunological applications, more specifically in immunotherapy and immunodiagnostic. The inventors call to mind that antibody molecules are immunoglobulins (Ig) belonging to 5 classes: IgM, IgG, IgD, IgE and IgA. In general, these molecules comprise a heavy chain (H) and a light chain (L) that is either the kappa chain (κ), or the lambda chain (λ).

Each class of immunoglobulins comprises a specific type of H chain: µ chain for IgM, γ for IgG, δ for IgD, ε for IgE and α for IgA. Each chain is formed by domains, each with an inner disulphide bond. An L chain has two domains and an H chain has 4 domains. The sequence of the domain comprising the amine end of each chain is variable (VH and VL regions), that of other domains is constant (CH1, CH2 and CH3 of the H chain, and CL of the L chain). The variable regions V comprise regions of hypervariable sequences called CDR together determining the complementarity.

In the H chains, the first two domains (VH-CH1) are followed by a hinge region. In an immunoglobulin, the L chain is connected to the H chain by a disulphide bond to form a heterodimer. This heterodimer is connected to the same heterodimer by several disulphide bonds at the hinge region to form the immunoglobulin. By splitting with a protease at the level of the hinge, we obtain two fragments: fragment Fab (antigen binding domain, comprising the VL-CL and VH-CH1 domains) and fragment Fc (effector domain, comprising domains $(CH2-CH3)_2$).

The invention more specifically refers to antibody fragments and different antibody formats created from these fragments, in particular formats of chimerised or humanised, multispecific and/or multivalent antibodies. The "antibody formats" as referred to in the invention correspond to different combinations of domains and regions of the types mentioned above.

By "chimerised antibody", the inventors refer to a VH domain of animal origin fused to constant regions of human immunoglobulin. By "humanised antibody", the inventors refer to a human VH domain on which hypervariable regions (CDRs) are grafted from a VH of animal origin, fused to constant regions of a human Ig.

These antibodies recognise the epitopes of targets corresponding to a given molecule. These epitopes may differ, and belong to different targets or the same target. Thereby "bispecific antibody" refers to a format with two different VH binding two different targets; "biepitopic antibody" refers to a format with two different VH binding two different epitopes on the same target. The "valence" corresponds to the number of times the same VH is found on the fragment considered.

The recognition specificity of antibodies to reach a determined target has been used for the diagnosis and treatment of different diseases and, in particular in oncology, where the target may be an antigen associated with a tumour, a growth factor receptor, an oncogene product or a muted "tumour suppressor" gene, or even a molecule linked to angiogenesis or a molecule also expressed on non-tumoural cells, but absent from progenitor cells (as in the case of CD20).

After over 20 years of experimental work, the immunotargeting of tumours by monoclonal antibodies is currently developing considerably. Thereby, the results of the different clinical studies have recently demonstrated the therapeutic possibilities of certain antibodies and have led to their approval by the FDA and the granting of a European AMM.

This progression is largely due to the use of so-called "second generation" recombinant antibodies: humanised antibodies, such as Herceptine, an anti-HER2/Neu antibody used in association with chemotherapy in certain breast carcinomas; and chimeric antibodies such as Rituximab, an anti-CD20 antibody used in the treatment of follicular B-cell lymphomas. Through gene engineering, it is possible to "graft" the variable or hypervariable regions of mouse antibodies on human Ig molecules. New techniques can now be used to obtain fully human antibodies either by selection of variable human domains expressed on phages (so-called "Phage display" technique), or by using transgenic mice producing human antibodies.

Moreover, the concept of bispecific antibodies has been used to stimulate the immune system and thereby favour the contact between the tumoural target cell and an effector cell. It consists in constructing an antibody endowed with a double specificity. This antibody should be able to bind a molecule produced at the surface of tumoural cells (such as CEA, HER2/Neu, GD2, etc.) and a molecule expressed at the surface of effector cells of the immunity, NK cells, killer T lymphocytes or CTL, polynuclear neutrophils, monocytes and macrophages (such as Fc receptors, etc.). A variant of this strategy consists of constructing an antibody linking a molecule produced at the surface of the tumoural cell and a molecule presenting direct or indirect properties of cytotoxicity (radio-element, toxin, prodrug).

Until now, most of the bispecific antibodies were developed by biochemically coupling 2 fragments of antibodies. However, this technique is rarely developed on an industrial scale. Several bispecific antibodies have been genetically developed, such as bispecific antibodies of the scFv type ("diabodies"). Unfortunately, they remain difficult to produce in *E. coli* in soluble form and they also are not very effective in terms of ADCC.

Within the search for candidate antibodies to generate antibody formats for immunotherapy and in particular to obtain multi-specific antibodies, the inventors directed their work towards specific antibodies, without a light chain, identified in the Camelidae (camel, dromedary, llama) (Hamers-Casterman et al., 1993).

Variable domains of heavy single chain antibodies from Camelidae (VHH), specifically recognising a type of antigen, were selected from immunised animals and were used to develop different formats of chimerised or humanised antibodies that may be produced from plasmid constructions. It turned out that the different formats were compatible to enable the production of any other VHH or humanised VHH, or human VH.

The invention aims at providing antibody formats comprising a part of the totality of VHH or humanised VHH, or human VH domains with properties to recognise the searched for targets and epitopes. It also aims at providing a method for the production of these different constructions. According to another aspect, the invention aims at immunotherapeutic and immunodiagnostic applications of the different formats provided. The invention also relates to antibody formats including a part or the totality of the VHH domains of Camelidae, in particular llamas and/or human VH, fused to constant regions of human antibodies.

According to a first means of achievement of the invention, the antibody formats are of Fab type and are characterised by the association of two identical or different VHH domains or two human VH domains, or two human VH domains on which are grafted the CDRs of the VHH, one of the domains being fused to the constant region Cκ or Cλ of a human immunoglobulin, the other to the constant region CH1 from a human immunoglobulin.

According to a second means of achievement of the invention, the antibody formats are of the Fab' type and are characterised by the association of two identical or different VHH domains or two human VH domains, or two human VH domains on which are grafted the CDRs of the VHH, one of the domains being fused to the constant region Cκ or Cλ of a human immunoglobulin, the other to the constant region CH1 followed by a hinge region H from a human immunoglobulin. These chimerised or humanised antibody formats are of monospecific/bivalent, bispecific/monovalent and biepitopic/monovalent types.

According to a third means of achievement of the invention, the antibody formats are of F(ab')$_2$ type and are characterised by the association of two formats of Fab' type as defined above. These chimerised or humanised antibody formats have a hinge region H, from a human immunoglobulin and allow for monospecific/tetravalent, bispecific/bivalent and biepitopic/bivalent combinations.

According to a fourth means of achievement of the invention, the antibody formats are of F(ab')$_2$ type and are characterised by the association of two Fab' obtained by reduction of formats of the above F(ab')$_2$ type. These chimerised or humanised antibody formats have a hinge region H from a human immunoglobulin and allow for monospecific/tetravalent to tetraspecifique/monovalent or tetraepitopic/monovalent combinations, including all of the intermediate possibilities.

According to a fifth means of achievement of the invention, the antibody formats are of (HCH2CH3)$_2$ type (H, representing the hinge region of a human immunoglobulin, CH2 and CH3, representing the second and third constant domain of a heavy chain from a human Ig, and are characterised by the association of two identical VHH or human VH, or two human VH on which are grafted the hypervariable regions of the VHH, each being fused at the region H—CH2-CH3 of a human Ig. These chimerised or humanised antibody formats allow for monospecific/bivalent combinations.

According to a sixth means of achievement of the invention, the antibody formats are of mAb* type (this type refers to variable domains of origin replaced by all or part of the VHH or humanised VHH or human VH domains, fused to constant regions of human antibodies) and are characterised by the association of two identical or different VHH or two human VH, or two human VH on which are grafter hypervariable regions of VHH, one being fused to the Cκ or human Cλ region, the other to the CH1-H—CH2-CH3 region of a human Ig. These chimerised or humanised antibody formats allow for monospecific/tetravalent and bispecific/bivalent and biepitopic/bivalent combinations.

In these different formats, the immunoglobulin is an IgG, corresponding to a human isoform IgG1, IgG2, IgG3 or IgG4, or a human IgA corresponding to an isoform IgA1, IgA2, or any other human Ig. The VHH may be replaced by human VH or humanised VHH by the grafting of CDRs from VHH on human VH.

In the examples of the above means of achievement of the invention, the VHH correspond to or comprise fragments of Camelidae VHH antibodies, in particular from llamas. In particular, it involves characteristic fragments in that it consists of a part or the totality of anti-carcinoembryonic antigen (anti-CEA in abbreviated form) or anti-receptor FcγRIII (anti-CD16 in abbreviated form) fragments.

The anti-CEA antibody fragments more specifically comprise an amino acid sequence selected from the group consisting of the sequences SEQ ID NO:77, SEQ ID NO:78, SEQ ID NO:79, SEQ ID NO:80 and SEQ ID NO:105. The anti-CD16 antibody fragments in a preferred manner comprise an amino acid sequence selected from the group consisting of the sequences SEQ ID NO:73, SEQ ID NO:74, SEQ ID NO:75, SEQ ID NO:76, SEQ ID NO:103 and SEQ ID NO:104. These fragments form new products and in this way also come into the scope of the invention.

The invention also includes the CDRs of these VHH fragments. The invention also includes a method for the production of chimerised or humanised, multispecific and/or multivalent antibodies for immunotherapy or immunodiagnostics, characterised in that it comprises the use of antibody formats defined above. The invention specifically aims at a method of said formats comprising anti-CEA and anti-CD16 Camelidae VHH, in particular llama VHH. More specifically, it refers to variable domains of anti-CEA and anti-CD16 VHH advantageously produced according to a protocol comprising: the immunisation of Camelidae, in particular of llamas with, as immunogen, a CEA or a CD 16; the purification of B lymphocytes obtained from blood; the construction of a VHH bank; and the isolation of VHH from the bank.

The construction of the bank comprises: the extraction of whole RNA from B lymphocytes; the reverse transcription of RNA to obtain the corresponding cDNA; the amplification by PCR of genes coding for the variable regions of single heavy chain anti-CD 16 and anti-CEA antibodies; and the ligation of VHH DNA fragments obtained by cutting, by enzymes, of DNA amplified with a phagemid. The VHH are isolated from banks by the phage display technique and are purified.

Said variable domains of anti-CEA and anti-CD16 VHH are advantageously produced according to a protocol comprising: the immunisation of Camelidae, in particular llamas with, as immunogen, a CEA or a CD16; the purification of B lymphocytes recovered from blood; the construction of a VHH bank; and the isolation of VHH from the bank.

In an advantageous manner, the construction of the bank comprises: the extraction of whole RNA from B lymphocytes; the reverse transcription of RNA to obtain the corresponding cDNA; the amplification by PCR of genes coding for the variable regions of single heavy chain anti-CD16 and anti-CEA antibodies; and the ligation of fragments of DNA VHH, obtained by cutting by enzymes of amplified DNA with a phagemid. The VHH are isolated from banks by the phage display technique and are purified. The different VHH have been validated in terms of specificity and affinity as illustrated by the examples.

According to the invention, the genes of the selected VHH are then introduced in expression vectors, in particular plasmids, to produce different chimerised multispecific and/or multivalent (anti-CEA/anti-CD16) antibodies, able to bind with tumoral cells expressing the CEA at their surface and recruit the effector cells from the immune system (monocytes, macrophages, NK, polynuclear neutrophils, et al.) that express CD16.

The invention also refers to expression vectors of the antibody formats defined above. It more specifically refers to expression vectors, in particular plasmids containing, between two unique sites of restriction enzymes, the promoters, the signal sequences, the nucleotide sequences able to code for the VHH domains defined above, and the constant regions of a human Ig, or for human VH domains, the CDRs regions of a VHH, and the constant regions of a human Ig.

The plasmids according to the invention are able to express high quantities of the antibody formats defined above, in soluble forms in bacteria and the regions coding for the antibody domains may easily be transferred to other systems of prokaryotic or even eukaryotic expression.

The invention therefore refers to plasmids pCκCH1γ1-TAG (SEQ ID NO:98 and SEQ ID NO:112) and pCκCH1γ1 (SEQ ID NO:100 and SEQ ID NO:114) allowing for the production of antibodies of Fab type according to a first means of achievement of the antibody formats defined above. These plasmids are more specifically characterised by the insertion of nucleotide sequences coding for the light region Cκ, and the constant heavy region CH1 of an Ig in the plasmid p55Flag/RBS/35cmyc6HisGS (SEQ ID NO:94 and SEQ ID NO:110).

The invention also refers to the plasmids pCκCH1 Hγ1-TAG (SEQ ID NO:99 and SEQ ID NO:113) and pCκCH1Hγ1 (SEQ ID NO:101 and SEQ ID NO:115) allowing for the production of antibodies of Fab' and F(ab')$_2$ type according to a second, third and fourth means of achievement of the antibody formats defined above. These plasmids are more specifically characterised by the insertion of nucleotide sequences coding for the heavy chain CH1 and the hinge region (H) of an Ig in p55CκFlag/RBS/35cmyc6HisGS (SEQ ID NO:97 and SEQ ID NO:111).

The invention also refers to the plasmids pHCH2CH3γ1-TAG (SEQ ID NO:95) and pHCH2CH3γ1 (SEQ ID NO:96) allowing for the production of antibodies of (HCH2CH3)$_2$ type according to a fifth means of achievement of the antibody formats defined above. These plasmids are more specifically characterised by the insertion of nucleotide sequences coding for the hinge region (H) and the constant regions CH2 and CH3 of an Ig in p55Flag/RBS/35cmyc6HisGS.

The invention also refers to plasmid pMabγI* (SEQ ID NO:102 and SEQ ID NO:116) allowing for the production of antibodies of mAb* type according to a sixth means of achievement of the invention. This plasmid is more specifically characterised by the insertion of nucleotide sequences coding for the constant heavy region CH1, the hinge region and the constant regions CH2 and CH3 of an Ig in pCκCH1γ1-TAG.

The diagrams of these plasmids are illustrated in FIG. 10B and their nucleotide sequences in FIG. 11. The intermediate plasmids used for the construction of the above plasmids also fall within the scope of the invention. More specifically, it involves plasmids p55PhoA6HisGS/N⁻ (SEQ ID NO:89), p55PhoA6HisGS/NAB' (SEQ ID NO:90), p55/MCS1 (SEQ ID NO:92), p55Flag/RBS/35 (SEQ ID NO:93 and SEQ ID NO:109), p55Flag/RBS/35cmyc6HisGS (SEQ ID NO:94 and SEQ ID NO:110) and p55CκFlag/RBS/35cmyc6HisGS (SEQ ID NO:97 and SEQ ID NO:111) constructed to develop the plasmids defined above. The domains CH1, CH2, CH3, H of an Ig in these plasmids belong to IgGl, IgG2, IgG3 or IgG4, or even IgA, or any other Ig.

The genes coding for the VHH or the human VH are introduced between the unique sites in the different plasmids. These genes may be replaced by genes coding for humanised VHH by grafting of CDRs of VHH on human VH. More generally, the plasmids used according to the invention may be designed to contain nucleotide sequences coding for VHH other than anti-CEA or anti-CD16 VHH, or for other human VH, or for other humanised VHH, able to bind on any molecule.

The invention also refers to plasmid p55PhoA6HisGS⁻/NAB⁻ (SEQ ID NO:91) characterised in that it comprises the nucleotide sequences to produce human VH domains fused to alkaline phosphatase according to the diagram in FIGS. 10A and 11.

A method to select the variable human fragments of heavy chains of immunoglobulins (VH) and isolate the best produced and best secreted clones has been developed. Advantageously, these human VH are used as a matrix to graft the CDR from previously selected VHH in order to humanise the variable regions.

The antibody formats defined above are of great interest in immunotherapy and immunodiagnostics. They are able to recognise different molecules or bind two different epitopes on the same molecule, and also provide access to new epitopes that are not recognised by the concentional antibodies. They may also be humanised, which opens the way to advantageous prospects, to have antibodies of low immunogenicity after injection in man. The fact that they are obtained in a soluble form is an additional characteristic of interest for these antibodies. Their applications in immunodiagnostics and immunotherapy are also part of the invention.

BRIEF DESCRIPTION OF DRAWINGS

Other characteristics and advantages of the invention will be provided in the following examples in which reference is made to FIGS. 1 to 13, that respectively represent:

FIGS. 1 and 2, the amino acid (SEQ ID NOs:73 to 76, 103 and 104) and nucleotide (SEQ ID NOs:81 to 84,106 and 107) sequences of 4 clones of anti-CD16 VHH and the amino acid (SEQ ID NOs:77 to 80 and 105) and nucleotide (SEQ ID NOs:85 to 88 and 108) sequences of 4 anti-CEA clones isolated according to the invention;

FIG. 6, the results of competition tests by ELISA between 2 anti-CD16 VHH and monoclonal anti-CD 16 antibodies;

FIG. 8, the activation results of CD16A by 2 anti-CD16 VHH, and by the bispecific anti-CEA 17/anti-CD16 c21 antibody of type F(ab')$_2$;

FIG. 9, the results of cell lysis by NK cells activated by the bi-specific antibodies;

FIG. 11, the plasmid sequences of the invention;

FIGS. 12A and 12B, antibody formats of type Fab, Fab', F(ab')$_2$, (HCH2CH3)$_2$ and mAb*;

DETAILED DESCRIPTION

Figure 3:
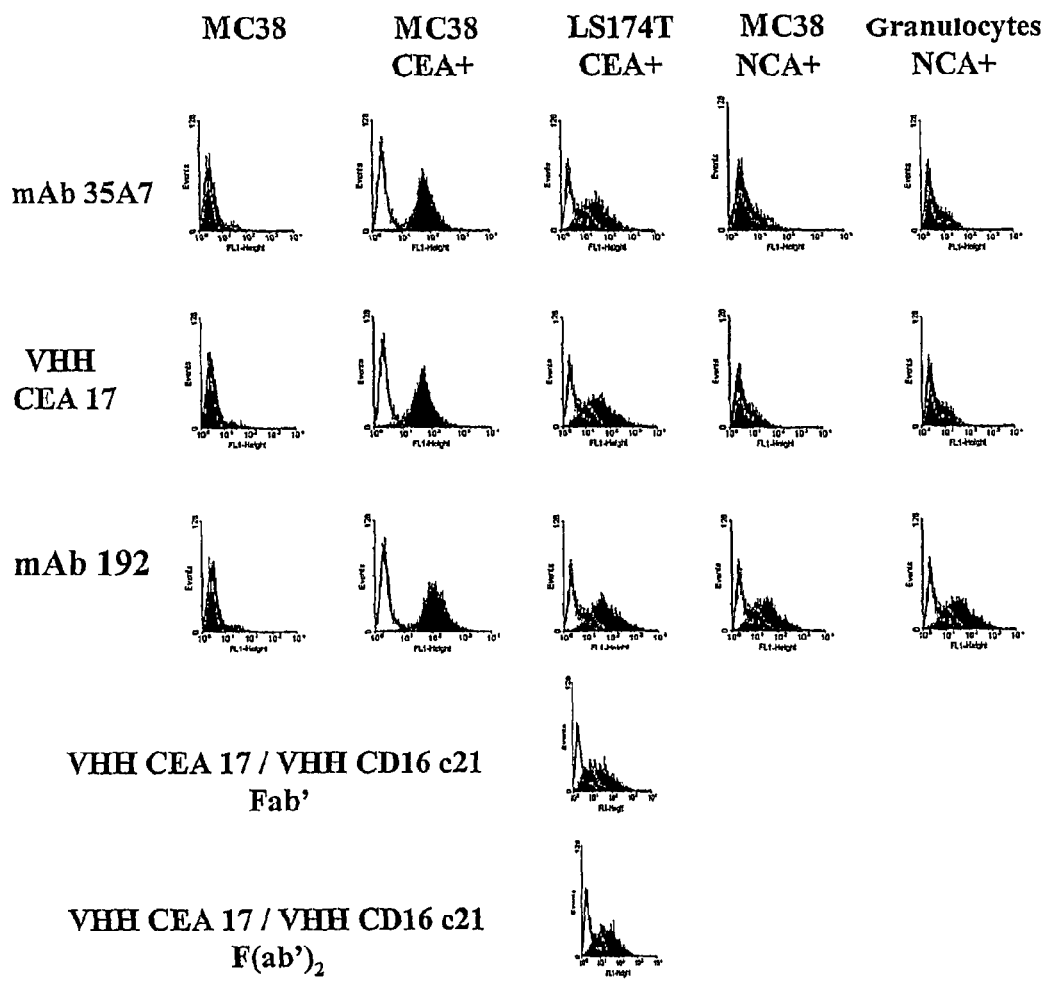
FIGS. 3 and 4, the results by FACS demonstrating the specificity of 8 VHH analysed, and the corresponding bispecific antibodies.

The following examples are provided by way of illustration and do not limit the extent of the present invention. Other advantages and characteristics of the invention will emerge in the light of the following examples.

EXAMPLE 1

Immunisation of Llamas, Titration of Serums and Purification of B Lymphocytes

A female llama was immunised with the extracellular region of human recombinant (CD16B) receptor FcγRIIIB (described in: Teillaud C et al., 1993). REF. A male llama was immunised with the extracellular region of the human recombinant carcinoembryonary antigen (CEA) (described in: Terskikh et al., 1993, and in patent: Terskikh A et al., 1993). REF The animals were immunised every month with 500 µg of each immunogen. 100 ml of blood was taken 15 days after each immunisation. For each sample taken, the serums and the purified antibodies (IgGI, 2 and 3) were titrated to detect the presence of antibodies against the different immunogens. The B lymphocytes were then purified on Ficoll gradient (histopaque-1077, Sigma-Aldrich), then washed twice with PBS.

Construction of VHH banks: purification of whole RNA, reverse transcription, PCR1, PCR2 and cloning in phagemid pHen1.

Construction of VHH banks:

Purification of whole RNA: The whole RNA of the B lymphocytes is extracted according to the method using guanidium isothiocyanate (Chomczynski and Sacchi, 1987) REF. After phenol/chloroform extractions in an acid medium, the whole RNA is precipitated with ethanol. The quality of the RNA and the quantification are evaluated on 1% agarose gel. They are then converted into cDNA by reverse transcription.

Reverse transcription and PCR: Sequences SEQ ID NOs:1 to 9 of the oligonucleotides used:

```
3'CH2FORTA4
SEQ ID NO.1: CGCCATCAAGGTACCAGTTGA

3'CH2-2
SEQ ID NO:2: GGTACGTGCTGTTGAACTGTTCC

3'RC-IgG2
SEQ ID NO:3: GGAGCTGGGGTCTTCGCTGTGGTGCG

3'RC-IgG3
SEQ ID NO:4: TGGTTGTGGTTTTGGTGTCTTGGGTT

5'VH1-Sfi
SEQ ID NO:5: CATGCCATGACTCGCGGCCCAGCCGGCCATGGCCCAG
GTGCAGCTGGTGCAGTCTGG

5'VH2-Sfi
SEQ ID NO:6: CATGCCATGACTCGCGGCCCAGCCGGCCATGGCCCAG
GTCACCTTGAAGGAGTCTGG

5'VH3-Sfi
SEQ ID NO:7: CATGCCATGACTCGCGGCCCAGCCGGCCATGGCCGAG
GTGCAGCTGGTGGAGTTGG

5'VH4-Sfi
SEQ ID NO:8: CATGCCATGACTCGCGGCCCAGCCGGCCATGGCCCAG
GTGCAGCTGCAGGAGTCGGG

3'VHH-Not
SEQ ID NO:9: CACGATTCTGCGGCCGCTGAGGAGAC(AG)GTGACCT
GGGTCC
```

Five µg of whole RNA are hybridised with 1 pmole of oligonucleotide 3' CH2FORTA4 (Arbabi Ghahroudi et al., 1997) REF or CH2-2 specific to the CH2 domain of the heavy single chain IgG of llama reverse transcribed with 150 U of superscript II (BRL) for 30 min at 50° C. The specific oligonucleotides of the hinge regions of IgG 2 and 3, 3' RC-IgG2 and 3' RC-IgG3, may also be used. The single strand cDNA are purified on beads (BioMag$^R$ Carboxyl Terminator, Polyscience Inc.) and eluted with 17 µl of 10 mM Tris-acetate pH 7.8.

PCR1 conditions: Four µl of cDNA are amplified by PCR with 0.5 U of Dynazyme Extend DNA polymerase (Finnzymes), 10 pmoles of the same primer 3' CH2FORTA4 or CH2-2 and 10 pmoles of 4 primers 5' VH1-4-Sfi specific to the VH domain of human IgG, in a volume of 50 µl. (94° C., 3 min; 94° C., 1 min; 60° C., 1 min; 72° C., 1 min; 37 cycles then 72° C., 10 min). Three fragments of DNA are amplified: one fragment of about 900 bp coding for the VH-CH1-CH2 domains of IgGI; and two fragments of about 600 bp coding for the VHH—CH2 domain of IgG2 and 3.

PCR2 conditions: The 600 bp fragments are purified on 1% agarose gel ("Qiaquick gel extraction" kit, Qiagen) then amplified by PCR with 1 U of Deep Vent (Biolabs) and 10 pmoles of 4 primers 5'VH1-4-Sfi specific for the VH domain of human IgG and 10 pmoles of primer 3' VHH-NotI. (94° C., 3 min; 94° C., 45 sec; 65° C., 45 sec; 72° C., 45 sec; 15 cycles, then 94° C., 45 sec; 60° C., 45 sec; 72° C., 45 sec; 15 further cycles, then 72° C., 10 min).

Fragments of about 400 bp coding for the VHH are purified on 1% agarose gel ("Qiaquick gel extraction" kit, Qiagen) assembled and precipitated with ethanol. They are then cut by restriction enzymes NcoI and NotI, or BgII and NotI (Biolabs) to be cloned in phagemid pHen1 (Hoogenboom et al., 1991) REF at sites NcoI and NotI or SfiI and NotI.

Preparation of the Vector: Twenty µg of phagemid pHen1 are digested in a 300 µl volume with 50 U of Sfi1 in the presence of BSA, at 50° C., 16 h; or with 50 U of NcoI in the presence of BSA, at 37° C., 16 h. The linearised phagemid is purified on 0.7% agarose gel ("Qiaquick gel extraction" kit, Qiagen). The eluted DNA is then cut by 50 U of NotI at 37° C. in a volume of 200 µl, 16 h. The enzyme is destroyed by heat for 15 min at 65° C. and the DNA is extracted with phenol/chloroform and precipitated by ethanol. The cut pHen1 is controlled on 0.7% agarose gel, quantified and adjusted to 200 ng/µl.

Preparation of the VHH DNA fragments: Five µg of VHH fragments are cut in a volume of 300 µl with 50 U of BgII and NotI in the presence of BSA, at 37° C., 16 h; or with 50 U of NcoI and NotI in the presence of BSA, at 37° C., 16 h. The enzymes are denatured at 65° C., 15 min; the DNA is then extracted with phenol/chloroform and precipitated with ethanol in the presence of 10 µg of glycogen (Roche). The VHH fragments cut by NcoI and NotI are purified on 1% agarose gel and then controlled on 2% agarose gel, quantified and adjusted at 100 ng/µl.

Ligation: One hundred and fifty ng of pHen1 digested by SfiI and NotI are ligated with 60 ng of VHH fragment digested by BgII and NotI in a volume of 20 µl with 2000 U of T4 DNA ligase (Biolabs) at 16° C., 17 h.

The ligase is inactivated at 65° C., 15 min, and the ligation product is cut by 20 U of XhoI (Biolabs) to eliminate the non-ligated residual vector, 37° C., 4 h. Six ligations are thereby made. The ligation products are then collected in 2 tubes and extracted with phenol/chloroform, precipitated in the presence of 10 µg of glycogen and taken up in 2×18 µl ultrapure $H_2O$. Two µl are used by electroporation.

The VHH bank from the male llama (ref.: 080101) represents $5.4 \times 10^6$ clones and the VHH bank from the female llama (ref.: 010301) $10^6$ clones.

Isolation of the VHH from the banks by phage-display technology.

Selection of anti-CEA and anti-CD16 VHH: The different VHH are isolated by the phage-display technique.

Production of phage banks: Ten μl of stock from bank 080101 or 010301 (TG1 cells transformed with phagemids) are inoculated in 50 ml of (2TY, 100 μg/ml of ampicillin, 2% glucose) and incubated at 37° C. until the $OD_{600}$ is equal to 0.5. Five ml of culture are then infected with 5 ml of M13KO7 at $10^{13}$ pfu/ml, 30 min, 37° C., without stirring. After centrifugation, the phage sediment is taken up in 25 ml of (2TY, 100 μg/ml of ampicillin, 25 μg/ml kanamycin). The culture is incubated 16 h at 30° C. with stirring. The phages are then precipitated with 1/5 vol of 2.5 M NaCl/20% PEG 6000 and concentrated 25 times in PBS.

VHH selection: Two hundred μ; of beads coated with streptavidin (Dynabeads M-280, Dynal) are equilibrated with 1 ml of 2% milk/PBS for 45 min at ambient temperature with stirring on a wheel. $10^{12}$ phages from the above production are also equilibrated with 2% milk/PBS in a final volume of 500 μl for 60 min at ambient temperature with stirring on a wheel.

The beads are compacted with a magnet, re-suspended with 250 μl of 2% milk/PBS and incubated with 200 μl of biotinylated antigen for 30 min at ambient temperature on a wheel. 150, 75 and 25 nM final of biotinyl antigen are used on the $1^{st}$, $2^{nd}$ and $3^{rd}$ rotation, respectively.

To 450 μl of beads/antigen-biotin are added the 500 μl of phages for 3 h at ambient temperature with stirring on a wheel. The beads/antigen-biotin/phages mixture is washed 5 times with 800 μl of 4% milk-PBS and then transferred to a new Eppendorf tube. Five other washings are carried out with 800 μl of PBS-0.1% Tween and the mixture is then transferred to another Eppendorf tube. Finally, 5 washings are carried out with 800 μl of PBS.

The antibody phages bound on the beads/antigen-biotin are re-suspended with 200 μl of PBS and incubated 30 min at 37° C., without stirring, with 1 ml of TG1 rendered competent for the binding of phages to pili (competent cells: from a culture of TG1 in 2YT overnight, a 1/100 dilution is made and 50 ml of 2YT is inoculated at 37° C. while stirring until the $OD_{600}$ is close to 0.5). At each selection, the phages are counted and amplified for another round of selection.

Counting of the selections: 1 μl dilutions are made of TG1 cells transfected with the phages (see above) of $10^{-2}$ to $10^{-5}$ with 2YT. One, 10 and 100 μl of each dilution are spread on a Petri dish (2YT/ampicillin 100 μg/ml/2% glucose). The dishes are incubated for 16 h at 30° C.

Spreading of the selection for the isolation of the colonies: Centrifuge the 5 ml of TGI transfected for 10 min at 3000 g to concentrate the cells and pick up the sediment with 1 ml of 2YT. Two hundred and fifty μl are used per Petri dish (12 cm×12 cm) (2TY/ampicillin 100 μg/ml/2% glucose) and are incubated for 16 h at 30° C.

The following VHH were isolated using this method: four anti-CEA VHH (clones: 3, 17, 25, 43) and four anti-CD16 VHH (clones: c13, c21, c28, c72) were obtained whose amino acid and nucleotide sequences are indicated in FIGS. 1 and 2.

Recloning, production and purification of VHH and bispecific antibodies.

VHH cloning: The VHH were cloned in plasmid p55PhoA6HisGS/NAB⁻ (construction described in section 1.3.6, see FIGS. 10A and 11) between the SfiI and HindIII restriction sites.

PCR conditions: Fifty ng of VHH were amplified by PCR with 1 U of Deep Vent (Biolabs), 10 pmoles of primers 5' pJF-VH3-Sfi and 3' cmyc-6His/HindIII in a final volume of 50 μl. (94° C., 3 min; 94° C., 45 sec; 52° C., 45 sec; 72° C., 45 sec; 30 cycles then, 72° C., 5 min).

The following oligonucleotide sequences SEQ ID NO:10 and SEQ ID NO:11 are used:

```
5' pJF-VH3-Sfi
SEQ ID NO: 10: CTTTACTATTCTCACGGCCATGGCGGCCGAGGTGC
AGCTGGTGG

3' cmyc-6His/HindIII
SEQ ID NO: 11: CCGCGCGCGCCAAGACCCAAGCTTGGGCTA(GA)T
G(GA)TG(GA)TG(GA)TG(GA) TG(GA)TGTGCGGCCCCATTCAGATC
```

The PCR products are purified on 1% agarose gel ("Qiaquick gel extraction" kit, Qiagen) and cut with 20 U of BglII and 20 U of HindIII (Biolabs) 16 h at 37° C. Ten μg of p55PhoA/NAB⁻ are first cut with 50 U of SfiI 16 h at 50° C., then with 20 U of HindIII 12 h at 37° C. The digestion products (vector and PCR fragments) are precipitated in ethanol. The DNA are re-suspended in 20 μl of $H_2O$ and quantified on 90.7% agarose gel.

The ligation is carried out with 200 U of T4 DNA ligase (50 ng of p55PhoA/NAB⁻ cut by SfiI and HindIII and 10 ng of PCR fragment cut by BgII and HindIII in a volume of 20 μl, 16 h at 16° C. After the inactivation of the T4 DNA ligase 15 min at 65° C., the non-recombinant vector is eliminated by enzyme digestion with 10 U of XhoI, 2 h at 37° C. After transformation of the ligation and analysis of several recombinant colonies, the VHH of interest are produced in *E. coli*.

Production of VHH: An isolated colony is inoculated in 3 ml of 2YT/ampicillin 100 μg/ml/2% glucose and incubated at 37° C. with stirring. Fifty ml of 2YT/ampicillin 100 μg/ml/2% glucose are then seeded with a dilution of the above culture and incubated for 16 h at 30° C. with stirring. Four hundred ml of 2YT/ampicillin 100 μg/ml are inoculated with the equivalent of 0.1 units $OD_{600}$, and incubated at 30° C. with stirring, until the $OD_{600}$ is 0.5 to 0.7. The culture is then induced with 400 μl of IPTG (isopropyl-β-D-thiogalactopyranoside) 0.1 mM final and cultivated at 30° C. for 16 h.

Production of bispecific antibodies: An isolated colony, derived from a transformation of plasmids carried out in the *E. coli* strain DH5α, is inoculated in 3 ml of 2YT/ampicillin 100 μg/ml/2% glucose and incubated at 30° C. with stirring. Fifty ml of LB/ampicillin 100 μg/ml/2% glucose are then seeded with a dilution of the previous culture and incubated for 16 h at 30° C. with stirring. Four hundred ml of LB/ampicillin 100 μg/ml are inoculated with the equivalent of 0.1 units $OD_{600}$, and incubated at 30° C. with stirring for 2.5 h, then the culture is incubated at 20° C. with stirring, until the $OD_{600}$ is 0.5 to 0.7. The culture is then induced with 400 μl of IPTG (isopropyl-β-D-thiogalactopyranoside) 0.1 mM final, cultivated at 20° C. for 72 h.

Extraction of the soluble fraction of the periplasma: The cultures used to produce the VHH or the bispecific antibodies are centrifuged at 4200 g, 4° C., 40 min. The sediment is taken up in 4 ml of glacial TES (0.2 M Tris-HCl pH 8.0; 0.5 mM EDTA; 0.5 M sucrose). 160 μl of lysozyme (10 mg/ml in TES, freshly prepared) is then added and then 24 ml of cold TES diluted to 1/2 in $H_2O$. The mixture is incubated for 30 min in ice.

After centrifugation at 4200 g, 4° C., 40 min, the supernatant is recovered (corresponding to the periplasmic fraction) and 150 μl of DNAse (10 mg/ml) and 5 mM final of $MgCl_2$ are added, 30 min at ambient temperature. The solution is dialysed for 16 h against the equilibrium buffer (50 mM sodium acetate, 0.1M NaCl pH 7.0).

Purification of the VHH: The column (BD TALON™ Metal affinity, BD Biosciences Clontech) is equilibrated with the equilibration buffer (50 mM sodium acetate, 0.1 M NaCl pH 7.0). The periplasmic fraction is deposited on the column. After washing the column with 5 volumes of equilibration buffer, the VHH is eluted by pH gradient or imidazole (gradient between the equilibration buffer pH 7.0 and the 50 mM sodium acetate solution pH 5.0 or the 200 mM imidazole solution. Each fraction is controlled on a SDS/PAGE gel (15% acrylamide) after colouration with Coomassie blue. The fractions of interest are assembled and dialysed against PBS. The VHH is concentrated on membrane (Amicon Ultra 5000MWCO, Millipore) and assayed with Lowry's colorimetric method using the Biorad Protein Assay kit.

Purification of the bispecific antibodies: The bispecific antibodies are purified from the soluble fraction of the periplasma (refer to extraction of the soluble fraction of the periplasma) in two steps. First on a BD TALON column (refer to VHH purification) and then on a protein G (HiTrap protein G 5 ml, Amersham biosciences).

The "Hi Trap protein G" column is equilibrated in PBS (NaCl 137 mM, KCl 2.67 mM, $Na_2HPO_4$ 1.2 mM, $KH_2PO_4$ 1.76 mM pH 7.4). The proteins eluted on the BD TALON column and dialysed on PBS are deposited on the protein G. After washing the column with 5 volumes of PBS, the bispecific antibody is eluted with 0.1 M glycine pH 2.7 then buffered with 1 M hepes pH 8. After control on SDS/PAGE gel (10% acrylamide), the bispecific antibody is dialysed in 0.1× PBS, frozen at −80° C. and lyophilised to be concentrated ten times. Finally, the $F(ab')_2$ is separated from the Fab' on a Tricorn Superdex 200 10/300 GL column (Amersham Biosciences) equilibrated in PBS.

Functional characterisation of the VHH and bispecific antibodies by ELISA, Biacore, immunofluorescence (flow cytometry, FACS) and by activation tests of CD16.
Characterisation of anti-CEA and anti-CD16 antibodies by ELISA: ELISA of phages-VHH: Five µg/ml of biotinylated antigen (CEA or CD16) are bound on a streptavidin plate (BioBind Assembly Streptavidin Coated, ThermoLabsystems) previously saturated with 2% milk-PBS. $5×10^{10}$ phages-antibodies are put in contact with the antigen. The antigen/antibody binding is detected by an ELISA comprising a monoclonal antibody directed against protein P8 of the phage (HRP/anti-M13 monoclonal conjugate, Pharmacia). The addition of the substrate, 10 mg ABTS (2,2'-azino bis(3-ethylbenzo-thiazoline-6-sulphonic acid, diammonium salt)) to 20 ml of detection buffer (18 ml PBS, 1 ml 1 M citric acid, 1 ml 1 M sodium citrate, 10 ml 30% $H_2O_2$), are used to read the reaction at 405 nm (Tecan).

ELISA of the VHH: Five µg/ml of biotinylated antibody are binded on a streptavidin plate (BioBind Assembly Streptavidin Coated, ThermoLabsystems) previously saturated in 2% milk-PBS. Each VHH (range from 0.001 µg/ml to 1 µg/ml) is bound to the adsorbed antigen in the microwells. The binding is detected with a monoclonal antibody directed against the c-myc label (Santa Cruz Biotechnology, Inc) diluted to 1/1000 and a goat polyclonal antibody directed against the IgG of mice coupled with peroxidase diluted to 1/5000 (ref 55556, ICN) in the presence of ABTS (2,2'-Azino-di-(3-ethylbenzthiazoline sulphonate)diammonium salt, Roche).

ELISA of the bispecific antibodies: Ten µg/ml of antigen (rhCD16 or rhCEA) are passively coated on a MaxiSorp plate (Nunc). After saturation of the plate in PBS/4% milk, the bispecific antibody ($F(ab')_2$, Fab', Fab) (range from 800 to 0.4 nM) is bound to the antigen adsorbed in the microwells. The binding is detected:

with a monoclonal antibody directed against the Flag tag (anti-Flag M2 mAb, Sigma) diluted to 1/5000 and a goat monoclonal antibody directed against mouse IgG coupled with alkaline phosphatase diluted to 1/5000 (ref 115-055-003, Jackson Immunoresearch) in the presence of DNPP (disodium 4-nitrophenyl phosphate hexahydrate); or with a monoclonal antibody directed against the c-myc tag (Santa Cruz Biotechnology) diluted to 1/500 and a goat polyclonal antibody directed against mouse IgG coupled with alkaline phosphatase diluted to 1/5000 (ref 115-055-003, Jackson Immunoresearch) in the presence of DNPP; or with a goat polyclonal antibody directed against the light human kappa chain coupled with alkaline phosphatase diluted to 1/500 (ref 2060-04, SouthernBiotech) in the presence of DNPP.

Demonstration of the accessibility of VHH CEA 17 when the VHH CD16 c21 is bound to rhCD16 adsorbed in the microwells with biotinylated rhCEA and streptavidin coupled with alkaline phosphatase diluted to 1/500 (DAKO, cat D0396).

Affinity constants for the anti-CEA and anti-CD16 antibodies by Biacore: BIACORE uses the principle of surface plasmon resonance (SPR) to monitor, in real time, the interactions between molecules without their labelling. One of the partners in the interaction is covalently immobilised on a biosensor while the other is injected in a continuous flow. The principle of detection by SPR allows the changes in the mass to be monitored at the surface of the biosensor due to the formation and then the dissociation of the molecular complexes. The response, quantified in resonance units (RU) is a direct indication of the rate of binding of the analyte by the measurement of the variation of the refraction index. The recorded signal (a sensorgram) is processed mathematically to obtain the association speed, $k_a$, dissociation speed $k_d$ constants and the association $K_A$ ($K_A=k_A/k_d$) and dissociation $K_D$ (KD=kd/ka) constants at equilibrium.

The interactions between the CEA or the CD16 and the VHH (that have a c-myc tag recognised by the monoclonal antibody 9E10, Santa Cruz Biotechnology, Inc) were studied on a BIACORE 3000 equipped with a CM5 biosensor on which the monoclonal antibody 9E10 was covalently immobilised following the standard coupling procedure by the amines proposed by BIACORE (activation by NHS/EDC). The VHH (in buffer: 10 mM HEPES; 150 mM NaCl; 3 mM EDTA; 0.005% surfactant P20) is then injected and then a range of CEA or CD16 is injected on the VHH immobilised on the 9E10. In parallel, the injections are carried out on a control channel that has been subjected to the same coupling chemistry without the injection of protein. The affinities of the VHH are indicated in Table 1 below. Equivalent affinities are obtained from the different formats of bispecific antibodies.

TABLE 1

| VHH | ka × $10^5$ (1/Ms) | kd × $10^{-3}$ (1/s) | KA × $10^7$ (1/M) | KD × $10^{-9}$ (M) |
|---|---|---|---|---|
| Anti-CEA 3 | 1.24 ± 0.014 | 1.68 ± 0.002 | 7.38 | 13.6 |
| Anti-CEA 17 | 1.56 ± 0.014 | 1.3 ± 0.002 | 12 | 8.3 |
| Anti-CEA 25 | 1.13 ± 0.014 | 3.6 ± 0.004 | 3.15 | 31.7 |
| Anti-CEA 43 | 1.78 ± 0.019 | 1.83 ± 0.002 | 9.72 | 10.3 |
| Anti-CD16 c13 | 0.53 ± 0.07 | 5.67 ± 0.02 | 0.94 | 100.6 |
| Anti-CD16 c21 | 2.86 ± 0.02 | 2.79 ± 0.006 | 10.3 | 9.7 |
| Anti-CD16 c28 | 0.42 ± 0.03 | 3.45 ± 0.006 | 1.22 | 81.9 |
| Anti-CD16 c72 | 0.39 ± 0.02 | 3.7 ± 0.006 | 1.06 | 94.6 |

Analysis by FACS of the specificity of anti-CEA and anti-CD16 VHH and the corresponding bispecific antibodies.
Specificity for CEA: (For effective immunotargeting, it is important that the anti-CEA antibodies do not recognise the NCA, a molecule that is very homologous to the CEA that is expressed at the surface of the granulocytes.)

The detection of the antigen-antibody bond is carried out on the non-transfected line MC38 (cell line of a murine colon cancer), the lines transfected with the CEA (MC38/CEA⁺) or the NCA (MC38/NCA⁺), the human tumoural line LS174T (cell line of human colon adenocarcinoma expressing the CEA at its surface) and the granulocytes that express the NCA at their surface.

The granulocytes are extracted from fresh blood in the presence of heparin, on Ficoll gradient at two densities (Histopaque 1119 and 1077). The granulocytes are found at the interface of two Histopaques.

Antibodies used for the binding to the cells:
35A7, anti-CEA monoclonal antibody (specific for CEA).
192, anti-CEA monoclonal antibody (that crosses with the NCA).
7.5.4 and 3G8 anti-CD16 monoclonal antibody.
anti-CD16 VHH (c13, c21, c28, c72).
anti-CEA VHH (3, 17, 25, 43).
anti-CEA/anti-CD16 bispecific antibodies constructed from the 8 VHH isolated.
Antibodies used for the detection:
9E10, mouse anti-cmyc monoclonal antibody (200 µg/ml, used at $1/10^{th}$) binding at the c-myc label of the purified VHH.
AP326F, sheep polyclonal antibody anti-IgG of mouse coupled with FITC (Silenus, used at $1/100^{th}$).
$0.5 \times 10^6$ cells are used per test. The VHH and monoclonal antibodies are diluted in 100 µl of PBS-1% BSA.
$0.5 \times 10^6$ cells (autofluorescence measurement of the cells).
$0.5 \times 10^6$ cells+anti-IgG of mouse-FITC 20 µg/ml.
$0.5 \times 10^6$ cells+anti-9E10 20 µg/ml, then anti-IgG of mouse-FITC 20 µg/ml.
$0.5 \times 10^6$ cells+VHH anti-CEA or anti-CD16 1 to 5 µg/ml, then 9E10 20 µg/ml, then anti-IgG of mouse-FITC 20 µg/ml.
$0.5 \times 10^6$ cells+monoclonal antibody (35A7, 192, 7.5.4) 20 µg/ml, then anti-IgG of mouse-FITC 20 µg/ml.
At each step, the samples are incubated for 45 min, 4° C., in the dark. Between each reaction, a washing is carried out with 2 ml of PBS/1% BSA. At the last step, the cells are taken up with 0.5 ml of PBS.

The results by FACS demonstrate the specificity of the 4 anti-CEA VHH analysed and the anti-CEA/anti-CD16 bispecific antibodies in Fab, Fab' and F(ab')₂ form. They are CEA specific and do not cross with the NCA. One example is illustrated in FIG. 3. In this example, the monoclonal antibodies of reference mAb 35A7 and 192 do not bond on the MC38 cells that do not express CEA but on the MC38 CEA⁺, and LS174T CEA⁺ cells that express CEA on their surface. The mAb 192 also bonds on the MC38 NCA⁺ cells and granulocytes that express NCA on their surface. CEA 17 VHH only bonds cells that express CEA on their surface. Equivalent results are obtained with other anti-CEA VHH antibodies (clones 3, 25 and 43). The CEA 17/VHH CD16 c21 VHH bispecific antibody is specific to tumoural cells both in Fab' and F(ab')₂ form. Equivalent results are obtained with other anti-CEA/anti-CD16 bispecific antibodies in Fab, Fab' and F(ab')₂ form (deriving 8 anti-CEA and anti-CD16 VHH).

Specificity for CD16: For the effective recognition of the effector cells in the immune system, the anti-CD16 antibodies selected from CD16B should also recognise CD16A. In addition, they should not present a cross-over reaction with CD32 (RFcγIIA and RFcγIIB).

Experiments are carried out with Jurkat cells (cells from a human T lymphoma line; ATCC TIB-152) transfected or not with the gene coding for CD16A (stable line expressing CD16A at their surface; Vivier et al., 1992), granulocytes expressing CD16B, K562 cells that only express CD32A and IIA 6huIIB1 cells that only express CD32B.

Antibodies used for the binding to cells:
3G8, anti-CD16 monoclonal antibody (human RFcγIIIA/IIIB), anti-site antibody recognising a conformational epitope and blocking the bond of the IgG to CD16A and CD16B.
7.5.4, anti-CD16 monoclonal antibody (human RFcγIIIA/IIIB), antibody recognising a linear epitope, localised outside the binding site of IgG of CD16 and only weakly affecting this bond at high concentrations in competition tests (Vely et al., 1997).
AT10 anti-CD32 monoclonal antibody (human RFcγIIA/IIB).
IV.3, anti-CD32 monoclonal antibody (human RFcγIIA).
anti-CD16 VHH (c13, c21, c28, c72).
anti-CEA VHH (3, 17, 25, 43).
35A7, anti-CEA monoclonal antibody.
192, anti-NCA monoclonal antibody (that crosses with CEA).
anti-CEA/anti-CD16 bispecific antibodies constructed from 8 isolated VHH.
Antibodies used for detection:
9E10, mouse anti-cmyc monoclonal antibody (200 µg/ml, used at 1/10th) binding at the c-myc label of the purified VHH.
Fab'2 of a goat antibody anti-IgG of mouse coupled with FITC (F(ab')₂/FITC) used at 20 µg/ml (Jackson Immunoresearch Lab. Inc., 115-096-003).
$0.5 \times 10^6$ cells are used per test. The VHH and monoclonal antibodies are diluted in 100 µl of PBS-1% BSA.
$0.5 \times 10^6$ cells (autofluorescence measurement of the cells)
$0.5 \times 10^6$ cells+(F(ab')₂/FITC) 20 µg/ml
$0.5 \times 10^6$ cells+anti-9E10 20 µg/ml, then (F(ab')₂/FITC) 20 µg/ml
$0.5 \times 10^6$ cells+VHH 1 at 5 µg/ml, then 9E10 20 µg/ml, then (F(ab')₂/FITC) 20 µg/ml
$0.5 \times 10^6$ cells+monoclonal antibodies (35A7, 192, 3G8, 7.5.4, AT10, N.3) 20 µ/ml, then (F(ab')₂/FITC) 20 µg/ml.
At each step, the samples are incubated for 45 min, 4° C., in the dark. Between each reaction, a washing is carried out with 2 ml of PBS/1% BSA. At the last step, the cells are taken up with 0.5 ml of PBS.

Figure 4:
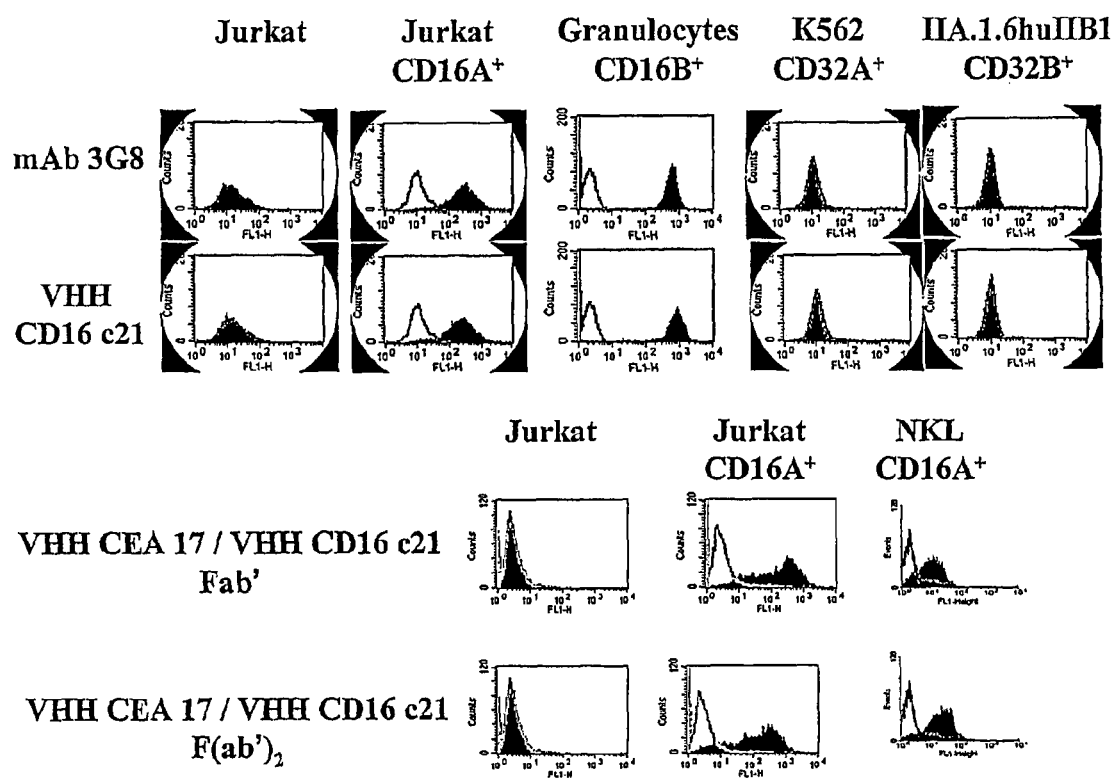

The results by FACS demonstrate the specificity of the 4 anti-CD16 VHH analysed and the anti-CEA/anti-CD16 bispecific antibodies in Fab, Fab' and F(ab')₂ form. They are CD16 specific and do not cross with CD32. One example is illustrated in FIG. 4. In this example, the reference monoclonal antibody mAb 3G8 does not bind on the Jurkat cells, K562 CD32A⁺ and IIA.1.6huIIB1 CD32B⁺ that do not express CD16 but on the Jurkat CD 16A⁺ cells, and the granulocytes that express CD16 on their surface. CD16 c21 VHH does not bind on cells that express CD16 on their surface. Equivalent results are obtained with other anti-CD16 VHH antibodies (clones: c13, c28 and c72). The bispecific antibody VHH CEA 17/VHH CD16 c21 is specific in Jurkat CD16A⁺ and NKL cells both in Fab' and F(ab')₂ form. Equivalent results are obtained with other anti-CEA/anti-CD16 bispecific antibodies in Fab, Fab' and F(ab')₂ form (deriving 8 anti-CEA and anti-CD16 VHH).

FACS Analysis of the accessibility of bispecific antibodies on cells:
The accessibility of anti-CD16 VHH domain: $5 \times 10^5$ LS174T cells are incubated for 30 min, in PBS-1% BSA in ice, in the presence of Fab, Fab' or F(ab')₂, (range from 10 µg/ml to 0.1 µg/ml). The cells are washed in PBS-BSA 1%. The binding of rhCD16 (µg/ml) on the anti-CD16 VHH domain of the different fragments of antibody is then detected, in two steps, by incubating monoclonal antibody 7.5.4 or 3G8 (3 µg/ml) with the cells for 30 min, in ice then by incubating the cells with goat F(ab')$_2$ anti-IgG of mouse (H+L) marked with FITC (Jackson Immunoresearch Laboratory, cat: 115-096-003), for 30 min in ice. After several washings, the immunofluoresence is analysed by flow cytometry with a FACScalibur 4C4 (Becton Dickinson) using the Cell Quest Pro programme.

The accessibility of the anti-CEA VHH domain: $5\times10^5$ Jurkat CD16A$^+$ cells are incubated for 30 min, in PBS-BSA 1% in ice, in the presence of Fab, Fab' or F(ab')$_2$, (range from 10 µg/ml to 0.1 g/ml). The cells are washed in PBS-1% BSA. The binding of the rhCEA (10 µg/ml) on the anti-CEA VHH domain of the Fab, Fab' or F(ab')$_2$, is then detected, in two steps, by incubating monoclonal antibody 192 (3 µ/ml) with the cells for 30 min, in ice, and then by incubating the cells with goat F(ab')$_2$ anti-IgG of mouse (H+L) marked with FITC (Jackson Immunoresearch Laboratory, cat: 115-096-003), for 30 min in ice. After several washings, the immunofluorescence is analysed by flow cytometry with a FACScalibur 4C4 (Becton Dickinson) using the Cell Quest Pro programme.

Figure 5:
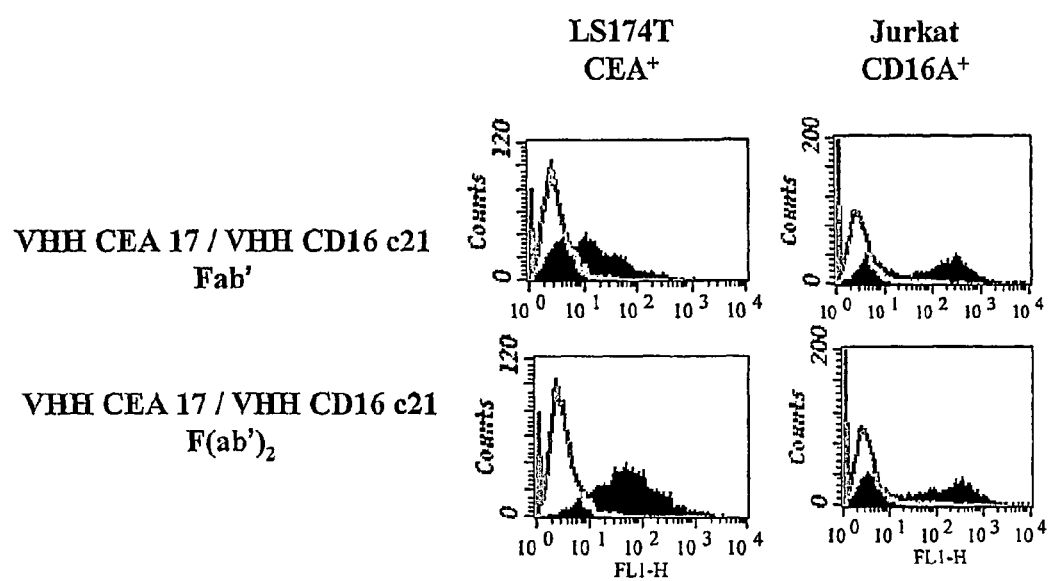
FIG. 5, the results by FACS demonstrating the accessibility on the cells of bispecific antibodies.

One example is illustrated in FIG. 5. The bispecific antibody VHH CEA 17/VHH CD16 c21 binds both with the LS174T and Jurkat CD16A$^+$ cells. Equivalent results are obtained with the other anti-CEA/anti-CD16 bispecific antibodies in Fab, Fab' and F(ab')$_2$ form (deriving 8 anti-CEA and anti-CD16 VHH).

Competition test between the anti-CD16 VHH and the monoclonal antibody 3G8 and 7.5.4:

ELISA: Five µg/ml of biotinyl VHH (c21, c28) are bound per well in a plate adsorbed with streptavidin (BioBind Assembly Streptavidin Coated, ThermoLabsystems) previously saturated in 2% milk-PBS. The CD16B with a concentration ranging from 0.07 to 20 µg/ml is then added. Secondly, the monoclonal antibody (3G8 or 7.5.4) at a constant concentration of 5 µg/ml is added. The CD16B-monoclonal antibody binding is detected with a goat F(ab')$_2$ anti-IgG of mouse coupled with alkaline phosphatase (SouthernBiotechnology, 1030-04) in the presence of p-nitrophenylphosphatase (Sigma, N9389).

The competition curves in ELISA are demonstrated in FIG. 6. The CD16 c21 VHH is shifted by monoclonal antibody 7.5.4. The CD16 c28 VHH is shifted by monoclonal antibody 3G8.

Indirect immunofluorescence (FACS): $5\times10^5$ Jurkat-CD16A cells are incubated for 30 min, in PBS-5% BSA in ice, in the presence of Cb16 c21 or c28 VHH (1 to 100 µg/ml). The cells are then incubated with 0.1 µg/ml of 3G8 or 1 µg/ml of 7.5.4 for 30 min in the same conditions, then washed in PBS-5% BSA. The binding of 3G8 or 7.5.4 is then detected by incubating the cells with the F(ab')$_2$ of a goat antibody anti-IgG of mouse (H+L) marked with FITC (Jackson ImmunoResearch Laboratories Inc., West Grove, Pa., USA, cat No.: 115-096-003) for 30 min in ice. After several washings, the immunofluorescence is analysed by flow cytometry with a FACScalibur 4CA (Becton Dickinson, Mountain View, Calif., USA) using the Cell Quest Pro programme.

Figure 7:
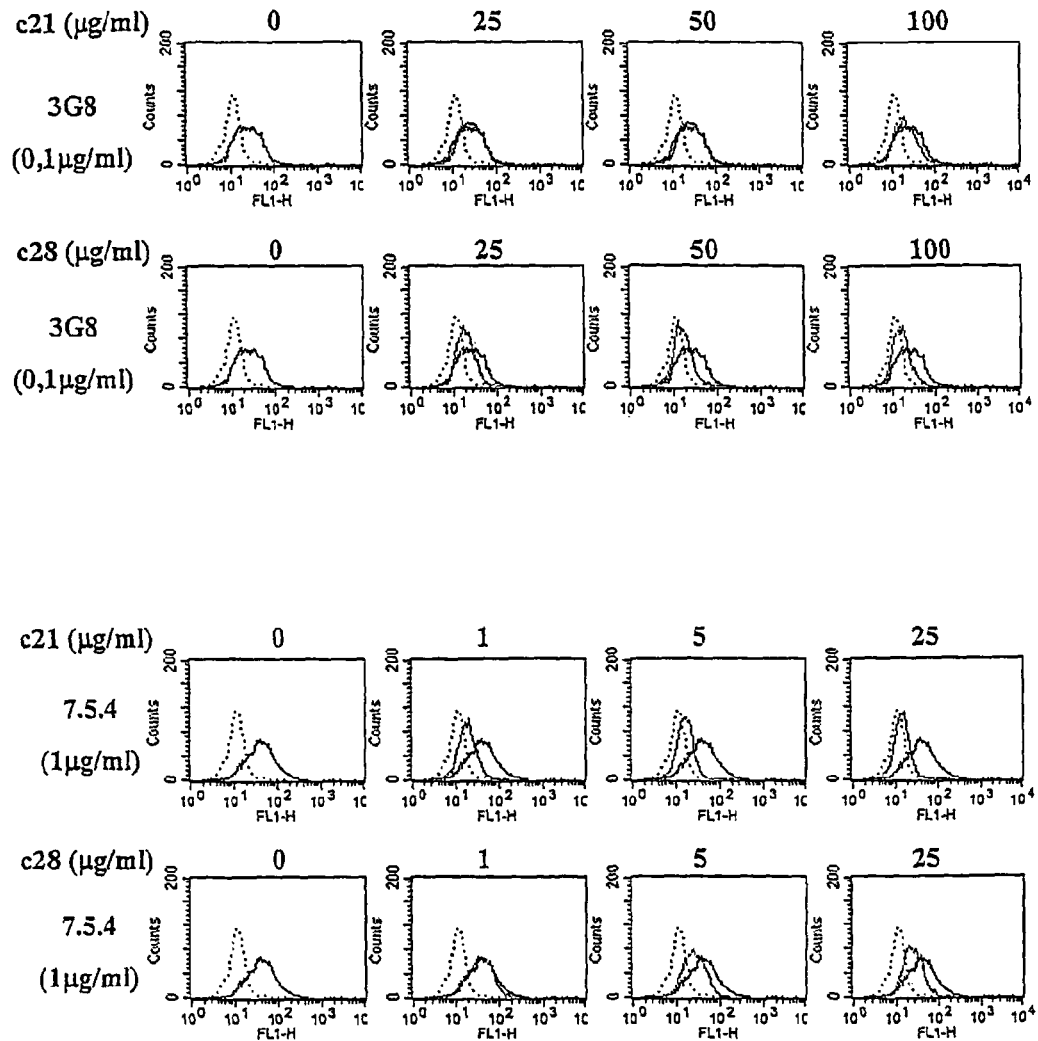
FIG. 7, the competition profiles on cells by FACS of 2anti-CD16 VHH and the monocolonal anti-CD 16 antibodies.

The competition profiles on cells are provided in FIG. 7. CD16 c21 VHH is shifted by monoclonal antibody 7.5.4. CD16 c28 VHH is shifted by monoclonal antibody 3G8. A high dose of CD16 c28 VHH is also shifted by mAb 7.5.4.

Activation by the anti-CD16 VHH and by the bispecific antibodies of Jurkat CD16$^+$ cells: The experiments are carried out with Jurkat cells (ATCC TIB-152) transfected with the gene that codes CD16A. The cells are cultivated in RPMI 1640 complemented with 10% FCS, 100 U/ml penicillin, 100 µg/ml streptomycin, 2 mM L-glutamine, 0.5 mg/ml G418.

$5\times10^5$ cells are then incubated for 18 h in microplate wells (250 µl of RPMI containing 10% FCS, 1% PS, 0.5 mg/ml G418). Ten ng/ml of phorbol myristate acetate (PMA) (concentration not perse inducing the production and secretion of IL2, but necessary as a "second signal" for this production) are then added, followed by the addition of 0.01 to 0.1 µg/ml of biotinylated VHH and 10 µg/ml of streptavidin (enabling the bridging of the VHH) or non-biotinylated bispecific antibodies.

The human IL2 produced in the cell supernatants is measured by ELISA using antibodies from the R&D kit (Duoset Human IL2; reference: DY202) and streptavidin coupled with alkaline phosphatase (DAKO, D0396) in the presence of p-nitrophenylphosphate (Sigma, cat 104-405).

The results of the activation of CD16A (production and secretion of interleukin 2) are provided in FIG. 8. The two anti-CD16 c21 and c28 VHH activate the production of IL2 of Jurkat CD16A$^+$ cells. Higher quantities of c28 are required to obtain an induction of the production and the secretion of IL2 similar to that induced by the c21. The anti-CEA 17/anti-CD16 c21 bispecific antibody in form F(ab')2 also activates the production of IL2 if the Jurkat cells express CD16A at their surface in the absence of bridging via the streptavidin. Equivalent results are obtained from other anti-CD16 VHH and anti-CEA/anti-CD16 bispecific antibodies.

Lysis of tumoural cells by NKL cells in the presence of bispecific antibody: For the cytotoxicity test of the NK cells, NKL cells are used as the cell lines (Robertson et al, 1996 (12)) obtained from leukemia with large granulocytic lymphocytes, whose functional properties are similar to that of the NK and whose expression of CD16 was first verified by flow cytometry. The target cells used are very NK sensitive HeLa cells obtained from a human leukemia, NK sensitive cells from murine colon C15.4.3 AP (MC38), and MC38 cells transfected with human CEA that are naturally NK resistant.

The target cells in culture are put into suspension (by tryptic reaction for the HeLa cells, mechanically for the MC38 and NKL cells) and counted using Trypan blue in a Malassay cell. Two thousand cells per well are incubated in 100 µl with $3.7\times10^6$ Bq of $^{51}$Cr and the different antibody formats (200, 100 or 50 µg/ml) 1 h at 37° C. The cells are then washed several times to eliminate the $^{51}$Cr remaining in the medium as well as the non-bound antibodies. The NKL cells in suspension are counted and added to the target cells with an effector/target ratio ranging from 60:1 to 0.2:1. After incubation for 4 h at 37° C., the radioactivity of the Cr released in the medium is counted using a γ counter. Examples showing the cell lysis obtained with the anti-CEA 17/anti-CD16 c21 and anti-CEA 17/anti-CD16 c28 bispecific antibodies in Fab' and F(ab')$_2$ form are represented in FIG. 9.

Construction of different plasmids (refer to FIGS. 10A, 10B, 11, 12A and 12B).

All of the non detailed protocols are described in Sambrook, Fritsch and Maniatis, Molecular Cloning: A Laboratory Manual, 2nd ed, Cold Spring Harbor Laboratory Press, 1989.

The digestions with the restriction enzymes are carried out according to the supplier's recommendations.

Genes of human origin inserted: The genes coding for regions Cκ, CH1, H, CH2 and CH3 respectively correspond to: the domains of genes coding for the constant region of a light kappa chain of human immunoglobulin, for the first constant region, for the hinge region, for the second constant region and for the third constant region of a heavy chain of human immunoglobulin IgG1. These genes were obtained by RT-PCR from an LFB pouch (Laboratoire francais du Fractionnement et des Biotechnologies). This material is subject to the legal authorisations and may be used for the experiments described.

The sequence of each plasmid is carried out on ABI 310 sequencer by using the oligonucleotides:

```
EcoRI-90 of sequence SEQ ID NO:12: GCGCCGACATCATAA
CGGTTCTGGC

HindIII+88 of sequence SEQ ID NO:13: CGCTACTGCC
GCCAGGC
```

Figure 10A:
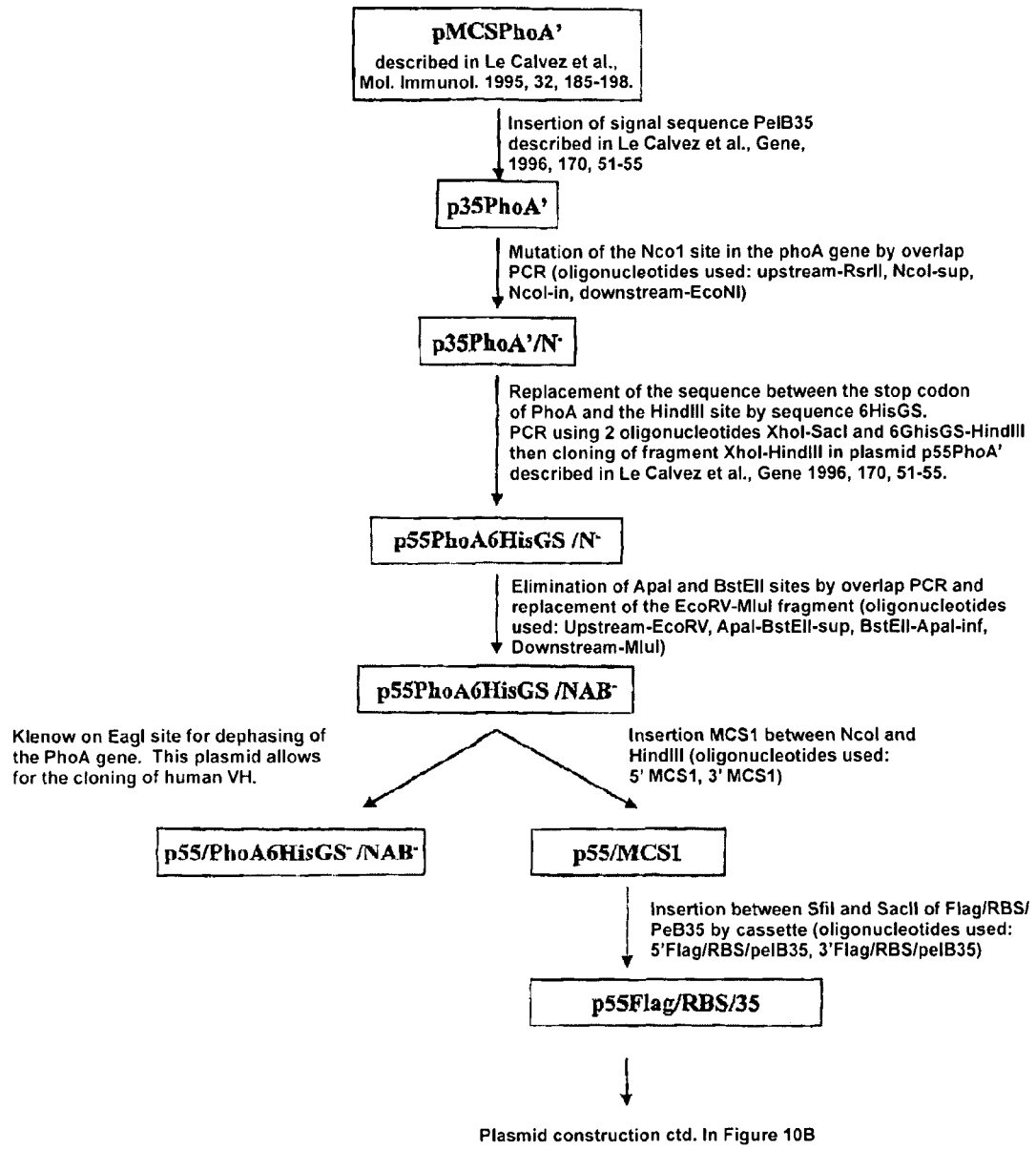
FIGS. 10A and 10B, plasmid constructions according to the invention.

All of the vectors are designed to allow for the introduction, between 2 unique sites of restriction enzymes, of: different promoters, different signal sequences of type PelB (or other), different RBS sequences, any VHH or humanised VHH domain, any Cλ domain, or domains CH1, H, CH2 and CH3 of any type of immunoglobulin.

pMCSPhoA* (FIG. 10A)

The construction of this plasmid is described in Le Calvez et al. (1995). REF. This plasmid codes for the mature form of the Alkaline Phosphatase (PhoA) starting at the sixth residue (Proline).

p35PhoA* (FIG. 10A)

The construction of this plasmid is described in Le Calvez (1996). A gene fragment (formed by degenerated oligonucleotides on the third base of codons 2 to 14 coding for the signal sequence of PelB) is inserted between the NdeI and EagI sites of plasmid pMCSPhoA'. The clones (1 to 60) presenting the best alkaline phosphatase activity were then selected.

p35PhoA'/N⁻ (FIGS. 10A and 11)

Suppression of the NcoI site in the phoA gene. An overlap PCR is carried out from pMCSPhoA' with the oligonucleotides: upstream-RsrII, NcoI-sup, NcoI-inf and downstream-EcoNI. Sequences SEQ ID NOs:14 to 17 of the oligonucleotides used:

```
upstream-RsrII
SEQ ID NO:14: GGCACATGTGACCTCGCGC

NcoI-sup
SEQ ID NO:15: GCAACGTACCACGGCAATATCG

NcoI-inf
SEQ ID NO:16: CGATATTGCCGTGGTACGTTGC downstream-EcoNI
SEQ ID NO:17: GCCATCTTTGGTATTTAGCGCC
```

Conditions for PCR 1 and PCR 2:

One µl of plasmid (5 ng), 10 pmoles of each oligonucleotide (upstream-RsrII and NcoI-inf for PCR 1 and NcoI-sup and downstream-EcoNI for PCR 2), 0.5 U Dynazyme (94° C., 3 min; 94° C., 45 s; 60° C., 45 s; 72° C., 45 s; for 25 cycles then 72° C., 10 min) in a final volume of 50 µl. The PCR products are purified from a 2% agarose gel (Qiagen Kit extraction gel, final volume 50 µl).

Conditions for the overlapping PCR 3:

One µl of each of PCR 1 and 2 and 0.5 U Deep Vent, in a final volume of 50 µl. After 5 cycles (94° C., 3 min; 94° C., 1 min; 60° C., 1 min; 72° C., 1.5 min) 10 pmoles of each oligonucleotide are added (upstream-RsrII and downstream-EcoNI) and the PCR is continued for 35 cycles then 72° C., 10 min. The product of the PCR 3 is purified, from a 2% agarose gel (Qiagen Kit extraction gel, final volume 50 µl). The sequence of the PCR fragment is carried out on sequencer ABI 310 using oligo 5' EcoRI-90.

Cloning of the PCR 3 fragment in plasmid p35PhoA':

Thirty-five µl of PCR 3 fragment and 5 µl (2.5 µg) of p35PhoA' are digested by 10 U of RsrII and EcoNI. After 16 h of incubation, the enzymes are destroyed for 10 min at 65° C. Each DNA is then precipitated and resuspended with 20 µl of H₂O. The ligation is carried out for 16 h at 16° C. with 5 µl of PCR fragment, 0.5 µl of vector and 3 U Weiss of T4 DNA ligase Biolabs in a final volume of 10 µl. Competent TG1 bacteria (CaCl₂ technique) are transformed with 5 µl of ligation.

p55PhoA6HisGS/N⁻ (FIGS. 10A and 11)

Insertion of the 6Histidine-Gly-Ser motif. A PCR is carried out from p35PhoA'/N⁻ using oligonucleotides XhoI-SacI and 6HisGS/HindIII. Sequences SEQ ID NOs:18 and 19 of the oligonucleotides used:

```
XhoI-SacI
SEQ ID NO:18: CCATGGCGGCCGATCCTCGAGAG

6HisGS/HindIII
SEQ ID NO: 19: CATGCAGTCCCAAGCTTATTAGCTCCCGTGATGGT
GATGATGATGTTTCAGCCCCAGA GCGGCTTTC
```

PCR conditions: A PCR is carried out with 5 ng of p35PhoA'/N⁻ vector, 10 pmoles of each oligonucleotide and 0.5 U Dynazyme (94° C., 3 min; 94° C., 1 min; 70° C., 1 min; 72° C., 1 min; 35 cycles then 72° C., 10 min) in a final volume of 50 µl. The PCR product is purified from a 1% agarose gel (Qiagen Kit extraction gel, final volume 50 µl).

Cloning of fragmentXhoI-HindIII: Twenty µl of the PCR fragment and 5 µl (2.5 µg) of p55PhoA' vector (Le Calvez et al. Gene 1996, 170, 51-55) are digested by 10 U of XhoI and HindIII in the presence of BSA. After 16 h of incubation, the enzymes are destroyed for 10 min at 65° C. Each DNA is then precipitated and resuspended with 20 µl of H₂O. The ligation is carried out for 16 h at 16° C. with 5 µl of PCR fragment, 0.5 µl of vector and 3 U Weiss of T4 DNA ligase Biolabs in a final volume of 10 µl. Competent TG1 bacteria (CaCl₂ technique) are transformed with 5 µl of ligation product.

p55PhoA6HisGS/NAB⁻ (FIGS. 10A and 11)

Suppression of sites ApaI and BstEII of p55PhoA6HisGS/N⁻. One overlap PCR is carried out from p55PhoA6HisGS/N⁻ with the oligonucleotides: upstream-EcoRV, ApaI-BstEII-sup, BstEII-ApaI-inf and downstream-MluI. Sequences SEQ ID NOs:20 to 23 of the oligonucleotides used:

```
upstream-EcoRV
SEQ ID NO:20: CATGAGCTGTCTTCGGTATC

ApaI-BstEII-sup
SEQ ID NO:21: TAATGGTCCCGCTAACAGCGC-
GATTTGCTGATGACCCA

BstEII-ApaI-inf
SEQ ID NO:22: TGGGTCATCAGCAAATCGCGCTGT-
TAGCGGGACCATTA downstream-MluI
SEQ ID NO:23: GAACGAAGCGGCGTCGAAG
```

PCR 1 and PCR 2 conditions: One µl (5 ng) of plasmid p55PhoA6HisGS/N⁻, 10 pmoles of each oligonucleotide (upstream-EcoRV and BstEII-ApaI-inf for PCR 1 and ApaI-BstEII-sup and downstream-MluI for PCR 2), 0.5 U Dynazyme (94° C., 3 min; 94° C., 45 s; 60° C., 45 s; 72° C., 45 s; 25 cycles then 72° C., 10 min. The PCR products are purified from a 2% agarose gel (Qiagen Kit extraction gel, final volume 50 µl).

Conditions for the overlap PCR 3: One µl of each of PCR 1 and 2 and 0.5 U Deep Vent, in a final volume of 50 µl. After 5 cycles (94° C., 3 min; 94° C., 1 min; 60° C., 1 min; 72° C., 1.5 min) 10 pmoles of each oligonucleotide are added (upstream-EcoRV and downstream-MluI) and the PCR is continued for 35 cycles then 72° C., 10 min. The PCR 3 product is purified from a 2% agarose gel (Qiagen Kit extraction gel, final volume 50 µl). The sequence of the PCR fragment is carried out on ABI 310 sequencer using oligo 5' EcoRI-90.

Cloning of the PCR 3 fragment in the p55PhoA6HisGS/N⁻ plasmid: Thirty-five µl of PCR 3 fragment and 5 µl (2.5 µg) of p55PhoA6HisGS/N⁻ are digested by 10 U of EcoRV and MluI. After 16 h of incubation, the enzymes are destroyed for 10 min at 65° C. Each DNA is then precipitated and resuspended with 20 µl of H$_2$O. The ligation is carried out for 16 h at 16° C. with 5 µl of PCR fragment, 0.5 µl of vector and 3 U Weiss of T4 DNA ligase Biolabs in a final volume of 10 µl. Competent TG1 bacteria (CaCl$_2$ technique) are transformed with 5 µl of ligation product.

p55PhoA6HisGS⁻/NAB⁻ (FIGS. 10A and 11)

Phase shift of the PhoA gene at the EagI site. This phase shift creates a single FseI site. Five µl (2.5 µg) of p55PhoA6HisGS/NAB⁻ are digested by 10 U of EagI. After 16 h of incubation, the enzyme is destroyed for 10 min at 65° C. The reaction mixture is then precipitated and resuspended with 20 µl of H$_2$O. An equimolar mixture of dGTP and dCTP (33 µM final) and 2.5 U of Klenow fragment exo (Biolabs) are added in a final volume of 50 µl 15 min at 25° C. The reaction is stopped with 2 µl of EDTA at 500 mM, 20 min at 75° C. The reaction mixture is precipitated in ethanol, resuspended with 5 µl of H$_2$O and ligated with 3 U Weiss of T4 DNA ligase Biolabs in a final volume of 10 µl Competent TG1 bacteria (CaCl$_2$ technique) are transformed with 5 µl of ligation. This plasmid allows for the cloning and selection of the best secreted fragments of human antibody VH.

p55/MCS1 (FIGS. 10A and 11)

Insertion of MCS1 in p55PhoA6HisGS/NAB⁻ between the NcoI and HindIII sites using the paired oligonucleotides 5' MCS1 and 3' MCS1. Sequences SEQ ID NOs:24 and 25 of the oligonucleotides used:

```
5' MCS1
SEQ ID NO:24: CATGGCCCAGGTCACCGTCTCCTCAAACCGCGGACTC

GAGGCGGCCCAGCCGGCCAT GGCCGCTAGCGCGGCCGCTCTAGATTA

3' MCS1
SEQ ID NO:25: AGCTTAATCTAGAGCGGCCGCGCTAGCGGCCATGGCC

GGCTGGGCCGCCTCGAGTCCG CGGTTTGAGGAGACGGTGACCTGGGC
```

Five µl (2.5 µg) of p55PhoA6HisGS/NAB⁻ vector are digested for 16 h by 10 U of each NcoI and HindIII enzyme. Ten pmoles of each of the oligonucleotides 5' MCS1 and 3' MCS1 are incubated for 5 min at 80° C.; the solution is then slowly reduced to ambient temperature. Ligate 5 µl of vector with 1.2 µl of the hybrid cassette (5' MCS1+3' MCS1) in the presence of 3 U Weiss of T4 DNA ligase Biolabs 1 h at ambient temperature. The ligase is destroyed by incubating for 10 min at 65° C. A reaction mixture (2 h) of 90 µl, containing 10 U of EagI is added to destroy the original vector. This mixture is precipitated with ethanol and resuspended with 10 µl of H$_2$O. Competent TG1 bacteria (CaCl$_2$ technique) are transformed with 5 µl of mixture.

p55Flag/RBS/35 (FIGS. 10A and 11)

Insertion of the Flag/RBS/PeIB35 motif in p55/MCS1 between the SfiI and Sac2 sites using the paired oligonucleotides 5' Flag/RBS/35-sup and 3' Flag/RBS/35-inf. Sequences SEQ ID NOs:26 and 27 of the oligonucleotides used:

```
5' Flag/RBS/35-sup
SEQ ID NO:26: GGAGAGTGTGCAGGTGATTACAAAGACGATGACGATA

AGTAATAAAGAGGAAACAGAAGTCCATATGAAATACCTATTGCCTACGGCA

GCCGCTGGATTGTTATTACTCGCGGCCCAGC

SEQ ID NO:117: GGAGAGTGTGCAGGTGATTACAAAGACGATGACGAT

AAGTAATAAACAGGAAACAGAAGTCCATATGAAATATCTTTTACCTACGGC

AGCCGCAGGTTTGTTGTTACTCGCGGCCCAGC

3' Flag/RBS/35-inf
SEQ ID NO:27: GGGCCGCGAGTAATAACAATCCAGCGGCTGCCGTAGG

CAATAGGTATTTGATATGGACTTCTGTTTCCTGTTTATTACTTATCGTCAT

CGTCTTTGTAATCACCTGCACACTCTCCGC

SEQ ID NO:118: GGGCCGCGAGTAACAACAAACCTGCGGCTGCCGTAG

GTAAAAGATATTTCATATGGACTTCTGTTTCCTGTTTATTACTTATCGTCA

TCGTCTTTGTAATCACCTGCACACTCTCCGC
```

Figure 10B:
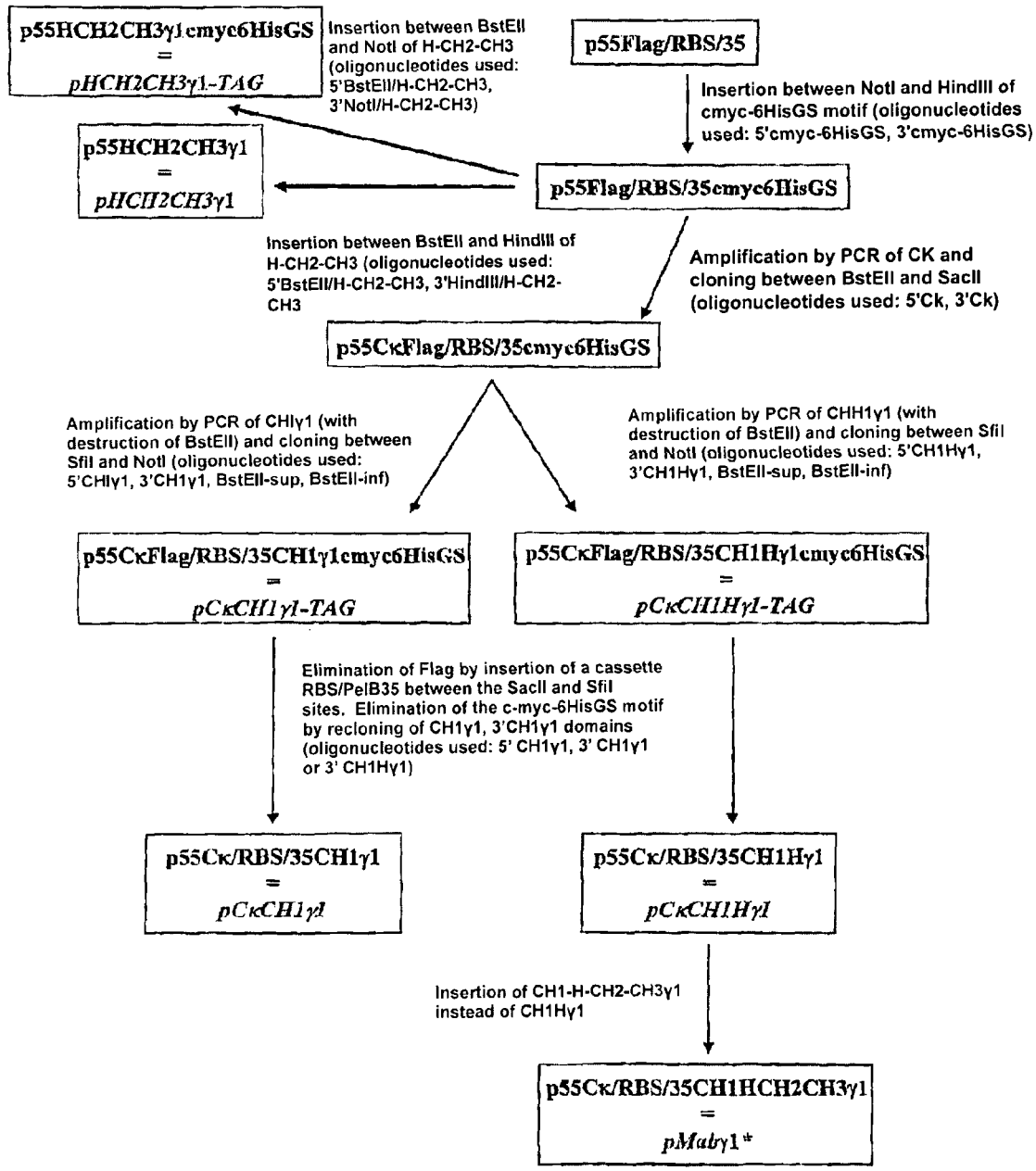

The cloning is carried out exactly according to the conditions previously described for the insertion of MCS1. After ligation, the reaction mixture is digested by 10 U of XhoI enzyme.

p55Flag/RBS/35cmyc6HisGS (FIGS. 10B and 11)

Insertion of the c-myc-6HisGS motif in p55Flag/RBS/35 between the NotI and HindIII sites using the paired oligonucleotides 5' c-myc-6HisGS and 3' c-myc-6HisGS. Sequences SEQ ID NOs:28 and 29 of the oligonucleotides used:

```
5' c-myc-6HisGS
SEQ ID NO:28: GGCCGCAGAACAAAAACTCATCTCAGAAGAGGATCTG

AATGGGGCCGTACATCACCACC ATCACCATGGGAGCTA

3' c-myc-6HisGS
SEQ ID NO:29: AGCTTAGCTCCCATGGTGATGGTGGTGATGTACGGCCC

CATTCAGATCCTCTTCTGAGA TGAGTTTTTGTTCTGC
```

The cloning is carried out exactly according to the conditions previously described for the insertion of MCS1. The ligation mixture is digested by 10 U of XbaI enzyme.

P55CκFlag/RBS/35cmyc6HisGS (FIGS. 10B and 11)

Insertion of the constant light Ckappa region of an immunoglobulin in p55Flag/RBS/35cmyc6HisGS. Sequences SEQ ID NOs:30 and 31 of the oligonucleotides used:

```
5' Cκ
SEQ ID NO:30: GGGGCCAGGGGACCCAGGTCACCGTCTCCTCAGGTAC

CGTGGCTGCACCATCTGTCTTC

SEQ ID NO:119: GGGGCCAGGGGACCCAGGTCACCGTCTCCTCACGTA

CGGTGGCTGCACCATCTGTGT TC

3' Cκ
SEQ ID NO:31: CGTCATCGTCTTTGTAATCACCTGCACACTCTCCGCG

GTTGAAGCTCTTTGTCACCG
```

Amplification of the Cκ domain: Human B lymphocytes are purified by Ficoll gradient from a pouch provided by LFB. The whole RNA is then prepared according to the protocol described in section 1.3.2.

Hybridisation: One µl of whole DNA is preincubated with 1 pmole of oligonucleotide 3' Cκ for 10 min at 70° C. in a final volume of 8 µl. The temperature is slowly decreased (45 min) to 37° C.

Reverse transcription: Take 8 µl and add 0.5 µl of RNAsine (20 U), 3 µl of 5× buffer (SuperScriptII, Invitrogen), 1 µl DTT, 100 mM, 2 µl dNTP 10 mM and incubate for 10 min at 50° C. Then, 0.75 µl of SuperScript (150 U) are added and the incubation is continued for 30 min at 50° C. and 15 min at 70° C. The cDNA obtained is purified on beads (BioMag Carboxyl Terminated, Polysciences) according to the supplier's recommendations. The final elution is made with 15 µl of Tris-acetate 10 mM pH 7.8.

PCR 1 and 2 conditions: The PCR1 is carried out with 1 µl of cDNA, 10 pmoles of each oligonucleotide 5' Cκ and 3' Cκ, 0.5 U Dynazyme (94° C., 3 min; 94° C., 1 min; 60° C., 1 min; 72° C., 1.5 min; 30 cycles then 72° C., 10 min) in a final volume of 50 µl. The PCR2 is carried out from 1 µl of PCR1 using 0.5 U Deep-Vent, (94° C., 3 min; 94° C., 45 s; 60° C., 45 s; 72° C., 45 s; 25 cycles then 72° C., 5 min) in a final volume of 50 µl. The PCR product is purified from a 2% agarose gel (Qiagen Kit extraction gel, final volume 50 µl). The PCR fragment is sequenced, before cloning, on ABI310 with oligonucleotides 5' Cκ and 3' Cκ.

The cloning of the Cκ domain is carried out between sites BstEII and SacII of p55Flag/RBS/35cmyc6HisGS: 20 µl of PCR 2 fragment and 5 µl (2.5 µg) of p55Flag/RBS/35cmyc6HisGS are digested by 10 U of BstEII and SacII. After 16 h of incubation, the enzymes are destroyed for 10 min at 65° C. Each DNA is then precipitated and resuspended with 20 µl of $H_2O$. Ligation is carried out for 16 h at 16° C. with 5 µl of PCR 2 fragment, 0.5 µl of vector and 3 U Weiss of T4 DNA ligase Biolabs in a final volume of 10 µl. Competent TG1 bacteria ($CaCl_2$ technique) are transformed with 5 µl of ligate.

p55CκFlag/RBS/35CH1γ1cmyc6HisGS (pCκCH1 γ1-TAG)

Insertion of the heavy constant region CH1 of an immunoglobulin of the IgG1 type in p55CκFlag/RBS/35cmyc6HisGS. Sequences SEQ ID NOs:32 to 35 of the oligonucleotides used:

```
5' CH1 γ1
SEQ ID NO:32: CTCGAGGCGGCCCAGCCGGCCATGGCCGCTAGCACCA

AGGGCCCATCGG

3' CH1 γ1
SEQ ID NO:33: AAGCTTAATCTAGAGCGGCCGCACAAGATTTGGGCTC

AACTTTC

BstEII-sup
SEQ ID NO:34: CCCTCAGCAGCGTAGTGACCGTGCCCTCC

BstEII-inf
SEQ ID NO:35: GGAGGGCACGGTCACTACGCTGCTGAGGG
```

The amplification of the CH1γ1 domain is carried out by overlapping PCR to destroy the BstEII site. The reverse transcription is carried out exactly as described above for the Cκ, but by using oligonucleotide 3' CH1γI. The PCR 1 after RT is carried out with 1 µl of cDNA, 10 pmoles of each oligonucleotide 5' CH1 γ1 and 3' CH1 γ1, 0.5 U of Dynazyme (94° C., 3 min; 94° C., 1 min; 60° C., 1 min; 72° C., 1.5 min; 30 cycles then 72° C., 10 min) in a final volume of 50 µl.

The PCR 2a is carried out from 1 µl of PCR 1, with oligonucleotides 5' CH1 γ1 and BstEII-inf using 0.5 U of Dynazyme (94° C., 3 min; 94° C., 45 s; 60° C., 45 s; 72° C., 45 s; 25 cycles then 72° C., 5 min) in a final volume of 50 µl. The PCR2b is carried out from 1 µl of PCR 1, with oligonucleotides BstEII-sup and 3' CH1 γ1 using 0.5 U of Dynazyme (94° C., 3 min; 94° C., 45 s; 60° C., 45 s; 72° C., 45 s; 25 cycles then 72° C., 5 min) in a final volume of 50 µl.

The PCR 3 is carried out from one µl of each of PCR 2a and PCR 2b, with oligonucleotides 5' CH1γ1 and 3' CH1γ1, using 0.5 U of Deep-Vent (94° C., 3 min; 94° C., 45 s; 60° C., 45 s; 72° C., 45 s; 25 cycles then 72° C., 5 min) in a final volume of 50 µl. The product of PCR 3 is purified from a 2% agarose gel (Qiagen Kit extraction gel, final volume 50 µl). The sequence of the PCR 3 fragment is carried out on ABI 310 sequencer using oligonucleotides: 5' CH1γ1 and 3' CH1γ1.

The cloning is carried out as described for the $C_κ$ domain but between the SfiI and NotI sites of p55CκFlag/RBS/35cmyc6HisGS. The resulting plasmid is more commonly called: PCκCH1γ1-TAG; it allows for the production of antibody fragments of Fab type where each chain has a label (FIG. 12A).

p55CκFlag/RBS/35CH1Hγ1cmyc6HisGS (pC5κCH1Hγ1-TAG) (FIGS. 10B and 11)

Insertion of the heavy constant region CH1 and the hinge region (H) of an immunoglobulin of IgG1 type in p55CκFlag/RBS/35cmyc6HisGS. The PCR1, 2a, 2b and 3 are carried out exactly as for the amplification of the CH1 domain described above by replacing oligonucleotide 3' Cγ1 by oligonucleotide 3' CH1 Hγ1 whose sequence SEQ ID NO:36 is indicated below:

```
3' CH1Hγ1
SEQ ID NO:36: AAGCTTAATCTAGAGCGGCCGCTGGGCACGGTGGGCA

TGTGTGAGTTTTGTCACAAGA TTTGGGCTCAACTTTC
```

The cloning is carried out as described for the CH1γ1 domain between the SfiI and NotI sites of p55CκFlag/RBS/35cmyc6HisGS. The resulting plasmid is commonly called: PCκCH1Hγ1-TAG, it allows for the production of antibody fragments of F(ab')$_2$ type where each chain has a label (FIG. 12A).

p55Cκ/RBS/35CH1γ1 (pCκH1γ1) (FIGS. 10B and 11)

Elimination of the Flag and c-myc-6hisGS labels from plasmid p55CκFlag/RBS/35CH1γ1cmyc6HisGS by the replacement of the DNA fragment included between SacI and SfiI by a new cassette using the paired oligonucleotides 5' RBS/35-sup and 3' RBS/35-inf. Sequences SEQ ID NOs:37 and 38 of the oligonucleotides used:

```
5' RBS/35-sup
SEQ ID NO:37: GGAGAGTGTTAATAAACAGGAAACAGAAGTCCATATG

AAATACCTATTGCCTACGGCA GCCGCTGGATTGTTATTACTCGCGGCCCA

GC

SEQ ID NO:120: GGAGAGTGTTAATAAACAGGAAACAGAAGTCCATAT

GAAATATCTTTTACCTACGG CAGCCGCAGGTTTGTTGTTACTCGCGGCCC

AGC

3' RBS/35-inf
SEQ ID NO:38: GGGCCGCGAGTAATAACAATCCAGCGGCTGCCGTAG

GCAATAGGTATTTCATATGGA CTTCTGTTTCCTGTTTATTAACACTCTC

CGC

SEQ ID NO:121: GGGCCGCGAGTAACAACAAACCTGCGGCTGCCGTAG

GTAAAAGATATTTCATATGGAC TTCTGTTTCCTGTTTATTAACACTCTC

CGC
```

The cloning is carried out exactly according to the conditions described for the insertion of MCS1. The resulting intermediate plasmid is called: p55Cκ/RBS/35CH1γ1cmyc6HisGS. The c-myc-6HisGS motif is removed by re-cloning the CH1γ1 domain in p55Cκ/RBS/35CH1γ1cmyc6HisGS.

One PCR is used by amplifying, from 5 ng of plasmid p55CκFlag/RBS/35CH1γ1cmyc6HisGS, the CH1γ1 domain with oligonucleotides 5' CH1γ1 and 3' CH1γ1-STOP. Sequence SEQ ID NO:39 of the oligonucleotide used:

3' CH1γ1-STOP
SEQ ID NO:39: CATGCAGTCCCAAGCTTAACAAGATTTGGGCTCAAC
TTTC

The cloning of the PCR fragment is carried out as described for the $C_\kappa$ domain, but between the SfiI and HindIII sites of plasmid p55Cκ/RBS/35CH1γ1cmyc6HisGS. The resulting plasmid is commonly called: pCκCH1γ1; it allows for the production of antibody fragments of Fab type (FIG. 12A).

p55Cκ/RBS/35CH1 Hγ1 (pCκCH1Hγ1) (FIGS. 10B and 11)

Elimination of the Flag and c-myc-6HisGS labels from the plasmid p55CκFlag/RBS/35CH1Hγ1cmyc6HisGS by replacement of the DNA fragment included between SacII and SfiI by a new cassette using the paired oligonucleotides 5' RBS/35-sup and 3' RBS/35-inf described above. The cloning is carried out exactly according to the conditions described for the insertion of MCS1. The resulting intermediate plasmid is called p55Cκ/RBS/35CH1Hγ1cmyc6HisGS. The c-myc-6HisGS motif is removed by re-cloning the CH1Hγ1 domain in p55Cκ/RBS/35CH1Hγ1cmyc6HisGS.

One PCR is used by amplifying, from 5 ng of plasmid p55CκFlag/RBS/35CH1 Hγ1cmyc6HisGS, the CH1 Hγ1 domain with oligonucleotides 5' CH1γ1 and 3' CH1 Hγ1-STOP. Sequence SEQ ID NO:40 of the oligonucleotide used:

3' CH1Hγ1-STOP
SEQ ID NO:40: CATGCAGTCCCAAGCTTATGGGCACGGTGGGCATGT
GTG

The cloning of the PCR fragment is carried out between the SfiI and HindIII sites as described above, but from plasmid p55Cκ/RBS/35CH1Hγ1cmyc6HisGS. The resulting plasmid is commonly called: PCκCH1Hγ1, it allows for the production of antibody fragment of F(ab')$_2$ type (FIG. 12A).

p55Cκ/RBS/35CH1HCH2CH3γ1 (pMabγ1*) (FIGS. 10B and 11)

Insertion of the constant heavy region CH1, of the hinge region (H) and the constant regions CH2 and CH3 of an immunoglobulin of IgG1 type in p55CκFlag/RBS/35CH1γ1cmyc6HisGS. The PCR1, 2a, 2b and 3 are carried out exactly as in the amplification of the CH1 domain described above by replacing oligonucleotide 3' CH1γ1 by oligonucleotide 3' HindIII/H—CH2-CH3 whose sequence SEQ ID NO.41 is indicated below:

3' HindIII/H-CH2-CH3
SEQ ID NO:41: CCGCCAAAACAGCCAAGCTTATTTACCCGGAGACAG
GGAG

The cloning is carried out as described for the CH17 domain between the SfiI and HindIII sites of p55CκFlag/RBS/35CH1γ1cmyc6HisGS. The resulting plasmid is more commonly called: pMAbγI*; it allows for the production of antibody fragments of mAb* type (FIG. 12B).

p55HCH2CH3γ1cmyc6HisGS (pHCH2CH3γ1-TAG) (FIGS. 10B and 11)

Insertion of the hinge region (H) and the constant regions CH2 and CH3 of an immunoglobulin of IgG1 type between the BstEII and NotI sites of p55Flag/RBS/35cmyc6HisGS. The reverse transcription is carried out exactly as described for Cκ, but by using oligonucleotide 3' NotI/H—CH2-CH3. Sequences SEQ ID NOs:42 and 43 of the oligonucleotides used:

5'BstE2/H-CH2-CH3
SEQ ID NO:42: CCGGCCATGGCCCAGGTCACCGTCTCCTCAGACAAA
ACTCACACATGCCC

3' NotI/H-CH2-CH3
SEQ ID NO:43: AAGCTTAATCTAGAGCGGCCGCTTTACCCGGAGACA
GGGAG

The PCR after RT is carried out with 1 μl of cDNA, 10 pmoles of each oligonucleotide 5' BstE2/H—CH2-CH3 and 3' NotI/H—CH2-CH3, 0.5 U of Dynazyme (94° C., 3 min; 94° C., 1 min; 60° C., 1 min; 72° C., 1.5 min; 30 cycles then 72° C., 10 min) in a final volume of 50 μl. The resulting plasmid is more commonly called: pHCH2CH3γ1-TAG; it allows for the production of antibody fragments of (HCH2CH3)$_2$ type with a label at the end of CH3 (FIG. 12B).

p55HCH2CH3γ1 (pHCH2CH3γ1) (FIGS. 10B and 11)

Insertion of the hinge region (H) and constant regions CH2 and CH3 of an immunoglobulin of IgG1 type between the BstEII and HindIII sites of p55Flag/RBS/35cmyc6HisGS. The reverse transcription is carried out exactly as described for Cκ, but by using oligonucleotide 3' HindIII/H—CH2-CH3. Sequences SEQ ID NOs:44 and 45 of the oligonucleotides used:

5' BstE2/H-CH2-CH3
SEQ ID NO:44: CCGGCCATGGCCCAGGTCACCGTCTCCTCAGACAAA
ACTCACACATGCCC

3' HindIII/H-CH2-C113
SEQ ID NO:45: CCGCCAAAACAGCCAAGCTTATTTACCCGGAGACAG
GGAG

The PCR after RT is carried out with 1 μl of cDNA, 10 pmoles each of oligonucleotides 5' BstE2/H—CH2-CH3 and 3' HindIII/H—CH2-CH3, 0.5 U of Dynazyme (94° C., 3 min; 94° C., 1 min; 60° C., 1 min; 72° C., 1.5 min; 30 cycles then 72° C., 10 min) in a final volume of 50 μl. The resulting plasmid is more commonly called: pHCH2CH3γ1; it allows for the production of antibody fragment of (HCH2CH3)$_2$ type (FIG. 12B).

Cloning of VHH

In the different formats, any VHH may be introduced between the unique sites: Upstream from Ck: between EcoRI and BstEII (or KpnI); Upstream from CH1: between SfiI and NheI; Upstream from H: EcoRI and BstEII. For this reason, we amplify the different VHH by PCR with the pairs of oligonucleotides 5' and 3' described below: Sequences SEQ ID NOs:46 to 52 of the oligonucleotides used:

5' EcoRI-PeIB55-PeIBPHen
SEQ ID NO:46: CGACACCGGAATTCCATATGAAATACCTATTACTTA
CAACAGCAGCAGCTGGGTTATTGCTCGCTGCGCAGCCGGCCATGGCCGAG
GTGCAGCTG

-continued

```
5'VH1-Sfi
SEQ ID NO:47:  CATGCCATGACTCGCGGCCCAGCCGGCCATGGCCCA

GGTGCAGCTGGTGCAGTCTGG

5'VH2-Sfi
SEQ ID NO:48:  CATGCCATGACTCGCGGCCCAGCCGGCCATGGCCCA

GGTCACCTTGAAGGAGTCTGG

5' VH3-Sfi
SEQ ID NO:49:  CATGCCATGACTCGCGGCCCAGCCGGCCATGGCCGA

GGTGCAGCTGGTGGAGTCTGG

5'VH4-Sfi
SEQ ID NO:50:  CATGCCATGACTCGCGGCCCAGCCGGCCATGGCCCA

GGTGCA GCTGCAGGAGTCGGG

3' BstEII/KpnI
SEQ ID NO:51:  GGTGCAGCCACGGTACCTGAGGAGACGGTGACCTG

3' BstE2/NheI
SEQ ID NO:52:  GGGCCCTTGGTGCTAGCTGAGGAGACGGTGACCTG
```

Production, purification and characterisation of bio-specific antibodies.

Figure 13:
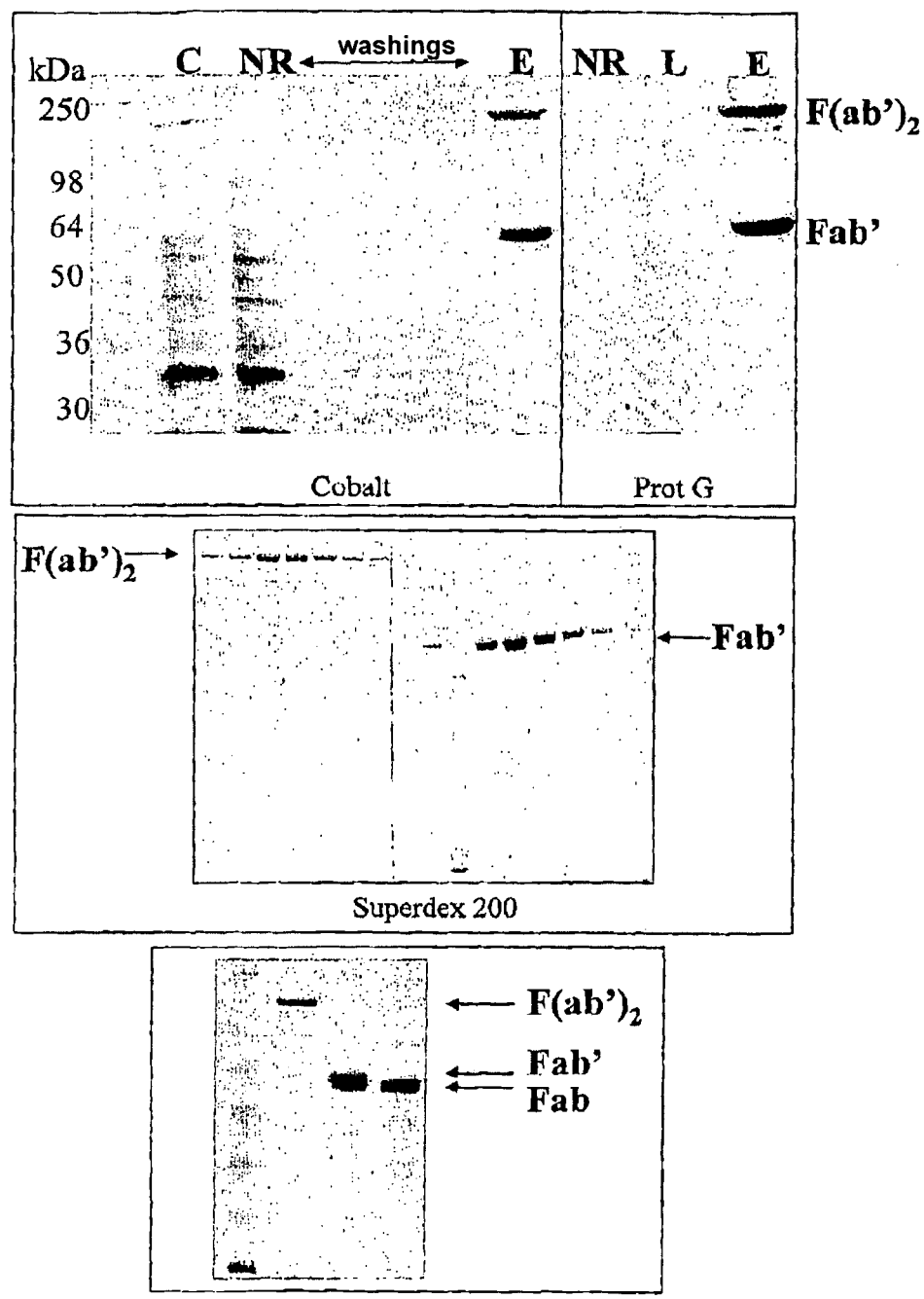
FIG. 13, electrophoresis gels of antibody fragments of type Fab, Fab' and F(ab')2 during different stages of their purification.

The production and purification of the different antibody fragments with the 6HisGS label are carried out as described above. For the purification of antibody fragments without label, the chromatography stage on base is replaced by an ion exchange column whose characteristics (anions or cations) depend on the characteristics of the antibody fragment. Electrophoresis gels are shown in FIG. 13. The Fab' and F(ab')$_2$ are purified on a cobalt column and then on protein G. The different antibody fragments are then separated on Superdex 200 (or possibly Superdex 75).

Method to isolate human VH and construction of vectors. The principle of the method consists of cloning human VH domains (isolated by RT-PCR from the LFB pouch) in plasmid p55PhoA6HisGS⁻/NAB⁻ (FIGS. 10A and 11). This plasmid has the gene coding for the alkaline phosphatase in a reading frame not allowing for its expression. The cloning of the VH restores the reading frame of the alkaline phosphatase and allows for the production of fused VH upstream from the alkaline phosphatase (bank for VH-PhoA cloned in TG1 bacteria). The different clones are then produced in 96-well microplates and the growth kinetics of the different clones is directly measured every 30 min (OD 620 nm) from the microplates. Thereby, the clones whose growth is not altered by the presence of VH are selected. The clones from the microplates are replicated and stored at −80° C. After 2 hours of induction at 37° C., or 16 hours of induction at 30° C., 24° C., or even 18° C., the growth is stopped and the phosphatase activity is directly measured from the supernatants in the culture medium. The phosphatase activity is then directly correlated with the number of bacteria found in each microplate well.

The alkaline phosphatase is only active if it is secreted in the bacterial periplasm, in dimer form with its disulphate bridges correctly formed. This approach allows for the selection of the clones producing the most fusion protein VH-PhoA secreted in the bacterial culture medium. It is thereby possible to select the VH that are correctly replicated and whose disulphide bridges are correctly formed, and therefore soluble. The selected VH are used as a matrix to exchange the CDR of human VH by the CDR from llama VHH previously described. The VH are chosen by selecting the VH whose amino acids at the CDR junctions are equivalent to those of the VHH.

RT-PCR and PCR conditions.

Hybridisation: One µl of whole RNA (purification described in section 1.3.2) is preincubated with 1 pmole of oligonucleotide (mixture of: 3' JH1-4-5; 3' J112; 3' JH3 and 3' JH6) for 10 min at 70° C. in a final volume of 8 µl. The temperature is slowly reduced (45 min) to 37° C.

Reverse transcription: Take 8 µl and add 0.5 µl of RNAsine (20 U), 3 µl of 5× buffer (SuperScriptII, Invitrogen), 1 µl DTT, 100 mM, 2 µl dNTP 10 mM and incubate for 10 min at 50° C. Then add 0.75 µl of SuperScript (150 U) and the incubation continues for 30 min at 50° C. and 15 min at 70° C. The cDNA obtained is purified on beads (BioMag Carboxyl Terminated, Polysciences) according to the supplier's recommendations. The final elution is made with 15 µl of 10 mM Tris-acetate pH 7.8.

The PCR1 is carried out with 1 µl of cDNA (obtained by RT-PCR), 10 pmoles of oligonucleotides 5' (0.625 pmole of each oligonucleotide 5' whose sequences are indicated below) and 3' (2.5 pmoles of each oligonucleotide 3' whose sequences are indicated below), 0.5 U of Dynazyme (95° C., 3 min; then 95° C., 1 min; 58° C., 1 min; 72° C., 1 min; for 35 cycles then 72° C., 10 min). The PCR products are deposited on a 2% agarose gel and the bands corresponding to the VH are purified (Qiagen Kit extraction gel). The PCR2 is carried out from 1 µl of PCR1 diluted to 1/1000th, the same quantity of oligonucleotides described above, 0.5 U Deep-Vent for a final volume of 50 µl. (94° C., 3 min; then 94° C., 1 min; 70° C., 1 min; 72° C., 1.5 min; for 40 cycles then 72° C., 10 min). The fragments are purified from 2% agarose gel as described above.

Sequences SEQ ID NO:53 to SEQ ID NO:72 of the oligonucleotides used:

```
5'VH1a
SEQ ID NO:53:  CG GCC CAG CCG GCC ATG GCC CAG GTG

CTG GTG CAG CAG TCT GG

5' VH1b
SEQ ID NO:54:  CG GCC CAG CCG GCC ATG GCC CAG GT(CT)

CAG CG(GT) GTG CAG TCT GG

5' VH1c
SEQ ID NO:55:  CG GCC CAG CCG GCC ATG GCC (CG)AG

GTC CAG CTG GTA CAG TCT GG

5' VH1d
SEQ ID NO:56:  CG GCC CAG CCG GCC ATG GCC CA(GA)

ATG CAG CTG GTG CAG TCT GG

5' VH2a
SEQ ID NO:57:  CG GCC CAG CCG GCC ATG GCC CAG GTC

ACC TTG AAG GAG TCT GG

5' VH2b
SEQ ID NO:58:  CG GCC CAG CCG GCC ATG GCC CAG ATC

ACC TTG AAG GAG TCT GG

5' VH3a
SEQ ID NO:59:  CG GCC CAG CCG GCC ATG GCC GAG GTG

CAG CTG GTG GAG TCT GG

5' VH3b
SEQ ID NO:60:  CG GCC CAG CCG GCC ATG GCC GAA GTG

CAG CTG GTG GAG TCT GG
```

-continued

5' VH3c
SEQ ID NO:61: CG GCC CAG CCG GCC ATG GCC CAG GTG
CAG CTG GTG GAG TCT GG

5' VH3d
SEQ ID NO:62: CG GCC CAG CCG GCC ATG GCC GAG GTG
CAG CTG GTG GAG (AT)C(TC) (GC)G

5' VH4a
SEQ ID NO:63: CG GCC CAG CCG GCC ATG GCC CAG GTG
CAG CTG CAG GAG TCG GG

5' VH4b
SEQ ID NO:64: CG GCC CAG CCG GCC ATG GCC CAG CTG
CAG CTG CAG GAG TC(GC) GG

5' VH4c
SEQ ID NO:65: CG GCC CAG CCG GCC ATG GCC CAG GTG
CAG CTA CAG CAG TGG GG

5' VH5a
SEQ ID NO:66: CG GCC CAG CCG GCC ATG GCC GA(GA)
GTG CAG CTG GTG CAG TCT GG

5' VH6a
SEQ ID NO:67: CG GCC CAG CCG GCC ATG GCC CAG) GTA
CAG CTG CAG CAG TCA GG

5' VH7a
SEQ ID NO:68: CG GCC CAG CCG GCC ATG GCC CAG GTG
CAG CTG GTG CAA TCT GG

3' JH1-4-5
SEQ ID NO:69: GTC TAG ACG TCC CCC CGG GGA GGA GAC
GGT GAC CAG GG

3' JH2
SEQ ID NO:70: GTC TAG ACG TCC CCC CGG GGA GGA GAC
AGT GAC CAG GG

3' JH3
SEQ ID NO:71: GTC TAG ACG TCC CCC CGG GGA AGA GAC
GGT GAC CAT TG

3' JH6
SEQ ID NO:72: GTC TAG ACG TCC CCC CGG GGA GGA GAC
GGT GAC CGT GG

The different purified fragments of PCR are digested by 10 U of NcoI and XmaI and inserted in cloning vector p55/PhoA6HisGS$^{-s/NAB-}$ by ligation. The ligation mixture is digested by FseI before transformation of the bacteria. The transformation is carried out by electroporation with electrocompetent TG1 bacteria. The clones with an inserted VH domain restore the phosphatase activity (blue colonies).

Production in 96 or 384 well microplate: Controls: negative medium control (2YT/ampicillin 100 µg/ml); negative control of vector p55/PhoA6HisGS$^-$/NAB$^-$; positive control of vector p55PhoA6HisGS/NAB$^-$. Distribution of 150 or 40 µl of culture medium (2YT/ampicillin 100 µg/ml) per well (Nunclon Surface, Nunc). Each well is inoculated with an isolated blue colony with a toothpick or a cell pick (Qpix) and the plate is then sealed with a sterile adhesive sheet. Place for 16 h or at 37° C. or 30° C. in an IEMS Thermo plate incubator with stirring at 900 rpm and then make a replica of the "mother" microplate with a 96 or 384 well replicator in a microplate containing 150 or 40 µl of 2YT/ampicillin 100 µg/ml then seal with a sterile adhesive sheet. (After making the replica, add in the mother microplate 37.5 or 10 µl of 80% glycerol per well and store at 80° C.). After 3 h of culture (about OD 620 nm 0.5), induce for 16 h with 100 µM final of IPTG. The OD at 620 nm is measured at the end of induction.

Assay of the alkaline phosphatase activity: Take 10 µl of the whole culture (cells+culture medium) and 10 µl of culture supernatant (for this, centrifuge for 3 min at 910×g). To each sample, add 65 µl 10 mM Tris-HCl pH 8.0 and add 25 µl of PNPP (paranitrophenyl phosphate) at 1 mg/ml in (diethanolamine pH 9.8 (HCl); MgCl$_2$ 0.5 mM). After 30 min of reaction while stirring, measure the OD at 405 nm.

The alkaline phosphatase activity measured at 405 nm is corrected according to the number of cells (OD measurement 620 nm) contained in each well at the end of induction. Each phosphatase activity, of the clones expressing a VH fused to the alkaline phosphatase, is compared with that of the positive control (non-fused alkaline phosphatase produced by p55PhoA6HisGS/NAB$^-$). Only the clones with an activity equal or greater than the control are taken into account and sequenced with oligonucleotides 5' EcoRI-90 and 3' inf-PstI+71 (sequence of oligonucleotide 3' inf-PstI+71: GTTAAACGGCGAGCACCG).

References

1. Hamers-Casterman C, Atarhouch T, Muyldermans S, Robinson G, Hamers C, Sanga E B, Bendahinan N, Harriers R. Naturally occurring antibodies devoid of light chains. *Nature* 1993, 363:446-448.
2. Teillaud C, Galon J, Zilber M T, Mazieres N, Spagnoli R, Kurrle R, Fridman W H, Sautes C. Soluble CD16 binds peripheral blood mononuclear cells and inhibits pokeweed-nitogen-induced responses. *Blood,* 1993, 82:3081-3090).
3. Terskikh, A, Mach, J P, and Pelegrin A. Marked increase in the secretion of a fully antigenic recombinant CEA obtained by deletion of its hydrophobic tail. *Mol Immunol,* 1993, 30:921-927.
4. Chomczynski P, Sacchi N. Single-step method of RNA isolation by acid guanidinium thiocyanate-phenol-chloroform extraction. *Anal Biochem,* 1987, 162:156-159.
5. Arbabi Ghahroudi M, Desmyter A, Wyns L, Hamers R, Muyldermans S. Selection and identification of single domain antibody fragments from camel heavy-chain antibodies. *FEBS Lett,* 1997, 414:521-526.
6. Vivier E, Rochet N, Ackerly M, Petrini J, Levine H, Daley J, Anderson P. Signaling function of reconstituted CD16: zeta: gamma receptor complex isoforms. *Int Immunol,* 1992, 4:1313-1323.
7. Vély F, Gruel N, Moncuit J, Cochet O, Rouard H, Dard S, Galon J, Sautes C, Fridman W H, Teillaud J-L. A new set of monoclonal antibodies against human FcgammaRIIl (CD32) and FcgammaRIII (CD16): characterization and use in various assays. *Hybridoma,* 1997, 16:519-528.
8. Le Calvez H, Fieschi J, Green J M, Marchesi N, Chauveau J, Baty D. Paratope characterisation by structural modelling of two anti-cortisol single-chain variable fragments produced in *E. coli. Mol. Immunol,* 1995, 32:185-198.
9. Le Calvez H, Green J M, Baty D. Increased efficiency of alkaline phosphatase production levels in *Escherichia coli* using a degenerate PelB signal sequence. *Gene,* 1996, 170: 51-55.

What is claimed:

1. An isolated chimeric antibody comprising all of the VHH or humanized VHH domains, fused to constant regions of human antibodies wherein said antibody is a chimeric antibody that does not contain a light chain variable domain, and wherein the antibody has a Fab type format and comprises two different VHH domains, or two human VH domains on which are grafted the VHH CDRs, wherein one of the domains is fused to the Cκ or Cλ constant region of a human immunoglobulin, the other domain is fused to the CH1 region of an immunoglobulin, wherein said chimeric antibody recognizes CD16 or CEA and wherein said antibody comprises an amino acid sequence encoded by a nucleotide sequence selected from the group consisting of, respectively, sequences SEQ ID NO:81,SEQ ID NO:82,SEQ ID NO:83, SEQ ID NO:84,SEQ ID NO:106 and SEQ ID NO:107 or SEQ ID NO:85,SEQ ID NO:86,SEQ ID NO:87, SEQ ID NO:88 and SEQ ID NO:108.

2. An antigen binding fragment of VHH antibodies from Camelidae, in particular llamas, said antigen binding fragments consisting of anti-CD16 or anti-CEA fragments comprising an amino acid sequence encoded by a nucleotide sequence selected from the group consisting of, respectively, sequences SEQ ID NO:81,SEQ ID NO:82,SEQ ID NO:83, SEQ ID NO:84,SEQ ID NO:106 and SEQ ID NO:107 or SEQ ID NO:85,SEQ ID NO:86,SEQ ID NO:87, SEQ ID NO:88 and SEQ ID NO:108.

3. The antigen binding fragment according to claim 2, wherein the fragment comprises VHH CDRs.

4. Method of production of chimerized or humanized, multispecific and/or multivalent antibodies, comprising the use of domains of antibody formats according to claim 1 or fragments of claim 2.

5. The method according to claim 4, wherein said formats comprise anti-CEA and anti-CD16 VHH from Camelidae, in particular llama.

6. The method according to claim 5, characterised in that said variable domains of anti-CEA and anti-CD16 VHH are advantageously produced according to a protocol comprising:
   the immunisation of Camelidae, in particular llamas, with as immunogen, a CEA or a CD16,
   the purification of the B lymphocytes obtained from blood,
   the construction of a VHH bank, and
   the isolation of VHH from the bank.

7. The method according to claim 6, characterised in that the construction of the bank comprises:
   the extraction of whole DNA from B lymphocytes,
   the reverse transcription of RNA to obtain the corresponding cDNA,
   the amplification by PCR of genes coding for the variable regions of single heavy chain anti-CD16 and anti-CEA antibodies,
   the ligation of DNA VHH fragments obtained by cutting, by enzymes, of DNA amplified with a phagemid.

8. The method according claim 6, wherein the VHH are isolated from banks by the phage display technique and purified.

9. The method according to claim 6, wherein the genes of selected VHH are introduced in the expression vectors, in particular plasmids, to produce formats comprising all or part of the VHH or humanised VHH or human VH domains, directly fused to constant regions of human antibodies.

10. A Pharmaceutical composition, comprising at least one isolated chimeric antibody according to claim 1.

* * * * *

SEQUENCE LISTING

<160> NUMBER OF SEQ ID NOS: 122

<210> SEQ ID NO 1
<211> LENGTH: 21
<212> TYPE: DNA
<213> ORGANISM: Artificial sequence
<220> FEATURE:
<223> OTHER INFORMATION: primer 3? CH2FORTA4

<400> SEQUENCE: 1
cgccatcaag gtaccagttg a                                       21

<210> SEQ ID NO 2
<211> LENGTH: 23
<212> TYPE: DNA
<213> ORGANISM: Artificial sequence
<220> FEATURE:
<223> OTHER INFORMATION: primer 3? CH2-2

<400> SEQUENCE: 2
ggtacgtgct gttgaactgt tcc                                     23

<210> SEQ ID NO 3
<211> LENGTH: 26
<212> TYPE: DNA
<213> ORGANISM: Artificial sequence
<220> FEATURE:
<223> OTHER INFORMATION: primer 3? RC-IgG2

<400> SEQUENCE: 3
ggagctgggg tcttcgctgt ggtgcg                                  26

<210> SEQ ID NO 4
<211> LENGTH: 57
<212> TYPE: DNA
<213> ORGANISM: Artificial sequence
<220> FEATURE:
<223> OTHER INFORMATION: primer 3? RC-IgG3

<400> SEQUENCE: 4
catgccatga ctcgcggccc agccggccat ggcccaggtg cagctggtgc agtctgg    57

<210> SEQ ID NO 5
<211> LENGTH: 26
<212> TYPE: DNA
<213> ORGANISM: Artificial sequence
<220> FEATURE:
<223> OTHER INFORMATION: primer 5? VH1-Sfi

<400> SEQUENCE: 5
tggttgtggt tttggtgtct tgggtt                                  26

<210> SEQ ID NO 6
<211> LENGTH: 57
<212> TYPE: DNA
<213> ORGANISM: Artificial sequence
<220> FEATURE:
<223> OTHER INFORMATION: primer 5? VH2-Sfi

<400> SEQUENCE: 6
catgccatga ctcgcggccc agccggccat ggcccaggtc accttgaagg agtctgg    57

<210> SEQ ID NO 7
<211> LENGTH: 57
<212> TYPE: DNA
<213> ORGANISM: Artificial sequence
<220> FEATURE:
<223> OTHER INFORMATION: primer 5?VH3-Sfi

<400> SEQUENCE: 7
catgccatga ctcgcggccc agccggccat ggccgaggtg cagctggtgg agtctgg      57

<210> SEQ ID NO 8
<211> LENGTH: 57
<212> TYPE: DNA
<213> ORGANISM: Artificial sequence
<220> FEATURE:
<223> OTHER INFORMATION: primer 5?VH4-Sfi

<400> SEQUENCE: 8
catgccatga ctcgcggccc agccggccat ggcccaggtg cagctgcagg agtcggg      57

<210> SEQ ID NO 9
<211> LENGTH: 41
<212> TYPE: DNA
<213> ORGANISM: Artificial sequence
<220> FEATURE:
<223> OTHER INFORMATION: primer 3?VHH-Not

<400> SEQUENCE: 9
cacgattctg cggccgctga ggagacaggt gacctgggtc c      41

<210> SEQ ID NO 10
<211> LENGTH: 44
<212> TYPE: DNA
<213> ORGANISM: Artificial sequence
<220> FEATURE:
<223> OTHER INFORMATION: primer 5?pJF-VH3-Sfi

<400> SEQUENCE: 10
ctttactatt ctcacggcca tggcggccga ggtgcagctg gtgg      44

<210> SEQ ID NO 11
<211> LENGTH: 72
<212> TYPE: DNA
<213> ORGANISM: Artificial sequence
<220> FEATURE:
<223> OTHER INFORMATION: primer 3'cmyc-6His/HindIII

<400> SEQUENCE: 11
ccgcgcgcgc caagacccaa gcttgggcta gatggatgga tggatggatg gatgtgcggc      60
cccattcaga tc      72

<210> SEQ ID NO 12
<211> LENGTH: 25
<212> TYPE: DNA
<213> ORGANISM: Artificial sequence
<220> FEATURE:
<223> OTHER INFORMATION: primer EcoRI-90

<400> SEQUENCE: 12
gcgccgacat cataacggtt ctggc      25

<210> SEQ ID NO 13
<211> LENGTH: 17
<212> TYPE: DNA
<213> ORGANISM: Artificial sequence
<220> FEATURE:
<223> OTHER INFORMATION: primer HindIII+88

<400> SEQUENCE: 13

```
cgctactgcc gccaggc                                                   17

<210> SEQ ID NO 14
<211> LENGTH: 19
<212> TYPE: DNA
<213> ORGANISM: Artificial sequence
<220> FEATURE:
<223> OTHER INFORMATION: primer amont-RsrII

<400> SEQUENCE: 14
ggcacatgtg acctcgcgc                                                 19

<210> SEQ ID NO 15
<211> LENGTH: 22
<212> TYPE: DNA
<213> ORGANISM: Artificial sequence
<220> FEATURE:
<223> OTHER INFORMATION: primer NcoI-sup

<400> SEQUENCE: 15
gcaacgtacc acggcaatat cg                                             22

<210> SEQ ID NO 16
<211> LENGTH: 22
<212> TYPE: DNA
<213> ORGANISM: Artificial sequence
<220> FEATURE:
<223> OTHER INFORMATION: primer NcoI-inf

<400> SEQUENCE: 16
cgatattgcc gtggtacgtt gc                                             22

<210> SEQ ID NO 17
<211> LENGTH: 22
<212> TYPE: DNA
<213> ORGANISM: Artificial sequence
<220> FEATURE:
<223> OTHER INFORMATION: primer aval-EcoNI

<400> SEQUENCE: 17
gccatctttg gtatttagcg cc                                             22

<210> SEQ ID NO 18
<211> LENGTH: 23
<212> TYPE: DNA
<213> ORGANISM: Artificial sequence
<220> FEATURE:
<223> OTHER INFORMATION: primer XhoI-SacI

<400> SEQUENCE: 18
ccatggcggc cgatcctcga gag                                            23

<210> SEQ ID NO 19
<211> LENGTH: 67
<212> TYPE: DNA
<213> ORGANISM: Artificial sequence
<220> FEATURE:
<223> OTHER INFORMATION: primer 6HisGS/HindIII

<400> SEQUENCE: 19
catgcagtcc caagcttatt agctcccgtg atggtgatga tgatgtttca gccccagagc   60
ggctttc                                                              67

<210> SEQ ID NO 20
<211> LENGTH: 20
```

```
<212> TYPE: DNA
<213> ORGANISM: Artificial sequence
<220> FEATURE:
<223> OTHER INFORMATION: primer amont-EcoRV

<400> SEQUENCE: 20
catgagctgt cttcggtatc                                                    20

<210> SEQ ID NO 21
<211> LENGTH: 38
<212> TYPE: DNA
<213> ORGANISM: Artificial sequence
<220> FEATURE:
<223> OTHER INFORMATION: primer ApaI-BstEII-sup

<400> SEQUENCE: 21
taatggtccc gctaacagcg cgatttgctg atgaccca                                 38

<210> SEQ ID NO 22
<211> LENGTH: 38
<212> TYPE: DNA
<213> ORGANISM: Artificial sequence
<220> FEATURE:
<223> OTHER INFORMATION: primer BstEII-ApaI-inf

<400> SEQUENCE: 22
tgggtcatca gcaaatcgcg ctgttagcgg gaccatta                                 38

<210> SEQ ID NO 23
<211> LENGTH: 19
<212> TYPE: DNA
<213> ORGANISM: Artificial sequence
<220> FEATURE:
<223> OTHER INFORMATION: primer aval-MluI

<400> SEQUENCE: 23
gaacgaagcg gcgtcgaag                                                     19

<210> SEQ ID NO 24
<211> LENGTH: 84
<212> TYPE: DNA
<213> ORGANISM: Artificial sequence
<220> FEATURE:
<223> OTHER INFORMATION: linker 5' MCS1

<400> SEQUENCE: 24
catggcccag gtcaccgtct cctcaaaccg cggactcgag gcggcccagc cggccatggc         60
cgctagcgcg gccgctctag atta                                               84

<210> SEQ ID NO 25
<211> LENGTH: 84
<212> TYPE: DNA
<213> ORGANISM: Artificial sequence
<220> FEATURE:
<223> OTHER INFORMATION: linker 3' MCS1

<400> SEQUENCE: 25
agcttaatct agagcggccg cgctagcggc catggccggc tgggccgcct cgagtccgcg         60
gtttgaggag acggtgacct gggc                                               84

<210> SEQ ID NO 26
<211> LENGTH: 119
<212> TYPE: DNA
<213> ORGANISM: Artificial sequence
<220> FEATURE:
```

<223> OTHER INFORMATION: linker 5' flag/rbs/35-sup

<400> SEQUENCE: 26
ggagagtgtg caggtgatta caaagacgat gacgataagt aataaacagg aaacagaagt    60
ccatatgaaa tacctattgc ctacggcagc cgctggattg ttattactcg cggcccagc    119

<210> SEQ ID NO 27
<211> LENGTH: 118
<212> TYPE: DNA
<213> ORGANISM: Artificial sequence
<220> FEATURE:
<223> OTHER INFORMATION: linker 3'flag/RBS/35-inf

<400> SEQUENCE: 27
gggccgcgag taataacaat ccagcggctg ccgtaggcaa taggtatttc atatggactt    60
ctgtttcctg tttattactt atcgtcatcg tctttgtaat cacctgcaca ctctccgc     118

<210> SEQ ID NO 28
<211> LENGTH: 75
<212> TYPE: DNA
<213> ORGANISM: Artificial sequence
<220> FEATURE:
<223> OTHER INFORMATION: linker 5' c-myc-6HISGS

<400> SEQUENCE: 28
ggccgcagaa caaaaactca tctcagaaga ggatctgaat ggggccgtac atcaccacca    60
tcaccatggg agcta                                                    75

<210> SEQ ID NO 29
<211> LENGTH: 75
<212> TYPE: DNA
<213> ORGANISM: Artificial sequence
<220> FEATURE:
<223> OTHER INFORMATION: linker 3' c-myc-6HISGS

<400> SEQUENCE: 29
agcttagctc ccatggtgat ggtggtgatg tacggcccca ttcagatcct cttctgagat    60 gagttttgt tctgc                                                     75

<210> SEQ ID NO 30
<211> LENGTH: 59
<212> TYPE: DNA
<213> ORGANISM: Artificial sequence
<220> FEATURE:
<223> OTHER INFORMATION: linker 5' Ck

<400> SEQUENCE: 30
ggggccaggg gacccaggtc accgtctcct caggtaccgt ggctgcacca tctgtcttc    59

<210> SEQ ID NO 31
<211> LENGTH: 57
<212> TYPE: DNA
<213> ORGANISM: Artificial sequence
<220> FEATURE:
<223> OTHER INFORMATION: linker 3'Ck

<400> SEQUENCE: 31
cgtcatcgtc tttgtaatca cctgcacact ctccgcggtt gaagctcttt gtcaccg    57

<210> SEQ ID NO 32
<211> LENGTH: 49
<212> TYPE: DNA
<213> ORGANISM: Artificial sequence
<220> FEATURE:
<223> OTHER INFORMATION: linker 5'CH1y1

<400> SEQUENCE: 32
ctcgaggcgg cccagccggc catggccgct agcaccaagg gcccatcgg          49

<210> SEQ ID NO 33
<211> LENGTH: 44
<212> TYPE: DNA
<213> ORGANISM: Artificial sequence
<220> FEATURE:
<223> OTHER INFORMATION: linker 3' CH1y1

<400> SEQUENCE: 33
aagcttaatc tagagcggcc gcacaagatt tgggctcaac tttc               44

<210> SEQ ID NO 34
<211> LENGTH: 29
<212> TYPE: DNA
<213> ORGANISM: Artificial sequence
<220> FEATURE:
<223> OTHER INFORMATION: linker BstEII-sup

<400> SEQUENCE: 34
ccctcagcag cgtagtgacc gtgccctcc                                29

<210> SEQ ID NO 35
<211> LENGTH: 29
<212> TYPE: DNA
<213> ORGANISM: Artificial sequence
<220> FEATURE:
<223> OTHER INFORMATION: linker BstEII-inf

<400> SEQUENCE: 35
ggagggcacg gtcactacgc tgctgaggg                                29

<210> SEQ ID NO 36
<211> LENGTH: 74
<212> TYPE: DNA
<213> ORGANISM: Artificial sequence
<220> FEATURE:
<223> OTHER INFORMATION: linker 3'CHHy1

<400> SEQUENCE: 36
aagcttaatc tagagcggcc gctgggcacg gtgggcatgt gtgagttttg tcacaagatt    60
tgggctcaac tttc                                                     74

<210> SEQ ID NO 37
<211> LENGTH: 89
<212> TYPE: DNA
<213> ORGANISM: Artificial sequence
<220> FEATURE:
<223> OTHER INFORMATION: linker 5'RBS/35-inf

<400> SEQUENCE: 37
ggagagtgtt aataaacagg aaacagaagt ccatatgaaa tacctattgc ctacggcagc    60
cgctggattg ttattactcg cggcccagc                                     89

<210> SEQ ID NO 38
<211> LENGTH: 88
<212> TYPE: DNA
<213> ORGANISM: Artificial sequence
<220> FEATURE:
<223> OTHER INFORMATION: linker 3'RBS/35-inf -continued

<400> SEQUENCE: 38
gggccgcgag taataacaat ccagcggctg ccgtaggcaa taggtatttc atatggactt    60
ctgtttcctg tttattaaca ctctccgc    88

<210> SEQ ID NO 39
<211> LENGTH: 40
<212> TYPE: DNA
<213> ORGANISM: Artificial sequence
<220> FEATURE:
<223> OTHER INFORMATION: primer 3' CH1y1-STOP

<400> SEQUENCE: 39
catgcagtcc caagcttaac aagatttggg ctcaactttc    40

<210> SEQ ID NO 40
<211> LENGTH: 39
<212> TYPE: DNA
<213> ORGANISM: Artificial sequence
<220> FEATURE:
<223> OTHER INFORMATION: primer 3' CH1Hy1-STOP

<400> SEQUENCE: 40
catgcagtcc caagcttatg ggcacggtgg gcatgtgtg    39

<210> SEQ ID NO 41
<211> LENGTH: 40
<212> TYPE: DNA
<213> ORGANISM: Artificial sequence
<220> FEATURE:
<223> OTHER INFORMATION: primer 3' HINDIII/H-CH2-CH3

<400> SEQUENCE: 41
ccgccaaaac agccaagctt atttacccgg agacagggag    40

<210> SEQ ID NO 42
<211> LENGTH: 50
<212> TYPE: DNA
<213> ORGANISM: Artificial sequence
<220> FEATURE:
<223> OTHER INFORMATION: primer 5' BstE2/H-CH2-CH3

<400> SEQUENCE: 42
ccggccatgg cccaggtcac cgtctcctca gacaaaactc acacatgccc    50

<210> SEQ ID NO 43
<211> LENGTH: 41
<212> TYPE: DNA
<213> ORGANISM: Artificial sequence
<220> FEATURE:
<223> OTHER INFORMATION: primer 3'Not/H-CH2-CH3

<400> SEQUENCE: 43
aagcttaatc tagagcggcc gctttacccg gagacaggga g    41

<210> SEQ ID NO 44
<211> LENGTH: 50
<212> TYPE: DNA
<213> ORGANISM: Artificial sequence
<220> FEATURE:
<223> OTHER INFORMATION: primer 5' BstE2/H-CH2-CH3

<400> SEQUENCE: 44
ccggccatgg cccaggtcac cgtctcctca gacaaaactc acacatgccc    50

```
<210> SEQ ID NO 45
<211> LENGTH: 40
<212> TYPE: DNA
<213> ORGANISM: Artificial sequence
<220> FEATURE:
<223> OTHER INFORMATION: primer 3'HindIII/H-CH2-CH3

<400> SEQUENCE: 45
ccgccaaaac agccaagctt atttacccgg agacagggag                          40

<210> SEQ ID NO 46
<211> LENGTH: 95
<212> TYPE: DNA
<213> ORGANISM: Artificial sequence
<220> FEATURE:
<223> OTHER INFORMATION: primer 5' EcoRl-PelB55-PelBPHen

<400> SEQUENCE: 46
cgacaccgga attccatatg aaatacctat taccaacagc agcagctggg ttattattgc    60
tcgctgcgca gccggccatg gccgaggtgc agctg                              95

<210> SEQ ID NO 47
<211> LENGTH: 57
<212> TYPE: DNA
<213> ORGANISM: Artificial sequence
<220> FEATURE:
<223> OTHER INFORMATION: primer 5'VH1-Sfi

<400> SEQUENCE: 47
catgccatga ctcgcggccc agccggccat ggcccaggtg cagctggtgc agtctgg       57

<210> SEQ ID NO 48
<211> LENGTH: 57
<212> TYPE: DNA
<213> ORGANISM: Artificial sequence
<220> FEATURE:
<223> OTHER INFORMATION: primer 5'VH2-Sfi

<400> SEQUENCE: 48
catgccatga ctcgcggccc agccggccat ggcccaggtc accttgaagg agtctgg       57

<210> SEQ ID NO 49
<211> LENGTH: 57
<212> TYPE: DNA
<213> ORGANISM: Artificial sequence
<220> FEATURE:
<223> OTHER INFORMATION: primer 5'VH3-Sfi

<400> SEQUENCE: 49
catgccatga ctcgcggccc agccggccat ggccgaggtg cagctggtgg agtctgg       57

<210> SEQ ID NO 50
<211> LENGTH: 57
<212> TYPE: DNA
<213> ORGANISM: Artificial sequence
<220> FEATURE:
<223> OTHER INFORMATION: primer 5'VH4-Sfi

<400> SEQUENCE: 50
catgccatga ctcgcggccc agccggccat ggcccaggtg cagctgcagg agtcggg       57

<210> SEQ ID NO 51
<211> LENGTH: 35
<212> TYPE: DNA
<213> ORGANISM: Artificial sequence
<220> FEATURE:
```

<223> OTHER INFORMATION: primer 3' BstE2/KpnI

<400> SEQUENCE: 51
ggtgcagcca cggtacctga ggagacggtg acctg                                      35

<210> SEQ ID NO 52
<211> LENGTH: 35
<212> TYPE: DNA
<213> ORGANISM: Artificial sequence
<220> FEATURE:
<223> OTHER INFORMATION: primer 3' BstE2/NheI

<400> SEQUENCE: 52
gggcccttgg tgctagctga ggagacggtg acctg                                      35

<210> SEQ ID NO 53
<211> LENGTH: 43
<212> TYPE: DNA
<213> ORGANISM: Artificial sequence
<220> FEATURE:
<223> OTHER INFORMATION: primer 5' VH1a

<400> SEQUENCE: 53
cggcccagcc ggccatggcc caggtgcagc tggtgcagtc tgg                             43

<210> SEQ ID NO 54
<211> LENGTH: 45
<212> TYPE: DNA
<213> ORGANISM: Artificial sequence
<220> FEATURE:
<223> OTHER INFORMATION: primer 5' VH1b

<400> SEQUENCE: 54
cggcccagcc ggccatggcc caggtctcag ctgtgtgcag tctgg                           45

<210> SEQ ID NO 55
<211> LENGTH: 44
<212> TYPE: DNA
<213> ORGANISM: Artificial sequence
<220> FEATURE:
<223> OTHER INFORMATION: primer 5'VH1c

<400> SEQUENCE: 55
cggcccagcc ggccatggcc cgaggtccag ctggtacagt ctgg                            44

<210> SEQ ID NO 56
<211> LENGTH: 44
<212> TYPE: DNA
<213> ORGANISM: Artificial sequence
<220> FEATURE:
<223> OTHER INFORMATION: primer 5'VH1d

<400> SEQUENCE: 56
cggcccagcc ggccatggcc cagaatgcag ctggtgcagt ctgg                            44

<210> SEQ ID NO 57
<211> LENGTH: 43
<212> TYPE: DNA
<213> ORGANISM: Artificial sequence
<220> FEATURE:
<223> OTHER INFORMATION: primer 5'VH2a

<400> SEQUENCE: 57
cggcccagcc ggccatggcc caggtcacct tgaaggagtc tgg                             43

```
<210> SEQ ID NO 58
<211> LENGTH: 43
<212> TYPE: DNA
<213> ORGANISM: Artificial sequence
<220> FEATURE:
<223> OTHER INFORMATION: primer 5' VH2b

<400> SEQUENCE: 58
cggcccagcc ggccatggcc cagatcacct tgaaggagtc tgg                    43

<210> SEQ ID NO 59
<211> LENGTH: 43
<212> TYPE: DNA
<213> ORGANISM: Artificial sequence
<220> FEATURE:
<223> OTHER INFORMATION: primer 5'VH3a

<400> SEQUENCE: 59
cggcccagcc ggccatggcc gaggtgcagc tggtggagtc tgg                    43

<210> SEQ ID NO 60
<211> LENGTH: 43
<212> TYPE: DNA
<213> ORGANISM: Artificial sequence
<220> FEATURE:
<223> OTHER INFORMATION: primer 5'VH3b

<400> SEQUENCE: 60
cggcccagcc ggccatggcc gaagtgcagc tggtggagtc tgg                    43

<210> SEQ ID NO 61
<211> LENGTH: 43
<212> TYPE: DNA
<213> ORGANISM: Artificial sequence
<220> FEATURE:
<223> OTHER INFORMATION: primer 5'VH3c

<400> SEQUENCE: 61
cggcccagcc ggccatggcc caggtgcagc tggtggagtc tgg                    43

<210> SEQ ID NO 62
<211> LENGTH: 46
<212> TYPE: DNA
<213> ORGANISM: Artificial sequence
<220> FEATURE:
<223> OTHER INFORMATION: primer 5'VH3d

<400> SEQUENCE: 62
cggcccagcc ggccatggcc gaggtgcagc tggtggagat ctcgcg                 46

<210> SEQ ID NO 63
<211> LENGTH: 43
<212> TYPE: DNA
<213> ORGANISM: Artificial sequence
<220> FEATURE:
<223> OTHER INFORMATION: primer 5' VH4a

<400> SEQUENCE: 63
cggcccagcc ggccatggcc caggtgcagc tgcaggagtc ggg                    43

<210> SEQ ID NO 64
<211> LENGTH: 44
<212> TYPE: DNA
<213> ORGANISM: Artificial sequence
<220> FEATURE:
<223> OTHER INFORMATION: primer 5'VH4b
```

```
<400> SEQUENCE: 64
cggcccagcc ggccatggcc cagctgcagc tgcaggagtc gcgg        44

<210> SEQ ID NO 65
<211> LENGTH: 43
<212> TYPE: DNA
<213> ORGANISM: Artificial sequence
<220> FEATURE:
<223> OTHER INFORMATION: primer 5' VH4c

<400> SEQUENCE: 65
cggcccagcc ggccatggcc caggtgcagc tacagcagtg ggg         43

<210> SEQ ID NO 66
<211> LENGTH: 44
<212> TYPE: DNA
<213> ORGANISM: Artificial sequence
<220> FEATURE:
<223> OTHER INFORMATION: primer 5'VH5a

<400> SEQUENCE: 66
cggcccagcc ggccatggcc gagagtgcag ctggtgcagt ctgg        44

<210> SEQ ID NO 67
<211> LENGTH: 43
<212> TYPE: DNA
<213> ORGANISM: Artificial sequence
<220> FEATURE:
<223> OTHER INFORMATION: primer 5'VH6a

<400> SEQUENCE: 67
cggcccagcc ggccatggcc caggtacagc tgcagcagtc agg         43

<210> SEQ ID NO 68
<211> LENGTH: 43
<212> TYPE: DNA
<213> ORGANISM: Artificial sequence
<220> FEATURE:
<223> OTHER INFORMATION: primer 5'VH7a

<400> SEQUENCE: 68
cggcccagcc ggccatggcc caggtgcagc tggtgcaatc tgg         43

<210> SEQ ID NO 69
<211> LENGTH: 38
<212> TYPE: DNA
<213> ORGANISM: Artificial sequence
<220> FEATURE:
<223> OTHER INFORMATION: primer 3' JH1-4-5

<400> SEQUENCE: 69
gtctagacgt cccccgggg aggagacggt gaccaggg               38

<210> SEQ ID NO 70
<211> LENGTH: 38
<212> TYPE: DNA
<213> ORGANISM: Artificial sequence
<220> FEATURE:
<223> OTHER INFORMATION: primer 3'JH2

<400> SEQUENCE: 70
gtctagacgt cccccgggg aggagacagt gaccaggg               38

<210> SEQ ID NO 71
<211> LENGTH: 38
```

-continued

```
<212> TYPE: DNA
<213> ORGANISM: Artificial sequence
<220> FEATURE:
<223> OTHER INFORMATION: primer 3'JH3

<400> SEQUENCE: 71
gtctagacgt ccccccgggg aagagacggt gaccattg                               38

<210> SEQ ID NO 72
<211> LENGTH: 38
<212> TYPE: DNA
<213> ORGANISM: Artificial sequence
<220> FEATURE:
<223> OTHER INFORMATION: primer 3'JH6

<400> SEQUENCE: 72
gtctagacgt ccccccgggg aggagacggt gaccgtgg                               38

<210> SEQ ID NO 73
<211> LENGTH: 126
<212> TYPE: PRT
<213> ORGANISM: Artificial sequence
<220> FEATURE:
<223> OTHER INFORMATION: CD 16 c13 amino acid sequence
<220> FEATURE:
<221> NAME/KEY: MISC_FEATURE
<222> LOCATION: (35)..(37)
<223> OTHER INFORMATION: Unknown amino acid
<220> FEATURE:
<221> NAME/KEY: MISC_FEATURE
<222> LOCATION: (55)..(57)
<223> OTHER INFORMATION: Unknown amino acid
<220> FEATURE:
<221> NAME/KEY: MISC_FEATURE
<222> LOCATION: (109)..(113)
<223> OTHER INFORMATION: Unknown amino acid

<400> SEQUENCE: 73

Glu Val Gln Leu Val Gln Ser Gly Gly Gly Leu Val Gln Pro Gly Gly
1               5                   10                  15

Ser Leu Arg Leu Ser Cys Ser Phe Pro Gly Ser Ile Phe Ser Leu Thr
            20                  25                  30

Met Gly Xaa Xaa Xaa Trp Tyr Arg Gln Ala Pro Gly Lys Glu Arg Glu
        35                  40                  45

Leu Val Thr Ser Ala Thr Xaa Xaa Xaa Pro Gly Gly Asp Thr Asn Tyr
    50                  55                  60

Ala Asp Phe Val Lys Gly Arg Phe Thr Ile Ser Arg Asp Asn Ala Arg
65                  70                  75                  80

Ser Ile Ile Tyr Leu Gln Met Asn Ser Leu Lys Pro Glu Asp Thr Ala
                85                  90                  95

Val Tyr Tyr Cys Tyr Ala Arg Thr Arg Asn Trp Gly Xaa Xaa Xaa Xaa
            100                 105                 110

Xaa Thr Val Trp Gly Gln Gly Thr Gln Val Thr Val Ser Ser
        115                 120                 125

<210> SEQ ID NO 74
<211> LENGTH: 126
<212> TYPE: PRT
<213> ORGANISM: Artificial sequence
<220> FEATURE:
<223> OTHER INFORMATION: CD 16 c21 aminoacid sequence
<220> FEATURE:
<221> NAME/KEY: MISC_FEATURE
<222> LOCATION: (36)..(37)
<223> OTHER INFORMATION: Unknown amino acid
<220> FEATURE:
```

<221> NAME/KEY: MISC_FEATURE
<222> LOCATION: (56)..(57)
<223> OTHER INFORMATION: Unknown amino acid

<400> SEQUENCE: 74

Glu Val Gln Leu Val Gln Ser Gly Gly Glu Leu Val Gln Ala Gly Gly
1               5                   10                  15

Ser Leu Arg Leu Ser Cys Ala Ala Ser Gly Leu Thr Phe Ser Ser Tyr
            20                  25                  30

Asn Met Gly Xaa Xaa Trp Phe Arg Arg Ala Pro Gly Lys Glu Arg Glu
        35                  40                  45

Phe Val Ala Ser Ile Thr Trp Xaa Xaa Ser Gly Arg Asp Thr Phe Tyr
50                  55                  60

Ala Asp Ser Val Lys Gly Arg Phe Thr Ile Ser Arg Asp Asn Ala Lys
65                  70                  75                  80

Asn Thr Val Tyr Leu Gln Met Ser Ser Leu Lys Pro Glu Asp Thr Ala
                85                  90                  95

Val Tyr Tyr Cys Ala Ala Asn Pro Trp Pro Val Ala Ala Pro Arg Ser
            100                 105                 110

Gly Thr Tyr Trp Gly Gln Gly Thr Gln Val Thr Val Ser Ser
        115                 120                 125

<210> SEQ ID NO 75
<211> LENGTH: 126
<212> TYPE: PRT
<213> ORGANISM: Artificial sequence
<220> FEATURE:
<223> OTHER INFORMATION: CD16 c28 aminoacid sequence
<220> FEATURE:
<221> NAME/KEY: MISC_FEATURE
<222> LOCATION: (35)..(37)
<223> OTHER INFORMATION: Unknown amino acid
<220> FEATURE:
<221> NAME/KEY: MISC_FEATURE
<222> LOCATION: (55)..(57)
<223> OTHER INFORMATION: Unknown amino acid
<220> FEATURE:
<221> NAME/KEY: MISC_FEATURE
<222> LOCATION: (113)..(113)
<223> OTHER INFORMATION: Unknown amino acid

<400> SEQUENCE: 75

Glu Val Gln Leu Val Glu Ser Gly Gly Gly Leu Val Gln Pro Gly Glu
1               5                   10                  15

Ser Leu Thr Leu Ser Cys Val Val Ala Gly Ser Ile Phe Ser Phe Ala
            20                  25                  30

Met Ser Xaa Xaa Xaa Trp Tyr Arg Gln Ala Pro Gly Lys Glu Arg Glu
        35                  40                  45

Leu Val Ala Arg Ile Gly Xaa Xaa Xaa Ser Asp Asp Arg Val Thr Tyr
50                  55                  60

Ala Asp Ser Val Lys Gly Arg Phe Thr Ile Ser Arg Asp Asn Ile Lys
65                  70                  75                  80

Arg Thr Ala Gly Leu Gln Met Asn Ser Leu Lys Pro Glu Asp Thr Ala
                85                  90                  95

Val Tyr Tyr Cys Asn Ala Gln Thr Asp Leu Arg Asp Trp Thr Val Arg
            100                 105                 110

Xaa Glu Tyr Trp Gly Gln Gly Thr Gln Val Thr Val Ser Ser
        115                 120                 125

<210> SEQ ID NO 76
<211> LENGTH: 126

<210> SEQ ID NO 76
<211> LENGTH: 126
<212> TYPE: PRT
<213> ORGANISM: Artificial sequence
<220> FEATURE:
<223> OTHER INFORMATION: CD 16 c72 aminoacid sequence
<220> FEATURE:
<221> NAME/KEY: MISC_FEATURE
<222> LOCATION: (35)..(37)
<223> OTHER INFORMATION: Unknown amino acid
<220> FEATURE:
<221> NAME/KEY: MISC_FEATURE
<222> LOCATION: (55)..(57)
<223> OTHER INFORMATION: Unknown amino acid
<220> FEATURE:
<221> NAME/KEY: MISC_FEATURE
<222> LOCATION: (113)..(113)
<223> OTHER INFORMATION: Unknown amino acid

<400> SEQUENCE: 76

Glu Val Gln Leu Val Glu Ser Gly Gly Gly Leu Val Gln Pro Gly Gly
1               5                   10                  15

Ser Leu Thr Leu Ser Cys Val Ala Ala Gly Ser Ile Phe Thr Phe Ala
            20                  25                  30

Met Ser Xaa Xaa Xaa Trp Tyr Arg Gln Ala Pro Arg Lys Glu Arg Glu
        35                  40                  45

Leu Val Ala Arg Ile Gly Xaa Xaa Xaa Thr Asp Glu Thr Met Tyr
50                  55                  60

Lys Asp Ser Val Lys Gly Arg Phe Thr Ile Ser Arg Asp Asn Val Lys
65                  70                  75                  80

Arg Thr Ala Gly Leu Gln Met Asn Asn Leu Lys Pro Glu Asp Thr Ala
                85                  90                  95

Val Tyr Tyr Cys Asn Ala Arg Thr Asp Tyr Arg Asp Trp Thr Val Arg
            100                 105                 110

Xaa Glu Tyr Trp Gly Gln Gly Thr Gln Val Thr Val Ser Ser
        115                 120                 125

<210> SEQ ID NO 77
<211> LENGTH: 126
<212> TYPE: PRT
<213> ORGANISM: Artificial sequence
<220> FEATURE:
<223> OTHER INFORMATION: CEA 3 aminoacid sequence
<220> FEATURE:
<221> NAME/KEY: MISC_FEATURE
<222> LOCATION: (36)..(37)
<223> OTHER INFORMATION: Unknown amino acid
<220> FEATURE:
<221> NAME/KEY: MISC_FEATURE
<222> LOCATION: (56)..(57)
<223> OTHER INFORMATION: Unknown amino acid
<220> FEATURE:
<221> NAME/KEY: MISC_FEATURE
<222> LOCATION: (111)..(113)
<223> OTHER INFORMATION: Unknown amino acid

<400> SEQUENCE: 77

Glu Val Gln Leu Val Glu Ser Gly Gly Gly Leu Val Gln Ala Gly Gly
1               5                   10                  15

Ser Leu Arg Leu Ser Cys Thr Ser Ser Thr Val Thr Phe Thr Pro Tyr
            20                  25                  30

Gln Met Gly Xaa Xaa Trp Tyr Arg Gln Ala Pro Gly Lys Gln Arg Ala
        35                  40                  45

Leu Val Ala Asp Ile Ser Thr Xaa Xaa Gly Gly Ser Arg Thr Asn Tyr
50                  55                  60

Ala Asp Phe Ala Lys Gly Arg Phe Thr Ile Ser Arg Asp Asp Val Lys
65                  70                  75                  80

Asn Thr Val Tyr Leu Gln Met Asn Asn Leu Lys Pro Glu Asp Thr Ala
            85                  90                  95

Val Tyr Tyr Cys Asn Thr Tyr Tyr Ala Met Ile Gly His Ala Xaa Xaa
                100                 105                 110

Xaa Arg Asn Trp Gly Gln Gly Thr Gln Val Thr Val Ser Ser
        115                 120                 125

<210> SEQ ID NO 78
<211> LENGTH: 126
<212> TYPE: PRT
<213> ORGANISM: Artificial sequence
<220> FEATURE:
<223> OTHER INFORMATION: CEA 17 aminoacid sequence
<220> FEATURE:
<221> NAME/KEY: MISC_FEATURE
<222> LOCATION: (36)..(37)
<223> OTHER INFORMATION: Unknown amino acid
<220> FEATURE:
<221> NAME/KEY: MISC_FEATURE
<222> LOCATION: (57)..(57)
<223> OTHER INFORMATION: Unknown amino acid
<220> FEATURE:
<221> NAME/KEY: MISC_FEATURE
<222> LOCATION: (111)..(113)
<223> OTHER INFORMATION: Unknown amino acid

<400> SEQUENCE: 78

Glu Val Gln Leu Val Glu Ser Gly Gly Gly Phe Val Gln Ala Gly Glu
1               5                   10                  15

Ser Leu Thr Leu Ser Cys Thr Ser Ser Thr Leu Thr Phe Thr Pro Tyr
            20                  25                  30

Arg Met Ala Xaa Xaa Trp Tyr Arg Gln Ala Pro Gly Lys Gln Arg Asp
        35                  40                  45

Leu Val Ala Asp Ile Ser Ser Gly Xaa Asp Gly Arg Thr Thr Asn Tyr
    50                  55                  60

Ala Asp Phe Ala Lys Gly Arg Phe Thr Ile Ser Arg Asp Asn Ile Lys
65                  70                  75                  80

Asn Thr Val Phe Leu Arg Met Thr Asn Leu Lys Pro Glu Asp Thr Ala
            85                  90                  95

Val Tyr Tyr Cys Asn Thr Phe Val Ser Phe Val Gly Ile Ala Xaa Xaa
                100                 105                 110

Xaa Arg Ser Trp Gly Gln Gly Thr Gln Val Thr Val Ser Ser
        115                 120                 125

<210> SEQ ID NO 79
<211> LENGTH: 126
<212> TYPE: PRT
<213> ORGANISM: Artificial sequence
<220> FEATURE:
<223> OTHER INFORMATION: CEA 25 aminoacid sequence
<220> FEATURE:
<221> NAME/KEY: MISC_FEATURE
<222> LOCATION: (36)..(37)
<223> OTHER INFORMATION: Unknown amino acid
<220> FEATURE:
<221> NAME/KEY: MISC_FEATURE
<222> LOCATION: (57)..(57)
<223> OTHER INFORMATION: Unknown amino acid
<220> FEATURE:
<221> NAME/KEY: MISC_FEATURE
<222> LOCATION: (111)..(113)
<223> OTHER INFORMATION: Unknown amino acid

<400> SEQUENCE: 79

Glu Val Gln Leu Val Glu Ser Gly Gly Gly Leu Val Gln Ala Gly Asp

```
                1               5                  10                 15
Ser Leu Thr Leu Thr Cys Thr Ser Pro Thr Leu Thr Phe Thr Pro Tyr
                20                  25                 30

Arg Met Gly Xaa Xaa Trp Tyr Arg Gln Ala Pro Gly Lys Gln Arg Asp
            35                  40                  45

Leu Val Ala Asp Ile Ser Gly Gly Xaa Asp Gly Arg Thr Thr Asn Tyr
        50                  55                  60

Ala Asp Phe Ala Lys Gly Arg Phe Thr Ile Ser Arg Asp Asn Val Lys
65                  70                  75                  80

Asn Ala Val Tyr Leu Gln Met Asn Asn Leu Lys Pro Glu Asp Thr Ala
                85                  90                  95

Ile Tyr Tyr Cys Asn Thr Tyr Val Ala Ile Val Gly His Ala Xaa Xaa
                100                 105                 110

Xaa Arg Ser Trp Gly Gln Gly Thr Gln Val Thr Val Ser Ser
            115                 120                 125
```

<210> SEQ ID NO 80
<211> LENGTH: 126
<212> TYPE: PRT
<213> ORGANISM: Artificial sequence
<220> FEATURE:
<223> OTHER INFORMATION: CEA 43 aminoacid sequence
<220> FEATURE:
<221> NAME/KEY: MISC_FEATURE
<222> LOCATION: (36)..(37)
<223> OTHER INFORMATION: Unknown amino acid
<220> FEATURE:
<221> NAME/KEY: MISC_FEATURE
<222> LOCATION: (57)..(57)
<223> OTHER INFORMATION: Unknown amino acid
<220> FEATURE:
<221> NAME/KEY: MISC_FEATURE
<222> LOCATION: (111)..(113)
<223> OTHER INFORMATION: Unknown amino acid

<400> SEQUENCE: 80

```
Gln Val Gln Leu Gln Glu Ser Gly Gly Gly Leu Val Gln Ala Gly Gly
1               5                  10                 15

Ser Leu Thr Leu Ser Cys Thr Ser Ser Thr Leu Thr Phe Thr Pro Tyr
                20                  25                 30

Arg Met Gly Xaa Xaa Trp Tyr Arg Gln Thr Pro Gly Lys Gln Arg Asp
            35                  40                  45

Leu Val Ala Asp Ile Ser Pro Gly Xaa Asp Gly Ser Thr Lys Asn Tyr
        50                  55                  60

Ala Gly Phe Ala Gln Gly Arg Phe Thr Ile Ser Arg Asp Asn Ile Lys
65                  70                  75                  80

Asn Thr Val Tyr Leu Gln Met Asn Asp Leu Lys Pro Glu Asp Thr Ala
                85                  90                  95

Val Tyr Tyr Cys Asn Thr Tyr Val Ala Phe Val Gly Arg Ala Xaa Xaa
                100                 105                 110

Xaa Arg Thr Trp Gly Gln Gly Thr Gln Val Thr Val Thr Ser
            115                 120                 125
```

<210> SEQ ID NO 81
<211> LENGTH: 345
<212> TYPE: DNA
<213> ORGANISM: Artificial sequence
<220> FEATURE:
<223> OTHER INFORMATION: CD16 cl3

<400> SEQUENCE: 81

```
gaggtgcagc tggtgcagtc tgggggaggc ttggtgcagc ctggggggtc tctgagactc    60
tcctgttcat tccctggaag catcttcagt ctcaccatgg gctggtaccg tcaggctcca   120
gggaaggagc gcgagttggt cacaagtgct actcctggtg gtgacacaaa ctatgcagac   180
ttcgtgaagg gccgattcac catctccaga gacaacgcca ggagcatcat atatctacaa   240
atgaatagcc tgaaacctga ggacacggcc gtctattatt gttatgcacg tacgaggaat   300
tggggtacgg tctggggcca ggggacccag gtcaccgtct cctca                   345
```

```
<210> SEQ ID NO 82
<211> LENGTH: 366
<212> TYPE: DNA
<213> ORGANISM: Artificial sequence
<220> FEATURE:
<223> OTHER INFORMATION: CD16 c21

<400> SEQUENCE: 82
gaggtgcagc tggtgcagtc tggggagag ttggtgcagg ctgggggctc tctgagactc     60
tcctgtgcag cctctggcct caccttcagt agctataaca tgggctggtt ccgccgggct   120
ccagggaagg agcgtgagtt tgtagcatct attacctgga gtggtcggga cacattctat   180
gcagactccg tgaagggccg attcaccatc tccagagaca cgccaagaa cactgtttat   240 ctgcaaatga gcagcctgaa acctgaggac acggccgttt attattgtgc tgcaaacccc   300
tggccagtgg cggcgccacg tagtggcacc tactggggcc aagggaccca ggtcaccgtc   360
tcctca                                                             366
```

```
<210> SEQ ID NO 83
<211> LENGTH: 357
<212> TYPE: DNA
<213> ORGANISM: Artificial sequence
<220> FEATURE:
<223> OTHER INFORMATION: anti CD16 nucleotide

<400> SEQUENCE: 83
gaggtgcagc tggtggagtc tgggggaggc ttagtgcagc ctggggagtc tctgacactc     60
tcctgtgtag ttgctggaag catcttcagc ttcgccatga gctggtatcg ccaggctcca   120
ggaaaagagc gcgaattggt cgcacgtatt ggttcggatg atcgggtaac gtacgcagat   180
tccgtgaagg gccgatttac catctccaga gacaacatca gcgcacggc gggcctgcag   240 atgaacagcc tgaaacctga ggacacggcc gtctactact gcaatgccca aacagatttg   300
agggattgga ctgtgcgaga gtactgggc caggggaccc aggtcaccgt ctcctca      357
```

```
<210> SEQ ID NO 84
<211> LENGTH: 357
<212> TYPE: DNA
<213> ORGANISM: Artificial sequence
<220> FEATURE:
<223> OTHER INFORMATION: anti CD16 nucleotide

<400> SEQUENCE: 84
gaggtgcagc tggtggagtc tgggggaggc ttggtgcagc ctggggggtc tctgacactc     60
tcctgtgttg ccgctggaag catcttcacc ttcgccatga gctggtaccg ccaggctcca   120
cgaaaagagc gcgaattggt cgcacgtatt ggtacggatg acgaaacaat gtacaaagac   180
tccgtgaagg gtcgattcac catctccaga gacaacgtca gcgcacggc gggtctgcag   240 atgaacaacc tgaaacccga ggacacggcc gtctactact gcaatgcccg gacagattat   300
agggactgga ctgtccgtga gtactgggc caggggaccc aggtcaccgt ctcctca      357
```

<210> SEQ ID NO 85
<211> LENGTH: 357
<212> TYPE: DNA
<213> ORGANISM: Artificial sequence
<220> FEATURE:
<223> OTHER INFORMATION: VHH anti-cea cea3

<400> SEQUENCE: 85

```
gaggtgcagc tggtggagtc tggggggaggc ttggtgcagg ctgggggctc tctgagactc      60
tcctgtacca gctctacggt taccttcact ccgtatcaaa tgggctggta ccgccaggct     120
ccagggaagc agcgtgcttt ggtcgcagat attagtacgg gtggtagccg cacaaattat     180
gcggatttcg cgaagggccg attcaccatc tccagagacg acgttaagaa cacggtgtat     240
ctgcaaatga acaacctgaa acctgaggac acggccgtct actactgtaa cacctactac     300
gcgatgatag ggcatgcgcg taattggggc caggggaccc aggtcactgt ctcctca        357
```

<210> SEQ ID NO 86
<211> LENGTH: 360
<212> TYPE: DNA
<213> ORGANISM: Artificial sequence
<220> FEATURE:
<223> OTHER INFORMATION: CEA 17

<400> SEQUENCE: 86

```
gaggtgcagc tggtggagtc tggggggaggc ttcgtgcagg cggggggaatc tctgacgctc     60 tcctgtacaa gttctacact gaccttcact ccgtatcgca tggcctggta ccgccaggct    120
ccagggaagc agcgtgattt agtcgcggat attagtagtg gtgatggtag gaccacaaac    180
tatgcggact cgcgaaggg ccgattcacc atctccagag acaacatcaa gaacacggtc     240
tttctgcgaa tgactaacct gaaacctgag gacacggccg tctactactg taacaccttc    300
gtttcgtttg tggggattgc gcgttcttgg ggccagggga cccaggtcac tgtctcctca    360
```

<210> SEQ ID NO 87
<211> LENGTH: 360
<212> TYPE: DNA
<213> ORGANISM: Artificial sequence
<220> FEATURE:
<223> OTHER INFORMATION: CEA 25

<400> SEQUENCE: 87

```
gaggtgcagc tggtggagtc tggggggaggc ttggtgcagg cgggggactc tctgacactg      60
acctgtacaa gccctacact taccttcact ccgtatcgca tggctggta ccgccaagct     120 ccagggaagc agcgtgattt ggtcgcagat attagtggtg gtgatggtcg taccacaaac    180
tatgcagact cgcgaaggg ccgattcacc atctccagag acaacgtcaa gaacgcggtc     240
tatctgcaaa tgaacaacct gaaacctgaa gacacggcca tttattactg taacacctac    300
gtcgcgattg tgggccatgc gcgttcctgg ggccagggga cccaggtcac cgtctcctca    360
```

<210> SEQ ID NO 88
<211> LENGTH: 360
<212> TYPE: DNA
<213> ORGANISM: Artificial sequence
<220> FEATURE:
<223> OTHER INFORMATION: nucleotide CEA 43

<400> SEQUENCE: 88

```
caggtgcagc tgcaggagtc tggggggaggc ttggtgcagg cgggggggctc tctgacactc     60
```

| | |
|---|---|
| tcctgcacaa gttctacact taccttcact ccgtatcgca tgggctggta ccgccagact | 120 |
| ccagggaagc agcgtgattt ggtcgcggac attagtcctg gtgatggtag taccaaaaat | 180 |
| tatgcaggct tcgcgcaggg ccgattcacc atctccagag acaacatcaa gaacacggtg | 240 |
| tatctgcaaa tgaacgacct gaaacctgag gacacggccg tctattactg caacacctac | 300 |
| gtcgcgtttg tggggcgtgc gcgtacttgg ggccagggga cccaggtcac tgtcacctca | 360 |

<210> SEQ ID NO 89
<211> LENGTH: 6715
<212> TYPE: DNA
<213> ORGANISM: Artificial sequence
<220> FEATURE:
<223> OTHER INFORMATION: plasmid p55PhoA5HisGS/N-

<400> SEQUENCE: 89

| | |
|---|---|
| ttgtttattt ttctaaatac attcaaatat gtatccgctc atgagacaat aaccctgata | 60 |
| aatgcttcaa taatattgaa aaaggaagag tatgagtatt caacatttcc gtgtcgccct | 120 |
| tattcccttt tttgcggcat tttgccttcc tgttttttgct cacccagaaa cgctggtgaa | 180 |
| agtaaaagat gctgaagatc agttgggtgc acgagtgggt tacatcgaac tggatctcaa | 240 |
| cagcggtaag atccttgaga gttttcgccc cgaagaacgt tttccaatga tgagcacttt | 300 |
| taaagttctg ctatgtggcg cggtattatc ccgtgttgac gccgggcaag agcaactcgg | 360 |
| tcgccgcata cactattctc agaatgactt ggttgagtac tcaccagtca cagaaaagca | 420 |
| tcttacggat ggcatgacag taagagaatt atgcagtgct gccataacca tgagtgataa | 480 |
| cactgcggcc aacttacttc tgacaacgat cggaggaccg aaggagctaa ccgcttttttt | 540 |
| gcacaacatg ggggatcatg taactcgcct tgatcgttgg gaaccggagc tgaatgaagc | 600 |
| cataccaaac gacgagcgtg acaccacgat gcctgtagca atggcaacaa cgttgcgcaa | 660 |
| actattaact ggcgaactac ttactctagc ttcccggcaa caattaatag actggatgga | 720 |
| ggcggataaa gttgcaggac cacttctgcg ctcggccctt ccggctggct ggtttattgc | 780 |
| tgataaatct ggagccggtg agcgtgggtc tcgcggtatc attgcagcac tggggccaga | 840 |
| tggtaagccc tcccgtatcg tagttatcta cacgacgggg agtcaggcaa ctatggatga | 900 |
| acgaaataga cagatcgctg agataggtgc ctcactgatt aagcattggt aactgtcaga | 960 |
| ccaagtttac tcatatatac tttagattga tttaaaactt catttttaat ttaaaaggat | 1020 |
| ctaggtgaag atcctttttg ataatctcat gaccaaaatc ccttaacgtg agttttcgtt | 1080 |
| ccactgagcg tcagaccccg tagaaaagat caaaggatct tcttgagatc ctttttttct | 1140 |
| gcgcgtaatc tgctgcttgc aaacaaaaaa accaccgcta ccagcggtgg tttgtttgcc | 1200 |
| ggatcaagag ctaccaactc tttttccgaa ggtaactggc ttcagcagag cgcagatacc | 1260 |
| aaatactgtc cttctagtgt agccgtagtt aggccaccac ttcaagaact ctgtagcacc | 1320 |
| gcctacatac ctcgctctgc taatcctgtt accagtggct gctgccagtg gcgataagtc | 1380 |
| gtgtcttacc gggttggact caagacgata gttaccggat aaggcgcagc ggtcgggctg | 1440 |
| aacggggggt tcgtgcacac agcccagctt ggagcgaacg acctacaccg aactgagata | 1500 |
| cctacagcgt gagcattgag aaagcgccac gcttcccgaa gggagaaagg cggacaggta | 1560 |
| tccggtaagc ggcagggtcg gaacaggaga gcgcacgagg gagcttccag ggggaaacgc | 1620 |
| ctggtatctt tatagtcctg tcgggtttcg ccacctctga cttgagcgtc gatttttgtg | 1680 |
| atgctcgtca ggggggcgga gcctatggaa aaacgccagc aacgcggcct ttttacggtt | 1740 |
| cctggccttt tgctggcctt ttgctcacat gttctttcct gcgttatccc ctgattctgt | 1800 |

```
ggataaccgt attaccgcct ttgagtgagc tgataccgct cgccgcagcc gaacgaccga   1860
gcgcagcgag tcagtgagcg aggaagcgga agagcgcctg atgcggtatt ttctccttac   1920
gcatctgtgc ggtatttcac accgcatata tggtgcactc tcagtacaat ctgctctgat   1980
gccgcatagt taagccagta tacactccgc tatcgctacg tgactgggtc atggctgcgc   2040
cccgacaccc gccaacaccc gctgacgcgc cctgacgggc ttgtctgctc ccggcatccg   2100
cttacagaca agctgtgacc gtctccggga gctgcatgtg tcagaggttt tcaccgtcat   2160
caccgaaacg cgcgaggcag ctgcggtaaa gctcatcagc gtggtcgtga agcgattcac   2220
agatgtctgc ctgttcatcc gcgtccagct cgttgagttt ctccagaagc gttaatgtct   2280
ggcttctgat aaagcgggcc atgttaaggg cggttttttc ctgtttggtc acttgatgcc   2340
tccgtgtaag ggggaatttc tgttcatggg ggtaatgata ccgatgaaac gagagaggat   2400
gctcacgata cgggttactg atgatgaaca tgcccggtta ctggaacgtt gtgagggtaa   2460
acaactggcg gtatggatgc ggcgggacca gagaaaaatc actcagggtc aatgccagcg   2520
cttcgttaat acagatgtag gtgttccaca gggtagccag cagcatcctg cgatgcagat   2580
ccggaacata atggtgcagg cgctgactt ccgcgtttcc agactttacg aaacacggaa   2640
accgaagacc attcatgttg ttgctcaggt cgcagacgtt ttgcagcagc agtcgcttca   2700
cgttcgctcg cgtatcggtg attcattctg ctaaccagta aggcaacccc gccagcctag   2760
ccgggtcctc aacgacagga gcacgatcat gcgcacccgt ggccaggacc caacgctgcc   2820
cgagatgcgc cgcgtgcggc tgctggagat ggcggacgcg atggatatgt tctgccaagg   2880
gttggtttgc gcattcacag ttctccgcaa gaattgattg gctccaattc ttggagtggt   2940
gaatccgtta gcgaggtgcc gccggcttcc attcaggtcg aggtggcccg gctccatgca   3000
ccgcgacgca acgcggggag gcagacaagg tatagggcgg cgcctacaat ccatgccaac   3060
ccgttccatg tgctcgccga ggcggcataa atcgccgtga cgatcagcgg tccagtgatc   3120
gaagttaggc tggtaagagc cgcgagcgat ccttgaagct gtccctgatg gtcgtcatct   3180
acctgcctgg acagcatggc ctgcaacgcg ggcatcccga tgccgccgga agcgagaaga   3240
atcataatgg ggaaggccat ccagcctcgc gtcgcgaacg ccagcaagac gtagcccagc   3300
gcgtcggcca gcttgcaatt cgcgctaact tacattaatt gcgttgcgct cactgcccgc   3360
tttccagtcg ggaaacctgt cgtgccagct gcattaatga atcggccaac gcgcggggag   3420
aggcggtttg cgtattgggc gccagggtgg ttttcttttt caccagtgag acgggcaaca   3480
gctgattgcc cttcaccgcc tggccctgag agagttgcag caagcggtcc acgctggttt   3540
gccccagcag gcgaaaatcc tgtttgatgg tggttgacgg cgggatataa catgagctgt   3600
cttcggtatc gtcgtatccc actaccgaga tatccgcacc aacgcgcagc ccggactcgg   3660
taatggcgcg cattgcgccc agcgccatct gatcgttggc aaccagcatc gcagtgggaa   3720
cgatgccctc attcagcatt tgcatggttt gttgaaaacc ggacatggca ctccagtcgc   3780
cttcccgttc cgctatcggc tgaatttgat tgcgagtgag atatttatgc cagccagcca   3840
gacgcagacg cgccgagaca gaacttaatg ggcccgctaa cagcgcgatt tgctggtgac   3900
ccaatgcgac cagatgctcc acgcccagtc gcgtaccgtc ttcatgggag aaaataatac   3960
tgttgatggg tgtctggtca gagacatcaa gaaataacgc cggaacatta gtgcaggcag   4020
cttccacagc aatggcatcc tggtcatcca gcggatagtt aatgatcagc ccactgacgc   4080
gttgcgcgag aagattgtgc accgccgctt tacaggcttc gacgccgctt cgttctacca   4140
```

```
tcgacaccac cacgctggca cccagttgat cggcgcgaga tttaatcgcc gcgacaattt      4200
gcgacggcgc gtgcagggcc agactggagg tggcaacgcc aatcagcaac gactgtttgc      4260
ccgccagttg ttgtgccacg cggttgggaa tgtaattcag ctccgccatc gccgcttcca      4320
cttttttccc g cgttttcgca gaaacgtggc tggcctggtt caccacgcgg gaaacggtct     4380
gataagagac accggcatac tctgcgacat cgtataacgt tactggtttc acattcacca      4440
ccctgaattg actctcttcc gggcgctatc atgccatacc gcgaaaggtt ttgcgccatt      4500
cgatggtgtc aacgtaaatg catgccgctt cgccttcgcg cgcgaattgc aagctgatcc      4560
ggagcttatc gactgcacgg tgcaccaatg cttctggcgt caggcagcca tcggaagctg      4620
tggtatggct gtgcaggtcg taaatcactg cataattcgt gtcgctcaag gcgcactccc      4680
gttctggata tgttttttg cgccgacatc ataacggttc tggcaaatat tctgaaatga      4740
gctgttgaca attaatcatc ggctcgtata atgtgtggaa ttgtgagcgg ataacaattt      4800
cacacaggaa acagaattcc atatgaaata cctattacca acagcagcag ctgggttatt      4860
attgctcgct gcgcagccgg ccatggcggc cgatcctcga gagctcccgg gctgcagccc      4920
tgttctggaa aaccgggctg ctcagggcga tattactgca cccggcggtg ctcgccgttt      4980
aacgggtgat cagactgccg ctctgcgtga ttctcttagc gataaacctg caaaaaatat      5040
tattttgctg attggcgatg ggatggggga ctcggaaatt actgccgcac gtaattatgc      5100
cgaaggtgcg ggcggctttt ttaaaggtat agatgcctta ccgcttaccg ggcaatacac      5160
tcactatgcg ctgaataaaa aaaccggcaa accggactac gtcaccgact cggctgcatc      5220
agcaaccgcc tggtcaaccg gtgtcaaaac ctataacggc gcgctgggcg tcgatattca      5280
cgaaaaagat cacccaacga ttctggaaat ggcaaaagcc gcaggtctgg cgaccggtaa      5340
cgtttctacc gcagagttgc aggatgccac gcccgctgcg ctggtggcac atgtgacctc      5400
gcgcaaatgc tacggtccga gcgcgaccag tgaaaaatgt ccgggtaacg ctctggaaaa      5460
aggcggaaaa ggatcgatta ccgaacagct gcttaacgct cgtgccgacg ttacgcttgg      5520
cggcggcgca aaaaccttg ctgaaacggc aaccgctggt gaatggcagg gaaaaacgct      5580
gcgtgaacag gcacaggcgc gtggttatca gttggtgagc gatgctgcct cactgaattc      5640
ggtgacggaa gcgaatcagc aaaaacccct gcttggcctg tttgctgacg gcaatatgcc      5700
agtgcgctgg ctaggaccga agcaacgta ccacggcaat atcgataagc ccgcagtcac      5760
ctgtacgcca aatccgcaac gtaatgacag tgtaccaacc ctggcgcaga tgaccgacaa      5820
agccattgaa ttgttgagta aaaatgagaa aggcttttc ctgcaagttg aaggtgcgtc      5880
aatcgataaa caggatcatg ctgcgaatcc ttgtgggcaa attggcgaga cggtcgatct      5940
cgatgaagcc gtacaacggg cgctggaatt cgctaaaaag gagggtaaca cgctggtcat      6000
agtcaccgct gatcacgccc acgccagcca gattgttgcg ccggatacca aagctccggg      6060
cctcacccag gcgctaaata ccaaagatgg cgcagtgatg gtgatgagtt acggaactc      6120 cgaagaggat tcacaagaac ataccggcag tcagttgcgt attgcggcgt atggcccgca      6180
tgccgccaat gttgttggac tgaccgacca gaccgatctc ttctacacca tgaaagccgc      6240
tctggggctg aaacatcatc atcaccatca cgggagctaa taagcttctg ttttggcgga      6300
tgagagaaga ttttcagcct gatacagatt aaatcagaac gcagaagcgg tctgataaaa      6360
cagaatttgc ctggcggcag tagcgcggtg gtcccacctg accccatgcc gaactcagaa      6420
gtgaaacgcc gtagcgccga tggtagtgtg gggtctcccc atgcgagagt agggaactgc      6480
caggcatcaa ataaaacgaa aggctcagtc gaaagactgg gcctttcgtt ttatctgttg      6540
```

```
tttgtcggtg aacgctctcc tgagtaggac aaatccgccg ggagcggatt tgaacgttgc    6600
gaagcaacgg cccggaggac cctggcgggc aggacgcccg ccataaactg ccaggcatca    6660
aattaagcag aaggccatcc tgacggatgg ccttttttgcg tttctacaaa ctctt        6715
```

<210> SEQ ID NO 90
<211> LENGTH: 6715
<212> TYPE: DNA
<213> ORGANISM: Artificial sequence
<220> FEATURE:
<223> OTHER INFORMATION: plasmid p55/PhoA6HisGS-/NAB-

<400> SEQUENCE: 90

```
ttgtttattt ttctaaatac attcaaatat gtatccgctc atgagacaat aaccctgata      60
aatgcttcaa taatattgaa aaaggaagag tatgagtatt caacatttcc gtgtcgccct     120
tattcccttt tttgcggcat tttgccttcc tgttttttgct cacccagaaa cgctggtgaa    180
agtaaaagat gctgaagatc agttgggtgc acgagtgggt tacatcgaac tggatctcaa    240
cagcggtaag atccttgaga gttttcgccc cgaagaacgt tttccaatga tgagcacttt    300
taaagttctg ctatgtggcg cggtattatc ccgtgttgac gccgggcaag agcaactcgg    360
tcgccgcata cactattctc agaatgactt ggttgagtac tcaccagtca cagaaaagca    420
tcttacggat ggcatgacag taagagaatt atgcagtgct gccataacca tgagtgataa    480
cactgcggcc aacttacttc tgacaacgat cggaggaccg aaggagctaa ccgcttttttt   540 gcacaacatg ggggatcatg taactcgcct tgatcgttgg gaaccggagc tgaatgaagc    600
cataccaaac gacgagcgtg acaccacgat gcctgtagca atggcaacaa cgttgcgcaa    660
actattaact ggcgaactac ttactctagc ttcccggcaa caattaatag actggatgga    720
ggcggataaa gttgcaggac cacttctgcg ctcggccctt ccggctggct ggtttattgc    780
tgataaatct ggagccggtg agcgtgggtc tcgcggtatc attgcagcac tggggccaga    840
tggtaagccc tcccgtatcg tagttatcta cacgacgggg agtcaggcaa ctatggatga    900
acgaaataga cagatcgctg agataggtgc ctcactgatt aagcattggt aactgtcaga    960
ccaagtttac tcatatatac tttagattga tttaaaactt cattttttaat ttaaaaggat   1020 ctaggtgaag atcctttttg ataatctcat gaccaaaatc ccttaacgtg agttttcgtt    1080
ccactgagcg tcagaccccg tagaaaagat caaaggatct tcttgagatc ctttttttct    1140
gcgcgtaatc tgctgcttgc aaacaaaaaa accaccgcta ccagcggtgg tttgtttgcc    1200
ggatcaagag ctaccaactc tttttccgaa ggtaactggc ttcagcagag cgcagatacc    1260
aaatactgtc cttctagtgt agccgtagtt aggccaccac ttcaagaact ctgtagcacc    1320
gcctacatac ctcgctctgc taatcctgtt accagtggct gctgccagtg gcgataagtc    1380
gtgtcttacc gggttggact caagacgata gttaccggat aaggcgcagc ggtcgggctg    1440
aacggggggt tcgtgcacac agcccagctt ggagcgaacg acctacaccg aactgagata    1500
cctacagcgt gagcattgag aaagcgccac gcttcccgaa gggagaaagg cggacaggta    1560
tccggtaagc ggcagggtcg gaacaggaga gcgcacgagg gagcttccag ggggaaacgc    1620
ctggtatctt tatagtcctg tcgggtttcg ccacctctga cttgagcgtc gatttttgtg    1680
atgctcgtca ggggggcgga gcctatggaa aaacgccagc aacgcggcct ttttacggtt    1740
cctggccttt tgctggcctt ttgctcacat gttctttcct gcgttatccc ctgattctgt    1800
ggataaccgt attaccgcct ttgagtgagc tgataccgct cgccgcagcc gaacgaccga    1860
```

-continued

```
gcgcagcgag tcagtgagcg aggaagcgga agagcgcctg atgcggtatt ttctccttac    1920
gcatctgtgc ggtatttcac accgcatata tggtgcactc tcagtacaat ctgctctgat    1980
gccgcatagt taagccagta tacactccgc tatcgctacg tgactgggtc atggctgcgc    2040
cccgacaccc gccaacaccc gctgacgcgc cctgacgggc ttgtctgctc ccggcatccg    2100
cttacagaca agctgtgacc gtctccggga gctgcatgtg tcagaggttt tcaccgtcat    2160
caccgaaacg cgcgaggcag ctgcggtaaa gctcatcagc gtggtcgtga agcgattcac    2220
agatgtctgc ctgttcatcc gcgtccagct cgttgagttt ctccagaagc gttaatgtct    2280
ggcttctgat aaagcgggcc atgttaaggg cggttttttc ctgtttggtc acttgatgcc    2340
tccgtgtaag ggggaatttc tgttcatggg ggtaatgata ccgatgaaac gagagaggat    2400
gctcacgata cggttactg atgatgaaca tgcccggtta ctggaacgtt gtgagggtaa     2460
acaactggcg gtatggatgc ggcgggacca gagaaaaatc actcagggtc aatgccagcg    2520
cttcgttaat acagatgtag gtgttccaca gggtagccag cagcatcctg cgatgcagat    2580
ccggaacata atggtgcagg cgctgacttc cgcgtttcc agactttacg aaacacggaa     2640
accgaagacc attcatgttg ttgctcaggt cgcagacgtt ttgcagcagc agtcgcttca    2700
cgttcgctcg cgtatcggtg attcattctg ctaaccagta aggcaacccc gccagcctag    2760
ccgggtcctc aacgacagga gcacgatcat gcgcacccgt ggccaggacc caacgctgcc    2820
cgagatgcgc cgcgtgcggc tgctggagat ggcggacgcg atggatatgt tctgccaagg    2880 gttggttttgc gcattcacag ttctccgcaa gaattgattg ctccaattc ttggagtggt    2940 gaatccgtta gcgaggtgcc gccggcttcc attcaggtcg aggtgcccg gctccatgca     3000 ccgcgacgca acgcggggag gcagacaagg tatagggcgg cgcctacaat ccatgccaac    3060
ccgttccatg tgctcgccga ggcggcataa atcgccgtga cgatcagcgg tccagtgatc    3120
gaagttaggc tggtaagagc cgcgagcgat ccttgaagct gtccctgatg gtcgtcatct    3180
acctgcctgg acagcatggc ctgcaacgcg ggcatcccga tgccgccgga agcgagaaga    3240
atcataatgg ggaaggccat ccagcctcgc gtcgcgaacg ccagcaagac gtagcccagc    3300
gcgtcggcca gcttgcaatt cgcgctaact tacattaatt gcgttgcgct cactgcccgc    3360
tttccagtcg ggaaacctgt cgtgccagct gcattaatga atcggccaac gcgcggggag    3420
aggcggtttg cgtattgggc gccagggtgg ttttctttt caccagtgag acgggcaaca    3480
gctgattgcc cttcaccgcc tggccctgag agagttgcag caagcggtcc acgctggttt    3540
gccccagcag gcgaaaatcc tgtttgatgg tggttgacgg cgggatataa catgagctgt    3600
cttcggtatc gtcgtatccc actaccgaga tatccgcacc aacgcgcagc ccggactcgg    3660
taatggcgcg cattgcgccc agcgccatct gatcgttggc aaccagcatc gcagtgggaa    3720
cgatgccctc attcagcatt tgcatggttt gttgaaaacc ggacatggca ctccagtcgc    3780
cttcccgttc cgctatcggc tgaatttgat tgcgagtgag atatttatgc cagccagcca    3840
gacgcagacg cgccgagaca gaacttaatg gtcccgctaa cagcgcgatt tgctgatgac    3900
ccaatgcgac cagatgctcc acgcccagtc gcgtaccgtc ttcatgggag aaaataatac    3960
tgttgatggg tgtctggtca gagacatcaa gaaataacgc cggaacatta gtgcaggcag    4020
cttccacagc aatggcatcc tggtcatcca gcggatagtt aatgatcagc ccactgacgc    4080
gttgcgcgag aagattgtgc accgccgctt tacaggcttc gacgccgctt cgttctacca    4140
tcgacaccac cacgctggca cccagttgat cggcgcgaga tttaatcgcc gcgacaattt    4200
gcgacggcgc gtgcagggcc agactggagg tggcaacgcc aatcagcaac gactgtttgc    4260
```

```
ccgccagttg ttgtgccacg cggttgggaa tgtaattcag ctccgccatc gccgcttcca    4320 cttttcccg cgttttcgca gaaacgtggc tggcctggtt caccacgcgg gaaacggtct     4380
gataagagac accggcatac tctgcgacat cgtataacgt tactggtttc acattcacca    4440
ccctgaattg actctcttcc gggcgctatc atgccatacc gcgaaaggtt ttgcgccatt    4500
cgatggtgtc aacgtaaatg catgccgctt cgccttcgcg cgcgaattgc aagctgatcc    4560
ggagcttatc gactgcacgg tgcaccaatg cttctggcgt caggcagcca tcggaagctg    4620
tggtatggct gtgcaggtcg taaatcactg cataattcgt gtcgctcaag gcgcactccc    4680
gttctggata tgttttttg cgccgacatc ataacggttc tggcaaatat tctgaaatga     4740
gctgttgaca attaatcatc ggctcgtata atgtgtggaa ttgtgagcgg ataacaattt    4800
cacacaggaa acagaattcc atatgaaata cctattacca acagcagcag ctgggttatt    4860
attgctcgct gcgcagccgg ccatggcggc cgatcctcga gagctcccgg gctgcagccc    4920
tgttctggaa aaccgggctg ctcagggcga tattactgca cccggcggtg ctcgccgttt    4980
aacgggtgat cagactgccg ctctgcgtga ttctcttagc gataaacctg caaaaaatat    5040 tatttgctg attggcgatg ggatggggga ctcggaaatt actgccgcac gtaattatgc     5100
cgaaggtgcg ggcggctttt ttaaaggtat agatgcctta ccgcttaccg gcaatacac     5160 tcactatgc ctgaataaaa aaaccggcaa accggactac gtcaccgact cggctgcatc     5220
agcaaccgcc tggtcaaccg tgtcaaaac ctataacggc gcgctgggcg tcgatattca     5280
cgaaaaagat cacccaacga ttctggaaat ggcaaaagcc gcaggtctgg cgaccggtaa    5340
cgtttctacc gcagagttgc aggatgccac gcccgctgcg ctggtggcac atgtgacctc    5400
gcgcaaatgc tacggtccga gcgcgaccag tgaaaaatgt ccgggtaacg ctctggaaaa    5460
aggcggaaaa ggatcgatta ccgaacagct gcttaacgct cgtgccgacg ttacgcttgg    5520
cggcggcgca aaacctttg ctgaaacggc aaccgctggt gaatggcagg aaaaacgct     5580 gcgtgaacag gcacaggcgc gtggttatca gttggtgagc gatgctgcct cactgaattc    5640
ggtgacggaa gcgaatcagc aaaaacccct gcttggcctg tttgctgacg caatatgcc    5700 agtgcgctgg ctaggaccga agcaacgta ccacggcaat atcgataagc ccgcagtcac     5760
ctgtacgcca aatccgcaac gtaatgacag tgtaccaacc ctggcgcaga tgaccgacaa    5820
agccattgaa ttgttgagta aaaatgagaa aggcttttc ctgcaagttg aaggtgcgtc     5880
aatcgataaa caggatcatg ctgcgaatcc ttgtgggcaa attggcgaga cggtcgatct    5940
cgatgaagcc gtacaacggg cgctggaatt cgctaaaaag gagggtaaca cgctggtcat    6000
agtcaccgct gatcacgccc acgccagcca gattgttgcg ccggatacca agctccggg     6060 cctcacccag cgctaaaata ccaaagatgg cgcagtgatg gtgatgagtt acgggaactc    6120
cgaagaggat tcacaagaac ataccggcag tcagttgcgt attgcggcgt atggcccgca    6180
tgccgccaat gttgttggac tgaccgacca gaccgatctc ttctacacca tgaaagccgc    6240
tctggggctg aaacatcatc atcaccatca cgggagctaa taagcttctg ttttggcgga    6300
tgagagaaga tttcagcct gatacagatt aaatcagaac gcagaagcgg tctgataaaa     6360
cagaatttgc ctggcggcag tagcgcggtg gtcccacctg accccatgcc gaactcagaa    6420
gtgaaacgcc gtagcgccga tggtagtgtg gggtctcccc atgcgagagt agggaactgc    6480
caggcatcaa ataaaacgaa aggctcagtc gaaagactgg gcctttcgtt ttatctgttg    6540
tttgtcggtg aacgctctcc tgagtaggac aaatccgccg ggagcggatt tgaacgttgc    6600
```

| | |
|---|---|
| gaagcaacgg cccggaggac cctggcgggc aggacgcccg ccataaactg ccaggcatca | 6660 |
| aattaagcag aaggccatcc tgacggatgg ccttttttgcg tttctacaaa ctctt | 6715 |

<210> SEQ ID NO 91
<211> LENGTH: 6721
<212> TYPE: DNA
<213> ORGANISM: Artificial sequence
<220> FEATURE:
<223> OTHER INFORMATION: plasmid p55/PhoAHisGS-/NAB-

<400> SEQUENCE: 91

| | |
|---|---|
| ttgtttattt ttctaaatac attcaaatat gtatccgctc atgagacaat aaccctgata | 60 |
| aatgcttcaa taatattgaa aaaggaagag tatgagtatt caacatttcc gtgtcgccct | 120 |
| tattcccttt tttgcggcat tttgccttcc tgttttttgct cacccagaaa cgctggtgaa | 180 |
| agtaaaagat gctgaagatc agttgggtgc acgagtgggt tacatcgaac tggatctcaa | 240 |
| cagcggtaag atccttgaga gttttcgccc cgaagaacgt tttccaatga tgagcacttt | 300 |
| taaagttctg ctatgtggcg cggtattatc ccgtgttgac gccgggcaag agcaactcgg | 360 |
| tcgccgcata cactattctc agaatgactt ggttgagtac tcaccagtca cagaaaagca | 420 |
| tcttacggat ggcatgacag taagagaatt atgcagtgct gccataacca tgagtgataa | 480 |
| cactgcggcc aacttacttc tgacaacgat cggaggaccg aaggagctaa ccgcttttttt | 540 |
| gcacaacatg ggggatcatg taactcgcct tgatcgttgg gaaccggagc tgaatgaagc | 600 |
| cataccaaac gacgagcgtg acaccacgat gcctgtagca atggcaacaa cgttgcgcaa | 660 |
| actattaact ggcgaactac ttactctagc ttcccggcaa caattaatag actggatgga | 720 |
| ggcggataaa gttgcaggac cacttctgcg ctcggccctt ccggctggct ggtttattgc | 780 |
| tgataaatct ggagccggtg agcgtgggtc tcgcggtatc attgcagcac tggggccaga | 840 |
| tggtaagccc tcccgtatcg tagttatcta cacgacgggg agtcaggcaa ctatggatga | 900 |
| acgaaataga cagatcgctg agataggtgc ctcactgatt aagcattggt aactgtcaga | 960 |
| ccaagtttac tcatatatac tttagattga tttaaaactt catttttaat ttaaaaggat | 1020 |
| ctaggtgaag atcctttttg ataatctcat gaccaaaatc ccttaacgtg agttttcgtt | 1080 |
| ccactgagcg tcagaccccg tagaaaagat caaaggatct tcttgagatc ctttttttct | 1140 |
| gcgcgtaatc tgctgcttgc aaacaaaaaa accaccgcta ccagcggtgg tttgtttgcc | 1200 |
| ggatcaagag ctaccaactc tttttccgaa ggtaactggc ttcagcagag cgcagatacc | 1260 |
| aaatactgtc cttctagtgt agccgtagtt aggccaccac ttcaagaact ctgtagcacc | 1320 |
| gcctacatac ctcgctctgc taatcctgtt accagtggct gctgccagtg gcgataagtc | 1380 |
| gtgtcttacc gggttggact caagacgata gttaccggat aaggcgcagc ggtcgggctg | 1440 |
| aacggggggt tcgtgcacac agcccagctt ggagcgaacg acctacaccg aactgagata | 1500 |
| cctacagcgt gagcattgag aaagcgccac gcttcccgaa gggagaaagg cggacaggta | 1560 |
| tccggtaagc ggcagggtcg gaacaggaga gcgcacgagg gagcttccag ggggaaacgc | 1620 |
| ctggtatctt tatagtcctg tcgggtttcg ccacctctga cttgagcgtc gatttttgtg | 1680 |
| atgctcgtca ggggggcgga gcctatggaa aaacgccagc aacgcggcct ttttacggtt | 1740 |
| cctggccttt tgctggcctt tgctcacat gttcttttcct gcgttatccc ctgattctgt | 1800 |
| ggataaccgt attaccgcct ttgagtgagc tgataccgct cgccgcagcc gaacgaccga | 1860 |
| gcgcagcgag tcagtgagcg aggaagcgga agagcgcctg atgcggtatt ttctccttac | 1920 |
| gcatctgtgc ggtatttcac accgcatata tggtgcactc tcagtacaat ctgctctgat | 1980 |

```
gccgcatagt taagccagta tacactccgc tatcgctacg tgactgggtc atggctgcgc    2040
cccgacaccc gccaacaccc gctgacgcgc cctgacgggc ttgtctgctc ccggcatccg    2100
cttacagaca agctgtgacc gtctccggga gctgcatgtg tcagaggttt tcaccgtcat    2160
caccgaaacg cgcgaggcag ctgccggtaaa gctcatcagc gtggtcgtga agcgattcac   2220
agatgtctgc ctgttcatcc gcgtccagct cgttgagttt ctccagaagc gttaatgtct   2280
ggcttctgat aaagcgggcc atgttaaggg cggttttttc ctgtttggtc acttgatgcc   2340
tccgtgtaag ggggaatttc tgttcatggg ggtaatgata ccgatgaaac gagagaggat   2400
gctcacgata cggttactg atgatgaaca tgcccggtta ctggaacgtt gtgagggtaa    2460
acaactggcg gtatggatgc ggcgggacca gagaaaaatc actcagggtc aatgccagcg   2520
cttcgttaat acagatgtag gtgttccaca gggtagccag cagcatcctg cgatgcagat   2580
ccggaacata atggtgcagg cgctgactt ccgcgtttcc agactttacg aaacacggaa    2640
accgaagacc attcatgttg ttgctcaggt cgcagacgtt ttgcagcagc agtcgcttca   2700
cgttcgctcg cgtatcggtg attcattctg ctaaccagta aggcaacccc gccagcctag   2760
ccgggtcctc aacgacagga gcacgatcat gcgcacccgt ggccaggacc caacgctgcc   2820
cgagatgcgc cgcgtgcggc tgctggagat ggcggacgcg atggatatgt tctgccaagg   2880
gttggtttgc gcattcacag ttctccgcaa gaattgattg ctccaattc ttggagtggt    2940 gaatccgtta gcgaggtgcc gccggcttcc attcaggtcg aggtggcccg gctccatgca   3000
ccgcgacgca acgcggggag gcagacaagg tatagggcgg cgcctacaat ccatgccaac   3060
ccgttccatg tgctcgccga ggcggcataa atcgccgtga cgatcagcgg tccagtgatc   3120
gaagttaggc tggtaagagc cgcgagcgat ccttgaagct gtccctgatg gtcgtcatct   3180
acctgcctgg acagcatggc ctgcaacgcg ggcatcccga tgccgccgga agcgagaaga   3240
atcataatgg ggaaggccat ccagcctcgc gtcgcgaacg ccagcaagac gtagcccagc   3300
gcgtcggcca gcttgcaatt cgcgctaact tacattaatt gcgttgcgct cactgcccgc   3360
tttccagtcg ggaaacctgt cgtgccagct gcattaatga atcggccaac gcgcggggag   3420
aggcggtttg cgtattgggc gccagggtgg ttttttcttt caccagtgag acgggcaaca   3480
gctgattgcc cttcaccgcc tggccctgag agagttgcag caagcggtcc acgctggttt   3540
gccccagcag gcgaaaatcc tgtttgatgg tggttgacgg cggatataa catgagctgt    3600 cttcggtatc gtcgtatccc actaccgaga tatccgcacc aacgcgcagc ccggactcgg   3660
taatggcgcg cattgcgccc agcgccatct gatcgttggc aaccagcatc gcagtgggaa   3720
cgatgccctc attcagcatt tgcatggttt gttgaaaacc ggacatggca ctccagtcgc   3780
cttcccgttc cgctatcggc tgaatttgat tgcgagtgag atatttatgc cagccagcca   3840
gacgcagacg cgccgagaca gaacttaatg gtcccgctaa cagcgcgatt tgctgatgac   3900
ccaatgcgac cagatgctcc acgcccagtc gcgtaccgtc ttcatgggag aaaataatac   3960
tgttgatggg tgtctggtca gagacatcaa gaaataacgc cggaacatta gtgcaggcag   4020
cttccacagc aatggcatcc tggtcatcca gcggatagtt aatgatcagc ccactgacgc   4080
gttgcgcgag aagattgtgc accgccgctt tacaggcttc gacgccgctt cgttctacca   4140
tcgacaccac cacgctggca cccagttgat cggcgcgaga tttaatcgcc gcgacaattt   4200
gcgacggcgc gtgcagggcc agactggagg tggcaacgcc aatcagcaac gactgtttgc   4260
ccgccagttg ttgtgccacg cggttgggaa tgtaattcag ctccgccatc gccgcttcca   4320
```

```
cttttttcccg cgttttcgca gaaacgtggc tggcctggtt caccacgcgg gaaacggtct    4380
gataagagac accggcatac tctgcgacat cgtataacgt tactggtttc acattcacca    4440
ccctgaattg actctcttcc gggcgctatc atgccatacc gcgaaaggtt ttgcgccatt    4500
cgatggtgtc aacgtaaatg catgccgctt cgccttcgcg cgcgaattgc aagctgatcc    4560
ggagcttatc gactgcacgg tgcaccaatg cttctggcgt caggcagcca tcggaagctg    4620
tggtatggct gtgcaggtcg taaatcactg cataattcgt gtcgctcaag gcgcactccc    4680
gttctggata atgttttttg cgccgacatc ataacggttc tggcaaatat tctgaaatga    4740
gctgttgaca attaatcatc ggctcgtata atgtgtggaa ttgtgagcgg ataacaattt    4800
cacacaggaa acagaattcc atatgaaata cctattacca acagcagcag ctgggttatt    4860
attgctcgct gcgcagccgg ccatggcggc cggccgatcc tcgagagctc ccgggctgca    4920
gccctgttct ggaaaaccgg gctgctcagg gcgatattac tgcacccggc ggtgctcgcc    4980
gtttaacggg tgatcagact gccgctctgc gtgattctct tagcgataaa cctgcaaaaa    5040
atattatttt gctgattggc gatgggatgg gggactcgga aattactgcc gcacgtaatt    5100
atgccgaagg tgcgggcggc ttttttaaag gtatagatgc cttaccgctt accgggcaat    5160
acactcacta tgcgctgaat aaaaaaaccg gcaaaccgga ctacgtcacc gactcggctg    5220
catcagcaac cgcctggtca accggtgtca aaacctataa cggcgcgctg ggcgtcgata    5280
ttcacgaaaa agatcaccca acgattctgg aaatggcaaa agccgcaggt ctggcgaccg    5340
gtaacgtttc taccgcagag ttgcaggatg ccacgcccgc tgcgctggtg cacatgtga    5400 cctcgcgcaa atgctacggt ccgagcgcga ccagtgaaaa atgtccgggt aacgctctgg    5460
aaaaaggcgg aaaaggatcg attaccgaac agctgcttaa cgctcgtgcc gacgttacgc    5520
ttggcggcgg cgcaaaaacc tttgctgaaa cggcaaccgc tggtgaatgg cagggaaaaa    5580
cgctgcgtga acaggcacag gcgcgtggtt atcagttggt gagcgatgct gcctcactga    5640
attcggtgac ggaagcgaat cagcaaaaac ccctgcttgg cctgtttgct gacggcaata    5700
tgccagtgcg ctggctagga ccgaaagcaa cgtaccacgg caatatcgat aagcccgcag    5760
tcacctgtac gccaaatccg caacgtaatg acagtgtacc aaccctggcg cagatgaccg    5820
acaaagccat tgaattgttg agtaaaaatg agaaaggctt tttcctgcaa gttgaaggtg    5880
cgtcaatcga taaacaggat catgctgcga atccttgtgg gcaaattggc gagacggtcg    5940
atctcgatga agccgtacaa cgggcgctgg aattcgctaa aaaggagggt aacacgctgg    6000
tcatagtcac cgctgatcac gcccacgcca gccagattgt tgcgccggat accaaagctc    6060
cgggcctcac ccaggcgcta ataccaaagg atggcgcagt gatggtgatg agttacggga    6120
actccgaaga ggattcacaa gaacataccg gcagtcagtt gcgtattgcg gcgtatggcc    6180
cgcatgccgc caatgttgtt ggactgaccg accagaccga tctcttctac accatgaaag    6240
ccgctctggg gctgaaacat catcatcacc atcacgggag ctaataagct tggctgtttt    6300
ggcggatgag agaagatttt cagcctgata cagattaaat cagaacgcag aagcggtctg    6360
ataaaacaga atttgcctgg cggcagtagc gcggtggtcc cacctgaccc catgccgaac    6420
tcagaagtga aacgccgtag cgccgatggt agtgtgggg ctccccatgc gagagtaggg    6480
aactgccagg catcaaataa aacgaaaggc tcagtcgaaa gactgggcct ttcgttttat    6540
ctgttgtttg tcggtgaacg ctctcctgag taggacaaat ccgccgggag cggatttgaa    6600
cgttgcgaag caacggcccg gagggacctg gcgggcagga cgcccgccat aaactgccag    6660
gcatcaaatt aagcagaagg ccatcctgac ggatggcctt tttgcgtttc tacaaactct    6720
```

<210> SEQ ID NO 92
<211> LENGTH: 5400
<212> TYPE: DNA
<213> ORGANISM: Artificial sequence
<220> FEATURE:
<223> OTHER INFORMATION: plasmid p55/MCS1

<400> SEQUENCE: 92

```
ttgtttattt ttctaaatac attcaaatat gtatccgctc atgagacaat aaccctgata     60
aatgcttcaa taatattgaa aaggaagag tatgagtatt caacatttcc gtgtcgccct    120
tattcccttt tttgcggcat tttgccttcc tgtttttgct cacccagaaa cgctggtgaa    180
agtaaaagat gctgaagatc agttgggtgc acgagtgggt tacatcgaac tggatctcaa    240
cagcggtaag atccttgaga gttttcgccc cgaagaacgt tttccaatga tgagcacttt    300
taaagttctg ctatgtggcg cggtattatc ccgtgttgac gccgggcaag agcaactcgg    360
tcgccgcata cactattctc agaatgactt ggttgagtac tcaccagtca cagaaaagca    420
tcttacggat ggcatgacag taagagaatt atgcagtgct gccataacca tgagtgataa    480
cactgcggcc aacttacttc tgacaacgat cggaggaccg aaggagctaa ccgcttttttt    540
gcacaacatg gggatcatg taactcgcct tgatcgttgg gaaccggagc tgaatgaagc    600
cataccaaac gacgagcgtg acaccacgat gcctgtagca atggcaacaa cgttgcgcaa    660
actattaact ggcgaactac ttactctagc ttcccggcaa caattaatag actggatgga    720
ggcggataaa gttgcaggac cacttctgcg ctcggccctt ccggctggct ggtttattgc    780
tgataaatct ggagccggtg agcgtgggtc tcgcggtatc attgcagcac tggggccaga    840
tggtaagccc tcccgtatcg tagttatcta cacgacgggg agtcaggcaa ctatggatga    900
acgaaataga cagatcgctg agataggtgc ctcactgatt aagcattggt aactgtcaga    960
ccaagtttac tcatatatac tttagattga tttaaaactt catttttaat ttaaaaggat   1020
ctaggtgaag atcctttttg ataatctcat gaccaaaatc ccttaacgtg agttttcgtt   1080
ccactgagcg tcagaccccg tagaaaagat caaaggatct tcttgagatc ctttttttct   1140
gcgcgtaatc tgctgcttgc aaacaaaaaa accaccgcta ccagcggtgg tttgtttgcc   1200
ggatcaagag ctaccaactc tttttccgaa ggtaactggc ttcagcagag cgcagatacc   1260
aaatactgtc cttctagtgt agccgtagtt aggccaccac ttcaagaact ctgtagcacc   1320
gcctacatac ctcgctctgc taatcctgtt accagtggct gctgccagtg cgataagtc   1380
gtgtcttacc gggttggact caagacgata gttaccggat aaggcgcagc ggtcgggctg   1440
aacggggggt tcgtgcacac agcccagctt ggagcgaacg acctacaccg aactgagata   1500
cctacagcgt gagcattgag aaagcgccac gcttcccgaa gggagaaagg cggacaggta   1560
tccggtaagc ggcagggtcg gaacaggaga gcgcacgagg gagcttccag ggggaaacgc   1620
ctggtatctt tatagtcctg tcgggtttcg ccacctctga cttgagcgtc gatttttgtg   1680
atgctcgtca gggggggcgga gcctatggaa aaacgccagc aacgcggcct ttttacggtt   1740
cctggccttt tgctggcctt tgctcacat gttctttcct gcgttatccc ctgattctgt   1800
ggataaccgt attaccgcct ttgagtgagc tgataccgct cgccgcagcc gaacgaccga   1860
gcgcagcgag tcagtgagcg aggaagcgga agagcgcctg atgcggtatt ttctccttac   1920
gcatctgtgc ggtatttcac accgcatata tggtgcactc tcagtacaat ctgctctgat   1980
``` t                                                                    6721

```
gccgcatagt taagccagta tacactccgc tatcgctacg tgactgggtc atggctgcgc    2040
cccgacaccc gccaacaccc gctgacgcgc cctgacgggc ttgtctgctc ccggcatccg    2100
cttacagaca agctgtgacc gtctccggga gctgcatgtg tcagaggttt tcaccgtcat    2160
caccgaaacg cgcgaggcag ctgcggtaaa gctcatcagc gtggtcgtga agcgattcac    2220
agatgtctgc ctgttcatcc gcgtccagct cgttgagttt ctccagaagc gttaatgtct    2280
ggcttctgat aaagcgggcc atgttaaggg cggttttttc ctgtttggtc acttgatgcc    2340
tccgtgtaag ggggaatttc tgttcatggg ggtaatgata ccgatgaaac gagagaggat    2400
gctcacgata cgggttactg atgatgaaca tgcccggtta ctggaacgtt gtgagggtaa    2460
acaactggcg gtatggatgc ggcgggacca gagaaaaatc actcagggtc aatgccagcg    2520
cttcgttaat acagatgtag gtgttccaca gggtagccag cagcatcctg cgatgcagat    2580
ccggaacata atggtgcagg cgctgactt ccgcgtttcc agactttacg aaacacggaa    2640
accgaagacc attcatgttg ttgctcaggt cgcagacgtt ttgcagcagc agtcgcttca    2700
cgttcgctcg cgtatcggtg attcattctg ctaaccagta aggcaacccc gccagcctag    2760
ccgggtcctc aacgacagga gcacgatcat gcgcacccgt ggccaggacc caacgctgcc    2820
cgagatgcgc cgcgtgcggc tgctggagat ggcgacgcg atggatatgt tctgccaagg    2880
gttggtttgc gcattcacag ttctccgcaa gaattgattg ctccaattc ttggagtggt    2940 gaatccgtta gcgaggtgcc gccggcttcc attcaggtcg aggtggcccg gctccatgca    3000
ccgcgacgca acgcggggag gcagacaagg tatagggcgg cgcctacaat ccatgccaac    3060
ccgttccatg tgctcgccga ggcggcataa atcgccgtga cgatcagcgg tccagtgatc    3120
gaagttaggc tggtaagagc cgcgagcgat ccttgaagct gtccctgatg gtcgtcatct    3180
acctgcctgg acagcatggc ctgcaacgcg ggcatcccga tgccgccgga agcgagaaga    3240
atcataatgg ggaaggccat ccagcctcgc gtcgcgaacg ccagcaagac gtagcccagc    3300
gcgtcggcca gcttgcaatt cgcgctaact tacattaatt gcgttgcgct cactgcccgc    3360
tttccagtcg ggaaacctgt cgtgccagct gcattaatga atcggccaac gcgcggggag    3420
aggcggtttg cgtattgggc gccagggtgg ttttcttt caccagtgag acgggcaaca    3480
gctgattgcc cttcaccgcc tggccctgag agagttgcag caagcggtcc acgctggttt    3540 gcccagcag cgaaaatcc tgtttgatgg tggttgacgg cgggatataa catgagctgt    3600
cttcggtatc gtcgtatccc actaccgaga tatccgcacc aacgcgcagc ccggactcgg    3660
taatggcgcg cattgcgccc agcgccatct gatcgttggc aaccagcatc gcagtgggaa    3720
cgatgccctc attcagcatt tgcatggttt gttgaaaacc ggacatggca ctccagtcgc    3780
cttcccgttc cgctatcggc tgaatttgat tgcgagtgag atatttatgc cagccagcca    3840
gacgcagacg cgccgagaca gaacttaatg gtcccgctaa cagcgcgatt tgctgatgac    3900
ccaatgcgac cagatgctcc acgcccagtc gcgtaccgtc ttcatgggag aaaataatac    3960
tgttgatggg tgtctggtca gagacatcaa gaaataacgc cggaacatta gtgcaggcag    4020
cttccacagc aatggcatcc tggtcatcca gcggatagtt aatgatcagc ccactgacgc    4080
gttgcgcgag aagattgtgc accgccgctt tacaggcttc gacgccgctt cgttctacca    4140
tcgacaccac cacgctggca cccagttgat cggcgcgaga tttaatcgcc gcgacaattt    4200
gcgacggcgc gtgcagggcc agactggagg tggcaacgcc aatcagcaac gactgtttgc    4260
ccgccagttg ttgtgccacg cggttgggaa tgtaattcag ctccgccatc gccgcttcca    4320
ctttttcccg cgttttcgca gaaacgtggc tggcctggtt caccacgcgg gaaacggtct    4380
```

```
gataagagac accggcatac tctgcgacat cgtataacgt tactggtttc acattcacca    4440
ccctgaattg actctcttcc gggcgctatc atgccatacc gcgaaaggtt ttgcgccatt    4500
cgatggtgtc aacgtaaatg catgccgctt cgccttcgcg cgcgaattgc aagctgatcc    4560
ggagcttatc gactgcacgg tgcaccaatg cttctggcgt caggcagcca tcggaagctg    4620
tggtatggct gtgcaggtcg taaatcactg cataattcgt gtcgctcaag gcgcactccc    4680
gttctggata tgttttttg cgccgacatc ataacggttc tggcaaatat tctgaaatga    4740
gctgttgaca attaatcatc ggctcgtata atgtgtggaa ttgtgagcgg ataacaattt    4800
cacacaggaa acagaattcc atatgaaata cctattacca acagcagcag ctgggttatt    4860
attgctcgct gcgcagccgg ccatggccca ggtcaccgtc tcctcaaacc gcggactcga    4920
ggcggcccag ccggccatgg ccgctagcgc ggccgctcta gattaagctt ggctgttttg    4980
gcggatgaga aagattttc agcctgatac agattaaatc agaacgcaga gcggtctga    5040 taaaacagaa tttgcctggc ggcagtagcg cggtggtccc acctgacccc atgccgaact    5100
cagaagtgaa acgccgtagc gccgatggta gtgtggggtc tccccatgcg agagtaggga    5160
actgccaggc atcaaataaa acgaaaggct cagtcgaaag actgggcctt tcgttttatc    5220
tgttgtttgt cggtgaacgc tctcctgagt aggacaaatc cgccgggagc ggatttgaac    5280
gttgcgaagc aacggcccgg aggacctgg cgggcaggac gccgccata aactgccagg    5340 catcaaatta agcagaaggc catcctgacg gatggccttt ttgcgtttct acaaactctt    5400
```

<210> SEQ ID NO 93
<211> LENGTH: 5500
<212> TYPE: DNA
<213> ORGANISM: Artificial sequence
<220> FEATURE:
<223> OTHER INFORMATION: plasmid P55Flag/RBS/35

<400> SEQUENCE: 93

```
ttgtttatttt ttctaaatac attcaaatat gtatccgctc atgagacaat aaccctgata     60
aatgcttcaa taatattgaa aaaggaagag tatgagtatt caacatttcc gtgtcgccct    120
tattcccttt tttgcggcat tttgccttcc tgttttgct cacccagaaa cgctggtgaa    180
agtaaaagat gctgaagatc agttgggtgc acgagtgggt tacatcgaac tggatctcaa    240
cagcggtaag atccttgaga gttttcgccc cgaagaacgt tttccaatga tgagcacttt    300
taaagttctg ctatgtggcg cggtattatc ccgtgttgac gccgggcaag agcaactcgg    360
tcgccgcata cactattctc agaatgactt ggttgagtac tcaccagtca cagaaaagca    420
tcttacggat ggcatgacag taagagaatt atgcagtgct gccataacca tgagtgataa    480
cactgcggcc aacttacttc tgacaacgat cggaggaccg aaggagctaa ccgcttttt    540 gcacaacatg ggggatcatg taactcgcct tgatcgttgg gaaccggagc tgaatgaagc    600
cataccaaac gacgagcgtg acaccacgat gcctgtagca atggcaacaa cgttgcgcaa    660
actattaact ggcgaactac ttactctagc ttcccggcaa caattaatag actggatgga    720
ggcggataaa gttgcaggac cacttctgcg ctcggccctt ccggctggct ggtttattgc    780
tgataaatct ggagccggtg agcgtgggtc tcgcggtatc attgcagcac tggggccaga    840
tggtaagccc tcccgtatcg tagttatcta cacgacgggg agtcaggcaa ctatggatga    900
acgaaataga cagatcgctg agataggtgc ctcactgatt aagcattggt aactgtcaga    960
ccaagtttac tcatatatac tttagattga tttaaaactt catttttaat ttaaaaggat   1020
```

```
ctaggtgaag atccttttg ataatctcat gaccaaaatc ccttaacgtg agttttcgtt    1080
ccactgagcg tcagacccg tagaaaagat caaaggatct tcttgagatc cttttttct     1140 gcgcgtaatc tgctgcttgc aaacaaaaaa accaccgcta ccagcggtgg tttgtttgcc   1200
ggatcaagag ctaccaactc ttttccgaa ggtaactggc ttcagcagag cgcagatacc    1260
aaatactgtc cttctagtgt agccgtagtt aggccaccac ttcaagaact ctgtagcacc   1320
gcctacatac ctcgctctgc taatcctgtt accagtggct gctgccagtg gcgataagtc   1380
gtgtcttacc gggttggact caagacgata gttaccggat aaggcgcagc ggtcgggctg   1440 aacgggggt tcgtgcacac agcccagctt ggagcgaacg acctacaccg aactgagata    1500
cctacagcgt gagcattgag aaagcgccac gcttcccgaa gggagaaagg cggacaggta   1560
tccggtaagc ggcagggtcg aacaggaga gcgcacgagg gagcttccag ggggaaacgc    1620
ctggtatctt tatagtcctg tcgggtttcg ccacctctga cttgagcgtc gatttttgtg   1680
atgctcgtca gggggcgga gcctatggaa aaacgccagc aacgcggcct ttttacggtt    1740
cctggccttt tgctggcctt tgctcacat gttctttcct gcgttatccc ctgattctgt    1800
ggataaccgt attaccgcct ttgagtgagc tgataccgct cgccgcagcc gaacgaccga   1860
gcgcagcgag tcagtgagcg aggaagcgga agagcgcctg atgcggtatt ttctccttac   1920
gcatctgtgc ggtatttcac accgcatata tggtgcactc tcagtacaat ctgctctgat   1980
gccgcatagt taagccagta tacactccgc tatcgctacg tgactgggtc atggctgcgc   2040
cccgacaccc gccaacaccc gctgacgcgc cctgacgggc ttgtctgctc ccggcatccg   2100
cttacagaca agctgtgacc gtctccggga gctgcatgtg tcagaggttt tcaccgtcat   2160
caccgaaacg cgcgaggcag ctgcggtaaa gctcatcagc gtggtcgtga agcgattcac   2220
agatgtctgc ctgttcatcc gcgtccagct cgttgagttt ctccagaagc gttaatgtct   2280
ggcttctgat aaagcgggcc atgttaaggg cggttttttc ctgtttggtc acttgatgcc   2340
tccgtgtaag ggggaatttc tgttcatggg ggtaatgata ccgatgaaac gagagaggat   2400
gctcacgata cgggttactg atgatgaaca tgcccggtta ctggaacgtt gtgagggtaa   2460
acaactggcg gtatgatgcc ggcgggacca gagaaaaatc actcagggtc aatgccagcg   2520
cttcgttaat acagatgtag gtgttccaca gggtagccag cagcatcctg cgatgcagat   2580
ccggaacata atggtgcagg cgctgactt ccgcgtttcc agactttacg aaacacggaa    2640
accgaagacc attcatgttg ttgctcaggt cgcagacgtt ttgcagcagc agtcgcttca   2700
cgttcgctcg cgtatcggtg attcattctg ctaaccagta aggcaacccc gccagcctag   2760
ccgggtcctc aacgacagga gcacgatcat gcgcacccgt ggccaggacc caacgctgcc   2820
cgagatgcgc cgcgtgcggc tgctggagat ggcggacgcg atggatatgt tctgccaagg   2880
gttggtttgc gcattcacag ttctccgcaa gaattgattg gctccaattc ttggagtggt   2940
gaatccgtta gcgaggtgcc gccggcttcc attcaggtcg aggtggcccg gctccatgca   3000
ccgcgacgca acgcggggag gcagacaagg tatagggcgg cgcctacaat ccatgccaac   3060
ccgttccatg tgctcgccga ggcggcataa atcgccgtga cgatcagcgg tccagtgatc   3120
gaagttaggc tggtaagagc cgcgagcgat ccttgaagct gtccctgatg gtcgtcatct   3180
acctgcctgg acagcatggc ctgcaacgcg ggcatcccga tgccgccgga agcgagaaga   3240
atcataatgg ggaaggccat ccagcctcgc gtcgcgaacg ccagcaagac gtagcccagc   3300
gcgtcggcca gcttgcaatt cgcgctaact tacattaatt gcgttgcgct cactgcccgc   3360
tttccagtcg ggaaacctgt cgtgccagct gcattaatga atcggccaac gcgcggggag   3420
```

```
aggcggtttg cgtattgggc gccagggtgg tttttcttt caccagtgag acgggcaaca    3480
gctgattgcc cttcaccgcc tggccctgag agagttgcag caagcggtcc acgctggttt    3540
gccccagcag gcgaaaatcc tgtttgatgg tggttgacgg cgggatataa catgagctgt    3600
cttcggtatc gtcgtatccc actaccgaga tatccgcacc aacgcgcagc ccggactcgg    3660
taatggcgcg cattgcgccc agcgccatct gatcgttggc aaccagcatc gcagtgggaa    3720
cgatgccctc attcagcatt tgcatggttt gttgaaaacc ggacatggca ctccagtcgc    3780
cttcccgttc cgctatcggc tgaatttgat tgcgagtgag atatttatgc cagccagcca    3840
gacgcagacg cgccgagaca gaacttaatg gtcccgctaa cagcgcgatt tgctgatgac    3900
ccaatgcgac cagatgctcc acgcccagtc gcgtaccgtc ttcatgggag aaaataatac    3960
tgttgatggg tgtctggtca gagacatcaa gaaataacgc cggaacatta gtgcaggcag    4020
cttccacagc aatggcatcc tggtcatcca gcggatagtt aatgatcagc ccactgacgc    4080
gttgcgcgag aagattgtgc accgccgctt tacaggcttc gacgccgctt cgttctacca    4140
tcgacaccac cacgctggca cccagttgat cggcgcgaga tttaatcgcc gcgacaattt    4200
gcgacggcgc gtgcagggcc agactggagg tggcaacgcc aatcagcaac gactgtttgc    4260
ccgccagttg ttgtgccacg cggttgggaa tgtaattcag ctccgccatc gccgcttcca    4320
ctttttcccg cgttttcgca gaaacgtggc tggcctggtt caccacgcgg gaaacggtct    4380
gataagagac accggcatac tctgcgacat cgtataacgt tactggtttc acattcacca    4440
ccctgaattg actctcttcc gggcgctatc atgccatacc gcgaaaggtt ttgcgccatt    4500
cgatggtgtc aacgtaaatg catgccgctt cgccttcgcg cgcgaattgc aagctgatcc    4560
ggagcttatc gactgcacgg tgcaccaatg cttctggcgt caggcagcca tcggaagctg    4620
tggtatggct gtgcaggtcg taaatcactg cataattcgt gtcgctcaag gcgcactccc    4680
gttctggata tgttttttg cgccgacatc ataacggttc tggcaaatat tctgaaatga    4740
gctgttgaca attaatcatc ggctcgtata atgtgtggaa ttgtgagcgg ataacaattt    4800
cacacaggaa acagaattcc atatgaaata cctattacca acagcagcag ctgggttatt    4860
attgctcgct gcgcagccgg ccatggccca ggtcaccgtc tcctcaaacc gcggagagtg    4920
tgcaggtgat tacaaagacg atgacgataa gtaataaaca ggaaacagaa gtccatatga    4980
aatacctatt gcctacggca gccgctggat tgttattact cgcggcccag ccggccatgg    5040
ccgctagcgc ggccgctcta gattaagctt ggctgttttg gcggatgaga agattttc    5100
agcctgatac agattaaatc agaacgcaga agcggtctga taaaacagaa tttgcctggc    5160
ggcagtagcg cggtggtccc acctgacccc atgccgaact cagaagtgaa acgccgtagc    5220
gccgatggta gtgtggggtc tccccatgcg agagtaggga actgccaggc atcaaataaa    5280
acgaaaggct cagtcgaaag actgggcctt tcgttttatc tgttgtttgt cggtgaacgc    5340
tctcctgagt aggacaaatc cgccgggagc ggatttgaac gttgcgaagc aacgcccgg    5400
aggaccctgg cgggcaggac gcccgccata aactgccagg catcaaatta agcagaaggc    5460
catcctgacg gatggccttt ttgcgtttct acaaactctt                          5500
```

<210> SEQ ID NO 94
<211> LENGTH: 5560
<212> TYPE: DNA
<213> ORGANISM: Artificial sequence
<220> FEATURE:
<223> OTHER INFORMATION: plasmid P55/RBS/35cmyc6HisGS

<400> SEQUENCE: 94

```
ttgtttattt ttctaaatac attcaaatat gtatccgctc atgagacaat aaccctgata        60
aatgcttcaa taatattgaa aaaggaagag tatgagtatt caacatttcc gtgtcgccct       120
tattcccttt tttgcggcat tttgccttcc tgttttgct cacccagaaa cgctggtgaa        180
agtaaaagat gctgaagatc agttgggtgc acgagtgggt tacatcgaac tggatctcaa       240
cagcggtaag atccttgaga gttttcgccc cgaagaacgt tttccaatga tgagcacttt       300
taaagttctg ctatgtggcg cggtattatc ccgtgttgac gccgggcaag agcaactcgg       360
tcgccgcata cactattctc agaatgactt ggttgagtac tcaccagtca cagaaaagca       420
tcttacggat ggcatgacag taagagaatt atgcagtgct gccataacca tgagtgataa       480
cactgcggcc aacttacttc tgacaacgat cggaggaccg aaggagctaa ccgctttttt       540
gcacaacatg gggatcatg taactcgcct tgatcgttgg gaaccggagc tgaatgaagc        600
cataccaaac gacgagcgtg acaccacgat gcctgtagca atggcaacaa cgttgcgcaa       660
actattaact ggcgaactac ttactctagc ttcccggcaa caattaatag actggatgga       720
ggcggataaa gttgcaggac cacttctgcg ctcggccctt ccggctggct ggtttattgc       780
tgataaatct ggagccggtg agcgtgggtc tcgcggtatc attgcagcac tggggccaga       840
tggtaagccc tcccgtatcg tagttatcta cacgacgggg agtcaggcaa ctatggatga       900
acgaaataga cagatcgctg agataggtgc ctcactgatt aagcattggt aactgtcaga       960
ccaagtttac tcatatatac tttagattga tttaaaactt cattttaat ttaaaaggat      1020
ctaggtgaag atcctttttg ataatctcat gaccaaaatc ccttaacgtg agttttcgtt      1080
ccactgagcg tcagaccccg tagaaaagat caaaggatct tcttgagatc ctttttttct      1140
gcgcgtaatc tgctgcttgc aaacaaaaaa accaccgcta ccagcggtgg tttgtttgcc      1200
ggatcaagag ctaccaactc ttttccgaa ggtaactggc ttcagcagag cgcagatacc       1260
aaatactgtc cttctagtgt agccgtagtt aggccaccac ttcaagaact ctgtagcacc      1320
gcctacatac ctcgctctgc taatcctgtt accagtggct gctgccagtg gcgataagtc      1380
gtgtcttacc gggttggact caagacgata gttaccggat aaggcgcagc ggtcgggctg      1440
aacggggggt tcgtgcacac agcccagctt ggagcgaacg acctacaccg aactgagata      1500
cctacagcgt gagcattgag aaagcgccac gcttcccgaa gggagaaagg cggacaggta      1560
tccggtaagc ggcagggtcg gaacaggaga gcgcacgagg gagcttccag ggggaaacgc      1620
ctggtatctt tatagtcctg tcgggtttcg ccacctctga cttgagcgtc gatttttgtg      1680
atgctcgtca gggggggcgga gcctatggaa aaacgccagc aacgcggcct ttttacggtt      1740
cctggccttt tgctggcctt ttgctcacat gttctttcct gcgttatccc ctgattctgt      1800
ggataaccgt attaccgcct tgagtgagc tgataccgct cgccgcagcc gaacgaccga       1860
gcgcagcgag tcagtgagcg aggaagcgga agagcgcctg atgcggtatt ttctccttac      1920
gcatctgtgc ggtatttcac accgcatata tggtgcactc tcagtacaat ctgctctgat      1980
gccgcatagt taagccagta tacactccgc tatcgctacg tgactgggtc atggctgcgc      2040
cccgacaccc gccaacaccc gctgacgcgc cctgacgggc ttgtctgctc ccggcatccg      2100
cttacagaca agctgtgacc gtctccggga gctgcatgtg tcagaggttt tcaccgtcat      2160
caccgaaacg cgcgaggcag ctgcggtaaa gctcatcagc gtggtcgtga agcgattcac      2220
agatgtctgc ctgttcatcc gcgtccagct cgttgagttt ctccagaagc gttaatgtct      2280
ggcttctgat aaagcgggcc atgttaaggg cggttttttc ctgtttggtc acttgatgcc      2340
```

```
tccgtgtaag ggggaatttc tgttcatggg ggtaatgata ccgatgaaac gagagaggat    2400
gctcacgata cgggttactg atgatgaaca tgcccggtta ctggaacgtt gtgagggtaa    2460
acaactggcg gtatggatgc ggcgggacca gagaaaaatc actcagggtc aatgccagcg    2520
cttcgttaat acagatgtag gtgttccaca gggtagccag cagcatcctg cgatgcagat    2580
ccggaacata atggtgcagg gcgctgactt ccgcgtttcc agactttacg aaacacggaa    2640
accgaagacc attcatgttg ttgctcaggt cgcagacgtt ttgcagcagc agtcgcttca    2700
cgttcgctcg cgtatcggtg attcattctg ctaaccagta aggcaacccc gccagcctag    2760
ccgggtcctc aacgacagga gcacgatcat gcgcacccgt ggccaggacc caacgctgcc    2820
cgagatgcgc cgcgtgcggc tgctggagat ggcggacgcg atggatatgt tctgccaagg    2880
gttggtttgc gcattcacag ttctccgcaa gaattgattg gctccaattc ttggagtggt    2940
gaatccgtta gcgaggtgcc gccggcttcc attcaggtcg aggtggcccg gctccatgca    3000
ccgcgacgca acgcggggag gcagacaagg tatagggcgg cgcctacaat ccatgccaac    3060
ccgttccatg tgctcgccga ggcggcataa atcgccgtga cgatcagcgg tccagtgatc    3120
gaagttaggc tggtaagagc cgcgagcgat ccttgaagct gtccctgatg gtcgtcatct    3180
acctgcctgg acagcatggc ctgcaacgcg ggcatcccga tgccgccgga agcgagaaga    3240
atcataatgg ggaaggccat ccagcctcgc gtcgcgaacg ccagcaagac gtagcccagc    3300
gcgtcggcca gcttgcaatt cgcgctaact tacattaatt gcgttgcgct cactgcccgc    3360
tttccagtcg ggaaacctgt cgtgccagct gcattaatga atcggccaac gcgcggggag    3420
aggcggtttg cgtattgggc gccagggtgg ttttcttttt caccagtgag acgggcaaca    3480
gctgattgcc cttcaccgcc tggccctgag agagttgcag caagcggtcc acgctggttt    3540
gccccagcag gcgaaaatcc tgtttgatgg tggttgacgg cgggatataa catgagctgt    3600
cttcggtatc gtcgtatccc actaccgaga tatccgcacc aacgcgcagc ccggactcgg    3660
taatggcgcg cattgcgccc agcgccatct gatcgttggc aaccagcatc gcagtgggaa    3720
cgatgccctc attcagcatt tgcatggttt gttgaaaacc ggacatggca ctccagtcgc    3780
cttcccgttc cgctatcggc tgaatttgat tgcgagtgag atatttatgc cagccagcca    3840
gacgcagacg cgccgagaca gaacttaatg gtcccgctaa cagcgcgatt tgctgatgac    3900
ccaatgcgac cagatgctcc acgcccagtc gcgtaccgtc ttcatgggag aaaataatac    3960
tgttgatggg tgtctggtca gagacatcaa gaaataacgc cggaacatta gtgcaggcag    4020
cttccacagc aatggcatcc tggtcatcca gcggatagtt aatgatcagc ccactgacgc    4080
gttgcgcgag aagattgtgc accgccgctt tacaggcttc gacgccgctt cgttctacca    4140
tcgacaccac cacgctggca cccagttgat cggcgcgaga tttaatcgcc gcgacaattt    4200
gcgacggcgc gtgcagggcc agactggagg tggcaacgcc aatcagcaac gactgtttgc    4260
ccgccagttt ttgtgccacg cggttgggaa tgtaattcag ctccgccatc gccgcttcca    4320
cttttttccg cgttttcgca gaaacgtggc tggcctggtt caccacgcgg gaaacggtct    4380
gataagagac accggcatac tctgcgacat cgtataacgt tactggtttc acattcacca    4440
ccctgaattg actctcttcc gggcgctatc atgccatacc gcgaaaggtt ttgcgccatt    4500
cgatggtgtc aacgtaaatg catgccgctt cgccttcgcg cgcgaattgc aagctgatcc    4560
ggagcttatc gactgcacgg tgcaccaatg cttctggcgt caggcagcca tcggaagctg    4620
tggtatggct gtgcaggtcg taaatcactg cataattcgt gtcgctcaag gcgcactccc    4680
```

| | |
|---|---|
| gttctggata atgttttttg cgccgacatc ataacggttc tggcaaatat tctgaaatga | 4740 |
| gctgttgaca attaatcatc ggctcgtata atgtgtggaa ttgtgagcgg ataacaattt | 4800 |
| cacacaggaa acagaattcc atatgaaata cctattacca acagcagcag ctgggttatt | 4860 |
| attgctcgct gcgcagccgg ccatggccca ggtcaccgtc tcctcaaacc gcggagagtg | 4920 |
| tgcaggtgat tacaaagacg atgacgataa gtaataaaca ggaaacagaa gtccatatga | 4980 |
| aatacctatt gcctacggca gccgctggat tgttattact cgcggcccag ccggccatgg | 5040 |
| ccgctagcgc ggccgcagaa caaaaactca tctcagaaga ggatctgaat ggggccgtac | 5100 |
| atcaccacca tcatcatggg agctaagctt ggctgttttg gcggatgaga agattttc | 5160 |
| agcctgatac agattaaatc agaacgcaga agcggtctga taaaacagaa tttgcctggc | 5220 |
| ggcagtagcg cggtggtccc acctgacccc atgccgaact cagaagtgaa acgccgtagc | 5280 |
| gccgatggta gtgtggggtc tccccatgcg agagtaggga actgccaggc atcaaataaa | 5340 |
| acgaaaggct cagtcgaaag actgggcctt tcgttttatc tgttgtttgt cggtgaacgc | 5400 |
| tctcctgagt aggacaaatc cgccgggagc ggatttgaac gttgcgaagc aacggcccgg | 5460 |
| agggaccctgg cgggcaggac gcccgccata aactgccagg catcaaatta agcagaaggc | 5520 |
| catcctgacg gatggccttt ttgcgtttct acaaactctt | 5560 |

<210> SEQ ID NO 95
<211> LENGTH: 6099
<212> TYPE: DNA
<213> ORGANISM: Artificial sequence
<220> FEATURE:
<223> OTHER INFORMATION: plasmid pHCH2CH3YI-TAG

<400> SEQUENCE: 95

| | |
|---|---|
| ttgtttattt ttctaaatac attcaaatat gtatccgctc atgagacaat aaccctgata | 60 |
| aatgcttcaa taatattgaa aaaggaagag tatgagtatt caacatttcc gtgtcgccct | 120 |
| tattcccttt tttgcggcat tttgccttcc tgttttttgct cacccagaaa cgctggtgaa | 180 |
| agtaaaagat gctgaagatc agttgggtgc acgagtgggt tacatcgaac tggatctcaa | 240 |
| cagcggtaag atccttgaga gttttcgccc cgaagaacgt tttccaatga tgagcacttt | 300 |
| taaagttctg ctatgtggcg cggtattatc ccgtgttgac gccgggcaag agcaactcgg | 360 |
| tcgccgcata cactattctc agaatgactt ggttgagtac tcaccagtca cagaaaagca | 420 |
| tcttacggat ggcatgacag taagagaatt atgcagtgct gccataacca tgagtgataa | 480 |
| cactgcggcc aacttacttc tgacaacgat cggaggaccg aaggagctaa ccgcttttttt | 540 |
| gcacaacatg ggggatcatg taactcgcct tgatcgttgg aaccggagct gaatgaagc | 600 |
| cataccaaac gacgagcgtg acaccacgat gcctgtagca atggcaacaa cgttgcgcaa | 660 |
| actattaact ggcgaactac ttactctagc ttcccggcaa caattaatag actggatgga | 720 |
| ggcggataaa gttgcaggac cacttctgcg ctcggccctt ccggctggct ggtttattgc | 780 |
| tgataaatct ggagccggtg agcgtgggtc tcgcggtatc attgcagcac tggggccaga | 840 |
| tggtaagccc tcccgtatcg tagttatcta cacgacgggg agtcaggcaa ctatggatga | 900 |
| acgaaataga cagatcgctg agataggtgc ctcactgatt aagcattggt aactgtcaga | 960 |
| ccaagtttac tcatatatac tttagattga tttaaaactt catttttaat ttaaaaggat | 1020 |
| ctaggtgaag atcctttttg ataatctcat gaccaaaatc ccttaacgtg agttttcgtt | 1080 |
| ccactgagcg tcagaccccg tagaaaagat caaaggatct tcttgagatc ctttttttct | 1140 |
| gcgcgtaatc tgctgcttgc aaacaaaaaa accaccgcta ccagcggtgg tttgtttgcc | 1200 |

```
ggatcaagag ctaccaactc tttttccgaa ggtaactggc ttcagcagag cgcagatacc    1260
aaatactgtc cttctagtgt agccgtagtt aggccaccac ttcaagaact ctgtagcacc    1320
gcctacatac ctcgctctgc taatcctgtt accagtggct gctgccagtg gcgataagtc    1380
gtgtcttacc gggttggact caagacgata gttaccggat aaggcgcagc ggtcgggctg    1440 aacgggggt tcgtgcacac agcccagctt ggagcgaacg acctacaccg aactgagata    1500
cctacagcgt gagcattgag aaagcgccac gcttcccgaa gggagaaagg cggacaggta    1560
tccggtaagc ggcagggtcg aacaggaga gcgcacgagg gagcttccag ggggaaacgc    1620
ctggtatctt tatagtcctg tcgggtttcg ccacctctga cttgagcgtc gattttgtg    1680 atgctcgtca gggggcgga gcctatggaa aaacgccagc aacgcggcct ttttacggtt    1740
cctggccttt tgctggcctt tgctcacat gttctttcct gcgttatccc ctgattctgt    1800
ggataaccgt attaccgcct ttgagtgagc tgataccgct cgccgcagcc gaacgaccga    1860
gcgcagcgag tcagtgagcg aggaagcgga agagcgcctg atgcggtatt ttctccttac    1920
gcatctgtgc ggtatttcac accgcatata tggtgcactc tcagtacaat ctgctctgat    1980
gccgcatagt taagccagta tacactccgc tatcgctacg tgactgggtc atggctgcgc    2040
cccgacaccc gccaacaccc gctgacgcgc cctgacgggc ttgtctgctc ccggcatccg    2100
cttacagaca agctgtgacc gtctccggga gctgcatgtg tcagaggttt tcaccgtcat    2160
caccgaaacg cgcgaggcag ctgcggtaaa gctcatcagc gtggtcgtga agcgattcac    2220
agatgtctgc ctgttcatcc gcgtccagct cgttgagttt ctccagaagc gttaatgtct    2280
ggcttctgat aaagcgggcc atgttaaggg cggttttttc ctgtttggtc acttgatgcc    2340
tccgtgtaag ggggaatttc tgttcatggg ggtaatgata ccgatgaaac gagagaggat    2400
gctcacgata cgggttactg atgatgaaca tgcccggtta ctggaacgtt gtgagggtaa    2460
acaactggcg gtatggatgc ggcgggacca gagaaaaatc actcagggtc aatgccagcg    2520
cttcgttaat acagatgtag gtgttccaca gggtagccag cagcatcctg cgatgcagat    2580
ccggaacata atggtgcagg cgctgactt ccgcgtttcc agactttacg aaacacggaa    2640
accgaagacc attcatgttg ttgctcaggt cgcagacgtt ttgcagcagc agtcgcttca    2700
cgttcgctcg cgtatcggtg attcattctg ctaaccagta aggcaacccc gccagcctag    2760
ccgggtcctc aacgacagga gcacgatcat gcgcacccgt ggccaggacc caacgctgcc    2820
cgagatgcgc cgcgtgcggc tgctggagat ggcggacgcg atggatatgt tctgccaagg    2880 gttggttgc gcattcacag ttctccgcaa gaattgattg gctccaattc ttggagtggt    2940
gaatccgtta gcgaggtgcc gccggcttcc attcaggtcg aggtggcccg gctccatgca    3000
ccgcgacgca acgcggggag gcagacaagg tatagggcgg cgcctacaat ccatgccaac    3060
ccgttccatg tgctcgccga ggcggcataa atcgccgtga cgatcagcgg tccagtgatc    3120
gaagttaggc tggtaagagc cgcgagcgat ccttgaagct gtccctgatg gtcgtcatct    3180
acctgcctgg acagcatggc ctgcaacgcg ggcatcccga tgccgccgga agcgagaaga    3240
atcataatgg ggaaggccat ccagcctcgc gtcgcgaacg ccagcaagac gtagcccagc    3300
gcgtcggcca gcttgcaatt cgcgctaact tacattaatt gcgttgcgct cactgcccgc    3360
tttccagtcg ggaaacctgt cgtgccagct gcattaatga atcggccaac gcgcggggag    3420
aggcggtttg cgtattgggc gccagggtgg ttttctttt caccagtgag acgggcaaca    3480
gctgattgcc cttcaccgcc tggccctgag agagttgcag caagcggtcc acgctggttt    3540
```

-continued

```
gccccagcag gcgaaaatcc tgtttgatgg tggttgacgg cgggatataa catgagctgt    3600
cttcggtatc gtcgtatccc actaccgaga tatccgcacc aacgcgcagc ccggactcgg    3660
taatggcgcg cattgcgccc agcgccatct gatcgttggc aaccagcatc gcagtgggaa    3720
cgatgccctc attcagcatt tgcatggttt gttgaaaacc ggacatggca ctccagtcgc    3780
cttcccgttc cgctatcggc tgaatttgat tgcgagtgag atatttatgc cagccagcca    3840
gacgcagacg cgccgagaca gaacttaatg gtcccgctaa cagcgcgatt tgctgatgac    3900
ccaatgcgac cagatgctcc acgcccagtc gcgtaccgtc ttcatgggag aaaataatac    3960
tgttgatggg tgtctggtca gagacatcaa gaaataacgc cggaacatta gtgcaggcag    4020
cttccacagc aatggcatcc tggtcatcca gcggatagtt aatgatcagc ccactgacgc    4080
gttgcgcgag aagattgtgc accgccgctt tacaggcttc gacgccgctt cgttctacca    4140
tcgacaccac cacgctggca cccagttgat cggcgcgaga tttaatcgcc gcgacaattt    4200
gcgacggcgc gtgcagggcc agactggagg tggcaacgcc aatcagcaac gactgtttgc    4260
ccgccagttg ttgtgccacg cggttgggaa tgtaattcag ctccgccatc gccgcttcca    4320
cttttttccg cgtttttcgca gaaacgtggc tggcctggtt caccacgcgg gaaacggtct    4380
gataagagac accggcatac tctgcgacat cgtataacgt tactggtttc acattccacca    4440
ccctgaattg actctcttcc gggcgctatc atgccatacc gcgaaaggtt ttgcgccatt    4500
cgatggtgtc aacgtaaatg catgccgctt cgccttcgcg cgcgaattgc aagctgatcc    4560
ggagcttatc gactgcacgg tgcaccaatg cttctggcgt caggcagcca tcggaagctg    4620
tggtatggct gtgcaggtcg taaatcactg cataattcgt gtcgctcaag cgcactccc    4680
gttctggata tgttttttg cgccgacatc ataacggttc tggcaaatat tctgaaatga    4740
gctgttgaca attaatcatc ggctcgtata atgtgtggaa ttgtgagcgg ataacaattt    4800
cacacaggaa acagaattcc atatgaaata cctattacca acagcagcag ctgggttatt    4860
attgctcgct gcgcagccgg ccatggccca ggtcaccgtc tcctcagaca aaactcacac    4920
atgcccaccg tgcccagcac ctgaactcct ggggggaccg tcagtcttcc tcttcccccc    4980
aaaacccaag gacaccctca tgatctcccg gaccccctgag gtcacatgcg tggtggtgga    5040
cgtgagccac gaagaccctg aggtcaagtt caactggtac gtggacggcg tggaggtgca    5100
taatgccaag acaaagccgc gggaggagca gtacaacagc acgtaccggg tggtcagcgt    5160
cctcaccgtc ctgcaccagg actggctgaa tggcaaggag tacaagtgca aggtctccaa    5220
caaagccctc ccagccccca tcgagaaaac catctccaaa gccaaagggc agccccgaga    5280
accacaggtg tacaccctgc cccatcccg ggatgagctg accaagaacc aggtcagcct    5340
gacctgcctg gtcaaaggct tctatcccag cgacatcgcc gtggagtggg agagcaatgg    5400
gcagccggag aacaactaca agaccacgcc tcccgtgctg gactccgacg gctccttctt    5460
cctctacagc aagctcaccg tggacaagag caggtggcag caggggaacg tcttctcatg    5520
ctccgtgatg catgaggctc tgcacaacca ctacacgcag aagagcctct ccctgtctcc    5580
gggtaaagcg gccgcagaac aaaaactcat ctcagaagag gatctgaatg ggccgtaca    5640
tcaccaccat catcatggga gctaagcttg gctgttttgg cggatgagag aagattttca    5700
gcctgataca gattaaatca gaacgcagaa gcggtctgat aaaacagaat ttgcctggcg    5760
gcagtagcgc ggtggtccca cctgacccca tgccgaactc agaagtgaaa cgccgtagcg    5820
ccgatggtag tgtggggtct ccccatgcga gagtaggaa ctgccaggca tcaaataaaa    5880
cgaaaggctc agtcgaaaga ctgggccttt cgttttatct gttgtttgtc ggtgaacgct    5940
```

```
ctcctgagta ggacaaatcc gccgggagcg gatttgaacg ttgcgaagca acggcccgga    6000
ggaccctggc gggcaggacg cccgccataa actgccaggc atcaaattaa gcagaaggcc    6060
atcctgacgg atggcctttt tgcgtttcta caaactctt                           6099

<210> SEQ ID NO 96
<211> LENGTH: 6024
<212> TYPE: DNA
<213> ORGANISM: Artificial sequence
<220> FEATURE:
<223> OTHER INFORMATION: plasmid pHCH2CH3Y

<400> SEQUENCE: 96
ttgtttattt ttctaaatac attcaaatat gtatccgctc atgagacaat aaccctgata      60
aatgcttcaa taatattgaa aaaggaagag tatgagtatt caacatttcc gtgtcgccct    120
tattcccttt tttgcggcat tttgccttcc tgttttgct cacccagaaa cgctggtgaa     180
agtaaaagat gctgaagatc agttgggtgc acgagtgggt tacatcgaac tggatctcaa    240
cagcggtaag atccttgaga gttttcgccc cgaagaacgt tttccaatga tgagcacttt    300
taaagttctg ctatgtggcg cggtattatc ccgtgttgac gccgggcaag agcaactcgg    360
tcgccgcata cactattctc agaatgactt ggttgagtac tcaccagtca cagaaaagca    420
tcttacggat ggcatgacag taagagaatt atgcagtgct gccataacca tgagtgataa    480
cactgcggcc aacttacttc tgacaacgat cggaggaccg aaggagctaa ccgcttttt     540 gcacaacatg ggggatcatg taactcgcct tgatcgttgg gaaccggagc tgaatgaagc    600
cataccaaac gacgagcgtg acaccacgat gcctgtagca atggcaacaa cgttgcgcaa    660
actattaact ggcgaactac ttactctagc ttcccggcaa caattaatag actggatgga    720
ggcggataaa gttgcaggac cacttctgcg ctcggccctt ccggctggct ggtttattgc    780
tgataaatct ggagccggtg agcgtgggtc tcgcggtatc attgcagcac tggggccaga    840
tggtaagccc tcccgtatcg tagttatcta cacgacgggg agtcaggcaa ctatggatga    900
acgaaataga cagatcgctg agataggtgc ctcactgatt aagcattggt aactgtcaga    960
ccaagtttac tcatatatac tttagattga tttaaaactt catttttaat ttaaaaggat   1020
ctaggtgaag atcctttttg ataatctcat gaccaaaatc ccttaacgtg agttttcgtt   1080
ccactgagcg tcagaccccg tagaaaagat caaaggatct tcttgagatc ctttttttct   1140
gcgcgtaatc tgctgcttgc aaacaaaaaa accaccgcta ccagcggtgg tttgtttgcc   1200
ggatcaagag ctaccaactc tttttccgaa ggtaactggc ttcagcagag cgcagatacc   1260
aaatactgtc cttctagtgt agccgtagtt aggccaccac ttcaagaact ctgtagcacc   1320
gcctacatac ctcgctctgc taatcctgtt accagtggct gctgccagtg gcgataagtc   1380
gtgtcttacc gggttggact caagacgata gttaccggat aaggcgcagc ggtcgggctg   1440
aacggggggt tcgtgcacac agcccagctt ggagcgaacg acctacaccg aactgagata   1500
cctacagcgt gagcattgag aaagcgccac gcttcccgaa gggagaaagg cggacaggta   1560
tccggtaagc ggcagggtcg gaacaggaga gcgcacgagg gagcttccag ggggaaacgc   1620
ctggtatctt tatagtcctg tcgggtttcg ccacctctga cttgagcgtc gatttttgtg   1680
atgctcgtca ggggggcgga gcctatggaa aaacgccagc aacgcggcct ttttacggtt   1740
cctggccttt tgctggcctt ttgctcacat gttctttcct gcgttatccc ctgattctgt   1800
ggataaccgt attaccgcct ttgagtgagc tgataccgct cgccgcagcc gaacgaccga   1860
```

```
gcgcagcgag tcagtgagcg aggaagcgga agagcgcctg atgcggtatt ttctccttac   1920
gcatctgtgc ggtatttcac accgcatata tggtgcactc tcagtacaat ctgctctgat   1980
gccgcatagt taagccagta tacactccgc tatcgctacg tgactgggtc atggctgcgc   2040
cccgacaccc gccaacaccc gctgacgcgc cctgacgggc ttgtctgctc ccggcatccg   2100
cttacagaca agctgtgacc gtctccggga gctgcatgtg tcagaggttt tcaccgtcat   2160
caccgaaacg cgcgaggcag ctgcggtaaa gctcatcagc gtggtcgtga agcgattcac   2220
agatgtctgc ctgttcatcc gcgtccagct cgttgagttt ctccagaagc gttaatgtct   2280
ggcttctgat aaagcgggcc atgttaaggg cggttttttc ctgtttggtc acttgatgcc   2340
tccgtgtaag ggggaatttc tgttcatggg ggtaatgata ccgatgaaac gagagaggat   2400
gctcacgata cgggttactg atgatgaaca tgcccggtta ctggaacgtt gtgagggtaa   2460
acaactggcg gtatggatgc ggcgggacca gagaaaaatc actcagggtc aatgccagcg   2520
cttcgttaat acagatgtag gtgttccaca gggtagccag cagcatcctg cgatgcagat   2580
ccggaacata atggtgcagg cgctgacttc cgcgtttcc agactttacg aaacacggaa    2640
```

```
ccgccagttg ttgtgccacg cggttgggaa tgtaattcag ctccgccatc gccgcttcca    4320
cttttttccg cgttttcgca gaaacgtggc tggcctggtt caccacgcgg gaaacggtct    4380
gataagagac accggcatac tctgcgacat cgtataacgt tactggtttc acattcacca    4440
ccctgaattg actctcttcc gggcgctatc atgccatacc gcgaaaggtt ttgcgccatt    4500
cgatggtgtc aacgtaaatg catgccgctt cgccttcgcg cgcgaattgc aagctgatcc    4560
ggagcttatc gactgcacgg tgcaccaatg cttctggcgt caggcagcca tcggaagctg    4620
tggtatggct gtgcaggtcg taaatcactg cataattcgt gtcgctcaag gcgcactccc    4680
gttctggata tgttttttg cgccgacatc ataacggttc tggcaaatat tctgaaatga    4740
gctgttgaca attaatcatc ggctcgtata atgtgtggaa ttgtgagcgg ataacaattt    4800
cacacaggaa acagaattcc atatgaaata cctattacca acagcagcag ctgggttatt    4860
attgctcgct gcgcagccgg ccatggccca ggtcaccgtc tcctcagaca aaactcacac    4920
atgcccaccg tgcccagcac ctgaactcct gggggaccg tcagtcttcc tcttccccc    4980 aaaacccaag gacaccctca tgatctcccg gacccctgag gtcacatgcg tggtggtgga    5040
cgtgagccac gaagaccctg aggtcaagtt caactggtac gtggacggcg tggaggtgca    5100
taatgccaag acaaagccgc gggaggagca gtacaacagc acgtaccggg tggtcagcgt    5160
cctcaccgtc ctgcaccagg actggctgaa tggcaaggag tacaagtgca aggtctccaa    5220
caaagccctc ccagccccca tcgagaaaac catctccaaa gccaagggc agccccgaga    5280 accacaggtg tacaccctgc ccccatcccg ggatgagctg accaagaacc aggtcagcct    5340
gacctgcctg gtcaaaggct tctatcccag cgacatcgcc gtggagtggg agagcaatgg    5400
gcagccggag aacaactaca agaccacgcc tcccgtgctg gactccgacg gctccttctt    5460
cctctacagc aagctcaccg tggacaagag caggtggcag caggggaacg tcttctcatg    5520
ctccgtgatg catgaggctc tgcacaacca ctacacgcag aagagcctct ccctgtctcc    5580
gggtaaataa gcttggctgt tttggcggat gagagaagat tttcagcctg atacagatta    5640
aatcagaacg cagaagcggt ctgataaaac agaatttgcc tggcggcagt agcgcggtgg    5700
tcccacctga ccccatgccg aactcagaag tgaaacgccg tagcgccgat ggtagtgtgg    5760
ggtctcccca tgcgagagta gggaactgcc aggcatcaaa taaaacgaaa ggctcagtcg    5820
aaagactggg ccttcgttt tatctgttgt ttgtcggtga acgctctcct gagtaggaca    5880
aatccgccgg gagcggattt gaacgttgcg aagcaacggc ccggaggacc ctggcgggca    5940
ggacgcccgc cataaactgc caggcatcaa attaagcaga aggccatcct gacggatggc    6000 cttttttgcgt tctacaaac tctt                                           6024
```

<210> SEQ ID NO 97
<211> LENGTH: 5866
<212> TYPE: DNA
<213> ORGANISM: Artificial sequence
<220> FEATURE:
<223> OTHER INFORMATION: plasmid p55/Flag/RBS/35cmyc6HisGS

<400> SEQUENCE: 97

```
ttgtttattt ttctaaatac attcaaatat gtatccgctc atgagacaat aaccctgata     60
aatgcttcaa taatattgaa aaaggaagag tatgagtatt caacatttcc gtgtcgccct    120
tattcccttt tttgcggcat tttgccttcc tgttttgct cacccagaaa cgctggtgaa    180
agtaaaagat gctgaagatc agttgggtgc acgagtgggt tacatcgaac tggatctcaa    240
```

-continued

```
cagcggtaag atccttgaga gttttcgccc cgaagaacgt tttccaatga tgagcacttt        300
taaagttctg ctatgtggcg cggtattatc ccgtgttgac gccgggcaag agcaactcgg        360
tcgccgcata cactattctc agaatgactt ggttgagtac tcaccagtca cagaaaagca        420
tcttacggat ggcatgacag taagagaatt atgcagtgct gccataacca tgagtgataa        480
cactgcggcc aacttacttc tgacaacgat cggaggaccg aaggagctaa ccgcttttt         540 gcacaacatg ggggatcatg taactcgcct tgatcgttgg gaaccggagc tgaatgaagc        600
cataccaaac gacgagcgtg acaccacgat gcctgtagca atggcaacaa cgttgcgcaa        660
actattaact ggcgaactac ttactctagc ttcccggcaa caattaatag actggatgga        720
ggcggataaa gttgcaggac cacttctgcg ctcggccctt ccggctggct ggtttattgc        780
tgataaatct ggagccggtg agcgtgggtc tcgcggtatc attgcagcac tggggccaga        840
tggtaagccc tcccgtatcg tagttatcta cacgacgggg agtcaggcaa ctatggatga        900
acgaaataga cagatcgctg ataggtgcc tcactgatt aagcattggt aactgtcaga         960
ccaagtttac tcatatatac tttagattga tttaaaactt catttttaat ttaaaaggat       1020
ctaggtgaag atcctttttg ataatctcat gaccaaaatc ccttaacgtg agttttcgtt       1080
ccactgagcg tcagaccccg tagaaaagat caaaggatct tcttgagatc ctttttttct       1140
gcgcgtaatc tgctgcttgc aaacaaaaaa accaccgcta ccagcggtgg tttgtttgcc       1200
ggatcaagag ctaccaactc tttttccgaa ggtaactggc ttcagcagag cgcagatacc       1260
aaatactgtc cttctagtgt agccgtagtt aggccaccac ttcaagaact ctgtagcacc       1320
gcctacatac ctcgctctgc taatcctgtt accagtggct gctgccagtg gcgataagtc       1380
gtgtcttacc gggttggact caagacgata gttaccggat aaggcgcagc ggtcgggctg       1440
aacggggggt tcgtgcacac agcccagctt ggagcgaacg acctacaccg aactgagata       1500
cctacagcgt gagcattgag aaagcgccac gcttcccgaa gggagaaagg cggacaggta       1560
tccggtaagc ggcagggtcg aacaggaga gcgcacgagg gagcttccag ggggaaacgc        1620
ctggtatctt tatagtcctg tcgggtttcg ccacctctga cttgagcgtc gatttttgtg       1680
atgctcgtca gggggggcgga gcctatggaa aaacgccagc aacgcggcct ttttacggtt      1740
cctggccttt tgctggcctt tgctcacat gttctttcct gcgttatccc ctgattctgt        1800
ggataaccgt attaccgcct ttgagtgagc tgataccgct cgccgcagcc gaacgaccga       1860
gcgcagcgag tcagtgagcg aggaagcgga agagcgcctg atgcggtatt ttctccttac       1920
gcatctgtgc ggtatttcac accgcatata tggtgcactc tcagtacaat ctgctctgat       1980
gccgcatagt taagccagta tacactccgc tatcgctacg tgactgggtc atggctgcgc       2040
cccgacaccc gccaacaccc gctgacgcgc cctgacgggc ttgtctgctc ccggcatccg       2100
cttacagaca agctgtgacc gtctccggga gctgcatgtg tcagaggttt tcaccgtcat       2160
caccgaaacg cgcgaggcag ctgcggtaaa gctcatcagc gtggtcgtga agcgattcac       2220
agatgtctgc ctgttcatcc gcgtccagct cgttgagttt ctccagaagc gttaatgtct       2280
ggcttctgat aaagcgggcc atgttaaggg cggttttttc ctgtttggtc acttgatgcc       2340
tccgtgtaag ggggaatttc tgttcatggg ggtaatgata ccgatgaaac gagagaggat       2400
gctcacgata cgggttactg atgatgaaca tgcccggtta ctggaacgtt gtgagggtaa       2460
acaactggcg gtatggatgc ggcgggacca gagaaaaatc actcagggtc aatgccagcg       2520
cttcgttaat acagatgtag gtgttccaca gggtagccag cagcatcctg cgatgcagat       2580
ccggaacata atggtgcagg cgctgactt ccgcgttcc agactttacg aaacacggaa        2640
```

```
accgaagacc attcatgttg ttgctcaggt cgcagacgtt ttgcagcagc agtcgcttca   2700
cgttcgctcg cgtatcggtg attcattctg ctaaccagta aggcaacccc gccagcctag   2760
ccgggtcctc aacgacagga gcacgatcat gcgcacccgt ggccaggacc caacgctgcc   2820
cgagatgcgc cgcgtgcggc tgctggagat ggcggacgcg atggatatgt tctgccaagg   2880
gttggtttgc gcattcacag ttctccgcaa gaattgattg gctccaattc ttggagtggt   2940
gaatccgtta gcgaggtgcc gccggcttcc attcaggtcg aggtggcccg gctccatgca   3000
ccgcgacgca acgcggggag gcagacaagg tatagggcgg cgcctacaat ccatgccaac   3060
ccgttccatg tgctcgccga ggcggcataa atcgccgtga cgatcagcgg tccagtgatc   3120
gaagttaggc tggtaagagc cgcgagcgat ccttgaagct gtccctgatg gtcgtcatct   3180
acctgcctgg acagcatggc ctgcaacgcg ggcatcccga tgccgccgga agcgagaaga   3240
atcataatgg ggaaggccat ccagcctcgc gtcgcgaacg ccagcaagac gtagcccagc   3300
gcgtcggcca gcttgcaatt cgcgctaact tacattaatt gcgttgcgct cactgcccgc   3360
tttccagtcg ggaaacctgt cgtgccagct gcattaatga atcggccaac gcgcggggag   3420
aggcggtttg cgtattgggc gccagggtgg ttttcttt caccagtgag acgggcaaca   3480
gctgattgcc cttcaccgcc tggccctgag agagttgcag caagcggtcc acgctggttt   3540
gccccagcag gcgaaaatcc tgtttgatgg tggttgacgg cgggatataa catgagctgt   3600
cttcggtatc gtcgtatccc actaccgaga tatccgcacc aacgcgcagc ccggactcgg   3660
taatggcgcg cattgcgccc agcgccatct gatcgttggc aaccagcatc gcagtgggaa   3720
cgatgccctc attcagcatt tgcatggttt gttgaaaacc ggacatggca ctccagtcgc   3780
cttcccgttc cgctatcggc tgaatttgat tgcgagtgag atatttatgc cagccagcca   3840
gacgcagacg cgccgagaca gaacttaatg gtcccgctaa cagcgcgatt tgctgatgac   3900
ccaatgcgac cagatgctcc acgcccagtc gcgtaccgtc ttcatgggag aaaataatac   3960
tgttgatggg tgtctggtca gagacatcaa gaaataacgc cggaacatta gtgcaggcag   4020
cttccacagc aatggcatcc tggtcatcca gcggatagtt aatgatcagc ccactgacgc   4080
gttgcgcgag aagattgtgc accgccgctt tacaggcttc gacgccgctt cgttctacca   4140
tcgacaccac cacgctggca cccagttgat cggcgcgaga tttaatcgcc gcgacaattt   4200
gcgacggcgc gtgcagggcc agactggagg tggcaacgcc aatcagcaac gactgtttgc   4260
ccgccagttg ttgtgccacg cggttgggaa tgtaattcag ctccgccatc gccgcttcca   4320
cttttttccg cgttttcgca gaaacgtggc tggcctggtt caccacgcgg gaaacggtct   4380
gataagagac accggcatac tctgcgacat cgtataacgt tactggtttc acattcacca   4440
ccctgaattg actctcttcc gggcgctatc atgccatacc gcgaaaggtt ttgcgccatt   4500
cgatggtgtc aacgtaaatg catgccgctt cgccttcgcg cgcgaattgc aagctgatcc   4560
ggagcttatc gactgcacgg tgcaccaatg cttctggcgt caggcagcca tcggaagctg   4620
tggtatggct gtgcaggtcg taaatcactg cataattcgt gtcgctcaag gcgcactccc   4680
gttctggata atgttttttg cgccgacatc ataacggttc tggcaaatat tctgaaatga   4740
gctgttgaca attaatcatc ggctcgtata atgtgtggaa ttgtgagcgg ataacaattt   4800
cacacaggaa acagaattcc atatgaaata cctattacca acagcagcag ctgggttatt   4860
attgctcgct gcgcagccgg ccatggccca ggtcaccgtc tcctcaggta ccgtggctgc   4920
accatctgtc ttcatcttcc cgccatctga tgagcagttg aaatctggaa ctgcctctgt   4980
```

| tgtgtgcctg ctgaataact tctatcccag agaggccaaa gtacagtgga aggtggataa | 5040 |
| cgccctccaa tcgggtaact cccaggagag tgtcacagag caggacagca aggacagcac | 5100 |
| ctacagcctc agcagcaccc tgacgctgag caaagcagac tacgagaaac acaaagtcta | 5160 |
| cgcctgcgaa gtcacccatc agggcctgag ctcgccggtg acaaagagct tcaaccgcgg | 5220 |
| agagtgtgca ggtgattaca agacgatga cgataagtaa taaacaggaa acagaagtcc | 5280 |
| atatgaaata cctattgcct acggcagccg ctggattgtt attactcgcg cccagccgg | 5340 |
| ccatggccgc tagcgcggcc gcagaacaaa aactcatctc agaagaggat ctgaatgggg | 5400 |
| ccgtacatca ccaccatcat catgggagct aagcttggct gttttggcgg atgagagaag | 5460 |
| attttcagcc tgatacagat taaatcagaa cgcagaagcg gtctgataaa acagaatttg | 5520 |
| cctggcggca gtagcgcggt ggtcccacct gaccccatgc cgaactcaga agtgaaacgc | 5580 |
| cgtagcgccg atggtagtgt ggggtctccc catgcgagag tagggaactg ccaggcatca | 5640 |
| aataaaacga aggctcagt cgaaagactg ggcctttcgt tttatctgtt gtttgtcggt | 5700 |
| gaacgctctc ctgagtagga caaatccgcc gggagcggat ttgaacgttg cgaagcaacg | 5760 |
| gcccggagga ccctggcggg caggacgccc gccataaact gccaggcatc aaattaagca | 5820 |
| gaaggccatc ctgacggatg ccttttttgc gtttctacaa actctt | 5866 |

<210> SEQ ID NO 98
<211> LENGTH: 6109
<212> TYPE: DNA
<213> ORGANISM: Artificial sequence
<220> FEATURE:
<223> OTHER INFORMATION: plasmid pcKCH1y1-TAG

<400> SEQUENCE: 98

| ttgtttattt ttctaaatac attcaaatat gtatccgctc atgagacaat aaccctgata | 60 |
| aatgcttcaa taatattgaa aaggaagag tatgagtatt caacatttcc gtgtcgccct | 120 |
| tattccctt tttgcggcat tttgccttcc tgttttgct cacccagaaa cgctggtgaa | 180 |
| agtaaaagat gctgaagatc agttgggtgc acgagtgggt tacatcgaac tggatctcaa | 240 |
| cagcggtaag atccttgaga gttttcgccc cgaagaacgt tttccaatga tgagcacttt | 300 |
| taaagttctg ctatgtggcg cggtattatc ccgtgttgac gccgggcaag agcaactcgg | 360 |
| tcgccgcata cactattctc agaatgactt ggttgagtac tcaccagtca cagaaaagca | 420 |
| tcttacggat ggcatgacag taagagaatt atgcagtgct gccataacca tgagtgataa | 480 |
| cactgcggcc aacttacttc tgacaacgat cggaggaccg aaggagctaa ccgcttttt | 540 |
| gcacaacatg gggatcatg taactcgcct tgatcgttgg aaccggagc tgaatgaagc | 600 |
| cataccaaac gacgagcgtg acaccacgat gcctgtagca atggcaacaa cgttgcgcaa | 660 |
| actattaact ggcgaactac ttactctagc ttcccggcaa caattaatag actggatgga | 720 |
| ggcggataaa gttgcaggac cacttctgcg ctcggccctt ccggctggct ggtttattgc | 780 |
| tgataaatct ggagccggtg agcgtgggtc tcgcggtatc attgcagcac tggggccaga | 840 |
| tggtaagccc tcccgtatcg tagttatcta cacgacgggg agtcaggcaa ctatggatga | 900 |
| acgaaataga cagatcgctg agataggtgc ctcactgatt aagcattggt aactgtcaga | 960 |
| ccaagtttac tcatatatac tttagattga tttaaaactt catttttaat ttaaaaggat | 1020 |
| ctaggtgaag atcctttttg ataatctcat gaccaaaatc ccttaacgtg agttttcgtt | 1080 |
| ccactgagcg tcagaccccg tagaaaagat caaaggatc tcttgagatc ctttttttct | 1140 |
| gcgcgtaatc tgctgcttgc aaacaaaaaa accaccgcta ccagcggtgg tttgtttgcc | 1200 |

```
ggatcaagag ctaccaactc tttttccgaa ggtaactggc ttcagcagag cgcagatacc    1260
aaatactgtc cttctagtgt agccgtagtt aggccaccac ttcaagaact ctgtagcacc    1320
gcctacatac ctcgctctgc taatcctgtt accagtggct gctgccagtg gcgataagtc    1380
gtgtcttacc gggttggact caagacgata gttaccggat aaggcgcagc ggtcgggctg    1440 aacgggggt tcgtgcacac agcccagctt ggagcgaacg acctacaccg aactgagata    1500
cctacagcgt gagcattgag aaagcgccac gcttcccgaa gggagaaagg cggacaggta    1560
tccggtaagc ggcagggtcg aacaggaga gcgcacgagg gagcttccag ggggaaacgc    1620
ctggtatctt tatagtcctg tcgggtttcg ccacctctga cttgagcgtc gattttttgtg   1680 atgctcgtca gggggcgga gcctatggaa aaacgccagc aacgcggcct ttttacggtt    1740
cctggccttt tgctggcctt tgctcacat gttctttcct gcgttatccc ctgattctgt     1800
ggataaccgt attaccgcct ttgagtgagc tgataccgct cgccgcagcc gaacgaccga    1860
gcgcagcgag tcagtgagcg aggaagcgga agagcgcctg atgcggtatt ttctccttac    1920
gcatctgtgc ggtatttcac accgcatata tggtgcactc tcagtacaat ctgctctgat    1980
gccgcatagt taagccagta tacactccgc tatcgctacg tgactgggtc atggctgcgc    2040
cccgacaccc gccaacaccc gctgacgcgc cctgacgggc ttgtctgctc ccggcatccg    2100
cttacagaca agctgtgacc gtctccggga gctgcatgtg tcagaggttt tcaccgtcat    2160
caccgaaacg cgcgaggcag ctgcggtaaa gctcatcagc gtggtcgtga agcgattcac    2220
agatgtctgc ctgttcatcc gcgtccagct cgttgagttt ctccagaagc gttaatgtct    2280
ggcttctgat aaagcgggcc atgttaaggg cggttttttc ctgtttggtc acttgatgcc    2340
tccgtgtaag ggggaatttc tgttcatggg ggtaatgata ccgatgaaac gagagaggat    2400
gctcacgata cgggttactg atgatgaaca tgcccggtta ctggaacgtt gtgagggtaa    2460
acaactggcg gtatggatgc ggcgggacca gagaaaaatc actcagggtc aatgccagcg    2520
cttcgttaat acagatgtag gtgttccaca gggtagccag cagcatcctg cgatgcagat    2580
ccggaacata atggtgcagg cgctgactt ccgcgtttcc agactttacg aaacacggaa     2640
accgaagacc attcatgttg ttgctcaggt cgcagacgtt ttgcagcagc agtcgcttca    2700
cgttcgctcg cgtatcggtg attcattctg ctaaccagta aggcaacccc gccagcctag    2760
ccgggtcctc aacgacagga gcacgatcat gcgcacccgt ggccaggacc caacgctgcc    2820
cgagatgcgc cgcgtgcggc tgctggagat ggcggacgcg atggatatgt tctgccaagg    2880 gttggttttgc gcattcacag ttctccgcaa gaattgattg gctccaattc ttggagtggt   2940
gaatccgtta gcgaggtgcc gccggcttcc attcaggtcg aggtggcccg gctccatgca    3000
ccgcgacgca acgcggggag gcagacaagg tatagggcgg cgcctacaat ccatgccaac    3060
ccgttccatg tgctcgccga ggcggcataa atcgccgtga cgatcagcgg tccagtgatc    3120
gaagttaggc tggtaagagc cgcgagcgat ccttgaagct gtccctgatg gtcgtcatct    3180
acctgcctgg acagcatggc ctgcaacgcg ggcatcccga tgccgccgga agcgagaaga    3240
atcataatgg ggaaggccat ccagcctcgc gtcgcgaacg ccagcaagac gtagcccagc    3300
gcgtcggcca gcttgcaatt cgcgctaact tacattaatt gcgttgcgct cactgcccgc    3360
tttccagtcg ggaaacctgt cgtgccagct gcattaatga atcggccaac gcgcggggag    3420
aggcggtttg cgtattgggc gccagggtgg ttttcttttt caccagtgag acgggcaaca    3480
gctgattgcc cttcaccgcc tggccctgag agagttgcag caagcggtcc acgctggttt    3540
```

```
gccccagcag gcgaaaatcc tgtttgatgg tggttgacgg cgggatataa catgagctgt    3600
cttcggtatc gtcgtatccc actaccgaga tatccgcacc aacgcgcagc ccggactcgg    3660
taatggcgcg cattgcgccc agcgccatct gatcgttggc aaccagcatc gcagtgggaa    3720
cgatgccctc attcagcatt tgcatggttt gttgaaaacc ggacatggca ctccagtcgc    3780
cttcccgttc cgctatcggc tgaatttgat tgcgagtgag atatttatgc cagccagcca    3840
gacgcagacg cgccgagaca gaacttaatg gtcccgctaa cagcgcgatt tgctgatgac    3900
ccaatgcgac cagatgctcc acgcccagtc gcgtaccgtc ttcatgggag aaaataatac    3960
tgttgatggg tgtctggtca gagacatcaa gaaataacgc cggaacatta gtgcaggcag    4020
cttccacagc aatggcatcc tggtcatcca gcggatagtt aatgatcagc ccactgacgc    4080
gttgcgcgag aagattgtgc accgccgctt tacaggcttc gacgccgctt cgttctacca    4140
tcgacaccac cacgctggca cccagttgat cggcgcgaga tttaatcgcc gcgacaattt    4200
gcgacggcgc gtgcagggcc agactggagg tggcaacgcc aatcagcaac gactgtttgc    4260
ccgccagttg ttgtgccacg cggttgggaa tgtaattcag ctccgccatc gccgcttcca    4320
cttttttccg cgttttcgca gaaacgtggc tggcctggtt caccacgcgg gaaacggtct    4380
gataagagac accggcatac tctgcgacat cgtataacgt tactggtttc acattccacca    4440
ccctgaattg actctcttcc gggcgctatc atgccatacc gcgaaaggtt ttgcgccatt    4500
cgatggtgtc aacgtaaatg catgccgctt cgccttcgcg cgcgaattgc aagctgatcc    4560
ggagcttatc gactgcacgg tgcaccaatg cttctggcgt caggcagcca tcggaagctg    4620
tggtatggct gtgcaggtcg taaatcactg cataattcgt gtcgctcaag cgcactccc    4680
gttctggata tgttttttg cgccgacatc ataacggttc tggcaaatat tctgaaatga    4740
gctgttgaca attaatcatc ggctcgtata atgtgtggaa ttgtgagcgg ataacaattt    4800
cacacaggaa acagaattcc atatgaaata cctattacca acagcagcag ctgggttatt    4860
attgctcgct cgcagccgg ccatggccca ggtcaccgtc tcctcaggta ccgtggctgc    4920
accatctgtc ttcatcttcc cgccatctga tgagcagttg aaatctggaa ctgcctctgt    4980
tgtgtgcctg ctgaataact tctatcccag agaggccaaa gtacagtgga aggtggataa    5040
cgccctccaa tcgggtaact cccaggagag tgtcacagag caggacagca aggacagcac    5100
ctacagcctc agcagcaccc tgacgctgag caaagcagac tacgagaaac acaaagtcta    5160
cgcctgcgaa gtcaccccatc agggcctgag ctcgccggtg acaaagagct caaccgcgg    5220
agagtgtgca ggtgattaca agacgatga cgataagtaa taaacaggaa acagaagtcc    5280
atatgaaata cctattgcct acggcagccg ctggattgtt attactcgcg gcccagccgg    5340
ccatggccgc tagcaccaag ggcccatcgg tcttccccct ggcaccctcc tccaagagca    5400
cctctggggg cacagcggcc ctgggctgcc tggtcaagga ctacttcccc gaaccggtga    5460
cggtgtcgtg gaactcaggc gccctgacca gcggcgtgca caccttcccg gctgtcctac    5520
agtcctcagg actctactcc ctcagcagcg tagtgaccgt gccctccagc agcttgggca    5580
cccagaccta catctgcaac gtgaatcaca agcccagcaa caccaaggtg gacaagaaag    5640
ttgagcccaa atcttgtgcg gccgcagaac aaaaactcat ctcagaagag gatctgaatg    5700
gggccgtaca tcaccaccat catcatggga gctaagcttg gctgttttgg cggatgagag    5760
aagattttca gcctgataca gattaaatca gaacgcagaa gcggtctgat aaaacagaat    5820
ttgcctggcg gcagtagcgc ggtggtccca cctgacccca tgccgaactc agaagtgaaa    5880
cgccgtagcg ccgatggtag tgtggggtct ccccatgcga gagtagggaa ctgccaggca    5940
```

```
tcaaataaaa cgaaaggctc agtcgaaaga ctgggccttt cgttttatct gttgtttgtc    6000
ggtgaacgct ctcctgagta ggacaaatcc gccgggagcg gatttgaacg ttgcgaagca    6060
gcagaaggcc atcctgacgg atggcctttt tgcgtttcta caaactctt              6109
```

<210> SEQ ID NO 99
<211> LENGTH: 6199
<212> TYPE: DNA
<213> ORGANISM: Artificial sequence
<220> FEATURE:
<223> OTHER INFORMATION: plasmid pcKCH1Hy1-TAG

<400> SEQUENCE: 99

```
ttgtttattt ttctaaatac attcaaatat gtatccgctc atgagacaat aaccctgata     60
aatgcttcaa taatattgaa aaaggaagag tatgagtatt caacatttcc gtgtcgccct    120
tattcccttt tttgcggcat tttgccttcc tgttttgct cacccagaaa cgctggtgaa     180
agtaaaagat gctgaagatc agttgggtgc acgagtgggt tacatcgaac tggatctcaa    240
cagcggtaag atccttgaga gttttcgccc cgaagaacgt tttccaatga tgagcacttt    300
taaagttctg ctatgtggcg cggtattatc ccgtgttgac gccgggcaag agcaactcgg    360
tcgccgcata cactattctc agaatgactt ggttgagtac tcaccagtca cagaaaagca    420
tcttacggat ggcatgacag taagagaatt atgcagtgct gccataacca tgagtgataa    480
cactgcggcc aacttacttc tgacaacgat cggaggaccg aaggagctaa ccgcttttt     540 gcacaacatg ggggatcatg taactcgcct tgatcgttgg gaaccggagc tgaatgaagc    600
cataccaaac gacgagcgtg acaccacgat gcctgtagca atggcaacaa cgttgcgcaa    660
actattaact ggcgaactac ttactctagc ttcccggcaa caattaatag actggatgga    720
ggcggataaa gttgcaggac cacttctgcg ctcggccctt ccggctggct ggtttattgc    780
tgataaatct ggagccggtg agcgtgggtc tcgcggtatc attgcagcac tggggccaga    840
tggtaagccc tcccgtatcg tagttatcta cacgacgggg agtcaggcaa ctatggatga    900
acgaaataga cagatcgctg agataggtgc ctcactgatt aagcattggt aactgtcaga    960
ccaagtttac tcatatatac tttagattga tttaaaactt catttttaat ttaaaaggat   1020
ctaggtgaag atcctttttg ataatctcat gaccaaaatc ccttaacgtg agttttcgtt   1080
ccactgagcg tcagaccccg tagaaaagat caaaggatct tcttgagatc ctttttttct   1140
gcgcgtaatc tgctgcttgc aaacaaaaaa accaccgcta ccagcggtgg tttgtttgcc   1200
ggatcaagag ctaccaactc tttttccgaa ggtaactggc ttcagcagag cgcagatacc   1260
aaatactgtc cttctagtgt agccgtagtt aggccaccac ttcaagaact ctgtagcacc   1320
gcctacatac ctcgctctgc taatcctgtt accagtggct gctgccagtg gcgataagtc   1380
gtgtcttacc gggttggact caagacgata gttaccggat aaggcgcagc ggtcgggctg   1440
aacggggggt tcgtgcacac agcccagctt ggagcgaacg acctacaccg aactgagata   1500
cctacagcgt gagcattgag aaagcgccac gcttcccgaa gggagaaagg cggacaggta   1560
tccggtaagc ggcagggtcg gaacaggaga gcgcacgagg gagcttccag ggggaaacgc   1620
ctggtatctt tatagtcctg tcgggtttcg ccacctctga cttgagcgtc gatttttgtg   1680
atgctcgtca ggggggcgga gcctatggaa aaacgccagc aacgcggcct ttttacggtt   1740
cctggccttt tgctggcctt ttgctcacat gttctttcct gcgttatccc ctgattctgt   1800
ggataaccgt attaccgcct ttgagtgagc tgataccgct cgccgcagcc gaacgaccga   1860
```

-continued

```
gcgcagcgag tcagtgagcg aggaagcgga agagcgcctg atgcggtatt ttctccttac   1920
gcatctgtgc ggtatttcac accgcatata tggtgcactc tcagtacaat ctgctctgat   1980
gccgcatagt taagccagta tacactccgc tatcgctacg tgactgggtc atggctgcgc   2040
cccgacaccc gccaacaccc gctgacgcgc cctgacgggc ttgtctgctc ccggcatccg   2100
cttacagaca agctgtgacc gtctccggga gctgcatgtg tcagaggttt tcaccgtcat   2160
caccgaaacg cgcgaggcag ctgcggtaaa gctcatcagc gtggtcgtga agcgattcac   2220
agatgtctgc ctgttcatcc gcgtccagct cgttgagttt ctccagaagc gttaatgtct   2280
ggcttctgat aaagcgggcc atgttaaggg cggttttttc ctgtttggtc acttgatgcc   2340
tccgtgtaag ggggaatttc tgttcatggg ggtaatgata ccgatgaaac gagagaggat   2400
gctcacgata cggttactg atgatgaaca tgcccggtta ctggaacgtt gtgagggtaa   2460
acaactggcg gtatggatgc ggcgggacca gagaaaaatc actcagggtc aatgccagcg   2520
cttcgttaat acagatgtag gtgttccaca gggtagccag cagcatcctg cgatgcagat   2580
ccggaacata atggtgcagg cgctgacttc cgcgtttcc agactttacg aaacacggaa   2640
accgaagacc attcatgttg ttgctcaggt cgcagacgtt ttgcagcagc agtcgcttca   2700
cgttcgctcg cgtatcggtg attcattctg ctaaccagta aggcaacccc gccagcctag   2760
ccgggtcctc aacgacagga gcacgatcat gcgcacccgt ggccaggacc caacgctgcc   2820
cgagatgcgc cgcgtgcggc tgctggagat ggcggacgcg atggatatgt ctgccaagg   2880 gttggtttgc gcattcacag ttctccgcaa gaattgattg ctccaattc ttggagtggt   2940 gaatccgtta gcgaggtgcc gccggcttcc attcaggtcg aggtggcccg gctccatgca   3000
ccgcgacgca acgcggggag gcagacaagg tatagggcgg cgcctacaat ccatgccaac   3060
ccgttccatg tgctcgccga ggcggcataa atcgccgtga cgatcagcgg tccagtgatc   3120
gaagttaggc tggtaagagc cgcgagcgat ccttgaagct gtccctgatg gtcgtcatct   3180
acctgcctgg acagcatggc ctgcaacgcg ggcatcccga tgccgccgga agcgagaaga   3240
atcataatgg ggaaggccat ccagcctcgc gtcgcgaacg ccagcaagac gtagcccagc   3300
gcgtcggcca gcttgcaatt cgcgctaact tacattaatt gcgttgcgct cactgcccgc   3360
tttccagtcg ggaaacctgt cgtgccagct gcattaatga atcggccaac gcgcggggag   3420
aggcggtttg cgtattgggc gccagggtgg ttttcttttt caccagtgag acgggcaaca   3480
gctgattgcc cttcaccgcc tggccctgag agagttgcag caagcggtcc acgctggttt   3540
gccccagcag gcgaaaatcc tgtttgatgg tggttgacgg cgggatataa catgagctgt   3600
cttcggtatc gtcgtatccc actaccgaga tatccgcacc aacgcgcagc ccggactcgg   3660
taatggcgcg cattgcgccc agcgccatct gatcgttggc aaccagcatc gcagtgggaa   3720
cgatgccctc attcagcatt tgcatggttt gttgaaaacc ggacatggca ctccagtcgc   3780
cttcccgttc cgctatcggc tgaatttgat tgcgagtgag atatttatgc cagccagcca   3840
gacgcagacg cgccgagaca gaacttaatg gtcccgctaa cagcgcgatt tgctgatgac   3900
ccaatgcgac cagatgctcc acgcccagtc gcgtaccgtc ttcatgggag aaaataatac   3960
tgttgatggg tgtctggtca gagacatcaa gaaataacgc cggaacatta gtgcaggcag   4020
cttccacagc aatggcatcc tggtcatcca gcggatagtt aatgatcagc ccactgacgc   4080
gttgcgcgag aagattgtgc accgccgctt tacaggcttc gacgccgctt cgttctacca   4140
tcgacaccac cacgctggca cccagttgat cggcgcgaga tttaatcgcc gcgacaattt   4200
gcgacggcgc gtgcagggcc agactggagg tggcaacgcc aatcagcaac gactgtttgc   4260
```

```
ccgccagttg ttgtgccacg cggttgggaa tgtaattcag ctccgccatc gccgcttcca    4320 cttttttccccg cgttttcgca gaaacgtggc tggcctggtt caccacgcgg gaaacggtct    4380
gataagagac accggcatac tctgcgacat cgtataacgt tactggtttc acattcacca    4440
ccctgaattg actctcttcc gggcgctatc atgccatacc gcgaaaggtt ttgcgccatt    4500
cgatggtgtc aacgtaaatg catgccgctt cgccttcgcg cgcgaattgc aagctgatcc    4560
ggagcttatc gactgcacgg tgcaccaatg cttctggcgt caggcagcca tcggaagctg    4620
tggtatggct gtgcaggtcg taaatcactg cataattcgt gtcgctcaag gcgcactccc    4680
gttctggata tgttttttg cgccgacatc ataacggttc tggcaaatat tctgaaatga    4740
gctgttgaca attaatcatc ggctcgtata atgtgtggaa ttgtgagcgg ataacaattt    4800
cacacaggaa acagaattcc atatgaaata cctattacca acagcagcag ctgggttatt    4860
attgctcgct gcgcagccgg ccatggccca ggtcaccgtc tcctcaggta ccgtggctgc    4920
accatctgtc ttcatcttcc cgccatctga tgagcagttg aaatctggaa ctgcctctgt    4980
tgtgtgcctg ctgaataact ctatcccag agaggccaaa gtacagtgga aggtggataa    5040
cgccctccaa tcgggtaact cccaggagag tgtcacagag caggacagca aggacagcac    5100
ctacagcctc agcagcaccc tgacgctgag caaagcagac tacgagaaac acaaagtcta    5160
cgcctgcgaa gtcacccatc agggcctgag ctcgccggtg acaaagagct tcaaccgcgg    5220
agagtgtgca ggtgattaca agacgatga cgataagtaa taaacaggaa acagaagtcc    5280
atatgaaata cctattgcct acggcagccg ctggattgtt attactcgcg gcccagccgg    5340
ccatggccgc tagcaccaag ggcccatcgg tcttccccct ggcaccctcc tccaagagca    5400
cctctggggg cacagcggcc ctgggctgcc tggtcaagga ctacttcccc gaaccggtga    5460
cggtgtcgtg gaactcaggc gccctgacca gcggcgtgca caccttcccg gctgtcctac    5520
agtcctcagg actctactcc ctcagcagcg tagtgaccgt gccctccagc agcttgggca    5580
cccagaccta catctgcaac gtgaatcaca agcccagcaa caccaaggtg gacaagaaag    5640
ttgagcccaa atcttgtgac aaaactcaca catgcccacc gtgcccagcg gccgcagaac    5700
aaaaactcat ctcagaagag gatctgaatg gggccgtaca tcaccaccat catcatggga    5760
gctaagcttg gctgttttgg cggatgagag aagattttca gcctgataca gattaaatca    5820
gaacgcagaa gcggtctgat aaaacagaat ttgcctggcg gcagtagcgc ggtggtccca    5880
cctgacccca tgccgaactc agaagtgaaa cgccgtagcg ccgatggtag tgtgggtct    5940 ccccatgcga gagtagggaa ctgccaggca tcaaataaaa cgaaaggctc agtcgaaaga    6000
ctgggccttt cgttttatct gttgtttgtc ggtgaacgct ctcctgagta ggacaaatcc    6060
gccgggagcg gatttgaacg ttgcgaagca acggcccgga ggaccctggc gggcaggacg    6120
cccgccataa actgccaggc atcaaattaa gcagaaggcc atcctgacgg atggcctttt    6180
tgcgtttcta caaactctt                                                  6199
```

<210> SEQ ID NO 100
<211> LENGTH: 6064
<212> TYPE: DNA
<213> ORGANISM: Artificial sequence
<220> FEATURE:
<223> OTHER INFORMATION: plasmid pcKCH1yl

<400> SEQUENCE: 100

```
ttgtttattt ttctaaatac attcaaatat gtatccgctc atgagacaat aaccctgata      60
```

```
aatgcttcaa taatattgaa aaaggaagag tatgagtatt caacatttcc gtgtcgccct    120 tattccctt tttgcggcat tttgccttcc tgttttgct cacccagaaa cgctggtgaa      180
agtaaaagat gctgaagatc agttgggtgc acgagtgggt tacatcgaac tggatctcaa    240
cagcggtaag atccttgaga gttttcgccc gaagaacgt tttccaatga tgagcacttt     300
taaagttctg ctatgtggcg cggtattatc ccgtgttgac gccgggcaag agcaactcgg    360
tcgccgcata cactattctc agaatgactt ggttgagtac tcaccagtca cagaaaagca   420
tcttacggat ggcatgacag taagagaatt atgcagtgct gccataacca tgagtgataa    480
cactgcggcc aacttacttc tgacaacgat cggaggaccg aaggagctaa ccgctttttt    540
gcacaacatg ggggatcatg taactcgcct tgatcgttgg aaccggagc tgaatgaagc     600 cataccaaac gacgagcgtg acaccacgat gcctgtagca atggcaacaa cgttgcgcaa    660
actattaact ggcgaactac ttactctagc ttcccggcaa caattaatag actggatgga    720
ggcggataaa gttgcaggac cacttctgcg ctcggcccctt ccggctggct ggtttattgc   780
tgataaatct ggagccggtg agcgtgggtc tcgcggtatc attgcagcac tggggccaga   840
tggtaagccc tcccgtatcg tagttatcta cacgacgggg agtcaggcaa ctatggatga    900
acgaaataga cagatcgctg ataggtgc ctcactgatt aagcattggt aactgtcaga      960
ccaagtttac tcatatatac tttagattga tttaaaactt catttttaat ttaaaaggat   1020
ctaggtgaag atccttttg ataatctcat gaccaaaatc ccttaacgtg agttttcgtt     1080
ccactgagcg tcagaccccg tagaaaagat caaaggatct tcttgagatc ctttttttct   1140
gcgcgtaatc tgctgcttgc aaacaaaaaa accaccgcta ccagcggtgg tttgtttgcc   1200
ggatcaagag ctaccaactc tttttccgaa ggtaactggc ttcagcagag cgcagatacc   1260
aaatactgtc cttctagtgt agccgtagtt aggccaccac ttcaagaact ctgtagcacc   1320
gcctacatac ctcgctctgc taatcctgtt accagtggct gctgccagtg gcgataagtc    1380
gtgtcttacc gggttggact caagacgata gttaccggat aaggcgcagc ggtcgggctg    1440 aacgggggt tcgtgcacac agcccagctt ggagcgaacg acctacaccg aactgagata     1500
cctacagcgt gagcattgag aaagcgccac gcttcccgaa gggagaaagg cggacaggta   1560
tccggtaagc ggcagggtcg aacaggaga gcgcacgagg gagcttccag ggggaaacgc    1620
ctggtatctt tatagtcctg tcgggtttcg ccacctctga cttgagcgtc gatttttgtg   1680
atgctcgtca gggggggcgga gcctatggaa aaacgccagc aacgcggcct ttttacggtt   1740
cctggccttt tgctggcctt ttgctcacat gttctttcct gcgttatccc ctgattctgt    1800
ggataaccgt attaccgcct tgagtgagc tgataccgct cgccgcagcc gaacgaccga    1860
gcgcagcgag tcagtgagcg aggaagcgga agagcgcctg atgcggtatt ttctccttac   1920
gcatctgtgc ggtatttcac accgcatata tggtgcactc tcagtacaat ctgctctgat   1980
gccgcatagt taagccagta tacactccgc tatcgctacg tgactgggtc atggctgcgc   2040
cccgacaccc gccaacaccc gctgacgcgc cctgacgggc ttgtctgctc ccggcatccg   2100
cttacagaca agctgtgacc gtctccggga gctgcatgtg tcagaggttt tcaccgtcat   2160
caccgaaacg cgcgaggcag ctgcggtaaa gctcatcagc gtggtcgtga agcgattcac   2220
agatgtctgc ctgttcatcc gcgtccagct cgttgagttt ctccagaagc gttaatgtct   2280
ggcttctgat aaagcgggcc atgttaaggg cggttttttc ctgtttggtc acttgatgcc   2340
tccgtgtaag ggggaatttc tgttcatggg ggtaatgata ccgatgaaac gagagaggat   2400
gctcacgata cgggttactg atgatgaaca tgcccggtta ctggaacgtt gtgagggtaa   2460
```

```
acaactggcg gtatggatgc ggcgggacca gagaaaaatc actcagggtc aatgccagcg   2520
cttcgttaat acagatgtag gtgttccaca gggtagccag cagcatcctg cgatgcagat   2580
ccggaacata atggtgcagg gcgctgactt ccgcgtttcc agactttacg aaacacggaa   2640
accgaagacc attcatgttg ttgctcaggt cgcagacgtt ttgcagcagc agtcgcttca   2700
cgttcgctcg cgtatcggtg attcattctg ctaaccagta aggcaacccc gccagcctag   2760
ccgggtcctc aacgacagga gcacgatcat gcgcacccgt ggccaggacc caacgctgcc   2820
cgagatgcgc cgcgtgcggc tgctggagat ggcggacgcg atggatatgt tctgccaagg   2880
gttggtttgc gcattcacag ttctccgcaa gaattgattg gctccaattc ttggagtggt   2940
gaatccgtta gcgaggtgcc gccggcttcc attcaggtcg aggtggcccg gctccatgca   3000
ccgcgacgca acgcggggag gcagacaagg tatagggcgg cgcctacaat ccatgccaac   3060
ccgttccatg tgctcgccga ggcggcataa atcgccgtga cgatcagcgg tccagtgatc   3120
gaagttaggc tggtaagagc cgcgagcgat ccttgaagct gtccctgatg gtcgtcatct   3180
acctgcctgg acagcatggc ctgcaacgcg ggcatcccga tgccgccgga agcgagaaga   3240
atcataatgg ggaaggccat ccagcctcgc gtcgcgaacg ccagcaagac gtagcccagc   3300
gcgtcggcca gcttgcaatt cgcgctaact tacattaatt gcgttgcgct cactgcccgc   3360
tttccagtcg ggaaacctgt cgtgccagct gcattaatga atcggccaac gcgcggggag   3420
aggcggtttg cgtattgggc gccagggtgg ttttctttt caccagtgag acgggcaaca   3480
gctgattgcc cttcaccgcc tggccctgag agagttgcag caagcggtcc acgctggttt   3540
gccccagcag gcgaaaatcc tgtttgatgg tggttgacgg cgggatataa catgagctgt   3600
cttcggtatc gtcgtatccc actaccgaga tatccgcacc aacgcgcagc ccggactcgg   3660
taatggcgcg cattgcgccc agcgccatct gatcgttggc aaccagcatc gcagtgggaa   3720
cgatgccctc attcagcatt tgcatggttt gttgaaaacc ggacatggca ctccagtcgc   3780
cttcccgttc cgctatcggc tgaatttgat tgcgagtgag atatttatgc cagccagcca   3840
gacgcagacg cgccgagaca gaacttaatg gtcccgctaa cagcgcgatt tgctgatgac   3900
ccaatgcgac cagatgctcc acgcccagtc gcgtaccgtc ttcatgggag aaaataatac   3960
tgttgatggg tgtctggtca gagacatcaa gaaataacgc cggaacatta gtgcaggcag   4020
cttccacagc aatggcatcc tggtcatcca gcggatagtt aatgatcagc ccactgacgc   4080
gttgcgcgag aagattgtgc accgccgctt acaggcttc gacgccgctt cgttctacca   4140
tcgacaccac cacgctggca cccagttgat cggcgcgaga tttaatcgcc gcgacaattt   4200
gcgacggcgc gtgcagggcc agactggagg tggcaacgcc aatcagcaac gactgtttgc   4260
ccgccagttt ttgtgccacg cggttgggaa tgtaattcag ctccgccatc gccgcttcca   4320
cttttttccg cgttttcgca gaaacgtggc tggcctggtt caccacgcgg gaaacggtct   4380
gataagagac accggcatac tctgcgacat cgtataacgt tactggtttc acattccacca   4440
ccctgaattg actctcttcc gggcgctatc atgccatacc gcgaaaggtt ttgcgccatt   4500
cgatggtgtc aacgtaaatg catgccgctt cgccttcgcg cgcgaattgc aagctgatcc   4560
ggagcttatc gactgcacgg tgcaccaatg cttctggcgt caggcagcca tcggaagctg   4620
tggtatggct gtgcaggtcg taaatcactg cataattcgt gtcgctcaag gcgcactccc   4680
gttctggata atgttttttg cgccgacatc ataacggttc tggcaaatat tctgaaatga   4740
gctgttgaca attaatcatc ggctcgtata atgtgtggaa ttgtgagcgg ataacaattt   4800
```

| | | |
|---|---|---|
| cacacaggaa acagaattcc atatgaaata cctattacca acagcagcag ctgggttatt | 4860 |
| attgctcgct gcgcagccgg ccatggccca ggtcaccgtc tcctcaggta ccgtggctgc | 4920 |
| accatctgtc ttcatcttcc cgccatctga tgagcagttg aaatctggaa ctgcctctgt | 4980 |
| tgtgtgcctg ctgaataact ctatcccag agaggccaaa gtacagtgga aggtggataa | 5040 |
| cgccctccaa tcgggtaact cccaggagag tgtcacagag caggacagca aggacagcac | 5100 |
| ctacagcctc agcagcaccc tgacgctgag caaagcagac tacgagaaac acaaagtcta | 5160 |
| cgcctgcgaa gtcaccccatc agggcctgag ctcgccggtg acaaagagct caaccgcgg | 5220 |
| agagtgttaa taaacaggaa acagaagtcc atatgaaata cctattgcct acggcagccg | 5280 |
| ctggattgtt attactcgcg gcccagccgg ccatggccgc tagcaccaag ggcccatcgg | 5340 |
| tcttccccct ggcaccctcc tccaagagca cctctggggg cacagcggcc ctgggctgcc | 5400 |
| tggtcaagga ctacttcccc gaaccggtga cggtgtcgtg gaactcaggc gccctgacca | 5460 |
| gcggcgtgca caccttcccg gctgtcctac agtcctcagg actctactcc ctcagcagcg | 5520 |
| tagtgaccgt gccctccagc agcttgggca cccagaccta catctgcaac gtgaatcaca | 5580 |
| agcccagcaa caccaaggtg gacaagaaag ttgagcccaa atcttgttaa gcttggctgt | 5640 |
| tttggcggat gagagaagat tttcagcctg atacagatta aatcagaacg cagaagcggt | 5700 |
| ctgataaaac agaatttgcc tggcggcagt agcgcggtgg tcccacctga ccccatgccg | 5760 |
| aactcagaag tgaaacgccg tagcgccgat ggtagtgtgg ggtctcccca tgcgagagta | 5820 |
| gggaactgcc aggcatcaaa taaaacgaaa ggctcagtcg aaagactggg cctttcgttt | 5880 |
| tatctgttgt ttgtcggtga cgctctcct gagtaggaca atccgccgg gagcggattt | 5940 |
| gaacgttgcg aagcaacggc ccggaggacc ctggcgggca ggacgcccgc cataaactgc | 6000 |
| caggcatcaa attaagcaga aggccatcct gacggatggc cttttttgcgt ttctacaaac | 6060 |
| tctt | 6064 |

<210> SEQ ID NO 101
<211> LENGTH: 6094
<212> TYPE: DNA
<213> ORGANISM: Artificial sequence
<220> FEATURE:
<223> OTHER INFORMATION: plasmid pcKCH1Hy1

<400> SEQUENCE: 101

| | | |
|---|---|---|
| ttgtttattt ttctaaatac attcaaatat gtatccgctc atgagacaat aaccctgata | 60 |
| aatgcttcaa taatattgaa aaggaagag tatgagtatt caacatttcc gtgtcgccct | 120 |
| tattcccttt tttgcggcat tttgccttcc tgttttgct cacccagaaa cgctggtgaa | 180 |
| agtaaaagat gctgaagatc agttgggtgc acgagtgggt tacatcgaac tggatctcaa | 240 |
| cagcggtaag atccttgaga gttttcgccc cgaagaacgt tttccaatga tgagcacttt | 300 |
| taaagttctg ctatgtggcg cggtattatc ccgtgttgac gccgggcaag agcaactcgg | 360 |
| tcgccgcata cactattctc agaatgactt ggttgagtac tcaccagtca cagaaaagca | 420 |
| tcttacggat ggcatgacag taagagaatt atgcagtgct gccataacca tgagtgataa | 480 |
| cactgcggcc aacttacttc tgacaacgat cggaggaccg aaggagctaa ccgcttttt | 540 |
| gcacaacatg gggatcatg taactcgcct tgatcgttgg gaaccggagc tgaatgaagc | 600 |
| cataccaaac gacgagcgtg acaccacgat gcctgtagca atggcaacaa cgttgcgcaa | 660 |
| actattaact ggcgaactac ttactctagc ttcccggcaa caattaatag actggatgga | 720 |
| ggcggataaa gttgcaggac cacttctgcg ctcggccctt ccggctggct ggtttattgc | 780 |

```
tgataaatct ggagccggtg agcgtgggtc tcgcggtatc attgcagcac tggggccaga    840
tggtaagccc tcccgtatcg tagttatcta cacgacgggg agtcaggcaa ctatggatga    900
acgaaataga cagatcgctg agataggtgc ctcactgatt aagcattggt aactgtcaga    960
ccaagtttac tcatatatac tttagattga tttaaaactt catttttaat ttaaaaggat   1020
ctaggtgaag atccttttg ataatctcat gaccaaaatc ccttaacgtg agttttcgtt   1080
ccactgagcg tcagaccccg tagaaaagat caaaggatct tcttgagatc ctttttttct   1140
gcgcgtaatc tgctgcttgc aaacaaaaaa accaccgcta ccagcggtgg tttgtttgcc   1200
ggatcaagag ctaccaactc tttttccgaa ggtaactggc ttcagcagag cgcagatacc   1260
aaatactgtc cttctagtgt agccgtagtt aggccaccac ttcaagaact ctgtagcacc   1320
gcctacatac ctcgctctgc taatcctgtt accagtggct gctgccagtg gcgataagtc   1380
gtgtcttacc gggttggact caagacgata gttaccggat aaggcgcagc ggtcgggctg   1440
aacggggggt tcgtgcacac agcccagctt ggagcgaacg acctacaccg aactgagata   1500
cctacagcgt gagcattgag aaagcgccac gcttcccgaa gggagaaagg cggacaggta   1560
tccggtaagc ggcagggtcg gaacaggaga gcgcacgagg gagcttccag ggggaaacgc   1620
ctggtatctt tatagtcctg tcgggtttcg ccacctctga cttgagcgtc gatttttgtg   1680
atgctcgtca gggggggcgga gcctatggaa aaacgccagc aacgcggcct ttttacggtt   1740
cctggccttt tgctggcctt tgctcacat gttctttcct gcgttatccc ctgattctgt   1800
ggataaccgt attaccgcct ttgagtgagc tgataccgct cgccgcagcc gaacgaccga   1860
gcgcagcgag tcagtgagcg aggaagcgga agagcgcctg atgcggtatt ttctccttac   1920
gcatctgtgc ggtatttcac accgcatata tggtgcactc tcagtacaat ctgctctgat   1980
gccgcatagt taagccagta tacactccgc tatcgctacg tgactgggtc atggctgcgc   2040
cccgacaccc gccaacaccc gctgacgcgc cctgacgggc ttgtctgctc ccggcatccg   2100
cttacagaca agctgtgacc gtctccggga gctgcatgtg tcagaggttt tcaccgtcat   2160
caccgaaacg cgcgaggcag ctgcggtaaa gctcatcagc gtggtcgtga agcgattcac   2220
agatgtctgc ctgttcatcc gcgtccagct cgttgagttt ctccagaagc gttaatgtct   2280
ggcttctgat aaagcgggcc atgttaaggg cggttttttc ctgtttggtc acttgatgcc   2340
tccgtgtaag ggggaatttc tgttcatggg ggtaatgata ccgatgaaac gagagaggat   2400
gctcacgata cgggttactg atgatgaaca tgcccggtta ctggaacgtt gtgagggtaa   2460
acaactggcg gtatggatgc ggcgggacca gagaaaaatc actcagggtc aatgccagcg   2520
cttcgttaat acagatgtag gtgttccaca gggtagccag cagcatcctg cgatgcagat   2580
ccggaacata atggtgcagg cgctgacttc cgcgtttcc agactttacg aaacacggaa   2640
accgaagacc attcatgttg ttgctcaggt cgcagacgtt ttgcagcagc agtcgcttca   2700
cgttcgctcg cgtatcggtg attcattctg ctaaccagta aggcaacccc gccagcctag   2760
ccgggtcctc aacgacagga gcacgatcat gcgcacccgt ggccaggacc caacgctgcc   2820
cgagatgcgc cgcgtgcggc tgctggagat ggcggacgcg atggatatgt tctgccaagg   2880
gttggtttgc gcattcacag ttctccgcaa gaattgattg gctccaattc ttggagtggt   2940
gaatccgtta gcgaggtgcc gccggcttcc attcaggtcg aggtggcccg gctccatgca   3000
ccgcgacgca acgcggggag gcagacaagg tatagggcgg cgcctacaat ccatgccaac   3060
ccgttccatg tgctcgccga ggcggcataa atcgccgtga cgatcagcgg tccagtgatc   3120
```

```
gaagttaggc tggtaagagc cgcgagcgat ccttgaagct gtccctgatg gtcgtcatct  3180
acctgcctgg acagcatggc ctgcaacgcg ggcatcccga tgccgccgga agcgagaaga  3240
atcataatgg ggaaggccat ccagcctcgc gtcgcgaacg ccagcaagac gtagcccagc  3300
gcgtcggcca gcttgcaatt cgcgctaact tacattaatt gcgttgcgct cactgcccgc  3360
tttccagtcg ggaaacctgt cgtgccagct gcattaatga atcggccaac gcgcggggag  3420
aggcggtttg cgtattgggc gccagggtgg ttttcttttt caccagtgag acgggcaaca  3480
gctgattgcc cttcaccgcc tggccctgag agagttgcag caagcggtcc acgctggttt  3540
gccccagcag gcgaaaatcc tgtttgatgg tggttgacgg cgggatataa catgagctgt  3600
cttcggtatc gtcgtatccc actaccgaga tatccgcacc aacgcgcagc ccggactcgg  3660
taatggcgcg cattgcgccc agcgccatct gatcgttggc aaccagcatc gcagtgggaa  3720
cgatgccctc attcagcatt tgcatggttt gttgaaaacc ggacatggca ctccagtcgc  3780
cttcccgttc cgctatcggc tgaatttgat tgcgagtgag atatttatgc cagccagcca  3840
gacgcagacg cgccgagaca gaacttaatg gtcccgctaa cagcgcgatt tgctgatgac  3900
ccaatgcgac cagatgctcc acgcccagtc gcgtaccgtc ttcatgggag aaaataatac  3960
tgttgatggg tgtctggtca gagacatcaa gaaataacgc cggaacatta gtgcaggcag  4020
cttccacagc aatggcatcc tggtcatcca gcggatagtt aatgatcagc ccactgacgc  4080
gttgcgcgag aagattgtgc accgccgctt tacaggcttc gacgccgctt cgttctacca  4140
tcgacaccac cacgctggca cccagttgat cggcgcgaga tttaatcgcc gcgacaattt  4200
gcgacggcgc gtgcagggcc agactggagg tggcaacgcc aatcagcaac gactgtttgc  4260
ccgccagttg ttgtgccacg cggttgggaa tgtaattcag ctccgccatc gccgcttcca  4320
cttttttcccg cgttttcgca gaaacgtggc tggcctggtt caccacgcgg gaaacggtct  4380
gataagagac accggcatac tctgcgacat cgtataacgt tactggtttc acattcacca  4440
ccctgaattg actctcttcc gggcgctatc atgccatacc gcgaaaggtt ttgcgccatt  4500
cgatggtgtc aacgtaaatg catgccgctt cgccttcgcg cgcgaattgc aagctgatcc  4560
ggagcttatc gactgcacgg tgcaccaatg cttctggcgt caggcagcca tcggaagctg  4620
tggtatggct gtgcaggtcg taaatcactg cataattcgt gtcgctcaag gcgcactccc  4680
gttctggata atgttttttg cgccgacatc ataacggttc tggcaaatat tctgaaatga  4740
gctgttgaca attaatcatc ggctcgtata atgtgtggaa ttgtgagcgg ataacaattt  4800
cacacaggaa acagaattcc atatgaaata cctattacca acagcagcag ctgggttatt  4860
attgctcgct gcgcagccgg ccatggccca ggtcaccgtc tcctcaggta ccgtggctgc  4920
accatctgtc ttcatcttcc cgccatctga tgagcagttg aaatctggaa ctgcctctgt  4980
tgtgtgcctg ctgaataact tctatcccag agaggccaaa gtacagtgga aggtggataa  5040
cgccctccaa tcgggtaact cccaggagag tgtcacagag caggacagca aggacagcac  5100
ctacagcctc agcagcaccc tgacgctgag caaagcagac tacgagaaac acaaagtcta  5160
cgcctgcgaa gtcacccatc agggcctgag ctcgccggtg acaaagagct tcaaccgcgg  5220
agagtgttaa taaacaggaa acagaagtcc atatgaaata cctattgcct acggcagccg  5280
ctggattgtt attactcgcg gcccagccgg ccatggccgc tagcaccaag ggcccatcgg  5340
tcttcccccct ggcaccctcc tccaagagca cctctggggg cacagcggcc ctgggctgcc  5400
tggtcaagga ctacttcccc gaaccggtga cggtgtcgtg gaactcaggc gccctgacca  5460
gcggcgtgca caccttcccg gctgtcctac agtcctcagg actctactcc ctcagcagcg  5520
```

| | |
|---|---|
| tagtgaccgt gccctccagc agcttgggca cccagaccta catctgcaac gtgaatcaca | 5580 |
| agcccagcaa caccaaggtg gacaagaaag ttgagcccaa atcttgtgac aaaactcaca | 5640 |
| catgcccacc gtgcccataa gcttggctgt tttggcggat gagagaagat tttcagcctg | 5700 |
| atacagatta aatcagaacg cagaagcggt ctgataaaac agaatttgcc tggcggcagt | 5760 |
| agcgcggtgg tcccacctga ccccatgccg aactcagaag tgaaacgccg tagcgccgat | 5820 |
| ggtagtgtgg ggtctcccca tgcgagagta gggaactgcc aggcatcaaa taaaacgaaa | 5880 |
| ggctcagtcg aaagactggg cctttcgttt tatctgttgt ttgtcggtga acgctctcct | 5940 |
| gagtaggaca atccgccgg gagcggattt gaacgttgcg aagcaacggc ccggaggacc | 6000 |
| ctggcgggca ggacgcccgc cataaactgc caggcatcaa attaagcaga aggccatcct | 6060 |
| gacggatggc cttttttgcgt ttctacaaac tctt | 6094 |

<210> SEQ ID NO 102
<211> LENGTH: 6745
<212> TYPE: DNA
<213> ORGANISM: Artificial sequence
<220> FEATURE:
<223> OTHER INFORMATION: plasmid pMabyl

<400> SEQUENCE: 102

| | |
|---|---|
| ttgtttattt ttctaaatac attcaaatat gtatccgctc atgagacaat aaccctgata | 60 |
| aatgcttcaa taatattgaa aaaggaagag tatgagtatt caacatttcc gtgtcgccct | 120 |
| tattcccttt tttgcggcat tttgccttcc tgttttttgct cacccagaaa cgctggtgaa | 180 |
| agtaaaagat gctgaagatc agttgggtgc acgagtgggt tacatcgaac tggatctcaa | 240 |
| cagcggtaag atccttgaga gttttcgccc cgaagaacgt tttccaatga tgagcacttt | 300 |
| taaagttctg ctatgtggcg cggtattatc ccgtgttgac gccgggcaag agcaactcgg | 360 |
| tcgccgcata cactattctc agaatgactt ggttgagtac tcaccagtca cagaaaagca | 420 |
| tcttacggat ggcatgacag taagagaatt atgcagtgct gccataacca tgagtgataa | 480 |
| cactgcggcc aacttacttc tgacaacgat cggaggaccg aaggagctaa ccgcttttttt | 540 |
| gcacaacatg gggatcatg taactcgcct tgatcgttgg gaaccggagc tgaatgaagc | 600 |
| cataccaaac gacgagcgtg acaccacgat gcctgtagca atggcaacaa cgttgcgcaa | 660 |
| actattaact ggcgaactac ttactctagc ttcccggcaa caattaatag actggatgga | 720 |
| ggcggataaa gttgcaggac cacttctgcg ctcggccctt ccggctggct ggtttattgc | 780 |
| tgataaatct ggagccggtg agcgtgggtc tcgcggtatc attgcagcac tggggccaga | 840 |
| tggtaagccc tcccgtatcg tagttatcta cacgacgggg agtcaggcaa ctatggatga | 900 |
| acgaaataga cagatcgctg agataggtgc ctcactgatt aagcattggt aactgtcaga | 960 |
| ccaagtttac tcatatatac tttagattga tttaaaactt catttttaat ttaaaaggat | 1020 |
| ctaggtgaag atcctttttg ataatctcat gaccaaaatc ccttaacgtg agttttcgtt | 1080 |
| ccactgagcg tcagaccccg tagaaaagat caaaggatct tcttgagatc cttttttttct | 1140 |
| gcgcgtaatc tgctgcttgc aaacaaaaaa accaccgcta ccagcggtgg tttgtttgcc | 1200 |
| ggatcaagag ctaccaactc tttttccgaa ggtaactggc ttcagcagag cgcagatacc | 1260 |
| aaatactgtc cttctagtgt agccgtagtt aggccaccac ttcaagaact ctgtagcacc | 1320 |
| gcctacatac ctcgctctgc taatcctgtt accagtggct gctgccagtg gcgataagtc | 1380 |
| gtgtcttacc gggttggact caagacgata gttaccggat aaggcgcagc ggtcgggctg | 1440 |

```
aacgggggggt tcgtgcacac agcccagctt ggagcgaacg acctacaccg aactgagata  1500
cctacagcgt gagcattgag aaagcgccac gcttcccgaa gggagaaagg cggacaggta  1560
tccggtaagc ggcagggtcg gaacaggaga gcgcacgagg gagcttccag ggggaaacgc  1620
ctggtatctt tatagtcctg tcgggtttcg ccacctctga cttgagcgtc gattttttgtg  1680
atgctcgtca gggggggcgga gcctatggaa aaacgccagc aacgcggcct ttttacggtt  1740
cctggccttt tgctggcctt tgctcacat gttctttcct gcgttatccc ctgattctgt  1800
ggataaccgt attaccgcct ttgagtgagc tgataccgct cgccgcagcc gaacgaccga  1860
gcgcagcgag tcagtgagcg aggaagcgga agagcgcctg atgcggtatt ttctccttac  1920
gcatctgtgc ggtatttcac accgcatata tggtgcactc tcagtacaat ctgctctgat  1980
gccgcatagt taagccagta tacactccgc tatcgctacg tgactgggtc atggctgcgc  2040
cccgacaccc gccaacaccc gctgacgcgc cctgacgggc ttgtctgctc ccggcatccg  2100
cttacagaca gctgtgaccc gtctccggga gctgcatgtg tcagaggttt tcaccgtcat  2160
caccgaaacg cgcgaggcag ctgcggtaaa gctcatcagc gtggtcgtga agcgattcac  2220
agatgtctgc ctgttcatcc gcgtccagct cgttgagttt ctccagaagc gttaatgtct  2280
ggcttctgat aaagcgggcc atgttaaggg cggttttttc ctgtttggtc acttgatgcc  2340
tccgtgtaag ggggaatttc tgttcatggg ggtaatgata ccgatgaaac gagagaggat  2400
gctcacgata cgggttactg atgatgaaca tgcccggtta ctggaacgtt gtgagggtaa  2460
acaactggcg gtatggatgc ggcgggacca gagaaaaatc actcagggtc aatgccagcg  2520
cttcgttaat acagatgtag gtgttccaca gggtagccag cagcatcctg cgatgcagat  2580
ccggaacata atggtgcagg gcgctgactt ccgcgtttcc agactttacg aaacacggaa  2640
accgaagacc attcatgttg ttgctcaggt cgcagacgtt ttgcagcagc agtcgcttca  2700
cgttcgctcg cgtatcggtg attcattctg ctaaccagta aggcaacccc gccagcctag  2760
ccgggtcctc aacgacagga gcacgatcat gcgcacccgt ggccaggacc caacgctgcc  2820
cgagatgcgc cgcgtgcggc tgctggagat ggcggacgcg atggatatgt tctgccaagg  2880
gttggttttgc gcattcacag ttctccgcaa gaattgattg gctccaattc ttggagtggt  2940
gaatccgtta gcgaggtgcc gccggcttcc attcaggtcg aggtggcccg gctccatgca  3000
ccgcgacgca acgcggggag gcagacaagg tatagggcgg cgcctacaat ccatgccaac  3060
ccgttccatg tgctcgccga ggcggcataa atcgccgtga cgatcagcgg tccagtgatc  3120
gaagttaggc tggtaagagc cgcgagcgat ccttgaagct gtccctgatg gtcgtcatct  3180
acctgcctgg acagcatggc ctgcaacgcg ggcatcccga tgccgccgga agcgagaaga  3240
atcataatgg ggaaggccat ccagcctcgc gtcgcgaacg ccagcaagac gtagcccagc  3300
gcgtcggcca gcttgcaatt cgcgctaact tacattaatt gcgttgcgct cactgcccgc  3360
tttccagtcg ggaaacctgt cgtgccagct gcattaatga atcggccaac gcgcggggag  3420
aggcggtttg cgtattgggc gccagggtgg ttttcttttt caccagtgag acgggcaaca  3480
gctgattgcc cttcaccgcc tggccctgag agagttgcag caagcggtcc acgctggttt  3540
gccccagcag gcgaaaatcc tgtttgatgg tggttgacgg cgggatataa catgagctgt  3600
cttcggtatc gtcgtatccc actaccgaga tatccgcacc aacgcgcagc ccggactcgg  3660
taatggcgcg cattgcgccc agcgccatct gatcgttggc aaccagcatc gcagtgggaa  3720
cgatgccctc attcagcatt tgcatggttt gttgaaaacc ggacatggca ctccagtcgc  3780
cttcccgttc cgctatcggc tgaatttgat tgcgagtgag atatttatgc cagccagcca  3840
```

```
gacgcagacg cgccgagaca gaacttaatg gtcccgctaa cagcgcgatt tgctgatgac    3900
ccaatgcgac cagatgctcc acgcccagtc gcgtaccgtc ttcatgggag aaaataatac    3960
tgttgatggg tgtctggtca gagacatcaa gaaataacgc cggaacatta gtgcaggcag    4020
cttccacagc aatggcatcc tggtcatcca gcggatagtt aatgatcagc ccactgacgc    4080
gttgcgcgag aagattgtgc accgccgctt tacaggcttc gacgccgctt cgttctacca    4140
tcgacaccac cacgctggca cccagttgat cggcgcgaga tttaatcgcc gcgacaattt    4200
gcgacggcgc gtgcagggcc agactggagg tggcaacgcc aatcagcaac gactgtttgc    4260
ccgccagttg ttgtgccacg cggttgggaa tgtaattcag ctccgccatc gccgcttcca    4320
cttttttcccg cgttttcgca gaaacgtggc tggcctggtt caccacgcgg gaaacggtct    4380
gataagagac accggcatac tctgcgacat cgtataacgt tactggtttc acattcacca    4440
ccctgaattg actctcttcc gggcgctatc atgccatacc gcgaaaggtt ttgcgccatt    4500
cgatggtgtc aacgtaaatg catgccgctt cgccttcgcg cgcgaattgc aagctgatcc    4560
ggagcttatc gactgcacgg tgcaccaatg cttctggcgt caggcagcca tcggaagctg    4620
tggtatggct gtgcaggtcg taaatcactg cataattcgt gtcgctcaag gcgcactccc    4680
gttctggata atgtttttg cgccgacatc ataacggttc tggcaaatat tctgaaatga    4740
gctgttgaca attaatcatc ggctcgtata atgtgtggaa ttgtgagcgg ataacaattt    4800
cacacaggaa acagaattcc atatgaaata cctattacca acagcagcag ctgggttatt    4860
attgctcgct gcgcagccgg ccatggccca ggtcaccgtc tcctcaggta ccgtggctgc    4920
accatctgtc ttcatcttcc cgccatctga tgagcagttg aaatctggaa ctgcctctgt    4980
tgtgtgcctg ctgaataact tctatcccag agaggccaaa gtacagtgga aggtggataa    5040
cgccctccaa tcgggtaact cccaggagag tgtcacagag caggacagca aggacagcac    5100
ctacagcctc agcagcaccc tgacgctgag caaagcagac tacgagaaac acaaagtcta    5160
cgcctgcgaa gtcacccatc agggcctgag ctcgccggtg acaaagagct caaccgcgg    5220
agagtgttaa taaacaggaa acagaagtcc atatgaaata cctattgcct acggcagccg    5280
ctggattgtt attactcgcg gcccagccgg ccatggccgc tagcaccaag ggcccatcgg    5340
tcttccccct ggcaccctcc tccaagagca cctctggggg cacagcggcc ctgggctgcc    5400
tggtcaagga ctacttcccc gaaccggtga cggtgtcgtg gaactcaggc gccctgacca    5460
gcggcgtgca caccttcccg gctgtcctac agtcctcagg actctactcc ctcagcagcg    5520
tggtgaccgt gccctccagc agcttgggca cccagaccta catctgcaac gtgaatcaca    5580
agcccagcaa caccaaggtg gacaagaaag ttgagcccaa atcttgtgac aaaactcaca    5640
catgcccacc gtgcccagca cctgaactcc tggggggacc gtcagtcttc ctcttccccc    5700
caaaacccaa ggacaccctc atgatctccc ggacccctga ggtcacatgc gtggtggtgg    5760
acgtgagcca cgaagaccct gaggtcaagt tcaactggta cgtggacggc gtggaggtgc    5820
ataatgccaa gacaaagccg cgggaggagc agtacaacag cacgtaccgg gtggtcagcg    5880
tcctcaccgt cctgcaccag gactggctga atggcaagga gtacaagtgc aaggtctcca    5940
acaaagcccc ccagccccc atcgagaaaa ccatctccaa agccaaaggg cagccccgag    6000
aaccacaggt gtacaccctg cccccatccc gggatgagct gaccaagaac caggtcagcc    6060
tgacctgcct ggtcaaaggc ttctatccca gcgacatcgc cgtggagtgg gagagcaatg    6120
ggcagccgga gaacaactac aagaccacgc ctcccgtgct ggactccgac ggctccttct    6180
```

-continued

| | | | | |
|---|---|---|---|---|
| tcctctacag | caagctcacc | gtggacaaga | gcaggtggca | gcaggggaac gtcttctcat | 6240 |
| gctccgtgat | gcatgaggct | ctgcacaacc | actacacgca | gaagagcctc tccctgtctc | 6300 |
| cgggtaaata | agcttggctg | ttttggcgga | tgagagaaga | ttttcagcct gatacagatt | 6360 |
| aaatcagaac | gcagaagcgg | tctgataaaa | cagaatttgc | ctggcggcag tagcgcggtg | 6420 |
| gtcccacctg | accccatgcc | gaactcagaa | gtgaaacgcc | gtagcgccga tggtagtgtg | 6480 |
| gggtctcccc | atgcgagagt | agggaactgc | caggcatcaa | ataaaacgaa aggctcagtc | 6540 |
| gaaagactgg | gcctttcgtt | ttatctgttg | tttgtcggtg | aacgctctcc tgagtaggac | 6600 |
| aaatccgccg | ggagcggatt | tgaacgttgc | gaagcaacgg | cccggaggac cctggcgggc | 6660 |
| aggacgcccg | ccataaactg | ccaggcatca | aattaagcag | aaggccatcc tgacggatgg | 6720 |
| cctttttgcg | tttctacaaa | ctctt | | | 6745 |

```
<210> SEQ ID NO 103
<211> LENGTH: 126
<212> TYPE: PRT
<213> ORGANISM: Artificial sequence
<220> FEATURE:
<223> OTHER INFORMATION: CD16 c13 aminoacid sequence
<220> FEATURE:
<221> NAME/KEY: MISC_FEATURE
<222> LOCATION: (35)..(37)
<223> OTHER INFORMATION: Unknown amino acid
<220> FEATURE:
<221> NAME/KEY: MISC_FEATURE
<222> LOCATION: (55)..(57)
<223> OTHER INFORMATION: Unknown amino acid
<220> FEATURE:
<221> NAME/KEY: MISC_FEATURE
<222> LOCATION: (109)..(113)
<223> OTHER INFORMATION: Unknown amino acid

<400> SEQUENCE: 103
```

Glu Val Gln Leu Val Glu Ser Gly Gly Gly Leu Val Gln Pro Gly Gly
1               5                   10                  15

Ser Leu Arg Leu Ser Cys Ser Phe Pro Gly Ser Ile Phe Ser Leu Thr
            20                  25                  30

Met Gly Xaa Xaa Xaa Trp Tyr Arg Gln Ala Pro Gly Lys Glu Arg Glu
        35                  40                  45

Leu Val Thr Ser Ala Thr Xaa Xaa Xaa Pro Gly Gly Asp Thr Asn Tyr
    50                  55                  60

Ala Asp Phe Val Lys Gly Arg Phe Thr Ile Ser Arg Asp Asn Ala Arg
65                  70                  75                  80

Ser Ile Ile Tyr Leu Gln Met Asn Ser Leu Lys Pro Glu Asp Thr Ala
                85                  90                  95

Val Tyr Tyr Cys Tyr Ala Arg Thr Arg Asn Trp Gly Xaa Xaa Xaa Xaa
            100                 105                 110

Xaa Thr Val Trp Gly Gln Gly Thr Gln Val Thr Val Ser Ser
        115                 120                 125

```
<210> SEQ ID NO 104
<211> LENGTH: 126
<212> TYPE: PRT
<213> ORGANISM: Artificial sequence
<220> FEATURE:
<223> OTHER INFORMATION: CD16 c21 aminoacid sequence
<220> FEATURE:
<221> NAME/KEY: MISC_FEATURE
<222> LOCATION: (36)..(37)
<223> OTHER INFORMATION: Unknown amino acid
<220> FEATURE:
<221> NAME/KEY: MISC_FEATURE
```

<222> LOCATION: (56)..(57)
<223> OTHER INFORMATION: Unknown amino acid

<400> SEQUENCE: 104

Glu Val Gln Leu Val Glu Ser Gly Gly Glu Leu Val Gln Ala Gly Gly
1               5                   10                  15

Ser Leu Arg Leu Ser Cys Ala Ala Ser Gly Leu Thr Phe Ser Ser Tyr
            20                  25                  30

Asn Met Gly Xaa Xaa Trp Phe Arg Arg Ala Pro Gly Lys Glu Arg Glu
        35                  40                  45

Phe Val Ala Ser Ile Thr Trp Xaa Xaa Ser Gly Arg Asp Thr Phe Tyr
50                  55                  60

Ala Asp Ser Val Lys Gly Arg Phe Thr Ile Ser Arg Asp Asn Ala Lys
65                  70                  75                  80

Asn Thr Val Tyr Leu Gln Met Ser Ser Leu Lys Pro Glu Asp Thr Ala
                85                  90                  95

Val Tyr Tyr Cys Ala Ala Asn Pro Trp Pro Val Ala Ala Pro Arg Ser
            100                 105                 110

Gly Thr Tyr Trp Gly Gln Gly Thr Gln Val Thr Val Ser Ser
        115                 120                 125

<210> SEQ ID NO 105
<211> LENGTH: 126
<212> TYPE: PRT
<213> ORGANISM: Artificial sequence
<220> FEATURE:
<223> OTHER INFORMATION: CEA 43 aminoacid sequence
<220> FEATURE:
<221> NAME/KEY: MISC_FEATURE
<222> LOCATION: (36)..(37)
<223> OTHER INFORMATION: Unknown amino acid
<220> FEATURE:
<221> NAME/KEY: MISC_FEATURE
<222> LOCATION: (57)..(57)
<223> OTHER INFORMATION: Unknown amino acid
<220> FEATURE:
<221> NAME/KEY: MISC_FEATURE
<222> LOCATION: (111)..(113)
<223> OTHER INFORMATION: Unknown amino acid

<400> SEQUENCE: 105

Glu Val Gln Leu Val Glu Ser Gly Gly Gly Leu Val Gln Ala Gly Gly
1               5                   10                  15

Ser Leu Thr Leu Ser Cys Thr Ser Ser Thr Leu Thr Phe Thr Pro Tyr
            20                  25                  30

Arg Met Gly Xaa Xaa Trp Tyr Arg Gln Thr Pro Gly Lys Gln Arg Asp
        35                  40                  45

Leu Val Ala Asp Ile Ser Pro Gly Xaa Asp Gly Ser Thr Lys Asn Tyr
50                  55                  60

Ala Gly Phe Ala Gln Gly Arg Phe Thr Ile Ser Arg Asp Asn Ile Lys
65                  70                  75                  80

Asn Thr Val Tyr Leu Gln Met Asn Asp Leu Lys Pro Glu Asp Thr Ala
                85                  90                  95

Val Tyr Tyr Cys Asn Thr Tyr Val Ala Phe Val Gly Arg Ala Xaa Xaa
            100                 105                 110

Xaa Arg Thr Trp Gly Gln Gly Thr Gln Val Thr Val Thr Ser
        115                 120                 125

<210> SEQ ID NO 106
<211> LENGTH: 345
<212> TYPE: DNA

<213> ORGANISM: Artificial sequence
<220> FEATURE:
<223> OTHER INFORMATION: nucleotide CD16 c13

<400> SEQUENCE: 106

```
gaggtgcagc tggtggagtc tgggggaggc ttggtgcagc ctggggggtc tctgagactc    60
tcctgttcat tccctggaag catcttcagt ctcaccatgg gctggtaccg tcaggctcca   120
gggaaggagc gcgagttggt cacaagtgct actcctggtg gtgacacaaa ctatgcagac   180
ttcgtgaagg gccgattcac catctccaga gacaacgcca ggagcatcat atatctacaa   240
atgaatagcc tgaaacctga ggacacggcc gtctattatt gttatgcacg tacgaggaat   300
tggggtacgg tctggggcca ggggacccag gtcaccgtct cctca                   345
```

<210> SEQ ID NO 107
<211> LENGTH: 366
<212> TYPE: DNA
<213> ORGANISM: Artificial sequence
<220> FEATURE:
<223> OTHER INFORMATION: nucleotide CD16 c21

<400> SEQUENCE: 107

```
gaggtgcagc tggtggagtc tgggggagag ttggtgcagg ctggggggctc tctgagactc    60
tcctgtgcag cctctggcct caccttcagt agctataaca tgggctggtt ccgccgggct   120
ccagggaagg agcgtgagtt tgtagcatct attacctgga gtggtcggga cacattctat   180
gcagactccg tgaagggccg attcaccatc tccagagaca cgccaagaa cactgtttat   240
ctgcaaatga gcagcctgaa acctgaggac acggccgttt attattgtgc tgcaaacccc   300
tggccagtgg cggcgccacg tagtggcacc tactggggcc aagggaccca ggtcaccgtc   360
tcctca                                                              366
```

<210> SEQ ID NO 108
<211> LENGTH: 360
<212> TYPE: DNA
<213> ORGANISM: Artificial sequence
<220> FEATURE:
<223> OTHER INFORMATION: nucleotide CEA 43

<400> SEQUENCE: 108

```
gaggtgcagc tggtggagtc tgggggaggc ttggtgcagg cgggggggctc tctgacactc    60
tcctgcacaa gttctacact taccttcact ccgtatcgca tgggctggta ccgccagact   120
ccagggaagc agcgtgattt ggtcgcggac attagtcctg gtgatggtag taccaaaaat   180
tatgcaggct tcgcgcaggg ccgattcacc atctccagag acaacatcaa gaacacggtg   240
tatctgcaaa tgaacgacct gaaacctgag gacacggccg tctattactg caacacctac   300
gtcgcgtttg tggggcgtgc gcgtacttgg ggccagggga cccaggtcac tgtcacctca   360
```

<210> SEQ ID NO 109
<211> LENGTH: 5500
<212> TYPE: DNA
<213> ORGANISM: Artificial sequence
<220> FEATURE:
<223> OTHER INFORMATION: plasmid p55Flag/RBS/35

<400> SEQUENCE: 109

```
ttgtttattt ttctaaatac attcaaatat gtatccgctc atgagacaat aaccctgata    60
aatgcttcaa taatattgaa aaaggaagag tatgagtatt caacatttcc gtgtcgccct   120
tattcccttt tttgcggcat tttgccttcc tgttttgct cacccagaaa cgctggtgaa   180
```

```
agtaaaagat gctgaagatc agttgggtgc acgagtgggt tacatcgaac tggatctcaa    240
cagcggtaag atccttgaga gttttcgccc cgaagaacgt tttccaatga tgagcacttt    300
taaagttctg ctatgtggcg cggtattatc ccgtgttgac gccgggcaag agcaactcgg    360
tcgccgcata cactattctc agaatgactt ggttgagtac tcaccagtca cagaaaagca    420
tcttacggat ggcatgacag taagagaatt atgcagtgct gccataacca tgagtgataa    480
cactgcggcc aacttacttc tgacaacgat cggaggaccg aaggagctaa ccgcttttt     540
gcacaacatg gggatcatg taactcgcct tgatcgttgg gaaccggagc tgaatgaagc     600
cataccaaac gacgagcgtg acaccacgat gcctgtagca atggcaacaa cgttgcgcaa    660
actattaact ggcgaactac ttactctagc ttcccggcaa caattaatag actggatgga    720
ggcggataaa gttgcaggac cacttctgcg ctcggccctt ccggctggct ggtttattgc    780
tgataaatct ggagccggtg agcgtgggtc tcgcggtatc attgcagcac tggggccaga    840
tggtaagccc tcccgtatcg tagttatcta cacgacgggg agtcaggcaa ctatggatga    900
acgaaataga cagatcgctg agataggtgc ctcactgatt aagcattggt aactgtcaga    960
ccaagtttac tcatatatac tttagattga tttaaaactt cattttaat ttaaaaggat     1020
ctaggtgaag atccttttg ataatctcat gaccaaaatc ccttaacgtg agttttcgtt     1080
ccactgagcg tcagaccccg tagaaaagat caaaggatct tcttgagatc ctttttttct    1140
gcgcgtaatc tgctgcttgc aaacaaaaaa accaccgcta ccagcggtgg tttgtttgcc    1200
ggatcaagag ctaccaactc tttttccgaa ggtaactggc ttcagcagag cgcagatacc    1260
aaatactgtc cttctagtgt agccgtagtt aggccaccac ttcaagaact ctgtagcacc    1320
gcctacatac ctcgctctgc taatcctgtt accagtggct gctgccagtg gcgataagtc    1380
gtgtcttacc gggttggact caagacgata gttaccggat aaggcgcagc ggtcgggctg    1440
aacgggggt tcgtgcacac agcccagctt ggagcgaacg acctacaccg aactgagata     1500
cctacagcgt gagcattgag aaagcgccac gcttcccgaa gggagaaagg cggacaggta    1560
tccggtaagc ggcagggtcg gaacaggaga gcgcacgagg gagcttccag ggggaaacgc    1620
ctggtatctt tatagtcctg tcgggtttcg ccacctctga cttgagcgtc gatttttgtg    1680
atgctcgtca gggggggcgga gcctatggaa aaacgccagc aacgcggcct ttttacggtt    1740
cctggccttt tgctggcctt ttgctcacat gttctttcct gcgttatccc ctgattctgt    1800
ggataaccgt attaccgcct ttgagtgagc tgataccgct cgccgcagcc gaacgaccga    1860
gcgcagcgag tcagtgagcg aggaagcgga agagcgcctg atgcggtatt ttctccttac    1920
gcatctgtgc ggtatttcac accgcatata tggtgcactc tcagtacaat ctgctctgat    1980
gccgcatagt taagccagta tacactccgc tatcgctacg tgactgggtc atggctgcgc    2040
cccgacaccc gccaacaccc gctgacgcgc cctgacgggc ttgtctgctc ccggcatccg    2100
cttacagaca agctgtgacc gtctccggga gctgcatgtg tcagaggttt tcaccgtcat    2160
caccgaaacg cgcgaggcag ctgcggtaaa gctcatcagc gtggtcgtga agcgattcac    2220
agatgtctgc ctgttcatcc gcgtccagct cgttgagttt ctccagaagc gttaatgtct    2280
ggcttctgat aaagcgggcc atgttaaggg cggttttttc ctgtttggtc acttgatgcc    2340
tccgtgtaag ggggaatttc tgttcatggg ggtaatgata ccgatgaaac gagagaggat    2400
gctcacgata cgggttactg atgatgaaca tgcccggtta ctggaacgtt gtgagggtaa    2460
acaactggcg gtatggatgc ggcgggacca gagaaaaatc actcagggtc aatgccagcg    2520
```

```
cttcgttaat acagatgtag gtgttccaca gggtagccag cagcatcctg cgatgcagat    2580
ccggaacata atggtgcagg gcgctgactt ccgcgtttcc agactttacg aaacacggaa    2640
accgaagacc attcatgttg ttgctcaggt cgcagacgtt ttgcagcagc agtcgcttca    2700
cgttcgctcg cgtatcggtg attcattctg ctaaccagta aggcaacccc gccagcctag    2760
ccgggtcctc aacgacagga gcacgatcat gcgcacccgt ggccaggacc caacgctgcc    2820
cgagatgcgc cgcgtgcggc tgctggagat ggcggacgcg atggatatgt tctgccaagg    2880
gttggtttgc gcattcacag ttctccgcaa gaattgattg gctccaattc ttggagtggt    2940
gaatccgtta gcgaggtgcc gccggcttcc attcaggtcg aggtggcccg gctccatgca    3000
ccgcgacgca acgcggggag gcagacaagg tatagggcgg cgcctacaat ccatgccaac    3060
ccgttccatg tgctcgccga ggcggcataa atcgccgtga cgatcagcgg tccagtgatc    3120
gaagttaggc tggtaagagc cgcgagcgat ccttgaagct gtccctgatg gtcgtcatct    3180
acctgcctgg acagcatggc ctgcaacgcg gcatcccga tgccgccgga agcgagaaga     3240
atcataatgg ggaaggccat ccagcctcgc gtcgcgaacg ccagcaagac gtagcccagc    3300
gcgtcggcca gcttgcaatt cgcgctaact tacattaatt gcgttgcgct cactgcccgc    3360
tttccagtcg ggaaacctgt cgtgccagct gcattaatga atcggccaac gcgcggggag    3420
aggcggtttg cgtattgggc gccagggtgg tttttctttt caccagtgag acgggcaaca    3480
gctgattgcc cttcaccgcc tggccctgag agagttgcag caagcggtcc acgctggttt    3540
gccccagcag gcgaaaatcc tgtttgatgg tggttgacgg cgggatataa catgagctgt    3600
cttcggtatc gtcgtatccc actaccgaga tatccgcacc aacgcgcagc ccggactcgg    3660
taatggcgcg cattgcgccc agcgccatct gatcgttggc aaccagcatc gcagtgggaa    3720
cgatgcccte attcagcatt tgcatggttt gttgaaaacc ggacatggca ctccagtcgc    3780
cttcccgttc cgctatcggc tgaatttgat tgcgagtgag atatttatgc cagccagcca    3840
gacgcagacg cgccgagaca gaacttaatg gtcccgctaa cagcgcgatt tgctgatgac    3900
ccaatgcgac cagatgctcc acgcccagtc gcgtaccgtc ttcatgggag aaaataatac    3960
tgttgatggg tgtctggtca gagacatcaa gaaataacgc cggaacatta gtgcaggcag    4020
cttccacagc aatggcatcc tggtcatcca gcggatagtt aatgatcagc ccactgacgc    4080
gttgcgcgag aagattgtgc accgccgctt tacaggcttc gacgccgctt cgttctacca    4140
tcgacaccac cacgctggca cccagttgat cggcgcgaga tttaatcgcc gcgacaattt    4200
gcgacggcgc gtgcagggcc agactggagg tggcaacgcc aatcagcaac gactgtttgc    4260
ccgccagttg ttgtgccacg cggttgggaa tgtaattcag ctccgccatc gccgcttcca    4320
ctttttcccg cgttttcgca gaaacgtggc tggcctggtt caccacgcgg gaaacggtct    4380
gataagagac accggcatac tctgcgacat cgtataacgt tactggtttc acattcacca    4440
ccctgaattg actctcttcc gggcgctatc atgccatacc gcgaaaggtt ttgcgccatt    4500
cgatggtgtc aacgtaaatg catgccgctt cgccttcgcg cgcgaattgc aagctgatcc    4560
ggagcttatc gactgcacgg tgcaccaatg cttctggcgt caggcagcca tcggaagctg    4620
tggtatggct gtgcaggtcg taaatcactg cataattcgt gtcgctcaag gcgcactccc    4680
gttctggata atgttttttg cgccgacatc ataacggttc tggcaaatat tctgaaatga    4740
gctgttgaca attaatcatc ggctcgtata atgtgtggaa ttgtgagcgg ataacaattt    4800
cacacaggaa acagaattcc atatgaaata cctattacca acagcagcag ctgggttatt    4860
attgctcgct gcgcagccgg ccatggccca ggtcaccgtc tcctcaaacc gcggagagtg    4920
```

```
tgcaggtgat tacaaagacg atgacgataa gtaataaaca ggaaacagaa gtccatatga    4980
aatatctttt acctacggca gccgcaggtt tgttgttact cgcggcccag ccggccatgg    5040
ccgctagcgc ggccgctcta gattaagctt ggctgttttg gcggatgaga gaagattttc    5100
agcctgatac agattaaatc agaacgcaga agcggtctga taaaacagaa tttgcctggc    5160
ggcagtagcg cggtggtccc acctgacccc atgccgaact cagaagtgaa acgccgtagc    5220
gccgatggta gtgtggggtc tccccatgcg agagtaggga actgccaggc atcaaataaa    5280
acgaaaggct cagtcgaaag actgggcctt tcgttttatc tgttgtttgt cggtgaacgc    5340
tctcctgagt aggacaaatc cgccgggagc ggatttgaac gttgcgaagc aacgccccgg    5400
aggaccctgg cgggcaggac gcccgccata aactgccagg catcaaatta gcagaaggc    5460 catcctgacg gatggccttt ttgcgtttct acaaactctt                         5500
```

<210> SEQ ID NO 110
<211> LENGTH: 5560
<212> TYPE: DNA
<213> ORGANISM: Artificial sequence
<220> FEATURE:
<223> OTHER INFORMATION: p55Flag/RBS/35cmyc6HisGS

<400> SEQUENCE: 110

```
ttgtttattt ttctaaatac attcaaatat gtatccgctc atgagacaat aaccctgata      60
aatgcttcaa taatattgaa aaggaagag tatgagtatt caacatttcc gtgtcgccct     120
tattcccttt tttgcggcat tttgccttcc tgttttttgct cacccagaaa cgctggtgaa     180
agtaaaagat gctgaagatc agttgggtgc acagtgggt tacatcgaac tggatctcaa     240
cagcggtaag atccttgaga gttttcgccc cgaagaacgt tttccaatga tgagcacttt     300
taaagttctg ctatgtggcg cggtattatc ccgtgttgac gccgggcaag agcaactcgg     360
tcgccgcata cactattctc agaatgactt ggttgagtac tcaccagtca cagaaaagca     420
tcttacggat ggcatgacag taagagaatt atgcagtgct gccataacca tgagtgataa     480
cactgcggcc aacttacttc tgacaacgat cggaggaccg aaggagctaa ccgcttttt     540 gcacaacatg gggatcatg taactcgcct tgatcgttgg gaaccggagc tgaatgaagc     600
cataccaaac gacgagcgtg acaccacgat gcctgtagca atggcaacaa cgttgcgcaa     660
actattaact ggcgaactac ttactctagc ttcccggcaa caattaatag actggatgga     720
ggcggataaa gttgcaggac cacttctgcg ctcggccctt ccggctggct ggtttattgc     780
tgataaatct ggagccggtg agcgtgggtc tcgcggtatc attgcagcac tggggccaga     840
tggtaagccc tcccgtatcg tagttatcta cacgacgggg agtcaggcaa ctatggatga     900
acgaaataga cagatcgctg agataggtgc ctcactgatt aagcattggt aactgtcaga     960
ccaagtttac tcatatatac tttagattga tttaaaactt cattttaat ttaaaaggat    1020 ctaggtgaag atccttttg ataatctcat gaccaaaatc ccttaacgtg agttttcgtt    1080
ccactgagcg tcagaccccg tagaaaagat caaaggatct tcttgagatc ctttttttct    1140
gcgcgtaatc tgctgcttgc aaacaaaaaa accaccgcta ccagcggtgg tttgtttgcc    1200
ggatcaagag ctaccaactc tttttccgaa ggtaactggc ttcagcagag cgcagatacc    1260
aaatactgtc cttctagtgt agccgtagtt aggccaccac ttcaagaact ctgtagcacc    1320
gcctacatac ctcgctctgc taatcctgtt accagtggct gctgccagtg cgataagtc    1380 gtgtcttacc gggttggact caagacgata gttaccggat aaggcgcagc ggtcgggctg    1440
```

```
aacgggggt  tcgtgcacac  agcccagctt  ggagcgaacg  acctacaccg  aactgagata    1500
cctacagcgt  gagcattgag  aaagcgccac  gcttcccgaa  gggagaaagg  cggacaggta    1560
tccggtaagc  ggcagggtcg  gaacaggaga  gcgcacgagg  gagcttccag  ggggaaacgc    1620
ctggtatctt  tatagtcctg  tcgggtttcg  ccacctctga  cttgagcgtc  gattttgtg     1680 atgctcgtca  ggggggcgga  gcctatggaa  aaacgccagc  aacgcggcct  ttttacggtt    1740
cctggccttt  tgctggcctt  tgctcacat   gttctttcct  gcgttatccc  ctgattctgt    1800
ggataaccgt  attaccgcct  ttgagtgagc  tgataccgct  cgccgcagcc  gaacgaccga    1860
gcgcagcgag  tcagtgagcg  aggaagcgga  agagcgcctg  atgcggtatt  ttctccttac    1920
gcatctgtgc  ggtatttcac  accgcatata  tggtgcactc  tcagtacaat  ctgctctgat    1980
gccgcatagt  taagccagta  tacactccgc  tatcgctacg  tgactgggtc  atggctgcgc    2040
cccgacaccc  gccaacaccc  gctgacgcgc  cctgacgggc  ttgtctgctc  ccggcatccg    2100
cttacagaca  agctgtgacc  gtctccggga  gctgcatgtg  tcagaggttt  tcaccgtcat    2160
caccgaaacg  cgcgaggcag  ctgcggtaaa  gctcatcagc  gtggtcgtga  agcgattcac    2220
agatgtctgc  ctgttcatcc  gcgtccagct  cgttgagttt  ctccagaagc  gttaatgtct    2280
ggcttctgat  aaagcgggcc  atgttaaggg  cggttttttc  ctgtttggtc  acttgatgcc    2340
tccgtgtaag  ggggaatttc  tgttcatggg  ggtaatgata  ccgatgaaac  gagagaggat    2400
gctcacgata  cgggttactg  atgatgaaca  tgcccggtta  ctggaacgtt  gtgagggtaa    2460
acaactggcg  gtatggatgc  ggcgggacca  gagaaaaatc  actcagggtc  aatgccagcg    2520
cttcgttaat  acagatgtag  gtgttccaca  gggtagccag  cagcatcctg  cgatgcagat    2580
ccggaacata  atggtgcagg  gcgctgactt  ccgcgtttcc  agactttacg  aaacacggaa    2640
accgaagacc  attcatgttg  ttgctcaggt  cgcagacgtt  ttgcagcagc  agtcgcttca    2700
cgttcgctcg  cgtatcggtg  attcattctg  ctaaccagta  aggcaacccc  gccagcctag    2760
ccgggtcctc  aacgacagga  gcacgatcat  gcgcacccgt  ggccaggacc  caacgctgcc    2820
cgagatgcgc  cgcgtgcggc  tgctggagat  ggcggacgcg  atggatatgt  tctgccaagg    2880
gttggtttgc  gcattcacag  ttctccgcaa  gaattgattg  gctccaattc  ttggagtggt    2940
gaatccgtta  gcgaggtgcc  gccggcttcc  attcaggtcg  aggtggcccg  gctccatgca    3000
ccgcgacgca  acgcggggag  gcagacaagg  tatagggcgg  cgcctacaat  ccatgccaac    3060
ccgttccatg  tgctcgccga  ggcggcataa  atcgccgtga  cgatcagcgg  tccagtgatc    3120
gaagttaggc  tggtaagagc  cgcgagcgat  ccttgaagct  gtccctgatg  gtcgtcatct    3180
acctgcctgg  acagcatggc  ctgcaacgcg  ggcatcccga  tgccgccgga  agcgagaaga    3240
atcataatgg  ggaaggccat  ccagcctcgc  gtcgcgaacg  ccagcaagac  gtagcccagc    3300
gcgtcggcca  gcttgcaatt  cgcgctaact  tacattaatt  gcgttgcgct  cactgcccgc    3360
tttccagtcg  ggaaacctgt  cgtgccagct  gcattaatga  atcggccaac  gcgcggggag    3420
aggcggtttg  cgtattgggc  gccagggtgg  ttttctttt   caccagtgag  acgggcaaca    3480
gctgattgcc  cttcaccgcc  tggccctgag  agagttgcag  caagcggtcc  acgctggttt    3540
gccccagcag  gcgaaaatcc  tgtttgatgg  tggttgacgg  cgggatataa  catgagctgt    3600
cttcggtatc  gtcgtatccc  actaccgaga  tatccgcacc  aacgcgcagc  cggactcgg    3660 taatggcgcg  cattgcgccc  agcgccatct  gatcgttggc  aaccagcatc  gcagtgggaa    3720
cgatgccctc  attcagcatt  tgcatggttt  gttgaaaacc  ggacatggca  ctccagtcgc    3780
cttcccgttc  cgctatcggc  tgaatttgat  tgcgagtgag  atatttatgc  cagccagcca    3840
```

-continued

```
gacgcagacg cgccgagaca gaacttaatg gtcccgctaa cagcgcgatt tgctgatgac      3900
ccaatgcgac cagatgctcc acgcccagtc gcgtaccgtc ttcatgggag aaaataatac      3960
tgttgatggg tgtctggtca gagacatcaa gaaataacgc cggaacatta gtgcaggcag      4020
cttccacagc aatggcatcc tggtcatcca gcggatagtt aatgatcagc ccactgacgc      4080
gttgcgcgag aagattgtgc accgccgctt tacaggcttc gacgccgctt cgttctacca      4140
tcgacaccac cacgctggca cccagttgat cggcgcgaga tttaatcgcc gcgacaattt      4200
gcgacggcgc gtgcagggcc agactggagg tggcaacgcc aatcagcaac gactgtttgc      4260
ccgccagttg ttgtgccacg cggttgggaa tgtaattcag ctccgccatc gccgcttcca      4320
cttttttccg cgttttcgca gaaacgtggc tggcctggtt caccacgcgg gaaacggtct      4380
gataagagac accggcatac tctgcgacat cgtataacgt tactggtttc acattcacca      4440
ccctgaattg actctcttcc gggcgctatc atgccatacc gcgaaaggtt ttgcgccatt      4500
cgatggtgtc aacgtaaatg catgccgctt cgccttcgcg cgcgaattgc aagctgatcc      4560
ggagcttatc gactgcacgg tgcaccaatg cttctggcgt caggcagcca tcggaagctg      4620
tggtatggct gtgcaggtcg taaatcactg cataattcgt gtcgctcaag gcgcactccc      4680
gttctggata atgttttttg cgccgacatc ataacggttc tggcaaatat tctgaaatga      4740
gctgttgaca attaatcatc ggctcgtata atgtgtggaa ttgtgagcgg ataacaattt      4800
cacacaggaa acagaattcc atatgaaata cctattacca acagcagcag ctgggttatt      4860
attgctcgct gcgcagccgg ccatggccca ggtcaccgtc tcctcaaacc gcggagagtg      4920
tgcaggtgat tacaaagacg atgacgataa gtaataaaca ggaaacagaa gtccatatga      4980
aatatctttt acctacggca gccgcaggtt tgttgttact cgcggcccag ccggccatgg      5040
ccgctagcgc ggccgcagaa caaaaactca tctcagaaga ggatctgaat ggggccgtac      5100
atcaccacca tcatcatggg agctaagctt ggctgttttg gcggatgaga gaagattttc      5160
agcctgatac agattaaatc agaacgcaga agcggtctga taaaacagaa tttgcctggc      5220
ggcagtagcg cggtggtccc acctgacccc atgccgaact cagaagtgaa acgccgtagc      5280
gccgatggta gtgtggggtc tccccatgcg agagtaggga actgccaggc atcaaataaa      5340
acgaaaggct cagtcgaaag actgggcctt tcgttttatc tgttgtttgt cggtgaacgc      5400
tctcctgagt aggacaaatc cgccgggagc ggatttgaac gttgcgaagc aacggcccgg      5460
aggaccctgg cgggcaggac gcccgccata aactgccagg catcaaatta agcagaaggc      5520
catcctgacg gatggccttt ttgcgtttct acaaactctt                           5560
```

<210> SEQ ID NO 111
<211> LENGTH: 5866
<212> TYPE: DNA
<213> ORGANISM: Artificial sequence
<220> FEATURE:
<223> OTHER INFORMATION: plasmid p55Flag/RBS/35cmyc6HisGS

<400> SEQUENCE: 111

```
ttgtttattt ttctaaatac attcaaatat gtatccgctc atgagacaat aaccctgata       60
aatgcttcaa taatattgaa aaaggaagag tatgagtatt caacatttcc gtgtcgccct      120
tattcccttt tttgcggcat tttgccttcc tgtttttgct cacccagaaa cgctggtgaa      180
agtaaaagat gctgaagatc agttgggtgc acgagtgggt tacatcgaac tggatctcaa      240
cagcggtaag atccttgaga gttttcgccc cgaagaacgt tttccaatga tgagcacttt      300
```

| | |
|---|---|
| taaagttctg ctatgtggcg cggtattatc ccgtgttgac gccgggcaag agcaactcgg | 360 |
| tcgccgcata cactattctc agaatgactt ggttgagtac tcaccagtca cagaaaagca | 420 |
| tcttacggat ggcatgacag taagagaatt atgcagtgct gccataacca tgagtgataa | 480 |
| cactgcggcc aacttacttc tgacaacgat cggaggaccg aaggagctaa ccgcttttt | 540 |
| gcacaacatg ggggatcatg taactcgcct tgatcgttgg gaaccggagc tgaatgaagc | 600 |
| cataccaaac gacgagcgtg acaccacgat gcctgtagca atggcaacaa cgttgcgcaa | 660 |
| actattaact ggcgaactac ttactctagc ttcccggcaa caattaatag actggatgga | 720 |
| ggcggataaa gttgcaggac cacttctgcg ctcggccctt ccggctggct ggtttattgc | 780 |
| tgataaatct ggagccggtg agcgtgggtc tcgcggtatc attgcagcac tggggccaga | 840 |
| tggtaagccc tcccgtatcg tagttatcta cacgacgggg agtcaggcaa ctatggatga | 900 |
| acgaaataga cagatcgctg agataggtgc ctcactgatt aagcattggt aactgtcaga | 960 |
| ccaagtttac tcatatatac tttagattga tttaaaactt cattttaat ttaaaaggat | 1020 |
| ctaggtgaag atcctttttg ataatctcat gaccaaaatc ccttaacgtg agttttcgtt | 1080 |
| ccactgagcg tcagaccccg tagaaaagat caaaggatct tcttgagatc cttttttct | 1140 |
| gcgcgtaatc tgctgcttgc aaacaaaaaa accaccgcta ccagcggtgg tttgtttgcc | 1200 |
| ggatcaagag ctaccaactc tttttccgaa ggtaactggc ttcagcagag cgcagatacc | 1260 |
| aaatactgtc cttctagtgt agccgtagtt aggccaccac ttcaagaact ctgtagcacc | 1320 |
| gcctacatac ctcgctctgc taatcctgtt accagtggct gctgccagtg cgataagtc | 1380 |
| gtgtcttacc gggttggact caagacgata gttaccggat aaggcgcagc ggtcgggctg | 1440 |
| aacggggggt tcgtgcacac agcccagctt ggagcgaacg acctacaccg aactgagata | 1500 |
| cctacagcgt gagcattgag aaagcgccac gcttcccgaa gggagaaagg cggacaggta | 1560 |
| tccggtaagc ggcagggtcg gaacaggaga gcgcacgagg gagcttccag ggggaaacgc | 1620 |
| ctggtatctt tatagtcctg tcgggtttcg ccacctctga cttgagcgtc gatttttgtg | 1680 |
| atgctcgtca ggggggcgga gcctatggaa aaacgccagc aacgcggcct ttttacggtt | 1740 |
| cctggccttt tgctggcctt ttgctcacat gttctttcct gcgttatccc ctgattctgt | 1800 |
| ggataaccgt attaccgcct ttgagtgagc tgataccgct cgccgcagcc gaacgaccga | 1860 |
| gcgcagcgag tcagtgagcg aggaagcgga agagcgcctg atgcggtatt ttctccttac | 1920 |
| gcatctgtgc ggtatttcac accgcatata tggtgcactc tcagtacaat ctgctctgat | 1980 |
| gccgcatagt taagccagta tacactccgc tatcgctacg tgactgggtc atggctgcgc | 2040 |
| cccgacaccc gccaacaccc gctgacgcgc cctgacgggc ttgtctgctc ccggcatccg | 2100 |
| cttacagaca agctgtgacc gtctccggga gctgcatgtg tcagaggttt tcaccgtcat | 2160 |
| caccgaaacg cgcgaggcag ctgcggtaaa gctcatcagc gtggtcgtga agcgattcac | 2220 |
| agatgtctgc ctgttcatcc gcgtccagct cgttgagttt ctccagaagc gttaatgtct | 2280 |
| ggcttctgat aaagcgggcc atgttaaggg cggtttttc ctgtttggtc acttgatgcc | 2340 |
| tccgtgtaag ggggaatttc tgttcatggg ggtaatgata ccgatgaaac gagagaggat | 2400 |
| gctcacgata cgggttactg atgatgaaca tgcccggtta ctggaacgtt gtgagggtaa | 2460 |
| acaactggcg gtatggatgc ggcgggacca gagaaaaatc actcagggtc aatgccagcg | 2520 |
| cttcgttaat acagatgtag gtgttccaca gggtagccag cagcatcctg cgatgcagat | 2580 |
| ccggaacata atggtgcagg cgctgacttc cgcgtttcc agactttacg aaacacggaa | 2640 |
| accgaagacc attcatgttg ttgctcaggt cgcagacgtt ttgcagcagc agtcgcttca | 2700 |

```
cgttcgctcg cgtatcggtg attcattctg ctaaccagta aggcaaccccc gccagcctag    2760
ccgggtcctc aacgacagga gcacgatcat gcgcacccgt ggccaggacc caacgctgcc    2820
cgagatgcgc cgcgtgcggc tgctggagat ggcggacgcg atggatatgt tctgccaagg    2880
gttggtttgc gcattcacag ttctccgcaa gaattgattg gctccaattc ttggagtggt    2940
gaatccgtta gcgaggtgcc gccggcttcc attcaggtcg aggtggcccg gctccatgca    3000
ccgcgacgca acgcggggag gcagacaagg tatagggcgg cgcctacaat ccatgccaac    3060
ccgttccatg tgctcgccga ggcggcataa atcgccgtga cgatcagcgg tccagtgatc    3120
gaagttaggc tggtaagagc cgcgagcgat ccttgaagct gtccctgatg gtcgtcatct    3180
acctgcctgg acagcatggc ctgcaacgcg gcatcccga tgccgccgga agcgagaaga    3240
atcataatgg ggaaggccat ccagcctcgc gtcgcgaacg ccagcaagac gtagcccagc    3300
gcgtcggcca gcttgcaatt cgcgctaact tacattaatt gcgttgcgct cactgcccgc    3360
tttccagtcg ggaaacctgt cgtgccagct gcattaatga atcggccaac gcgcggggag    3420
aggcggtttg cgtattgggc gccagggtgg ttttctttt caccagtgag acgggcaaca    3480
gctgattgcc cttcaccgcc tggccctgag agagttgcag caagcggtcc acgctggttt    3540
gccccagcag gcgaaaatcc tgtttgatgg tggttgacgg cgggatataa catgagctgt    3600
cttcggtatc gtcgtatccc actaccgaga tatccgcacc aacgcgcagc ccggactcgg    3660
taatggcgcg cattgcgccc agcgccatct gatcgttggc aaccagcatc gcagtgggaa    3720
cgatgccctc attcagcatt tgcatggttt gttgaaaacc ggacatggca ctccagtcgc    3780
cttcccgttc cgctatcggc tgaatttgat tgcgagtgag atatttatgc cagccagcca    3840
gacgcagacg cgccgagaca gaacttaatg gtcccgctaa cagcgcgatt tgctgatgac    3900
ccaatgcgac cagatgctcc acgcccagtc gcgtaccgtc ttcatgggag aaaataatac    3960
tgttgatggg tgtctggtca gagacatcaa gaaataacgc cggaacatta gtgcaggcag    4020
cttccacagc aatggcatcc tggtcatcca gcggatagtt aatgatcagc ccactgacgc    4080
gttgcgcgag aagattgtgc accgccgctt tacaggcttc gacgccgctt cgttctacca    4140
tcgacaccac cacgctggca cccagttgat cggcgcgaga tttaatcgcc gcgacaattt    4200
gcgacggcgc gtgcagggcc agactggagg tggcaacgcc aatcagcaac gactgtttgc    4260
ccgccagttg ttgtgccacg cggttgggaa tgtaattcag ctccgccatc gccgcttcca    4320
cttttttcccg cgttttcgca gaaacgtggc tggcctggtt caccacgcgg gaaacggtct    4380
gataagagac accggcatac tctgcgacat cgtataacgt tactggtttc acattccacca    4440
ccctgaattg actctcttcc gggcgctatc atgccatacc gcgaaaggtt ttgcgccatt    4500
cgatggtgtc aacgtaaatg catgccgctt cgccttcgcg cgcgaattgc aagctgatcc    4560
ggagcttatc gactgcacgg tgcaccaatg cttctggcgt caggcagcca tcggaagctg    4620
tggtatggct gtgcaggtcg taaatcactg cataattcgt gtcgctcaag gcgcactccc    4680
gttctggata atgttttttg cgccgacatc ataacggttc tggcaaatat tctgaaatga    4740
gctgttgaca attaatcatc ggctcgtata atgtgtggaa ttgtgagcgg ataacaattt    4800
cacacaggaa acagaattcc atatgaaata cctattacca acagcagcag ctgggttatt    4860
attgctcgct gcgcagccgg ccatggccca ggtcaccgtc tcctcacgta cggtggctgc    4920
accatcgtc ttcatcttcc cgccatctga tgagcagttg aaatctggaa ctgcctctgt    4980
tgtgtgcctg ctgaataact tctatcccag agaggccaaa gtacagtgga aggtggataa    5040
```

| | |
|---|---:|
| cgccctccaa tcgggtaact cccaggagag tgtcacagag caggacagca aggacagcac | 5100 |
| ctacagcctc agcagcaccc tgacgctgag caaagcagac tacgagaaac acaaagtcta | 5160 |
| cgcctgcgaa gtcacccatc agggcctgag ctcgccggtg acaaagagct tcaaccgcgg | 5220 |
| agagtgtgca ggtgattaca aagacgatga cgataagtaa taaacaggaa acagaagtcc | 5280 |
| atatgaaata tcttttacct acggcagccg caggtttgtt gttactcgcg gcccagccgg | 5340 |
| ccatggccgc tagcgcggcc gcagaacaaa aactcatctc agaagaggat ctgaatgggg | 5400 |
| ccgtacatca ccaccatcat catgggagct aagcttggct gttttggcgg atgagagaag | 5460 |
| attttcagcc tgatacagat taaatcagaa cgcagaagcg gtctgataaa acagaatttg | 5520 |
| cctggcggca gtagcgcggt ggtcccacct gaccccatgc cgaactcaga agtgaaacgc | 5580 |
| cgtagcgccg atggtagtgt ggggtctccc catgcgagag tagggaactg ccaggcatca | 5640 |
| aataaaacga aaggctcagt cgaaagactg ggcctttcgt tttatctgtt gtttgtcggt | 5700 |
| gaacgctctc ctgagtagga caaatccgcc gggagcggat ttgaacgttg cgaagcaacg | 5760 |
| gcccggagga ccctggcggg caggacgccc gccataaact gccaggcatc aaattaagca | 5820 |
| gaaggccatc ctgacggatg gcctttttgc gtttctacaa actctt | 5866 |

<210> SEQ ID NO 112
<211> LENGTH: 6169
<212> TYPE: DNA
<213> ORGANISM: Artificial sequence
<220> FEATURE:
<223> OTHER INFORMATION: plasmid pCkCH1y1-TAG

<400> SEQUENCE: 112

| | |
|---|---:|
| ttgtttattt ttctaaatac attcaaatat gtatccgctc atgagacaat aaccctgata | 60 |
| aatgcttcaa taatattgaa aaaggaagag tatgagtatt caacatttcc gtgtcgccct | 120 |
| tattcccttt tttgcggcat tttgccttcc tgtttttgct cacccagaaa cgctggtgaa | 180 |
| agtaaaagat gctgaagatc agttgggtgc acgagtgggt tacatcgaac tggatctcaa | 240 |
| cagcggtaag atccttgaga gttttcgccc cgaagaacgt tttccaatga tgagcacttt | 300 |
| taaagttctg ctatgtggcg cggtattatc ccgtgttgac gccgggcaag agcaactcgg | 360 |
| tcgccgcata cactattctc agaatgactt ggttgagtac tcaccagtca cagaaaagca | 420 |
| tcttacggat ggcatgacag taagagaatt atgcagtgct gccataacca tgagtgataa | 480 |
| cactgcggcc aacttacttc tgacaacgat cggaggaccg aaggagctaa ccgcttttttt | 540 |
| gcacaacatg ggggatcatg taactcgcct tgatcgttgg gaaccggagc tgaatgaagc | 600 |
| cataccaaac gacgagcgtg acaccacgat gcctgtagca atggcaacaa cgttgcgcaa | 660 |
| actattaact ggcgaactac ttactctagc ttcccggcaa caattaatag actggatgga | 720 |
| ggcggataaa gttgcaggac cacttctgcg ctcggccctt ccggctggct ggtttattgc | 780 |
| tgataaatct ggagccggtg agcgtgggtc tcgcggtatc attgcagcac tggggccaga | 840 |
| tggtaagccc tcccgtatcg tagttatcta cacgacgggg agtcaggcaa ctatggatga | 900 |
| acgaaataga cagatcgctg agataggtgc ctcactgatt aagcattggt aactgtcaga | 960 |
| ccaagtttac tcatatatac tttagattga tttaaaactt cattttttaat ttaaaaggat | 1020 |
| ctaggtgaag atccttttttg ataatctcat gaccaaaatc ccttaacgtg agttttcgtt | 1080 |
| ccactgagcg tcagaccccg tagaaaagat caaaggatct tcttgagatc ctttttttct | 1140 |
| gcgcgtaatc tgctgcttgc aaacaaaaaa accaccgcta ccagcggtgg tttgtttgcc | 1200 |
| ggatcaagag ctaccaactc tttttccgaa ggtaactggc ttcagcagag cgcagatacc | 1260 |

```
aaatactgtc cttctagtgt agccgtagtt aggccaccac ttcaagaact ctgtagcacc   1320
gcctacatac ctcgctctgc taatcctgtt accagtggct gctgccagtg gcgataagtc   1380
gtgtcttacc gggttggact caagacgata gttaccggat aaggcgcagc ggtcgggctg   1440
aacgggggt  tcgtgcacac agcccagctt ggagcgaacg acctacaccg aactgagata   1500
cctacagcgt gagcattgag aaagcgccac gcttcccgaa gggagaaagg cggacaggta   1560
tccggtaagc ggcagggtcg gaacaggaga gcgcacgagg gagcttccag ggggaaacgc   1620
ctggtatctt tatagtcctg tcgggtttcg ccacctctga cttgagcgtc gattttgtg   1680
atgctcgtca gggggcgga gcctatggaa aaacgccagc aacgcggcct ttttacggtt   1740
cctggccttt tgctggcctt ttgctcacat gttctttcct gcgttatccc ctgattctgt   1800
ggataaccgt attaccgcct ttgagtgagc tgataccgct cgccgcagcc gaacgaccga   1860
gcgcagcgag tcagtgagcg aggaagcgga agagcgcctg atgcggtatt ttctccttac   1920
gcatctgtgc ggtatttcac accgcatata tggtgcactc tcagtacaat ctgctctgat   1980
gccgcatagt taagccagta tacactccgc tatcgctacg tgactgggtc atggctgcgc   2040
cccgacaccc gccaacaccc gctgacgcgc cctgacgggc ttgtctgctc ccggcatccg   2100
cttacagaca agctgtgacc gtctccggga gctgcatgtg tcagaggttt tcaccgtcat   2160
caccgaaacg cgcgaggcag ctgcggtaaa gctcatcagc gtggtcgtga agcgattcac   2220
agatgtctgc ctgttcatcc gcgtccagct cgttgagttt ctccagaagc gttaatgtct   2280
ggcttctgat aaagcgggcc atgttaaggg cggttttttc ctgtttggtc acttgatgcc   2340
tccgtgtaag ggggaatttc tgttcatggg ggtaatgata ccgatgaaac gagagaggat   2400
gctcacgata cgggttactg atgatgaaca tgcccggtta ctggaacgtt gtgagggtaa   2460
acaactggcg gtatggatgc ggcgggacca gagaaaaatc actcagggtc aatgccagcg   2520
cttcgttaat acagatgtag gtgttccaca gggtagccag cagcatcctg cgatgcagat   2580
ccggaacata atggtgcagg cgctgactt  ccgcgtttcc agactttacg aaacacggaa   2640
accgaagacc attcatgttg ttgctcaggt cgcagacgtt ttgcagcagc agtcgcttca   2700
cgttcgctcg cgtatcggtg attcattctg ctaaccagta aggcaacccc gccagcctag   2760
ccgggtcctc aacgacagga gcacgatcat gcgcacccgt ggccaggacc caacgctgcc   2820
cgagatgcgc cgcgtgcggc tgctggagat ggcggacgcg atggatatgt tctgccaagg   2880
gttggtttgc gcattcacag ttctccgcaa gaattgattg gctccaattc ttggagtggt   2940
gaatccgtta gcgaggtgcc gccggcttcc attcaggtcg aggtggcccg gctccatgca   3000
ccgcgacgca acgcggggag gcagacaagg tatagggcgg cgcctacaat ccatgccaac   3060
ccgttccatg tgctcgccga ggcggcataa atcgccgtga cgatcagcgg tccagtgatc   3120
gaagttaggc tggtaagagc cgcgagcgat ccttgaagct gtccctgatg gtcgtcatct   3180
acctgcctgg acagcatggc ctgcaacgcg gcatcccga  tgccgccgga agcgagaaga   3240
atcataatgg ggaaggccat ccagcctcgc gtcgcgaacg ccagcaagac gtagcccagc   3300
gcgtcggcca gcttgcaatt cgcgctaact tacattaatt gcgttgcgct cactgcccgc   3360
tttccagtcg ggaaacctgt cgtgccagct gcattaatga atcggccaac gcgcggggag   3420
aggcggtttg cgtattgggc gccagggtgg ttttttcttt caccagtgag acgggcaaca   3480
gctgattgcc cttcaccgcc tggccctgag agagttgcag caagcggtcc acgctggttt   3540
gccccagcag gcgaaaatcc tgtttgatgg tggttgacgg cgggatataa catgagctgt   3600
```

```
cttcggtatc gtcgtatccc actaccgaga tatccgcacc aacgcgcagc ccggactcgg    3660
taatggcgcg cattgcgccc agcgccatct gatcgttggc aaccagcatc gcagtgggaa    3720
cgatgccctc attcagcatt tgcatggttt gttgaaaacc ggacatggca ctccagtcgc    3780
cttcccgttc cgctatcggc tgaatttgat tgcgagtgag atatttatgc cagccagcca    3840
gacgcagacg cgccgagaca gaacttaatg gtcccgctaa cagcgcgatt tgctgatgac    3900
ccaatgcgac cagatgctcc acgcccagtc gcgtaccgtc ttcatgggag aaaataatac    3960
tgttgatggg tgtctggtca gagacatcaa gaaataacgc cggaacatta gtgcaggcag    4020
cttccacagc aatggcatcc tggtcatcca gcggatagtt aatgatcagc ccactgacgc    4080
gttgcgcgag aagattgtgc accgccgctt tacaggcttc gacgccgctt cgttctacca    4140
tcgacaccac cacgctggca cccagttgat cggcgcgaga tttaatcgcc gcgacaattt    4200
gcgacggcgc gtgcagggcc agactggagg tggcaacgcc aatcagcaac gactgtttgc    4260
ccgccagttg ttgtgccacg cggttgggaa tgtaattcag ctccgccatc gccgcttcca    4320
ctttttcccg cgttttcgca gaaacgtggc tggcctggtt caccacgcgg gaaacggtct    4380
gataagagac accggcatac tctgcgacat cgtataacgt tactggtttc acattcacca    4440
ccctgaattg actctcttcc gggcgctatc atgccatacc gcgaaaggtt ttgcgccatt    4500
cgatggtgtc aacgtaaatg catgccgctt cgccttcgcg cgcgaattgc aagctgatcc    4560
ggagcttatc gactgcacgg tgcaccaatg cttctggcgt caggcagcca tcggaagctg    4620
tggtatggct gtgcaggtcg taaatcactg cataattcgt gtcgctcaag gcgcactccc    4680
gttctggata atgttttttg cgccgacatc ataacggttc tggcaaatat tctgaaatga    4740
gctgttgaca attaatcatc ggctcgtata atgtgtggaa ttgtgagcgg ataacaattt    4800
cacacaggaa acagaattcc atatgaaata cctattacca acagcagcag ctgggttatt    4860
attgctcgct gcgcagccgg ccatggccca ggtcaccgtc tcctcacgta cggtggctgc    4920
accatctgtc ttcatcttcc cgccatctga tgagcagttg aaatctggaa ctgcctctgt    4980
tgtgtgcctg ctgaataact tctatcccag agaggccaaa gtacagtgga aggtggataa    5040
cgccctccaa tcgggtaact cccaggagag tgtcacagag caggacagca aggacagcac    5100
ctacagcctc agcagcaccc tgacgctgag caaagcagac tacgagaaac acaaagtcta    5160
cgcctgcgaa gtcacccatc agggcctgag ctcgccggtg acaaagagct caaccgcgg    5220
agagtgtgca ggtgattaca agacgatga cgataagtaa taaacaggaa acagaagtcc    5280
atatgaaata tcttttacct acggcagccg caggtttgtt gttactcgcg gcccagccgg    5340
ccatggccgc tagcaccaag ggcccatcgg tcttccccct ggcaccctcc tccaagagca    5400
cctctggggg cacagcggcc ctgggctgcc tggtcaagga ctacttcccc gaaccggtga    5460
cggtgtcgtg gaactcaggc gccctgacca gcggcgtgca caccttcccg gctgtcctac    5520
agtcctcagg actctactcc ctcagcagcg tagtgaccgt gccctccagc agcttgggca    5580
cccagaccta catctgcaac gtgaatcaca agcccagcaa caccaaggtg gacaagaaag    5640
ttgagcccaa atcttgtgcg gccgcagaac aaaaactcat ctcagaagag gatctgaatg    5700
gggccgtaca tcaccaccat catcatggga gctaagcttg gctgttttgg cggatgagag    5760
aagattttca gcctgataca gattaaatca gaacgcagaa gcggtctgat aaaacagaat    5820
ttgcctggcg gcagtagcgc ggtggtccca cctgacccca tgccgaactc agaagtgaaa    5880
cgccgtagcg ccgatggtag tgtggggtct ccccatgcga gagtagggaa ctgccaggca    5940
tcaaataaaa cgaaaggctc agtcgaaaga ctgggccttt cgttttatct gttgtttgtc    6000
```

```
ggtgaacgct ctcctgagta ggacaaatcc gccgggagcg gatttgaacg ttgcgaagca      6060
acggcccgga ggaccctggc gggcaggacg cccgccataa actgccaggc atcaaattaa      6120
gcagaaggcc atcctgacgg atggcctttt tgcgtttcta caaactctt                  6169

<210> SEQ ID NO 113
<211> LENGTH: 6199
<212> TYPE: DNA
<213> ORGANISM: Artificial sequence
<220> FEATURE:
<223> OTHER INFORMATION: plasmid pCkCH1Hy1-TAG

<400> SEQUENCE: 113
ttgtttattt ttctaaatac attcaaatat gtatccgctc atgagacaat aaccctgata        60
aatgcttcaa taatattgaa aaaggaagag tatgagtatt caacatttcc gtgtcgccct       120
tattcccttt tttgcggcat tttgccttcc tgttttgct cacccagaaa cgctggtgaa        180
agtaaaagat gctgaagatc agttgggtgc acgagtgggt tacatcgaac tggatctcaa       240
cagcggtaag atccttgaga gttttcgccc cgaagaacgt tttccaatga tgagcacttt       300
taaagttctg ctatgtggcg cggtattatc ccgtgttgac gccgggcaag agcaactcgg       360
tcgccgcata cactattctc agaatgactt ggttgagtac tcaccagtca cagaaaagca       420
tcttacggat ggcatgacag taagagaatt atgcagtgct gccataacca tgagtgataa       480
cactgcggcc aacttacttc tgacaacgat cggaggaccg aaggagctaa ccgcttttt        540 gcacaacatg gggatcatg taactcgcct tgatcgttgg gaaccggagc tgaatgaagc        600
cataccaaac gacgagcgtg acaccacgat gcctgtagca atggcaacaa cgttgcgcaa       660
actattaact ggcgaactac ttactctagc ttcccggcaa caattaatag actggatgga       720
ggcggataaa gttgcaggac cacttctgcg ctcggccctt ccggctggct ggtttattgc       780
tgataaatct ggagccggtg agcgtgggtc tcgcggtatc attgcagcac tggggccaga       840
tggtaagccc tcccgtatcg tagttatcta cacgacgggg agtcaggcaa ctatggatga       900
acgaaataga cagatcgctg agataggtgc ctcactgatt aagcattggt aactgtcaga       960
ccaagtttac tcatatatac tttagattga tttaaaactt catttttaat ttaaaaggat      1020
ctaggtgaag atcctttttg ataatctcat gaccaaaatc ccttaacgtg agttttcgtt      1080
ccactgagcg tcagaccccg tagaaaagat caaaggatct tcttgagatc ctttttttct      1140
gcgcgtaatc tgctgcttgc aaacaaaaaa accaccgcta ccagcggtgg tttgtttgcc      1200
ggatcaagag ctaccaactc tttttccgaa ggtaactggc ttcagcagag cgcagatacc      1260
aaatactgtc cttctagtgt agccgtagtt aggccaccac ttcaagaact ctgtagcacc      1320
gcctacatac ctcgctctgc taatcctgtt accagtggct gctgccagtg gcgataagtc      1380
gtgtcttacc gggttggact caagacgata gttaccggat aaggcgcagc ggtcgggctg      1440
aacggggggt tcgtgcacac agcccagctt ggagcgaacg acctacaccg aactgagata      1500
cctacagcgt gagcattgag aaagcgccac gcttcccgaa gggagaaagg cggacaggta      1560
tccggtaagc ggcagggtcg gaacaggaga gcgcacgagg gagcttccag ggggaaacgc      1620
ctggtatctt tatagtcctg tcgggtttcg ccacctctga cttgagcgtc gatttttgtg      1680
atgctcgtca ggggggcgga gcctatggaa aaacgccagc aacgcggcct ttttacggtt      1740
cctggccttt tgctggcctt ttgctcacat gttctttcct gcgttatccc ctgattctgt      1800
ggataaccgt attaccgcct ttgagtgagc tgataccgct cgccgcagcc gaacgaccga      1860
```

```
gcgcagcgag tcagtgagcg aggaagcgga agagcgcctg atgcggtatt ttctccttac    1920
gcatctgtgc ggtatttcac accgcatata tggtgcactc tcagtacaat ctgctctgat    1980
gccgcatagt taagccagta tacactccgc tatcgctacg tgactgggtc atggctgcgc    2040
cccgacaccc gccaacaccc gctgacgcgc cctgacgggc ttgtctgctc ccggcatccg    2100
cttacagaca agctgtgacc gtctccggga gctgcatgtg tcagaggttt tcaccgtcat    2160
caccgaaacg cgcgaggcag ctgcggtaaa gctcatcagc gtggtcgtga agcgattcac    2220
agatgtctgc ctgttcatcc gcgtccagct cgttgagttt ctccagaagc gttaatgtct    2280
ggcttctgat aaagcgggcc atgttaaggg cggttttttc ctgtttggtc acttgatgcc    2340
tccgtgtaag ggggaatttc tgttcatggg ggtaatgata ccgatgaaac gagagaggat    2400
gctcacgata cggggttactg atgatgaaca tgcccggtta ctggaacgtt gtgagggtaa    2460
acaactggcg gtatggatgc ggcgggacca gagaaaaatc actcagggtc aatgccagcg    2520
cttcgttaat acagatgtag gtgttccaca gggtagccag cagcatcctg cgatgcagat    2580
ccggaacata atggtgcagg cgctgacttc cgcgtttcc agactttacg aaacacggaa    2640
accgaagacc attcatgttg ttgctcaggt cgcagacgtt ttgcagcagc agtcgcttca    2700
cgttcgctcg cgtatcggtg attcattctg ctaaccagta aggcaacccc gccagcctag    2760
ccgggtcctc aacgacagga gcacgatcat gcgcacccgt ggccaggacc caacgctgcc    2820
cgagatgcgc cgcgtgcggc tgctggagat ggcggacgcg atggatatgt ctgccaagg    2880 gttggtttgc gcattcacag ttctccgcaa gaattgattg ctccaattc ttggagtggt    2940 gaatccgtta gcgaggtgcc gccggcttcc attcaggtcg aggtggcccg gctccatgca    3000
ccgcgacgca acgcggggag gcagacaagg tatagggcgg cgcctacaat ccatgccaac    3060
ccgttccatg tgctcgccga ggcggcataa atcgccgtga cgatcagcgg tccagtgatc    3120
gaagttaggc tggtaagagc cgcgagcgat ccttgaagct gtccctgatg gtcgtcatct    3180
acctgcctgg acagcatggc ctgcaacgcg ggcatcccga tgccgccgga agcgagaaga    3240
atcataatgg ggaaggccat ccagcctcgc gtcgcgaacg ccagcaagac gtagcccagc    3300
gcgtcggcca gcttgcaatt cgcgctaact tacattaatt gcgttgcgct cactgcccgc    3360
tttccagtcg ggaaacctgt cgtgccagct gcattaatga atcggccaac gcgcgggag    3420 aggcggtttg cgtattgggc gccagggtgg ttttcttttt caccagtgag acgggcaaca    3480
gctgattgcc cttcaccgcc tggccctgag agagttgcag caagcggtcc acgctggttt    3540
gccccagcag gcgaaaatcc tgtttgatgg tggttgacgg cgggatataa catgagctgt    3600
cttcggtatc gtcgtatccc actaccgaga tatccgcacc aacgcgcagc ccggactcgg    3660
taatggcgcg cattgcgccc agcgccatct gatcgttggc aaccagcatc gcagtgggaa    3720
cgatgccctc attcagcatt tgcatggttt gttgaaaacc ggacatggca ctccagtcgc    3780
cttcccgttc cgctatcggc tgaatttgat tgcgagtgag atatttatgc cagccagcca    3840
gacgcagacg cgccgagaca gaacttaatg gtcccgctaa cagcgcgatt tgctgatgac    3900
ccaatgcgac cagatgctcc acgcccagtc gcgtaccgtc ttcatgggag aaaataatac    3960
tgttgatggg tgtctggtca gagacatcaa gaaataacgc cggaacatta gtgcaggcag    4020
cttccacagc aatggcatcc tggtcatcca gcggatagtt aatgatcagc ccactgacgc    4080
gttgcgcgag aagattgtgc accgccgctt tacaggcttc gacgccgctt cgttctacca    4140
tcgacaccac cacgctggca cccagttgat cggcgcgaga tttaatcgcc gcgacaattt    4200
gcgacggcgc gtgcagggcc agactggagg tggcaacgcc aatcagcaac gactgtttgc    4260
```

```
ccgccagttg ttgtgccacg cggttgggaa tgtaattcag ctccgccatc gccgcttcca    4320
cttttttccg cgttttcgca gaaacgtggc tggcctggtt caccacgcgg gaaacggtct    4380
gataagagac accggcatac tctgcgacat cgtataacgt tactggtttc acattcacca    4440
ccctgaattg actctcttcc gggcgctatc atgccatacc gcgaaaggtt ttgcgccatt    4500
cgatggtgtc aacgtaaatg catgccgctt cgccttcgcg cgcgaattgc aagctgatcc    4560
ggagcttatc gactgcacgg tgcaccaatg cttctggcgt caggcagcca tcggaagctg    4620
tggtatggct gtgcaggtcg taaatcactg cataattcgt gtcgctcaag cgcactccc     4680 gttctggata tgttttttg cgccgacatc ataacggttc tggcaaatat tctgaaatga    4740
gctgttgaca attaatcatc ggctcgtata atgtgtggaa ttgtgagcgg ataacaattt    4800
cacacaggaa acagaattcc atatgaaata cctattacca acagcagcag ctgggttatt    4860
attgctcgct gcgcagccgg ccatggccca ggtcaccgtc tcctcacgta cggtggctgc    4920
accatctgtc ttcatcttcc cgccatctga tgagcagttg aaatctggaa ctgcctctgt    4980
tgtgtgcctg ctgaataact tctatcccag agaggccaaa gtacagtgga aggtggataa    5040
cgccctccaa tcgggtaact cccaggagag tgtcacagag caggacagca aggacagcac    5100
ctacagcctc agcagcaccc tgacgctgag caaagcagac tacgagaaac acaaagtcta    5160
cgcctgcgaa gtcacccatc agggcctgag ctcgccggtg acaaagagct caaccgcgg     5220 agagtgtgca ggtgattaca agacgatga cgataagtaa taaacaggaa acagaagtcc    5280
atatgaaata tctttttacct acggcagccg caggtttgtt gttactcgcg gcccagccgg    5340
ccatggccgc tagcaccaag ggcccatcgg tcttccccct ggcaccctcc tccaagagca    5400
cctctggggg cacagcggcc ctgggctgcc tggtcaagga ctacttcccc gaaccggtga    5460
cggtgtcgtg gaactcaggc gccctgacca gcggcgtgca caccttcccg gctgtcctac    5520
agtcctcagg actctactcc ctcagcagcg tagtgaccgt gccctccagc agcttgggca    5580
cccagaccta catctgcaac gtgaatcaca agcccagcaa caccaaggtg gacaagaaag    5640
ttgagcccaa atcttgtgac aaaactcaca catgcccacc gtgccagcg gccgcagaac     5700 aaaaactcat ctcagaagag gatctgaatg gggccgtaca tcaccaccat catcatggga    5760
gctaagcttg gctgttttgg cggatgagag aagattttca gcctgataca gattaaatca    5820
gaacgcagaa gcggtctgat aaaacagaat ttgcctggcg gcagtagcgc ggtggtccca    5880
cctgacccca tgccgaactc agaagtgaaa cgccgtagcg ccgatggtag tgtggggtct    5940
ccccatgcga gagtagggaa ctgccaggca tcaaataaaa cgaaaggctc agtcgaaaga    6000
ctgggccttt cgttttatct gttgtttgtc ggtgaacgct ctcctgagta ggacaaatcc    6060
gccgggagcg gatttgaacg ttgcgaagca acggcccgga ggaccctggc gggcaggacg    6120
cccgccataa actgccaggc atcaaattaa gcagaaggcc atcctgacgg atggcctttt    6180
tgcgtttcta caaactctt                                                 6199
```

<210> SEQ ID NO 114
<211> LENGTH: 6064
<212> TYPE: DNA
<213> ORGANISM: Artificial sequence
<220> FEATURE:
<223> OTHER INFORMATION: plasmid pCkCH1y1

<400> SEQUENCE: 114

```
ttgtttattt ttctaaatac attcaaatat gtatccgctc atgagacaat aaccctgata      60
```

```
aatgcttcaa taatattgaa aaaggaagag tatgagtatt caacatttcc gtgtcgccct    120 tattccctttt tttgcggcat tttgccttcc tgttttttgct cacccagaaa cgctggtgaa    180
agtaaaagat gctgaagatc agttgggtgc acgagtgggt tacatcgaac tggatctcaa    240
cagcggtaag atccttgaga gttttcgccc gaagaacgt tttccaatga tgagcacttt    300
taaagttctg ctatgtggcg cggtattatc ccgtgttgac gccgggcaag agcaactcgg    360
tcgccgcata cactattctc agaatgactt ggttgagtac tcaccagtca cagaaaagca    420
tcttacggat ggcatgacag taagagaatt atgcagtgct gccataacca tgagtgataa    480
cactgcggcc aacttacttc tgacaacgat cggaggaccg aaggagctaa ccgcttttt    540 gcacaacatg ggggatcatg taactcgcct tgatcgttgg gaaccggagc tgaatgaagc    600
cataccaaac gacgagcgtg acaccacgat gcctgtagca atggcaacaa cgttgcgcaa    660
actattaact ggcgaactac ttactctagc ttcccggcaa caattaatag actggatgga    720
ggcggataaa gttgcaggac cacttctgcg ctcggccctt ccggctggct ggtttattgc    780
tgataaatct ggagccggtg agcgtgggtc tcgcggtatc attgcagcac tggggccaga    840
tggtaagccc tcccgtatcg tagttatcta cacgacgggg agtcaggcaa ctatggatga    900
acgaaataga cagatcgctg agataggtgc ctcactgatt aagcattggt aactgtcaga    960
ccaagtttac tcatatatac tttagattga tttaaaactt catttttaat ttaaaaggat   1020
ctaggtgaag atccttttg ataatctcat gaccaaaatc ccttaacgtg agttttcgtt   1080
ccactgagcg tcagaccccg tagaaaagat caaaggatct tcttgagatc cttttttct   1140 gcgcgtaatc tgctgcttgc aaacaaaaaa accaccgcta ccagcggtgg tttgtttgcc   1200
ggatcaagag ctaccaactc tttttccgaa ggtaactggc ttcagcagag cgcagatacc   1260
aaatactgtc cttctagtgt agccgtagtt aggccaccac ttcaagaact ctgtagcacc   1320
gcctacatac ctcgctctgc taatcctgtt accagtggct gctgccagtg gcgataagtc   1380
gtgtcttacc gggttggact caagacgata gttaccggat aaggcgcagc ggtcgggctg   1440
aacggggggt tcgtgcacac agcccagctt ggagcgaacg acctacaccg aactgagata   1500
cctacagcgt gagcattgag aaagcgccac gcttcccgaa gggagaaagg cggacaggta   1560
tccggtaagc ggcagggtcg gaacaggaga gcgcacgagg gagcttccag ggggaaacgc   1620
ctggtatctt tatagtcctg tcgggtttcg ccacctctga cttgagcgtc gatttttgtg   1680
atgctcgtca gggggcgga gcctatggaa aaacgccagc aacgcggcct ttttacggtt   1740
cctggccttt tgctggcctt ttgctcacat gttctttcct gcgttatccc ctgattctgt   1800
ggataaccgt attaccgcct ttgagtgagc tgataccgct cgccgcagcc gaacgaccga   1860
gcgcagcgag tcagtgagcg aggaagcgga agagcgcctg atgcggtatt ttctccttac   1920
gcatctgtgc ggtatttcac accgcatata tggtgcactc tcagtacaat ctgctctgat   1980
gccgcatagt taagccagta tacactccgc tatcgctacg tgactgggtc atggctgcgc   2040
cccgacaccc gccaacaccc gctgacgcgc cctgacgggc ttgtctgctc ccggcatccg   2100
cttacagaca agctgtgacc gtctccggga gctgcatgtg tcagaggttt tcaccgtcat   2160
caccgaaacg cgcgaggcag ctgcggtaaa gctcatcagc gtggtcgtga agcgattcac   2220
agatgtctgc ctgttcatcc gcgtccagct cgttgagttt ctccagaagc gttaatgtct   2280
ggcttctgat aaagcgggcc atgttaaggg cggttttttc ctgtttggtc acttgatgcc   2340
tccgtgtaag ggggaatttc tgttcatggg ggtaatgata ccgatgaaac gagagaggat   2400
gctcacgata cgggttactg atgatgaaca tgcccggtta ctggaacgtt gtgagggtaa   2460
```

```
acaactggcg gtatggatgc ggcgggacca gagaaaaatc actcagggtc aatgccagcg   2520
cttcgttaat acagatgtag gtgttccaca gggtagccag cagcatcctg cgatgcagat   2580
ccggaacata atggtgcagg gcgctgactt ccgcgtttcc agactttacg aaacacggaa   2640
accgaagacc attcatgttg ttgctcaggt cgcagacgtt ttgcagcagc agtcgcttca   2700
cgttcgctcg cgtatcggtg attcattctg ctaaccagta aggcaacccc gccagcctag   2760
ccgggtcctc aacgacagga gcacgatcat gcgcacccgt ggccaggacc caacgctgcc   2820
cgagatgcgc cgcgtgcggc tgctggagat ggcggacgcg atggatatgt tctgccaagg   2880
gttggtttgc gcattcacag ttctccgcaa gaattgattg gctccaattc ttggagtggt   2940
gaatccgtta gcgaggtgcc gccggcttcc attcaggtcg aggtggcccg gctccatgca   3000
ccgcgacgca acgcggggag gcagacaagg tatagggcgg cgcctacaat ccatgccaac   3060
ccgttccatg tgctcgccga ggcggcataa atcgccgtga cgatcagcgg tccagtgatc   3120
gaagttaggc tggtaagagc cgcgagcgat ccttgaagct gtccctgatg gtcgtcatct   3180
acctgcctgg acagcatggc ctgcaacgcg ggcatcccga tgccgccgga agcgagaaga   3240
atcataatgg ggaaggccat ccagcctcgc gtcgcgaacg ccagcaagac gtagcccagc   3300
gcgtcggcca gcttgcaatt cgcgctaact tacattaatt gcgttgcgct cactgcccgc   3360
tttccagtcg ggaaacctgt cgtgccagct gcattaatga atcggccaac gcgcggggag   3420
aggcggtttg cgtattgggc gccagggtgg ttttctttt caccagtgag acgggcaaca   3480
gctgattgcc cttcaccgcc tggccctgag agagttgcag caagcggtcc acgctggttt   3540
gccccagcag gcgaaaatcc tgtttgatgg tggttgacgg cgggatataa catgagctgt   3600
cttcggtatc gtcgtatccc actaccgaga tatccgcacc aacgcgcagc ccggactcgg   3660
taatggcgcg cattgcgccc agcgccatct gatcgttggc aaccagcatc gcagtgggaa   3720
cgatgccctc attcagcatt tgcatggttt gttgaaaacc ggacatggca ctccagtcgc   3780
cttcccgttc cgctatcggc tgaatttgat tgcgagtgag atatttatgc cagccagcca   3840
gacgcagacg cgccgagaca gaacttaatg gtcccgctaa cagcgcgatt tgctgatgac   3900
ccaatgcgac cagatgctcc acgcccagtc gcgtaccgtc ttcatgggag aaaataatac   3960
tgttgatggg tgtctggtca gagacatcaa gaaataacgc cggaacatta gtgcaggcag   4020
cttccacagc aatggcatcc tggtcatcca gcggatagtt aatgatcagc ccactgacgc   4080
gttgcgcgag aagattgtgc accgccgctt tacaggcttc gacgccgctt cgttctacca   4140
tcgacaccac cacgctggca cccagttgat cggcgcgaga tttaatcgcc gcgacaattt   4200
gcgacggcgc gtgcagggcc agactggagg tggcaacgcc aatcagcaac gactgtttgc   4260
ccgccagttg ttgtgccacg cggttgggaa tgtaattcag ctccgccatc gccgcttcca   4320
cttttttccg cgttttcgca gaaacgtggc tggcctggtt caccacgcgg gaaacggtct   4380
gataagagac accggcatac tctgcgacat cgtataacgt tactggtttc acattccacca   4440 ccctgaattg actctcttcc gggcgctatc atgccatacc gcgaaaggtt ttgcgccatt   4500
cgatggtgtc aacgtaaatg catgccgctt cgccttcgcg cgcgaattgc aagctgatcc   4560
ggagcttatc gactgcacgg tgcaccaatg cttctggcgt caggcagcca tcggaagctg   4620
tggtatggct gtgcaggtcg taaatcactg cataattcgt gtcgctcaag gcgcactccc   4680
gttctggata atgttttttg cgccgacatc ataacggttc tggcaaatat tctgaaatga   4740
gctgttgaca attaatcatc ggctcgtata atgtgtggaa ttgtgagcgg ataacaattt   4800
```

```
cacacaggaa acagaattcc atatgaaata cctattacca acagcagcag ctgggttatt    4860
attgctcgct gcgcagccgg ccatggccca ggtcaccgtc tcctcacgta cggtggctgc    4920
accatctgtc ttcatcttcc cgccatctga tgagcagttg aaatctggaa ctgcctctgt    4980
tgtgtgcctg ctgaataact ctatcccag agaggccaaa gtacagtgga aggtggataa    5040
cgccctccaa tcgggtaact cccaggagag tgtcacagag caggacagca aggacagcac    5100
ctacagcctc agcagcaccc tgacgctgag caaagcagac tacgagaaac acaaagtcta    5160
cgcctgcgaa gtcaccccatc agggcctgag ctcgccggtg acaaagagct caaccgcgg    5220
```

```
cacacaggaa acagaattcc atatgaaata cctattacca acagcagcag ctgggttatt    4860
attgctcgct gcgcagccgg ccatggccca ggtcaccgtc tcctcacgta cggtggctgc    4920
accatctgtc ttcatcttcc cgccatctga tgagcagttg aaatctggaa ctgcctctgt    4980
tgtgtgcctg ctgaataact ctatcccag  agaggccaaa gtacagtgga aggtggataa    5040
cgccctccaa tcgggtaact cccaggagag tgtcacagag caggacagca aggacagcac    5100
ctacagcctc agcagcaccc tgacgctgag caaagcagac tacgagaaac acaaagtcta    5160
cgcctgcgaa gtcaccccatc agggcctgag ctcgccggtg acaaagagct caaccgcgg    5220 agagtgttaa taaacaggaa acagaagtcc atatgaaata tcttttacct acggcagccg    5280
caggtttgtt gttactcgcg gcccagccgg ccatggccgc tagcaccaag ggcccatcgg    5340 tcttcccct  ggcaccctcc tccaagagca cctctggggg cacagcggcc ctgggctgcc    5400
tggtcaagga ctacttcccc gaaccggtga cggtgtcgtg gaactcaggc gccctgacca    5460
gcggcgtgca caccttcccg gctgtcctac agtcctcagg actctactcc ctcagcagcg    5520
tagtgaccgt gccctccagc agcttgggca cccagaccta catctgcaac gtgaatcaca    5580
agcccagcaa caccaaggtg gacaagaaag ttgagcccaa atcttgttaa gcttggctgt    5640
tttggcggat gagagaagat tttcagcctg atacagatta aatcagaacg cagaagcggt    5700
ctgataaaac agaatttgcc tggcggcagt agcgcggtgg tcccacctga ccccatgccg    5760
aactcagaag tgaaacgccg tagcgccgat ggtagtgtgg ggtctcccca tgcgagagta    5820
gggaactgcc aggcatcaaa taaaacgaaa ggctcagtcg aaagactggg cctttcgttt    5880
tatctgttgt ttgtcggtga acgctctcct gagtaggaca aatccgccgg agcggatttt    5940
gaacgttgcg aagcaacggc ccggaggacc ctggcgggca ggacgcccgc cataaactgc    6000
caggcatcaa attaagcaga aggccatcct gacggatggc cttttgcgt ttctacaaac    6060 tctt                                                                6064
```

<210> SEQ ID NO 115
<211> LENGTH: 6094
<212> TYPE: DNA
<213> ORGANISM: Artificial sequence
<220> FEATURE:
<223> OTHER INFORMATION: plasmid pCkCH1Hy1

<400> SEQUENCE: 115

```
ttgtttattt ttctaaatac attcaaatat gtatccgctc atgagacaat aaccctgata      60
aatgcttcaa taatattgaa aaggaagag tatgagtatt caacatttcc gtgtcgccct     120
tattcccttt tttgcggcat tttgccttcc tgttttgct  cacccagaaa cgctggtgaa     180
agtaaaagat gctgaagatc agttgggtgc acgagtgggt tacatcgaac tggatctcaa     240
cagcggtaag atccttgaga gttttcgccc cgaagaacgt tttccaatga tgagcacttt     300
taaagttctg ctatgtggcg cggtattatc ccgtgttgac gccgggcaag agcaactcgg     360
tcgccgcata cactattctc agaatgactt ggttgagtac tcaccagtca cagaaaagca     420
tcttacggat ggcatgacag taagagaatt atgcagtgct gccataacca tgagtgataa     480
cactgcggcc aacttacttc tgacaacgat cggaggaccg aaggagctaa ccgcttttt     540 gcacaacatg gggatcatg  taactcgcct tgatcgttgg gaaccggagc tgaatgaagc     600
cataccaaac gacgagcgtg acaccacgat gcctgtagca atggcaacaa cgttgcgcaa     660
actattaact ggcgaactac ttactctagc ttcccggcaa caattaatag actggatgga     720
ggcggataaa gttgcaggac cacttctgcg ctcggccctt ccggctggct ggtttattgc     780
```

```
tgataaatct ggagccggtg agcgtgggtc tcgcggtatc attgcagcac tggggccaga    840
tggtaagccc tcccgtatcg tagttatcta cacgacgggg agtcaggcaa ctatggatga    900
acgaaataga cagatcgctg agataggtgc ctcactgatt aagcattggt aactgtcaga    960
ccaagtttac tcatatatac tttagattga tttaaaactt catttttaat ttaaaaggat   1020
ctaggtgaag atccttttg ataatctcat gaccaaaatc ccttaacgtg agttttcgtt   1080
ccactgagcg tcagacccccg tagaaaagat caaaggatct tcttgagatc ctttttttct   1140
gcgcgtaatc tgctgcttgc aaacaaaaaa accaccgcta ccagcggtgg tttgtttgcc   1200
ggatcaagag ctaccaactc tttttccgaa ggtaactggc ttcagcagag cgcagatacc   1260
aaatactgtc cttctagtgt agccgtagtt aggccaccac ttcaagaact ctgtagcacc   1320
gcctacatac ctcgctctgc taatcctgtt accagtggct gctgccagtg gcgataagtc   1380
gtgtcttacc gggttggact caagacgata gttaccggat aaggcgcagc ggtcgggctg   1440
aacggggggt tcgtgcacac agcccagctt ggagcgaacg acctacaccg aactgagata   1500
cctacagcgt gagcattgag aaagcgccac gcttcccgaa gggagaaagg cggacaggta   1560
tccggtaagc ggcagggtcg gaacaggaga gcgcacgagg gagcttccag ggggaaacgc   1620
ctggtatctt tatagtcctg tcgggtttcg ccacctctga cttgagcgtc gatttttgtg   1680
atgctcgtca ggggggcgga gcctatggaa aaacgccagc aacgcggcct ttttacggtt   1740
cctggccttt tgctggcctt tgctcacat gttctttcct gcgttatccc ctgattctgt   1800
ggataaccgt attaccgcct ttgagtgagc tgataccgct cgccgcagcc gaacgaccga   1860
gcgcagcgag tcagtgagcg aggaagcgga agagcgcctg atgcggtatt ttctccttac   1920
gcatctgtgc ggtatttcac accgcatata tggtgcactc tcagtacaat ctgctctgat   1980
gccgcatagt taagccagta tacactccgc tatcgctacg tgactgggtc atggctgcgc   2040
cccgacaccc gccaacaccc gctgacgcgc cctgacgggc ttgtctgctc ccggcatccg   2100
cttacagaca agctgtgacc gtctccggga gctgcatgtg tcagaggttt tcaccgtcat   2160
caccgaaacg cgcgaggcag ctgcggtaaa gctcatcagc gtggtcgtga agcgattcac   2220
agatgtctgc ctgttcatcc gcgtccagct cgttgagttt ctccagaagc gttaatgtct   2280
ggcttctgat aaagcgggcc atgttaaggg cggttttttc ctgtttggtc acttgatgcc   2340
tccgtgtaag ggggaatttc tgttcatggg ggtaatgata ccgatgaaac gagagaggat   2400
gctcacgata cgggttactg atgatgaaca tgcccggtta ctggaacgtt gtgagggtaa   2460
acaactggcg gtatggatgc ggcgggacca gagaaaaatc actcagggtc aatgccagcg   2520
cttcgttaat acagatgtag gtgttccaca gggtagccag cagcatcctg cgatgcagat   2580
ccggaacata atggtgcagg cgctgactt ccgcgtttcc agactttacg aaacacggaa   2640
accgaagacc attcatgttg ttgctcaggt cgcagacgtt ttgcagcagc agtcgcttca   2700
cgttcgctcg cgtatcggtg attcattctg ctaaccagta aggcaacccc gccagcctag   2760
ccgggtcctc aacgacagga gcacgatcat gcgcacccgt ggccaggacc caacgctgcc   2820
cgagatgcgc cgcgtgcggc tgctggagat ggcggacgcg atggatatgt tctgccaagg   2880
gttggtttgc gcattcacag ttctccgcaa gaattgattg gctccaattc ttggagtggt   2940
gaatccgtta gcgaggtgcc gccggcttcc attcaggtcg aggtggcccg gctccatgca   3000
ccgcgacgca acgcggggag gcagacaagg tatagggcgg cgcctacaat ccatgccaac   3060
ccgttccatg tgctcgccga ggcggcataa atcgccgtga cgatcagcgg tccagtgatc   3120
```

```
gaagttaggc tggtaagagc cgcgagcgat ccttgaagct gtccctgatg gtcgtcatct    3180
acctgcctgg acagcatggc ctgcaacgcg ggcatcccga tgccgccgga agcgagaaga    3240
atcataatgg ggaaggccat ccagcctcgc gtcgcgaacg ccagcaagac gtagcccagc    3300
gcgtcggcca gcttgcaatt cgcgctaact tacattaatt gcgttgcgct cactgcccgc    3360
tttccagtcg ggaaacctgt cgtgccagct gcattaatga atcggccaac gcgcggggag    3420
aggcggtttg cgtattgggc gccagggtgg ttttctttt caccagtgag acgggcaaca    3480
gctgattgcc cttcaccgcc tggccctgag agagttgcag caagcggtcc acgctggttt    3540
gccccagcag gcgaaaatcc tgtttgatgg tggttgacgg cgggatataa catgagctgt    3600
cttcggtatc gtcgtatccc actaccgaga tatccgcacc aacgcgcagc ccggactcgg    3660
taatggcgcg cattgcgccc agcgccatct gatcgttggc aaccagcatc gcagtgggaa    3720
cgatgccctc attcagcatt tgcatggttt gttgaaaacc ggacatggca ctccagtcgc    3780
cttcccgttc cgctatcggc tgaatttgat tgcgagtgag atatttatgc cagccagcca    3840
gacgcagacg cgccgagaca gaacttaatg gtcccgctaa cagcgcgatt tgctgatgac    3900
ccaatgcgac cagatgctcc acgcccagtc gcgtaccgtc ttcatgggag aaaataatac    3960
tgttgatggg tgtctggtca gagacatcaa gaaataacgc cggaacatta gtgcaggcag    4020
cttccacagc aatggcatcc tggtcatcca gcggatagtt aatgatcagc ccactgacgc    4080
gttgcgcgag aagattgtgc accgccgctt tacaggcttc gacgccgctt cgttctacca    4140
tcgacaccac cacgctggca cccagttgat cggcgcgaga tttaatcgcc gcgacaattt    4200
gcgacggcgc gtgcagggcc agactggagg tggcaacgcc aatcagcaac gactgtttgc    4260
ccgccagttg ttgtgccacg cggttgggaa tgtaattcag ctccgccatc gccgcttcca    4320
cttttttcccg cgttttcgca gaaacgtggc tggcctggtt caccacgcgg gaaacggtct    4380
gataagagac accggcatac tctgcgacat cgtataacgt tactggtttc acattcacca    4440
ccctgaattg actctcttcc gggcgctatc atgccatacc gcgaaaggtt ttgcgccatt    4500
cgatggtgtc aacgtaaatg catgccgctt cgccttcgcg cgcgaattgc aagctgatcc    4560
ggagcttatc gactgcacgg tgcaccaatg cttctggcgt caggcagcca tcggaagctg    4620
tggtatggct gtgcaggtcg taaatcactg cataattcgt gtcgctcaag gcgcactccc    4680
gttctggata atgttttttg cgccgacatc ataacggttc tggcaaatat tctgaaatga    4740
gctgttgaca attaatcatc ggctcgtata atgtgtggaa ttgtgagcgg ataacaattt    4800
cacacaggaa acagaattcc atatgaaata cctattacca acagcagcag ctgggttatt    4860
attgctcgct gcgcagccgg ccatggccca ggtcaccgtc tcctcacgta cggtggctgc    4920
accatctgtc ttcatcttcc cgccatctga tgagcagttg aaatctggaa ctgcctctgt    4980
tgtgtgcctg ctgaataact tctatcccag agaggccaaa gtacagtgga aggtggataa    5040
cgccctccaa tcgggtaact cccaggagag tgtcacagag caggacagca aggacagcac    5100
ctacagcctc agcagcaccc tgacgctgag caaagcagac tacgagaaac acaaagtcta    5160
cgcctgcgaa gtcacccatc agggcctgag ctcgccggtg acaaagagct tcaaccgcgg    5220
agagtgttaa taaacaggaa acagaagtcc atatgaaata tcttttacct acggcagccg    5280
caggtttgtt gttactcgcg gcccagccgg ccatggccgc tagcaccaag ggcccatcgg    5340
tcttcccccct ggcaccctcc tccaagagca cctctggggg cacagcggcc ctgggctgcc    5400
tggtcaagga ctacttcccc gaaccggtga cggtgtcgtg gaactcaggc gccctgacca    5460
gcggcgtgca caccttcccg gctgtcctac agtcctcagg actctactcc ctcagcagcg    5520
```

```
tagtgaccgt gccctccagc agcttgggca cccagaccta catctgcaac gtgaatcaca      5580
agcccagcaa caccaaggtg gacaagaaag ttgagcccaa atcttgtgac aaaactcaca      5640
catgcccacc gtgcccataa gcttggctgt tttggcggat gagagaagat tttcagcctg      5700
atacagatta aatcagaacg cagaagcggt ctgataaaac agaatttgcc tggcggcagt      5760
agcgcggtgg tcccacctga ccccatgccg aactcagaag tgaaacgccg tagcgccgat      5820
ggtagtgtgg ggtctcccca tgcgagagta gggaactgcc aggcatcaaa taaaacgaaa      5880
ggctcagtcg aaagactggg cctttcgttt tatctgttgt ttgtcggtga acgctctcct      5940
gagtaggaca atccgccgg gagcggattt gaacgttgcg aagcaacggc ccggaggacc       6000
ctggcgggca ggacgcccgc cataaactgc caggcatcaa attaagcaga aggccatcct      6060
gacggatggc cttttgcgt ttctacaaac tctt                                   6094

<210> SEQ ID NO 116
<211> LENGTH: 6745
<212> TYPE: DNA
<213> ORGANISM: Artificial sequence
<220> FEATURE:
<223> OTHER INFORMATION: plasmid pMaby1*

<400> SEQUENCE: 116
ttgtttattt ttctaaatac attcaaatat gtatccgctc atgagacaat aaccctgata        60
aatgcttcaa taatattgaa aaggaagag tatgagtatt caacatttcc gtgtcgccct        120
tattcccttt tttgcggcat tttgccttcc tgttttttgct cacccagaaa cgctggtgaa       180
agtaaaagat gctgaagatc agttgggtgc acagtgggt tacatcgaac tggatctcaa        240
cagcggtaag atccttgaga gttttcgccc cgaagaacgt tttccaatga tgagcacttt        300
taaagttctg ctatgtggcg cggtattatc ccgtgttgac gccgggcaag agcaactcgg       360
tcgccgcata cactattctc agaatgactt ggttgagtac tcaccagtca cagaaaagca      420
tcttacggat ggcatgacag taagagaatt atgcagtgct gccataacca tgagtgataa      480
cactgcggcc aacttacttc tgacaacgat cggaggaccg aaggagctaa ccgctttttt     540
gcacaacatg gggatcatg taactcgcct tgatcgttgg gaaccggagc tgaatgaagc      600
cataccaaac gacgagcgtg acaccacgat gcctgtagca atggcaacaa cgttgcgcaa    660
actattaact ggcgaactac ttactctagc ttcccggcaa caattaatag actggatgga    720 gcggataaa gttgcaggac cacttctgcg ctcggccctt ccggctggct ggtttattgc      780
tgataaatct ggagccggtg agcgtgggtc tcgcggtatc attgcagcac tggggccaga    840
tggtaagccc tcccgtatcg tagttatcta cacgacgggg agtcaggcaa ctatggatga    900
acgaaataga cagatcgctg agataggtgc ctcactgatt aagcattggt aactgtcaga    960
ccaagtttac tcatatatac tttagattga tttaaaactt cattttaat ttaaaaggat      1020 ctaggtgaag atccttttg ataatctcat gaccaaaatc ccttaacgtg agttttcgtt      1080
ccactgagcg tcagaccccg tagaaaagat caaaggatct tcttgagatc ctttttttct    1140
gcgcgtaatc tgctgcttgc aaacaaaaaa accaccgcta ccagcggtgg tttgtttgcc    1200
ggatcaagag ctaccaactc tttttccgaa ggtaactggc ttcagcagag cgcagatacc    1260
aaatactgtc cttctagtgt agccgtagtt aggccaccac ttcaagaact ctgtagcacc    1320
gcctacatac ctcgctctgc taatcctgtt accagtggct gctgccagtg gcgataagtc    1380
gtgtcttacc gggttggact caagacgata gttaccggat aaggcgcagc ggtcgggctg    1440
```

```
aacgggggt  tcgtgcacac  agcccagctt  ggagcgaacg  acctacaccg  aactgagata   1500
cctacagcgt  gagcattgag  aaagcgccac  gcttcccgaa  gggagaaagg  cggacaggta   1560
tccggtaagc  ggcagggtcg  aacaggaga   gcgcacgagg  gagcttccag  ggggaaacgc   1620
ctggtatctt  tatagtcctg  tcgggtttcg  ccacctctga  cttgagcgtc  gattttgtg    1680 atgctcgtca  ggggggcgga  gcctatggaa  aaacgccagc  aacgcggcct  ttttacggtt   1740
cctggccttt  tgctggcctt  ttgctcacat  gttctttcct  gcgttatccc  ctgattctgt   1800
ggataaccgt  attaccgcct  ttgagtgagc  tgataccgct  cgccgcagcc  gaacgaccga   1860
gcgcagcgag  tcagtgagcg  aggaagcgga  agagcgcctg  atgcggtatt  ttctccttac   1920
gcatctgtgc  ggtatttcac  accgcatata  tggtgcactc  tcagtacaat  ctgctctgat   1980
gccgcatagt  taagccagta  tacactccgc  tatcgctacg  tgactgggtc  atggctgcgc   2040
cccgacaccc  gccaacaccc  gctgacgcgc  cctgacgggc  ttgtctgctc  ccggcatccg   2100
cttacagaca  agctgtgacc  gtctccggga  gctgcatgtg  tcagaggttt  tcaccgtcat   2160
caccgaaacg  cgcgaggcag  ctgcggtaaa  gctcatcagc  gtggtcgtga  agcgattcac   2220
agatgtctgc  ctgttcatcc  gcgtccagct  cgttgagttt  ctccagaagc  gttaatgtct   2280
ggcttctgat  aaagcgggcc  atgttaaggg  cggttttttc  ctgtttggtc  acttgatgcc   2340
tccgtgtaag  ggggaatttc  tgttcatggg  ggtaatgata  ccgatgaaac  gagagaggat   2400
gctcacgata  cgggttactg  atgatgaaca  tgcccggtta  ctggaacgtt  gtgagggtaa   2460
acaactggcg  gtatggatgc  ggcgggacca  gagaaaaatc  actcagggtc  aatgccagcg   2520
cttcgttaat  acagatgtag  gtgttccaca  gggtagccag  cagcatcctg  cgatgcagat   2580
ccggaacata  atggtgcagg  gcgctgactt  ccgcgtttcc  agactttacg  aaacacggaa   2640
accgaagacc  attcatgttg  ttgctcaggt  cgcagacgtt  ttgcagcagc  agtcgcttca   2700
cgttcgctcg  cgtatcggtg  attcattctg  ctaaccagta  aggcaacccc  gccagcctag   2760
ccgggtcctc  aacgacagga  gcacgatcat  gcgcacccgt  ggccaggacc  caacgctgcc   2820
cgagatgcgc  cgcgtgcggc  tgctggagat  ggcggacgcg  atggatatgt  tctgccaagg   2880
gttggtttgc  gcattcacag  ttctccgcaa  gaattgattg  gctccaattc  ttggagtggt   2940
gaatccgtta  gcgaggtgcc  gccggcttcc  attcaggtcg  aggtggcccg  gctccatgca   3000
ccgcgacgca  acgcggggag  gcagacaagg  tatagggcgg  cgcctacaat  ccatgccaac   3060
ccgttccatg  tgctcgccga  ggcggcataa  atcgccgtga  cgatcagcgg  tccagtgatc   3120
gaagttaggc  tggtaagagc  cgcgagcgat  ccttgaagct  gtccctgatg  gtcgtcatct   3180
acctgcctgg  acagcatggc  ctgcaacgcg  ggcatcccga  tgccgccgga  agcgagaaga   3240
atcataatgg  ggaaggccat  ccagcctcgc  gtcgcgaacg  ccagcaagac  gtagcccagc   3300
gcgtcggcca  gcttgcaatt  cgcgctaact  tacattaatt  gcgttgcgct  cactgcccgc   3360
tttccagtcg  ggaaacctgt  cgtgccagct  gcattaatga  atcggccaac  gcgcggggag   3420
aggcggtttg  cgtattgggc  gccagggtgg  ttttcttttt  caccagtgag  acgggcaaca   3480
gctgattgcc  cttcaccgcc  tggccctgag  agagttgcag  caagcggtcc  acgctggttt   3540
gccccagcag  gcgaaaatcc  tgtttgatgg  tggttgacgg  cgggatataa  catgagctgt   3600
cttcggtatc  gtcgtatccc  actaccgaga  tatccgcacc  aacgcgcagc  ccggactcgg   3660
taatggcgcg  cattgcgccc  agcgccatct  gatcgttggc  aaccagcatc  gcagtgggaa   3720
cgatgccctc  attcagcatt  tgcatggttt  gttgaaaacc  ggacatggca  ctccagtcgc   3780
cttcccgttc  cgctatcggc  tgaatttgat  tgcgagtgag  atatttatgc  cagccagcca   3840
```

```
gacgcagacg cgccgagaca gaacttaatg gtcccgctaa cagcgcgatt tgctgatgac    3900
ccaatgcgac cagatgctcc acgcccagtc gcgtaccgtc ttcatgggag aaaataatac    3960
tgttgatggg tgtctggtca gagacatcaa gaaataacgc cggaacatta gtgcaggcag    4020
cttccacagc aatggcatcc tggtcatcca gcggatagtt aatgatcagc ccactgacgc    4080
gttgcgcgag aagattgtgc accgccgctt tacaggcttc gacgccgctt cgttctacca    4140
tcgacaccac cacgctggca cccagttgat cggcgcgaga tttaatcgcc gcgacaattt    4200
gcgacggcgc gtgcagggcc agactggagg tggcaacgcc aatcagcaac gactgtttgc    4260
ccgccagttg ttgtgccacg cggttgggaa tgtaattcag ctccgccatc gccgcttcca    4320
ctttttcccg cgttttcgca gaaacgtggc tggcctggtt caccacgcgg aaacggtct     4380
gataagagac accggcatac tctgcgacat cgtataacgt tactggtttc acattcacca    4440
ccctgaattg actctcttcc gggcgctatc atgccatacc gcgaaaggtt ttgcgccatt    4500
cgatggtgtc aacgtaaatg catgccgctt cgccttcgcg cgcgaattgc aagctgatcc    4560
ggagcttatc gactgcacgg tgcaccaatg cttctggcgt caggcagcca tcggaagctg    4620
tggtatggct gtgcaggtcg taaatcactg cataattcgt gtcgctcaag gcgcactccc    4680
gttctggata atgttttttg cgccgacatc ataacggttc tggcaaatat tctgaaatga    4740
gctgttgaca attaatcatc ggctcgtata atgtgtggaa ttgtgagcgg ataacaattt    4800
cacacaggaa acagaattcc atatgaaata cctattacca acagcagcag ctgggttatt    4860
attgctcgct gcgcagccgg ccatggccca ggtcaccgtc tcctcacgta cggtggctgc    4920
accatctgtc ttcatcttcc cgccatctga tgagcagttg aaatctggaa ctgcctctgt    4980
tgtgtgcctg ctgaataact tctatcccag agaggccaaa gtacagtgga aggtggataa    5040
cgccctccaa tcgggtaact cccaggagag tgtcacagag caggacagca aggacagcac    5100
ctacagcctc agcagcaccc tgacgctgag caaagcagac tacgagaaac acaaagtcta    5160
cgcctgcgaa gtcacccatc agggcctgag ctcgccggtg acaaagagct caaccgcgg    5220
agagtgttaa taaacaggaa acagaagtcc atatgaaata tcttttacct acggcagccg    5280
caggtttgtt gttactcgcg gcccagccgg ccatggccgc tagcaccaag ggcccatcgg    5340
tcttccccct ggcaccctcc tccaagagca cctctggggg cacagcggcc ctgggctgcc    5400
tggtcaagga ctacttcccc gaaccggtga cggtgtcgtg gaactcaggc gccctgacca    5460
gcggcgtgca caccttcccg gctgtcctac agtcctcagg actctactcc ctcagcagcg    5520
tggtgaccgt gccctccagc agcttgggca cccagaccta catctgcaac gtgaatcaca    5580
agcccagcaa caccaaggtg gacaagaaag ttgagcccaa atcttgtgac aaaactcaca    5640
catgcccacc gtgcccagca cctgaactcc tggggggacc gtcagtcttc ctcttccccc    5700
caaaacccaa ggacaccctc atgatctccc ggacccctga ggtcacatgc gtggtggtgg    5760
acgtgagcca cgaagaccct gaggtcaagt tcaactggta cgtggacggc gtggaggtgc    5820
ataatgccaa gacaaagccg cgggaggagc agtacaacag cacgtaccgg gtggtcagcg    5880
tcctcaccgt cctgcaccag gactggctga atggcaagga gtacaagtgc aaggtctcca    5940
acaaagcccc cccagccccc atcgagaaaa ccatctccaa agccaaaggg cagccccgag    6000
aaccacaggt gtacaccctg cccccatccc gggatgagct gaccaagaac caggtcagcc    6060
tgacctgcct ggtcaaaggc ttctatccca gcgacatcgc cgtggagtgg gagagcaatg    6120
ggcagccgga gaacaactac aagaccacgc ctcccgtgct ggactccgac ggctccttct    6180
```

| | | |
|---|---|---|
| tcctctacag caagctcacc gtggacaaga gcaggtggca gcaggggaac gtcttctcat | 6240 | |
| gctccgtgat gcatgaggct ctgcacaacc actacacgca gaagagcctc tccctgtctc | 6300 | |
| cgggtaaata agcttggctg ttttggcgga tgagagaaga ttttcagcct gatacagatt | 6360 | |
| aaatcagaac gcagaagcgg tctgataaaa cagaatttgc ctggcggcag tagcgcggtg | 6420 | |
| gtcccacctg accccatgcc gaactcagaa gtgaaacgcc gtagcgccga tggtagtgtg | 6480 | |
| gggtctcccc atgcgagagt agggaactgc caggcatcaa ataaaacgaa aggctcagtc | 6540 | |
| gaaagactgg gcctttcgtt ttatctgttg tttgtcggtg aacgctctcc tgagtaggac | 6600 | |
| aaatccgccg ggagcggatt tgaacgttgc gaagcaacgg cccggaggac cctggcgggc | 6660 | |
| aggacgcccg ccataaactg ccaggcatca aattaagcag aaggccatcc tgacggatgg | 6720 | |
| ccttttttgcg tttctacaaa ctctt | 6745 | |

```
<210> SEQ ID NO 117
<211> LENGTH: 119
<212> TYPE: DNA
<213> ORGANISM: Artificial sequence
<220> FEATURE:
<223> OTHER INFORMATION: oligonuclotide 5'Flag/RBS/35-sup

<400> SEQUENCE: 117
```

| | |
|---|---|
| ggagagtgtg caggtgatta caaagacgat gacgataagt aataaacagg aaacagaagt | 60 |
| ccatatgaaa tatctttttac ctacggcagc cgcaggtttg ttgttactcg cggcccagc | 119 |

```
<210> SEQ ID NO 118
<211> LENGTH: 118
<212> TYPE: DNA
<213> ORGANISM: Artificial sequence
<220> FEATURE:
<223> OTHER INFORMATION: oligonucleotide 5'Flag/RBS/35-inf

<400> SEQUENCE: 118
```

| | |
|---|---|
| gggccgcgag taacaacaaa cctgcggctg ccgtaggtaa aagatatttc atatggactt | 60 |
| ctgtttcctg tttattactt atcgtcatcg tctttgtaat cacctgcaca ctctccgc | 118 |

```
<210> SEQ ID NO 119
<211> LENGTH: 59
<212> TYPE: DNA
<213> ORGANISM: Artificial sequence
<220> FEATURE:
<223> OTHER INFORMATION: oligonuclotide 5'Ck

<400> SEQUENCE: 119
```

| | |
|---|---|
| ggggccaggg gacccaggtc accgtctcct cacgtacggt ggctgcacca tctgtcttc | 59 |

```
<210> SEQ ID NO 120
<211> LENGTH: 89
<212> TYPE: DNA
<213> ORGANISM: Artificial sequence
<220> FEATURE:
<223> OTHER INFORMATION: oligonucleotide 5'RBS/35-sup

<400> SEQUENCE: 120
```

| | |
|---|---|
| ggagagtgtt aataaacagg aaacagaagt ccatatgaaa tatctttttac ctacggcagc | 60 |
| cgcaggtttg ttgttactcg cggcccagc | 89 |

```
<210> SEQ ID NO 121
<211> LENGTH: 88
<212> TYPE: DNA
<213> ORGANISM: Artificial sequence
```

```
<220> FEATURE:
<223> OTHER INFORMATION: oligonucleotide 3'RBS/35-inf

<400> SEQUENCE: 121
gggccgcgag taacaacaaa cctgcggctg ccgtaggtaa aagatatttc atatggactt      60
ctgtttcctg tttattaaca ctctccgc                                        88

<210> SEQ ID NO 122
<211> LENGTH: 18
<212> TYPE: DNA
<213> ORGANISM: Artificial sequence
<220> FEATURE:
<223> OTHER INFORMATION: oligonucleotide 3' inf-Pst1+ 71

<400> SEQUENCE: 122
gttaaacggc gagcaccg                                                   18
```